(12) United States Patent
Cost et al.

(10) Patent No.: US 10,174,331 B2
(45) Date of Patent: Jan. 8, 2019

(54) METHODS AND COMPOSITIONS FOR NUCLEASE-MEDIATED TARGETED INTEGRATION OF TRANSGENES

(71) Applicants: Sangamo BioSciences, Inc., Richmond, CA (US); Dow AgroSciences LLC, Indianapolis, IN (US)

(72) Inventors: Gregory J. Cost, Richmond, CA (US); Fyodor Urnov, Richmond, CA (US); W. Michael Ainley, Indianapolis, IN (US); Joseph F. Petolino, Indianapolis, IN (US); Jayakumar Pon Samuel, Indianapolis, IN (US); Steven R. Webb, Indianapolis, IN (US); Lakshmi Sastry-Dent, Indianapolis, IN (US)

(73) Assignees: Sangamo Therapeutics, Inc., Richmond, CA (US); Dow AgroSciences LLC, Indianapolis, IN (US)

( * ) Notice: Subject to any disclaimer, the term of this patent is extended or adjusted under 35 U.S.C. 154(b) by 24 days.

(21) Appl. No.: 13/889,162

(22) Filed: May 7, 2013

(65) Prior Publication Data
US 2013/0326645 A1 Dec. 5, 2013

Related U.S. Application Data

(60) Provisional application No. 61/643,812, filed on May 7, 2012.

(51) Int. Cl.
| | | |
|---|---|---|
| C12N 15/82 | (2006.01) | |
| C12N 15/87 | (2006.01) | |
| C12N 15/85 | (2006.01) | |
| C12N 15/10 | (2006.01) | |

(52) U.S. Cl.
CPC ....... *C12N 15/8201* (2013.01); *C12N 15/102* (2013.01); *C12N 15/8209* (2013.01); *C12N 15/8213* (2013.01); *C12N 15/8216* (2013.01); *C12N 15/8241* (2013.01); *C12N 15/8247* (2013.01); *C12N 15/8274* (2013.01); *C12N 15/8278* (2013.01); *C12N 15/8286* (2013.01); *C12N 15/85* (2013.01); *C12N 15/87* (2013.01); *C12N 2800/80* (2013.01); *Y02A 40/162* (2018.01)

(58) Field of Classification Search
None
See application file for complete search history.

(56) References Cited

U.S. PATENT DOCUMENTS

| | | |
|---|---|---|
| 4,536,475 A | 8/1985 | Anderson |
| 4,693,977 A | 9/1987 | Jensen et al. |
| 4,886,937 A | 12/1989 | Chilton et al. |
| 5,015,580 A | 5/1991 | Barton et al. |
| 5,302,523 A | 4/1994 | Coffee et al. |
| 5,384,253 A | 1/1995 | Anderson et al. |
| 5,464,765 A | 11/1995 | Coffee et al. |
| 5,501,967 A | 3/1996 | De Groot et al. |
| 5,508,184 A | 4/1996 | Negrutiu et al. |
| 5,538,880 A | 4/1996 | Lundquist et al. |
| 5,550,318 A | 8/1996 | Adams et al. |
| 5,563,055 A | 10/1996 | Thomas et al. |
| 5,591,616 A | 1/1997 | Hiei et al. |
| 5,693,512 A | 12/1997 | Finer et al. |
| 5,789,538 A | 8/1998 | Pabo et al. |
| 5,824,877 A | 10/1998 | Connor-Ward et al. |
| 5,925,523 A | 7/1999 | Dove et al. |
| 5,981,840 A | 11/1999 | Cai et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Carlos, III et al. |
| 6,160,208 A | 12/2000 | Kirihara et al. |
| 6,200,759 B1 | 3/2001 | Dove et al. |
| 6,242,568 B1 | 6/2001 | Barbas et al. |
| 6,384,301 B1 | 5/2002 | Martinell et al. |
| 6,399,861 B1 | 6/2002 | Anderson et al. |
| 6,403,865 B1 | 6/2002 | Koziel et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | George, III et al. |
| 6,599,692 B1 | 7/2003 | Case et al. |
| 6,607,882 B1 | 8/2003 | George, III et al. |
| 6,689,558 B2 | 2/2004 | Case |
| 6,794,136 B1 | 9/2004 | Eisenberg et al. |
| 6,824,978 B1 | 11/2004 | George, III et al. |
| 6,903,185 B2 | 6/2005 | Kim et al. |
| 6,933,113 B2 | 8/2005 | Case et al. |
| 6,979,539 B2 | 12/2005 | Case et al. |

(Continued)

FOREIGN PATENT DOCUMENTS

| | | |
|---|---|---|
| EP | 0 122 791 B1 | 3/1989 |
| EP | 0 120 516 A2 | 10/1991 |

(Continued)

OTHER PUBLICATIONS

Chen et al 2003 (Molecular Breeding 11: p. 287-293).*

(Continued)

*Primary Examiner* — Matthew R Keogh
(74) *Attorney, Agent, or Firm* — Pasternak Patent Law

(57) ABSTRACT

Disclosed herein are methods and compositions for homology-independent targeted insertion of donor molecules into the genome of a cell.

10 Claims, 60 Drawing Sheets
Specification includes a Sequence Listing.

(56) References Cited

U.S. PATENT DOCUMENTS

| | | |
|---|---|---|
| 7,013,219 B2 | 3/2006 | Case et al. |
| 7,030,215 B2 | 4/2006 | Jamieson et al. |
| 7,067,317 B2 | 6/2006 | Rebar et al. |
| 7,070,934 B2 | 7/2006 | Case et al. |
| 7,153,949 B2 | 12/2006 | Kim et al. |
| 7,163,824 B2 | 1/2007 | Case et al. |
| 7,179,902 B2 | 2/2007 | Armstrong et al. |
| 7,253,273 B2 | 8/2007 | Collingwood |
| 7,262,054 B2 | 8/2007 | Jamieson et al. |
| 7,361,635 B2 | 4/2008 | Collingwood et al. |
| 7,838,733 B2 | 11/2010 | Arnold et al. |
| 7,888,121 B2 | 2/2011 | Holmes et al. |
| 7,951,925 B2 | 5/2011 | Ando et al. |
| 8,110,379 B2 | 2/2012 | DeKelver et al. |
| 8,329,986 B2 | 9/2012 | Butler et al. |
| 2003/0232410 A1 | 12/2003 | Aspland et al. |
| 2005/0026157 A1 | 2/2005 | Baltimore et al. |
| 2005/0064474 A1 | 3/2005 | Holmes et al. |
| 2005/0208489 A1 | 9/2005 | Carroll et al. |
| 2005/0267061 A1 | 12/2005 | Martin |
| 2006/0063231 A1 | 3/2006 | Li et al. |
| 2006/0188987 A1 | 8/2006 | Guschin et al. |
| 2007/0014275 A1 | 1/2007 | Bettink et al. |
| 2007/0218528 A1 | 9/2007 | Miller |
| 2008/0131962 A1 | 6/2008 | Miller |
| 2008/0159996 A1 | 7/2008 | Ando et al. |
| 2008/0182332 A1* | 7/2008 | Cai et al. ............ 435/468 |
| 2009/0042250 A1 | 2/2009 | Collingwood et al. |
| 2009/0068164 A1 | 3/2009 | Barbas et al. |
| 2009/0111119 A1 | 4/2009 | Doyon et al. |
| 2009/0117617 A1 | 5/2009 | Holmes |
| 2009/0263900 A1 | 10/2009 | DeKelver et al. |
| 2009/0305346 A1 | 12/2009 | Miller |
| 2010/0047805 A1 | 2/2010 | Wang |
| 2010/0129869 A1 | 5/2010 | Liu |
| 2011/0119786 A1 | 5/2011 | Butler et al. |
| 2011/0145940 A1 | 6/2011 | Voytas et al. |
| 2011/0201055 A1 | 8/2011 | Doyon et al. |
| 2011/0207221 A1 | 8/2011 | Cost et al. |
| 2011/0239315 A1 | 9/2011 | Bonas et al. |
| 2011/0281361 A1 | 11/2011 | DeKelver et al. |
| 2011/0301073 A1 | 12/2011 | Gregory et al. |

FOREIGN PATENT DOCUMENTS

| | | | |
|---|---|---|---|
| GB | 2338237 A | 12/1999 | |
| WO | WO 1995/19431 A1 | 7/1995 | |
| WO | WO 1996/06166 A1 | 2/1996 | |
| WO | WO 1998/37186 A1 | 8/1998 | |
| WO | 1998/041645 | 9/1998 | |
| WO | WO 1998/53057 A1 | 11/1998 | |
| WO | WO 1998/53058 A1 | 11/1998 | |
| WO | WO 1998/53059 A1 | 11/1998 | |
| WO | WO 1998/53060 A1 | 11/1998 | |
| WO | WO 1998/54311 A1 | 12/1998 | |
| WO | WO 2000/27878 A1 | 5/2000 | |
| WO | WO 2001/60970 A2 | 8/2001 | |
| WO | WO 2001/88197 A2 | 11/2001 | |
| WO | WO 2002/016536 A1 | 2/2002 | |
| WO | WO 2002/077227 A2 | 10/2002 | |
| WO | WO 2002/099084 A2 | 12/2002 | |
| WO | WO 2003/080809 A2 | 2/2003 | |
| WO | WO 2005/014791 A3 | 2/2005 | |
| WO | WO 2005/084190 A2 | 9/2005 | |
| WO | WO 2007/014275 A2 | 2/2007 | |
| WO | WO 2003/016496 A2 | 2/2008 | |
| WO | WO 2008/148223 A1 | 12/2008 | |
| WO | WO 2009/042163 A2 | 4/2009 | |
| WO | WO 2009/046384 A1 | 4/2009 | |
| WO | WO 2010/065123 A1 | 6/2010 | |
| WO | WO 2010/079430 A1 | 7/2010 | |
| WO | WO2010143917 A2 * | 12/2010 | ............ C12N 15/10 |
| WO | 2011/011767 A2 | 1/2011 | |
| WO | 2011/017315 A2 | 2/2011 | |
| WO | 2011/090804 A1 | 7/2011 | |
| WO | WO 2011/091317 A2 | 7/2011 | |

OTHER PUBLICATIONS

Orlando et al 2010 (Nucleic Acids Research 38:15, p. 1-15).*
Shukla et al 2009 (Nature 459, p. 437-441).*
Beerli et al., "Engineering Polydactyl Zinc-Finger Transcription Factors," *Nat. Biotechnol.* 20:135-141 (2002).
Bevan et al., "A Chimaeric Antibiotic Resistance Gene as a Selectable Marker for Plant Cell Transformation," *Nature* 304:184-187 (1983).
Boch, et al., "Breaking the Code of DNA Binding Specificity of TAL-Type III Effectors," *Science* 326:1509-1512 (2009).
Bonas et al., "Genetic and Structural Characterization of the Avirulence Gene AVRBS3 From Xanthomonas Campestris PV. Vesicatoria," *Mol. Gen. Genet.* 218:127-136 (1989).
Burgess, "Technology: A CRISPR Genome-Editing Tool," *Nature Reviews Genetics* 14:80-81 (2013).
Choo et al., "Advances in Zinc Finger Engineering," *Curr. Opin. Struct. Biol.* 10:411-416 (2000).
Christian et al., "TAL Effector Nucleases Create Targeted DNA Double-Strand Breaks," *Genetics* epub 10.1534/genetics.110. 102717 (2010).
Chu et al., "Establishment of an Efficient Medium for Another Culture in Rice Through Comparative Experiments on the Nitrogen Sources," *Scientia Sinica* 18:659-668 (1975).
Cong et al., "Multiplex Genome Engineering Using CRISPR/CAS Systems," *Sciencexpress* 1/10.1126/science 1231143 (2013).
DeKelver et al., "Functional Genomics, Proteomics, and Regulatory DNA Analysis in Isogenic Settings Using Zinc Finger Nuclease-Driven Transgenesis Into a Safe Harbor Locus in the Human Genome," *Genome Research* 20(8):1133-1142 (2010).
Doyon et al., "Heritable Targeted Gene Disruption in Zebrafish Using Designed Zinc-Finger Nucleases," *Nat. Biotechnol.* 26:702-708 (2008).
Doyon et al., "Enhancing Zinc-Finger-Nuclease Activity With Improved Obligate Heterodimeric Architecture," *Nature Methods* 8(1):74-79 (2010).
Guerts et al., "Knockout Rats via Embryo Microinjection of Zinc-Finger Nucleases," *Science* 325:433 (2009).
Guo et al., "Directed Evolution of an Enhanced and Highly Efficient FOKI Cleavage Domain for Zinc Finger Nucleases," *J. Mol. Biol.* 400(1):96-107 (2010).
Haft et al., "A Guild of 45 CRISPR-Associated (CAS) Protein Families and Multiple CRISPR/CAS Subtypes Exist in Prokaryotic Genomes," *PLoS Comput. Biol.* 1:e60 (2005).
Herrera-Estrella et al., "Expression of Chimaeric Genes Transferred Into Plant Cells Using a Ti-Plasmid-Derived Vector," *Nature* 303:209-213 (1983).
Heuer et al., "Repeat Domain Diversity of AVRBS3-Like Genes in Ralstonia Solanacearum Strains and Association With Host Preferences in the Field," *Appl. and Envir. Micro.* 73(13):4379-4384 (2007).
Hockemeyer et al., "Efficient Targeting of Expressed and Silent Genes in Human ESCS and IPSCS Using Zinc-Finger Nucleases," *Nat. Biotech.* 27(9):851-857 (2009).
Isalan et al., "A Rapid, Generally Applicable Method to Engineer Zinc Fingers Illustrated by Targeting the HIV-1 Promoter," *Nat. Biotech.* 19: 656-660 (2001).
Jansen et al., "Identification of Genes That Are Associated With DNA Repeats in Prokaryotes," *Mol. Microbiol.* 43:1565-1575 (2002).
Jinek et al., "RNA-Programmed Genome Editing in Human Cells," *eLife* 2:e00471(2013).
Jinek et al., "A Programmable Dual-RNA-Guided DNA Endonuclease in Adaptive Bacterial Immunity," *Science* 337:816-821 (2012).
Kay et al., "A Bacterial Effector Acts As a Plant Transcription Factor and Induces a Cell Size Regulator," *Science* 318:648-651 (2007).
Klee et al., "Vectors for Transformation of Higher Plants," *Nature Biotechnology.* 3:637-642 (1985).

(56) References Cited

OTHER PUBLICATIONS

Koller et al., "Germ-Line Transmission of a Planned Alteration Made in Hypoxanthine Phosphorylbosyltransferase Gene by Homologous Recombination in Embryonic Stem Cells," *PNAS USA* 86(22):8927-8931 (1989).

Liu et al., "Generation of a Triple-Gene Knockout Mammalian Cell Line Using Engineered Zinc Finger Nucleases," *Biotechnol. and Bioeng.* 106(1):97-105 (2010).

Lombardo et al., "Gene Editing in Human Stem Cells Using Zinc Finger Nucleases and Integrase-Defective Lentiviral Vector Delivery," *Nature Biotech.* 25(11):1298-1306 (2007).

Makarova et al., "A Putative RNA-Interference-Based Immune System in Prokaryotes: Computational Analysis of the Predicted Enzymatic Machinery, Functional Analogies With Eukaryotic RNA, and Hypothetical Mechanisms of Action," *Biol. Direct* 1:7 (2006).

Makarova et al., "A DNA Repair System Specific for Thermophilic Archaea and Bacteria Predicted by Genomic Context Analysis," *Nucleic Acids Research* 30:482-496 (2002).

Malanowska et al., "CTNDOT Integrase Performs Ordered Homology-Independent Strand Exchanges," *Nucleic Acids Research* 35(17):5861-5873 (2007).

Malphettes et al., "Highly Efficient Deletion of FUT8 in Cho Cell Lines Using Zinc-Finger Nucleases Yields Cells That Produce Completely Nonfucosylated Antibodies," *Biotechnol. and Bioeng.* 106(5):774-783 (2010).

Moehle et al., "Targeted Gene Addition Into a Specified Location in the Human Genome Using Designed Zinc Finger Nucleases," *Proc. Natl. Acad. Sci. USA* 104(9):3055-3060 (2007).

Moscou and Bogdanove, "A Simple Cipher Governs DNA Recognition by TAL Effectors," *Science* 326:1501 (2009).

Orlando et al., "Zinc-Finger Nuclease-Driven Targeted Integration Into Mammalian Genomes Using Donors With Limited Chromosomal Homology," *Nucleic Acids Res.* 38(15):e152 (2010).

Pabo et al., "Design and Selection of Novel CYS2HIS2 Zinc Finger Proteins," *Ann. Rev. Biochem.* 70:313-340 (2001).

Perez et al., "Establishment of HIV-1 Resistance in CD4+ T Cells by Genome Editing Using Zinc-Finger Nucleases," *Nat. Biotech.* 26(7):808-816 (2008).

Potrykus et al., "Direct Gene Transfer to Cells of a Graminaceous Monocot," *Mol. Gen. Genet.* 199:183-188 (1985).

Povirk, "Role of BRACA1 in Nonhomologous DNA End Joining," *U.S. Army Medical Research and Material Command* 1-11. Award No. DAMD17-03-1-0620 (1994).

Rebar, "Development of Pro-Angiogenic Engineered Transcription Factors for the Treatment of Cardiovascular Disease," *Expert Opinion Invest. Drugs* 13(7):829-839 (2004).

Rossi et al., "Genetic Therapies Against HIV," *Nature Biotech.* 25(12):1444-1454 (2007).

Rouet et al., "Expression of a Site-Specific Endonuclease Stimulates Homologous Recombination in Mammalian Cells," *PNAS USA* 91(13):6064-6068 (1994).

Schornack et al., "Gene-For-Gene-Mediated Recognition of Nuclear-Targeted AVRBS3-Like Bacterial Effector Proteins," *J. Plant Physiol.* 163(3):256-272 (2006).

Segal et al., "Custom DNA-Binding Proteins Come of Age: Polydactyl Zinc-Finger Proteins," *Curr. Opin. Biotechnol.* 12:632-637 (2001).

Segal, "Bacteria Herald a New Era of Gene Editing," *eLife* 2:e00563 (2013).

Shukla et al., "Precise Genome Modification in the Crop Species *Zea mays* Using Zinc-Finger Nucleases," *Nature* 459:437-441(2009).

Thomas et al., "High Frequency Targeting of Genes to Specific Sites in the Mammalian Genome," *Cell* 44(3):419-428 (1986).

Urnov et al., "Highly Efficient Endogenous Human Gene Correction Using Designed Zinc-Finger Nucleases," *Nature* 435(7042):646-651 (2005).

Chilton, et al., "Targeted Integration of T-DNA Into the Tobacco Genome at Double-Stranded Breaks: New Insights on the Mechanism of T-DNA Integration," Plant Physiology 133:956-965 (2003).

Haviv-Chesner, et al., "Capture of Linear Fragments At a Double-Strand Break in Yeast," Nucleic Acids Research 35(15):5192-5202 (2007).

Tzfira, et al., "Genome Modifications in Plant Cells by Custom-Made Restriction Enzymes," Plant Biotechnology Journal 10:373-389 (2012).

Tzfira, et al., "Site-Specific Integration of Agrobacterium Tumefaciens T-DNA via Double-Stranded Intermediates," Plant Physiology 133:1011-1023 (2003).

\* cited by examiner

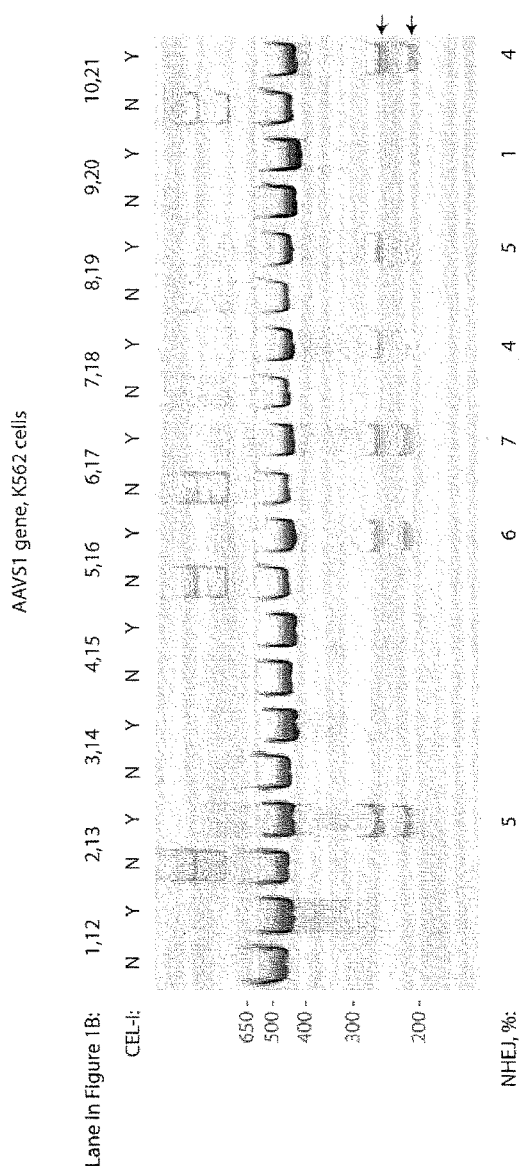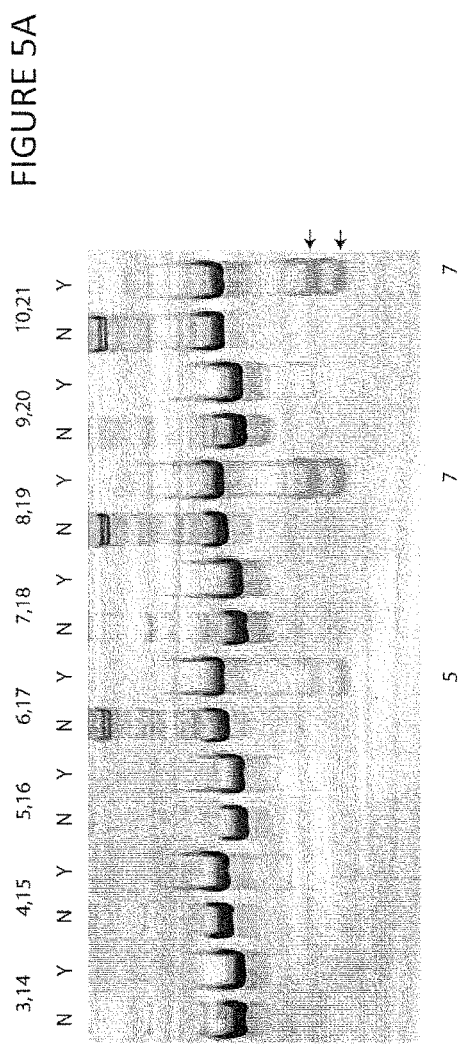
FIGURE 5A

*AAVS1* single cell-derived clones, AB insertions

Left (5') junction

| | | SEQ ID NO: |
|---|---|---|
| Expected | TTATCTGTCCCCTCCACCCCACAGTGGGGCCCACT*AGGGACAGGAT*TATCCATCACACTGG | 28 |
| Clone 1 | TTATCTGTCCCCTCCACCCCACAGTGGGGCCCACT*AGGGACAGGAT*TATCCATCACACTGG | 28 |
| Clone 3 | TTATCTGTCCCCTCCACCCCACAGTGGGGCCCACT*AGGGACAGGAT*TATCCATCACACTGG | 28 |

Right (3') junction

| | | |
|---|---|---|
| Expected | CGAATTCTGCAGATCACCCCACAGTGGGCCCACT*AGGGACAGGAT*TGGTGACAGAAAAGCC | 29 |
| Clone 1 | CGAATTCTGCAGATCACCCCACAGTGGGCCCACT*AGGGACAGGAT*TGGTGACAGAAAAGCC | 29 |
| Clone 3 | CGAATTCTGCAGATCACCCCACAGTGGGCCCACT*AGGGACAGGAT*TGGTGACAGAAAAGCC | 29 |

*AAVS1* single cell-derived clones, BA insertions

Left (5') junction

| | | |
|---|---|---|
| Expected | TTATCTGTCCCCTCCACCCCACAGTGGGCCCACTGTGGGG*T*GATCTGCAGAATTCG | 30 |
| Clone 2 | TTATCTGTCCCCTCCACCCCACAGTGGG..........GTGATCT*G*CAGAATTCG | 31 |
| Clone 3 | TTATCTGTCCCCTCCACCCCACAGTGGG..........GT*G*ATCTGCAGAATTCG | 31 |

Right (3') junction

| | | |
|---|---|---|
| Expected | CCAGTGTGATGGATA*ATCCTGTCCTA*GCT*AGGGACAGGAT*TGGTGACAGAAAAGC | 32 |
| Clone 2 | | |
| Clone 3 | | |

FIGURE 7

```
                                                                    SEQ ID NO
AAVS1 pool alleles, AB insertions
Left (5') junction
Expected TTATCTGTCCCCTCCACCCCACAGTGGGG:CCAC::TAGGGACAGGATTGGTGACAGAATCGA    33
         TTATCTGTCCCCTCCACCCCACAGTGGGG:CCAC::TAGGGACAGGATTGGTGACAGAATCGA    33
         TTATCTGTCCCCTCCACCCCACAGTGGGGCCAC::TAGGGACAGGATTGGTGACAGAATCGA     34
         TTATCTGTCCCCTCCA:::::::::::CCAC::TAGGGACAGGATTGGTGACAGAATCGA       35
         TTATCTGTCCCCTCCACCCCACAG::::::CCAC::TAGGGACAGGATTGGTGACAGAATCGA    36
         TTATCTGTCCCCTCCACCCCACAGTGGGG:CCACACTAGGGACAGGATTGGTGACAGAATCGA    37

AAVS1 pool alleles, BA insertions
Right (3') junction
Expected TCGATTCTGTCACCAATCCTGTCCCTAG::::::CTAGGGACAGGATTGGTGACAGAAAAGC    38
         TCGATTCTGTCACCAATCCTGTCCC:::::::::TAGGGACAGGATTGGTGACAGAAAAGC     39
         TCGATTCTGTCACCAATC:::::::::::CAGGATTGGTGACAGAAAAGC                40
         TCGATTCTGTCACCAATCCTGTCCCTAGTG:GCACTAGGGACAGGATTGGTGACAGAAAAGC    41
         TCGATTCTGTCACCAATCCTGTCCCTAGTGGCCACTAGGGACAGGATTGGTGACAGAAAAGC    42
         TCGATTCTGTCACCAATCCTGTCCCTA::::::::GGGACAGGATTGGTGACAGAAAAGC      43
```

FIGURE 8A

```
CCR5 pool alleles, BA insertions                                                                                      SEQ ID NO
Left (5') junction
Expected GTGGGCAACATGCTGGTCATCCTCATC::::::GATGAGGATGACCAAGGGCGAATTCTG                                                  44
         GTGGGCAACATGCTGGTCATCCTCATC::::::GATGAGGATGACCAAGGGCGAATTCTG                                                  44
         GTGGGCAACATGCTGGTCATCCTCATCCTGATCAGGATGAGGATGACCAAGGGCGAATTCTG(4X)                                            45
         GTGGGCAACATGCTGGTCATCCTCAT::::ATCAGGATGAGGATGACCAAGGGCGAATTCTG                                                46
         GTGGGCAACATGCTGGTCATCCTCATCCTGAT:::GATGAGGATGACCAAGGGCGAATTCTG                                                47

CCR5 pool alleles, AB insertions
Right (3') junction
Expected CAGAATTCGCCCTTGGTCATCCTCATCCT::::GATAAACTGCAAAAGGCTGAAGAGCATGAC                                               48
         CAGAATTCGCCCTTGGTCATCCTCATCCT::::GATAAACTGCAAAAGGCTGAAGAGCATGAC                                               48
         CAGAATTCGCCCTTGGTC:::::::::::::::::::::::::CTGAAGAGCATGAC                                                    49
         CAGAATTCGCCCTTGGTCATCC:::::::::GATAAACTGCAAAAGGCTGAAGAGCATGAC                                                 50
         CAGAATTCGCCCTTGGTCATCC:::::::::::GATAAACTGCAAAAGGCTGAAGAGCATGAC                                               51
         CAGAATTCGCCCTTGGTCA:::::::::::::::::CTGCAAAAGGCTGAAGAGCATGAC                                                  52
         CAGAATTCGCCCTTGGTCATCCTCATCCTGAGTTATTTTCTGCAAAAGGCTGAAGAGCATGAC                                               53
```

FIGURE 8B

```
                                                                          SEQ ID NO
GS pool alleles, BA insertions
Left (5') junction
Expected  AGCAACCTTTGACCCAAGCCCATTCCTGGGAA::::TTCCCAGGAATGGGCTTGGGGTCATCGAATTC    54
          AGCAACCTTTGACCCAAGCCCATTCCTGGGAACTGGTTCCCAGGAATGGGCTTGGGGTCATCGAATTC    55
          AGCAACCTTTGACCCAAGCCCATTCCTGG:::::TTCCCAGGAATGGGCTTGGGGTCATCGAATTC      56
          AGCAACCTTTGACCCAAGCCCATTCCTGGGAAC::::TTCCCAGGAATGGGCTTGGGGTCATCGAATTC   57
          AGCAACCTTTGACCCAAGCCCATTCCTGGGAAACTAGTTCTCAGGAATGGGCTTGGGGTCATCGAATTC   58
          AGCAACCTTTGACCCAAGCCCATTCCTGGGAACCAGTTCCCAGGAATGGGCTTGGGGTCATCGAATTC (3X) 59
          AGCAACCTTTGACCCAAGCCCATTCCTGGGAAG:::TTCCCAGGAATGGGCTTGGGGTCATCGAATTC    60

GS pool alleles, AB insertions
Right (3') junction
Expected  GGAATTCGATGACCCCAAGCCCATTCCTGGGAA:::::CTGGAATGGTGCAGGCTGCCATACCAACTTT    61
          GGAATTCGATGACCCCAAGCCCATTCCTGGG::::::::::TGCAGGCTGCCATACCAACTTT (2X)    62
          GGAATTCGATGACCCCAAGCCCATTCCTGGGAAC:::::CTGGAATGGTGCAGGCTGCCATACCAACTTT  63
          GGAATTCGATGACCCCAAGCCCATTCCTGGGAACTGGACTGGAATGGTGCAGGCTGCCATACCAACTTT   64
          GGAATTCGATGACCCCAAGCCCATTCCTGGGAACTGG::CTGGAATGGTGCAGGCTGCCATACCAACTTT  65
          GGAATTCGATGACCCCAAGCCCATTCCTGGGAAC::::CATGGAATGGTGCAGGCTGCCATACCAACTTT  66
          GGAATTCGATGACCCCAAGCCCATTCCTGGGAA::::::::::::::::TACCAACTTT            67

IL2Rg pool alleles, AB insertions
Right (3') junction
Expected  TCGATGTTTCGTGTTCGGAGCCGCTTTAACCC::ACTCTGTGTGGAAGTGCTCAGCATTGGAG          68
          TCGATGTTTCGTGTTCGGAGCCGCTTTAACCCTGACTCTGTGTGGAAGTGCTCAGCATTGGAG          69
          TCGATGTTTCGTGTTCGGAGCCGCTTTA::::::ACTCTGTGTGGAAGTGCTCAGCATTGGAG (2X)    70
          TCGATGTTTCGTGTTCGGAGCCGCTTTAAAAACCCACTCTGTGTGGAAGTGCTCAGCATTGGAG         71
```

FIGURE 8C

```
GS single cell-derived clones, BA orientation                                                                    SEQ ID
Left (5') junction
Expected AGCAACCTTTGACCCCAAGCCCCATTCCTGGGAA::::TTCCCAGGAATGGGCTTGGGGTCATCGAATTC                                   72
Clone 1  AGCAACCTTTGACCCCAAGCCCCATTCCTGGGAACCAGTTCCCAGGAATGGGCTTGGGGTCATCGAATTC                                   73
Clone 2  AGCAACCTTTGACCCCAAGCCCCATTCCTGGGAAC:TGTTCCCAGGAATGGGCTTGGGGTCATCGAATTC                                   74
Clone 3  AGCAACCTTTGACCCCAAGCCCCATTCCTGGGAACCAGTTCCCAGGAATGGGCTTGGGGTCATCGAATTC                                   75
Clone 4  AGCAACCTTTGACCCCAAGCCCCATTCCTGGGAACCAGTTCCCAGGAATGGGCTTGGGGTCATCGAATTC                                   76
Clone 5  AGCAACCTTTGACCCCAAGCCCCATTCCTGGGAAC:TGTTCCCAGGAATGGGCTTGGGGTCATCGAATTC                                   77
Clone 6  AGCAACCTTTGACCCCAAGCCCCATTCCTGGGAAC:TGTTCCCAGGAATGGGCTTGGGGTCATCGAATTC                                   77
Clone 7  AGCAACCTTTGACCCCAAGCCCCATTCCTGGGAACCAGTTCCCAGGAATGGGCTTGGGGTCATCGAATTC                                   78
Clone 8  AGCAACCTTTGACCCCAAGCCCCATTCCTGGGAACCAGTTCCCAGGAATGGGCTTGGGGTCATCGAATTC                                   78

Right (3') junction
Expected TTGATTTGGTATGGCAGCCTGCACCATT::::AATGGTGCAGGCTGCCATACCAACTTTAGCACCA                                      79
Clone 1
Clone 2
Clone 3
Clone 4  TTGATTTGGTATGGCAGCCTGCACCATTCCGGAATGGTGCAGGCAGCAATAAAAACTTTNGNACCT                                        80
Clone 5
Clone 6
Clone 7
Clone 8
```

FIGURE 9

```
FUT8 single cell-derived clones, AB orientation, cleaved by ZFNs                                                                    SEQ ID
Left (5') junction
Expected   TGGATAAAAAAAGAGTGTATCTGGCCACTGATGACCCTTCTTTGTTAAAGGAGGCAAAGACAAAGTAAGGCCGCGAATTC                                          81
           TGGATAAAAAAAGAGTGTATCTGGCCACTGATGACCCTTCTTT::::AAGGAGGCAAAGACAAAGACAAAGTAAGGCCGCGAATTC                                    82
      (X2) TGGATAAAAAAAGAGTGTATCTGGCCACTGATGACCCT::::::GTTAAAGGAGGCAAAGACAAAGACAAAGTAAGGCCGCGAATTC                                  83
           TGGATAAAAAAAGAGTGTATCTGGCCACTGATGACCCTTC:ATGTTAAAGGAGGCAAAGACAAAGTAAGGCCGCGAATTC                                         84

Right (3') junction
Expected   TTAGCGGCCGTGTATCTGGCCACTGATGACCCTTCTTTGTTAAAGGAGGCAAAGACAAAGTAAGTTAGACCAACAAGTGG                                          85
           TTAGCGGCCGTGTATCTGGCCACT:::::::GGTTAAAGGAGGCAAAGACAAAGACAAGTAAGTTAGACCAACAAGTGG                                           86
           TTAGCGGCCGTGTATCTGGCCACTGACCC:::::::AGGCAAAGAGGCAAAGACAAAGTAAGTTAGACCAACAAGTGG                                            87
           TTAGCGGCCGTGTATCTGGCCACTGATGACTGATGACCCTTCTT::::TTAAAGGAGGCAAAGACAAAGTAAGTTAGACCAACAAGTGG                                 88
      (X3) TTAGCGGCCGTGTATCTGGCCACTGATGACCCT::::::AAAGACAAAGTAAGTTAGACCAACAAGTGG                                                    89

FUT8 single cell-derived clones, BA orientation, cleaved by ZFNs
Left (5') junction
Expected   TGGATAAAAAAAGAGTGTATCTGGCCACTGATGACCCTTCTTAAGAAGGGTCATCAGTGGCCAGATACACGGCCGCTAAATTCA                                      90
     (X20) TGGATAAAAAAAGAGTGTATCTGGCCACTGATGACCCTTC::::::::::::::TACACGGCCGCTAAATTCA                                                91

Right (3') junction
Expected   GAATTCGGCCGCCTTACTTTGTCTTTGCCTCCCTTTAACATGTTAAAGGAGGCAAAGACAAAGTAAGTTAGACCAACAA                                          92
           GAATTCG:::::::::::ACTTTGTCTTTG::::::::::::CAAAGACAAAGTAAGTTAGACCAACAA           (X2)                                      93
           GAATTCGGCCGCCTTACTTTGTCTTT::::::::::GTTAAAGGAGGCAAAGACAAAGTAAGTTAGACCAACAA                                                94
           GAATTCGGCCGCCTTACTTTGTCTTT::::::::::GTTAAAGGAGGCAAAGACAAAGTAAGTTAGACCAACAA       (X2)                                     95
           GAATTCGGCCGCCTTACTTTGTCTTTGCCTCCCTTTAA:::TGTTAAAGGAGGCAAAGACAAAGTAAGTTAGACCAACAA                                          96
           GAATTCGCGCCTTACTTTGTCTTTGCCTCCCTTTAA:::GTTAAAGGAGGCAAAGACAAAGTAAGTTAGACCAACAA                                             
```

FIGURE 10A

```
                                                                                    SEQ ID
FUT8 single cell-derived clones, AB orientation, cleaved by TALENs
Left (5') junction
Expected  TGGATAAAAAAGAGTGTATCTGGCCACTGATGACCCTTATTTGTTAAAGGAGGCAAAGACAAAGTAAGGCCGCGAATTC    97
    (X2)  TGGATAAAAAAGAGTGTATCTGGCCACTGATGACCCT::::::TTAAAGGAGGCAAAGACAAAGTAAGGCCGCGAATTC    98
    (X2)  TGGATAAAAAAGAGTGTATCTGGCCACT::::::CTTTGTTAAAGGAGGCAAAGACAAAGTAAGGCCGCGAATTC        99
    (X2)  TGGATAAAAAAGAGTGTATCTGGCCACTGATG::::::TTAAAGGAGGCAAAGACAAAGTAAGGCCGCGAATTC         100
Right (3') junction
Expected  TTAGCGGCCGTGTATCTGGCCACTGATGACCCTTCCTTTGTTAAAGGAGGCAAAGACAAAGTAAGTTAGACCAACAAGTG  101

FUT8 single cell-derived clones, BA orientation, cleaved by TALENs
Left (5') junction
Expected  TGGATAAAAAAGAGTGTATCTGGCCACTGATCAGTGGCCAGATACACGGCCGCTAAATTCAA                    102
   (X10)  TGGATAAAAAAGAGTGTATCTGGCCACTGATGACCCTTC::::::TACACGGCCGCTAAATTCAA                 103
Right (3') junction
Expected  GAATTCGCGGCCTTACTTTGTCTTTGCCTCCTTTAACAAATCTTTGTTAAAGGAGGCAAAGACAAAGTAAGTTAGACCAA  104
    (X2)  GAATTCGCGGCCTTACTTTGTCTTTGCCTCCTTTAA::::::TTTGTTAAAGGAGGCAAAGACAAAGTAAGTTAGACCAA  105
    (X8)  GAATTCGCGGCCTTACTTTGTCTTTGCCTCCT::::::CTTTGTTAAAGGAGGCAAAGACAAAGTAAGTTAGACCAA     106
```

(A) Sequences amplified from the junction of the tGFP cassette from pDAS000341 with Fad3C at the DSB recognised by ZFN 28051-2A-28052
":" indicates deletions at cut-site 5' junction of tGFP cassette with Fad3C

| Fad3 | ZFN recognition site 28051 | Inserted Bases | ZFN recognition site 28052 | AtUbi10p |
|---|---|---|---|---|
| TTCTGGCCTCTTTATTGGCCGCCAAGGAACCCTTTCTGGGCCATCT | | | TCGTACTCGGCCACGACTGGTAATTTAATGGATCCACTAGTAA | |
| TTCTGGCCTCTTTATTGGCCGCCAAGGAACCCTTTCTGGGCCATCT | | | TCGTACTCGGCCACGACTGGTAATTTAATGGATCCACTAGTAA | |
| TTCTGGCCTCTTTATTGGCCGCCAAGGAACCCTTTCTGGGCCATC: | | | :::TACTCGGCCACGACTGGTAATTTAATGGATCCACTAGTAA | |
| TTCTGGCCTCTTTATTGGCCGCCAAGGAACCCTTTCTGGGCCATC: | | CAGTCGTGGCCGAGATCCGAAGATGCCCAAGA | :::TACTCGGCCACGACTGGTAATTTAATGGATCCACTAGTAA | |
| TTCTGGCCTCTTTATTGGCCGCCAAGGAACCCTTTCTGGGCCATCT | | | :::GTACTCGGCCACGACTGGTAATTTAATGGATCCACTAGTAA | |
| TTCTGGCCTCTTTATTGGCCGCCAAGGAACCCTTTCTCTTAGG:::: | TATCTCAGTTCGGTGTAGGTGTGGTTGCCTCGTTCGCCCAAGCTGGGTGCTGGCACGAAC:CG | :CGTACTCGGCCACGACTGGTAATTTAATGGATCCACTAGTAA | |
| TTCTGGCCTCTTTATTGGCCGCCAAGGAACCCTTTCTGGGCCCA::: | | | :::GACTGGTAATTTAATGGATCCACTAGTAA | |

3' junction of tGFP cassette with Fad3C

| AtuOrf23t | ZFN recognition site 28051 | Inserted Bases | ZFN recognition site 28052 | Fad3C |
|---|---|---|---|---|
| TCCAAGGTTGCGGCGCGGCGCCAAGGAACCCTTTCTGGGCCATCT | | | TCGTACTCGGCCACGACTGGTAATTTAATTTCAATTTATT | |
| TCCAAGGTTGCGGCGCGGCGCCAAGGAACCCTTTCTGGGCCAT:: | | | :::TACTCGGCCACGACTGGTAATTTAATTTCAATTTATT | |
| TCCAAGGTTGCGGCGCGGCGCCAAGGAACCCTTTCTGGGCCAT:T | | | :::TACTCGGCCACGACTGGTAATTTAATTTCAATTTATT | |
| ::::78 bases deleted ::::::::::::::::::::::::::: | | | :CGTACTCGGCCACGACTGGTAATTTAATTTCAATTTATT | |
| TCCAAGGTTGCGGCGCGGCGCCAAGGAACCCTTTCTGGGCCATCT | | | TCGTACTCGGCCACGACTGGTAATTTAATTTCAATTTATT | |
| TCCAAGGTTGCGGCGCGGCGCCAAGGAACCCTTTCTGGGCCATC:C | | TAGCCGTGGTTTTTTGTTTGCAAGCAGCAGATTACGCGCAGAAAAAAGGA | :TGGTAATTTAATTTAATTTCAATTTATT | |
| TCCAAGGTTGCGGCGCGGCGCCAAGGAACCCTTTCTGGGCCATCT:TACGAGCGTGAGTGCTGCCGTTGAAGAAGTCTGGAAAGAAATCCATAAACATAATCCCAGCCAGCACT | | | TCGTACTCGGCCACGACTGGTAATTTAATTTCAATTTATT | |
| TCCAAGGTTGCGGCGCGGCGCCAAGGAACCCTTTCTGGGCCATCT | | | :GGTAATTTAATTTCAATTTATT | |

FIGURE 29A (B) Sequences amplified from the junction of the tGFP cassette from pDAS000343 with Fad3C at the DSBs recognised by ZFNs 28051-2A-28052 and 28053-2A-28054. ":" indicates deletions at cut-site

METHODS AND COMPOSITIONS FOR NUCLEASE-MEDIATED TARGETED INTEGRATION OF TRANSGENES

CROSS-REFERENCE TO RELATED APPLICATIONS

The present application claims the benefit of U.S. Provisional Application No. 61/643,812, filed May 7, 2012, the disclosure of which is hereby incorporated by reference in its entirety.

STATEMENT OF RIGHTS TO INVENTIONS MADE UNDER FEDERALLY SPONSORED RESEARCH

Not applicable.

TECHNICAL FIELD

The present disclosure is in the field of genome engineering, particularly targeted modification of the genome of a cell.

BACKGROUND

Integration of foreign DNA into the genome of organisms and cell lines is a widely utilized method for interrogation and manipulation of biological systems. Traditionally, transgene insertion is targeted to a specific locus by provision of a plasmid carrying a transgene, and containing substantial DNA sequence identity flanking the desired site of integration. Spontaneous breakage of the chromosome followed by repair using the homologous region of the plasmid DNA as a template results in the transfer of the intervening transgene into the genome. See, e.g., Koller et al. (1989) *Proc. Nat'l. Acad. Sci. USA* 86(22):8927-8931; Thomas et al. (1986) *Cell* 44(3):419-428. The frequency of this type of homology-directed targeted integration can be increased by up to a factor of $10^5$ by deliberate creation of a double-strand break in the vicinity of the target region (Hockemeyer et al. (2009) *Nature Biotech.* 27(9):851-857; Lombardo et al. (2007) *Nature Biotech.* 25(11):1298-1306; Moehle et al. (2007) *Proc. Nat'l Acad. Sci. USA* 104(9):3055-3060; Rouet et al. (1994) *Proc. Nat'l Acad. Sci. USA* 91(13):6064-6068.

A double-strand break (DSB) or nick for can be created by a site-specific nuclease such as a zinc-finger nuclease (ZFN) or TAL effector domain nuclease (TALEN), or using the CRISPR/Cas9 system with an engineered crRNA/tract RNA (single guide RNA) to guide specific cleavage. See, for example, Burgess (2013) Nature Reviews Genetics 14:80-81, Urnov et al. (2010) *Nature* 435(7042):646-51; United States Patent Publications 20030232410; 20050208489; 20050026157; 20050064474; 20060188987; 20090263900; 20090117617; 20100047805; 20110207221; 20110301073 and International Publication WO 2007/014275, the disclosures of which are incorporated by reference in their entireties for all purposes. In many organisms, transgene insertion can be accomplished via homology-directed repair (HDR) processes, which require the inserted transgene to include regions of homology to the site of insertion (cleavage). However, some organisms and cell lines lack traditional HDR process and targeted integration occurs primarily via the homology-independent non-homologous end joining (NHEJ) DNA repair machinery. As such, to date, in organisms and cell lines (e.g., CHO cells) that are recalcitrant to HDR processes, only relatively short (<100 bp) oligonucleotides have been integrated via homology-independent pathways following nuclease-mediated cleavage of the target locus. See, e.g., Orlando et al. (2010) *Nucleic Acids Res.* 38(15):e152 and U.S. Patent Publication No. 20110207221.

Thus, there remains a need for compositions and methods for homology-independent targeted integration of transgenes, including larger transgenes, directly into the site of cleavage, for example in organisms and cell lines that lack, or are deficient in, traditional homology-driven approaches.

SUMMARY

Disclosed herein are methods and compositions for homology-independent targeted integration of a transgene.

In one aspect, described herein are double-stranded donor polynucleotides for integration into an endogenous locus of choice following in vivo cleavage of the donor using at least one nuclease. The donor polynucleotides include an exogenous sequence (transgene) to be integrated into the endogenous locus and contain at least one target site for a nuclease, for example two paired nuclease binding sites separated by a "spacer" sequence separating near edges of binding sites. The spacer can be of any size, for example, between 4 and 20 base pairs (or any value therebetween). Donors having multiple nuclease target sites may have the same or different target sites, for example, two of the same paired sites flanking the transgene or two different paired sites flanking the transgene. The donor nucleotides do not require the presence of homology arms flanking the transgene sequence. The only chromosomal homology that may be present in the donor sequence is(are) the nuclease binding site(s). In embodiments in which the nuclease target sites exhibit homology to the genome, the homology to the genome is less than 50 to 100 (or any number of base pairs between 50 and 100) contiguous base pairs in length. In certain embodiments, where the nuclease used to cleave the donor is not the same as the nuclease used to cleave the chromosome, there may be no homology between the chromosomal locus cleaved by the nuclease(s) and the donor sequence. In addition, the nuclease target site(s) are not within the transgene and, as such, cleavage of the donor polynucleotide by the nuclease(s) that bind(s) to the target site(s) does not modify the transgene. In certain embodiments, the donor nucleic acid comprises two target sites and the spacer sequence between the two target sites is non-naturally occurring, for example when the spacer sequence does not occur in a genomic sequence between the two target sites present in the genome. In certain embodiments, the donor molecules are integrated into the endogenous locus via homology-independent mechanisms (e.g., NHEJ). In other embodiments, the double-stranded donor comprises a transgene of at least 1 kb in length and nuclease target site(s) 3' and/or 5' of the transgene for in vivo cleavage. In certain embodiments, the nuclease target site(s) used to cleave the donor are not re-created upon integration of the transgene, for example when the spacer between paired target sites is not present in and/or does not exhibit homology to an endogenous locus. The donor molecule may be, for example, a plasmid. In certain embodiments, the donor is integrated following nuclease-mediated cleavage of the endogenous locus. In any nuclease-mediated integration of the donor molecule, the one or more of the nucleases used to cleave the donor may be the same as one or more of the nucleases used to cleave the endogenous locus. Alternatively, one or more of the nucleases used to cleave the donor may be different from one or more of the nucleases used to cleave the endogenous locus.

In some embodiments, the donor is contained on a plasmid. The donor may be integrated following nuclease-mediated cleavage where the sequence to be integrated (donor or transgene) is flanked in the plasmid by at least two nuclease cleavage sites. In other embodiments, the donor is contained on a plasmid, wherein the donor may be integrated following nuclease-mediated cleavage where the sequence to be integrated (donor or transgene) is the plasmid comprising a single nuclease cleavage site. In certain embodiments, the sequence of the nuclease cleavage sites in the donor plasmid is the same as the sequence of the nuclease cleavage site in the chromosomal locus to be targeted. In embodiments in which the cleavage sites are the same as between the donor and the genome, the sequences separating the cleavage sites may be the same or different. In certain embodiments, the sequences separating the cleavage sites (spacers) are different in the donor as compared to the genome such that following cleavage of the donor, the target sites is(are) not re-created and the donor cannot be cleaved again by the same nuclease(s). In other embodiments, the nuclease cleavage sites flanking the donor on the donor-containing plasmid are different from the cleavage site in the chromosome. In further embodiments, the nuclease cleavage sites flanking the donor in the donor-containing plasmid are not the same, and also may be different from the nuclease cleavage site in the chromosome. In further embodiments, the donor may be contained on a plasmid flanked by at least two nuclease cleavage sites and may be integrated into a deletion in the chromosome created by the action of two nucleases. In this embodiment, the nuclease cleavage sites flanking the donor on the plasmid and the nuclease cleavage sites in the chromosome may either be the same or may be different.

The sequence of interest of the donor molecule may comprise one or more sequences encoding a functional polypeptide (e.g., a cDNA), with or without a promoter. In certain embodiments, the nucleic acid sequence comprises a sequence encoding an antibody, an antigen, an enzyme, a growth factor, a receptor (cell surface or nuclear), a hormone, a lymphokine, a cytokine, a reporter, an insect resistant gene, a herbicide tolerance gene, a transcription factor, sequestration protein or functional fragments of any of the above and combinations of the above. The sequence of interest of the donor molecule may comprise one or more sequences that encode an RNA molecule that encodes a functional or structural RNA, for example, an RNAi, sRNAi, and/or mRNAi. In embodiments in which the functional polypeptide encoding sequences are promoterless, expression of the integrated sequence is then ensured by transcription driven by an endogenous promoter or other control element in the region of interest. In other embodiments, a "tandem" cassette is integrated into the selected site in this manner, the first component of the cassette comprising a promoterless sequence as described above, followed by a transcription termination sequence, and a second sequence, encoding an autonomous expression cassette. Additional sequences (coding or non-coding sequences) may be included in the donor molecule, including but not limited to, sequences encoding a 2A peptide, SA site, IRES, etc. In certain embodiments, the donor nucleic acid (transgene) comprises sequences encoding functional RNAs for example, miRNAs or shRNAs.

In another aspect, described herein are methods of integrating a donor nucleic acid (e.g., a donor molecule as described herein) into the genome of a cell via homology-independent mechanisms. The methods comprise creating a double-stranded break (DSB) in the genome of a cell and cleaving the donor molecule using one or more nucleases, such that the donor nucleic acid is integrated at the site of the DSB. In certain embodiments, the donor nucleic acid is integrated via non-homology dependent methods (e.g., NHEJ). As noted above, upon in vivo cleavage the donor sequences can be integrated in a targeted manner into the genome of a cell at the location of a DSB. The donor sequence can include one or more of the same target sites for one or more of the nucleases used to create the DSB. Thus, the donor sequence may be cleaved by one or more of the same nucleases used to cleave the endogenous gene into which integration is desired. In certain embodiments, the donor sequence includes different nuclease target sites from the nucleases used to induce the DSB. DSBs in the genome of the target cell may be created by any mechanism. In certain embodiments, the DSB is created by one or more (e.g., a dimerizing pair of) zinc-finger nucleases (ZFNs), fusion proteins comprising a zinc finger binding domain, which is engineered to bind a sequence within the region of interest, and a cleavage domain or a cleavage half-domain. In other embodiments, the DSB is created by one or more TALE DNA-binding domains (naturally occurring or non-naturally occurring) fused to a nuclease domain (TALEN). In still further embodiments, cleavage is performed using a nuclease system such as CRISPR/Cas with an engineered crRNA/tracr RNA.

Furthermore, in any of the methods described herein, the first and second cleavage half-domains may be from a Type IIS restriction endonuclease, for example, FokI or StsI. Furthermore, in any of the methods described herein, at least one of the fusion proteins may comprise an alteration in the amino acid sequence of the dimerization interface of the cleavage half-domain, for example such that obligate heterodimers of the cleavage half-domains are formed. Alternatively, in any of the methods described herein the cleavage domain may be a naturally or non-naturally occurring (engineered) meganuclease.

In any of the methods described herein, the cell can be any eukaryotic cells, for example a plant cell or a mammalian cell or cell line, including COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO, MDCK or HEK293 cell line. Suitable cells also include stem cells such as, by way of example, embryonic stem cells, induced pluripotent stem cells, hematopoietic stem cells, neuronal stem cells and mesenchymal stem cells. Furthermore, the cell may be arrested in the G2 phase of the cell cycle. In some embodiments of the methods described herein, the cell may be one lacking efficient homology-based DNA repair, for example a CHO cell. In certain embodiments, the cells may be primary or non-dividing cells which preferentially use the NHEJ DNA repair pathway. In some embodiments, the cell can be a plant or fungal cell. In other embodiments, the methods described herein may be used in cells with unsequenced genomes. These cells can be used to create cell lines and/or transgenic organisms (e.g., animals or plants) bearing the transgene(s).

In another aspect, transgenic organisms (e.g., plants or animals) comprising a transgene integrated according to any of the methods described herein are provided. In one embodiment, a cell, cell line or transgenic organism carrying a heterozygous genotype for the selected gene is constructed, while in another embodiment, a homozygous cell, cell line or transgenic organism is made carrying two mutant copies in both alleles of a desired locus.

A kit, comprising the methods and compositions of the invention, is also provided. The kit may comprise the nucleases, (e.g. RNA molecules or ZFN, TALEN or CRISPR/Cas system encoding genes contained in a suitable expression vector), or aliquots of the nuclease proteins, donor molecules, suitable host cell lines, instructions for performing the methods of the invention, and the like. The kit may also comprise donor molecules of interest (e.g. reporter genes, specific transgenes and the like).

These and other aspects will be readily apparent to the skilled artisan in light of disclosure as a whole.

BRIEF DESCRIPTION OF THE DRAWINGS

FIG. 1, panels A to F, show capture of a transgene cleaved in vivo at an AAVS1 locus in K562 cells.

FIG. 2, panels A and B, show that in vivo donor cleavage promotes transgene capture at several loci in two different cell types.

FIG. 4, panels A and C, depict disruption of alpha-(1,6)-fucosyltransferase (FUT8) in CHO-K1 cells by ZFN- and TALEN-mediated targeted insertion of a monoclonal antibody transgene.

FIG. 5, panels A to C, show ZFN activity for experiments described in the Examples. FIG. 5A shows ZFN cleavage at the AAVS1 locus (top) and of the donor plasmid (bottom). The corresponding lanes in FIG. 5A from FIG. 1D are indicated above the gel (ex.: "1,12"), as is the presence ("Y") or absence ("N") of the Surveyor™ nuclease enzyme. The percentage of molecules modified is shown below the lanes with signal.

FIG. 7 shows partial DNA sequence of junction PCR products from CHO K1 clones into which in vivo cleaved donors were integrated into the AAVS1 locus. Chromosomal sequence is shown in plain text, and donor sequence is shown in italics. ZFN binding sites are underlined and in bold. Microhomology is shaded in grey. The expected allele sequences in the AB orientation are shown across the top of the AB group and are defined as perfect ligation of the 5' overhangs; the expected allele sequences in the BA orientation are shown across the top of the BA group and are defined as removal of the 5' overhangs followed by ligation. Sequence identifiers are indicated in the Figure.

FIG. 8, panels A to C, show DNA sequences of junction PCR assays from CHO K1 cell pools with transgene integrations at AAVS1 (FIG. 8A), CCR5 (FIG. 8B), GS (FIG. 8C), and IL2Rγ (FIG. 8C). Chromosomal sequence is shown in plain text, donor sequence is shown in italics. ZFN binding sites are underlined and in bold. The expected allele sequences are shown as above, and are also as defined above for FIG. 7. Identical sequences isolated more than once are indicated and sequence identifiers are indicated in the Figure.

FIG. 9 shows DNA sequences of junction PCRs from GS single cell-derived clones. Chromosomal sequence is shown in plain text, donor sequence is shown in italics. ZFN binding sites are underlined and in bold. The expected alleles in the AB orientation are defined as perfect ligation of the 5' overhangs; the expected alleles in the BA orientation are defined as removal of the 5' overhangs followed by ligation. Sequence identifiers are indicated in the Figure.

FIG. 10, panels A and B, show DNA sequences of junction PCRs from single cell-derived clones with integrations at FUT8. Chromosomal sequence is shown in plain text, donor sequence is shown in italics. FIG. 10A shows integration following cleavage with FUT8-targeted ZFNs (ZFN binding sites are underlined and in bolded). FIG. 10B shows integration following cleavage with FUT8-targeted TALENs (TALEN binding sites are underlined and bolded). Sequence identifiers are indicated in the Figure.

FIG. 19, panels A and B, depict exogenous marker-free, sequential transgene stacking at an endogenous AHAS locus in the wheat genome of *Triticum aestivum* using ZFN-mediated, NHEJ-directed DNA repair.

FIG. 20, panels A and B, depict exogenous marker-free, sequential transgene stacking at an endogenous AHAS locus in the wheat genome of *Triticum aestivum* using ZFN-mediated, HDR-directed DNA repair.

FIG. 28, panels A and B, show the locations of the primers and their position relative to the start and stop codon of Fad3C. FIG. 28A shows the location of the primer sites for the wild type Fad3C locus. FIG. 28B shows the location of the primer sites to confirm donor integration, and the possible orientations by which the donor could integrate within the Fad3C locus.

FIG. 29, panels A and B, shows sequences alignments of various targeted integrations. FIG. 29A shows a sequence alignment amplified from the junction of the tGFP cassette of pDAS000341 with Fad3C at the double strand break as recognized by ZFN 28051-2A-28052. Sequences shown are SEQ ID NOs: 547-560 from top to bottom. The ":" indicates the deletions located at the cut sites. FIG. 29B shows a sequence alignment amplified from the junction of the tGFP cassette of pDAS000343 with Fad3C at the double strand break as recognized by ZFN 28051-2A-28052 and ZFN 28053-2A-28054. The ":" indicates the deletions located at the cut sites. Sequences shown are SEQ ID NOs: 561-572 and 506-507 from top to bottom.

FIG. 30, panels A and B, show a sequence alignment amplified from the junction of the hph cassette of pDAS000340 with FAD3C at the double strand break as recognized by ZFN 28051-2A-28052. The ":" indicates the deletions located at the cut sites. Sequences shown are SEQ ID NOs:508 to 52Th from top to bottom. FIG. 30A shows sequences for the 5' junction and the sequences shown in FIG. 30B are for the 3' junction.

FIG. 31, panels A and B, show a sequence alignment amplified from the junction of the hph cassette of pDAS00034 with FAD3C at the double strand break as recognized by ZFN 28051-2A-28052 and 28053-2A-28054. The ":" indicates the deletions located at the cut sites. Sequences shown are SEQ ID NOs:524 to 532 from top to bottom. The sequences shown in FIG. 31A are for the 5' junction and the sequences shown in FIG. 31B are for the 3' junction.

FIG. 43, panels A and B, shows the junction sequence from in-out PCR reactions. The left and right sequences are partial sequences of the AAD1 and ELP, respectively. The sequence expected from an insertion restoring the eZFN binding site is shown in the blue font. The eZFN binding site is highlighted green and deletions are black bars. The sequence for the direct orientation (FIG. 43A) and the reverse orientation (FIG. 43B) are shown. The sequences are in blocks according to the PCR reaction from which they were cloned.

DETAILED DESCRIPTION

Figure 1A:
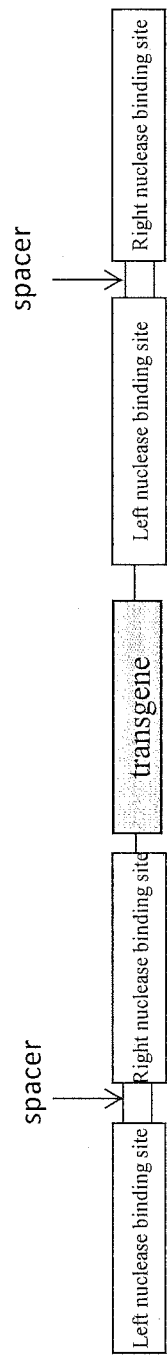
FIG. 1A is a schematic depicting an exemplary donor molecule having two paired binding sites (4 binding sites total), with each pair separated by spacers), which sites flank a transgene to be integrated into the genome. The target sites may be the same or different.
Figure 1B:
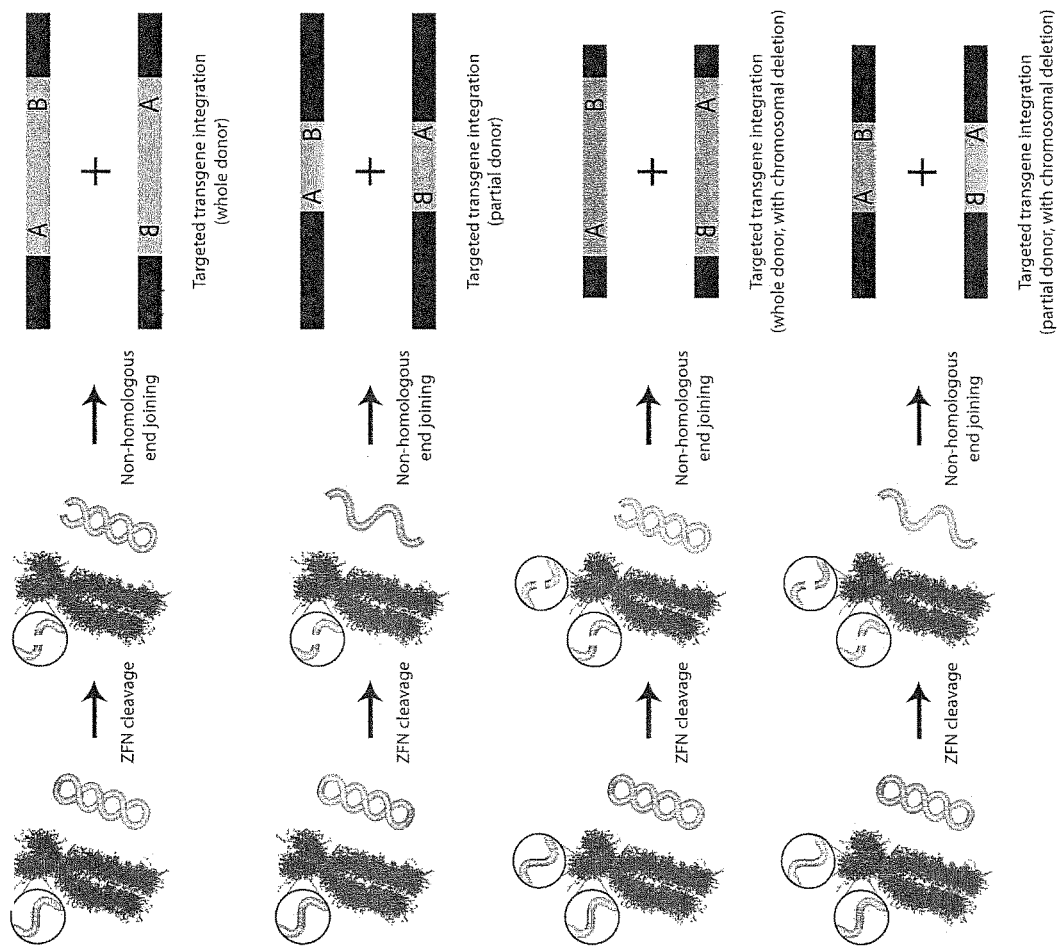
FIG. 1B is a schematic depicting four different in vivo donor cleavage techniques. In the first embodiment, when both the chromosome and the donor plasmid contain a ZFN cleavage site (dark grey region), cleavage of the donor and chromosome are synchronized, allowing efficient integration of the donor into the chromosome. Integration can occur in both forward and reverse orientations, termed "AB" and "BA," respectively. In the second embodiment, the donor contains more than one nuclease cleavage site. Nuclease action liberates a linear fragment of DNA which is integrated into the chromosome. In the third embodiment, the chromosome is cleaved by more than one nuclease and the donor by one nuclease, resulting in integration of the donor into a deletion in the chromosome. In the fourth embodiment, both the donor DNA and the chromosomal DNA are cleaved by more than one nuclease, resulting in integration of a linear fragment into a deletion in the chromosome.

Disclosed herein are compositions and methods for nuclease-mediated homology-independent (e.g., NHEJ capture) targeted integration of a transgene. While insertion of oligonucleotides can be performed via simple co-transfection of DNA with compatible 5' overhangs, it has now been shown that NHEJ capture of transgene-size fragments (e.g., >0.5 kb) is greatly facilitated by in vivo nuclease-mediated cleavage of the donor plasmid in addition to cleavage of the chromosome. In this way, transgenes of larger size (e.g., between 1 and 14 kb or longer in length) can be integrated in a targeted manner into organisms and cell lines, such as Chinese hamster ovary (CHO) cells, which are recalcitrant to HDR-based integration. For example, in vivo donor cleavage allowed targeted integration at high frequency (6%) in unselected CHO cells, a cell type otherwise recalcitrant to targeted insertion of large DNA sequences.

Co-cleavage of the chromosome and transgene-containing double-stranded donor as described herein results in successful integration into any endogenous target locus in a selected host cell. The methods and compositions described herein allow for efficient non-homology-driven targeted integration that is not generally achievable by simple co-transfection of pre-cut donors.

Thus, the compositions and methods described herein allow for homology-independent targeted integration of large transgenes into sites of nuclease-cleavage, including into deletions created by engineered nucleases such as ZFNs and/or TALENs. Alternately, a donor plasmid with nuclease sites flanking a transgene to be integrated can be used such that the transgene portion is liberated upon nuclease cleavage and efficiently integrated at a targeted location. Further, use of the methods and compositions of the invention allow for nuclease-mediated in vivo cleavage of a large donor molecule such as a bacterial or yeast artificial chromosome permits the targeted integration of large transgenes in mammalian and plant cells. Finally, the in vivo cleavage compositions and methods described will find use in the targeted genetic modification of other organisms and cells, especially those which perform homology-direct DNA repair poorly.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P.B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Patent Publication No. 20110301073, incorporated by reference herein in its entirety.

Zinc finger and TALE binding domains can be "engineered" to bind to a predetermined nucleotide sequence, for example via engineering (altering one or more amino acids) of the recognition helix region of a naturally occurring zinc finger. Similarly, TALEs can be "engineered" to bind to a predetermined nucleotide sequence, for example by engineering of the amino acids involved in DNA binding (the repeat variable diresidue or RVD region). Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication Nos. 20110301073, 20110239315 and 20119145940.

A "selected" zinc finger protein or TALE is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084 and U.S. Publication Nos. 20110301073, 20110239315 and 20119145940.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide. For HR-directed integration, the donor molecule contains at least 2 regions of homology to the genome ("homology arms") of least 50-100 base pairs in length. See, e.g., U.S. Patent Publication No. 20110281361.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins or TALEN can be used for additional double-stranded cleavage of additional target sites within the cell.

Any of the methods described herein can be used for insertion of a donor of any size and/or partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence (transgene) may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528 and 2008/0131962, incorporated herein by reference in their entireties.

The term "sequence" refers to a nucleotide sequence of any length, which can be DNA or RNA; can be linear, circular or branched and can be either single-stranded or double stranded. The term "donor sequence" or "transgene" refers to a nucleotide sequence that is inserted into a genome. A donor sequence can be of any length, for example between 2 and 100,000,000 nucleotides in length (or any integer value therebetween or thereabove), preferably between about 100 and 100,000 nucleotides in length (or any integer therebetween), more preferably between about 2000 and 60,000 nucleotides in length (or any value therebetween) and even more preferable, between about 3 and 15 kb (or any value therebetween).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE or Cas DNA-binding domain is fused to an activation domain, the ZFP, TALE or Cas DNA-binding domain and the activation domain are in operative linkage if, in the fusion polypeptide, the ZFP, TALE or Cas DNA-binding domain portion is able to bind its target site and/or its binding site, while the activation domain is able to upregulate gene expression. When a fusion polypeptide in which a ZFP, TALE or Cas DNA-binding domain is fused to a cleavage domain, the ZFP, TALE or Cas DNA-binding domain and the cleavage domain are in operative linkage if, in the fusion polypeptide, the ZFP, TALE or Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

A "safe harbor" locus is a locus within the genome wherein a gene may be inserted without any deleterious effects on the host cell. Most beneficial is a safe harbor locus in which expression of the inserted gene sequence is not perturbed by any read-through expression from neighboring genes. Non-limiting examples of safe harbor loci in mammalian cells are the AAVS1 gene (see U.S. Pat. No. 8,110,379), the CCR5 gene (see U.S. Publication No. 20080159996), the Rosa locus (see WO 2010/065123) and/or the albumin locus (U.S. application Ser. No. 13/624,193). Non-limiting examples of safe harbor loci in plant cells are the ZP15 locus (U.S. Pat. No. 8,329,986)

Nucleases

Described herein are compositions, particularly nucleases, that are useful for in vivo cleavage of a donor molecule carrying a transgene and nucleases for cleavage of the genome of a cell such that the transgene is integrated into the genome in a targeted manner. In certain embodiments, one or more of the nucleases are naturally occurring. In other embodiments, one or more of the nucleases are non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains).

A. DNA-Binding Domains

In certain embodiments, the composition and methods described herein employ a meganuclease (homing endonuclease) DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG family ("LAGLIDADG" disclosed as SEQ ID NO: 115), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue.

In certain embodiments, the methods and compositions described herein make use of a nuclease that comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue. In addition, the DNA-binding specificity of homing endonucleases and meganucleases can be engineered to bind non-natural target sites. See, for example, Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus Xanthomonas are known to cause many diseases in important crop plants. Pathogenicity of Xanthomonas depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et at (2007) Science 318:648-651). These proteins contain a DNA binding domain and a transcriptional activation domain. One of the most well characterized TAL-effectors is AvrBs3 from Xanthomonas campestgris pv. Vesicatoria (see Bonas et al (1989) Mol Gen Genet. 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) J Plant Physiol 163(3): 256-272). In addition, in the phytopathogenic bacteria Ralstonia solanacearum two genes, designated brg11 and hpx17 have been found that are homologous to the AvrBs3 family of Xanthomonas in the R. solanacearum biovar 1 strain GMI1000 and in the biovar 4 strain RS1000 (See Heuer et al (2007) Appl and Envir Micro 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of Xanthomonas. See, e.g., U.S. Patent Publication Nos. 20110239315, 20110145940 and 20110301073, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target). See, e.g., U.S. Patent Publication No. 20110301073; Christian et al ((2010)<Genetics epub 10.1534/genetics.110.120717).

In other embodiments, the nuclease is a system comprising the CRISPR (Clustered Regularly Interspaced Short Palindromic Repeats)/Cas (CRISPR Associated) nuclease system. The CRISPR/Cas is an engineered nuclease system based on a bacterial system that can be used for genome engineering. It is based on part of the adaptive immune response of many bacteria and archea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer". Cas9 cleaves the DNA to generate blunt ends at the DSB at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al (2012) *Science* 337, p. 816-821, Jinek et al, (2013), *eLife* 2:e00471, and David Segal, (2013) *eLife* 2:e00563). Thus, the CRISPR/Cas system can be engineered to create a DSB at a desired target in a genome, and repair of the DSB can be influenced by the use of repair inhibitors to cause an increase in error prone repair.

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Wastson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Thus, the nuclease comprises a DNA-binding domain in that specifically binds to a target site in any gene into which it is desired to insert a donor (transgene).

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Natl Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014,275. Likewise, TALE DNA-binding domains have been fused to nuclease domains to create TALENs. See, e.g., U.S. Publication No. 20110301073.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a Fok I cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987; 20070305346 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KIK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055). In other embodiments, the engineered cleavage half domain comprises the "Sharkey" and/or "Sharkey'" mutations (see Guo et al, (2010) *J. Mol. Biol.* 400(1):96-107).

Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014,275. Expression of the nuclease may be under the control of a constitutive promoter or an inducible promoter, for example the galactokinase promoter which is activated (de-repressed) in the presence of raffinose and/or galactose and repressed in presence of glucose.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek ibid and Cong, ibid).

Target Sites

As described in detail above, DNA domains can be engineered to bind to any sequence of choice. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Publication No. 20110301073.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Publication No. 20110301073.

As noted above, the DNA-binding domains of the nucleases may be targeted to any gene. In certain embodiments, the nuclease (DNA-binding domain component) is targeted to a "safe harbor" locus, which includes, by way of example only, the AAVS1 gene (see U.S. Pat. No. 8,110,379), the CCR5 gene (see U.S. Publication No. 20080159996), the Rosa locus (see WO 2010/065123) and/or the albumin locus (see, U.S. application Ser. No. 13/624,193).

Donors

Described herein are methods of targeted insertion of any polynucleotides for insertion into a chosen location. Polynucleotides for insertion can also be referred to as "exogenous" polynucleotides, "donor" polynucleotides or molecules or "transgenes."

Surprisingly, it is demonstrated herein that double-stranded donor nucleotides (e.g., plasmids) without homology arms flanking the exogenous sequence (transgene) can be effectively integrated into a selected target region of the genome of cell following in vivo cleavage of the double-stranded donor. Thus, the double-stranded donors include one or more nuclease binding sites for cleavage of the donor in vivo (in the cell). In certain embodiments, the donor includes two nuclease binding sites. In methods in which targeted integration is achieved by making a double-stranded cut in the target region of the genome (see, e.g., U.S. Pat. Nos. 7,888,121; 7,951,925; 8,110,379 and U.S. Patent Publication Nos. 20090263900; 20100129869 and 20110207221), one or more of then nucleases used to cleave the target region may also be used to cleave the donor molecule.

In certain embodiments, the double-stranded donor includes sequences (e.g., coding sequences, also referred to as transgenes) greater than 1 kb in length, for example between 2 and 200 kb, between 2 and 10 kb (or any value therebetween). The double-stranded donor also includes at least one nuclease target site, for example. In certain embodiments, the donor includes at least 2 target sites, for example for a pair of ZFNs or TALENs. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

As noted above, the donor can be cleaved in vivo and integrated into the genome in a forward ("AB") or in a reverse ("BA") orientation. Targeted integration via in vivo donor cleavage that results in a perfectly ligated AB-orientation insertion will recreate the paired nuclease (e.g., ZFN or TALEN) binding sites with the original spacing between the sites. Such recreated sites are potential substrates for a second round of cleavage by the nucleases. Nuclease cleavage at the recreated sites could result in DNA deletion at the transgene-chromosome junctions (as a result of inaccurate NHEJ-based repair) or even transgene excision. In contrast, reverse (BA) orientation insertions result in formation of two different nuclease pair binding sites (e.g., homodimers of the left and right nucleases). If obligate heterodimer (EL/KK, ELD/KKR, etc.) FokI nuclease domains are used, recreated BA sites will not be re-cleavable since the recreated binding sites are both homodimer sites. See, also, FIG. 1C.

Figure 1C:
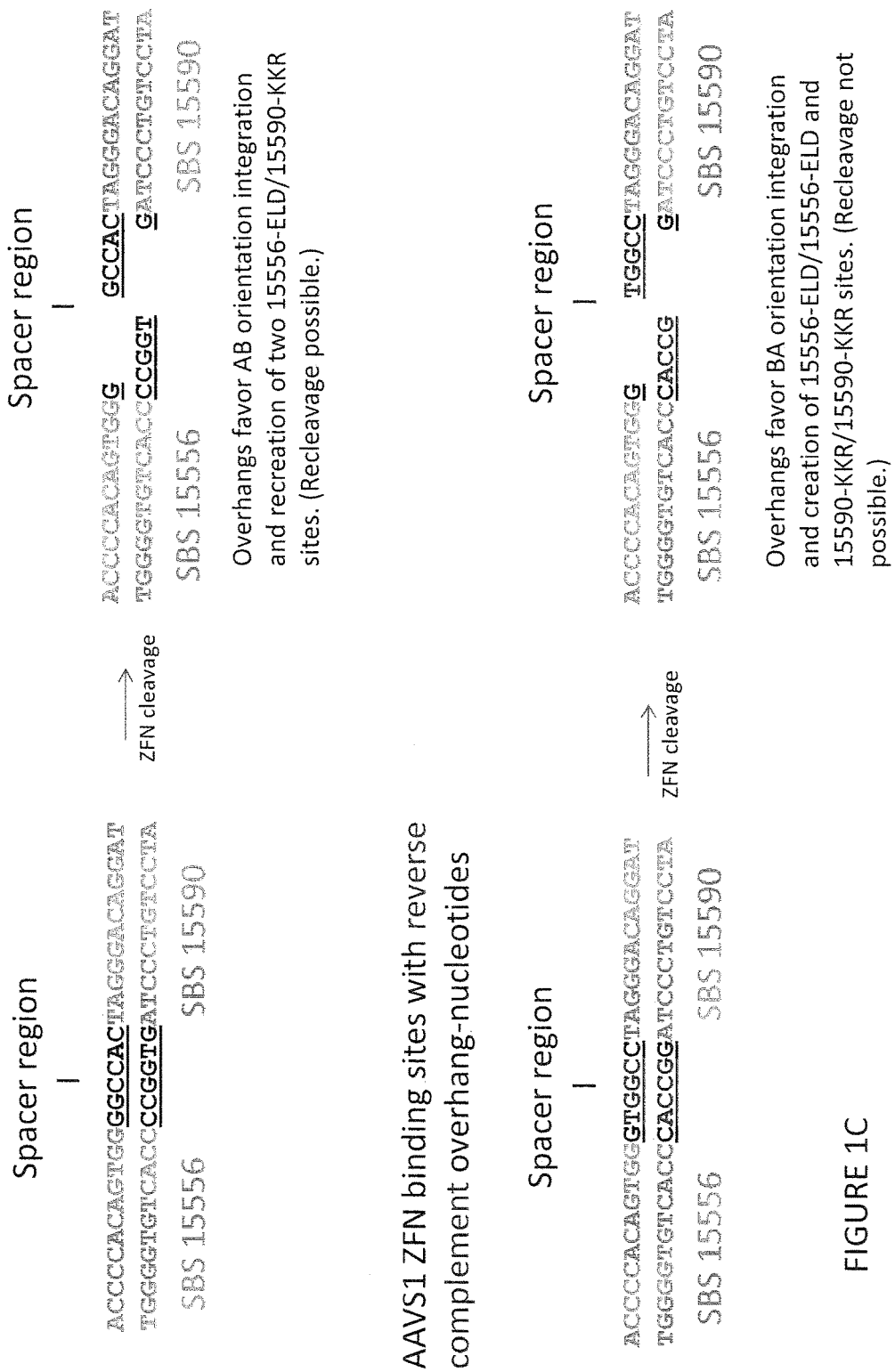
FIG. 1C shows a comparison of donors that favor the forward (AB) integration of the transgene and re-create the same nuclease target site (top panels) with donors the favor reverse (BA) integration of the transgene and do not re-create the same nuclease target site (bottom panels). The sequence between the binding sites (spacers) is underlined and the overhangs of the wild-type (top panels) and reverse-complement (bottom panels) spacers created after cleavage are shown on the right of the top and bottom panels. The sequences shown in the top left are SEQ ID NOs:107 and 108. The sequences shown in the top right are SEQ ID NOs:109, 543, 110, and 544, respectively, in order of appearance. The sequences shown in the bottom left are SEQ ID NOs:111 and 112 and the sequences shown in the bottom right are SEQ ID NOs:113, 545, 114, and 546, respectively, in order of appearance.

Furthermore, changing the nucleotides in the transgene donor nuclease spacer that make up the single-strand 5' overhang as compared to the wild-type (genomic) sequence, to the reverse complement of the wild-type sequence favors BA-orientation insertion of the cleaved donor (via Watson-Crick base-pairing with the overhangs on the cleaved chromosome) which would create an un-recleavable transgene integration (FIG. 1C).

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The double-stranded donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In a preferred embodiment, the exogenous sequence (transgene) comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, insect resistant, transcription factors and functional fragments of any of the above. The coding sequences may be, for example, cDNAs.

For example, the exogenous sequence may comprise a sequence encoding a polypeptide that is lacking or non-functional in the subject having a genetic disease, including but not limited to any of the following genetic diseases: achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted integration include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, $\alpha$-thalassemia, $\beta$-thalassemia) and hemophilias.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

Additional gene sequences that can be inserted may include, for example, wild-type genes to replace mutated sequences. For example, a wild-type Factor IX gene sequence may be inserted into the genome of a stem cell in which the endogenous copy of the gene is mutated. The wild-type copy may be inserted at the endogenous locus, or may alternatively be targeted to a safe harbor locus.

In some embodiments, the exogenous nucleic acid sequence (transgene) comprising an agronomic gene or nucleotide sequence encoding a polypeptide of interest may include, for example and without limitation: a gene that confers resistance to a pests or disease (See, e.g., Jones et al. (1994) *Science* 266:789 (cloning of the tomato Cf-9 gene for resistance to *Cladosporium fulvum*); Martin et al. (1993) Science 262:1432; Mindrinos et al. (1994) Cell 78:1089 (RSP2 gene for resistance to *Pseudomonas syringae*); PCT International Patent Publication No. WO 96/30517 (resistance to soybean cyst nematode); PCT International Patent Publication No. WO 93/19181); a gene that encodes a *Bacillus thuringiensis* protein, a derivative thereof, or a synthetic polypeptide modeled thereon (See, e.g., Geiser et al. (1986) Gene 48:109 (cloning and nucleotide sequence of a Bt δ-endotoxin gene; moreover, DNA molecules encoding δ-endotoxin genes can be purchased from American Type Culture Collection (Manassas, Va.), for example, under ATCC Accession Nos. 40098; 67136; 31995; and 31998)); a gene that encodes a lectin (See, e.g., Van Damme et al. (1994) Plant Molec. Biol. 24:25 (nucleotide sequences of several *Clivia miniata* mannose-binding lectin genes)); a gene that encodes a vitamin-binding protein, e.g., avidin (See PCT International Patent Publication No. US93/06487 (use of avidin and avidin homologues as larvicides against insect pests)); a gene that encodes an enzyme inhibitor, e.g., a protease, proteinase inhibitor, or amylase inhibitor (See, e.g., Abe et al. (1987) J. Biol. Chem. 262:16793 (nucleotide sequence of rice cysteine proteinase inhibitor); Huub et al. (1993) Plant Molec. Biol. 21:985 (nucleotide sequence of cDNA encoding tobacco proteinase inhibitor I); Sumitani et al. (1993) Biosci. Biotech. Biochem. 57:1243 (nucleotide sequence of *Streptomyces nitrosporeus* alpha-amylase inhibitor) and U.S. Pat. No. 5,494,813); a gene encoding an insect-specific hormone or pheromone, e.g., an ecdysteroid or juvenile hormone, a variant thereof, a mimetic based thereon, or an antagonist or agonist thereof (See, e.g., Hammock et al. (1990) Nature 344:458 (baculovirus expression of cloned juvenile hormone esterase, an inactivator of juvenile hormone)); a gene encoding an insect-specific peptide or neuropeptide that, upon expression, disrupts the physiology of the affected pest (See, e.g., Regan (1994) J. Biol. Chem. 269:9 (expression cloning yields DNA coding for insect diuretic hormone receptor); Pratt et al. (1989) Biochem. Biophys. Res. Comm. 163:1243 (an allostatin in *Diploptera puntata*); and U.S. Pat. No. 5,266,317 (genes encoding insect-specific, paralytic neurotoxins)); a gene encoding an insect-specific venom produced in nature by a snake, a wasp, or other organism (See, e.g., Pang et al. (1992) Gene 116:165 (heterologous expression in plants of a gene coding for a scorpion insectotoxic peptide)); a gene encoding an enzyme responsible for a hyperaccumulation of a monoterpene, a sesquiterpene, a steroid, hydroxamic acid, a phenylpropanoid derivative or other molecule with insecticidal activity; a gene encoding an enzyme involved in the modification, including the post-translational modification, of a biologically active molecule, e.g., a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, or a glucanase, whether natural or synthetic (See, e.g., PCT International Patent Publication No. WO 93/02197 (nucleotide sequence of a callase gene); moreover, DNA molecules containing chitinase-encoding sequences can be obtained, for example, from the ATCC, under Accession Nos. 39637 and 67152; Kramer et al. (1993) Insect Biochem. Molec. Biol. 23:691 (nucleotide sequence of a cDNA encoding tobacco hornworm chitinase); and Kawalleck et al. (1993) Plant Molec. Biol. 21:673

(nucleotide sequence of the parsley ubi4-2 polyubiquitin gene)); a gene encoding a molecule that stimulates signal transduction (See, e.g., Botella et al. (1994) Plant Molec. Biol. 24:757 (nucleotide sequences for mung bean calmodulin cDNA clones); and Griess et al. (1994) Plant Physiol. 104:1467 (nucleotide sequence of a maize calmodulin cDNA clone)); a gene that encodes a hydrophobic moment peptide (See, e.g., PCT International Patent Publication No. WO 95/16776 (peptide derivatives of Tachyplesin which inhibit fungal plant pathogens); and PCT International Patent Publication No. WO 95/18855 (synthetic antimicrobial peptides that confer disease resistance)); a gene that encodes a membrane permease, a channel former, or a channel blocker (See, e.g., Jaynes et al. (1993) Plant Sci 89:43 (heterologous expression of a cecropin-β lytic peptide analog to render transgenic tobacco plants resistant to *Pseudomonas solanacearum*)); a gene that encodes a viral-invasive protein or complex toxin derived therefrom (See, e.g., Beachy et al. (1990) Ann. rev. Phytopathol. 28:451); a gene that encodes an insect-specific antibody or immunotoxin derived therefrom (See, e.g., Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments)); a gene encoding a virus-specific antibody (See, e.g., Tavladoraki et al. (1993) Nature 366:469 (transgenic plants expressing recombinant antibody genes are protected from virus attack)); a gene encoding a developmental-arrestive protein produced in nature by a pathogen or a parasite (See, e.g., Lamb et al. (1992) Bio/Technology 10:1436 (fungal endo α-1,4-D-polygalacturonases facilitate fungal colonization and plant nutrient release by solubilizing plant cell wall homo-α-1,4-D-galacturonase); Toubart et al. (1992) Plant J. 2:367 (cloning and characterization of a gene which encodes a bean endopolygalacturonase-inhibiting protein)); a gene encoding a developmental-arrestive protein produced in nature by a plant (See, e.g., Logemann et al. (1992) Bio/Technology 10:305 (transgenic plants expressing the barley ribosome-inactivating gene have an increased resistance to fungal disease)).

In some embodiments, nucleic acids comprising an agronomic gene or nucleotide sequence encoding a polypeptide of interest may also and/or alternatively include, for example and without limitation: genes that confer resistance to an herbicide, such as an herbicide that inhibits the growing point or meristem, for example, an imidazolinone or a sulfonylurea (exemplary genes in this category encode mutant ALS and AHAS enzymes, as described, for example, by Lee et al. (1988) EMBO J. 7:1241, and Miki et al. (1990) Theor. Appl. Genet. 80:449, respectively); glyphosate resistance as conferred by, e.g., mutant 5-enolpyruvylshikimate-3-phosphate synthase (EPSPs) genes (via the introduction of recombinant nucleic acids and/or various forms of in vivo mutagenesis of native EPSPs genes); aroA genes and glyphosate acetyl transferase (GAT) genes, respectively); other phosphono compounds, such as glufosinate phosphinothricin acetyl transferase (PAT) genes from *Streptomyces* species, including *Streptomyces hygroscopicus* and *Streptomyces viridichromogenes*); and pyridinoxy or phenoxy proprionic acids and cyclohexones (ACCase inhibitor-encoding genes). See, e.g., U.S. Pat. Nos. 4,940,835 and 6,248,876 (nucleotide sequences of forms of EPSPs which can confer glyphosate resistance to a plant). A DNA molecule encoding a mutant aroA gene can be obtained under ATCC accession number 39256. See also U.S. Pat. No. 4,769,061 (nucleotide sequence of a mutant aroA gene). European patent application No. 0 333 033 and U.S. Pat. No. 4,975,374 disclose nucleotide sequences of glutamine synthetase genes, which may confer resistance to herbicides such as L-phosphinothricin. Nucleotide sequences of exemplary PAT genes are provided in European application No. 0 242 246, and DeGreef et al. (1989) Bio/Technology 7:61 (production of transgenic plants that express chimeric bar genes coding for PAT activity). Exemplary of genes conferring resistance to phenoxy proprionic acids and cyclohexones, such as sethoxydim and haloxyfop, include the Acc1-S1, Acc1-S2 and Acc1-S3 genes described by Marshall et al. (1992) Theor. Appl. Genet. 83:435. GAT genes capable of conferring glyphosate resistance are described, for example, in WO 2005012515. Genes conferring resistance to 2,4-D, phenoxyproprionic acid and pyridyloxy auxin herbicides are described, for example, in WO 2005107437.

Nucleic acids comprising an agronomic gene or nucleotide sequence encoding a polypeptide of interest may also include, for example and without limitation: a gene conferring resistance to an herbicide that inhibits photosynthesis, such as a triazine (psbA and gs+ genes) or a benzonitrile (nitrilase gene). See, e.g., Przibila et al. (1991) Plant Cell 3:169 (transformation of *Chlamydomonas* with plasmids encoding mutant psbA genes). Nucleotide sequences for nitrilase genes are disclosed in U.S. Pat. No. 4,810,648, and DNA molecules containing these genes are available under ATCC Accession Nos. 53435; 67441; and 67442. See also Hayes et al. (1992) Biochem. J. 285:173 (cloning and expression of DNA coding for a glutathione S-transferase).

In some embodiments, nucleic acids comprising an agronomic gene or nucleotide sequence encoding a polypeptide of interest may also and/or alternatively include, genes that confer or contribute to a value-added trait, for example and without limitation: modified fatty acid metabolism, e.g., by transforming a plant with an antisense gene of stearyl-ACP desaturase to increase stearic acid content of the plant (See, e.g., Knultzon et al. (1992) *Proc. Natl. Acad. Sci. U.S.A.* 89:2624); decreased phytate content, e.g., introduction of a phytase-encoding gene may enhance breakdown of phytate, adding more free phosphate to the transformed plant (See, e.g., Van Hartingsveldt et al. (1993) Gene 127:87 (nucleotide sequence of an *Aspergillus niger* phytase gene); a gene may be introduced to reduce phytate content—in maize, for example, this may be accomplished by cloning and then reintroducing DNA associated with the single allele which may be responsible for maize mutants characterized by low levels of phytic acid (See Raboy et al. (1990) Maydica 35:383)); and modified carbohydrate composition effected, e.g., by transforming plants with a gene encoding an enzyme that alters the branching pattern of starch (See, e.g., Shiroza et al. (1988) J. Bacteol. 170:810 (nucleotide sequence of *Streptococcus* mutant fructosyltransferase gene); Steinmetz et al. (1985) Mol. Gen. Genet. 20:220 (levansucrase gene); Pen et al. (1992) Bio/Technology 10:292 (α-amylase); Elliot et al. (1993) Plant Molec. Biol. 21:515 (nucleotide sequences of tomato invertase genes); Sogaard et al. (1993) J. Biol. Chem. 268:22480 (barley α-amylase gene); and Fisher et al. (1993) Plant Physiol. 102:1045 (maize endosperm starch branching enzyme II)).

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences (transgenes) may also include transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of a transgene of non-coding nucleic acid sequence may also be achieved. Transgenes encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Methods for Targeted Transgene Integration

The donor molecules disclosed herein are integrated into a genome of a cell via targeted, homology-independent methods. For such targeted integration, the genome is cleaved at a desired location (or locations) using a nuclease, for example, a fusion between a DNA-binding domain (e.g., zinc finger binding domain or TAL effector domain is engineered to bind a site at or near the predetermined cleavage site) and nuclease domain (e.g., cleavage domain or cleavage half-domain). In certain embodiments, two fusion proteins, each comprising a DNA-binding domain and a cleavage half-domain, are expressed in a cell, and bind to sites which are juxtaposed in such a way that a functional cleavage domain is reconstituted and DNA is cleaved in the vicinity of the target site(s). In one embodiment, cleavage occurs between the binding sites of the two DNA-binding domains. One or both of the DNA-binding domains can be engineered. See, also, U.S. Pat. No. 7,888,121; U.S. Patent Publication 20050064474 and International Patent Publications WO05/084190, WO05/014791 and WO 03/080809.

The nucleases as described herein can be introduced as polypeptides and/or polynucleotides. For example, two polynucleotides, each comprising sequences encoding one of the aforementioned polypeptides, can be introduced into a cell, and when the polypeptides are expressed and each binds to its target sequence, cleavage occurs at or near the target sequence. Alternatively, a single polynucleotide comprising sequences encoding both fusion polypeptides is introduced into a cell. Polynucleotides can be DNA, RNA or any modified forms or analogues or DNA and/or RNA.

Following the introduction of a double-stranded break in the region of interest, the transgene is integrated into the region of interest in a targeted manner via non-homology dependent methods (e.g., non-homologous end joining (NHEJ)) following linearization of a double-stranded donor molecule as described herein. The double-stranded donor is preferably linearized in vivo with a nuclease, for example one or more of the same or different nucleases that are used to introduce the double-stranded break in the genome. Synchronized cleavage of the chromosome and the donor in the cell may limit donor DNA degradation (as compared to linearization of the donor molecule prior to introduction into the cell). The nuclease target site(s) used for linearization of the donor preferably do not disrupt the transgene(s) sequence(s).

The transgene may be integrated into the genome in the direction expected by simple ligation of the nuclease overhangs (designated "forward" or "AB" orientation) or in the alternate direction (designated "reverse" or "BA" orientation). In certain embodiments, the transgene is integrated following accurate ligation of the donor and chromosome overhangs. In other embodiments, integration of the transgene in either the BA or AB orientation results in deletion of several nucleotides.

Delivery

The nucleases, polynucleotides encoding these nucleases, donor polynucleotides and compositions comprising the proteins and/or polynucleotides described herein may be delivered in vivo or ex vivo by any suitable means into any cell type.

Suitable cells include eukaryotic (e.g., animal or plant) and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces* as well as plant cells from monocotyledonous or dicotyledonous plants including but not limited to maize, soybean, cotton, *Arabidopsis*, wheat, barley, oats, sugar cane, sorghum, forage grasses, alfalfa, tomato, tobacco potato, rice, sunflower and *Brassica*. In certain embodiments, the cell line is a CHO, MDCK or HEK293 cell line. Suitable cells also include stem cells such as, by way of example, embryonic stem cells, induced pluripotent stem cells, hematopoietic stem cells, neuronal stem cells and mesenchymal stem cells. In certain embodiments, the plant cells are but not limited to suspension culture, protoplasts, or organized tissues such as embryos, immature-embryos, leaf discs, cotyledons, hypotcols, and microspores. Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the zinc finger protein(s). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of in vivo delivery of engineered DNA-binding proteins and fusion proteins comprising these binding proteins, see, e.g., Rebar (2004) *Expert Opinion Invest. Drugs* 13(7):829-839; Rossi et al. (2007) *Nature Biotech.* 25(12):1444-1454 as well as general gene delivery references such as Anderson, *Science* 256:808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example US6008336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiamid et al (2009) *Nature Biotechnology* 27(7):643).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV2, AAV3, AAV4, AAV5, AAV6, AAV7, AAV8, AAV9 and AAVrh.10 and any novel AAV serotype can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and w2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides (e.g. nuclease-encoding and/or double-stranded donors) described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

It will be apparent that the nuclease-encoding sequences and donor constructs can be delivered using the same or different systems. For example, the nucleases and donors can be carried by the same vector. Alternatively, a donor polynucleotide can be carried by a plasmid, while the one or more nucleases can be carried by a AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Thus, the instant disclosure includes in vivo or ex vivo treatment of diseases and conditions that are amenable to insertion of a transgenes encoding a therapeutic protein, for example treatment of hemophilias via nuclease-mediated integration of clotting factors such as Factor VIII (F8). The compositions are administered to a human patient in an amount effective to obtain the desired concentration of the therapeutic polypeptide in the serum or the target organ or cells. Administration can be by any means in which the polynucleotides are delivered to the desired target cells. For example, both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree. Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al., (1994) Nature Genetics, 6:335-341.

The effective amount of nuclease(s) and donor to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) Human Gene Ther., 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

The delivery of nucleic acids may be introduced into a plant cell in embodiments of the invention by any method known to those of skill in the art, including, for example and without limitation: by transformation of protoplasts (See, e.g., U.S. Pat. No. 5,508,184); by desiccation/inhibition-mediated DNA uptake (See, e.g., Potrykus et al. (1985) Mol. Gen. Genet. 199:183-8); by electroporation (See, e.g., U.S. Pat. No. 5,384,253); by agitation with silicon carbide fibers (See, e.g., U.S. Pat. Nos. 5,302,523 and 5,464,765); by Agrobacterium-mediated transformation (See, e.g., U.S. Pat. Nos. 5,563,055, 5,591,616, 5,693,512, 5,824,877, 5,981, 840, and 6,384,301); by acceleration of DNA-coated particles (See, e.g., U.S. Pat. Nos. 5,015,580, 5,550,318, 5,538, 880, 6,160,208, 6,399,861, and 6,403,865) and by Nanoparticles, nanocarriers and cell penetrating peptides (WO201126644A2; WO2009046384A1; WO2008148223A1) in the methods to deliver DNA, RNA, Peptides and/or proteins or combinations of nucleic acids and peptides into plant cells.

Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more nucleic acid sequences of the invention in the genome of the transgenic plant.

The most widely-utilized method for introducing an expression vector into plants is based on the natural transformation system of Agrobacterium. A. tumefaciens and A. rhizogenes are plant pathogenic soil bacteria that genetically transform plant cells. The $T_i$ and $R_i$ plasmids of A. tumefaciens and A. rhizogenes, respectively, carry genes responsible for genetic transformation of the plant. The $T_i$ (tumor-inducing)-plasmids contain a large segment, known as T-DNA, which is transferred to transformed plants. Another segment of the $T_i$ plasmid, the vir region, is responsible for T-DNA transfer. The T-DNA region is bordered by left-hand and right-hand borders that are each composed of terminal repeated nucleotide sequences. In some modified binary vectors, the tumor-inducing genes have been deleted, and the functions of the vir region are utilized to transfer foreign DNA bordered by the T-DNA border sequences. The T-region may also contain, for example, a selectable marker for efficient recovery of transgenic plants and cells, and a multiple cloning site for inserting sequences for transfer such as a nucleic acid encoding a fusion protein of the invention.

Thus, in some embodiments, a plant transformation vector is derived from a $T_i$ plasmid of A. tumefaciens (See, e.g., U.S. Pat. Nos. 4,536,475, 4,693,977, 4,886,937, and 5,501, 967; and European Patent EP 0 122 791) or a $R_i$ plasmid of A. rhizogenes. Additional plant transformation vectors include, for example and without limitation, those described by Herrera-Estrella et al. (1983) Nature 303:209-13; Bevan et al. (1983), supra; Klee et al. (1985) Bio/Technol. 3:637-42; and in European Patent EP 0 120 516, and those derived from any of the foregoing. Other bacteria, such as Sinorhizobium, Rhizobium, and Mesorhizobium that naturally interact with plants can be modified to mediate gene transfer to a number of diverse plants. These plant-associated symbiotic bacteria can be made competent for gene transfer by acquisition of both a disarmed $T_i$ plasmid and a suitable binary vector.

The following Examples relate to exemplary embodiments of the present disclosure in which the nuclease comprises a zinc finger nuclease (ZFN) or a TALEN. It will be appreciated that this is for purposes of exemplification only and that other nucleases can be used, for instance a CRISPR/Cas nuclease system or homing endonucleases (meganucleases) with engineered DNA-binding domains and/or fusions of naturally occurring of engineered homing endonucleases (meganucleases) DNA-binding domains and heterologous cleavage domains.

EXAMPLES

Example 1: Materials and Methods

Cell Growth, Transfection, and ZFN/TALEN Assay.

Transfection of K562 (ATCC CCL-243) used Amaxa Solution V and program T-016; CHO-K1 (ATCC CCl-61), Amaxa Solution T and program U-023. All transfections contained $10^6$ cells and the following plasmids: AAVS1, 3 μg of 2A-linked ZFNs and donor; IL2Rγ and CCR5, 2 μg of each unlinked ZFN plasmid and 10 μg of the donor plasmid; GS, FUT8, 3 μg of 2A-linked ZFNs and 10 μg of donor plasmid. See, U.S. Pat. No. 8,110,379 and U.S. Patent Publication Nos. 20100129869 and 20090042250 and DeKelver et al. (2010) *Genome Res.* 20(8):1133-1142; Liu et al. (2009) *Biotechnol. Bioeng.* 106(1):97-105; Malphettes et al. (2010) *Biotechnology and Bioengineering* 106(5):774-83; Perez et al. (2008) *Nature Biotech.* 26(7):808-816; Urnov et al. (2005) *Nature* 435(7042):646-651 for further details including ZFN designs.

The FUT8 TALE nuclease pair (SBS 101082 and SBS 101086) directly overlaps the ZFN binding site in exon 10 of FUT8 and was constructed using the Δ152/+63 N- and C-terminal truncation points (Miller et al. 2011). The binding site of SBS 101082 FUT8 TALE is 5'-tgt atc tgg cca ctg at-3' (SEQ ID NO:1); SBS 101086, 5'-ttt gtc ttt gcc tcc tt-3' (SEQ ID NO:2).

Donor Plasmid Design and Construction

Oligos containing ZFN target sites for the AAVS1 (5"-tgt ccc ctc cAC CCC ACA GTG Ggg cca cTA GGG ACA GGA Ttg gtg aca ga-3', SEQ ID NO:3), spaced-flipped AAVS1 (5"-tgt ccc ctc cAC CCC ACA GTG Ggt ggc cTA GGG ACA GGA Ttg gtg aca ga-3', SEQ ID NO:541), GS (5"-gac cCC AAG CCC ATT CCT GGG Aac tgg aAT GGT GCA GGC Tgc cat acc aa-3', SEQ ID NO:4), and IL2Rγ (5'-gtt tcg tgt tCG GAG CCG CTT Taa ccc ACT CTG TGG AAG tgc tca gca tt-3', SEQ ID NO:5) ZFN pairs were annealed to their reverse complements in 50 mM NaCl, 10 mM Tris pH 7.5, and 1 mM EDTA. See, also, U.S. Patent Publication Nos. 20100129869 and U.S. Pat. Nos. 7,951,925 and 8,110,379. Capital letters denote the ZFN binding sites while lowercase letters denote flanking and spacer sequence.

The double-stranded products were then cloned into the EcoRV site of the pBluescript II KS-vector (Agilent). The CCR5 donor plasmid resulted from insertion of the CCR5 target site oligonucleotides (5'-GTC ATC CTC ATC CTG ATA AAC TGC AAA AGa-3', SEQ ID NO:6); 5-CTT TTG CAG TTT ATC AGG ATG AGG ATG ACa-3' SEQ ID NO:7, see, also, U.S. Pat. No. 7,951,925) into pCR2.1 (Invitrogen). The second AAVS1 donor plasmid (see, FIG. 1E) was made by insertion of the above AAVS1 target site oligos into the EcoRV site of a pCR2.1-based plasmid also containing the GFP open reading frame driven by the pGK promoter.

The FUT8 donor plasmid was made via insertion of the ZFN/TALEN binding site (5'-ggc CGT GTA TCT GGC CAC TGA TGA CCC TTC TTt gtt aAA GGA GGC AAA GAC AAA Gta a-3', SEQ ID NO:8) into a donor plasmid containing IgG and puromycin resistance transgenes (Moehle et al. (2007) *Proc. Nat'l Acad. Sci. USA* 104(9):3055-3060).

Assay of Targeted Integration

All PCR reactions were performed with 100 ng genomic DNA as a template, using Accuprime HiFi™ polymerase (Invitrogen). Genomic DNA was purified with the Masterpure™ kit (Epicentre).

Targeted integration of the AAVS1 GFP donor plasmid at AAVS1 (also known as PPP1R12C) was assayed at all four possible chromosome-donor junctions via PCR amplification. PCR reactions used a 60° annealing temperature, a 30 second extension time, 30 cycles of amplification, and the following primers: AB left, AAVS1 CEL-I F (5'-ccc ctt acc tct cta gtc tgt gc-3', SEQ ID NO:9) and AAVS1 Junction R (5'-ggc gat taa gtt ggg taa cg-3', SEQ ID NO:10); AB right, AAVS1 Junction F (5'-ggc ctc ttg gtc aag ttg tt-3', SEQ ID NO:11) and AAVS1 CEL-I R (5'-ctc agg ttc tgg gag agg gta g-3', SEQ ID NO:12); BA left, AAVS1 CEL-I F and AAVS1 Junction F; BA right, AAVS1 Junction R and AAVS1 CEL-I R. For the sequences in FIG. 8A, the following primers were used: AB left, M13F (5'-gta aaa cga cgg cca gt-3', SEQ ID NO:13) and AAVS1 CEL-F; BA right, M13F and AAVS1 CEL-I R.

Targeted integration at IL2Rγ, CCR5, and GS was assayed via PCR amplification. PCR reactions used a 58° annealing temperature, a 30 second extension time, 5% DMSO, 26 cycles of amplification, and the M13F primer in combination with the following primers: IL2RγBA left, IL2Rγ CEL-I F (5'-acc agt gag ttt tca tta gg-3', SEQ ID NO:14); IL2RγAB right, IL2Rγ CEL-I R (5'-tgg agc aaa aga cag tgg tg-3', SEQ ID NO:15); CCR5BA left, R5F (5'-aag atg gat tat caa gtg tca agt cc-3', SEQ ID NO:16); CCR5AB right, R5R (5'-caa gtg ccc act ggg cg-3', SEQ ID NO:17); GS BA left, GJC 172F (5'-atc cgc atg gga gat cat ct-3', SEQ ID NO:18); GS AB right, GJC 173R (5'-gtg tat gtt cgt tca ccc ac-3', SEQ ID NO:19).

Targeted integration of the AAVS1 donor at GS (FIG. 2B) was assayed via PCR amplification. PCR reactions used a 58° C. annealing temperature, a 30 second extension time, 5% DMSO, 26 cycles of amplification, and the following primers: AB left, Jcn1F (5'-caa ata gga ccc tgt gaa gga-3', SEQ ID NO:20) and Jcn1R (5'-gat taa gtt ggg taa cgc cag-3', SEQ ID NO:21); BA left, Jcn3F (5'-aat agg acc ctg tga agg a-3', SEQ ID NO:22) and Jcn3R (5'-gtg tgg aat tgt gag cgg ata-3', SEQ ID NO:23).

Targeted integration of the IgG donor at FUT8 (FIG. 4) was assayed via PCR amplification. PCR reaction used a 60° annealing temperature, a 30 second extension time, 30 cycles of amplification (35 cycles for screening of crude lysates), and the following primers: AB left junction, GJC 75F (5'-agt cca tgt cag acg cac tg-3', SEQ ID NO:24) and SC seqpfzR (5'-aga gtg agg ctc tgt ctc aa-3', SEQ ID NO:25); AB right junction, FUT8 donor CELIF2 (5'-tac gta tag gct gcg caa ct-3', SEQ ID NO:26) and GJC 115R (5'-gca cat gta gtc ttt gat ttt g-3', SEQ ID NO:27); BA left junction, GJC75F and FUT8 donor CELIF2; BA right junction, SC seqpfzR and GJC115R.

The Southern blot of AAVS1 GFP donor integration at AAVS1 was probed as previously described (DeKelver et al. 2010, ibid). Expected results from this Southern blot are as follows: an AAVS1 probe will hybridize to either a 2092 or 6592 bp band for the AB and BA orientations, respectively. The wild-type, triploid AAVS1 locus will be seen as a 3287 bp band. The Southern blot of AAVS1 GFP donor integration elsewhere in the genome was probed with the complete open reading frame of GFP. Integration at AAVS1 will produce either 3323 or 4482 bp bands for the AB and BA orientations, respectively; non-targeted integrations elsewhere in the genome will produce secondary bands of indeterminable size. The Southern blot of GS donor integration at GS was probed with a 424 bp fragment of the GS gene bounded by 5'-ctg cag gtg aag aca gga tg-3' (SEQ ID NO: 523) and 5'-ccc act aga aag aac atg tt-3' (SEQ ID NO: 542). Integration at GS will be revealed as a hybridizing band at 2933 bp; the wild-type GS locus will produce a 1977 bp band. The Southern blot of GS donor integration elsewhere in the genome was probed with a BsaI-ScaI fragment of the *E. coli* bla gene. Correctly integrated transgenes will give a 2055 bp band; integrations into the GS pseudogenes will give bands of 4878, 4214, 10080, and 9416 bp depending on the pseudogene and insert orientation; other non-targeted integrations will produce a single band of unpredictable size. The Southern blot of integration at FUT8 was probed with a 407 bp HindIII-XmnI fragment of the FUT8 locus. For both FUT8 Southerns, the genomic DNA was cut with HindIII.

Contigs containing FUT8, GS, and GS pseudogenes were extracted from the whole-CHO genome sequencing data using a custom Python script (Xu et al. (2011) *Nat Biotechnol* 29(8):735-41). FUT8 is present on contig AFTD01065932.1; GS on contig AFTD01107178.1. One GS pseudogene (contained in AFTD01043599.1) has perfect conservation of the ZFN binding sites, 120/128 (94%) of homology to the exon 5 portion of the probe, and is expected to be present in a 6333 bp ScaI fragment. The second GS pseudogene (contained in AFTD01154859.1) has one mismatch in the ZFN binding sites, 116/128 (91%) by of homology to the exon 5 portion of the probe and is expected to be present in a 13320 bp ScaI fragment.

Antibody concentrations were measured using the Pierce Easy-Titer IgG Assay Kit (23310) according to the manufacturer's instructions. Clones with at least two-fold higher than background were classified as positive.

Example 2: Targeted Integration Following In Vivo Cleavage of a Double-Stranded Donor

A. AAVS1

To test whether transgene cleavage in vivo using the same ZFN that cuts the genomic target site would synchronize donor and chromosome cleavage, minimizing the vulnerability of the transgene to degradation, K562 cells were transfected with AAVS1-targeted ZFNs and a donor plasmid that includes the AAVS1 ZFN target sites for cleavage of the donor plasmid in vivo. Briefly, as described in Example 1, we cloned the recognition site for the well-characterized and highly active AAVS1 ZFNs into a donor plasmid containing an autonomous GFP expression cassette but lacking homology to the AAVS1 locus. See, U.S. Pat. No. 8,110,379 and DeKelver et al. (2010) *Genome Res.* 20(8):1133-1142. The donor plasmid (with or without the ZFN target site) was co-transfected into K562 cells along with a second plasmid encoding the AAVS1 ZFNs.

Insertion into the chromosomal AAVS1 site assayed by PCR amplification of the unique junctions formed by targeted donor integration from genomic DNA isolated 3 days post-transfection as described above in Example 1.

As shown in FIG. 1, when co-transfected with the cognate ZFNs, simultaneous cleavage of both a ZFN site-containing donor plasmid and the chromosome will occur, allowing insertion of the plasmid into the chromosome. Insertion of the donor plasmid in the direction expected by simple ligation of the ZFN overhangs was designated as the AB orientation, the alternate direction was designated as the BA orientation. As shown in FIG. 1D, the BA (reverse) orientation is favored when the nucleotides between the target sites (spacer) is the reverse complement of the genomic (wild-type) sequence.

Figure 1D:
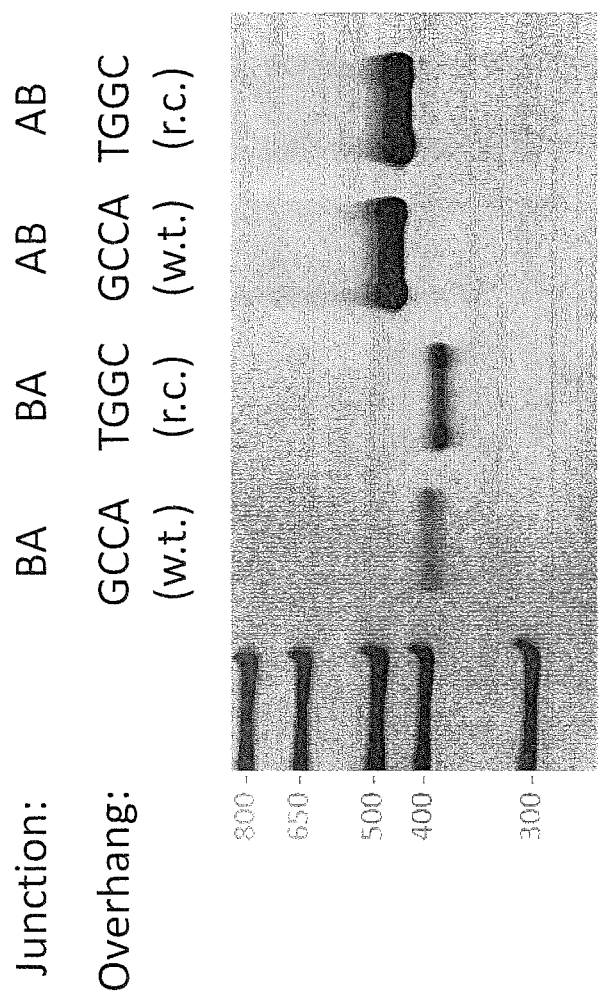
FIG. 1D is a gel showing detection of targeted integration from donors with wild-type ("w.t.") sequences (or spacers) between the ZFN binding sites (the same spacer sequences as in the genome) and reverse-complement ("r.c.") sequences between the ZFN binding sites. As shown, more signal is seen in the BA orientation with reverse-complement overhang-nucleotides
Figure 1E:
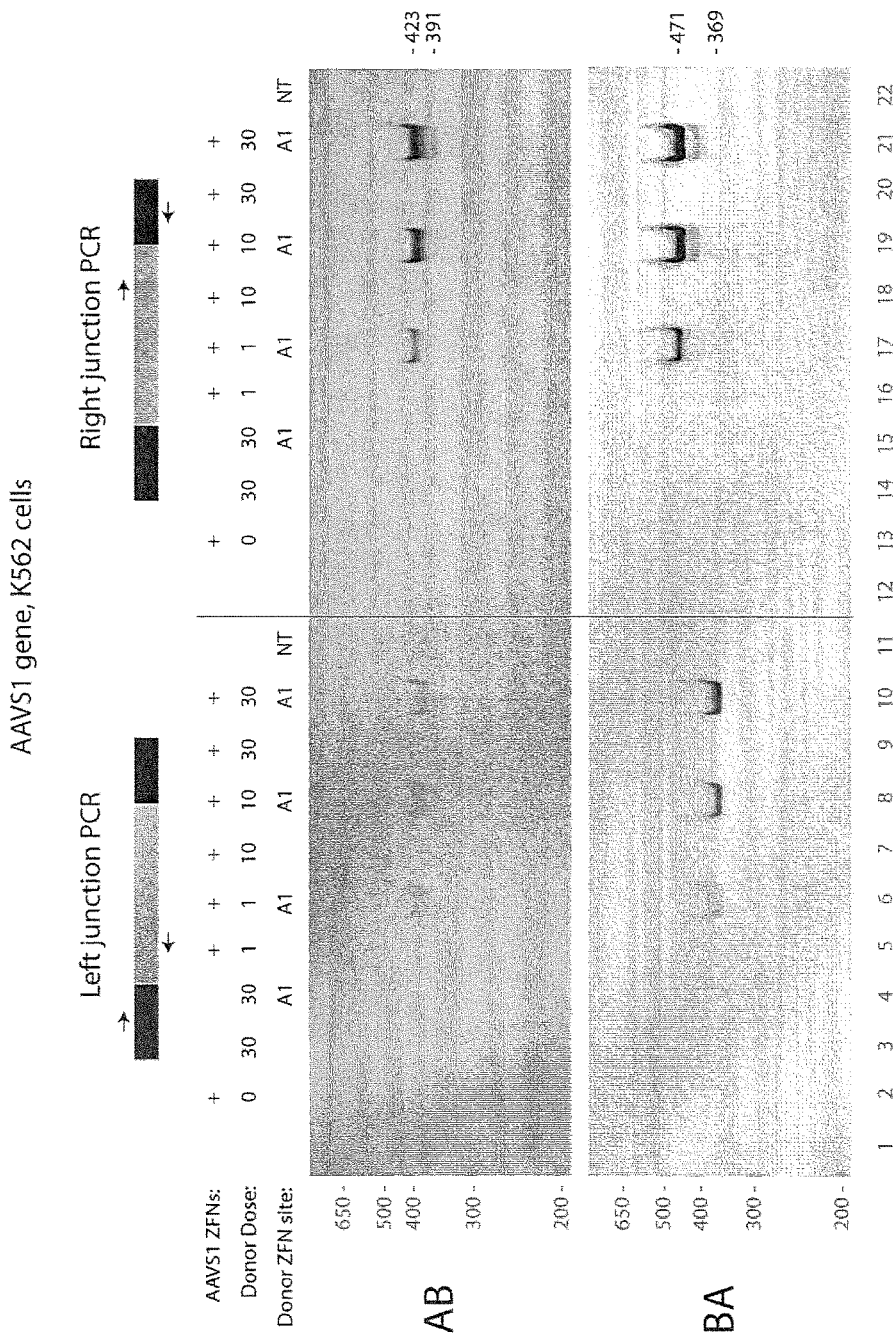
FIG. 1E is a gel depicting integration of a donor plasmid at AAVS1 following in vivo cleavage by the AAVS-specific ZFNs. A donor plasmid either containing or lacking the AAVS1 ZFN site was co-transfected with the AAVS1-specific ZFNs into K562 cells. Integration in both the AB and BA orientations was monitored by PCR of chromosome-donor junctions. Insertion in the AB orientation produces 391 and 423 bp PCR products for the left and right junctions, respectively; insertion in the BA orientation produces 369 and 471 bp junction PCR products for the left and right junctions, respectively. "A1" refers to the PCR reaction designed to amplify the AAVS1 ZFN site and "NT" refers to those reactions lacking DNA template.

Furthermore, as shown in FIGS. 1D and 1E (see lanes 6, 8, 10, 17, 19 and 21 of 1E), consistent with successful capture of the cleaved donor DNA, we detected the expected 5' and 3' junctions formed by donor integration in both the AB and the BA orientations. The BA orientation was favored with the reverse complement spacers (FIG. 1D). Donor integration required ZFN-mediated cleavage as both (i) donor without an AAVS1 ZFN site was not integrated despite efficient cleavage of the AAVS1 locus (see, FIG. 1E, lanes 5, 7, 9, and lanes 16, 18, and 20; FIG. 5A) and (ii) transfection of a donor without co-transfection of the corresponding ZFN also failed to yield targeted integration.

Figure 1F:
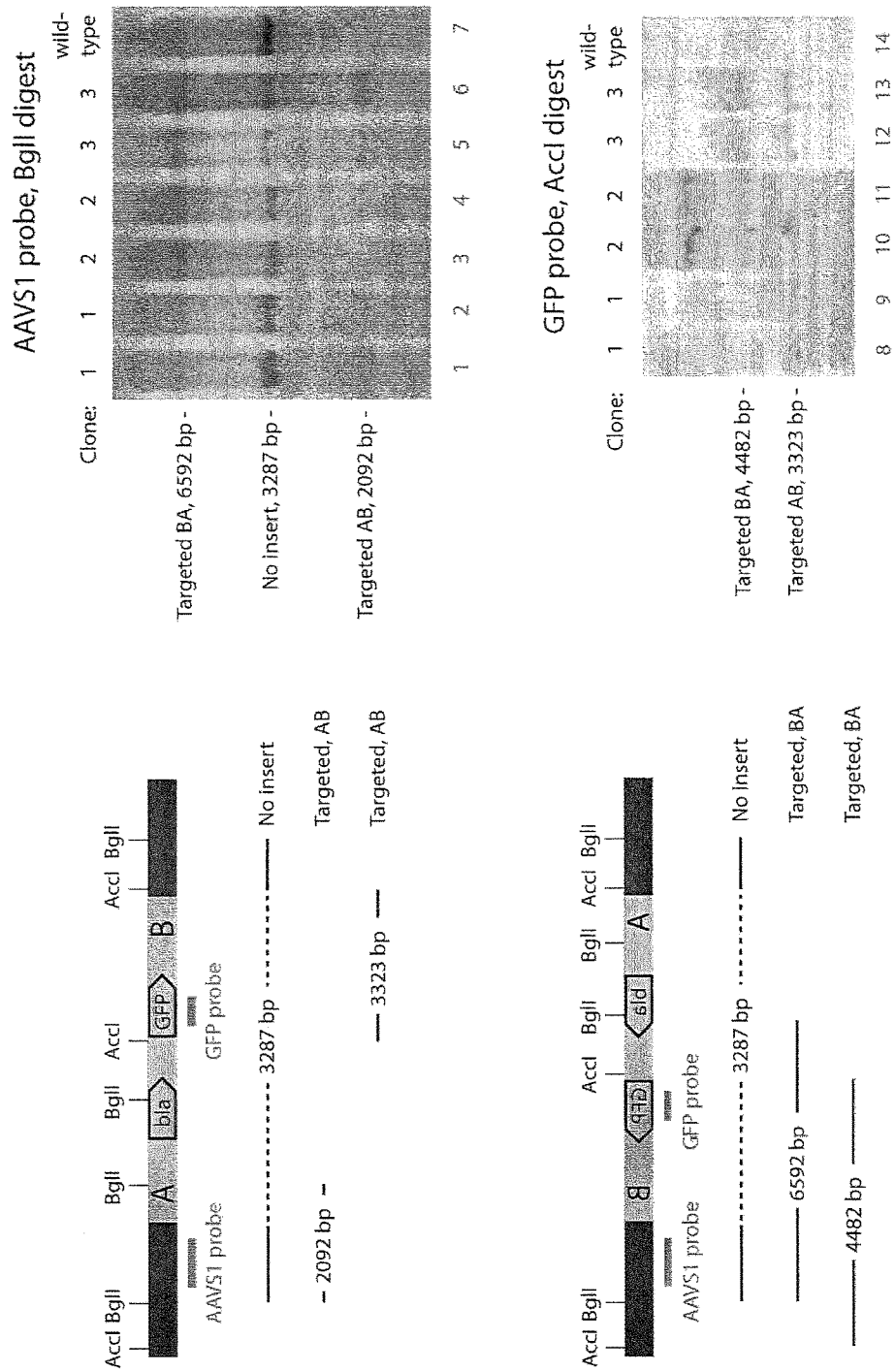
FIG. 1F depicts both schematics of the triploid AAVS1locus and results of interrogation of targeted integration, as assayed by Southern blot. Three clones were assayed in duplicate. Genomic DNA from the three clones was either cut with BglI and probed with an AAVS1-specific probe (top gel) or cut with AccI and probed with a transgene specific probe (bla).

Cell clones were obtained by limiting dilution from the pool transfected with both ZFN and donor (lane 8/19). Three GFP-positive and junction PCR-positive clones were analyzed in duplicate by Southern blot to confirm integration of the donor plasmid. The clones fall into three classes: clone one contains one AB insertion; clone two contains one BA insertion; clone three contains both AB and BA insertions in addition to a non-inserted allele (FIG. 1F).

The three clones were also analyzed for off-target integration by Southern blotting with a GFP-specific probe. Clone one contains only the expected insertion at AAVS1 whereas clones 2 and 3 contain a transgene insertion elsewhere in the genome in addition to the AAVS1 insertions (FIG. 1F).

PCR amplicons of the chromosome-donor integration junctions from these three cell lines were cloned and sequenced. As shown in FIG. 7, clones 1 and 3 contained AB insertions with perfect ligation of the donor and chromosomal overhangs at both the 5' and 3' junctions. Clones 2 and 3 contained BA insertions with alleles produced by microhomology-driven repair at the left, 5' junction.

B. IL2Rγ, GS and CCR

To demonstrate that capture of a cleaved donor was not restricted to integration into AAVS1 in K562 cells, we performed analogous experiments at three other loci (IL2Rγ, CCR and GS) in K562 and CHO cells. Successful targeted integration was monitored at one chromosome-donor junction for each orientation (AB and BA) as described above.

Figure 2A:
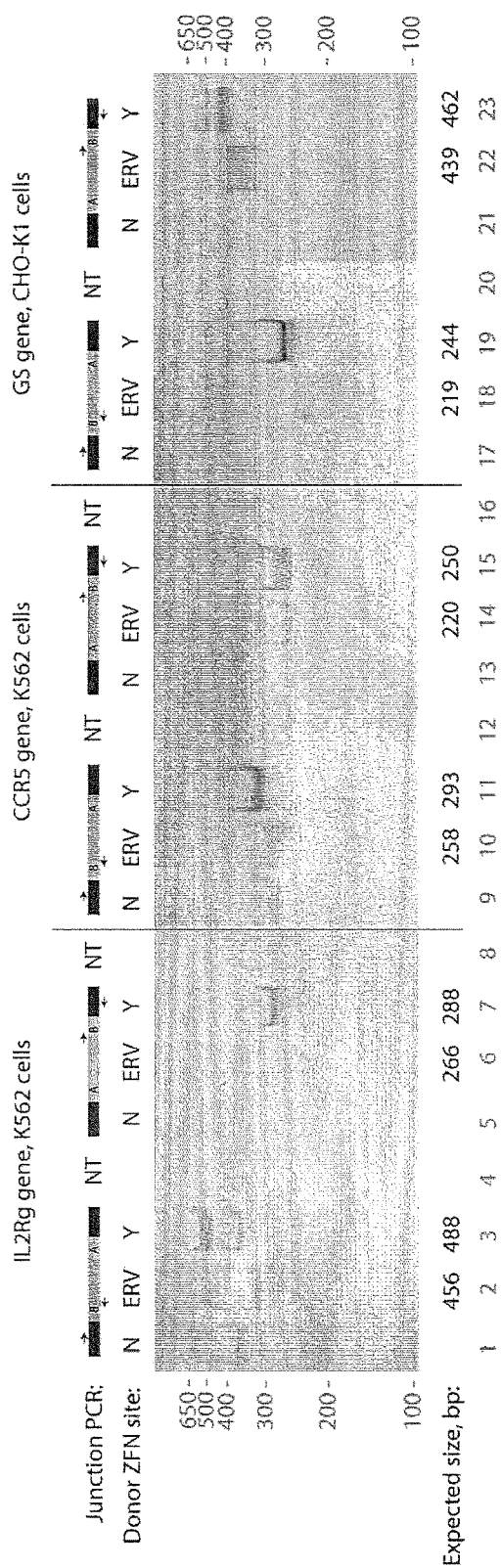
FIG. 2A shows that targeted integration via NHEJ at sites in the IL2Rγ, CCR5, and glutamine synthetase (GS) loci is more efficient when the donor plasmid is co-cleaved with the chromosome rather than being cut prior to transfection. One junction PCR for each orientation was performed for all three loci, the left junction for the BA orientation and the right junction for the AB orientation. The experimental conditions that were used are labeled as follows: "N" refers to transfections wherein the donor lacked a ZFN site; "ERV" refers to the sample in which the donor was pre-cut with EcoRV prior to introduction into the cell; "Y" refers to a transfection where the donor and the targeted gene both contained the ZFN site; and "NT" refers to PCR reactions with no template DNA. The amplicon size expected from PCR amplification of successfully integrated donors is shown below each lane in base pairs ("Expected size, bp"). The picture shown is a color-inverted image of an ethidium bromide-stained gel.
Figure 2B:
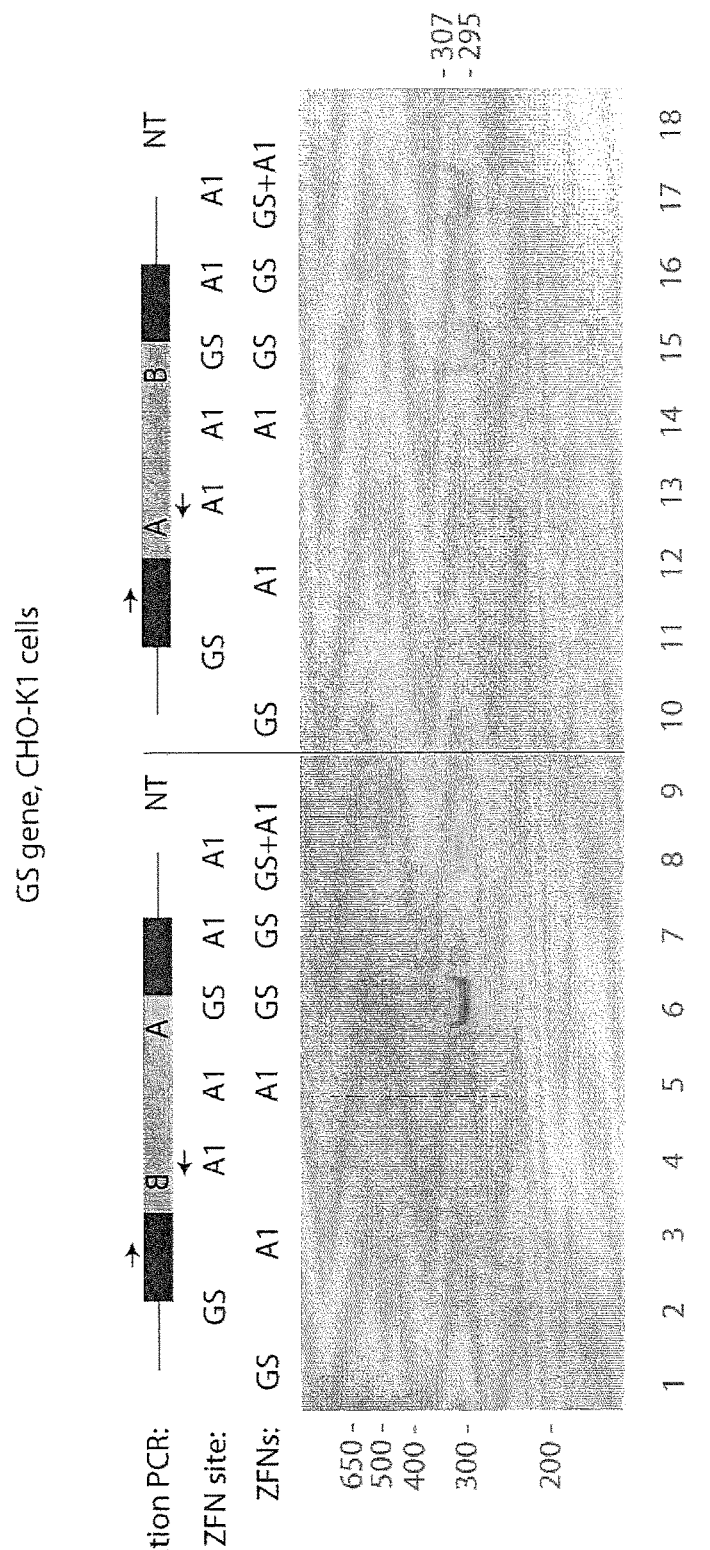
FIG. 2B depicts that donor cleavage does not need to be done with the same ZFNs as those used to cut the target site in the chromosome. Junction-specific PCR assays were used to detect transgene integration into the chromosomal target and to detect the orientation of the integrated transgenes. These assays demonstrated that the transgene could integrate in either orientation following ZFN cleavage. Experimental conditions are labeled as follows: GS, GS-specific ZFNs or donor plasmid with the GS ZFN cleavage site; A1, AAVS1-specific ZFNs or donor with the AAVS1ZFN cleavage site.
Figure 5B:
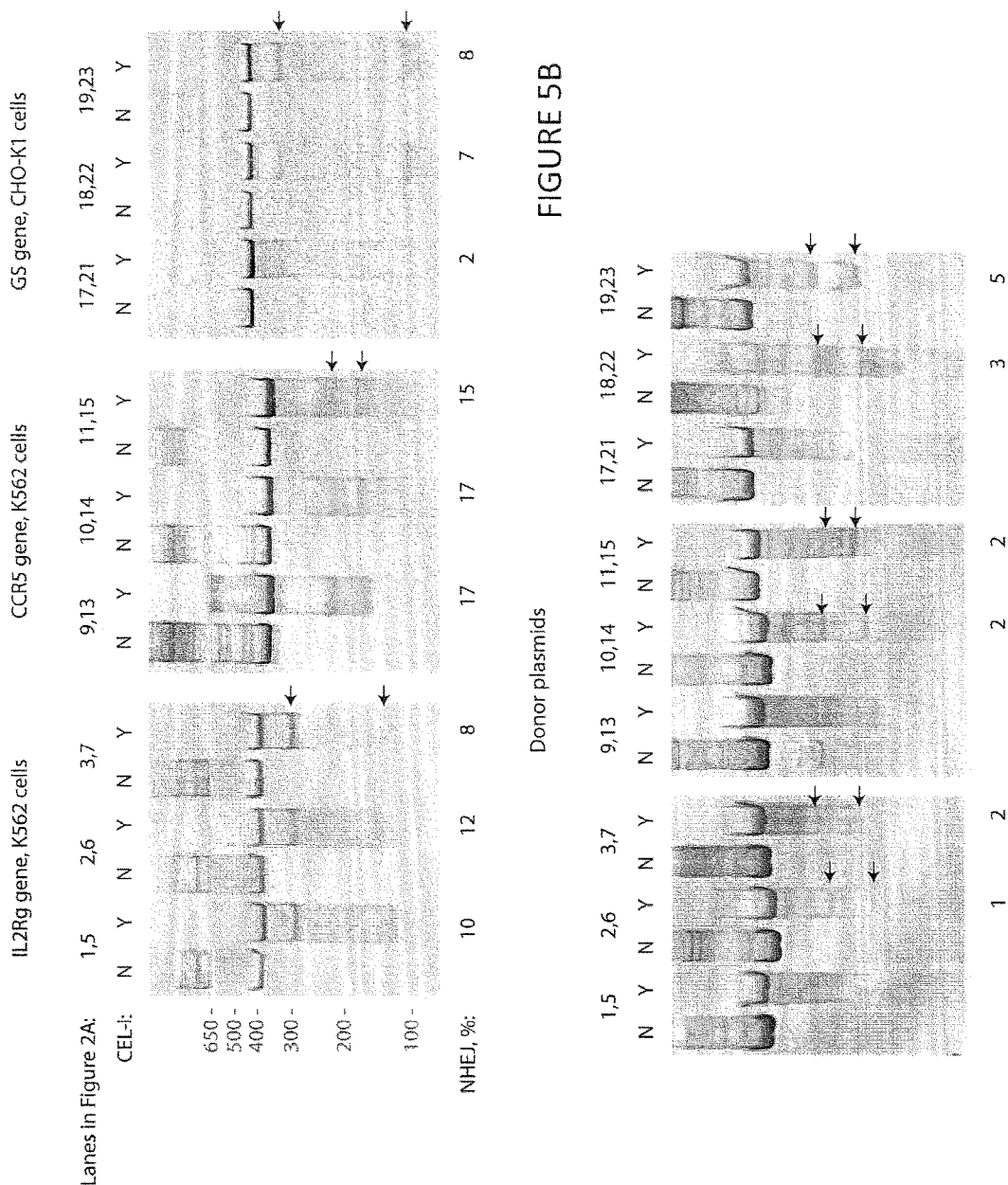
FIG. 5B shows ZFN cleavage at IL2Rγ, CCR5, and GS using the corresponding gene-specific ZFNs. As described above for 5A, the corresponding lanes in 5B from FIG. 2A are shown above the gel, as is the presence ("Y") or absence ("N") of the Surveyor™ nuclease enzyme. While the gels across the top of FIG. 5B depict the results from integration into the gene loci, the gels on the bottom of the figure depict the results of cleavage in the donors.

Site-specific integration targeted to the site of ZFN cleavage was observed for the IL2Rγ, and CCR5 loci in K562 cells and for the GS locus in CHO-K1 cells. (FIG. 2A, lanes 3, 7, 11, 15, 19, and 23). As with integration into AAVS1, integration at IL2Rγ, CCR5, and GS was dependent upon inclusion of the ZFN cleavage site in the donor plasmid (FIG. 2A, lanes 1, 5, 9, 13, 17, and 21) and the co-delivery of the ZFNs themselves. ZFN activity, both at the chromosomal target and on the donor plasmid was essentially uniform across all samples (FIG. 5B).

Sequencing of chromosome-donor junction PCR products from these loci, as well as from an analogous pool of AAVS1 integrants, revealed a spectrum of insertion events consistent with correct integration at the targeted locus (FIG. 8).

Thus, the ability to capture an in vivo cleaved transgene donor at a DSB is a general property of the mammalian DNA repair machinery and is independent of the specific target site or cell type.

Example 3: In Vivo and In Vitro Cleavage

To confirm that in vivo cleavage was necessary to support the observed levels of targeted gene insertion, we performed a direct comparison of targeted integration using in vivo cleaved donors and donors cleaved in vitro using EcoRV, as described in Example 1.

As shown in FIG. 2, while integration of pre-cleaved donor plasmids was occasionally detectable, it was markedly less efficient compared to the in vivo-cleaved donors (FIG. 2A, compare lanes 2/3, 6/7, 10/11, 14/15, 18/19, and 22/23). Moreover, the use of pre-cleaved donor DNAs showed an increased range of junction PCR sizes consistent with an increased level of donor DNA degradation prior to chromosomal capture (see, e.g., FIG. 2A, lane 22).

To confirm targeted integration could be stimulated via the use of two different nucleases (ZFNs), we used the GS ZFN pair (Example 1) to cut the chromosome of CHO-K1 cells and the AAVS1 ZFN pair to cleave a donor plasmid in the same cell. Integration at GS was detected at a similar frequency both when the GS ZFN pair cut the chromosome and the donor (as in FIG. 2A) and when the GS ZFNs cut the chromosome while the AAVS1 ZFNs cut the donor (FIG.

Figure 5C:
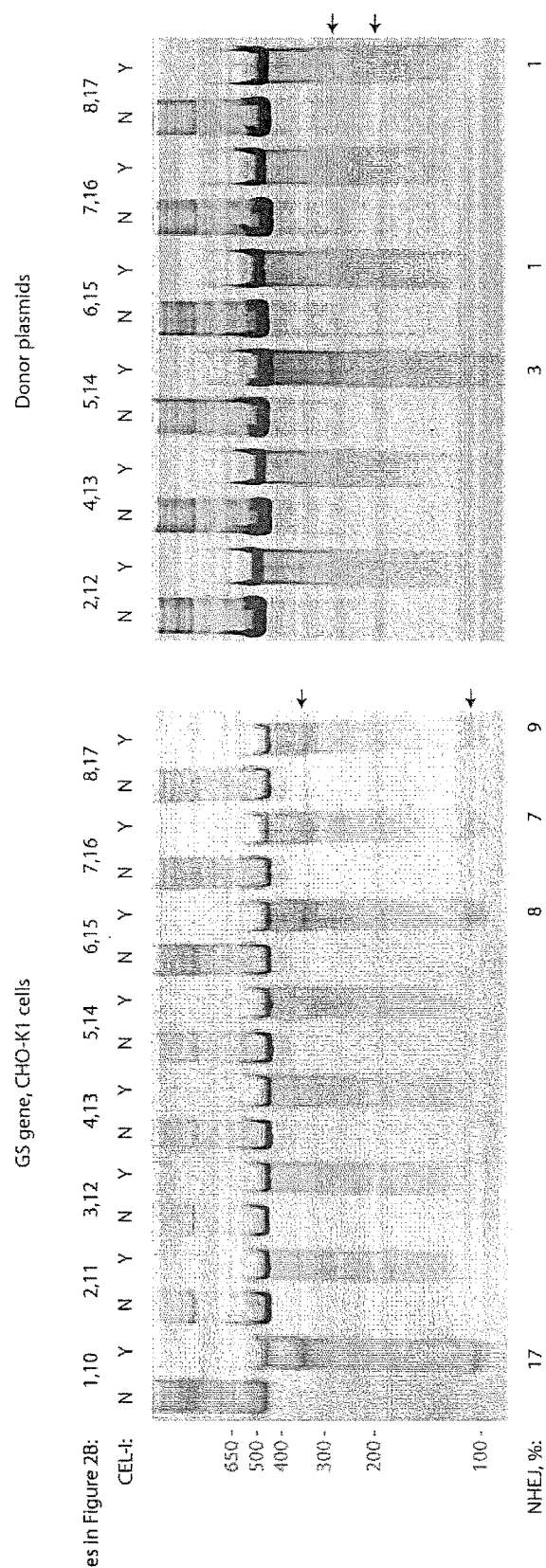
FIG. 5C shows ZFN cleavage at GS where the gel on the left depicts the results from the gene locus in CHO cells, while the gel on the right depicts the results of ZFN cleavage of the donor. As above, the corresponding lanes in FIG. 5C from FIG. 2B is shown above the gel, as is the presence ("Y") or absence ("N") of the Surveyor™ nuclease enzyme. Arrows indicate the expected cleavage products.

2B, lanes 6 and 8, lanes 15 and 17). Cleavage efficiency at GS was again uniform over all GS ZFN-transfected samples (FIG. 5C).

Thus, in vivo cleavage is more efficient than pre-cleavage of the donor molecule.

Example 4: Homology-Independent Targeted Integration into CHO Cells

Targeted integration in CHO cells has particularly important applications in biotechnology yet CHO cells perform HDR-based targeted integration of several kilobase transgenes very poorly. To highlight this point, we compared HDR-mediated targeted integration in both HEK-293 cells and CHO-K1 cells using a system designed to deliver a promoterless GFP gene into a promoter-containing acceptor locus, essentially as described in Moehle et al. (2007) Proc. Nat'l Acad. Sci. USA 104(9):3055-3060). Targeted integration results in expression of GFP and allows quantitation by flow cytometry.

Figure 6:
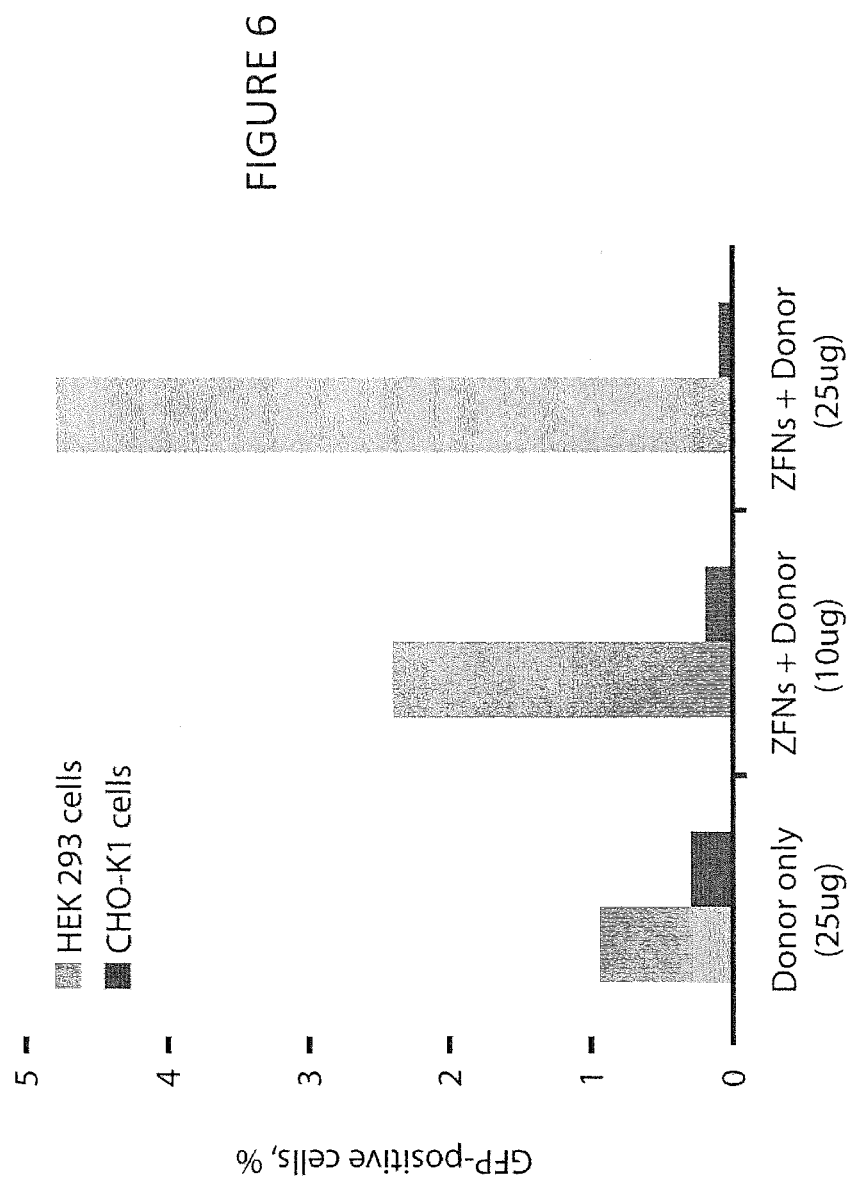
FIG. 6 is a graph depicting homology-directed targeted integration of a GFP encoding transgene in HEK 293 and CHO-K1 cells. The percentage of cells that are GFP-positive is shown in light grey (HEK 293 cells) or dark grey (CHO-K1 cells). The amount of donor used is indicated below each grouping.

When transfected with ZFNs and a homology-containing donor plasmid (for integration via HDR), between 0.5 and 3% of HEK-293 cells became GFP-positive (FIG. 6). In contrast, none of the CHO-K1 cells became GFP-positive when similarly transfected. Given that CHO cells perform HDR-based targeted integration poorly, and yet have proven their utility for recombinant protein production, we next asked whether in vivo cleavage of donor DNA could be exploited to drive targeted integration in CHO cells.

Figure 3A:
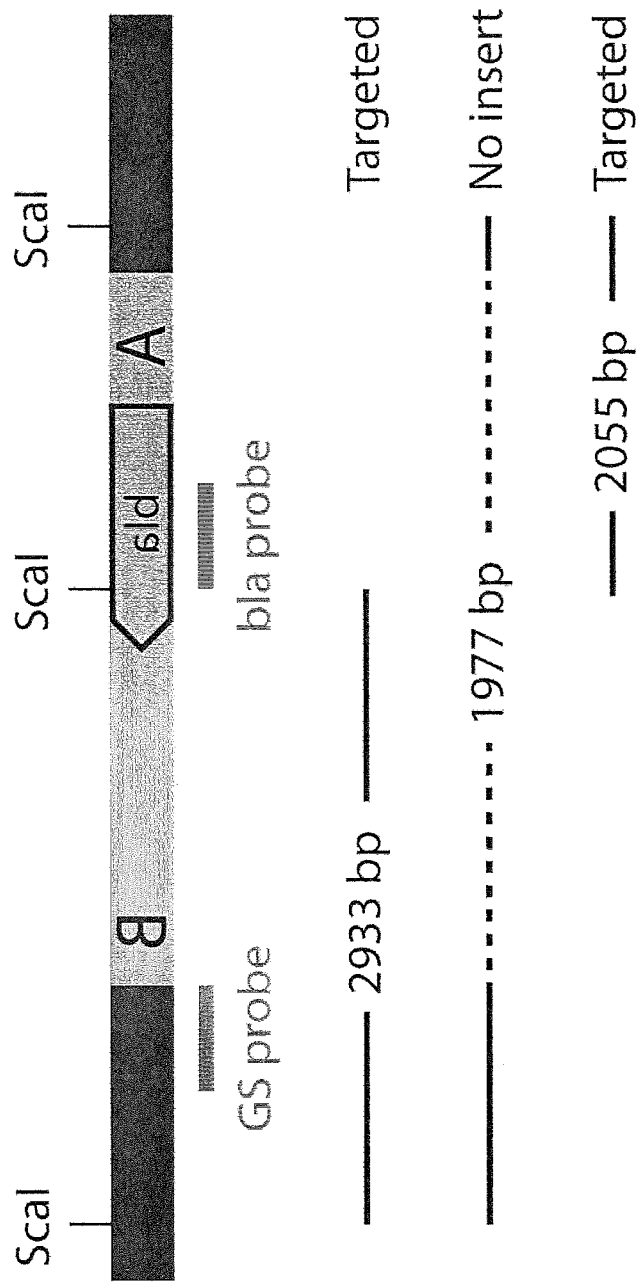
FIG. 3A is a schematic of the GS locus showing the transgene integrated in the BA orientation.
Figure 3B:
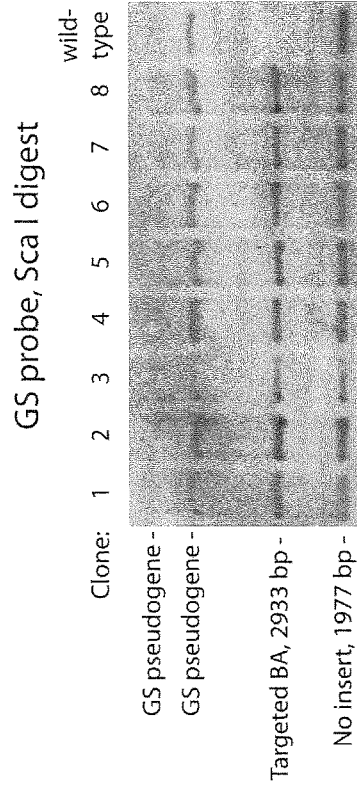
FIG. 3B shows a Southern blot assay of cell clones for targeted integration of the donor at the GS locus. The exonic GS probe also detects two GS pseudogenes. The same panel of clones was assayed for total transgene integration by probing for the E. coli bla gene (FIG. 3C). Integration of the transgene at the GS locus is seen along with transgene integration elsewhere in the genome in three of the eight clones analyzed.
Figure 3C:
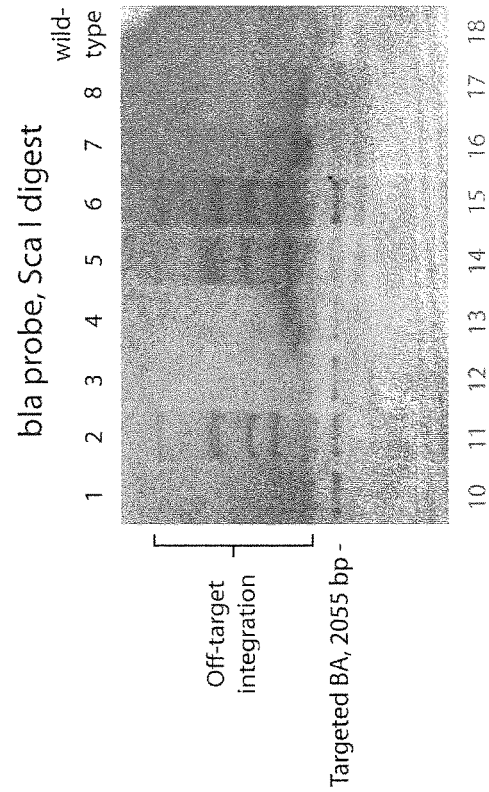
FIG. 3, panels A to C, depict high-frequency targeted transgene integration at the GS locus in CHO-K1 cells.

CHO-K1 cells from the pool bearing targeted integration at GS (FIG. 2A, lanes 19/23) were cloned by limiting dilution and single-cell derived clones screened by PCR for site-specific integration. In contrast to the negative results obtained with the HDR-based approach, homology-independent capture of the in vivo cleaved donor DNA yielded 10% (17/157) single-cell derived clones that were PCR-positive for the left chromosome-donor BA junction, 8% (13) positive for the right BA junction, and 6% (10) positive for both BA junctions. Eight of these ten clones were chosen randomly for analysis by Southern blotting. All 8 clones contained the expected targeted transgene insertion at the GS target site, a wild-type GS allele, and two GS pseudogenes (FIG. 3). Only the wild-type GS allele and the pseudogenes are present in wild-type CHO-K1 cells (FIG. 3, lane 9). Furthermore, when probed with a transgene-specific sequence, five of the 8 clones were shown to contain only one copy of the transgene at GS, whereas 3 contained a transgene copy at GS along with one or more randomly integrated copies at other sites in the CHO genome, one of which corresponded to integration into a GS pseudogene (FIG. 3, lanes 10, 12, 13, 16, 17 and lanes 11, 14, 15, respectively). The chromosome-transgene junctions were sequenced and are shown in FIG. 9.

Example 5: Targeted Integration into and Disruption of FUT8

Transgenes are routinely inserted into the CHO cell genome to produce biopharmaceutical proteins, notably antibodies. CHO cells with a deletion of the FUT8 gene yield fucosylated antibodies with 100-fold higher antibody-dependent cellular cytotoxicity (Malphettes et al. (2010) Biotechnology and Bioengineering 106(5):774-83; Yamane-Ohnuki et al. (2004) Biotech. Bioeng. 87(5):614-22). Moreover, knockout of FUT8 expression can be selected for, thus potentially coupling targeted integration with this selectable trait. We therefore used the previously described FUT8-specific ZFNs to disrupt the FUT8 gene via insertion of an in vivo-cleaved antibody production cassette (Moehle et al. (2007) Proc. Nat'l Acad. Sci. USA 104(9):3055-3060). Furthermore, we wished to determine whether capture of an in vivo cleaved donor could occur at a double-strand break produced by a TALE nuclease (TALEN) specific for FUT8.

Briefly, ZFNs or TALENs that cleave FUT8 were cotransfected with an antibody expression plasmid containing a FUT8 nuclease cleavage site as described in Example 1. The transfected pool was selected for biallelic FUT8 knockout using Lens culinaris agglutinin and cells cloned by limiting dilution (see, Malphettes et al. (2010) Biotechnology and Bioengineering 106(5):774-83). Clones were screened for secretion of IgG and for insertion of the IgG transgene by PCR of both left and right transgene/chromosome junctions.

Figure 4A:
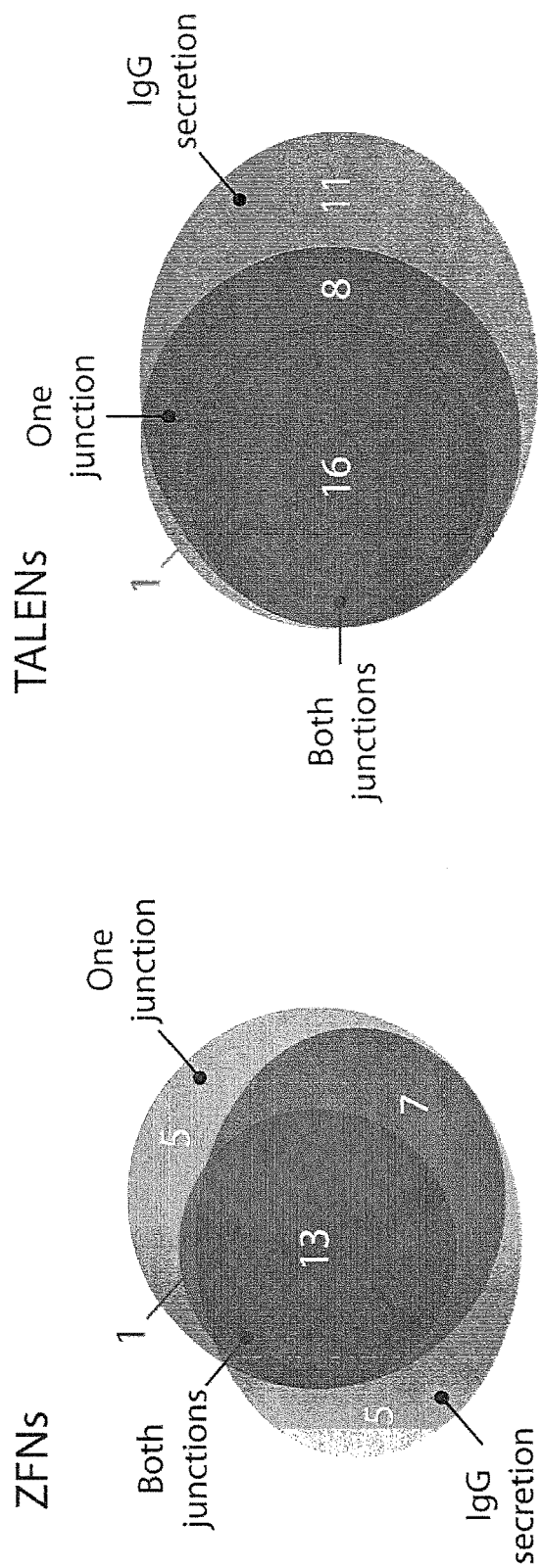
FIG. 4A depicts area-proportional Venn diagrams showing concordance between clones screened for transgene insertion by junction-specific PCR and for IgG expression.

As shown in FIG. 4, ZFN-treated clones, 25/96 (26%) of clones expressed IgG and 14/96 (15%) of clones were positive for insertion of the complete IgG transgene. All but one clone positive for insertion by PCR expressed IgG. Similar results were obtained with the FUT8 TALENs: 35/171 (20%) of clones expressed IgG and all 16 (9%) of clones with complete transgene insertion expressed IgG. Clones with one (but not both) transgene integration junctions detectable by PCR accounted for a significant fraction of the remaining IgG-expressing clones (FIG. 4A).

Figure 4B:
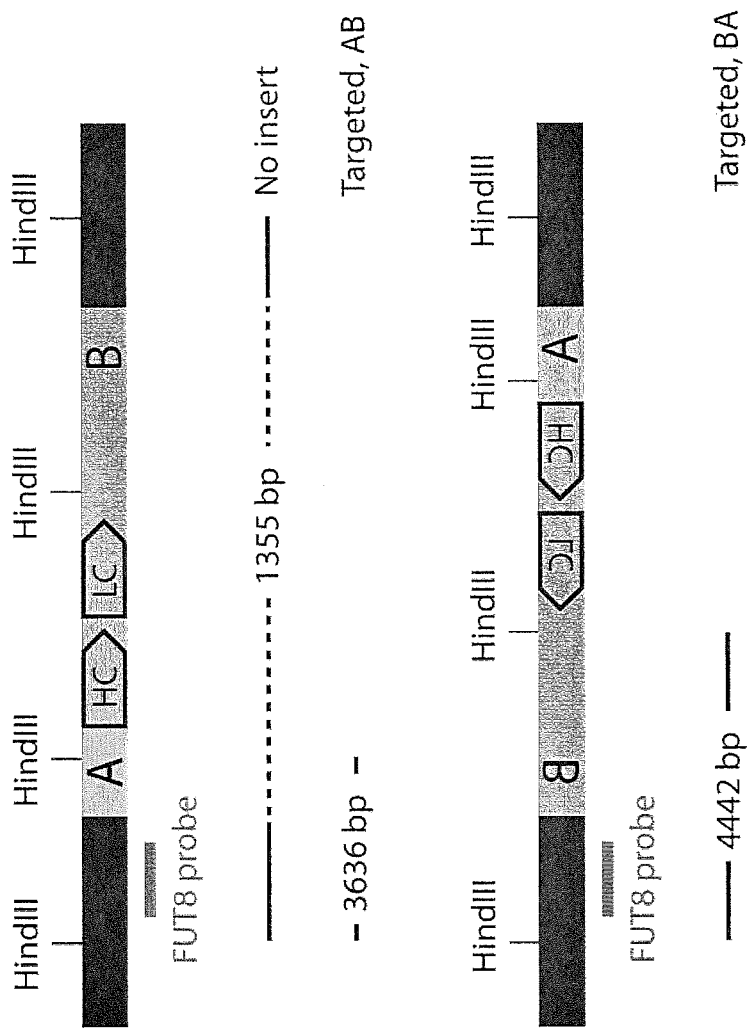
FIG. 4B is a schematic of the FUT8 locus containing the inserted transgene (depicted in light grey), labeling the orientation of the transgene in either the "AB" or "BA" nomenclature.
Figure 4C:
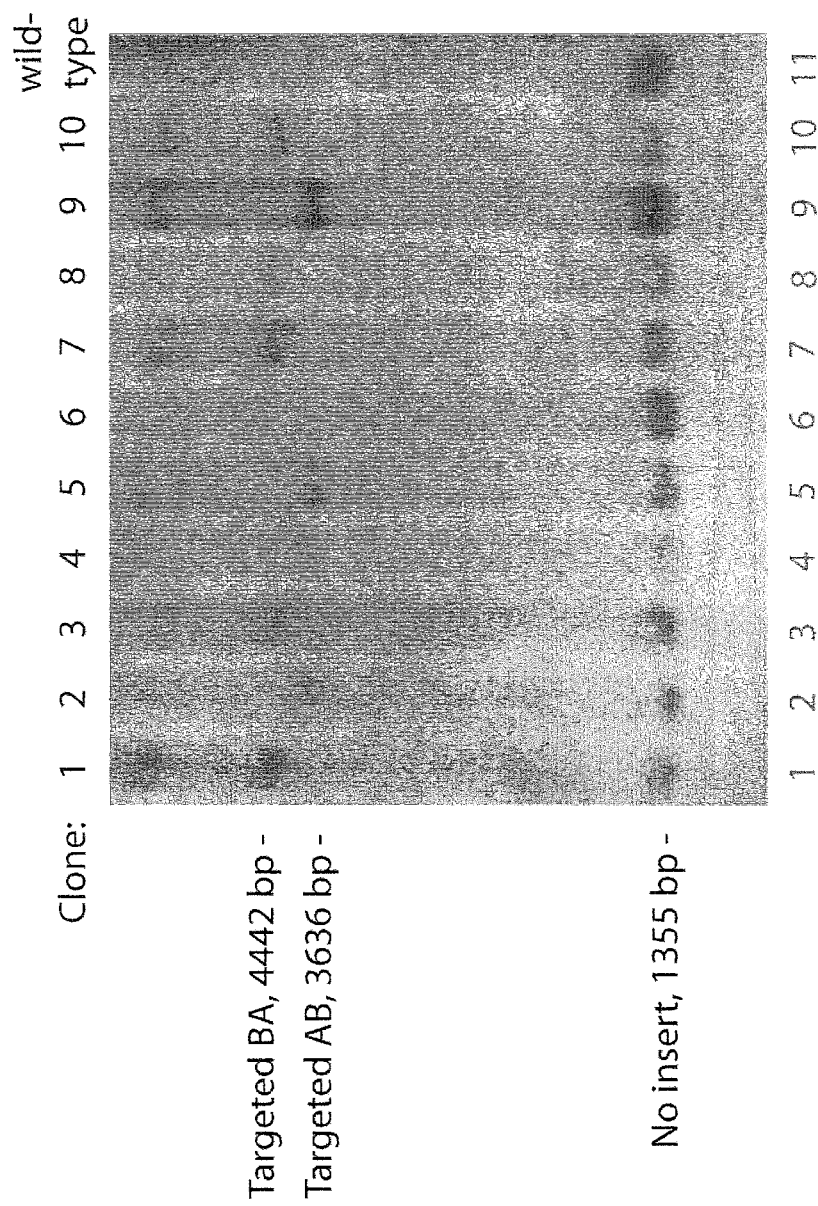
FIG. 4C shows Southern blot confirmation of integration at FUT8. Integrants containing the transgenes inserted in the BA and AB orientations are indicated.
Figure 12:
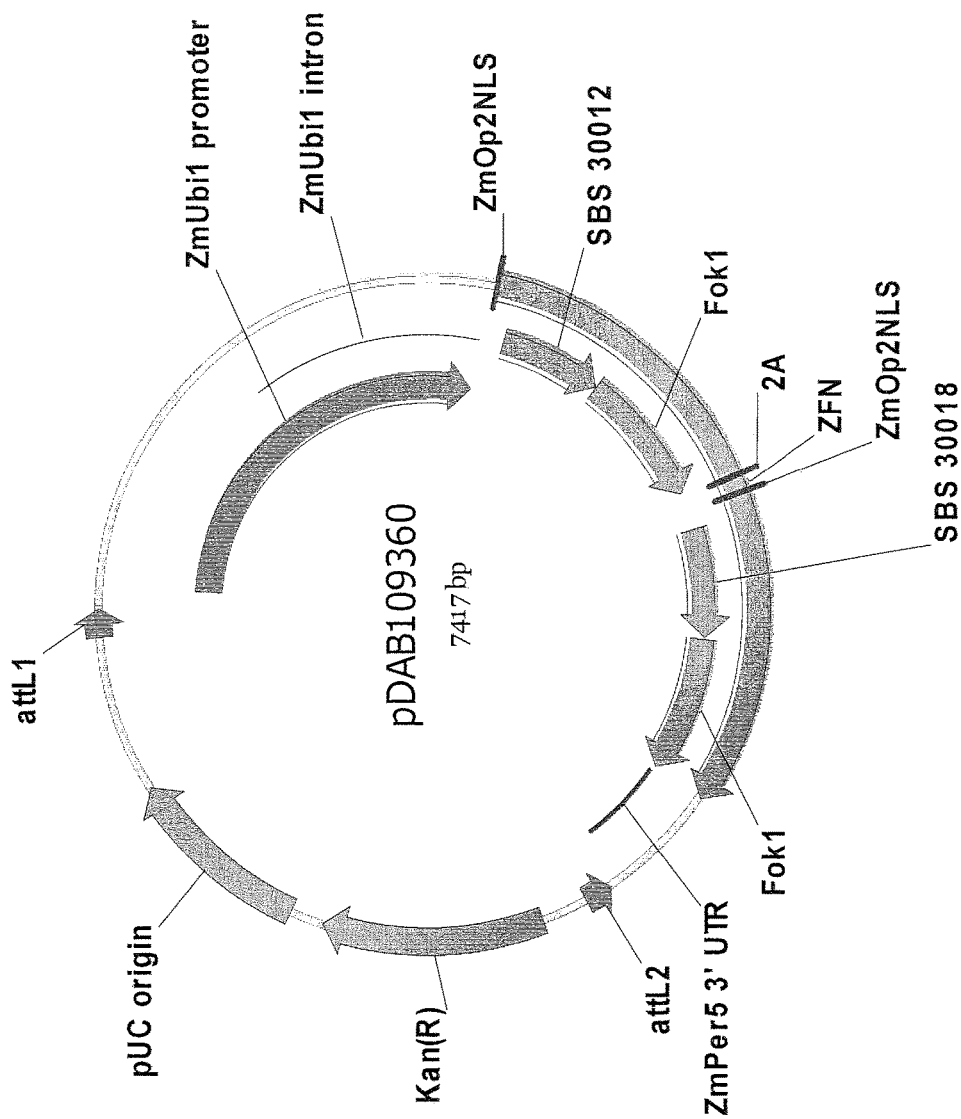
FIG. 12 shows a plasmid map of pDAB109360.

These experiments were also performed using TALE-nucleases targeted to FUT8. Transgene integration at FUT8 was confirmed by Southern blot analysis for ten PCR- and IgG-positive clones derived from TALEN-mediated transgene insertion (FIGS. 4B and 4C). In addition, FIG. 12 shows sequences obtained by sequencing of PCR junctions of FUT8-integrated donors using ZFNs (FIG. 10A) or TALENs (FIG. 10B).

In sum, the methods and compositions described herein provide for the facile and targeted integration of large transgenes via homology-independent methods, including in cell lines (e.g., CHO cells) that are resistant to homology-driven integration.

Example 6: Targeted Integration into and Disruption of Wheat AHAS Loci Characterization and Identification of AHAS Genomic Target Sequences The transcribed regions for three homoeologous AHAS genes were identified and determined, zinc finger nucleases were designed to bind and cleave the sites for NHEJ-mediated targeting of a donor sequence as described in U.S. Provisional Patent Filing No. 61/809,097, incorporated herein by reference. These novel sequences are listed as SEQ ID NO:116, SEQ ID NO:117, and SEQ ID NO:118. Previous sequencing efforts identified and genetically mapped homoeologous copies of AHAS genes from Triticum aestivum to the long arms of chromosomes 6A, 6B and 6D (Anderson et al., (2004) Weed Science 52:83-90; and, Li et al., (2008) Molecular Breeding 22:217-225). Sequence analysis of Expressed Sequence Tags (EST) and genomic sequences available in Genbank (Accession Numbers: AY210405.1, AY210407.1, AY210406.1, AY210408.1, FJ997628.1, FJ997629.1, FJ997631.1, FJ997630.1, FJ997627.1, and AY273827.1) were used to determine the transcribed region for the homoeologous copies of the AHAS gene (SEQ ID NOs: 116-118).

The novel, non-coding AHAS gene sequences located upstream and downstream of the transcribed region were characterized for the first time. To completely characterize theses non-coding sequences, the transcribed sequences for each of the three homoeologous copies of the AHAS gene were used as BLASTN™ queries to screen unassembled ROCHE 454™ sequence reads that had been generated from whole genome shotgun sequencing of *Triticum aestivum* cv. Chinese Spring. The ROCHE 454™ sequence reads of *Triticum aestivum* cv. Chinese Spring had been generated to 5-fold sequence coverage. Sequence assembly was completed using the SEQUENCHER SOFTWARE™ (Gene-Codes, Ann Arbor, Mich.) of the ROCHE 454™ Sequence reads with a significant BLASTN™ hit (E-value<0.0001) were used to characterize these non-transcribed region. Iterative rounds of BLASTN™ analysis and sequence assembly were performed. Each iteration incorporated the assembled AHAS sequence from the previous iteration so that all of the sequences were compiled as a single contiguous sequence. Overall, 4,384, 7,590 and 6,205 of genomic sequences for the homoeologous AHAS genes located on chromosomes 6A, 6B and 6D, respectively, were characterized (SEQ ID NOs:119-121).

Sequence Analysis of AHAS Genes Isolated from *Triticum aestivum* Cv. Bobwhite MPB26RH The homoeologous copies of the AHAS gene were cloned and sequenced from *Triticum aestivum* cv. Bobwhite MPB26RH to obtain nucleotide sequence suitable for designing specific zinc finger proteins that could bind the sequences with a high degree of specificity. The sequence analysis of the AHAS nucleotide sequences obtained from *Triticum aestivum* cv. Bobwhite MPB26RH was required to confirm the annotation of nucleotides present in Genbank and the ROCHE 454™ AHAS gene sequences and due to allelic variation between cv. Bobwhite MPB26RH and the other wheat varieties from which the Genbank and ROCHE 454™ sequences were obtained.

A cohort of PCR primers were designed for amplification of the AHAS genes (Table 1). The primers were designed from a consensus sequence which was produced from multiple sequence alignments generated using CLUSTALW™ (Thompson et al., (1994) *Nucleic Acids Research* 22:4673-80). The sequence alignments were assembled from the cv. Chinese Spring sequencing data generated from ROCHE 454™ sequencing which was completed at a 5-fold coverage.

As indicated in Table 1, the PCR primers were designed to amplify all three homoeologous sequences or to amplify only a single homoeologous sequence. For example, the PCR primers used to amplify the transcribed region of the AHAS gene were designed to simultaneously amplify all three homoeologous copies in a single multiplex PCR reaction. The PCR primers used to amplify the non-transcribed region were either designed to amplify all three homoeologous copies or to amplify only a single homoeologous copy. All of the PCR primers were designed to be between 18 and 27 nucleotides in length and to have a melting temperature of 60 to 65° C., optimal 63° C. In addition, several primers were designed to position the penultimate base (which contained a phosphorothioate linkage and is indicated in Table 1 as an asterisk [*]) over a nucleotide sequence variation that distinguished the gene copies from each wheat sub-genome. Table 1 lists the PCR primers that were designed and synthesized.

TABLE 1

Primer sequences used for PCR amplification of AHAS sequences

| Primer Name | Genome Region Amplified | SEQ ID NO. | Sequence (5' →3') |
|---|---|---|---|
| AHAS-p_Fwd5 | 5' UTR D | 122 | TCTGTAAGTTATCGCCT GAATTGCTT |
| AHAS-p_Rvs6 | 5' UTR D | 123 | CATTGTGACATCAGCA TGACACAA |
| AHAS-p_Fwd4 | 5' UTR D | 124 | AAGCAYGGCTTGCCTA CAGC |
| AHAS-p_Rvs3 | 5' UTR D | 125 | AACCAAATRCCCCTAT GTCTCTCC |
| AHAS-p_Fwd1 | 5' UTR A, B, and D | 126 | CGTTCGCCCGTAGACC ATTC |
| AHAS-p_Rvs1 | 5' UTR A, B, and D | 127 | GGAGGGGTGATGKTTT TGTCTTT |
| AHAS_1F1_transcribed | Coding A, B, and D | 128 | TCG CCC AAA CCC TCG CC |
| AHAS_1R1_transcribed | Coding A, B, and D | 129 | GGG TCG TCR CTG GGG AAG TT |
| AHAS_2F2_transcribed | Coding A, B, and D | 130 | GCC TTC TTC CTY GCR TCC TCT GG |
| AHAS_2R2_transcribed | Coding A, B, and D | 131 | GCC CGR TTG GCC TTG TAA AAC CT |
| AHAS_3F1_transcribed | Coding A, B, and D | 132 | AYC AGA TGT GGG CGG CTC AGT AT |
| AHAS_3R1_transcribed | Coding A, B, and D | 133 | GGG ATA TGT AGG ACA AGA AAC TTG CAT GA |

TABLE 1-continued

Primer sequences used for PCR amplification of AHAS sequences

| Primer Name | Genome Region Amplified | SEQ ID NO. | Sequence (5' →3') |
|---|---|---|---|
| AHAS-6A.PS.3'.F1 | 3'UTR A | 134 | AGGGCCATACTTGTTGGATATCAT*C |
| AHAS-6A.PS.3'.R2 | 3'UTR A | 135 | GCCAACACCCTACACTGCCTA*T |
| AHAS-6B.PS.3'.F1 | 3'UTR B | 136 | TGCGCAATCAGCATGATACC*T |
| AHAS-6B.PS.3'.R1 | 3'UTR B | 137 | ACGTATCCGCAGTCGAGCAA*T |
| AHAS-6D.PS.3'.F1 | 3'UTR D | 138 | GTAGGGATGTGCTGTCATAAGAT*G |
| AHAS-6D.PS.3'.R3 | 3'UTR D | 139 | TTGGAGGCTCAGCCGATCA*C |

UTR = untranslated region
Coding = primers designed for the transcribed regions
asterisk (*) indicates the incorporation of a phosphorothioate sequence Sub-genome-specific amplification was achieved using on-off PCR (Yang et al., (2005) Biochemical and Biophysical Research Communications 328:265-72) with primers that were designed to position the penultimate base (which contained a phosphorothioate linkage) over a nucleotide sequence variation that distinguished the gene copies from each wheat sub-genome. Two different sets of PCR conditions were used to amplify the homoeologous copies of the AHAS gene from cv. Bobwhite MPB26RH. For the transcribed regions, the PCR reaction contained 0.2 mM dNTPs, 1× IMMOLASE PCR™ buffer (Bioline, Taunton, Mass.), 1.5 mM $MgCl_2$, 0.25 units IMMOLASE DNA POLYMERASE™ (Bioline, Taunton, Mass.), 0.2 µM each of forward and reverse primer, and about 50 ng genomic DNA. Reactions containing the AHAS_1F1 and AHAS_1R1 primers were supplemented with 8% (v/v) DMSO. For the non-transcribed regions, the PCR reactions contained 0.2 mM dNTP, 1× PHUSION GC BUFFER™ (New England Biolabs Ipswich, Mass.), 0.5 units HOT-START PHUSION DNA™ polymerase (New England Biolabs), 0.2 µM each of forward and reverse primer, and about 50 ng genomic DNA. PCR was performed in a final 25 µl reaction volume using an MJ PTC200® thermocycler (BioRad, Hercules, Calif.). Following PCR cycling, the reaction products were purified and cloned using PGEM-T EASY VECTOR™ (Promega, Madison, Wis.) into E. coli JM109 cells. Plasmid DNA was extracted using a DNAEASY PLASMID DNA PURIFICATION KIT™ (Qiagen, Valencia, Calif.) and Sanger sequenced using BIGDYE® v3.1 chemistry (Applied Biosystems, Carlsbad, Calif.) on an ABI3730XL® automated capillary electrophoresis platform. Sequence analysis performed using SEQUENCHER SOFTWARE™ (GeneCodes, Ann Arbor, Mich.) was used to generate a consensus sequence for each homoeologous gene copy (SEQ ID NO:140, SEQ ID NO:141, and SEQ ID NO:142) from cv. Bobwhite MPB26RH. CLUSTALW™ was used to produce a multiple consensus sequence alignment from which homoeologous sequence variation distinguishing between the AHAS gene copies was confirmed.

Design of Zinc Finger Binding Domains Specific to AHAS Gene Sequences

Zinc finger proteins directed against the identified DNA sequences of the homoeologous copies of the AHAS genes were designed as previously described. See, e.g., Urnov et al., (2005) Nature 435:646-551. Exemplary target sequence and recognition helices are shown in Table 2 (recognition helix regions designs) and Table 3 (target sites). In Table 3, nucleotides in the target site that are contacted by the ZFP recognition helices are indicated in uppercase letters; non-contacted nucleotides are indicated in lowercase. Zinc Finger Nuclease (ZFN) target sites were designed for 4 regions in the AHAS gene: a region about 500-bp upstream of the serine 653 amino acid residue, an upstream region adjacent (within 30-bp) to the serine 653 amino acid residue, a downstream region adjacent (within 80-bp) to the serine 653 amino acid residue, and a region about 400-bp downstream of the serine 653 amino acid residue. Numerous ZFP designs were developed and tested to identify the fingers which bound with the highest level of efficiency with 22 different AHAS target sites which were identified in wheat as described in U.S. Provisional Patent Filing No. 61809097, incorporated herein by reference. The specific ZFP recognition helices (Table 2) which bound with the highest level of efficiency to the zinc finger recognition sequences were used for NHEJ-mediated targeting and integration of a donor sequence (homology-independent targeted integration) within the AHAS locus of the wheat genome.

TABLE 2

AHAS zinc finger designs (N/A indicates "not applicable")

| ZFP# | F1 | F2 | F3 | F4 | F5 | F6 |
|---|---|---|---|---|---|---|
| 29730 | TSGNLTR SEQ ID NO: 143 | HRTSLTD SEQ ID NO: 144 | QSSDLSR SEQ ID NO: 145 | HKYHLRS SEQ ID NO: 146 | QSSDLSR SEQ ID NO: 145 | QWSTRKR SEQ ID NO: 147 |
| 29732 | RSDSLSA_ SEQ ID NO: 148 | RSDALAR_ SEQ ID NO: 149 | RSDDLTR_ SEQ ID NO: 150 | QKSNLSS_ SEQ ID NO: 151 | DSSDRKK SEQ ID NO: 152 | N/A |
| 30012 | HSNARKT SEQ ID NO: 153 | QSGNLAR SEQ ID NO: 154 | DRSALAR SEQ ID NO: 155 | RSDNLST SEQ ID NO: 156 | AQWGRTS SEQ ID NO: 157 | N/A |
| 30018 | QSGDLTR SEQ ID NO: 158 | MRNRLNR SEQ ID NO: 159 | DRSNLSR SEQ ID NO: 160 | WRSCRSA SEQ ID NO: 161 | QRSNLDS SEQ ID NO: 162 | N/A |

TABLE 3

Target site of AHAS zinc fingers

| ZFP | AHAS Region | Target Site (5'→3') | SEQ ID NO: |
|---|---|---|---|
| 29730 | Within 30-bp upstream of S653 | agGCAGCACGTGCTCCTGATgcgggact | 163 |
| 29732 | Within 30-bp upstream of S653 | gaTCCCAAGCGGTGGTGctttcaaggac | 164 |
| 30012 | Within 80-bp downstream of S653N | tcTTGTAGGTCGAAATTtcagtacgagg | 165 |
| 30018 | Within 80-bp downstream of S653N | taCAAgTGTGACaTGCGCAatcagcatg | 166 |

The AHAS zinc finger designs were incorporated into zinc finger expression vectors encoding a protein having at least one finger with a CCHC structure. See, U.S. Patent Publication No. 2008/0182332. In particular, the last finger in each protein had a CCHC backbone for the recognition helix. The non-canonical zinc finger-encoding sequences were fused to the nuclease domain of the type IIS restriction enzyme FokI (amino acids 384-579 of the sequence of Wah et al., (1998) Proc. Natl. Acad. Sci. USA 95:10564-10569) via a four amino acid ZC linker and an opaque-2 nuclear localization signal derived from Zea mays to form AHAS zinc-finger nucleases (ZFNs). See, U.S. Pat. No. 7,888,121.

The optimal zinc fingers were verified for cleavage activity using a budding yeast based system previously shown to identify active nucleases. See, e.g., U.S. Patent Publication No. 2009/0111119; Doyon et al., (2008) Nat Biotechnology 26:702-708; Geurts et al., (2009) Science 325:433. Zinc fingers for the various functional domains were selected for in vivo use. Of the numerous ZFNs that were designed, produced and tested to bind to the putative AHAS genomic polynucleotide target site. The ZFNs described in Table 2 above, were identified as having in vivo activity at high levels, and were characterized as being capable of efficiently binding and cleaving the unique AHAS genomic polynucleotide target sites in planta.

Evaluation of Zinc Finger Nuclease Cleavage of AHAS Genes Using Transient Assays ZFN construct assembly: Plasmid vectors containing ZFN gene expression constructs, which were identified using the yeast assay as previously described, were designed and completed using skills and techniques commonly known in the art. (see, for example, Ausubel or Maniatis). Each ZFN-encoding sequence was fused to a sequence encoding an opaque-2 nuclear localization signal (Maddaloni et al., (1989) Nuc. Acids Res. 17:7532), that was positioned upstream of the zinc finger nuclease.

Expression of the fusion proteins was driven by the strong constitutive promoter from the Zea mays Ubiquitin gene, (which includes the 5' untranslated region (UTR) (Toki et al., (1992) Plant Physiology 100; 1503-07). The expression cassette also included the 3' UTR (comprising the transcriptional terminator and polyadenylation site) from the Zea mays peroxidase 5 gene (Per5) gene (US Patent Publication No. 2004/0158887). The self-hydrolyzing 2A encoding the nucleotide sequence from Thosea asigna virus (Szymczak et al., (2004) Nat. Biotechnol. 22:760-760) was added between the two Zinc Finger Nuclease fusion proteins that were cloned into the construct.

The plasmid vectors were assembled using the IN-FUSION™ Advantage Technology (Clontech, Mountain View, Calif.). Restriction endonucleases were obtained from New England BioLabs (Ipswich, Mass.) and T4 DNA Ligase (Invitrogen, Carlsbad, Calif.) was used for DNA ligation. Plasmid preparations were performed using NUCLEOSPIN® Plasmid Kit (Macherey-Nagel Inc., Bethlehem, Pa.) or the Plasmid Midi Kit (Qiagen) following the instructions of the suppliers. DNA fragments were isolated using QIAQUICK GEL EXTRACTION KIT™ (Qiagen) after agarose tris-acetate gel electrophoresis. Colonies of all ligation reactions were initially screened by restriction digestion of miniprep DNA. Plasmid DNA of selected clones was sequenced by a commercial sequencing vendor (Eurofins MWG Operon, Huntsville, Ala.). Sequence data were assembled and analyzed using the SEQUENCHER™ software (Gene Codes Corp., Ann Arbor, Mich.).

Figure 11:
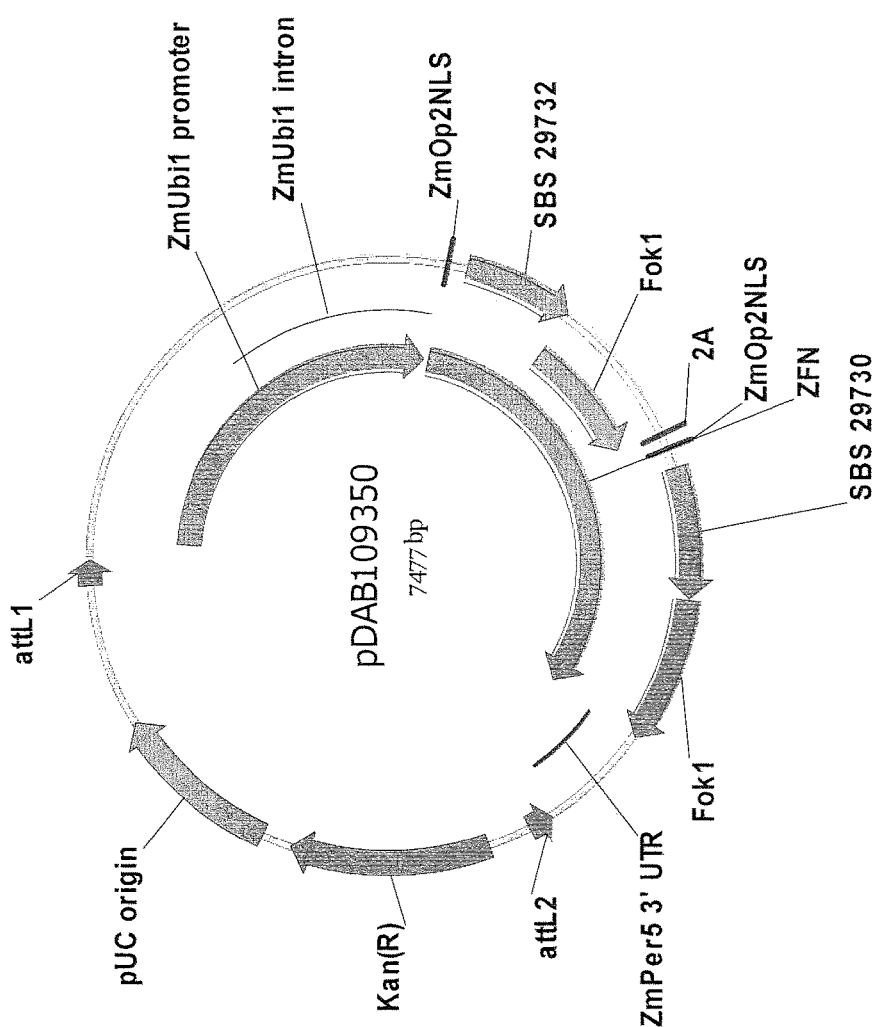
FIG. 11 shows a plasmid map of pDAB109350.

Representative plasmids pDAB109350 and pDAB109360 are shown in FIG. 11 and FIG. 12 and were confirmed via restriction enzyme digestion and via DNA sequencing.

Preparation of ZFN Constructs DNA for Transfection

Before delivery to Triticum aestivum protoplasts, plasmid DNA for each ZFN construct was prepared from cultures of E. coli using the PURE YIELD PLASMID MAXIPREP SYSTEM® (Promega Corporation, Madison, Wis.) or PLASMID MAXI KIT® (Qiagen, Valencia, Calif.) following the instructions of the suppliers.

Isolation of Wheat Mesophyll Protoplasts

Mesophyll protoplasts from the wheat line cv. Bobwhite MPB26RH were prepared for transfection using polyethylene glycol (PEG)-mediated DNA delivery as follows.

Mature seed was surface sterilized by immersing in 80% (v/v) ethanol for 30 secs, rinsing twice with tap water, followed by washing in 20% DOMESTOS® (0.8% v/v available chlorine) on a gyratory shaker at 140 rpm for 20 mins. The DOMESTOS® was removed by decanting and the seeds were rinsed four times with sterile water. Excess water was removed by placing the seed on WHATMAN™ filter paper. The seeds were placed in a sterile PETRI™ dish on several sheets of dampened sterile WHATMAN™ filter paper and incubated for 24 h at 24° C. Following incubation, the seeds were surface sterilized a second time in 15% DOMESTOS® with 15 min shaking, followed by rinsing with sterile water as described previously. The seeds were placed on Murashige and Skoog (MS) solidified media for 24 hr at 24° C. Finally, the seeds were surface sterilized a third time in 10% DOMESTOS® with 10 min shaking, followed by rinsing in sterile water as previously described. The seeds were placed, crease side down, onto MS solidified media with 10 seeds per PETRI™ dish and germinated in the dark at 24° C. for 14-21 days.

About 2-3 grams of leaf material from the germinated seeds was cut into 2-3 cm lengths and placed in a pre-weighed PETRI™ dish. Leaf sheath and yellowing leaf material was discarded. Approximately 10 mL of leaf enzyme digest mix (0.6 M mannitol, 10 mM MES, 1.5% w/v cellulase R10, 0.3% w/v macerozyme, 1 mM $CaCl_2$, 0.1% bovine serum albumin, 0.025% v/v pluronic acid, 5 mM (3-mercaptoethanol, pH 5.7) was pipetted into the PETRI™ dish and the leaf material was chopped transversely into 1-2 mm segments using a sharp scalpel blade. The leaf material was chopped in the presence of the leaf digest mix to prevent cell damage resulting from the leaf material drying out. Additional leaf enzyme digest mix was added to the PETRI™ dish to a volume of 10 mL per gram fresh weight of leaf material and subject to vacuum (20" Hg) pressure for 30 min. The PETRI™ dish was sealed with PARAFILM® and incubated at 28° C. with gentle rotational shaking for 4-5 hours.

Mesophyll protoplasts released from the leaf segments into the enzyme digest mix were isolated from the plant debris by passing the digestion suspension through a 100 micron mesh and into a 50 mL collection tube. To maximize the yield of protoplasts, the digested leaf material was washed three times. Each wash was performed by adding 10 mL wash buffer (20 mM KCl, 4 mM MES, 0.6 M mannitol, pH 5.6) to the PETRI™ dish, swirling gently for 1 min, followed by passing of the wash buffer through the 100 micron sieve into the same 50 mL collection tube. Next, the filtered protoplast suspension was passed through a 70 micron sieve, followed by a 40 micron sieve. Next, 6 mL aliquots of the filtered protoplast suspension were transferred to 12 mL round bottomed centrifugation tubes with lids and centrifuged at 70 g and 12° C. for 10 min. Following centrifugation, the supernatant was removed and the protoplast pellets were each resuspended in 7 mL wash buffer. The protoplasts were pelleted a second time by centrifugation, as described above. The protoplasts were each resuspended in 1 mL wash buffer and pooled to two centrifugation tubes. The wash buffer volume was adjusted to a final volume of 7 mL in each tube before centrifugation was performed, as described above. Following removal of the supernatant, the protoplast pellets were resuspended in 1 mL wash buffer and pooled to a single tube. The yield of mesophyll protoplasts was estimated using a Neubauer haemocytometer. Evans Blue stain was used to determine the proportion of live cells recovered.

PEG-Mediated Transfection of Mesophyll Protoplasts

About $10^6$ mesophyll protoplasts were added to a 12 mL round bottomed tube and pelleted by centrifugation at 70 g before removing the supernatant. The protoplasts were gently resuspended in 600 μl wash buffer containing 70 μg of plasmid DNA. The plasmid DNA consisted of the Zinc Finger Nuclease constructs described above. Next, an equal volume of 40% PEG solution (40% w/v PEG 4,000, 0.8 M mannitol, 1M $Ca(NO_3)_2$, pH 5.6) was slowly added to the protoplast suspension with simultaneous mixing by gentle rotation of the tube. The protoplast suspension was allowed to incubate for 15 min at room temperature without any agitation.

An additional 6 mL volume of wash buffer was slowly added to the protoplast suspension in sequential aliquots of 1 mL, 2 mL and 3 mL. Simultaneous gentle mixing was used to maintain a homogenous suspension with each sequential aliquot. Half of the protoplast suspension was transferred to a second 12 mL round bottomed tube and an additional 3 mL volume of wash buffer was slowly added to each tube with simultaneous gentle mixing. The protoplasts were pelleted by centrifugation at 70 g for 10 min and the supernatant was removed. The protoplast pellets were each resuspended in 1 mL wash buffer before protoplasts from the paired round bottomed tubes were pooled to a single 12 mL tube. An additional 7 mL wash buffer was added to the pooled protoplasts before centrifugation as described above. The supernatant was completely removed and the protoplast pellet was resuspended in 2 mL Qiao's media (0.44% w/v MS plus vitamins, 3 mM MES, 0.0001% w/v 2,4-D, 0.6 M glucose, pH 5.7). The protoplast suspension was transferred to a sterile 3 cm PETRI™ dish and incubated in the dark for 24° C. for 72 h.

Genomic DNA Isolation from Mesophyll Protoplasts

Transfected protoplasts were transferred from the 3 cm PETRI™ dish to a 2 mL microfuge tube. The cells were pelleted by centrifugation at 70 g and the supernatant was removed. To maximize the recovery of transfected protoplasts, the PETRI™ dish was rinsed three times with 1 mL of wash buffer. Each rinse was performed by swirling the wash buffer in the PETRI™ dish for 1 min, followed by transfer of the liquid to the same 2 ml microfuge tube. At the end of each rinse, the cells were pelleted by centrifugation at 70 g and the supernatant was removed. The pelleted protoplasts were snap frozen in liquid nitrogen before freeze drying for 24 h in a LABCONCO FREEZONE 4.5® (Labconco, Kansas City, Mo.) at −40° C. and $133 \times 10^{-3}$ mBar pressure. The lyophilized cells were subjected to DNA extraction using the DNEASY® PLANT DNA EXTRACTION MINI kit (Qiagen) following the manufacturer's instructions, with the exception that tissue disruption was not required and the protoplast cells were added directly to the lysis buffer.

PCR Assay of Protoplast Genomic DNA for ZFN Sequence Cleavage

To enable the cleavage efficacy and target site specificity of ZFNs designed for the AHAS gene locus to be investigated, PCR primers were designed to amplify up to a 300-bp fragment within which one or more ZFN target sites were captured. One of the primers was designed to be within a 100-bp window of the captured ZFN target site(s). This design strategy enabled Illumina short read technology to be used to assess the integrity of the target ZFN site in the transfected protoplasts. In addition, the PCR primers were designed to amplify the three homoeologous copies of the AHAS gene and to capture nucleotide sequence variation that differentiated between the homoeologs such that the Illumina sequence reads could be unequivocally attributed to the wheat sub-genome from which they were derived.

A total of four sets of PCR primers were designed to amplify the ZFN target site loci (Table 4). Each primer set was synthesized with the Illumina SP1 and SP2 sequences at the 5' end of the forward and reverse primer, respectively, to provide compatibility with Illumina short read sequencing chemistry. The synthesized primers also contained a phosphorothioate linkage at the penultimate 5' and 3' nucleotides (indicated in Table 4 as an asterisk [*]). The 5' phosphorothioate linkage afforded protection against exonuclease degradation of the Illumina SP1 and SP2 sequences, while the 3' phosphorothioate linkage improved PCR specificity for amplification of the target AHAS sequences using on-off PCR (Yang et al., (2005)). All PCR primers were designed to be between 18 and 27 nucleotides in length and to have a melting temperature of 60 to 65° C., optimal 63° C.

In Table 4, nucleotides specific for the AHAS gene are indicated in uppercase type; nucleotides corresponding to the Illumina SP1 and SP2 sequences are indicated in lowercase type. Each primer set was empirically tested for amplification of the three homoeologous AHAS gene copies through Sanger-based sequencing of the PCR amplification products.

DNA molecules in the correct format for Illumina-based sequencing-by-synthesis technology. Each PCR assay was optimized to work on 200 ng starting DNA (about 12,500 cell equivalents of the *Triticum aestivum* genome). Multiple reactions were performed per transfected sample to ensure sufficient copies of the *Triticum aestivum* genome were assayed for reliable assessment of ZFN efficiency and target site specificity. About sixteen PCR assays, equivalent to 200,000 copies of the *Triticum aestivum* genome taken from individual protoplasts, were performed per transfected sample. A single PCR master-mix was prepared for each transfected sample. To ensure optimal PCR amplification of the ZFN target site (i.e. to prevent PCR reagents from becoming limiting and to ensure that PCR remained in the exponential amplification stage) an initial assay was performed using a quantitative PCR method to determine the optimal number of cycles to perform on the target tissue. The initial PCR was performed with the necessary negative control reactions on a MX3000P THERMOCYCLER™ (Stratagene). From the data output gathered from the quantitative PCR instrument, the relative increase in fluorescence was plotted from cycle-to-cycle and the cycle number was determined per assay that would deliver sufficient amplification, while not allowing the reaction to become reagent limited, in an attempt to reduce over-cycling and biased amplification of common molecules. The unused master mix remained on ice until the quantitative PCR analysis was concluded and the optimal cycle number determined. The remaining master mix was then aliquoted into the desired number of reaction tubes (about 16 per ZFN assay) and PCR

TABLE 4

Primer sequences used to assess AHAS ZFN cleavage efficacy and target site specificity

| Primer Name | AHAS Region | Primer Sequence (5'→3') | SEQ ID NO: |
|---|---|---|---|
| AHAS-500ZFN.F3 | 500-bp upstream of S653 | a*cactctttccctacacgacgctcttccgatctT CCTCTAGGATTCAAGACTTTT G*G | 167 |
| AHAS-500ZFN.R1 | 500-bp upstream of S653 | g*tgactggagttcagacgtgtgctcttccgatct CGTGGCCGCTTGTAAGTGTA*A | 168 |
| AHASs653ZFN.F1 | Within 30-bp upstream of S653 | a*cactctttccctacacgacgctcttccgatctG AGACCCCAGGGCCATACTT*G | 169 |
| AHASs653ZFN.R3 | Within 30-bp upstream of S653 | g*tgactggagttcagacgtgtgctcttccgatct CAAGCAAACTAGAAAACGCA TG*G | 170 |
| AHASs653ZFN.F5 | Within 80-bp downstream of S653N | a*cactctttccctacacgacgctcttccgatctA TGGAGGGTGATGGCAGGA*C | 171 |
| AHASs653ZFN.R1 | Within 80-bp downstream of S653N | g*tgactggagttcagacgtgtgctcttccgatct ATGACAGCACATCCCTACAAA AG*A | 172 |
| AHAS + 400ZFN.F1 | 400-bp downstream of S653 | a*cactctttccctacacgacgctcttccgatctA ACAGTGTGCTGGTTCCTTTCT*G | 173 |
| AHAS + 400ZFN.R3 | 400-bp downstream of S653 | g*tgactggagttcagacgtgtgctcttccgatct TYTYYCCTCCCAACTGTATTC AG*A | 174 | asterisk (*) is used to indicate a phosphorothioate

PCR amplification of ZFN target site loci from the genomic DNA extracted from transfected wheat mesophyll protoplasts was used to generate the requisite loci specific amplification was performed for the optimal cycle number. Following amplification, samples for the same ZFN target site were pooled together and 200 µl of pooled product per ZFN was purified using a QIAQUICK MINIELUTE PCR PURIFICATION KIT™ (Qiagen) following the manufacturer's instructions.

To enable the sample to be sequenced using Illumina short read technology, an additional round of PCR was performed to introduce the Illumina P5 and P7 sequences onto the amplified DNA fragments, as well as a sequence barcode index that could be used to unequivocally attribute sequence reads to the sample from which they originated. This was achieved using primers that were in part complementary to the SP1 and SP2 sequences added in the first round of amplification, but also contained the sample index and P5 and P7 sequences. The optimal number of PCR cycles required to add the additional sequences to the template without over-amplifying common fragments was determined by quantitative PCR cycle analysis, as described above. Following amplification, the generated product was purified using AMPURE MAGNETIC BEADS® (Beckman-Coulter) with a DNA-to-bead ratio of 1:1.7. The purified DNA fragment were titrated for sequencing by Illumina short read technology using a PCR-based library quantification kit (KAPA) according the manufacturer's instructions. The samples were prepared for sequencing using a cBot cluster generation kit (Illumina) and were sequenced on an ILLUMINA GAII$_X$™ or HISEQ2000™ instrument (Illumina) to generate 100-bp paired end sequence reads, according to the manufacturer's instructions.

Data Analysis for Detecting NHEJ at Target ZFN Sites

Following generation of Illumina short read sequence data for sample libraries prepared for transfected mesophyll protoplasts, bioinformatics analysis was performed to identify deleted nucleotides at the target ZFN sites. Such deletions are known to be indicators of in planta ZFN activity that result from non-homologous end joining (NHEJ) DNA repair.

To identify sequence reads with NHEJ deletions, the manufacturer's supplied scripts for processing sequence data generated on the HISEQ2000™ instrument (Illumina) was used to first computationally assign the short sequence reads to the protoplast sample from which they originated. Sample assignment was based on the barcode index sequence that was introduced during library preparation, as described previously. Correct sample assignment was assured as the 6-bp barcode indexes used to prepare the libraries were differentiated from each other by at least a two-step sequence difference.

Following sample assignment, a quality filter was passed across all sequences. The quality filter was implemented in custom developed PERL script. Sequence reads were excluded if there were more than three ambiguous bases, or if the median Phred score was less than 20, or if there were three or more consecutive bases with a Phred score less than 20, or if the sequence read was shorter than 40 nucleotides in length.

Next, the quality trimmed sequences were attributed to the wheat sub-genome from which they originated. This was achieved using a second custom developed PERL script in which sub-genome assignment was determined from the haplotype of the nucleotide sequence variants that were captured by the PCR primers used to amplify the three homoeologous copies of the AHAS gene, as described above.

Finally, the frequency of NHEJ deletions at the ZFN cleavage site in the sub-genome-assigned sequence reads was determined for each sample using a third custom developed PERL script and manual data manipulation in Microsoft Excel 2010 (Microsoft Corporation). This was achieved by counting the frequency of unique NHEJ deletions on each sub-genome within each sample.

Two approaches were used to assess the cleavage efficiency and specificity of the ZFNs tested. Cleavage efficiency was expressed (in parts per million reads) as the proportion of sub-genome assigned sequences that contained a NHEJ deletion at the ZFN target site. Rank ordering of the ZFNs by their observed cleavage efficiency was used to identify ZFNs with the best cleavage activity for each of the four target regions of the AHAS genes in a sub-genome-specific manner.

All of the ZFNs tested showed NHEJ deletion size distributions consistent with that expected for in planta ZFN activity. Cleavage specificity was expressed as the ratio of cleavage efficiencies observed across the three sub-genomes. The inclusion of biological replicates in the data analyses did not substantially affect the rank order for cleavage activity and specificity of the ZFNs tested.

From these results, the ZFNs encoded on plasmid pDAB109350 (i.e. ZFN 29732 and 29730) and pDAB109360 (i.e. ZFN 30012 and 30018) were selected for in planta targeting in subsequent experiments, given their characteristics of significant genomic DNA cleavage activity in each of the three wheat sub-genomes.

Evaluation of Donor Designs for ZFN-Mediated AHAS Gene Editing Using Transient Assays To investigate ZFN-mediated genomic editing at the endogenous AHAS gene locus in wheat, a series of experiments were undertaken to assess the effect of donor design on the efficiency of non-homologous end joining (NHEJ)-directed DNA repair. These experiments used transient assays to monitor the efficiency for ZFN-mediated addition of the previously described S653N mutation conferring tolerance to imidazolinone class herbicides (Li et al., (2008) Molecular Breeding 22:217-225) at the endogenous AHAS gene locus in wheat, or alternatively for ZFN-mediated introduction of an EcoRI restriction endonuclease sequence site at the double strand DNA break created in the endogenous AHAS genes by targeted ZFN cleavage.

Donor Designs for NHEJ-Directed DNA Repair

Two types of donor DNA designs were used for NHEJ-directed DNA repair.

The first type of donor design was a linear, double stranded DNA molecule comprising 41-bp of sequence that shared no homology with the endogenous AHAS genes in wheat. Two donor DNA molecules were designed, each to target the three homoeologous copies of the AHAS gene. Both donor DNA molecules had protruding 5' and 3' ends to provide ligation overhangs to facilitate ZFN-mediated NHEJ-directed DNA repair. The two donor DNA molecules differed by the sequence at their protruding 3' end. The first donor DNA molecule, pDAS000152 (SEQ ID NO:175 and SEQ ID NO:176), was designed to provide ligation overhangs that were compatible with those generated by cleavage of the endogenous AHAS genes by ZFNs 29732 and 29730 (encoded on plasmid pDAB109350) and to result in the insertion of the 41-bp donor molecule into the endogenous AHAS gene at the site of the double strand DNA break via NHEJ-directed DNA repair. The second donor DNA molecule pDAS000149 (SEQ ID NO:177 and SEQ ID NO:178) was designed to provide ligation overhangs that were compatible with those generated by the dual cleavage of the endogenous AHAS genes by ZFNs 29732 and 29730 (encoded on plasmid pDAB109350) and ZFNs 30012 and 30018 (encoded on plasmid pDAB109360) and to result in the replacement of the endogenous AHAS sequence contained between the two double strand DNA breaks created by the ZFNs with the 41-bp donor molecule via NHEJ-directed DNA repair.

Figure 13:
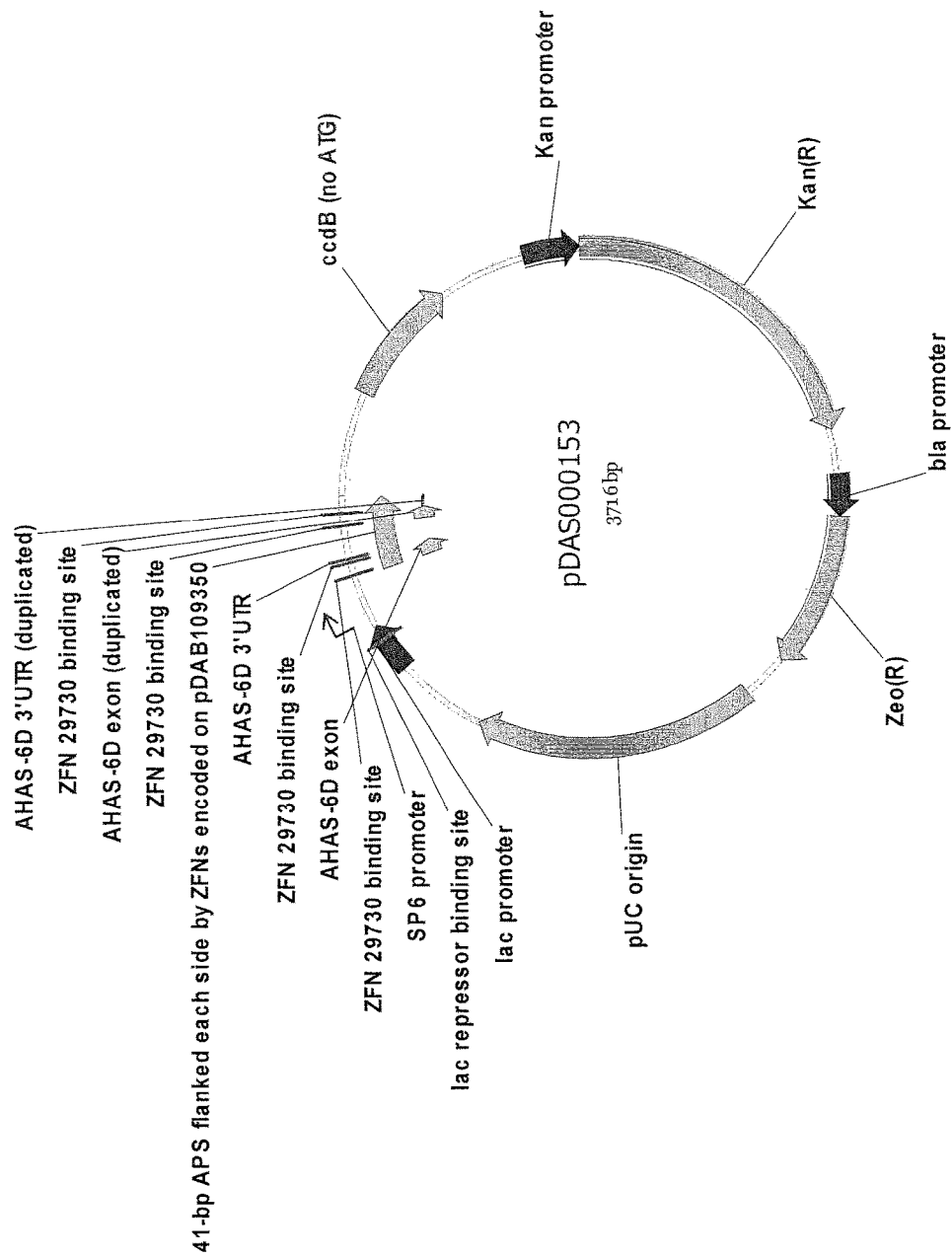
FIG. 13 shows a plasmid map of pDAS000153.
Figure 14:
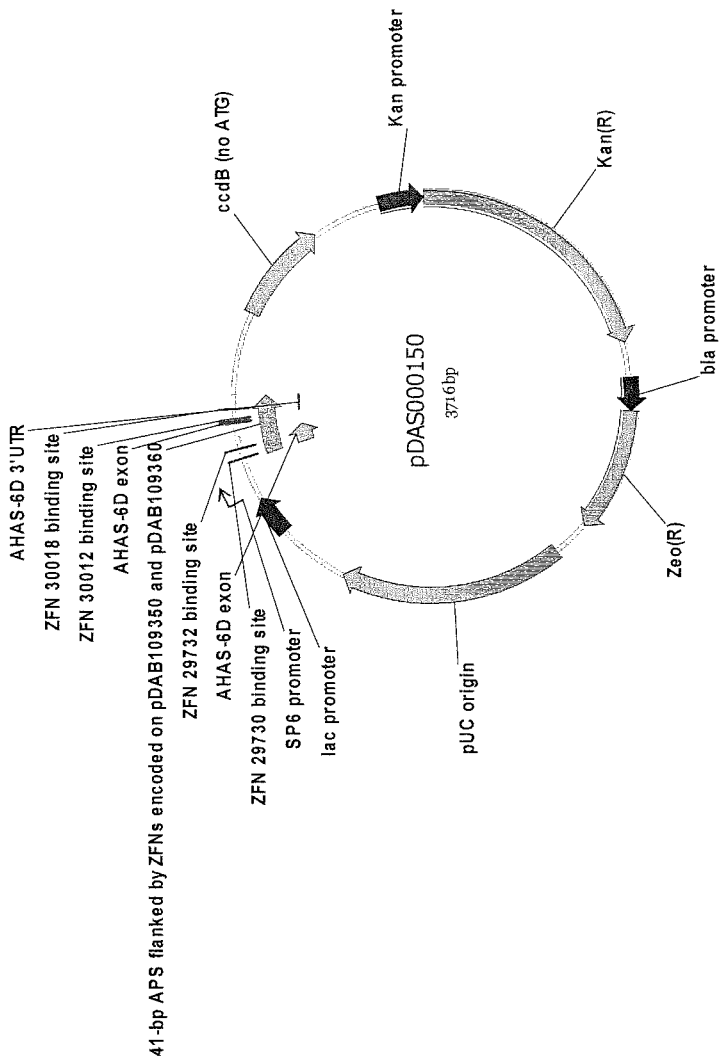
FIG. 14 shows a plasmid map of pDAS000150.

The second type of donor was a plasmid DNA vector containing 41-bp of sequence that shared no homology with the endogenous AHAS genes in wheat and that was flanked on either side by sequence that was recognized by the ZFN(s) used to create double strand DNA breaks in the endogenous AHAS genes. This donor design allowed in planta release of the unique 41-bp sequence from the plasmid DNA molecule by the same ZFN(s) used to cleave target sites in the endogenous AHAS genes, and simultaneous generation of protruding ends that were suitable for overhang ligation of the released 41-bp sequence into the endogenous AHAS genes via NHEJ-directed DNA repair. Two plasmid donor DNA molecules were designed, each to target the three homoeologous copies of the AHAS gene. The first plasmid donor molecule, pDAS000153 (SEQ ID NO:179 and SEQ ID NO:180) (FIG. 13), was designed to provide ligation overhangs on the released 41-bp DNA fragment that were compatible with those generated by cleavage of the endogenous AHAS genes by ZFNs 29732 and 29730 (encoded on plasmid pDAB109350). The second plasmid donor molecule, pDAS000150 (SEQ ID NO:181 and SEQ ID NO:182) (FIG. 14), was designed to provide ligation overhangs on the released 41-bp DNA fragment that were at one end compatible with those generated by ZFNs 29732 and 29730 (encoded on plasmid pDAB109350) and at the other end compatible with those generated by ZFNs 30012 and 30018 (encoded on plasmid pDAB109360). This design allowed the replacement of the endogenous AHAS sequence contained between the two double strand DNA breaks created by ZFNs 29732 and 29730 and ZFNs 30012 and 30018 with the 41-bp donor molecule sequence.

Synthesis of Donor DNA for NHEJ-Directed DNA Repair

Standard cloning methods commonly known by one skilled in the art were used to build the plasmid vectors. Before delivery to *Triticum aestivum*, plasmid DNA for each donor construct was prepared from cultures of *E. coli* using the PURE YIELD PLASMID MAXIPREP SYSTEM® (Promega Corporation, Madison, Wis.) or PLASMID MAXI KIT® (Qiagen, Valencia, Calif.) following the instructions of the suppliers.

Standard phosphoramidite chemistry was used to synthetically synthesize the double stranded DNA donor molecules (Integrated DNA Technologies, Coralville, Iowa). For each donor molecule, a pair of complementary single stranded DNA oligomers was synthesized, each with two phosphorothioate linkages at their 5' ends to provide protection against in planta endonuclease degradation. The single stranded DNA oligomers were purified by high performance liquid chromatography to enrich for full-length molecules and purified of chemical carryover from the synthesis steps using $Na^+$ exchange. The double stranded donor molecule was formed by annealing equimolar amounts of the two complementary single-stranded DNA oligomers using standard methods commonly known by one skilled in the art. Before delivery to *Triticum aestivum*, the double stranded DNA molecules were diluted to the required concentration in sterile water.

Isolation of Wheat Protoplasts Derived from Somatic Embryogenic Callus

Protoplasts derived from somatic embryogenic callus (SEC) from the donor wheat line cv. Bobwhite MPB26RH were prepared for transfection using polyethylene glycol (PEG)-mediated DNA delivery as follows:

Seedlings of the donor wheat line were grown in an environment controlled growth room maintained at 18/16° C. (day/night) and a 16/8 hour (day/night) photoperiod with lighting provided at 800 mmol $m^2$ per sec. Wheat spikes were collected at 12-14 days post-anthesis and were surface sterilized by soaking for 1 min in 70% (v/v) ethanol. The spikes were threshed and the immature seeds were sterilized for 15 min in 17% (v/v) bleach with gentle shaking, followed by rinsing at least three times with sterile distilled water. The embryos were aseptically isolated from the immature seeds under a dissecting microscope. The embryonic axis was removed using a sharp scalpel and discarded. The scutella were placed into a 9 cm PETRI™ dish containing 2-4 medium without TIMENTIN™, with the uncut scutellum oriented upwards. A total of 25 scutella were plated onto each 9 cm PETRI™ dish. Somatic embryogenic callus (SEC) formation was initiated by incubating in the dark at 24° C. for 3 weeks. After 3 weeks, SEC was separated from non-embryogenic callus, placed onto fresh 2-4 medium without TIMENTIN™ and incubated for a further 3 weeks in the dark at 24° C. Sub-culturing of SEC was repeated for a total of three times before being used for protoplast preparation.

About one gram of SEC was chopped into 1-2 mm pieces using a sharp scalpel blade in a 10 cm PETRI™ dish contained approximately 10 mL of wheat callus digest mix (2.5% w/v Cellulase RS, 0.2% w/v pectolyase Y23, 0.1% w/v DRISELASE®, 14 mM $CaCl_2$, 0.8 mM $MgSO_4$, 0.7 mM $KH_2PO_4$, 0.6 M Mannitol, pH 5.8) to prevent the callus from dehydrating. Additional callus digest mix was added to the PETRI™ dish to a volume of 10 mL per gram fresh weight of callus and subject to vacuum (20" Hg) pressure for 30 min. The PETRI™ dish was sealed with PARAFILM® and incubated at 28° C. with gentle rotational shaking at 30-40 rpm for 4-5 hours.

SEC protoplasts released from the callus were isolated by passing the digestion suspension through a 100 micron mesh and into a 50 mL collection tube. To maximize the yield of protoplasts, the digested callus material was washed three times. Each wash was performed by adding 10 mL SEC wash buffer (0.6 M Mannitol, 0.44% w/v MS, pH 5.8) to the PETRI™ dish, swirling gently for 1 min, followed by passing of the SEC wash buffer through the 100 micron sieve into the same 50 mL collection tube. Next, the filtered protoplast suspension was passed through a 70 micron sieve, followed by a 40 micron sieve. Next, 6 mL aliquots of the filtered protoplast suspension were transferred to 12 mL round bottomed centrifugation tubes with lids and centrifuged in at 70 g and 12° C. for 10 min. Following centrifugation, the supernatant was removed, leaving approximately 0.5 mL supernatant behind, and the protoplast pellets were each resuspended in 7 mL of 22% sucrose solution. The sucrose/protoplast mixture was carefully overlaid with 2 mL SEC wash buffer, ensuring that there was no mixing of the two solutions. The protoplasts were centrifuged a second time by centrifugation, as described above. The band of protoplasts visible between the SEC wash buffer and sucrose solution was collected using a pipette and placed into a clean 12 mL round bottom tube. Seven mL of SEC wash buffer was added to the protoplasts and the tubes were centrifuged, as described above. The supernatant was removed and the SEC protoplasts were combined to a single tube and resuspended in a final volume 1-2 mL of SEC wash buffer. The yield of SEC protoplasts was estimated using a Neubauer haemocytometer. Evans Blue stain was used to determine the proportion of live cells recovered.

PEG-Mediated Transfection of SEC Protoplasts

About two million SEC protoplasts were added to a 12 mL round bottomed tube and pelleted by centrifugation at 70 g before removing the supernatant. The protoplasts were gently resuspended in 480 µl SEC wash buffer containing 70 µg of DNA. The DNA consisted of the Zinc Finger Nuclease and donor DNA constructs described above, with each construct present at the molar ratio required for the experiment being undertaken. Next, 720 µl of 50% PEG solution (50% w/v PEG 4000, 0.8 M mannitol, 1M $Ca(NO_3)_2$, pH 5.6) was slowly added to the protoplast suspension with simultaneous mixing by gentle rotation of the tube. The protoplast suspension was allowed to incubate for 15 min at room temperature without any agitation.

An additional 7 mL volume of SEC wash buffer was slowly added to the protoplast suspension in sequential aliquots of 1 mL, 2 mL and 3 mL. Simultaneous gentle mixing was used to maintain a homogenous suspension with each sequential aliquot. Half of the protoplast suspension was transferred to a second 12 mL round bottomed tube and an additional 3 mL volume of SEC wash buffer was slowly added to each tube with simultaneous gentle mixing. The protoplasts were pelleted by centrifugation at 70 g for 10 min and the supernatant was removed. The protoplast pellets were each resuspended in 1 mL SEC wash buffer before protoplasts from the paired round bottomed tubes were pooled to a single 12 mL tube. An additional 7 mL SEC wash buffer was added to the pooled protoplasts before centrifugation as described above. The supernatant was completely removed and the protoplast pellet was resuspended in 2 mL Qiao's media. The protoplast suspension was transferred to a sterile 3 cm PETRI™ dish and incubated in the dark for 24° C. for 72 h.

Isolation of Scutella from Immature Zygotic Wheat Embryos

Scutella of immature zygotic wheat embryos from the donor wheat line cv. Bobwhite MPB26RH were prepared for transfection using biolistics-mediated DNA delivery as follows.

Seedlings of the donor wheat line were grown in an environment controlled growth room maintained at 18/16° C. (day/night) and a 16/8 hour (day/night) photoperiod with lighting provided at 800 mmol $m^2$ per sec. Wheat spikes were collected at 12-14 days post-anthesis and were surface sterilized by soaking for 1 min in 70% (v/v) ethanol. The spikes were threshed and the immature seeds were sterilized for 15 min in 17% (v/v) bleach with gentle shaking, followed by rinsing at least three times with sterile distilled water. The embryos were aseptically isolated from the immature seeds under a dissecting microscope. The embryonic axis was removed using a sharp scalpel and discarded. The scutella were placed into a 9 cm PETRI™ dish containing osmotic MS (E3 maltose) medium, with the uncut scutellum oriented upwards. A total of 20 scutella were plated onto each 9 cm PETRI™ dish. The prepared embryos were pre-cultured in the dark at 26° C. for a minimum of 4 h before transfection using biolistics-mediated DNA delivery.

Transfection of Scutella of Immature Zygotic Wheat Embryos by Biolistic-Mediated DNA Delivery Gold particles for biolistic-mediated DNA delivery were prepared by adding 40 mg of 0.6 micron colloidal gold particles (BioRad) to 1 mL of sterile water in a 1.5 mL microtube. The gold particles were resuspended by vortexing for 5 min. To prepare sufficient material for 10 bombardments, a 50 µL aliquot of the gold particle suspension was transferred to a 1.5 mL microtube containing 5 µg of DNA resuspended in 5 µL of sterile water. Following thorough mixing by vortexing, 50 µL of 2.5 M $CaCl_2$ and 20 µL of 0.1 M spermidine were added to the microtube, with thorough mixing after the addition of each reagent. The DNA-coated gold particles were pelleted by centrifugation for 1 min at maximum speed in a bench top microfuge. The supernatant was removed and 1 mL of 100% ethanol was added to wash and resuspend the gold particles. The gold particles were pelleted by centrifugation, as described above, and the supernatant discarded. The DNA-coated gold particles were resuspended in 110 µL of 100% ethanol and maintained on ice. Following a brief vortex, 10 µL of the gold particle solution was placed centrally onto a macrocarrier membrane and allowed to air dry.

The PDS-1000/HE PARTICLE GUN DELIVERY SYSTEM™ (BioRad) was used to transfect the scutella of immature zygotic wheat embryos by biolistic-mediated DNA delivery. Delivery of the DNA-coated gold particles was performed using the following settings: gap 2.5 cm, stopping plate aperture 0.8 cm, target distance 6.0 cm, vacuum 91.4-94.8 kPa, vacuum flow rate 5.0 and vent flow rate 4.5. The scutella of immature zygotic wheat embryos were bombarded using a 900 psi rupture disc. Each PETRI™ dish containing 20 scutella was bombarded once. The bombarded scutella were incubated at 26° C. in the dark for 16 h before being transferred onto medium for callus induction. The scutella were cultured on callus induction medium in the dark at 26° C. for 7d.

Genomic DNA Isolation from SEC Protoplasts

Genomic DNA was extracted from SEC protoplasts using the procedure previously described for mesophyll protoplasts. An additional purification step was performed to reduce the presence of the donor DNA used for transfection. This was achieved using gel electrophoresis to separate the genomic DNA from the SEC protoplasts from the donor DNA used for transfection. The extracted DNA was electrophoresed for 3 h in a 0.5% agarose gel using 0.5×TBE. The DNA was visualized by SYBR® SAFE staining and the band corresponding to genomic DNA from the SEC protoplasts was excised. The genomic DNA was purified from the agarose gel using a QIAQUICK DNA PURIFICATION KIT™ (Qiagen), following the manufacturer's instructions, except that the QIAQUICK™ DNA purification column was replaced with a DNA binding column from the DNEASY PLANT DNA EXTRACTION MINI KIT™ (Qiagen).

Genomic DNA Isolation from Scutella of Immature Zygotic Embryos

The 20 scutella of immature zygotic wheat embryos transfected for each biolistic-mediated DNA delivery were transferred to a 15 ml tube and snap frozen in liquid nitrogen before freeze drying for 24 h in a LABCONCO FREEZONE 4.5® (Labconco, Kansas City, Mo.) at −40° C. and $133 \times 10^{-3}$ mBar pressure. The lyophilized calli were subjected to DNA extraction using the DNEASY® PLANT DNA EXTRACTION MAXI™ KIT (Qiagen) following the manufacturer's instructions.

An additional purification step was performed to reduce the presence of the donor DNA used for transfection. This was achieved using gel electrophoresis to separate the genomic DNA from the calli from the donor DNA used for transfection. The extracted DNA was electrophoresed for 3 h in a 0.5% agarose gel using 0.5×TBE. The DNA was visualized by SYBR® SAFE staining and the band corresponding to genomic DNA from the calli was excised. The genomic DNA was purified from the agarose gel using a QIAQUICK™ DNA PURIFICATION kit (Qiagen), following the manufacturer's instructions, except that the QIA- QUICK™ DNA purification column was replaced with a DNA binding column from the DNEASY® PLANT DNA EXTRACTION MAXI™ KIT (Qiagen).

PCR Assay of Genomic DNA for ZFN-Mediated AHAS Editing

To investigate ZFN-mediated genomic editing at the endogenous AHAS genes in wheat using NHEJ-directed DNA repair, and assess the effect of donor DNA design on the efficacy of each DNA repair pathway, PCR assays were used to amplify the target AHAS regions from genomic DNA of transfected wheat cells. PCR assays were performed as described previously to generate requisite loci specific DNA molecules in the correct format for Illumina-based sequencing-by-synthesis technology. Each assay was performed using the previously described primer pair (SEQ ID NO: 160 and SEQ ID NO: 170) that were designed to amplify the region targeted by ZFNs 29732 and 29730 (encoded on plasmid pDAB109350) and ZFNs 30012 and 30018 (encoded on plasmid pDAB109360) for each of the three homoeologous copies of the AHAS genes. Multiple reactions were performed per transfected sample to ensure that sufficient copies of the *Triticum aestivum* genome were assayed for reliable assessment of ZFN-mediated gene editing. For transfected SEC protoplasts, up to sixteen PCR assays, equivalent to 200,000 copies of the *Triticum aestivum* genome taken from individual protoplasts, were performed per transfected sample. For transfected scutella of immature zygotic embryos, about forty eight (48) PCR assays, equivalent to 600,000 copies of the *Triticum aestivum* genome taken from individual protoplasts, were performed per transfected sample. Each transfected sample was prepared for sequencing using a CBOT CLUSTER GENERATION KIT™ (Illumina) and was sequenced on an ILLUMINA GAII$_X$™ or HISEQ2000™ instrument (Illumina) to generate 100-bp paired end sequence reads, as described previously.

Data Analysis for Detecting ZFN-Mediated NHEJ-Directed Editing at AHAS Genes

Following generation of Illumina short read sequence data for sample libraries prepared for transfected SEC protoplasts and scutella of immature zygotic wheat embryos, analyses were performed to identify molecular evidence for ZFN-mediated NHEJ-directed editing at the target ZFN sites.

To identify sequence reads with molecular evidence for NHEJ-directed gene editing, the short sequence reads were first computationally processed, as previously described, to assign each read to the sample and sub-genome from which they originated, and to perform quality filtering to ensure that only high quality sequences were used for subsequent analyses. Next, custom developed PERL scripts and manual data manipulation in Microsoft Excel 2010 (Microsoft Corporation) was used to identify reads that contained sequence for both the donor DNA molecule used for transfection and the endogenous AHAS locus. The editing frequency (expressed in parts per million reads) was calculated as the proportion of sub-genome-assigned sequence reads that showed evidence for ZFN-mediated NHEJ-directed gene editing.

From the results of three biological replicates performed for each linear double stranded DNA donor design, molecular evidence was obtained for the enrichment of sequence reads showing ZFN-mediated NHEJ-directed editing at the three homoeologous copies of the endogenous AHAS genes in wheat (Table 7 and Table 8). Strong molecular evidence was obtained for the integration of the linear, double-stranded 41-bp donor molecule at the position of the double strand DNA break created by cleavage of the homoeologous copies of the AHAS gene by ZFNs 29732 and 29730 in samples of both SEC protoplasts and scutella of immature zygotic embryos that were transfected with pDAB109350 and pDAS000152. Similar editing efficiency was observed across the three wheat sub-genomes in these samples. In contrast, samples of SEC protoplasts and scutella of immature zygotic embryos transfected with pDAB109350 and pDAS000153 showed poor evidence for ZFN-mediated NHEJ-directed gene editing, presumably due to the prerequisite requirement for in planta release of the 41-bp donor sequence from the plasmid backbone. Molecular evidence for the replacement of endogenous AHAS sequence with the 41-bp donor molecule was observed in both SEC protoplasts and scutella of immature zygotic embryos that were transfected with pDAB109350, pDAB109360 and pDAS000149. However, the frequency of editing was significantly lower than that observed for transfections performed using pDAB109350 and pDAS000152, presumably due to the requirement for dual ZFN cleavage of the endogenous AHAS sequence. Limited evidence was obtained for the replacement of endogenous AHAS sequence with the 41-bp donor molecule that required in planta release from plasmid backbone in samples of SEC protoplast and scutella of immature zygotic embryos that were transfected with pDAB109350, pDAB109360 and pDAS000150.

TABLE 7

Average NHEJ editing frequency in parts per million (ppm) across three biological replicates of scutella transfected with linear double-stranded donor DNA designs. "na" indicates "not applicable."

| Donor | ZFN | Donor-to-ZFN molar ratio | Editing Frequency in Wheat Sub-Genome | Editing Frequency (ppm) |
|---|---|---|---|---|
| pDAS000152 | n/a | n/a | A | 0 |
| pDAS000152 | 29732-2A-29730 | 5:1 | A | 0 |
| pDAS000152 | 29732-2A-29730 | 10:1 | A | 131 |
| pDAS000152 | n/a | n/a | B | 0 |
| pDAS000152 | 29732-2A-29730 | 5:1 | B | 0 |
| pDAS000152 | 29732-2A-29730 | 10:1 | B | 47 |
| pDAS000152 | n/a | n/a | D | 0 |
| pDAS000152 | 29732-2A-29730 | 5:1 | D | 0 |
| pDAS000152 | 29732-2A-29730 | 10:1 | D | 75 |
| pDAS000153 | n/a | n/a | A | 0 |
| pDAS000153 | 29732-2A-29730 | 5:1 | A | 4 |
| pDAS000153 | 29732-2A-29730 | 10:1 | A | 0 |
| pDAS000153 | n/a | n/a | B | 0 |
| pDAS000153 | 29732-2A-29730 | 5:1 | B | 0 |
| pDAS000153 | 29732-2A-29730 | 10:1 | B | 0 |
| pDAS000153 | n/a | n/a | D | 0 |
| pDAS000153 | 29732-2A-29730 | 5:1 | D | 0 |
| pDAS000153 | 29732-2A-29730 | 10:1 | D | 0 |
| pDAS000149 | n/a | n/a | A | 0 |
| pDAS000149 | 29732-2A-29730 | 5:1 | A | 23 |
| pDAS000149 | 29732-2A-29730 | 10:1 | A | 9 |
| pDAS000149 | n/a | n/a | B | 0 |
| pDAS000149 | 29732-2A-29730 | 5:1 | B | 7 |

TABLE 7-continued

Average NHEJ editing frequency in parts per million (ppm) across three biological replicates of scutella transfected with linear double-stranded donor DNA designs. "na" indicates "not applicable."

| Donor | ZFN | Donor-to-ZFN molar ratio | Editing Frequency in Wheat Sub-Genome | Editing Frequency (ppm) |
|---|---|---|---|---|
| pDAS000149 | 29732-2A-29730 | 10:1 | B | 3 |
| pDAS000149 | n/a | n/a | D | 0 |
| pDAS000149 | 29732-2A-29730 | 5:1 | D | 7 |
| pDAS000149 | 29732-2A-29730 | 10:1 | D | 0 |
| pDAS000150 | n/a | n/a | A | 0 |
| pDAS000150 | 29732-2A-29730 | 5:1 | A | 1 |
| pDAS000150 | 29732-2A-29730 | 10:1 | A | 0 |
| pDAS000150 | n/a | n/a | B | 0 |
| pDAS000150 | 29732-2A-29730 | 5:1 | B | 0 |
| pDAS000150 | 29732-2A-29730 | 10:1 | B | 0 |
| pDAS000150 | n/a | n/a | D | 0 |
| pDAS000150 | 29732-2A-29730 | 5:1 | D | 4 |
| pDAS000150 | 29732-2A-29730 | 10:1 | D | 0 |

TABLE 8

Average NHEJ editing frequency in parts per million (ppm) across three biological replicates of SEC protoplast transfected with linear double-stranded donor DNA designs. "na" indicates "not applicable."

| Donor | ZFN | Donor-to-ZFN molar ratio | Editing Frequency in Wheat Sub-Genome | Editing Frequency (ppm) |
|---|---|---|---|---|
| pDAS000152 | n/a | n/a | A | 0 |
| pDAS000152 | 29732-2A-29730 | 5:1 | A | 0 |
| pDAS000152 | 29732-2A-29730 | 10:1 | A | 6717 |
| pDAS000152 | 29732-2A-29730 | 20:1 | A | 5404 |
| pDAS000152 | n/a | n/a | B | 0 |
| pDAS000152 | 29732-2A-29730 | 5:1 | B | 0 |
| pDAS000152 | 29732-2A-29730 | 10:1 | B | 6306 |
| pDAS000152 | 29732-2A-29730 | 20:1 | B | 4106 |
| pDAS000152 | n/a | n/a | D | 0 |
| pDAS000152 | 29732-2A-29730 | 5:1 | D | 0 |
| pDAS000152 | 29732-2A-29730 | 10:1 | D | 7911 |
| pDAS000152 | 29732-2A-29730 | 20:1 | D | 4059 |
| pDAS000153 | n/a | n/a | A | 0 |
| pDAS000153 | 29732-2A-29730 | 5:1 | A | 0 |
| pDAS000153 | 29732-2A-29730 | 10:1 | A | 0 |
| pDAS000153 | 29732-2A-29730 | 20:1 | A | 0 |
| pDAS000153 | n/a | n/a | B | 0 |
| pDAS000153 | 29732-2A-29730 | 5:1 | B | 0 |
| pDAS000153 | 29732-2A-29730 | 10:1 | B | 0 |
| pDAS000153 | 29732-2A-29730 | 20:1 | B | 0 |
| pDAS000153 | n/a | n/a | D | 0 |
| pDAS000153 | 29732-2A-29730 | 5:1 | D | 0 |
| pDAS000153 | 29732-2A-29730 | 10:1 | D | 0 |
| pDAS000153 | 29732-2A-29730 | 20:1 | D | 0 |
| pDAS000149 | n/a | n/a | A | 0 |
| pDAS000149 | 29732-2A-29730 | 5:1 | A | 0 |
| pDAS000149 | 29732-2A-29730 | 10:1 | A | 0 |
| pDAS000149 | 29732-2A-29730 | 20:1 | A | 344 |
| pDAS000149 | n/a | n/a | B | 0 |
| pDAS000149 | 29732-2A-29730 | 5:1 | B | 0 |
| pDAS000149 | 29732-2A-29730 | 10:1 | B | 0 |
| pDAS000149 | 29732-2A-29730 | 20:1 | B | 210 |
| pDAS000149 | n/a | n/a | D | 0 |
| pDAS000149 | 29732-2A-29730 | 5:1 | D | 4 |
| pDAS000149 | 29732-2A-29730 | 10:1 | D | 0 |
| pDAS000149 | 29732-2A-29730 | 20:1 | D | 24 |
| pDAS000150 | n/a | n/a | A | 0 |
| pDAS000150 | 29732-2A-29730 | 5:1 | A | 0 |
| pDAS000150 | 29732-2A-29730 | 10:1 | A | 0 |
| pDAS000150 | 29732-2A-29730 | 20:1 | A | 0 |
| pDAS000150 | n/a | n/a | B | 0 |
| pDAS000150 | 29732-2A-29730 | 5:1 | B | 0 |
| pDAS000150 | 29732-2A-29730 | 10:1 | B | 0 |
| pDAS000150 | 29732-2A-29730 | 20:1 | B | 0 |
| pDAS000150 | n/a | n/a | D | 0 |
| pDAS000150 | 29732-2A-29730 | 5:1 | D | 0 |
| pDAS000150 | 29732-2A-29730 | 10:1 | D | 0 |
| pDAS000150 | 29732-2A-29730 | 20:1 | D | 0 |

Collectively, the results provide strong molecular evidence for precise ZFN-mediated NHEJ-directed editing at the endogenous AHAS gene locus in wheat. These results show that all three sub-genomes can be targeted with a single ZFN and donor. The results clearly demonstrate a higher frequency of editing for linear donor DNA designs as compared to plasmid donor DNA designs. Presumably, these results are due to the prerequisite requirement for in planta linearization of the plasmid donor molecules before they can participate in NHEJ-directed DNA repair. The results also indicate that sub-genome-specific mediated NHEJ-directed gene editing is facilitated by a double strand break. The ZFNs that were designed to induce the double strand DNA breaks resulted in a sub-genome-specific mediated NHEJ-directed gene editing when delivered with the donor DNA to the *Triticum aestivum* plant cells.

Development of a Transformation System for Producing AHAS Edited Plants

The endogenous AHAS gene locus in wheat was selected as a model locus to develop a transformation system for generating plants with precise genome modifications induced by ZFN-mediated gene editing. The endogenous AHAS gene was selected as a model locus due to its ability to produce a selectable phenotype (i.e., tolerance to group B herbicides—ALS inhibitors), knowledge of prerequisite information of sub-genome-specific gene coding sequence, and knowledge of specific mutations conferring tolerance to group B herbicides from the characterization of wheat with chemically induced mutations in the AHAS genes. The S653N mutation conferring tolerance to imidazolinone class herbicide was chosen as a target for ZFN-mediated gene editing due to the availability of commercially released wheat varieties carrying the S653N mutation that could be used as positive controls to develop a chemical selection system to enrich for precisely edited events.

Molecular Characterization of *Triticum aestivum* cv. Clearfield Janz

*Triticum aestivum* cv. Clearfield Janz, a commercially released bread wheat variety carrying the S653N mutation in the D-genome, was selected for use as a positive control to develop a chemical selection strategy to enrich for AHAS edited wheat plants produced by ZFN-mediated gene editing. To generate a pure genetic seed stock, 48 seedlings were screened with 96 microsatellite (SSR) markers using Multiplex-Ready PCR technology (Hayden et al., (2008) BMC Genomics 9; 80). Seedlings with identical SSR haplotypes were used to produce seed that was used in subsequent experiments.

To ensure that the wheat plants used to produce seed carried the S653N mutation, a PCR assay was developed to amplify the region of the AHAS gene carrying the mutation from the D-genome of wheat. Sub-genome-specific amplification was achieved using on-off PCR (Yang et al., (2005) Biochemical and Biophysical Research Communications 328:265-72) with primers AHAS-PS-6DF2 and AHAS-PS-6DR2 (SEQ ID NO:183 and SEQ ID NO:184) designed to position the penultimate base (which contained a phosphorothioate linkage) over nucleotide sequence variation that distinguished between the homoeologous copies of the AHAS genes. The PCR primers were designed to be between 18 and 27 nucleotides in length and to have a melting temperature of 60 to 65° C., optimal 63° C. The amplified PCR products were purified using a QIAQUICK MINIELUTE PCR PURIFICATION KIT™ (Qiagen) and sequenced using a direct Sanger sequencing method. The sequencing products were purified with ethanol, sodium acetate and EDTA following the BIGDYE® v3.1 protocol (Applied Biosystems) and electrophoresis was performed on an ABI3730XL® automated capillary electrophoresis platform.

Analysis of the amplified AHAS gene sequences using SEQUENCHER v3.7™ (GeneCodes, Ann Arbor, Mich.) revealed segregation for the S653N mutation and enabled the identification of plants that were homozygous (N653/N653) and heterozygous (N653/S653) for the S653N mutation or homozygous (S653/S653) for the herbicide-susceptible allele. The harvest of seed from individual plants provided a seed source having different levels of zygosity for the S653N mutation in the cv. Clearfield Janz genetic background.

Optimization of Chemical Selection Conditions Based on IMAZAMOX™

A series of experiments were performed to determine optimal selection conditions for regenerating AHAS edited wheat plants. These experiments were based on testing the basal tolerance to IMAZAMOX™ of the donor wheat line cv. Bobwhite MPB26RH(S653/S653 genotype) at the callus induction, plant regeneration and rooting stages of an established wheat transformation system. Similar experiments were performed to determine the basal tolerance and resistance of cv. Clearfield Janz genotypes carrying the different doses of the S653N mutation; i.e., plants with N653/N653 and S653/S653 genotypes.

The basal tolerance of the donor wheat line cv. Bobwhite MPB26RH and basal resistance of cv. Clearfield Janz (N653/N653) genotype to IMAZAMOX® at the callus induction stage was determined as follows: Scutella of immature zygotic embryos from each wheat line were isolated as described previously and placed in 10 cm PETRI™ dishes containing CIM medium supplemented with 0, 50, 100, 200, 300, 400 and 500 nM IMAZAMOX® respectively. Twenty scutella were placed in each PETRI™ dish. A total of 60 scutella from each of the donor wheat line cv. Bobwhite MPB26RH and cv. Clearfield Janz genotype were tested for basal tolerance and basal resistance response, respectively, at each IMAZAMOX® concentration. After incubation at 24° C. in the dark for 4 weeks, the amount of somatic embryogenic callus formation (SEC) at each IMAZAMOX® concentration was recorded. The results showed that SEC formation for cv. Bobwhite MPB26RH was reduced by about 70% at 100 nM IMAZAMOX®, compared to untreated samples. Callus formation for the cv. Clearfield Janz genotype was unaffected, relative to the untreated control, at any IMAZAMOX® concentrations tested.

The basal tolerance of the donor wheat line cv. Bobwhite MPB26RH to IMAZAMOX® at the plant regeneration stage was determined as follows: Scutella of immature zygotic embryos from the donor wheat line were isolated as described previously and placed in 10 cm PETRI™ dishes containing CIM medium. Somatic embryogenic callus was allowed to form by incubating at 24° C. in the dark for 4 weeks. The SEC was transferred to 10 cm PETRI™ dishes containing DRM medium supplemented with 0, 100, 200, 300, 400, 500 and 1000 nM IMAZAMOX® respectively. Twenty CIM were placed in each PETRI™ dish. A total of 60 CIM were tested for basal tolerance response at each IMAZAMOX® concentration. After incubation for 2 weeks at 24° C. under a 16/8 (light/dark) hour photoperiod in a growth room, the regeneration response was recorded. The results showed that plant regeneration was reduced by about 80% at 200 nM IMAZAMOX®, compared to untreated samples.

The basal tolerance of the cv. Clearfield Janz (S653/S653) genotype and basal resistance of the cv. Clearfield Janz (N653/N653) genotype to IMAZAMOX® at the plant regeneration stage was determined using a modified approach, as cv. Clearfield Janz was observed to have poor plant regeneration response (i.e., poor embryogenesis) in tissue culture. Seed for each cv. Clearfield Janz genotype was germinated using the aseptic approach described above for producing wheat mesophyll protoplasts. The germinated seedlings were multiplied in vitro by sub-culturing on multiplication medium. Following multiplication, plants for each genotype were transferred to 10 cm PETRI™ dishes containing plant growth medium (MS+10 µM BA+0.8% agar) supplemented with 0, 100, 300, 600, 900, 1200, 1500 and 3000 nM IMAZAMOX®, respectively. Ten plants were placed in each PETRI™ dish. A total of 30 plants per genotype were tested for basal response at each IMAZAMOX® concentration. After incubation for 3 weeks at 24° C. under a 16/8 (light/dark) hour photoperiod in a growth room, the growth response was recorded. The results showed that plant growth for the cv. Clearfield Janz (S653/S653) genotype was severely reduced in medium containing at least 200 nM IMAZAMOX®, compared to untreated samples. This response was similar to that observed for the cv. Bobwhite MPB26RH(S653/S653) genotype. In contrast, plant growth for the cv. Clearfield Janz (N653/N653) genotype was not strongly suppressed, relative to untreated samples, until the IMAZAMOX® concentration exceeded 2,000 nM.

The basal tolerance of the donor wheat line cv. Bobwhite MPB26RH to IMAZAMOX® at the plant rooting stage was determined as follows: Scutella of immature zygotic embryos from the donor wheat line were isolated as described previously and placed in 10 cm PETRI™ dishes containing CIM medium. Somatic embryogenic callus was allowed to form by incubating at 24° C. in the dark for 4 weeks. The SEC was transferred to 10 cm PETRI™ dishes containing DRM medium and incubated for 2 weeks at 24° C. under a 16/8 (light/dark) hour photoperiod to allow plant regeneration to take place. Regenerated plants were transferred to 10 cm PETRI™ dishes containing RM medium supplemented with 0, 100, 200, 300, 400, 500 nM IMAZAMOX®, respectively. Twenty regenerated plants were placed in each PETRI™ dish. A total of 60 regenerated plants were tested for basal tolerance response at each IMAZAMOX® concentration. After incubation for 3 weeks at 24° C. under a 16/8 (light/dark) hour photoperiod in a growth room, the root formation response was recorded. The results showed that root formation was severely restricted at all concentrations of IMAZAMOX® tested, compared to untreated samples.

The basal tolerance of the cv. Clearfield Janz (S653/S653) genotype and basal resistance of the cv. Clearfield Janz (N653/N653) genotype to IMAZAMOX® at the plant rooting stage was determined using a modified approach, as cv. Clearfield Janz was observed to have poor plant regeneration response (i.e., poor embryogenesis) in tissue culture. Seed for each cv. Clearfield Janz genotype was germinated using the aseptic approach described above for producing wheat mesophyll protoplasts. The germinated seedlings were multiplied in vitro by sub-culturing on multiplication medium. Following multiplication, plants for each genotype were transferred to 10 cm PETRI™ dishes containing plant rooting medium (½ MS, 0.5 mg/L NAA, 0.8% agar) supplemented with 0, 50, 100, 200 and 250 nM IMAZAMOX®, respectively. Three plants were placed in each PETRI™ dish. A total of 6 plants per genotype were tested for basal response at each IMAZAMOX® concentration. After incubation for 2 weeks at 24° C. under a 16/8 (light/dark) hour photoperiod in a growth room, the root formation response was recorded.

The results showed that root formation for the cv. Clearfield Janz (N653/N653) genotype was restricted, compared to untreated samples, at 250 nM IMAZAMOX®. Root formation was severely restricted in the cv. Clearfield Janz (S653/S653) genotype at all concentrations of IMAZAMOX® tested, compared to untreated samples.

Design and Synthesis of Donor DNA for ZFN-Mediated AHAS Gene Editing

Donor DNA molecules were designed to promote precise ZFN-mediated NHEJ-directed gene editing at the endogenous AHAS genes in wheat. The donor designs allowed for the introduction of the S653N mutation known to confer tolerance to imidazolinone class herbicides (Li et al., (2008) Molecular Breeding 22:217-225).

The first design was based on the integration of a 95-bp double stranded donor molecule at the position of the double strand DNA break created by cleavage of a homoeologous copy of the endogenous AHAS gene by ZFNs 29732 and 29730 (encoded on plasmid pDAB109350). The donor DNA molecule, pDAS000267 (SEQ ID NO:423 and SEQ ID NO:424), comprised two portions of the integrating donor polynucleotide. The 5' end contained sequence near identical to the endogenous AHAS gene encoded in the D-genome, starting from the target ZFN cleavage site and finishing at the AHAS stop codon. Six intentional mutations were introduced into this sequence: two mutations encoded the S653N mutation (AGC→AAT), and four mutations were synonymous (in which a silent mutation was incorporated into the donor sequence). The 3' end of the donor molecule contained a unique sequence that could be used for diagnostic PCR to detect ZFN-mediated NHEJ-directed gene editing events. The donor molecule was designed with protruding 5' and 3' ends to provide ligation overhangs to facilitate ZFN-mediated NHEJ-directed DNA repair.

The second design was based on replacement of the endogenous AHAS sequence located between a pair of ZFN target sites with a 79-bp double stranded donor molecule. Specifically, the donor was designed to replace the endogenous AHAS sequence released from chromatin upon dual cleavage of a homoeologous copy of the AHAS gene by ZFNs 29732 and 29730 (encoded on plasmid pDAB109350) and ZFNs 30012 and 30018 (encoded on plasmid pDAB109360). The donor molecule, pDAS000268 (SEQ ID NO:425 and SEQ ID NO:426), comprised sequence near identical to the endogenous AHAS gene encoded in the D-genome, starting from the cleavage site for ZFNs 29732 and 29730, and finishing at the cleavage site for ZFNs 30012 and 30018. Ten deliberate mutations were introduced into this sequence. Six mutations were located at the 5' end of the donor: two mutations encoded the S653N mutation (AGC→AAT) and four mutations were synonymous. Four mutations were located at the 3' end of the donor and were located in non-coding sequence. The donor molecule was designed with protruding 5' and 3' ends to provide ligation overhangs to facilitate ZFN-mediated NHEJ-directed DNA repair.

Standard phosphoramidite chemistry was used to synthetically synthesize the double stranded DNA donor molecules (Integrated DNA Technologies). For each donor molecule, a pair of complementary single stranded DNA oligomers was synthesized, each with two phosphorothioate linkages at their 5' ends to provide protection against in planta endonuclease degradation. The single stranded DNA oligomers were purified by high performance liquid chromatography to enrich for full-length molecules and purified of chemical carryover from the synthesis steps using $Na^+$ exchange. The double stranded donor molecule was formed by annealing equimolar amounts of the two complementary single-stranded DNA oligomers using standard methods commonly known by one skilled in the art. Before delivery to *Triticum aestivum*, the double stranded DNA molecules were diluted to the required concentration in sterile water.

Design and Production of Binary Vector Encoding AHAS (S653N)

Figure 15:
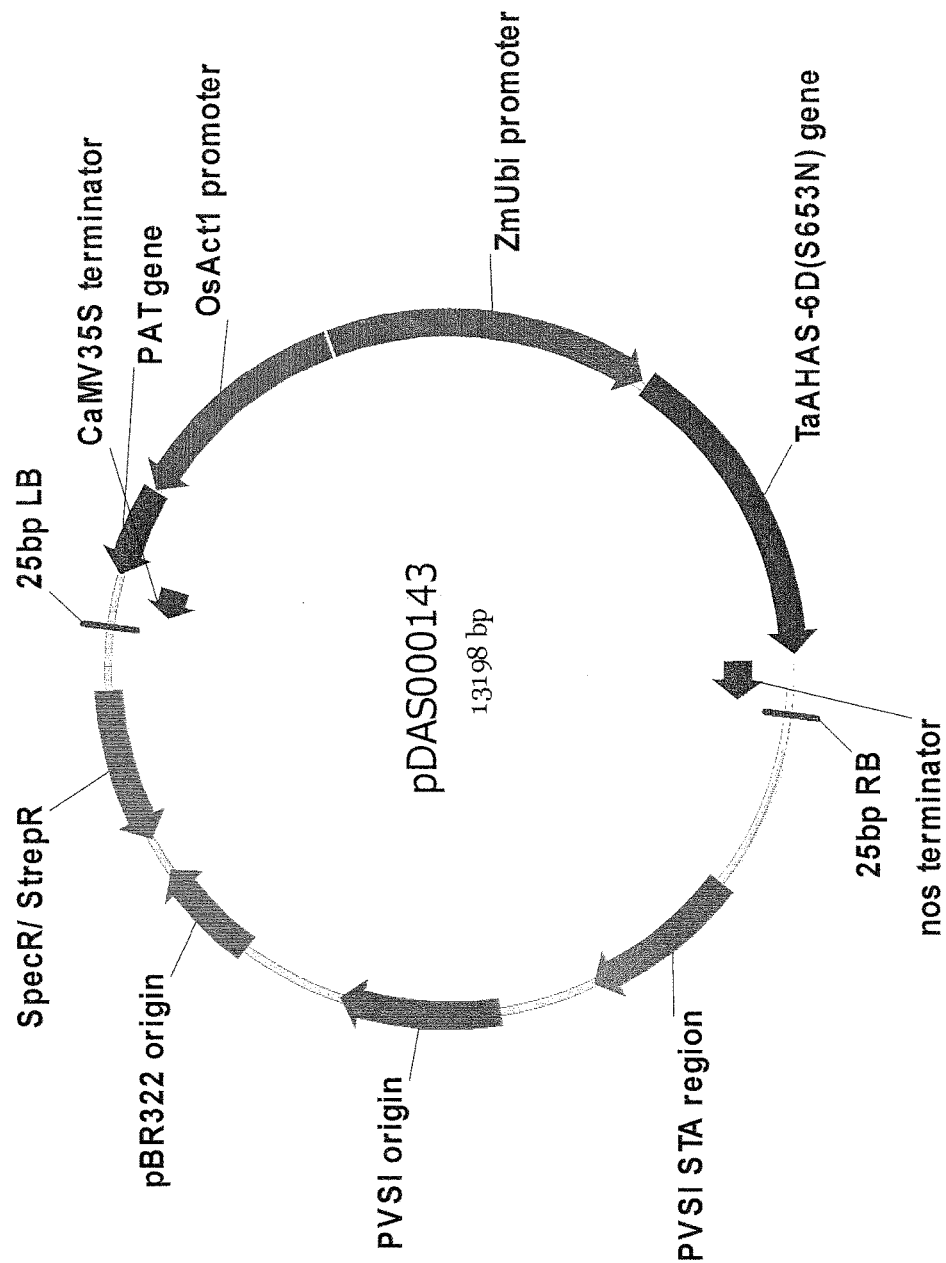
FIG. 15 shows a plasmid map of pDAS000143.

Standard cloning methods were used in the construction of binary vector pDAS000143 (SEQ ID:185) (FIG. 15). The AHAS (S653N) gene expression cassette consists of the promoter, 5' untranslated region and intron from the Ubiquitin (Ubi) gene from *Zea mays* (Toki et al., (1992) Plant Physiology 100; 1503-07) followed by the coding sequence (1935 bp) of the AHAS gene from *T. aestivum* with basepairs 1880 and 1181 mutated from CG to AT in order to induce an amino acid change from serine (S) to asparagine (N) at amino acid residue 653. The AHAS expression cassette included the 3' untranslated region (UTR) of the nopaline synthase gene (nos) from *A. tumefaciens* pTi15955 (Fraley et al., (1983) Proceedings of the National Academy of Sciences U.S.A. 80(15); 4803-4807). The selection cassette was comprised the promoter, 5' untranslated region and intron from the actin 1 (Act1) gene from *Oryza sativa* (McElroy et al., (1990) *The Plant Cell* 2(2); 163-171) followed by a synthetic, plant-optimized version of phosphinothricin acetyl transferase (PAT) gene, isolated from *Streptomyces viridochromogenes*, which encodes a protein that confers resistance to inhibitors of glutamine synthetase comprising phosphinothricin, glufosinate, and bialaphos (Wohlleben et al., (1988) Gene 70(1); 25-37). This cassette was terminated with the 3' UTR from the 35S gene of cauliflower mosaic virus (CaMV) (Chenault et al., (1993) Plant Physiology 101 (4); 1395-1396).

The selection cassette was synthesized by a commercial gene synthesis vendor (GeneArt, Life Technologies) and cloned into a Gateway-enabled binary vector with the RfA Gateway cassette located between the Ubiquitin (Ubi) gene from *Zea mays* and the 3' untranslated region (UTR) comprising the transcriptional terminator and polyadenylation site of the nopaline synthase gene (nos) from *A. tumefaciens* pTi15955. The AHAS(S653N) coding sequence was amplified with flanking attB sites and sub-cloned into pDONR221. The resulting ENTRY clone was used in a LR CLONASE II™ (Invitrogen, Life Technologies) reaction with the Gateway-enabled binary vector encoding the phosphinothricin acetyl transferase (PAT) expression cassette. Colonies of *E. coli* cells transformed with all ligation reactions were initially screened by restriction digestion of miniprep DNA. Restriction endonucleases were obtained from New England BioLabs and Promega. Plasmid preparations were performed using the QIAPREP SPIN MINIPREP KIT™ or the PURE YIELD PLASMID MAXIPREP SYSTEM™ (Promega Corporation, WI) following the manufacturer's instructions. Plasmid DNA of selected clones was sequenced using ABI Sanger Sequencing and BIG DYE TERMINATOR v3.1™ cycle sequencing protocol (Applied Biosystems, Life Technologies). Sequence data were assembled and analyzed using the SEQUENCHER SOFTWARE™ (Gene Codes Corporation, Ann Arbor, Mich.).

Biolistic-Mediated Transformation System for Generating AHAS Edited Wheat Plants About 23,000 scutella of immature zygotic embryos from the donor wheat line cv. Bobwhite MPB26RH were prepared for biolistics-mediated DNA delivery, as described previously. DNA-coated gold particles were prepared as described above with the following formulations. For transfections performed using pDAS000267, the donor DNA was mixed at a 5:1 molar ratio with plasmid DNA for pDAB109350 (encoding ZFNs 29732 and 29730). For transfections performed using pDAS000268, the donor DNA was mixed at a 10:1:1 molar ratio with plasmid DNA for pDAB109350 (encoding ZFNs 29732 and 29730) and pDAB109360 (encoding ZFNs 30012 and 30018). Transfections performed using pDAS000143 were performed using gold particles that were coated only with plasmid DNA for pDAS000143.

Biolistic-mediated transfections were performed as described previously. A total of 15,620 scutella were bombarded with gold particles coated with DNA containing pDAS000267, a total of 7,310 scutella were bombarded with gold particles coated with DNA containing pDAS000268, and a total of 2,120 scutella were bombarded with gold particles coated with pDAS000143. Following bombardment, the transfected scutella were incubated at 26° C. in the dark for 16 h before being transferred onto medium for callus induction.

Four different chemical selection strategies based on IMAZAMOX® were used to enrich for regenerated wheat plants that had the S653N mutation precisely integrated into one or more homoeologous copies of the endogenous AHAS gene by ZFN-mediated NHEJ-directed gene editing. The four chemical selection strategies are described in Table 9. For each strategy, scutella were cultured in the dark on callus induction medium at 24° C. for 2 weeks. The resultant calli were sub-cultured once onto fresh callus induction medium and kept in the same conditions for a further two weeks. Somatic embryogenic callus (SEC) was transferred onto plant regeneration medium and cultured for 2 weeks at 24° C. under a 16/8 (light/dark) hour photoperiod in a growth room. Regenerated plantlets were transferred onto rooting medium and cultured under the same conditions for 2-3 weeks. To increase stringency for the selection of regenerated plants having the S653N mutation, the roots of regenerated plants were removed and the plants were again sub-cultured on rooting media under the same conditions. Plantlets rooting a second time were transferred to soil and grown under glasshouse containment conditions. $T_1$ seed was harvested from individual plants, following bagging of individual spikes to prevent out-crossing.

The scutella explants bombarded with gold particles coated with pDAS000143 were used to monitor the selection stringency across the four chemical selection strategies for regenerating wheat plants carrying the AHAS S653N mutation. Plants transformed with pDAS000143 were regenerated using process described above.

TABLE 9

Chemical selection strategies used to regenerate wheat plants that had the S653N mutation precisely integrated into one or more homoeologous copies of the endogenous AHAS gene by ZFN-mediated NHEJ-directed gene editing. (IMI = IMAZAMOX ™)

| Plant Regeneration Stage | Strategy 1 | Strategy 2 | Strategy 3 | Strategy 4 |
|---|---|---|---|---|
| Callus induction (CIM) | 150 nM IMI | 250 nM IMI | 150 nM IMI | 250 nM IMI |
| Plant Regeneration (DRM) | 150 nM IMI | 0 nM IMI | 250 nM IMI | 250 nM IMI |
| Rooting (RM) | 200 nM IMI | 200 nM IMI | 200 nM IMI | 200 nM IMI |

Overall, 14 putatively ZFN-mediated NHEJ-directed AHAS edited wheat plants were recovered from the transfection of 22,930 scutella of immature zygotic embryos from the donor wheat line cv. Bobwhite MPB26RH. Putatively edited plants were obtained from all four selection strategies for scutella bombarded with gold particles coated with DNA containing pDAS000267. Two putatively edited plants were obtained from the second selection strategy for scutella bombarded with gold particles coated with DNA containing pDAS000268. A total of 129 putatively transformed wheat plants carrying at least one randomly integrated copy of the AHAS (S653N) donor polynucleotide were recovered across the four chemical selection strategies.

Molecular Characterization of Edited Wheat Plants

The wheat plants resulting from bombardments with a donor polynucleotide encoding the S653N mutation were obtained and molecularly characterized to identify the wheat sub-genomes that comprised an integration of the S653N mutation that occurred as a result of the donor integration at a genomic double strand cleavage site. Two series of bombardments were completed. The first set of experiments was completed with pDAS000143, and the second set of experiments was completed with pDAS000267 and pDAS000268. Individual wheat plants were obtained from both sets of experiments and assayed via a molecular method to identify plants which contained an integrated copy of the AHAS donor polynucleotide encoding the S653N mutation.

A hydrolysis probe assay (analogous to the TAQMAN® based assay) for quantitative PCR analysis was used to confirm that recovered wheat plants that had been bombarded with pDAS000143 carried at least one randomly integrated copy of the AHAS donor polynucleotide encoding the S653N mutation. Confirmation via Sanger sequence analysis indicated that wheat plants recovered from bombardments performed with pDAS000267 and pDAS000268 comprised the S653N donor polynucleotide in at least one of the homoeologous copies of the AHAS gene at the position expected for ZFN-mediated NHEJ-directed gene editing.

Genomic DNA Isolation from Regenerated Wheat Plants

Genomic DNA was extracted from freeze-dried leaf tissue harvested from each regenerated wheat plant. Freshly harvested leaf tissue was snap frozen in liquid nitrogen and freeze-dried for 24 h in a LABCONCO FREEZONE 4.5® (Labconco, Kansas City, Mo.) at −40° C. and $133 \times 10^{-3}$ mBar pressure. The lyophilized material was subjected to DNA extraction using the DNEASY® PLANT DNA EXTRACTION MINI KIT™ (Qiagen) following the manufacturer's instructions.

PCR Assay to Confirm Random Integration of AHAS Donor Polynucleotide Encoding S653N Mutation To confirm that the regenerated wheat plants from bombardments performed with pDAS000143 carried at least one randomly integrated copy of the AHAS donor polynucleotide encoding the S653N mutation, a duplex hydrolysis probe qPCR assay (analogous to TAQMAN®) was used to amplify the endogenous single copy gene, puroindoline-b (Pinb), from the D genome of hexaploid wheat (Gautier et al., (2000) Plant Science 153, 81-91; SEQ ID NO:186, SEQ ID NO:187 and SEQ ID NO:188 for forward and reverse primers and probe sequence, respectively) and a region of the Actin (Act1) promoter present on pDAS000143 (SEQ ID NO:189, SEQ ID NO:190 and SEQ ID NO:191 for forward and reverse primers and probe sequence, respectively). Hydrolysis probe qPCR assays were performed on 24 randomly chosen wheat plants that were recovered from each of the four chemical selection strategies. Assessment for the presence, and estimated copy number of pDAS00143 was performed according to the method described in Livak and Schmittgen (2001) Methods 25(4):402-8.

From the results, conclusive evidence was obtained for the integration of at least one copy of the AHAS donor polynucleotide encoding the S653N mutation into the genome of each of the wheat plants tested. These results indicate that the four chemical selection strategies provided stringent selection for the recovery of plants expressing the S653N mutation.

PCR Assay of Genomic DNA for ZFN-Mediated AHAS Editing

To characterize the sub-genomic location and outcome of ZFN-mediated NHEJ-directed gene editing in the recovered wheat plants, PCR with primers AHAS_3F1 and AHAS_3R1 (SEQ ID NO:192 and SEQ ID NO:193) was used to amplify the target region from the homoeologous copies of the AHAS genes. The resulting PCR products were cloned into plasmid vector and Sanger sequenced using BIGDYE® v3.1 chemistry (Applied Biosystems) on an ABI3730XL® automated capillary electrophoresis platform. Sanger sequencing of up to 120 independent plasmid clones was performed to ensure that each allele at the endogenous AHAS homoeologs was sequenced. Sequence analysis performed using SEQUENCHER SOFTWARE™ was used to generate a consensus sequence for each allele of the three homoeologous copies of the AHAS gene in each of the recovered wheat plants, and to determine the sub-genomic origin and sequence for each edited allele.

From the results, conclusive evidence for precise ZFN-mediated NHEJ-directed gene editing at the endogenous AHAS loci was demonstrated for 11 of the 12 recovered wheat plants that were transformed using pDAB109350 and pDAS000267 (Table 10), and both of the recovered wheat plants that were transformed using pDAB109350, pDAB109360 and pDAS000268 (Table 11). Plants with a range of editing outcomes were observed including: (1) independent events with perfect sub-genome-specific allele edits; (2) events with single perfect edits in the A-genome, B-genome and D-genomes; (3) events with simultaneous editing in multiple sub-genomes; and, (4) events demonstrating hemizygous and homozygous sub-genome-specific allele editing. Disclosed for the first time is a method which can be utilized to mutate a gene locus within all three genomes of a wheat plant. Wheat plants comprising an integrated AHAS donor polynucleotide encoding a S653N mutation are exemplified; integration of the polynucleotide sequence provides tolerance to imidazolinone class herbicides. The utilization of ZFN-mediated genomic editing at an endogenous gene locus in wheat allows for the introduction of agronomic traits (via mutation) without time consuming wheat breeding techniques which require backcrossing and introgression steps that can increase the amount of time required for introgressing the trait into all three sub-genomes. Consensus Sanger sequences for the alleles present in each sub-genome for the edited wheat plants are provided as SEQ ID NO:194-277 in Tables 10 and 11.

TABLE 10

ZFN-mediated NHEJ-directed AHAS editing outcomes for wheat plants transformed using pDAB109350 and pDAS000267

| | | A-genome | | B-genome | | D-genome | | |
|---|---|---|---|---|---|---|---|---|
| | | Allele 1 | Allele 2 | Allele 1 | Allele 2 | Allele 1 | Allele 2 | SEQ ID NO: |
| Plant No. 1 | Status | PE | NHEJ | IE | UE | IE | UE | 194-199 |
| | No. clones[1] | 13 | 20 | 12 | 19 | 14 | 22 | |
| Plant No. 2 | Status | NHEJ | UE | UE | nd | IE | UE | 200-205 |
| | No. clones[1] | 9 | 3 | 16 | 0 | 75 | 17 | |
| Plant No. 3 | Status | PE | UE | UE | nd | UE | nd | 206-211 |
| | No. clones[1] | 7 | 11 | 29 | 0 | 35 | 0 | |
| Plant No. 4 | Status | PE | UE | IE | UE | PE | IE | 212-217 |
| | No. clones[1] | 6 | 11 | 44 | 30 | 6 | 11 | |
| Plant No. 5 | Status | PE | UE | NHEJ | UE | UE | nd | 218-223 |
| | No. clones[1] | 10 | 9 | 15 | 26 | 21 | 0 | |
| Plant No. 6 | Status | UE | nd | PE | UE | UE | nd | 224-229 |
| | No. clones[1] | 22 | 0 | 11 | 18 | 43 | 0 | |
| Plant No. 7 | Status | PE | UE | UE | nd | UE | nd | 230-235 |
| | No. clones[1] | 5 | 12 | 26 | 0 | 22 | 0 | |
| Plant No. 8 | Status | UE | nd | UE | nd | UE | nd | 236-241 |
| | No. clones[1] | 32 | 0 | 40 | 0 | 26 | 0 | |
| Plant No. 9 | Status | PE | nd | IE | UE | UE | nd | 242-247 |
| | No. clones[1] | 24 | 0 | 13 | 21 | 33 | 0 | |
| Plant No. 10 | Status | PE | UE | UE | nd | UE | nd | 248-253 |
| | No. clones[1] | 10 | 19 | 37 | 0 | 29 | 0 | |
| Plant No. 11 | Status | UE | nd | UE | nd | PE | UE | 254-259 |
| | No. clones[1] | 35 | 0 | 37 | 0 | 15 | 11 | |
| Plant No. 12 | Status | UE | nd | UE | nd | IE | NHEJ | 260-265 |
| | No. clones[1] | 34 | 0 | 40 | 0 | 14 | 8 | |

[1]Number of independent plasmid clones sequenced.
PE = perfect edit; i.e., ZFN-mediated NHEJ-directed genome editing produced a predicted outcome.
IE = imperfect edit; i.e., ZFN-mediated NHEJ-directed genome editing produced an unpredicted outcome.
UE = unedited allele; i.e., allele had wild-type sequence.
nd = not detected; i.e., sufficient independent plasmid clones were sequenced to conclude that an alternate allele was not present and that the locus was homozygous for a single allele.
NHEJ = Non Homologous End Joining; i.e., evidence for a non-homologous end joining DNA repair outcome that did not result in the integration of a donor molecule at the ZFN cleavage site.

TABLE 11

ZFN-mediated NHEJ-directed AHAS editing outcomes for wheat plants transformed using pDAB109350, pDAB109360 and pDAS000268.

| | | A-genome | | B-genome | | D-genome | | |
|---|---|---|---|---|---|---|---|---|
| | | Allele 1 | Allele 2 | Allele 1 | Allele 2 | Allele 1 | Allele 2 | SEQ ID NO: |
| Plant No. 12a | Status | IE | UE | UE | nd | IE | nd | 266-271 |
| | No. clones[1] | 5 | 14 | 53 | 0 | 1 | 24 | |
| Plant No. 13a | Status | IE | UE | UE | nd | UE | nd | 272-277 |
| | No. clones[1] | 10 | 12 | 49 | 0 | 18 | 0 | |

[1]Number of independent plasmid clones sequenced.
IE = imperfect edit; i.e., ZFN-mediated NHEJ-directed genome editing produced unexpected outcome.
UE = unedited allele; i.e., allele had wild-type sequence.
nd = not detected; i.e., sufficient independent plasmid clones were sequenced to conclude that an alternate allele was not present and that the locus was homozygous for a single allele.

Design of Zinc Finger Binding Domains Specific to Region in AHAS Genes Encoding the P197 Amino Acid Residue Zinc finger proteins directed against DNA sequence of the homoeologous copies of the AHAS genes were designed as previously described. Exemplary target sequence and recognition helices are shown in Table 12 (recognition helix regions designs) and Table 13 (target sites). In Table 13, nucleotides in the target site that are contacted by the ZFP recognition helices are indicated in uppercase letters; non-contacted nucleotides are indicated in lowercase. Zinc Finger Nuclease (ZFN) target sites were designed upstream (from 2 to 510 nucleotides upstream) of the region in the AHAS gene encoding the proline 197 (P197) amino acid residue.

TABLE 12

AHAS zinc finger designs
(N/A indicates "Not Applicable")

| ZFP# | F1 | F2 | F3 | F4 | F5 | F6 |
|---|---|---|---|---|---|---|
| 34470 | SEQ ID NO: 278 RSADLSR | SEQ ID NO: 279 RSDHLSA | SEQ ID NO: 280 QSSDLRR | SEQ ID NO: 160 DRSNLSR | SEQ ID NO: 281 RSDDRKT | N/A |
| 34471 | SEQ ID NO: 158 QSGDLTR | SEQ ID NO: 282 RRADRAK | SEQ ID NO: 150 RSDDLTR | SEQ ID NO: 283 TSSDRKK | SEQ ID NO: 284 RSADLTR | SEQ ID NO: 285 RNDDRKK |
| 34472 | SEQ ID NO: 284 RSADLTR | SEQ ID NO: 286 DRSNLTR | SEQ ID NO: 287 ERGTLAR | SEQ ID NO: 150 RSDDLTR | SEQ ID NO: 288 DRSDLSR | SEQ ID NO: 289 DSSTRRR |
| 34473 | SEQ ID NO: 290 RSDHLSE | SEQ ID NO: 291 HSRTRTK | SEQ ID NO: 292 RSDTLSE | SEQ ID NO: 293 NNRDRTK | SEQ ID NO: 287 ERGTLAR | SEQ ID NO: 155 DRSALAR |
| 34474 | SEQ ID NO: 287 ERGTLAR | SEQ ID NO: 150 RSDDLTR | SEQ ID NO: 294 DRSDLSR | SEQ ID NO: 289 DSSTRRR | SEQ ID NO: 286 DRSNLTR | N/A |
| 34475 | SEQ ID NO: 296 RSDHLSR | SEQ ID NO: 297 QQWDRKQ | SEQ ID NO: 298 DRSHLTR | SEQ ID NO: 152 DSSDRKK | SEQ ID NO: 160 DRSNLSR | SEQ ID NO: 299 VSSNLTS |

TABLE 13

Target site of AHAS zinc fingers

| pDAB# | Approximate Cleavage Site Relative to AHAS Pro-197 | ZFP # and Binding Site (5'→3') | SEQ ID NO: |
|---|---|---|---|
| pDAB111850 (34456-2A-34457) | 499-bp upstream | 34456: cnGCGGCCATGGCGGCGGCGaggg gtttg | 300 |
| | | 34457: acCTCcCCCGCCGTCGCAttctcnggcg | 301 |
| pDAB111855 (34470-2A-34471) | 109-bp upstream | 34470: ggCCGGACGCGCGGGCGtanccgga cgc | 302 |
| | | 34471: cgTCGGCGTCTGCGTCGCCAcctcc ggc | 303 |
| pDAB111856 (34472-2A-34473) | 99-bp upstream | 34472: acGCCGACGCGGCCgGACGCGcgg gcgt | 304 |
| | | 34473: gcGTCGCCaCCTCCGGCCCGGggg ccac | 305 |
| pDAB111857 (34474-2A-34475) | 96-bp upstream | 34474: caGACGCCGACGCGGCCggacgcgc ggg | 306 |
| | | 34475: gtCGCCACcTCCGGCCCGGGGgcc acca | 307 |
| pDAB111858 (34476-2A-34477) | 90-bp upstream | 34476: gcGACGCAGACGCCGACgcggccgg acg | 308 |
| | | 34477: ccTCCGGCCCGGGGGCCaccaacctc gt | 309 |

TABLE 13-continued

Target site of AHAS zinc fingers

| pDAB# | Approximate Cleavage Site Relative to AHAS Pro-197 | ZFP # and Binding Site (5'→3') | SEQ ID NO: |
|---|---|---|---|
| pDAB111859 (34478-2A-34479) | 24-bp upstream | 34478: gggGATGGAGTCGAGGAGngcgtcng cga | 310 |
| | | 34479: tgGTCGCCATCACGGGCCAGgtccc ccg | 311 |
| pDAB111860 (34480-2A-34481) | 18-bp upstream | 34480: acCATGGGGATGGAGTCGAGgagn gcgt | 312 |
| | | 34481: ccATCACGGGCCAGGTCccccgccgc at | 313 |
| pDAB111861 (34482-2A-34483) | 16-bp upstream | 34482: cgACCATGGGGATGGAGTCGagga gngc | 314 |
| | | 34483: caTCACGGGCCAGGTCCcccgccgca tg | 315 |

The AHAS zinc finger designs were incorporated into zinc finger expression vectors and verified for cleavage activity using a budding yeast system, as described previously. Of the numerous ZFNs that were designed, produced and tested to bind to the putative AHAS genomic polynucleotide target sites, the ZFNs described above were identified as having in vivo activity at high levels, and selected for further experimentation. These ZFNs were designed to bind to the three homoeologous AHAS and were characterized as being capable of efficiently binding and cleaving the unique AHAS genomic polynucleotide target sites in planta.

Evaluation of Zinc Finger Nuclease Cleavage of AHAS Genes Using Transient Assays ZFN Construct Assembly;

Plasmid vectors containing ZFN expression constructs verified for cleavage activity using the yeast system were designed and completed as previously described. The resulting plasmid constructs; pDAB111855 (ZFNs 34470-2A-34471), pDAB111856 (ZFNs 34472-2A-34473), and pDAB111857 (ZFNs 34474-2A-34475) were confirmed via restriction enzyme digestion and via DNA sequencing.

Preparation of DNA from ZFN Constructs for Transfection

Before delivery to *Triticum aestivum* protoplasts, plasmid DNA for each ZFN construct was prepared from cultures of *E. coli* using the PURE YIELD PLASMID MAXIPREP SYSTEM® (Promega Corporation, Madison, Wis.) or PLASMID MAXI KIT® (Qiagen, Valencia, Calif.) following the instructions of the suppliers.

Isolation and Transfection of Wheat Mesophyll Protoplasts

Mesophyll protoplasts from the donor wheat line cv. Bobwhite MPB26RH were prepared and transfected using polyethylene glycol (PEG)-mediated DNA delivery as previously described.

PCR Assay of Protoplast Genomic DNA for ZFN Sequence Cleavage

Genomic DNA was isolated from transfected protoplasts and used for PCR assays to assess the cleavage efficiency and target site specificity of ZFNs designed to the region of the AHAS gene encoding P197, as previously described. Five sets of PCR primers which contained a phosphorothioate linkage as indicated by the asterisk [*] were used to amplify the ZFN target site loci (Table 14). Each primer set was designed according to criteria previously described.

TABLE 14

Primer sequences used to assess AHAS ZFN cleavage efficacy and target site specificity.

| Primer Name | Primer Set | Primer Sequence (5'→3') | SEQ ID NO: |
|---|---|---|---|
| AHAS-P197ZFN.F2 | Set 1 | a*cactctttccctacacgacgctcttccgatctTCC CCAATTCCAACCCTCT*C | 316 |
| AHAS-P197ZFN.R1 | Set 1 | g*tgactggagttcagacgtgtgctcttccgatctC GTCAGCGCCTGGTGGATC*T | 317 |
| AHASs653ZFN.F5 | Set 2 | a*cactctttccctacacgacgctcttccgatctGC CCGTCCGAGCCCCGCA*A | 318 |
| AHASs653ZFN.R1 | Set 2 | g*tgactggagttcagacgtgtgctcttccgatctC GTCAGCGCCTGGTGGATC*T | 319 |

TABLE 14-continued

Primer sequences used to assess AHAS ZFN
cleavage efficacy and target site specificity.

| Primer Name | Primer Set | Primer Sequence (5'→3') | SEQ ID NO: |
|---|---|---|---|
| AHASs653ZFN.F7 | Set 3 | a*cactctttccctacacgacgctcttccgatctGC GCTCGCCCGTCATCA*C | 320 |
| AHASs653ZFN.R5 | Set 3 | g*tgactggagttcagacgtgtgctcttccgatctA TGGGGATGGAGTCGAGGA*G | 321 |
| AHAS + 400ZFN.F9 | Set 4 | a*cactctttccctacacgacgctcttccgatctCTT CCGCCACGAGCAGG*G | 322 |
| AHAS + 400ZFN.R5 | Set 4 | g*tgactggagttcagacgtgtgctcttccgatctA TGGGGATGGAGTCGAGGA*G | 323 |
| AHAS + 400ZFN.F11 | Set 5 | a*cactctttccctacacgacgctcttccgatctTC GTCTCCGCGCTCGCTG*A | 324 |
| AHAS + 400ZFN.R6 | Set 5 | g*tgactggagttcagacgtgtgctcttccgatctTC CACTATGGGCGTCTCCT*G | 325 |

Data Analysis for Detecting NHEJ at Target ZFN Sites

Following generation of Illumina short read sequence data for sample libraries prepared for transfected mesophyll protoplasts, bioinformatics analysis (as previously described) was performed to identify deleted nucleotides at the target ZFN sites. Such deletions are known to be indicators of in planta ZFN activity that result from non-homologous end joining (NHEJ) DNA repair.

Two approaches were used to assess the cleavage efficiency and specificity of the ZFNs tested. Cleavage efficiency was expressed (in parts per million reads) as the proportion of sub-genome assigned sequences that contained a NHEJ deletion at the ZFN target site (Table 15). Rank ordering of the ZFNs by their observed cleavage efficiency was used to identify ZFNs with the best cleavage activity for the target region of the AHAS genes in a sub-genome-specific manner. All of the ZFNs tested showed NHEJ deletion size distributions consistent with that expected for in planta ZFN activity. Cleavage specificity was expressed as the ratio of cleavage efficiencies observed across the three sub-genomes.

TABLE 15

ZFN cleavage efficacy (expressed as number of NHEJ events per million reads) and target site specificity.

| ZFN | A-genome | B-genome | D-genome |
|---|---|---|---|
| pDAB111855 (34470-2A-34471) | 177,866 | 156,139 | 134,694 |
| pDAB111856 (34472-2A-34473) | 119,857 | 100,300 | 87,770 |
| pDAB111857 (34474-2A-34475) | 248,115 | 251,142 | 202,711 |

From these results, the ZFNs encoded on plasmids pDAB111855 (34470-2A-34471), pDAB111856 (34472-2A-34473) and pDAB111857 (34474-2A-34475) were selected for in planta targeting in subsequent experiments, given their characteristics of significant genomic DNA cleavage activity in each of the three wheat sub-genomes.

Generation of Molecular Evidence for ZFN-Mediated, Exogenous Marker-Free Sequential Transgene Stacking at an Endogenous AHAS Locus Using Transient Assays The generation of molecular evidence using transient assays for ZFN-mediated, sequential exogenous marker-free transgene stacking at an endogenous AHAS locus within the genome of *Triticum aestivum* cells via homology directed DNA repair is achieved as follows.

The AHAS (S653N) edited wheat plants, which were produced via transformation with donor pDAS000267 and the Zinc Finger Nuclease encoded on plasmid pDAB109350, demonstrate the first step for sequential, exogenous marker-free transgene stacking at an endogenous AHAS locus in the genome of wheat. These edited plants are used to generate explant material (e.g., protoplasts or scutella of immature zygotic embryos) for transfection using the previously described methods. The explant material is subsequently co-transfected with a donor DNA molecule and a plasmid encoding a ZFN (e.g., pDAB111855, pDAB111856 or pDAB111857) that is designed to target a Zinc Finger binding site located in the AHAS genes upstream of the region encoding the P197 amino acid residue. The ZFN cleaves an AHAS locus and the donor molecule is integrated within the genome of *Triticum aestivum* cells via homology directed repair. As a result of NHEJ-mediated donor molecule integration, the AHAS (P197S) mutation conferring tolerance to sulfonylurea class herbicides is introduced into the endogenous AHAS sequence and simultaneously, the AHAS(S653N) mutation introduced in the first round of transgene stacking is removed. Consequently, the expression of the endogenous AHAS gene is changed from conferring tolerance to imidazolinones and susceptibility to sulfonylureas (the phenotype of correctly targeted wheat cells in the first round of transgene stacking) to conferring susceptibility for imidazolinones and tolerance for sulfonylureas, thus allowing for the regeneration of correctly targeted cells using a sulfonylurea selection agent. Molecular evidence for the integration of the donor DNA and generation of correctly targeted wheat cells is confirmed using the previously described methods.

It is appreciated by those skilled in the art that co-transformation of wheat cells with a donor DNA molecule that contains one or more transgenes and a plasmid encoding a Zinc Finger Nuclease enables both parallel (simultaneous) or sequential transgene integration (transgene stacking) in plant genomes at precisely the same genomic location, including simultaneous editing of multiple alleles across multiple genomes in polyploid plant species.

Development of a Transformation System for Sequential, Exogenous Marker-Free Transgene Stacking at the Endogenous AHAS Loci in Wheat The endogenous AHAS gene in wheat was selected as a model locus to develop a ZFN-mediated, exogenous marker-free transformation system for generating plants with one or more transgenes precisely positioned at the same genomic location. The transformation system enables parallel (simultaneous integration of one or more transgenes) or sequential stacking (consecutive integration of one or more transgenes) at precisely the same genomic location, including simultaneous parallel or sequential stacking at multiple alleles across multiple sub-genomes, by exploiting known mutations in the AHAS gene that confer tolerance to Group B herbicides. ZFN-mediated integration of a donor DNA into the wild-type (herbicide susceptible) AHAS locus is used to introduce transgene(s) and a mutation to the endogenous AHAS gene that confers tolerance to imidazolinones, thus allowing the regeneration of correctly targeted plants using an imidazolinone selection agent. Stacking of a second transgene(s) at the AHAS locus is achieved by integration of a donor DNA that introduces one or more additional transgenes and confers susceptibility to imidazolinones but tolerance to sulfonylureas, thus allowing the regeneration of correctly targeted plants using a sulfonylurea selection agent. Stacking of a third transgene can be achieved by integration of a donor molecule that introduces further transgene(s) and confers susceptibility to sulfonylurea and tolerance to imidazolinones, thus allowing the regeneration of correctly targeted plants using an imidazolinone selection agent. As such, continued rounds of sequential transgene stacking are possible by the use of donor DNA that introduce transgene(s) and mutations at the endogenous AHAS genes for differential cycling between imidazolinone and sulfonylurea selection agents. The transgenes can be integrated within the AHAS gene and stacked via an NHEJ pathway. The NHEJ repair and recombination pathway can be determined by the design of the donor transgene. In an embodiment, transgenes that are integrated and stacked within the AHAS gene would be designed to contain single or double cut ZFN sites that flank the payload (e.g., AHAS mutation and gene of interest). Accordingly, such a design would utilize an NHEJ pathway for the integration and stacking of the donor polynucleotide within the chromosome.

Figure 16:
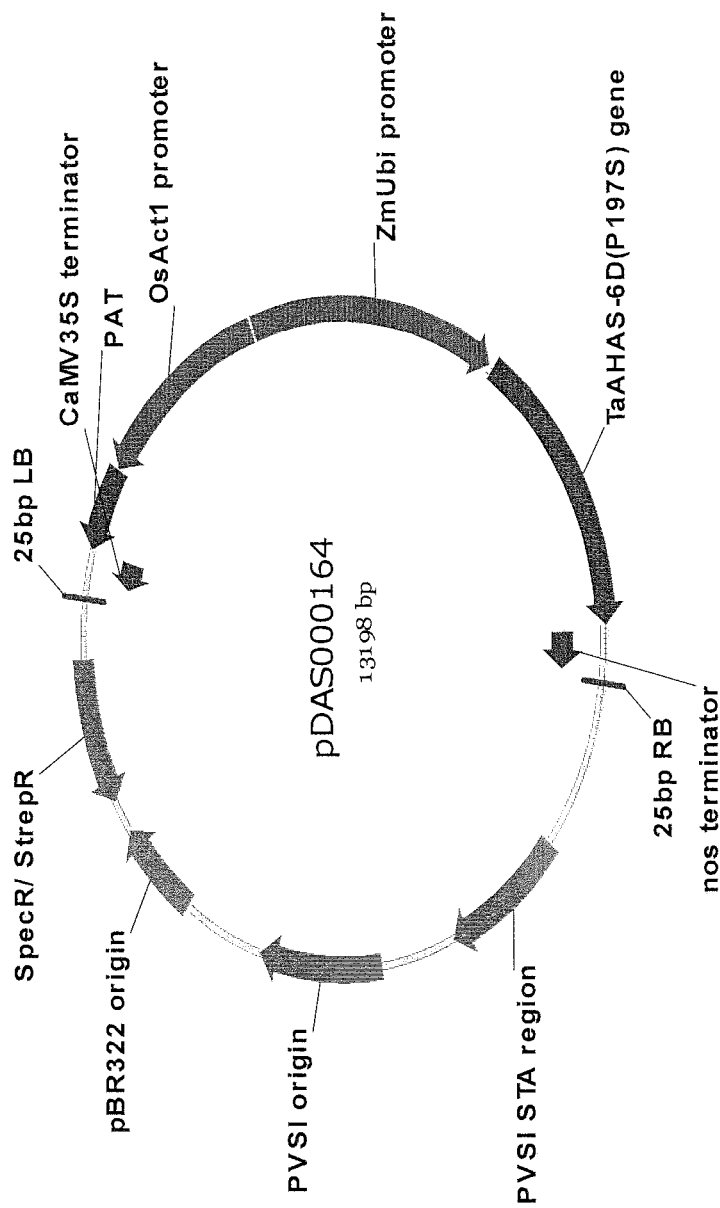
FIG. 16 shows a plasmid map of pDAS000164.

Generation of Low-Copy, Randomly Integrated T-DNA Wheat Plants with AHAS(P197S) Expression Constructs A binary vector pDAS000164 (SEQ ID NO:326, FIG. 16) containing the AHAS(P197S) expression and PAT selection cassettes was designed and assembled using skills and techniques commonly known in the art. The AHAS (P197S) expression cassette consisted of the promoter, 5' untranslated region and intron from the Ubiquitin (Ubi) gene from *Zea mays* (Toki et al., (1992) *Plant Physiology*, 100; 1503-07) followed by the coding sequence (1935 bp) of the AHAS gene from *T. aestivum* cv. Bobwhite MPB26RH with nucleotide 511 mutated from C to T in order to induce an amino acid change from proline (P) to serine (S). The AHAS expression cassette included the 3' untranslated region (UTR) comprising of the nopaline synthase gene (nos) from *A. tumefaciens* pTi15955 (Fraley et al., (1983) *Proceedings of the National Academy of Sciences U.S.A.* 80(15): 4803-4807). The selection cassette was comprised of the promoter, 5' untranslated region and intron from the actin 1(Act1) gene from *Oryza sativa* (McElroy et al., (199) *The Plant Cell* 2(2): 163-171) followed by a synthetic, plant-optimized version of phosphinothricin acetyl transferase (PAT) gene, isolated from *Streptomyces viridochromogenes*, which encodes a protein that confers resistance to inhibitors of glutamine synthetase comprising phosphinothricin, glufosinate, and bialaphos (Wohlleben et al., (1988) *Gene*, 70(1): 25-37). This cassette was terminated with the 3' UTR from the 35S gene of cauliflower mosaic virus (CaMV) (Chenault et al., (1993) *Plant Physiology* 101 (4): 1395-1396).

The selection cassette was synthesized by a commercial gene synthesis vendor (e.g., GeneArt, Life Technologies, etc.) and cloned into a GATEWAY®-enabled binary vector with the RfA Gateway cassette located between the Ubiquitin (Ubi) gene from *Zea mays* and the 3' untranslated region (UTR) comprising the transcriptional terminator and polyadenylation site of the nopaline synthase gene (nos) from *A. tumefaciens* pTi15955. The AHAS (P197S) coding sequence was amplified with flanking attB sites and subcloned into pDONR221. The resulting ENTRY clone was used in a LR CLONASE II® (Invitrogen, Life Technologies) reaction with the Gateway-enabled binary vector encoding the phosphinothricin acetyl transferase (PAT) expression cassette. Colonies of all assembled plasmids were initially screened by restriction digestion of miniprep DNA. Restriction endonucleases were obtained from New England BioLabs (NEB; Ipswich, Mass.) and Promega (Promega Corporation, WI). Plasmid preparations were performed using the QIAPREP SPIN MINIPREP KIT® (Qiagen, Hilden) or the PURE YIELD PLASMID MAXIPREP SYSTEM® (Promega Corporation, WI) following the instructions of the suppliers. Plasmid DNA of selected clones was sequenced using ABI Sanger Sequencing and BIG DYE TERMINATOR V3.1® cycle sequencing protocol (Applied Biosystems, Life Technologies). Sequence data were assembled and analyzed using the SEQUENCHER™ software (Gene Codes Corporation, Ann Arbor, Mich.).

The resulting binary expression clone pDAS000164 was transformed into *Agrobacterium tumefaciens* strain EHA105. Transgenic wheat plants with randomly integrated T-DNA were generated by *Agrobacterium*-mediated transformation using the donor wheat line cv. Bobwhite MPB26RH, following a protocol similar to Wu et al. (2008) *Transgenic Research* 17:425-436. Putative $T_0$ transgenic events expressing the AHAS (P197) expression constructs were selected for phosphinothricin (PPT) tolerance, the phenotype conferred by the PAT selectable marker, and transferred to soil. The $T_0$ plants were grown under glasshouse containment conditions and $T_1$ seed was produced.

Genomic DNA from each $T_0$ plant was extracted from leaf tissue, as previously described, and tested for the presence of *Agrobacterium tumefaciens* and for the number of integrated copies of the T-DNA encoding AHAS(P197S). The presence of *A. tumefaciens* was performed using a duplex hydrolysis probe qPCR assay (analogous to TAQMAN™) to amplify the endogenous ubiquitin gene (SEQ ID NO:327, SEQ ID NO:328, and SEQ ID NO:329 for forward and reverse primers and probe sequence, respectively) from the wheat genome, and virC from pTiBo542 (SEQ ID NO:330, SEQ ID NO:331, and SEQ ID NO:332 for forward and reverse primers and probe sequence, respectively). The number of integrated T-DNA copies was estimated using a duplex hydrolysis probe qPCR assay, as previously described, based on the puroindoline-b (Pinb) from the D genome of hexaploid wheat and a region of the Actin (Act1) promoter present on pDAS000164. Overall, 35 independent $T_0$ events with fewer than three randomly integrated copies of T-DNA were generated.

Optimization of Chemical Selection Conditions Based on Sulfometuron Methyl

A series of experiments were performed to determine optimal selection conditions for regenerating wheat plants expressing the AHAS(P197S) mutation conferring tolerance to sulfonylurea class herbicides. These experiments were based on testing the basal tolerance of the wild-type donor wheat line cv. Bobwhite MPB26RH (P197/P197 genotype, which confers susceptibility to sulfonylureas) at the callus induction, plant regeneration and rooting stages of an established wheat transformation system. Similar experiments were performed to determine the basal tolerance of transgenic cv. Bobwhite MPB26RH events that had randomly integrated T-DNA expressing the AHAS(P197) mutation, which confers tolerance to sulfonylurea selection agents.

The basal tolerance of the wild-type donor wheat line to sulfometuron methyl at the callus induction stage was determined as follows: Scutella of immature zygotic embryos were isolated, as previously described, and placed in 10 cm PETRI™ dishes containing CIM medium supplemented with 0, 100, 500, 1000, 1500 and 2000 nM sulfometuron methyl, respectively. Twenty scutella were placed in each PETRI™ dish. A total of 60 scutella were tested at each sulfometuron methyl concentration. After incubation at 24° C. in the dark for 4 weeks, the amount of somatic embryogenic callus formation (SEC) at each sulfometuron methyl concentration was recorded. The results showed that SEC transformation for cv. Bobwhite MPB26RH was reduced by about 70% at 100 nM sulfometuron methyl, compared to untreated samples.

The basal tolerance of the wild-type donor wheat line to sulfometuron methyl at the plant regeneration stage was determined as follows: Scutella of immature zygotic embryos from the donor wheat line were isolated and placed in 10 cm PETRI™ dishes containing CIM medium. Somatic embryogenic callus was allowed to form by incubating at 24° C. in the dark for 4 weeks. The SEC was transferred to 10 cm PETRI™ dishes containing DRM medium supplemented with 0, 100, 500, 1000, 1500, 2000, 2500 and 3000 nM sulfometuron methyl, respectively. Twenty CIM were placed in each PETRI™ dish. A total of 60 CIM were tested for basal tolerance response at each sulfometuron methyl concentration. After incubation for 2 weeks at 24° C. under a 16/8 (light/dark) hour photoperiod in a growth room, the regeneration response was recorded. The results showed that plant regeneration was reduced by about 80% at 2000 nM sulfometuron methyl, compared to untreated samples.

The basal tolerance of the wild-type donor wheat line to sulfometuron methyl at the plant rooting stage was determined as follows: Scutella of immature zygotic embryos were isolated and placed in 10 cm PETRI™ dishes containing CIM medium. Somatic embryogenic callus was allowed to form by incubating at 24° C. in the dark for 4 weeks. The SEC was transferred to 10 cm PETRI™ dishes containing DRM medium and incubated for 2 weeks at 24° C. under a 16/8 (light/dark) hour photoperiod to allow plant regeneration to take place. Regenerated plants were transferred to 10 cm PETRI™ dishes containing RM medium supplemented with 0, 100, 200, 250, 300, 400, 500, 1000 and 2000 nM sulfometuron methyl, respectively. Ten regenerated plants were placed in each PETRI™ dish. A total of 30 regenerated plants were tested for basal tolerance response at each sulfometuron methyl concentration. After incubation for 3 weeks at 24° C. under a 16/8 (light/dark) hour photoperiod in a growth room, the root formation response was recorded. The results showed that root formation was severely inhibited when concentrations of sulfometuron methyl higher than 400 nM, compared to untreated samples.

The basal tolerance of transgenic wheat events with randomly integrated, low-copy (≤3) T-DNA expressing the AHAS(P197S) mutation to sulfometuron methyl at the plant rooting stage was determined as follows: Four independent transgenic events were randomly selected and multiplied in vitro by sub-culturing on multiplication medium. Following multiplication, plants for each event were transferred to 10 cm PETRI™ dishes containing RM medium supplemented with 0, 400, 450, 500, 550 and 600 nM sulfometuron methyl, respectively. Four plants (one from each of the four events) were placed in each PETRI™ dish. A total of 3 plants per event was tested for basal tolerance at each sulfometuron methyl concentration. After incubation for 2 weeks at 24° C. under a 16/8 (light/dark) hour photoperiod in a growth room, the root formation response was recorded. The results showed that root formation was not restricted, compared to untreated controls, at any of the concentrations tested, indicating that the AHAS(P197S) mutation conferred high tolerance to sulfometuron methyl.

Figure 17:
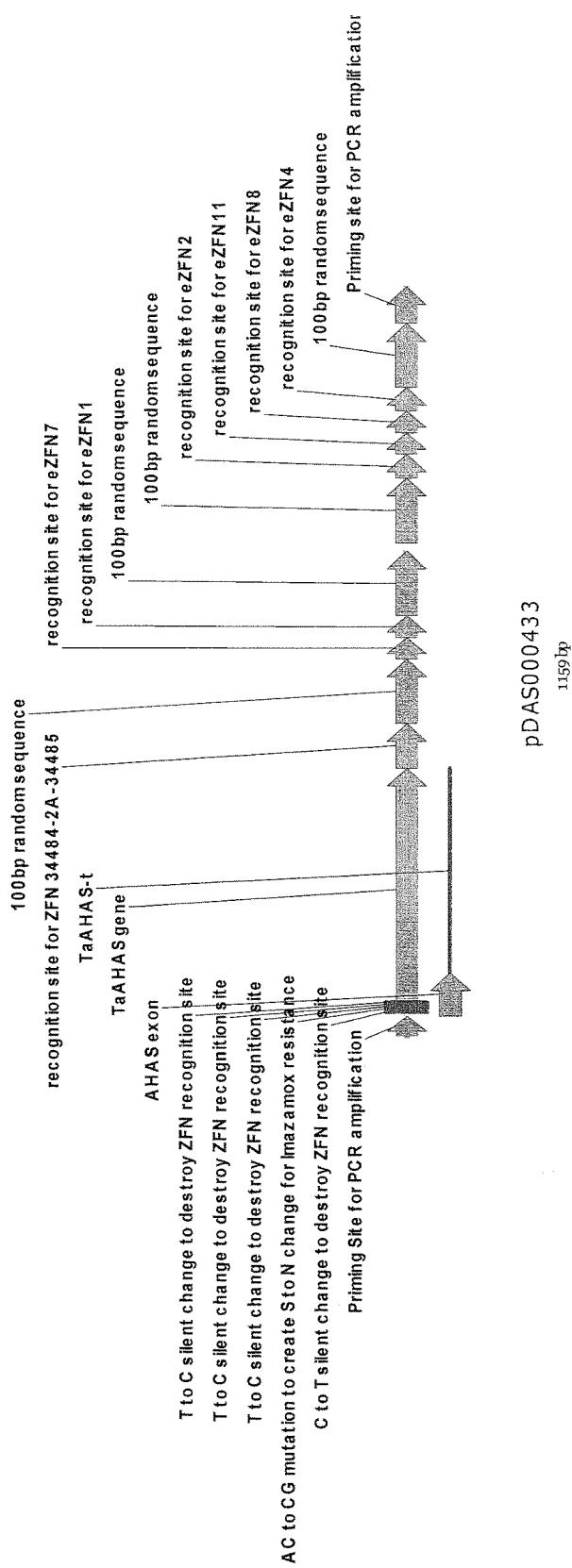
FIG. 17 shows a plasmid map of pDAS000433.

Design and Synthesis of Donor DNA for First Sequential Transgene Stacking at an Endogenous AHAS Locus Using NHEJ-Directed DNA Repair The donor DNA for the first round of transgene stacking is designed to promote precise donor integration at an endogenous AHAS locus via ZFN-mediated, NHEJ-directed repair. The design is based on the integration of a double stranded donor molecule at the position of the double strand DNA break created by cleavage of a homoeologous copy of the endogenous AHAS gene by ZFNs 29732 and 29730 (encoded on plasmid pDAB109350). The donor molecule (pDAS000433; SEQ ID NO:333, FIG. 17) several portions of polynucleotide sequences. The 5' end contains sequence near identical to the endogenous AHAS gene encoded in the D-genome, starting from the target ZFN cleavage site and finishing at the AHAS stop codon. Seven deliberate mutations are introduced into this sequence: two mutations encode the S653N mutation and five codon-optimized, synonymous mutations positioned across the binding site of ZFN 29732 to prevent re-cleavage of the integrated donor. Following the stop codon is 316-bp of non-coding sequence corresponding to the conserved 3' untranslated region (3'UTR) across the AHAS homoeologs. The 3'UTR sequence is followed by Zinc Finger binding sites for ZFNs 34480 and 34481 (encoded on plasmid pDAB111860) and ZFNs 34482 and 34483 (encoded on plasmid pDAB111861). These Zinc Finger binding sites allow for self-excision of donor-derived AHAS (coding and 3'UTR) sequence integrated at the endogenous locus during the next round of transgene stacking. The self-excision Zinc Finger binding sites are followed by several additional Zinc Finger binding sites (each of which is separated by 100-bp of random sequence) that flank two unique restriction endonuclease cleavage sites and which enable the insertion of a transgene expression cassette (e.g. the PAT expression cassette, as described previously) into the donor molecule. The additional Zinc Finger binding sites enable future excision of transgenes integrated at an AHAS locus by sequential marker-free transgene stacking, or continued sequential transgene stacking at the same genomic location using an alternate stacking method.

The donor cassette is synthesized by a commercial gene service vendor (e.g., GeneArt, Life Sciences, etc.) with a short stretch of additional flanking sequence at the 5' and 3' ends to enable generation of a donor molecule with protruding 5' and 3' ends that are compatible with the ligation overhangs generated by ZFNs 29732 and 29730 (encoded on plasmid pDAB109350) upon cleavage of an endogenous AHAS locus. The donor molecule with protruding 5' and 3' ends is generated by digesting plasmid DNA containing the donor molecule with the restriction endonuclease BbsI using standard methods known to the person having skill in the art.

Figure 18:
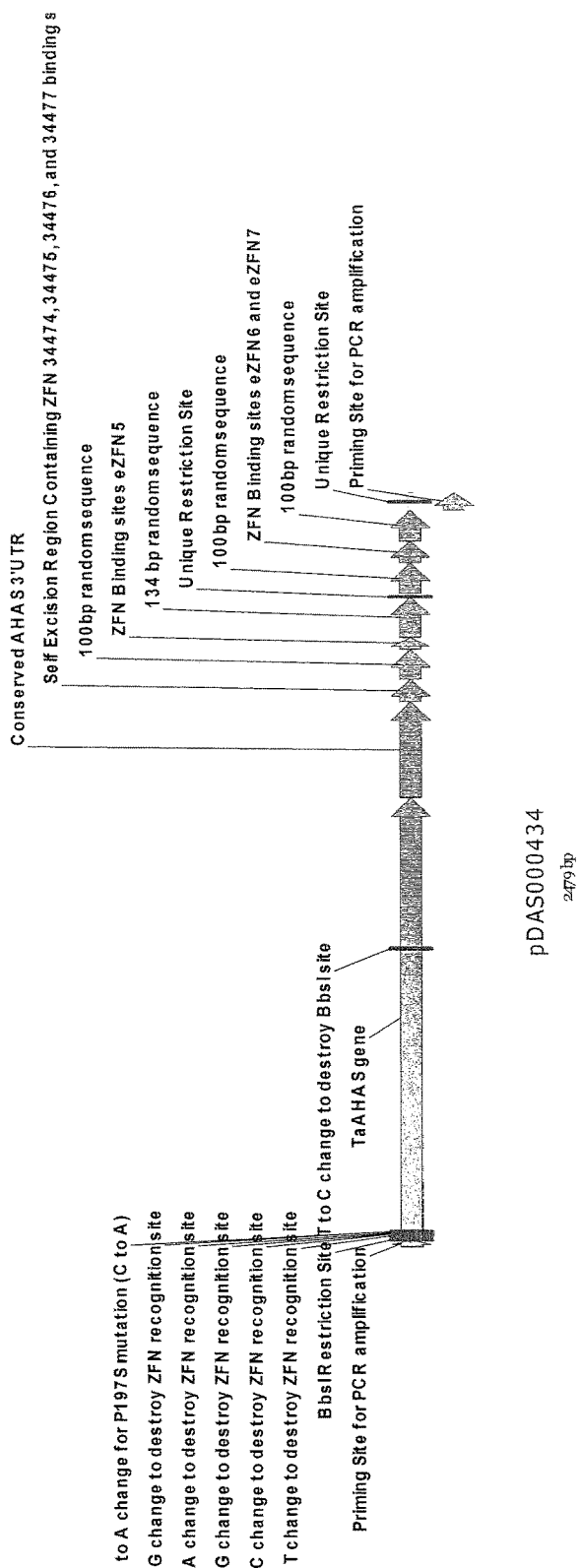
FIG. 18 shows a plasmid map of pDAS000434.

Design and Synthesis of Donor DNA for Second Sequential Transgene Stack at an Endogenous AHAS Locus Using NHEJ-Directed DNA Repair The donor DNA for the second round of transgene stacking is designed to promote precise donor integration at the same AHAS locus targeted in the first transgene stack via ZFN-mediated, NHEJ-directed repair. The design is based on the integration of a double stranded donor molecule at the double strand DNA break created by cleavage of the AHAS gene copy containing the first stacked transgene by ZFNs 34480 and 34481 (encoded on plasmid pDAB111860) or ZFNs 34482 and 34483 (encoded on plasmid pDAB111861). The donor molecule (pDAS000434; SEQ ID NO:334, FIG. 18) comprises several portions of polynucleotide sequences. The 5' end contains sequence near identical to the endogenous AHAS gene encoded in the D-genome, starting from the target ZFN cleavage site and finishing at the AHAS stop codon. Several deliberate mutations are introduced into this sequence: mutations encoding the P197S mutation and codon-optimized, synonymous mutations positioned across the binding site of ZFNs 34481 and 34483 to prevent re-cleavage of the integrated donor. Following the stop codon is 316-bp of non-coding sequence corresponding to the conserved 3' untranslated region (3'UTR) in the AHAS homoeologs. The 3'UTR sequence is followed by Zinc Finger binding sites for ZFNs 34474 and 34475 (encoded on plasmid pDAB111857) and ZFNs 34476 and 34477 (encoded on plasmid pDAB111858). These Zinc Finger binding sites allow for self-excision of donor-derived AHAS (coding and 3'UTR) sequence integrated at an endogenous locus in the next round of transgene stacking. The self-excision Zinc Finger binding sites are followed by several additional Zinc Finger binding sites (each of which is separated by 100-bp of random sequence) that flanks unique restriction endonuclease cleavage sites and which enable insertion of a transgene expression cassette (e.g. the DGT-28 expression cassette, as described in Patent Application Number 13757536). The additional Zinc Finger binding sites enable future excision of transgenes which can be integrated at an AHAS locus by sequential marker-free transgene stacking, or continued sequential transgene stacking at the same genomic location using an alternate stacking method. The donor cassette is synthesized by a commercial gene service vendor (e.g., GeneArt, Life Sciences) with a short stretch of additional flanking sequence at the 5' and 3' ends to enable generation of a donor molecule with protruding 5' and 3' ends that are compatible with the ligation overhangs generated by ZFNs 34474 and 34475 (encoded on plasmid pDAB111857) or ZFNs 34476 and 34477 (encoded on plasmid pDAB111858), upon cleavage of an endogenous AHAS locus. The donor molecule with protruding 5' and 3' ends is generated by digesting plasmid DNA containing the donor molecule with the restriction endonuclease BbsI using standard methods known to one in the art.

Figure 19A:
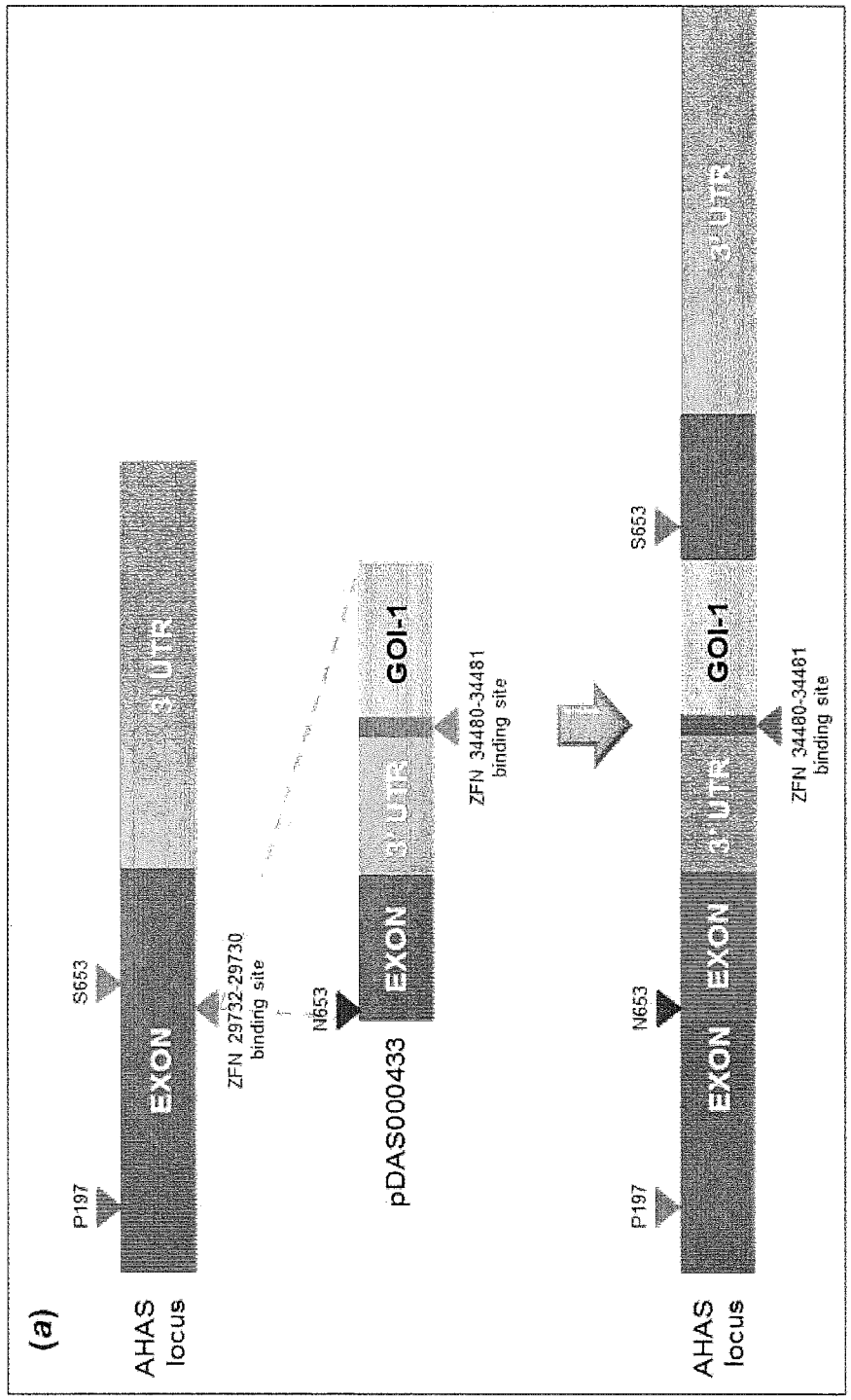
FIG. 19A depicts the first transgene stack.
Figure 19B:
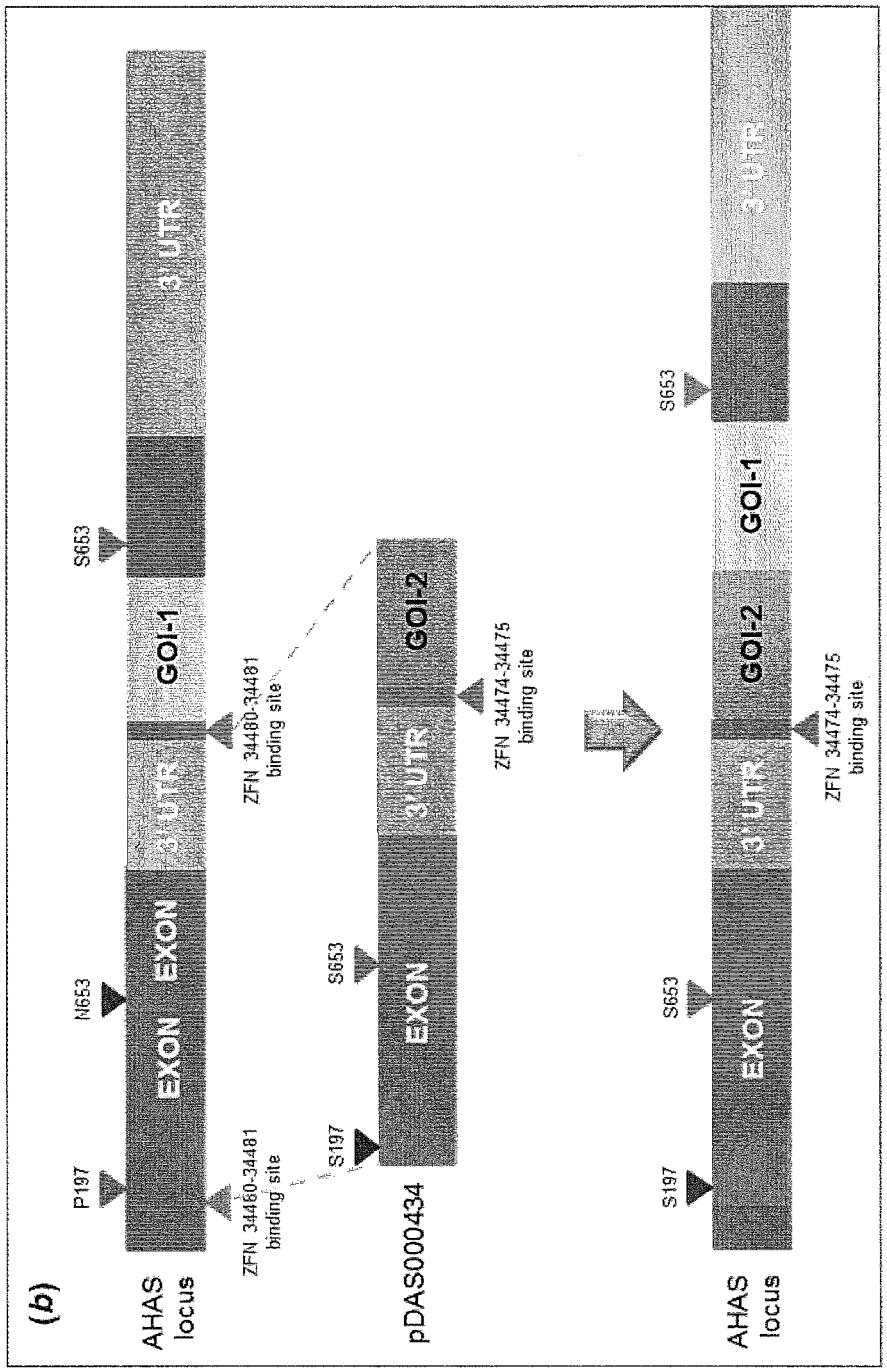
FIG. 19B depicts the second transgene stack.

Transformation System for Exogenous Marker-Free, Sequential Transgene Stacking at an Endogenous AHAS Locus in Wheat Using NHEJ-Directed DNA Repair Transgenic wheat events with multiple transgenes stacked at the same endogenous AHAS locus are produced by exogenous marker-free, sequential transgene stacking via transformation with donor pDAS000433 and ZFNs 29732 and 29730 (encoded on plasmid pDAB109350). Precise ZFN-mediated, NHEJ-directed donor integration introduces the first transgene and S653N mutation conferring tolerance to imidazolinones at an AHAS locus, thus allowing for the regeneration of correctly targeted plants using IMAZAMOX® as a selection agent, as previously described. FIG. 19a depicts the integration. Subsequent transformation of wheat cells, derived from first transgene stacked events, with donor pDAS000434 and ZFNs 34480 and 34481 (encoded on plasmid pDAB111860) results in the replacement of the endogenous chromatin located between the ZFN binding sites positioned upstream of P197 and at the self-excision site integrated during the first transgene stack with the donor molecule. This results in integration of the second transgene and a P197S mutation conferring tolerance to sulfonylurea, thus allowing for the regeneration of correctly targeted plants using sulfometuron methyl as a selection agent. At the same time, integration of the second donor removes the S653N mutation, thus restoring susceptibility to imidazolinones (FIG. 19B). One skilled in the art will appreciate that stacking of a third transgene can be achieved by transformation with appropriate zinc finger nucleases and a donor that contains an additional transgene and confers susceptibility to sulfonylurea and tolerance to imidazolinones, thus allowing the regeneration of correctly targeted plants using IMAZAMOX® as a selection agent. As such, continued rounds of sequential transgene stacking are possible via transformation with donors that introduce transgenes and mutations in the endogenous AHAS genes for differential cycling between imidazolinone and sulfonylurea selection agents.

Figure 21:
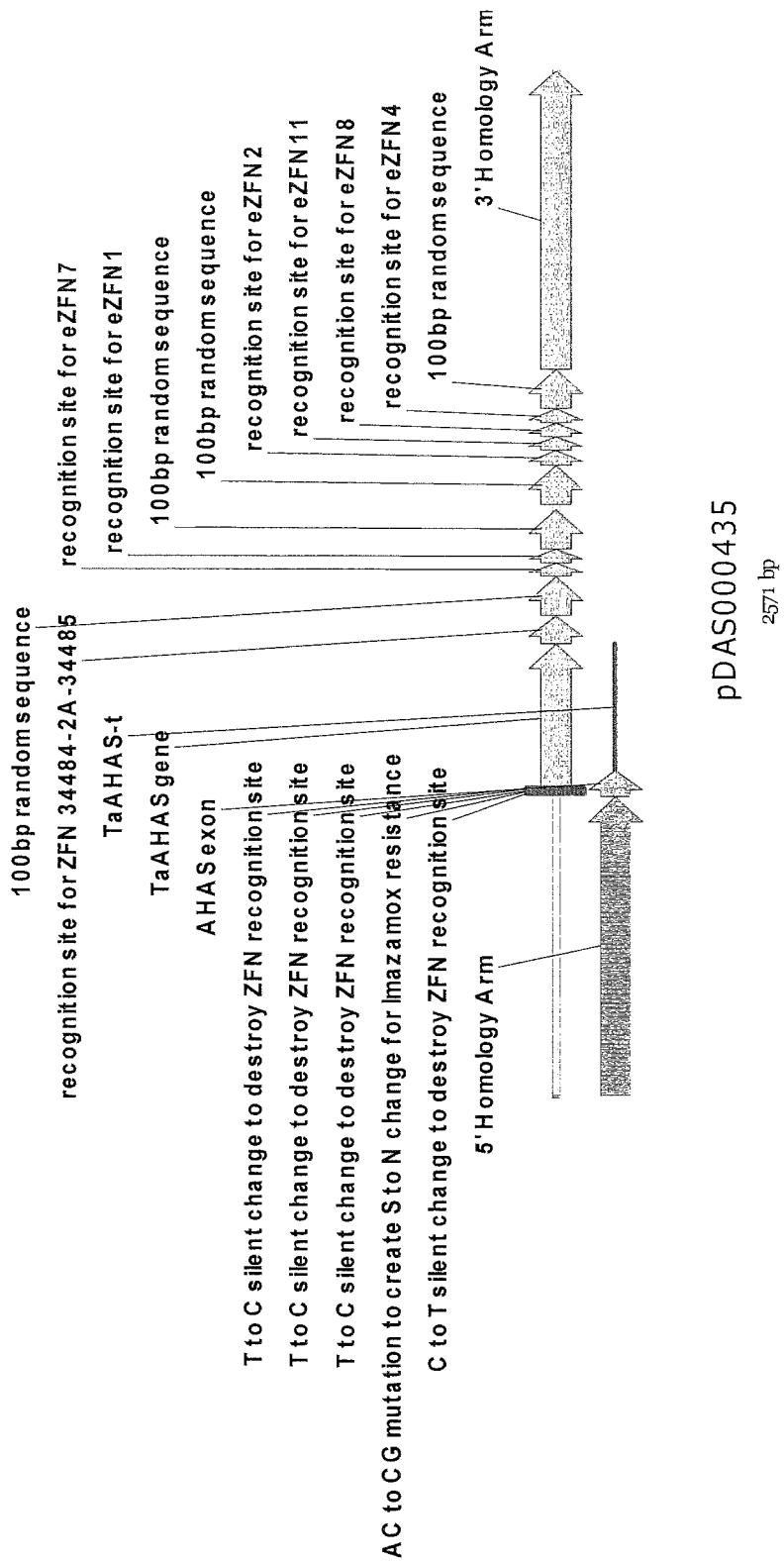
FIG. 21 shows a plasmid map of pDAS000435.

Design and Synthesis of Donor DNA for First Sequential Transgene Stacking at an Endogenous AHAS Locus Using HDR-Directed DNA Repair The donor DNA for the first round of transgene stacking is designed to promote precise donor integration at an endogenous AHAS locus via ZFN-mediated repair. The design is based on the integration of a double stranded donor molecule at the position of the double strand DNA break created by cleavage of a homoeologous copy of the endogenous AHAS gene by ZFNs 29732 and 29730 (encoded on plasmid pDAB109350). The donor molecule (pDAS000435; SEQ ID NO: 335, FIG. 21) is identical in sequence to pDAS000433 (SEQ ID NO:333).

Figure 20A:
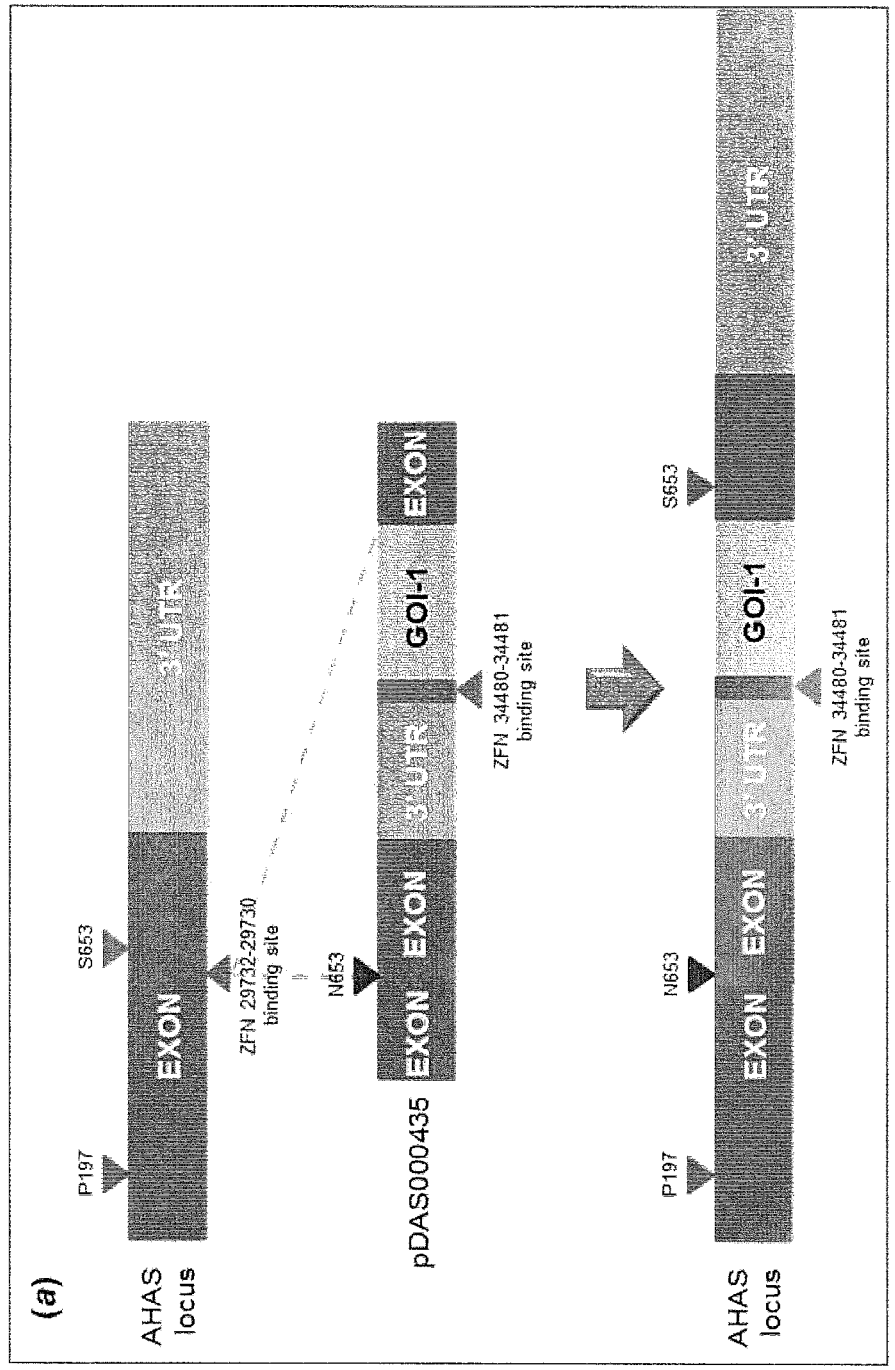
FIG. 20A depicts the first transgene stack.
Figure 20B:
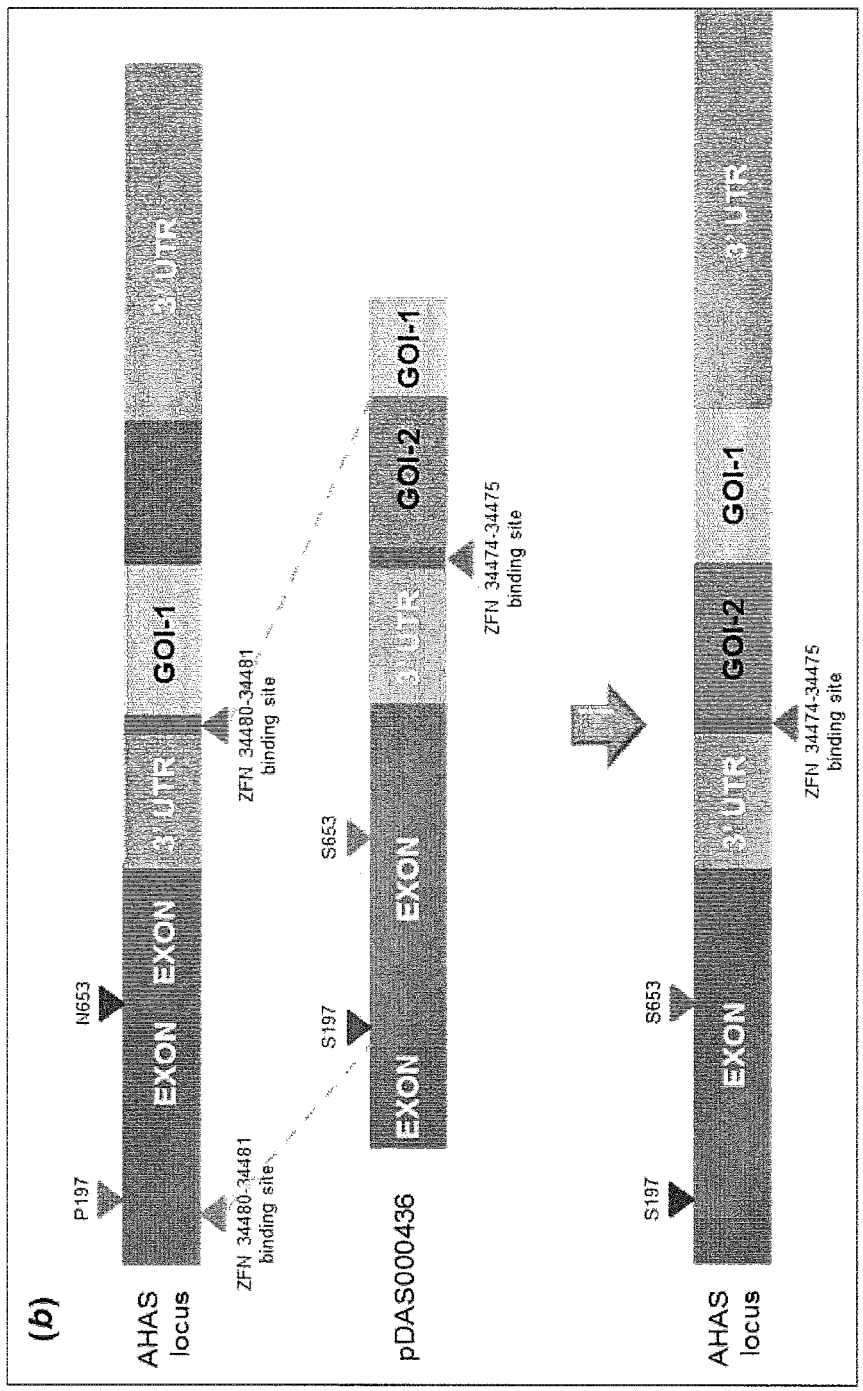
FIG. 20B depicts the second transgene stack.

Transformation System for Exogenous Marker-Free, Sequential Transgene Stacking at an Endogenous AHAS Locus in Wheat Using HDR-Directed DNA Repair Transgenic wheat events with multiple transgenes stacked at the same endogenous AHAS locus are produced by exogenous marker-free, sequential transgene stacking via transformation with donor pDAS000435 and ZFNs 29732 and 29730 (encoded on plasmid pDAB109350). Precise ZFN-mediated, HDR-directed donor integration introduces the first transgene and S653N mutation conferring tolerance to imidazolinones at an AHAS locus, thus allowing for the regeneration of correctly targeted plants using IMAZAMOX® as a selection agent, as previously described. FIG. 20a depicts the integration. Subsequent transformation of wheat cells, derived from first transgene stacked events, with donor pDAS000436 and ZFNs 34480 and 34481 (encoded on plasmid pDAB111860) results in the replacement of the endogenous chromatin located between the ZFN binding sites positioned upstream of P197 and at the self-excision site integrated during the first transgene stack with the donor molecule. This results in integration of the second transgene and a P197S mutation conferring tolerance to sulfonylurea, thus allowing for the regeneration of correctly targeted plants using sulfometuron methyl as a selection agent. At the same time, integration of the second donor removes the S653N mutation, thus restoring susceptibility to imidazolinones (FIG. 20b). As will be obvious to one skilled in the art, stacking of a third transgene can be achieved by transformation with appropriate zinc finger nucleases and a donor that contains an additional transgene and confers susceptibility to sulfonylurea and tolerance to imidazolinones, thus allowing the regeneration of correctly targeted plants using IMAZAMOX® as a selection agent. As such, continued rounds of sequential transgene stacking are possible via transformation with donors that introduce transgenes and mutations in the endogenous AHAS genes for differential cycling between imidazolinone and sulfonylurea selection agents.

Artificial Crossing and Molecular Analysis to Recover Transgenic Plants with Specific Combinations of Precise Genome Modifications The *Triticum aestivum* events which are produced via transformation with donor DNA and zinc finger nuclease constructs result in the integration of donor molecule sequence at one or more copies the target endogenous locus. As shown previously, ZFN-mediated genome modification can include simultaneous editing of multiple alleles across multiple sub-genomes. Artificial crossing of transformation events can be subsequently used to select for specific combinations of precise genome modifications. For example, artificial crossing of transformation events produced that have precisely modified AHAS genes with the S653N mutation can be used to produce wheat plants that have the S653N mutation on a specific sub-genome, on multiple sub-genomes, or on all three sub-genomes. Subsequent artificial crossing of transformation events facilitates the generation plants that have specific combinations of precise genome modifications. One skilled in the art can deploy molecular assays, such as those previously described, to track the inheritance of specific genome modification during artificial crossing in subsequent generations.

Example 7: Targeted Integration into and Disruption of *Brassica napus* Omega-3 Fatty Acid Desaturase (Fad3)

Selection of Zinc Finger Binding Domains Specific to Fad3C and Fad3A

The transcribed regions for homoeologous Fad3 genes were identified and characterized, zinc finger nucleases that were designed to bind and cleave these sites for NHEJ-mediated targeting of a donor sequence as described herein were designed and constructed. See, U.S. Provisional Patent Filing No. 61/697,854, herein incorporated by referenced. Zinc finger proteins (ZFPs) directed against DNA sequences from homeologues of Fad3 sequences were designed and tested as previously described in the U.S. Provisional Patent Filing No. 61/697,854. From the ZFNs showing on-target activity, two zinc finger proteins were selected that cut the Fad3 target at high efficiency: ZFP 28051-2A-28052 recognizes SEQ ID NO:336 5'-GCCCAAGGAAC-CCTTTTCTGGGCCATCTTCGTACTCGGCCAC-GACTGGTAATT TAAT-3' and was previously shown to specifically bind and cleave the Fad3C genomic locus. Likewise Zinc finger protein 28053-2A-28054 recognizes SEQ ID NO:337 5'-AGCGAGAGAAAGCTTATTG-CAACTTCAACTACTTGCTGGTCGATCGTGTTGGC CACTC-3' and was previously shown to specifically bind and cleave the Fad3A and Fad3C genomic locus. Nucleotides in the target sites that are contacted by the ZFP recognition helices are shown in Table 16.

TABLE 16

Zinc Finger Protein Binding Sites specific to Fad3C (28051-2A-28052) or Fad3A and Fad3C (28053-2A-28054). Nucleotides in the target site that are contacted by the ZFP recognition helices are indicated in uppercase letters; non-contact nucleotides are indicated in lowercase. Nucleotides in copies of Fad3 that differ from Fad3C are identified by underlining.

| | | | |
|---|---|---|---|
| 28051-2A-28052 | SEQ ID NO: | SEQ ID NO: 356 | gcccaaggaacCCTTTTCTGGGCCATct |
| | | SEQ ID NO: 357 | cgTACTCGGCCACGactggtaatttaat |
| Fad3C | | 338 | GCCCAAGGAACCCTTTTCTGGGCCATCTTCGTACTCGGC CACGACTGGTAATTTAAT |
| Fad3A | | 339 | GCCCAAGGAACCCT<u>G</u>TTCTGGGC<u>T</u>ATCTTCGTACTCGGC CACGACTGGTAATTTAAT |
| Fad3C' | | 340 | GCCCAAGGAACCCTTTTCTGGGCCATCTTCGT<u>CC</u>TCGGC CACGACTGGTAA<u>AGTTTC</u> |
| Fad3A' | | 341 | GCCCAAGGAACCCTTTTCTGGGCCATCTT<u>C</u>GTCCTCGGC CACGACTGGTAA<u>AGTTTC</u> |
| Fad3A" | | 342 | GCCCAAGGAACCCTTTTCTGGGCCATCTTCGT<u>T</u>CT<u>T</u>GGC CACGACTGGTAA<u>A</u>TTAA<u>A</u> |
| Fad3C" | | 343 | GCCCAAGGAACCCTTTTCTGGGCCATCTTCGT<u>T</u>CT<u>T</u>GGC CACGACTGGTAA<u>A</u>TTAA<u>A</u> |
| 28053-2A-28054 | SEQ ID NO: | SEQ ID NO: 358 | agcgagagaaAGCTTAtTGCAACTTCaa |
| | | SEQ ID NO: 359 | acTTGCTGGTCGATCGTGTTggccactc |
| Fad3C | | 344 | AGCGAGAGAAAGCTTATTGCAACTTCAACTACTTGCTG GTCGATCGTGTTGGCCACTC |

TABLE 16-continued

Zinc Finger Protein Binding Sites specific to Fad3C
(28051-2A-28052) or Fad3A and Fad3C (28053-2A-28054).
Nucleotides in the target site that are contacted by the
ZFP recognition helices are indicated in uppercase letters;
non-contact nucleotides are indicated in lowercase.
Nucleotides in copies of Fad3 that differ from Fad3C are
identified by underlining.

| | | |
|---|---|---|
| Fad3A | 345 | AGCGAGAGAAAGCTTATTGCAACTTCAACTACTTGCTG GTCGATCATGTTGGCCACTC |
| Fad3C' | 346 | AGCGAGAGAAAGCTTATTGCAACTTCAACTACTTGCTG GTCCATAATGTTGGCCATTC |
| Fad3A' | 347 | AGCGAGAGAAAGCTTATTGCAACTTCGACTACTTGCTG GTCCATAATGTTGGCAATTC |
| Fad3A" | 348 | AGCGAGAGGAAGCTTATTGCAACTTCAACAACTTGCTG GTCCATAATGTTGGCCACTC |
| Fad3C" | 349 | AGCGAGAGGAAGCTTATTGCAACTTCAACTACTTGCTG GTCCATAATGTTGGCCACTC |

Design and Construction of Expression Vectors Encoding Zinc Finger Nucleases Specific to Fad3C and Fad3A The Fad3 zinc finger designs were incorporated into zinc finger expression vectors encoding a protein having at least one finger with a CCHC structure (U.S. Patent Publication No. 2008/0182332). In particular, the last finger in each protein had a CCHC backbone for the recognition helix. The non-canonical, zinc finger-encoding-sequences were fused to the nuclease domain of the type IIS restriction enzyme FokI (amino acids 384-579 of the sequence of Wah et al., (1998) Proc. Natl. Acad. Sci. USA 95:10564-10569) via a four amino acid ZC linker and a sop2 nuclear localization signal. The self-hydrolyzing 2A encoding nucleotide sequence from Thosea asigna virus (Szymczak et al., 2004) was added between the two Zinc Finger Nuclease fusion proteins. Expression of the ZFNs was driven by the strong constitutive promoter and 5' untranslated region (UTR) from Cassava Vein Mosaic Virus (Verdaguer et al, Plant Molecular Biology 1996, 31(6); 1129-1139) and flanked by the 3' UTR (including the transcriptional terminator and polyadenylation site) from open reading frame 23 (ORF23) of Agrobacterium tumefaciens pTi15955 (Barker et al., Plant Molecular Biology 1983, 2(6); 335-50).

Figure 22:
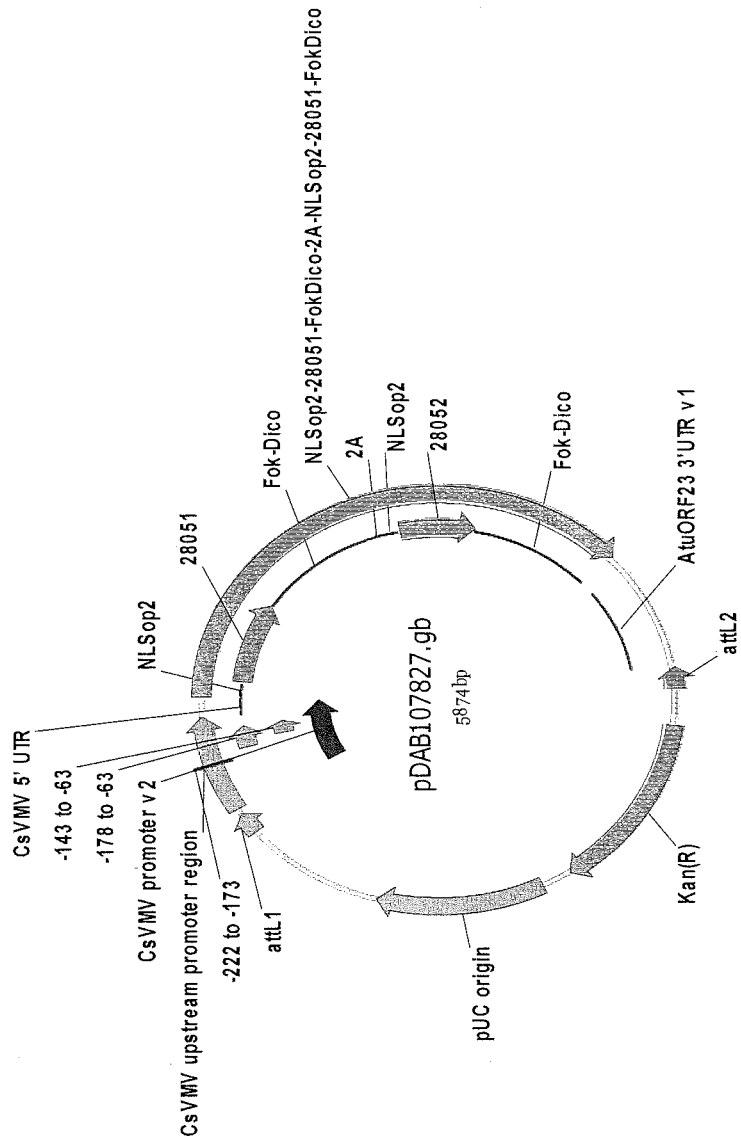
FIG. 22 shows a plasmid map of pDAB107827.
Figure 23:
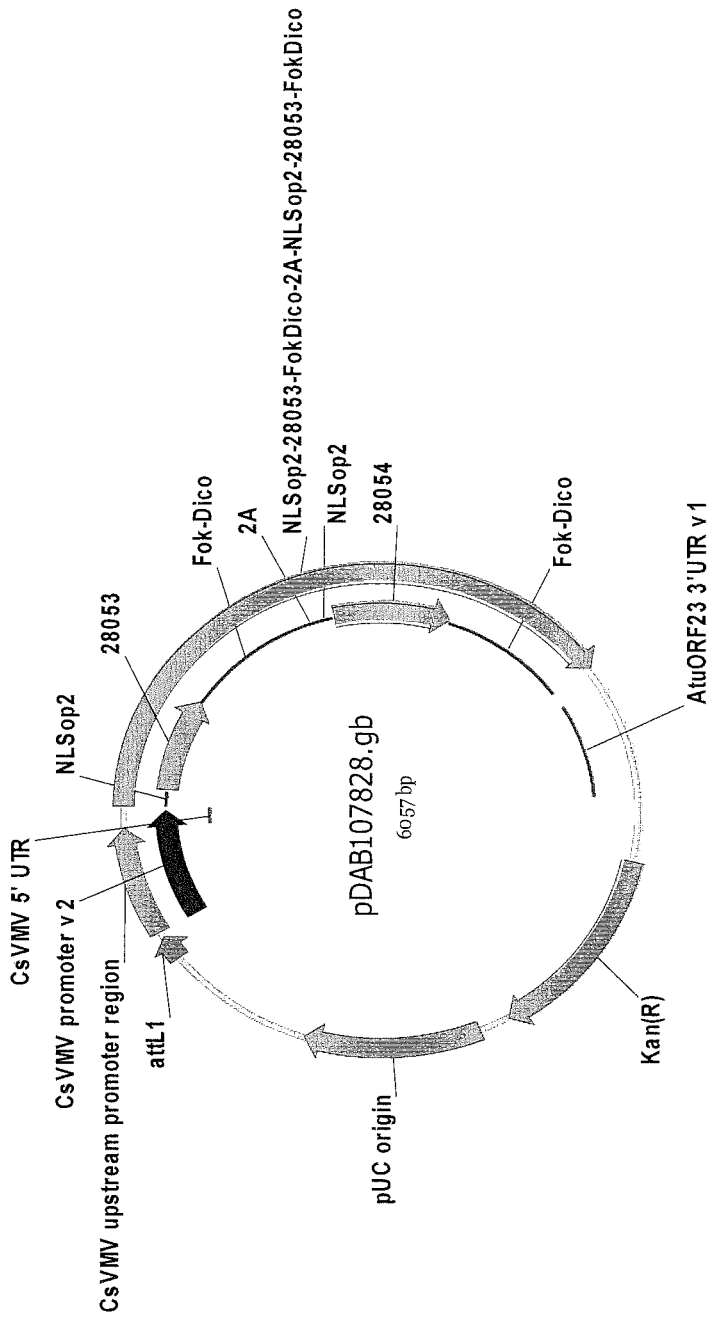
FIG. 23 shows a plasmid map of pDAB107828.

The vectors were assembled using the IN-FUSION™ Advantage Technology (Clontech, Mountain View, Calif.). Restriction endonucleases were obtained from New England BioLabs (NEB; Ipswich, Mass.) and T4 DNA Ligase (Invitrogen) was used for DNA ligation. Plasmid preparations were performed using NUCLEOSPIN® Plasmid Kit (Macherey-Nagel Inc., Bethlehem, Pa.) or the PLASMID MIDI KIT™ (Qiagen) following the instructions of the suppliers. DNA fragments were isolated using QIAQUICK GEL EXTRACTION KIT™ (Qiagen) after agarose Tris-acetate gel electrophoresis. Colonies of assembled plasmids were initially screened by restriction digestion of miniprep DNA. Plasmid DNA of selected clones was sequenced by a commercial sequencing vendor (Eurofins MWG Operon, Huntsville, Ala.). Sequence data were assembled and analyzed using the SEQUENCHER™ software (Gene Codes, Ann Arbor, Mich.). The resulting plasmid constructs: pDAB107827 (ZFN 28051-2A-28052, FIG. 22, SEQ ID NO:350) and pDAB107828 (ZFN 28053-2A-28054, FIG. 23, SEQ ID NO:351) were confirmed via restriction enzyme digestion and via DNA sequencing.

Design and Construction of "Donor" Vectors for NHEJ-Directed DNA Repair

Two strategies of integration of DNA into Fad3 were undertaken; gene splicing, where an expression cassette was inserted into a single ZFN-induced double-stranded break and gene-editing where a portion of the gene was removed by the use of two ZFN-induced double-stranded breaks and an expression cassette was inserted to repair the gap.

For each integration method, gene splicing or gene-editing, two vectors were constructed. The first encoded a turboGFP (tGFP) gene expression cassette and the second encoded a gene expression cassette to confer resistance to the antibiotic hygromycin. The tGFP expression cassette consisted of the promoter, 5' untranslated region and intron from the Arabidopsis thaliana polyubiquitin 10 (UBQ10) gene (Norris et al, Plant Molecular Biology 1993, 21(5), 895-906) followed by the tGFP coding sequence (Evrogen, Moscow, Russia). The tGFP coding sequence was codon-optimized for expression in dicot plants and the 3' untranslated region (UTR) comprising the transcriptional terminator and polyadenylation site of open reading frame 23 (ORF23) of A. tumefaciens pTi15955 (Barker et al, Plant Molecular Biology 1983, 2(6), 335-50). The hygromycin resistance gene expression cassette consisted of the 19S promoter including a 5' UTR from cauliflower mosaic virus (CaMV) (Cook and Penon Plant Molecular Biology 1990 14(3), 391-405) followed by the hygromycin phosphotransferase (hph) gene (Kaster et al Nucleic Acids Research 1983 11 (19), 6895-6911). The hph gene been codon-optimized for expression in dicots and was flanked by a 3'UTR comprising the transcriptional terminator and polyadenylation site of Open Reading Frame 1 (ORF1) of A. tumefaciens pTi15955 (Barker et al, Plant Molecular Biology 1983, 2(6), 335-50). Both cassettes were synthesized by a commercial gene synthesis vendor (GeneArt, Life Technologies, Regensberg, Germany).

Figure 24:
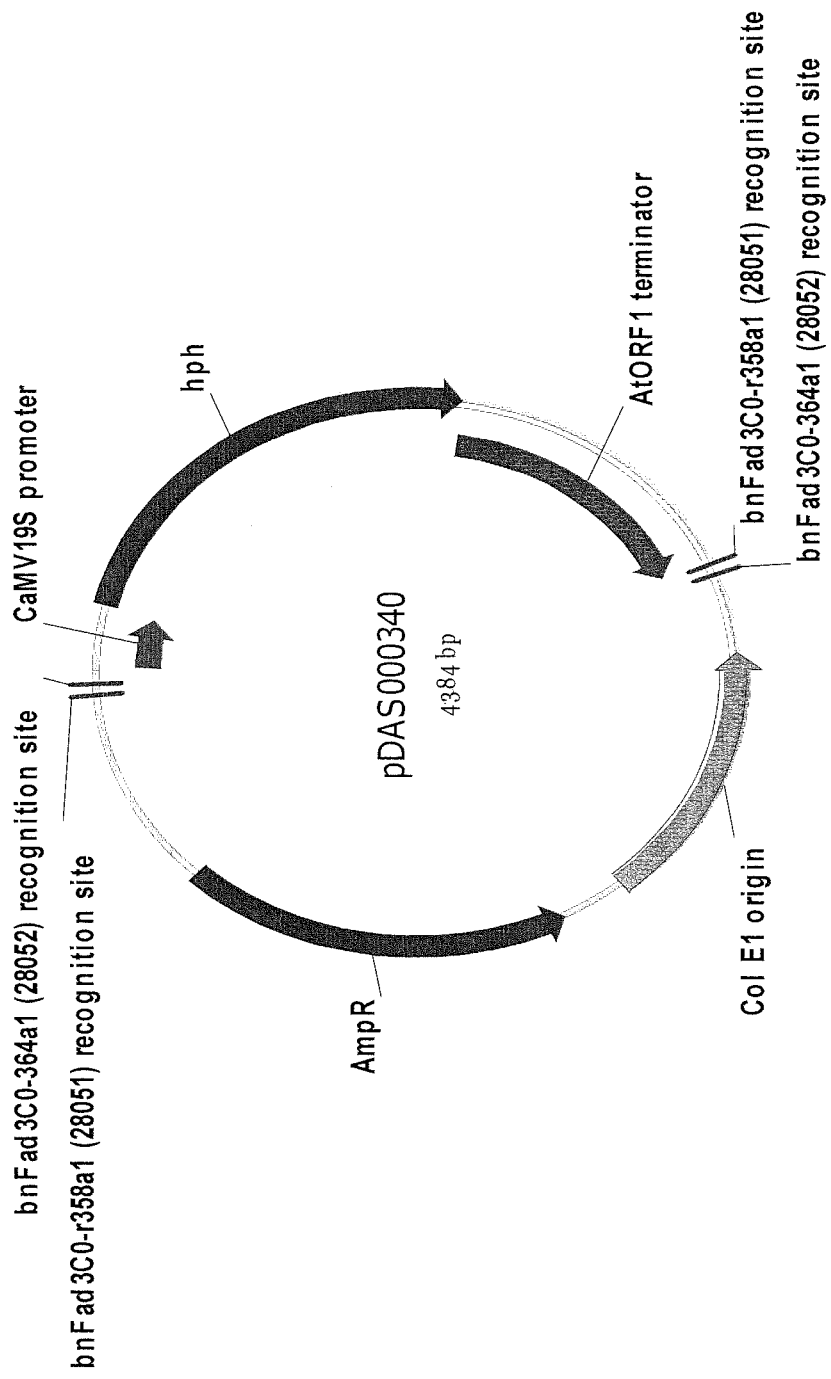
FIG. 24 shows a plasmid map of pDAS000340.
Figure 25:
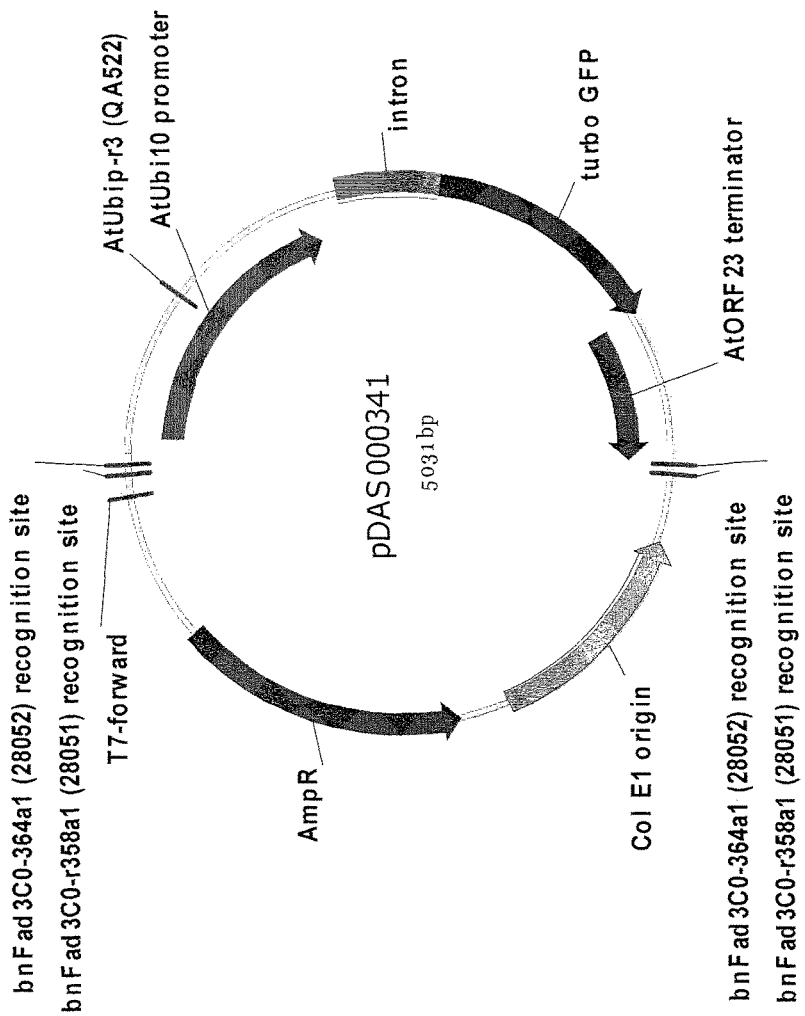
FIG. 25 shows a plasmid map of pDAS000341.
Figure 26:
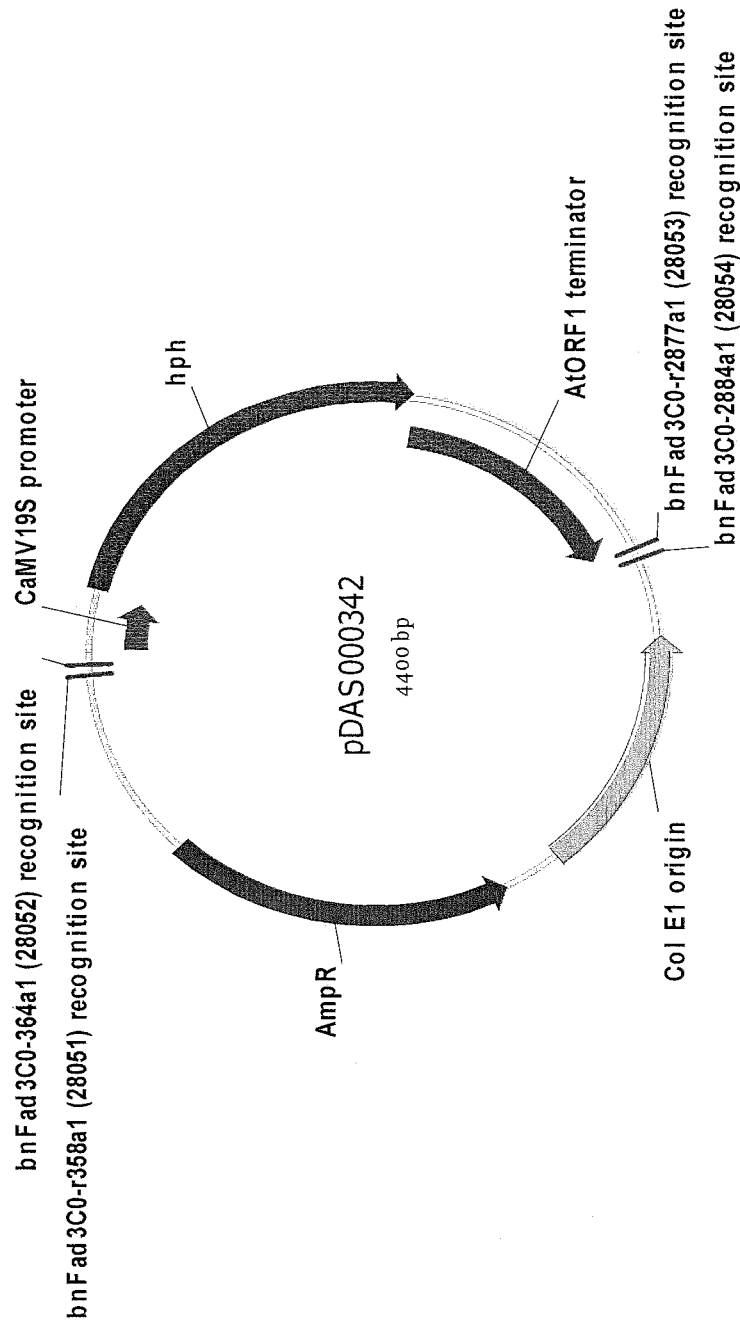
FIG. 26 shows a plasmid map of pDAS000342.
Figure 27:
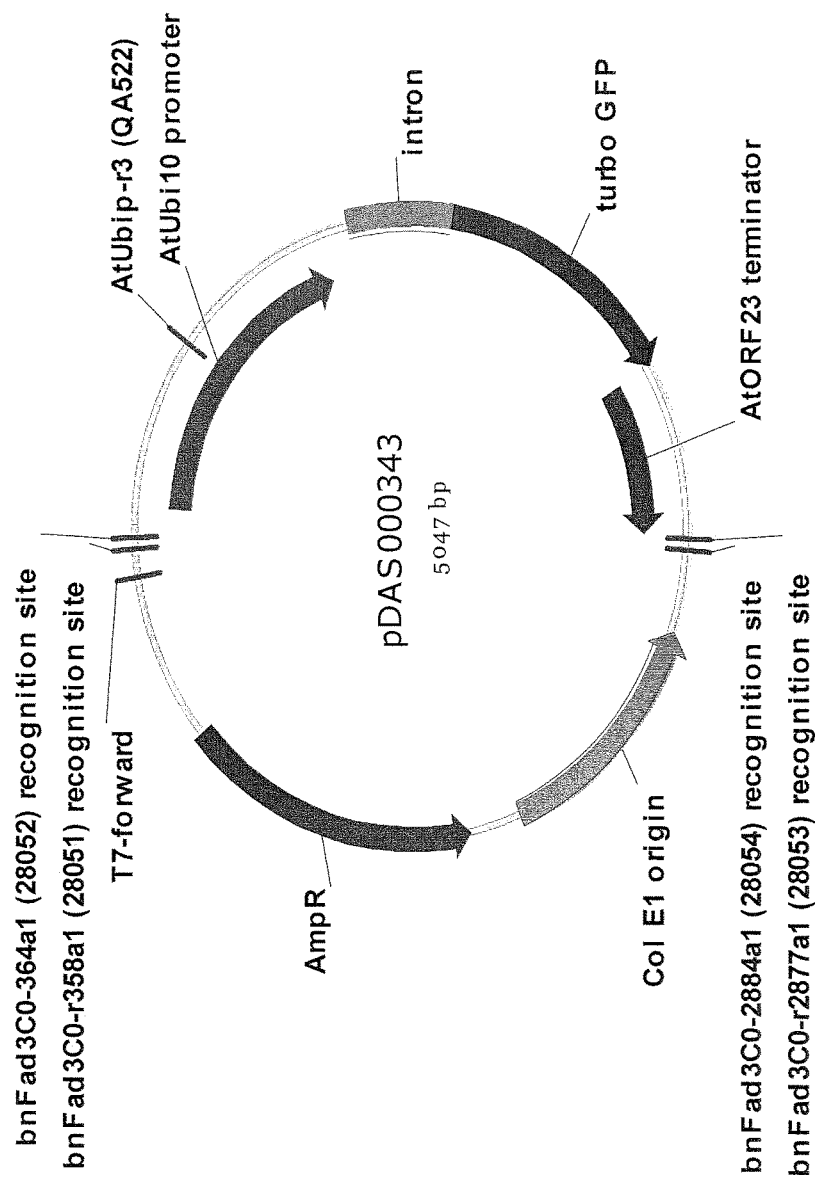
FIG. 27 shows a plasmid map of pDAS000343.

Vectors for gene splicing were constructed by cloning two tandem copies of the ZFN recognition sequence targeted by the ZFN encoded in the vector pDAB10782. Vectors for gene editing were constructed by cloning one copy of each of the ZFN recognition sequences targeted by the ZFNs encoded in the vectors pDAB107827 and pDAB107828. In both cases the two ZFN recognition sequences were separated by the recognition sequences for BamHI and NotI restriction endonucleases. The tGFP and HPH cassettes were cloned into the BamHI and NotI sites of each vector resulting in four "donor" vectors: pDAS000340 (hygromycin-resistant gene-splicing donor: SEQ ID NO:352, FIG. 24), pDAS000341 (tGFP reporter gene splicing donor: SEQ ID NO:353, FIG. 25), pDAS00342 (hygromycin-resistant gene-editing donor: SEQ ID NO:354, FIG. 26) and pDAS000343 (tGFP reporter gene editing donor: SEQ ID NO:355, FIG. 27).

Colonies of the assembled plasmids were initially screened by restriction endonuclease digestion of DNA purified from overnight cultures of *E. coli*. Restriction endonucleases were obtained from New England BioLabs (NEB, Ipswich, Mass.) and Promega (Promega Corporation, WI). Plasmid preparations were performed using the QIAPREP SPIN MINIPREP KIT™ (Qiagen, Hilden, Germany) or the PURE YIELD PLASMID MAXIPREP SYSTEM™ (Promega Corporation, WI) following the instructions of the suppliers. After the restriction fragments were confirmed by agarose gel electrophoresis of resulting fragments, plasmid DNA of selected clones were sequenced using ABI Sanger Sequencing and BIG DYE TERMINATOR V3.1™ cycle sequencing protocol (Applied Biosystems, Life Technologies). Sequence data were assembled and analyzed using the Sequencher™ software (Gene Codes, Ann Arbor, Mich.).

Maintenance of Plant Material for Protoplast Isolation

Mesophyll derived protoplasts were isolated from three-week old sterile shoot cultures of *Brassica napus* (DH10275). The corresponding seeds were germinated following the methods herein described. The seeds were surface-sterilized using 70% ethanol for 1 minute and gently shaken followed by 3-4 rinses in sterile double-distilled water. The seeds were subsequently sterilized using 20% bleach and 10 µl of Tween 20. The seeds were further treated with the bleach on a table top shaker at approximately 100 RPM, for 15 minutes followed by 3-4 rinses in sterile double-distilled water, seeds were carefully transferred to a sterile filter paper to remove the excess moisture and plated on seed germination medium (½ strength MS/B5 Vitamins+1% sucrose+0.8% Agar; pH 5.8.

Approximately, 50-60 ml of media was poured into each PETRI™ dish (15×100 mm) and placed with a slight angle using a support). Approximately 50 seeds were placed per plate. The plates were incubated upright at 22° C. in 16 h/d light (20 µmol m$^{-2}$ s$^{-1}$) for 6 days. Hypocotyl segments of 0.5 cm size were dissected from the six day old seedlings and cultured on shoot induction medium (MS/B5 Vitamins+3% sucrose+500 mg/L MES+BAP (13 µm)+Zeatin (5 µm)+Silver Nitrate (5 mg/L)+0.8% Agar (pH 5.8). The medium was poured in 100×20 mm sterile PETRI™ dish; approximately 20 explants were placed per plate. Shoot meristems that appeared after 3-4 weeks were transferred to shoot elongation medium (MS/B5 Vitamins+2% sucrose+500 mg/L MES+BAP (2 µm)+GA-3 (0.1 µm)+0.8% Agar (pH 5.8) and poured in 250 ml culture vessels) and the cultures were maintained in this medium for 4 weeks with one round of sub-culturing in between. Shoots of 2-3 cm height were then transferred to root initiation media (½ strength MS/B5 Vitamins+1% sucrose+500 mg/L MES+IBA (2.5 µm)+0.6% Agar (pH 5.8) and poured in 700 ml culture vessels) for root development. Rooted shoots were sub-cultured in fresh root initiation media at 3-4 weeks intervals as stem cuttings for two-three rounds before use. The cultures were maintained throughout at 22° C. in 16 h/d light (30 µmol m$^{-2}$ s$^{-1}$).

Isolation and Purification of Mesophyll Protoplasts

In vitro grown DH12075 *Brassica napus* plants were used as the explant source for isolating mesophyll protoplasts. To isolate the protoplasts, the 3rd to 4$^{th}$ upper fully expanded leaves from 3-4 weeks old plantlets were cut with a sharp scalpel into small strips (0.5 to 1 mm) for protoplast isolation. Enzymatic digestion was carried out by treating 250-500 mg of leaf material with 25 ml of digestion buffer (1.2% (w/v) Cellulase "ONOZUKA™" R10 and 0.2% (w/v) MACEROZYME® R10 (Source—Duchefa) dissolved in K4 media (Spangenberg et al., 1998)). The PETRI™ dish containing the leaf material and digestion buffer was sealed with PARAFILM™ and incubated at room temperature for 12 to 15 h in darkness. After overnight incubation the digests were filtered through a BD® cell strainer (mesh size 70 µm). Protoplast suspensions (5-6 ml) collected in a 14 ml round bottomed tube was over layered with 1 ml of W5 washing buffer (154 mM NaCl, 125 mM CaCl$_2$, 5 mM KCl and 5 mM glucose; pH 5.8 Menzel et al. (1981)).

The protoplast suspensions were further centrifuged at 400 RPM for 10 min. After centrifugation, protoplasts that floated in the interphase were withdrawn and washed by centrifugation using 10 ml of W5 buffer at 400 RPM for 10 min. After the final wash, isolated protoplasts were resuspended at a density of 1×10$^6$ protoplasts per mL of W5 buffer and incubated for 1 hour before transfections.

Assessment of Protoplast Yield and Viability

Protoplasts yield was assessed using a haemocytometer following the method of Sambrook and Russell, (2006). The cell viability was tested using 400 mg/L of Evans blue stain dissolved in 0.5 M of Mannitol as described by Huang et al. (1996) with few minor modifications to the protocol.

PEG 4000 Mediated DNA Delivery

Before delivery to *B. napus* protoplasts, plasmid DNA of each donor and ZFN construct was prepared from cultures of *E. coli* using the PURE YIELD PLASMID MAXIPREP SYSTEM® (Promega Corporation, Madison, Wis.) following the instructions of the suppliers. Aliquots of donor and ZFN plasmid DNA were prepared in three molar ratios: 1:1 (30 µg of each plasmid), 5:1 (donor plasmid to ZFN plasmid to a total of 30 µg of plasmid DNA) and 10:1 (donor plasmid to ZFN plasmid to a total of 30 µg of plasmid DNA). Additionally, donor-only and ZFN-only aliquots (30 µg) were prepared as controls. The amounts of DNA delivered to the *B. napus* protoplasts via the PEG4000 mediated transformation are summarized in Table 17.

TABLE 17

Quantities of ZFN and donor DNA delivered to protoplasts

| | Molar Ratio of plasmid DNA | Total quantity of DNA (µg) delivered to 1 million protoplasts |
|---|---|---|
| Splicing | Donor plasmid only | 30 |
| | ZFN plasmid only (pDAB107827) | 30 |
| | 1:1 Donor:ZFN | 60 |
| | 5:1 Donor:ZFN | 30 |
| | 10: Donor:ZFN | 30 |
| Editing | Donor plasmid only | 30 |
| | 1:1: ZFN plasmids (pDAB107827 and pDAB107828) | 30 |
| | 1:1:1 Donor:ZFN:ZFN | 90 |
| | 5:1:1 Donor:ZFN:ZFN | 30 |
| | 10:1:1 Donor:ZFN:ZFN | 30 |

Each aliquot of plasmid DNA was applied to one million protoplasts (viability≥95) suspended in 100 µl of transformation buffer (15 mM MgCl$_2$, 0.1% (w/v) morpholinoethanesulphonic acid (MES) and 0.5 M Mannitol; pH 5.8) followed by 150 µl of PEG solution (40% (w/v) PEG 4000 in 0.4 M Mannitol and 0.1 M Ca (NO$_3$)$_2$ (pH 6-7) Spangenberg and Potrykus (1995). After 10-15 min of incubation at room temperature, 5 ml of W5 buffer was added in a drop wise manner and the protoplasts were gently mixed. Another 5 ml of W5 buffer was added as a slow stream to the protoplasts suspension. Protoplasts were mixed gently and centrifuged at 400 RPM for 10 min and the W5 supernatant was removed carefully leaving behind the protoplasts in the form of a pellet. Transfected protoplasts were then incubated in 1 ml of W5 buffer at room temperature until they were embedded in bead type cultures. The transfected protoplasts were embedded following the sodium alginate method as described below.

Culturing of Mesophyll Derived Protoplasts to Recover Viable Microcalli

Before embedding the transfected protoplasts were centrifuged at 400 RPM for 10 min and the W5 buffer was carefully removed. The protoplasts were then resuspended in 1.0 ml of 0.5 M Mannitol and incubated on ice. To this equal volume of 1.0% sodium alginate was added and mixed gently. The protoplasts suspension was incubated in ice until it was embedded. Bead forming solution (0.4 M Mannitol+50 mM $CaCl_2$ (pH 5.8)) was transferred to a sterile six well plate (3-4 ml per well) using a serological pipette. Exactly 1.0 ml of the protoplasts suspension was added in a drop wise manner using a 1 ml pipette into the bead forming solution and each transfected sample (ca. $5\times10^5$ protoplasts) was embedded per well. The protoplasts suspension was incubated for 1-2 hours at room temperature to form sodium alginate beads. After the incubation period the bead forming solution was carefully removed and replaced with 4-5 ml of 1:2 mixture of K3+H:A media (Spangenberg et al 1998) supplemented with 1.5 mg/L of Hygromycin. The protoplasts were cultured for 3-4 weeks in darkness at 22° C. in a shaker (50 RPM). After 3-4 weeks the resistant microcalli (0.5-1.0 mm) were released by treating with depolymerisation buffer (0.3 M Mannitol+20 mM Sodium Citrate (pH 5.8)). After removing the liquid media 3-4 ml of depolymerisation buffer was added to each well containing the bead-type cultures and incubated at room temperature for 2 hours. Using a sterile forceps the beads were gently mixed to enhance the efficient release of the microcalli. Next a sterile 1.0 ml pipette was used to gently mix gelling agent that was released in the depolymerisation buffer and subsequently removed. The microcalli was washed twice using 5 ml of liquid A media and the microcalli was resuspended in sufficient quantity of liquid A (50 ml of liquid A was used for one ml of the settled cell volume (SCV: this was measured after transferring all the released microcalli to a sterile 50 or 15 ml falcon tube and allowed to settle down for 5 min)). After mixing the microcalli uniformly, 0.5 ml of the microcalli suspended in the liquid A media was transferred to B1 media (MS/MS Vitamins+3.5% Sucrose+500 mg/L MES+BAP (5 μm)+NAA (5 μm)+2,4-D (5 μm)+1.5 mg/L Hygromycin+0.7% Agarose Type I (pH 6.0) and poured in 100×20 mm sterile PETRI™ dish) and using 1-2 ml of additional liquid A media the microcalli was distributed uniformly in the B1 media and the excess liquid A media was carefully removed from each plate. The plates were sealed using a micropore tape which enhanced the embryo maturation. The cultures were maintained at 22° C. in 16 h/d light (30 μmol $m^{-2}$ $s^{-1}$).

Proliferation and Regeneration of Shoots from Mesophyll Derived Protoplasts

Hygromycin resistant colonies were picked from B1 media (microcalli derived from both SA and SP methods) after 2-3 weeks of incubation and transferred to B2 media (MS/MS Vitamins+3.0% Sucrose+500 mg/L MES+500 mg/L PVP+5 mg/L Silver nitrate+5 mg/L 2i P+NAA (0.5 μm)+GA-3 (0.3 μm)+1.5 mg/L Hygromycin+0.7% Agarose Type I (pH 5.8) and poured in 100×20 mm sterile PETRI™ dish). Approximately 25-30 calli were placed per plate and the plates were sealed using PARAFILM™ and incubated at 22° C. in 16 h/d light (30 μmol $m^{-2}$ $s^{-1}$). Hygromycin resistant colonies were subsequently recovered after 5-6 rounds of sub-culturing in B2 media at two weeks interval. The number of calli per plate was reduced to 12-15 after a third round of sub-culturing. Shoot primordias that appear after 10-12 weeks were carefully recovered along with the residual calli and transferred to shoot elongation medium (MS/B5 Vitamins+2% sucrose+500 mg/L MES+BAP (2 μm)+GA-3 (0.1 μm)+300 mg/L Timentin+1.5 mg/L Hygromycin+0.8% Agar (pH 5.8) and poured in 250 ml culture vessels). The shoots that survive after 2-3 rounds of Hygromycin selection were transferred to rooting media (½ strength MS/B5 Vitamins+1% sucrose+500 mg/L MES+IBA (2.5 μm)+1.5 mg/L Hygromycin+0.6% Agar (pH 5.8) and poured in 700 ml culture vessels).

Isolation of Genomic DNA from Mesophyll Protoplasts

Transfected protoplasts were transferred from the 3 cm PETRI™ dish to a 2 mL microfuge tube. The cells were pelleted by centrifugation at 70 g and the supernatant was removed. To maximize the recovery of transfected protoplasts, the PETRI™ dish was rinsed three times with 1 mL of wash buffer. Each rinse was performed by swirling the wash buffer in the PETRI™ dish for 1 minute, followed by transfer of the liquid to the same 2 ml microfuge tube. At the end of each rinse, the cells were pelleted by centrifugation at 70 g and the supernatant was removed. The pelleted protoplasts were snap frozen in liquid nitrogen before freeze drying for 24 h in a LABCONCO FREEZONE 4.5® (Labconco, Kansas City, Mo.) at −40° C. and $133\times10^{-3}$ mBar pressure. The lyophilized cells were subjected to DNA extraction using the DNEASY® PLANT DNA EXTRACTION MINI KIT (Qiagen) following the manufacturer's instructions, with the exception that tissue disruption was not required and the protoplast cells were added directly to the lysis buffer.

Isolation of Genomic DNA from Callus Tissue

Individual calli was snap frozen in liquid nitrogen before freeze drying for 24 h in a LABCONCO FREEZONE 4.5® (Labconco, Kansas City, Mo.) at −40° C. and $133\times10^{-3}$ mBar pressure. The lyophilized calli was subjected to DNA extraction using the DNEASY® PLANT DNA EXTRACTION MAXI kit (Qiagen, Hilden, Germany) following the manufacturer's instructions.

Isolation of Genomic DNA from Leaf Tissue

Thirty (30) mg of young leaf tissue from regenerated plants was snap frozen in liquid nitrogen before freeze drying for 24 h in a LABCONCO FREEZONE 4.5® (Labconco, Kansas City, Mo.) at −40° C. and $133\times10^{-3}$ mBar pressure. The lyophilized calli was subjected to DNA extraction using the DNEASY® PLANT DNA EXTRACTION MAXI KIT (Qiagen, Hilden, Germany) following the manufacturer's instructions.

PCR Assays of Genomic DNA for NHEJ-Mediated Splicing and Editing of Fad3C

Figure 28:
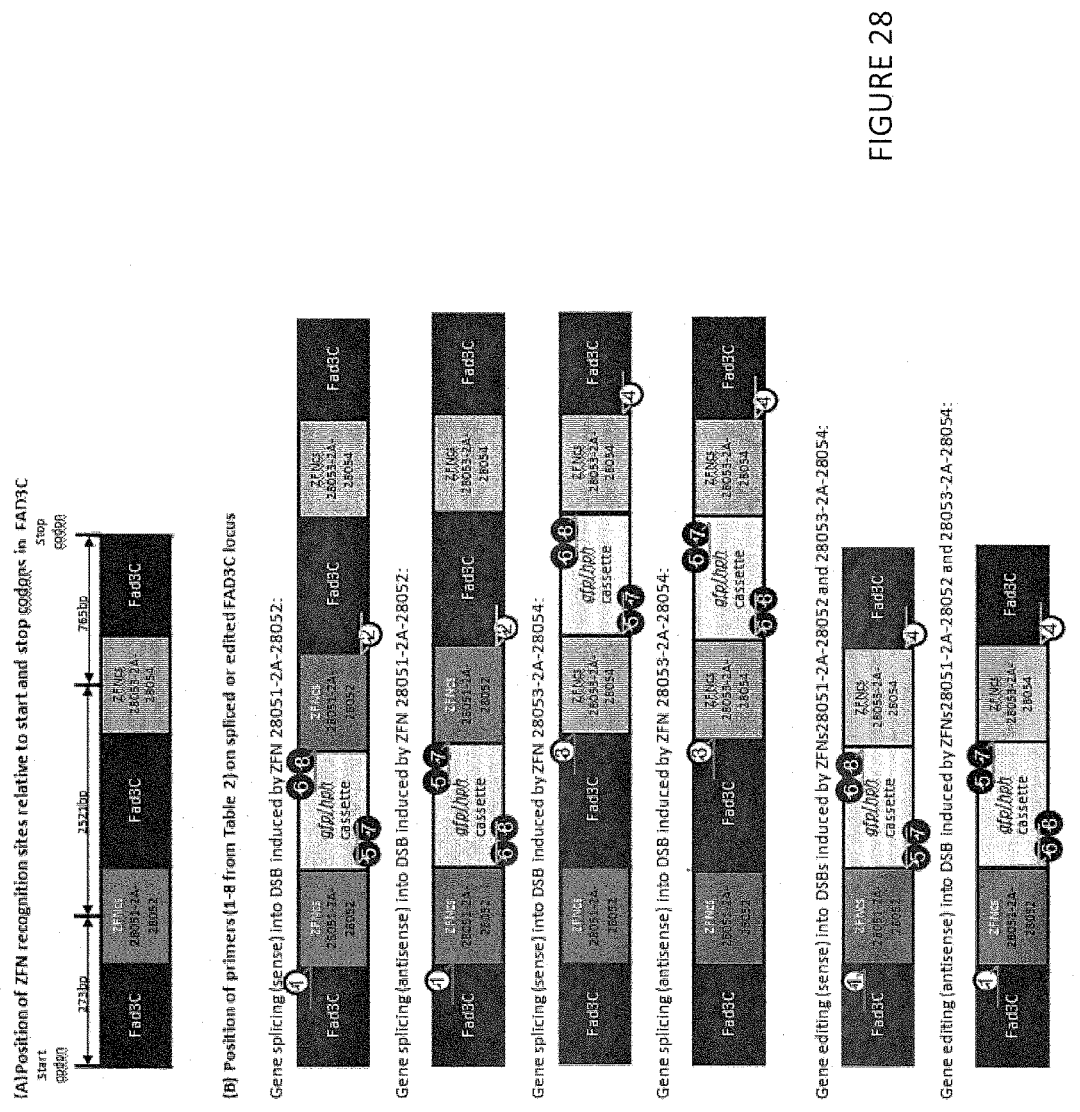

Detection of integration of donor DNA to the Fad3C gene of B. napus was done by a series of PCR where at least one primer was specific to the Fad3C locus (Table 18) and a second primer specific to either the promoter or terminator of the gfp cassette (Table 18 and FIG. 28A). Specificity was obtained by designing oligonucleotides where the last base pair aligned to a SNP that differentiated Fad3C genomic sequence from the other copies of Fad3 genes and including a phosphorothioate internucleotide linkage before this base pair as indicated by an asterisk [*]. This design, used in combination with a polymerase having proofreading activity, directed specific amplification of each Fad3C or Fad3A allele and excluded other Fad3 copies as noted. Each primer set was empirically tested for amplification of the correct gene copies through Sanger-based sequencing of the PCR amplification products obtained from wild type *B. napus*.

clones were sequenced on an ABI3730XL® automated capillary electrophoresis platform. Analysis of gene sequences was done using SEQUENCHER SOFTWARE V5.0™ (GeneCodes, Ann Arbor, Mich.).

Evidence of gene addition to Fad3C locus by editing or splicing was provided by amplification of both the 5' and 3' Fad3C-cassette junctions from genomic DNA extracted from protoplasts using the primers described in Table 18.

TABLE 18

Oligonucleotide sequences used to detect integration of DNA into ZFN-induced double-stranded breaks.

| | Primer Name | Primer Sequence | SEQ ID NO: | Specificity |
|---|---|---|---|---|
| 1 | FAD3CNHEJ-L4-F2 | gattcctaagcattgttgggt*c | 360 | Fad3C only |
| 2 | FAD3CNHEJ-L4-R2 | gaaaatctcatatcgaacgtgcg*t | 361 | Fad3C only |
| 3 | FAD3CNHEJ-L6-F1 | cgcttaccctctctatctggta*a | 362 | Does not amplify Fad3C' or Fad3C" |
| 4 | FAD3CNHEJ-L6-R2 | ccttgcctctgtaccaaggca*g | 363 | Fad3C only |
| 5 | 19SPNHEJ-R2 | gtgtgtgggaatcttatcttcgg | 364 | n/a |
| 6 | AtORF1NHEJ-F1 | caagtcaggtattatagtccaagca | 365 | n/a |
| 7 | AtUbiNHEJ-R1 | caagaatatcctgatccgttgac | 366 | n/a |
| 8 | AtORF23tNHEJ-F1 | tggcagttgaaatactcaaacc | 367 | n/a |
| 9 | FAD3aCNHEJ-L4-F1 | gtcctttgagatccatgagcta*t | 368 | Fad3A only |
| 10 | FAD3aCNHEJ-L4-F2 | gattcctaagcattgttgggt*a | 369 | Fad3A only |
| 11 | FAD3aNHEJ-L4-R1 | tgcgttcaagaaatcaaagac*a | 370 | Fad3A only |
| 12 | FAD3aNHEJ-L4-R2 | gaaaatctcatatcgaacgtgcg*g | 371 | Fad3A only |
| 13 | FAD3aNHEJ-L6-F1 | tctggtaaatcctaattcct*c | 372 | Fad3A only |
| 14 | FAD3aNHEJ-L6-R2 | ccttgcctctgtaccaaggca*a | 373 | Fad3A only |
| 15 | FAD3aNHEJ-L6-R1 | cttgcctctgtaccaaggcaactt*c | 374 | Excludes Fad3C |

*Indicates phosphorothioate internucleotide linkages to direct specific amplification (with proofreading polymerase) of Fad3C or Fad3A to exclusion of other copies of Fad3 as noted. Each primer set was empirically tested for amplification of the correct gene copies by Sanger-based sequencing of the PCR amplification products obtained from wild type *B. napus*.

Detection of Gene Addition to Fad3C by Non-Homologous End Joining in Protoplasts Genomic DNA was extracted from protoplast pools (one million protoplast per pool) to which donor DNA encoding a functional tGFP reporter cassette (pDAS000341 or pDAS000343), ZFN DNA (pDAB107827 or pDAB107828) or a mixture of donor and ZFN DNA had been delivered twenty-four hours earlier. Quantities of DNA delivered for transformation are described above. PCR products were cloned into plasmid vectors. The genomic editing occurs independently in each cell giving rise to a variety of different insertion events, by cloning into a plasmid vector, each genomic edit can be sequenced without ambiguity. Several Products of PCR amplification with primers "FAD3CNHEJ-L4-F2" and "AtUbiNHEJ-R1" was completed to amplify the 5' junction of tGFP cassette and Fad3C. PCR amplification with primers "FAD3CNHEJ-L4-R2" and "AtORF23tNHEJ-F1" was completed to amplify the 3' junction of tGFP cassette and Fad3C. PCR amplification with primers "FAD3CNHEJ-L4-F2" and "FAD3CNHEJ-L4-R2" was completed to amplify across the double strand breaks induced by ZFN 28051-2A-28052. No amplification was observed from protoplasts to which ZFN plasmid or donor plasmid alone had been delivered. All junction sequences were indicative of insertion of the tGFP cassette at the Fad3C locus via an NHEJ-mediated repair pathway. Deletions of varying lengths from either or both the genome and the cassette were observed as well as the addition of sequences derived from the vector backbones (either from the donor or ZFN) being inserted between the genome and the cassette.

Detection of Gene Addition to Fad3C by Non-Homologous End Joining in Callus Tissue Regenerated from Protoplasts Further evidence of splicing and editing of the Fad3C locus was obtained from callus tissue regenerated from protoplasts on selection (1.5 mg/L hygromycin, as described above) to which donor DNA encoding an hph cassette (pDAS000340 or pDAS000342), ZFN DNA only (pDAB107827 or pDAB107828) or donor and ZFN DNA had been delivered (quantities of DNA delivered are given in Table 17). DNA was extracted from approximately 80 calli for each ratio, except editing 1:1:1, for which no calli survived, four weeks after protoplast transfection.

Integration of the hph cassette into the *B. napus* genome (fwat Fad3C or randomly) was confirmed by TAQMAN™ qPCR using primers (SEQ ID NO:402; F-5'CTTACATGCT-TAGGATCGGACTTG 3', SEQ ID NO:403; R-5'AGTTC-CAGCACCAGATCTAACG 3') and probe (SEQ ID NO:404; 5' CCCTGAGCCCAAGCAGCATCATCG 3') specific to the hph gene. These primer-probe pairs were used in a duplex reaction with primers (SEQ ID NO:405; F-5' CGGAGAGGGCGTGGAAGG 3', SEQ ID NO:406; R-5' TTCGATTTGCTACAGCGTCAAC 3') and probe (SEQ ID NO:407; 5'AGGCACCATCGCAGGCTTCGCT 3') specific to the *B. napus* high mobility group protein I/I (HMG FY), which is present as a single copy on the A genome (Weng et al., 2004, Plant Molecular Biology Reporter). Amplification was performed on a C1000 thermal cycler with the CFX96 or CF384 REAL-TIME PCR DETECTION SYSTEM™ (BioRad, Hercules, Calif.). Results were analyzed using the CFX MANAGER™ (BioRad) software package. Relative quantification was calculated according to the $2^{-\Delta\Delta Ct}$ method (Livak and Schmittgen, 2001), which provided an estimation of the number of copies of hph cassette inserted into the genome. Evidence of NHEJ-mediated splicing and editing of Fad3C was obtained by conducting PCR assays with one primer specific to Fad3C and a second primer specific to either the promoter or terminator of the hph cassette (Table 17 and FIG. 28B). Due to limited quantities of DNA obtained from callus tissue, only integration in the sense orientation was assayed. PCR products were gel-purified using QIAQUICK MINIELUTE PCR PURIFICATION KIT™ (Qiagen) and sequenced using a direct Sanger sequencing method. The sequencing products were purified with ethanol, sodium acetate and EDTA following the BIG-DYE® v3.1 protocol (Applied Biosystems) and sequenced and analyzed as above.

The numbers of calli containing the donor cassette in each experiment are given in Table 18. Evidence of donor gene addition to the Fad3C locus by editing and/or splicing was provided by PCR amplification (with primers shown in Table 19) across the ZFN cut sites and both the 5' and 3' Fad3C-hph cassette junctions. PCR amplification of the genomic DNA isolated from callus tissue recovered from control protoplasts which were transformed with only the hph plasmid (pDAS000340 and pDAS000342) or only the ZFN plasmid (pDAB107827 and pDAB107828) did not result in the production of PCR amplification products.

The PCR amplicons produced from the amplification of the 5' and 3' Fad3C-hph cassette junctions were purified from the agarose gel and sequenced to confirm specificity of the integration within the Fad3C genomic locus. The results of the sequencing analysis of the PCR products indicated that each isolated callus which was generated from an individually transformed protoplast only produced a single PCR amplification product and did not contain cells of mixed genotypes.

Figure 30:
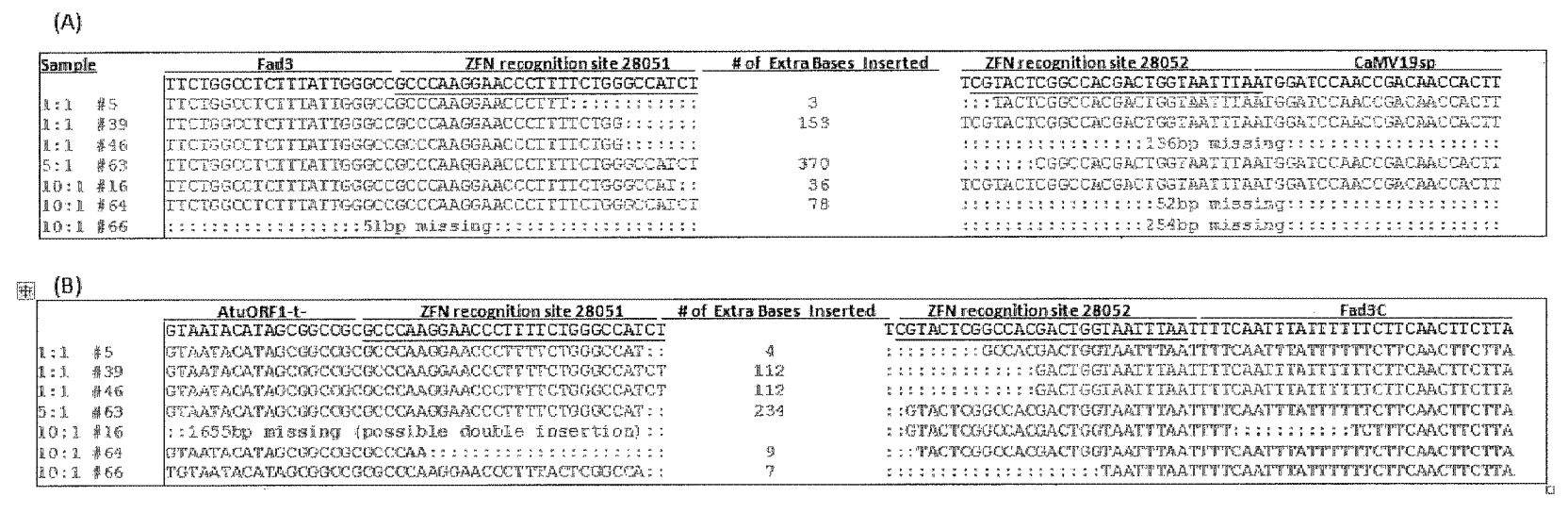
Figure 31:
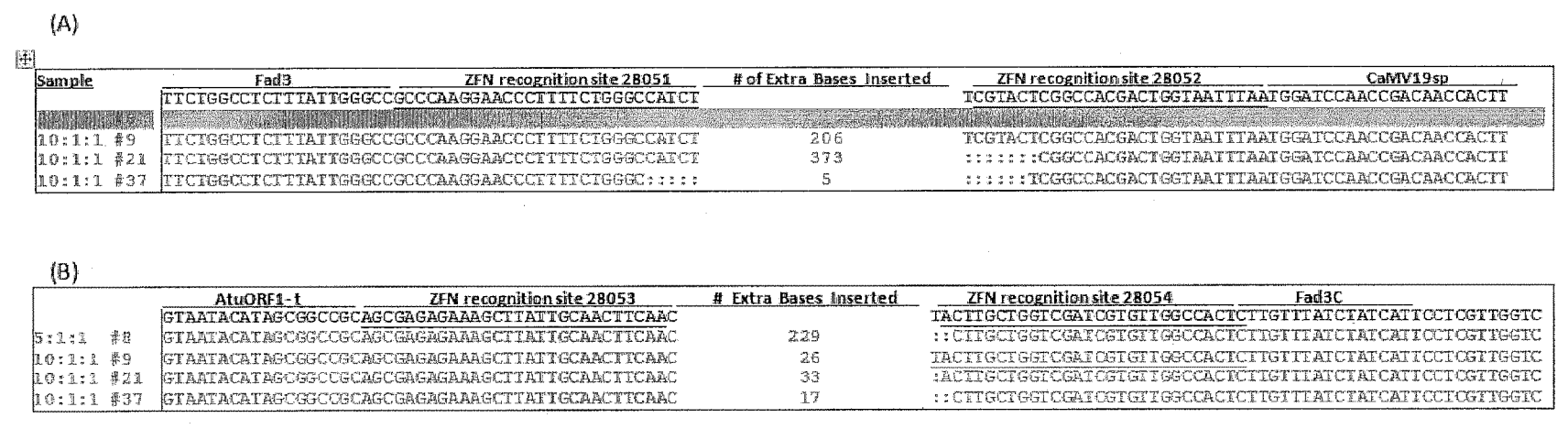

In NHEJ-mediated integration of donor sequences within the Fad3C genomic locus experiments the frequency of addition to the target locus (as defined by any part of the donor DNA vector being amplified from the target locus) was 42%, 46% and 32% for the DNA concentrations of 1:1, 5:1, and 10:1 (Donor DNA: ZFN DNA), respectively. See, Table 20. The frequency of on-target splicing was determined by assaying whether both cassette junctions were amplifiable and from the sequencing of the PCR products. These results verified that the cassette was inserted at the target locus in the correct orientation. The frequency of integration was calculated as 4%, 3% and 3% for the 1:1, 5:1 and 10:1 of Donor plasmid DNA: ZFN plasmid DNA concentrations, respectively. In gene editing experiments the frequency of addition to the target locus defined by any part of the donor DNA vector being amplified from the target locus, was 66% and 65% for the 5:1:1 and 10:1:1 of Donor plasmid DNA: ZFN plasmid DNA concentrations, respectively. See, Table 21. The frequency of on-target editing, was determined by both cassette junctions being amplifiable and producing a sequence of PCR products. These results verified that the cassette was inserted at the target locus in the correct orientation at frequencies of 3% and 6% for the 5:1:1 and 10:1:1 of Donor plasmid DNA: ZFN plasmid DNA concentrations, respectively. As observed in the protoplast assays, the base pairs were either deleted or additional bases were inserted between the genome and the cassette as a result of the cleavage of the genomic locus by the ZFN (FIGS. 30-31).

In certain instances the PCR products resulted in an addition of nucleotide sequences within the target locus, no PCR product, or a larger PCR product than observed in wild-type samples. These results which were produced from the PCR amplification using primers flanking the cut site indicated that the locus had been disrupted in both pairs of chromosomes (FIGS. 30-31). In some of the instances more than one band was amplified at the splice junctions (FIGS. 30-31) indicating that different insertions had occurred independently in each copy of the genome.

TABLE 19

Number of calli positive for presence of hph after four weeks on selection

| Vectors delivered | Molar Ratio of Donor DNA:ZFN DNA | Number of calli sampled | Number of calli positive for hph after four weeks on selection |
|---|---|---|---|
| pDAS000340 | 1:1 | 88 | 76 |
| DAB107827 | 5:1 | 88 | 35 |
|  | 10:1 | 87 | 37 |
| pDAS000342 | 1:1:1 | — | — |
| DAB107827 | 5:1:1 | 80 | 38 |
| DAB107828 | 10:1:1 | 79 | 52 |

TABLE 20

Number of calli with hph inserted by splicing at FadC locus at the DSB induced by ZFN28051-2A-28052

| Vectors delivered | Molar Ratio of Donor DNA: ZFN DNA | Number of calli positive for hph after four weeks on selection | Number of calli from which at least one splicing border amplified | Number of calli from which at least one perfect* border amplified | Number of calli from which both splicing borders amplified |
|---|---|---|---|---|---|
| pDAS000340 + DAB107827 | 1:1 | 76 | 32 | 0 | 3 |
|  | 5:1 | 35 | 16 | 0 | 1 |
|  | 10:1 | 37 | 12 | 0 | 1 |

*no base pairs deleted or additional base pairs inserted at cut site

TABLE 21

Number of calli with hph inserted by editing at FadC locus at the cut sites induced by ZFN28051-2A-28052 and ZFN28053-2A-28054

| Vectors delivered | Molar Ratio of Donor DNA: ZFN DNA | Number of calli positive for hph after four weeks on selection | Number of calli from which at least one splicing border amplified | Number of calli from which at least one perfect* border amplified | Number of calli from which both editing borders amplified |
|---|---|---|---|---|---|
| pDAS000342 + DAB107827 + DAB107828 | 5:1:1 | 38 | 25 | 2 | 1 |
|  | 10:1:1 | 52 | 34 | 2 | 3 |

*no base pairs deleted or additional base pairs inserted at cut site

Detection of Gene Addition to Fad3C by Non-Homologous End Joining in Plants

DNA was extracted from plants that were regenerated from protoplasts and transferred to potting medium (as described above). The majority of plants recovered were estimated to contain only 1-2 copies of the hph cassette encoded in the donor DNA. Plants were analyzed with the same suite of assays described for callus tissue as well as with assays to determine if the cassette had inserted in an antisense orientation or donor integration at the Fad3A locus.

TABLE 22

Estimated copy number of plants regenerated from protoplasts. For each ratio three transfections of one million protoplasts were performed.

| Vectors delivered | Molar Ratio of Donor DNA:ZFN DNA | # plants with 1-2 copies hph | # plants with 3-4 copies hph | # plants with 5 or more copies hph |
|---|---|---|---|---|
| pDAS000340 DAB107827 | 1:1 | 28 | 10 | 22 |
|  | 5:1 | 14 | 6 | 17 |
|  | 10:1 | 24 | 12 | 10 |
| pDAS000342 DAB107827 DAB107828 | 1:1:1 | 1 | 0 | 0 |
|  | 5:1:1 | 22 | 7 | 10 |
|  | 10:1:1 | 24 | 13 | 26 |
| Total | — | 109 | 48 | 85 |

The frequency of on-target splicing, where the hph cassette was inserted into Fad3C in either direction, was 51%, 32% and 56% for Donor DNA: ZFN DNA at concentrations of 1:1, 5:1 and 10:1, respectively (Table 23). Of these results, 35% 32% and 50% (1:1, 5:1 and 10:1) were inserted in the forward orientation (Table 23).

The frequency of on-target editing, where the hph cassette was inserted into Fad3C in either direction, replacing the area from locus 4 to locus 6, was 2% and 0% for Donor DNA:ZFN DNA:ZFN DNA at concentrations of 5:1:1 and 10:1:1, respectively (Table 24). In addition, when both ZFNs were delivered at 5:1:1, 2% and spliced into locus 4 and 10% spliced into locus 6 and when both ZFNs were delivered at 10:1:1 10% and spliced into locus 4 and 15% spliced into locus 6.

The bands obtained can be sequenced to determine the number of perfect borders. Additionally, plants can be screened for off-target insertions to determine the frequency of integration of hph at sites other than Fad3, and the frequency of integration at Fad3A rather than Fad3C.

TABLE 23

Number of plants with hph inserted by splicing at FadC locus at the DSB induced by ZFN28051-2A-28052

| Vectors delivered | Molar Ratio of Donor DNA: ZFN DNA | Number of plants analysed (positive for hph) | Number of plants from which at least one splicing border amplified (forward/reverse/either) | Number of plants from which both splicing borders amplified (forward/reverse/either) |
|---|---|---|---|---|
| pDAS000340 + DAB107827 | 1:1 | 60 | 21/23/31 | 4/7/8 |
|  | 5:1 | 37 | 12/4/12 | 3/1/3 |
|  | 10:1 | 46 | 23/12/26 | 4/4/7 |

* no base pairs deleted or additional base pairs inserted at cut site

TABLE 24

Number of plants with hph inserted by editing at FadC locus at the cut sites induced by ZFN28051-2A-28052 and ZFN28053-2A-28054

| Vectors delivered | Molar Ratio of Donor DNA:ZFN DNA:ZFN DNA | Number of plants analysed (positive for hph) | Number of plants from which at least one splicing border amplified (forward/reverse/either) | Number of plants from which both editing borders amplified (forward/reverse/either) |
|---|---|---|---|---|
| pDAS000342 + DAB107827 + DAB107828 | 5:1:1 | 39 | 17/11/24 | 0/1/1 |
|  | 10:1:1 | 63 | 27/27/34 | 0/0/0 |

* no base pairs deleted or additional base pairs inserted at cut site

Example 8: Targeted Integration into and Disruption of Corn Event DAS-59132
Characterization of an Endogenous Genomic Locus for Gene Targeting The genomic locus of Corn Event DAS-59132 was described in International Patent Application No. WO 2009/100188 A2. Corn Event DAS-59132 comprises the Cry34Ab1, Cry35Ab1, and PAT transgene expression cassettes. These transgene expression cassettes were integrated into chromosome 8 of the B73 maize genome derived region of Hi-II maize germplasm (D. D. Songstad, W. L. Petersen, C. L. Armstrong, *American Journal of Botany*, Vol. 79, pp. 761-764, 1992) as a full length T-strand insert. In addition, the genomic DNA surrounding the transgenic locus lacked any large deletions relative to the native B73 sequence, and was generally devoid of repetitive elements except for a single, small repetitive element.

The genomic locus in which Corn Event DAS-59132 integrated was selected as an endogenous genomic locus for gene targeting. The selection of this endogenous genomic locus was based on the characterization of Corn Event DAS-59132. This event resulted from the integration of a T-strand into the endogenous genomic locus, and the subsequent expression of three transgene expression cassettes. In addition, there was minimal alteration of normal growth and development of corn plants which comprise Corn Event DAS-59132. The event retained the agronomic and breeding characteristics and was comparable in agronomic performance to non-transformed control plants.

An embodiment of the disclosure includes polynucleotide sequences that can be targeted for the integration of a transgene. The full length DNA molecule (PHI17662A) used to transform Corn Event DAS-59132, the 3' end of the genomic flanking sequence, and the PHI17662A/3' maize genome junction were described in the disclosure of International Patent Application No. WO 2009/100188 A2, and are disclosed in this filing as SEQ ID NO:427, SEQ ID NO:428 and SEQ ID NO:429, respectively. The 5' end of the genomic flanking sequence, and the genomic locus where Corn Event DAS-59132 integrated into the corn genome is disclosed in this filing as SEQ ID NO:430 and SEQ ID NO:431, respectively. The genomic locus listed as SEQ ID NO:431 was used to design zinc finger proteins for gene targeting.

Production of Zinc Finger Proteins Designed to Bind the Genomic Locus for Corn Event DAS-59132

Figure 32:
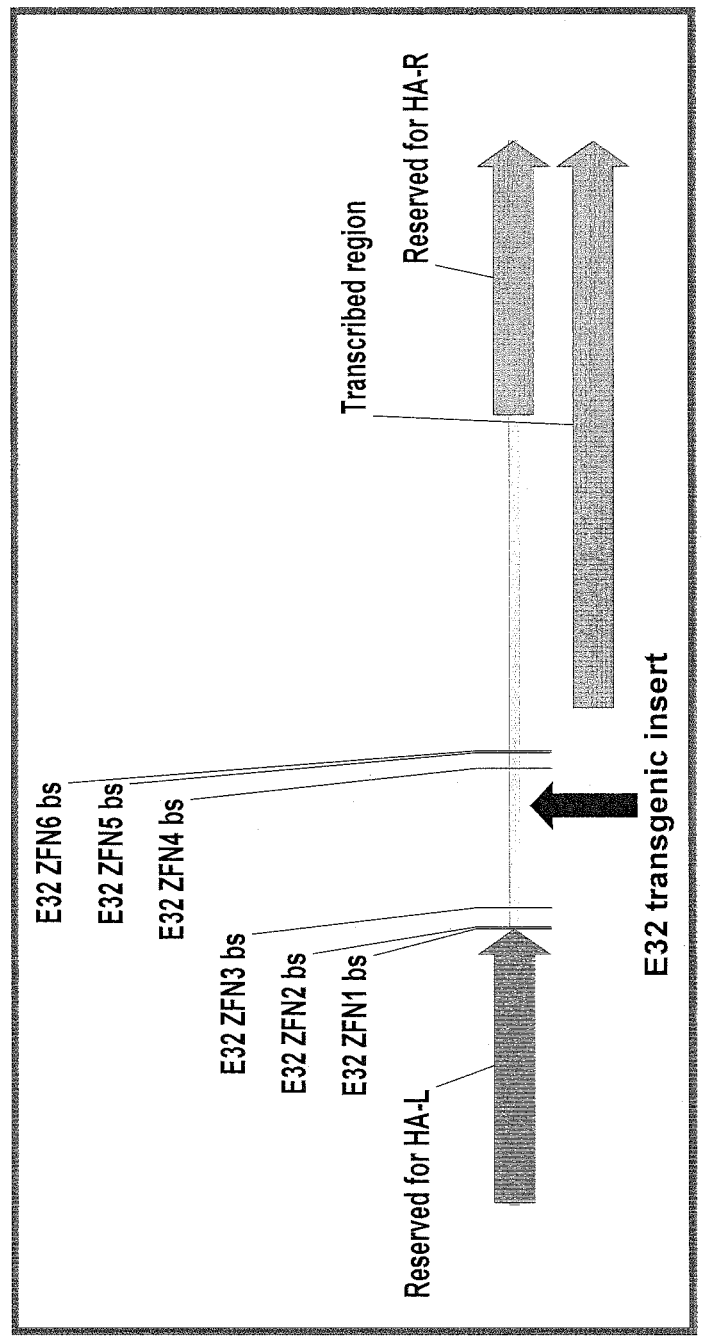
FIG. 32 depicts the relation of the ZFNs designed to bind the genomic locus of transgenic insert in Corn Event DAS-59132. Six ZFNs (E32 ZFN1-6) were identified from the yeast assay and four ZFNs were advanced for evaluation in plants.

Zinc finger proteins directed against DNA sequences which comprise the genomic locus for Corn Event DAS-59132 (see, FIG. 32) were designed as previously described. See, e.g., Urnov et al. (2005) Nature 435:646-651. Exemplary target sequence and recognition helices are shown in Tables 25A (recognition helix regions designs) and Table 25B (target sites). In Table 25B, nucleotides in the target site that are contacted by the ZFP recognition helices are indicated in uppercase letters.

TABLE 25A

Genomic locus for Corn Event DAS-59132-binding zinc finger designs

| ZFP# | F1 | F2 | F3 | F4 | F5 |
|---|---|---|---|---|---|
| 25716 | RSDDLSK SEQ ID NO: 533 | QSGSLTR SEQ ID NO: 534 | RSDNLRE SEQ ID NO: 535 | QSGDLTR SEQ ID NO: 158 | DTGARLK SEQ ID NO: 536 |
| 25717 | RSADRKT SEQ ID NO: 537 | DRSHLSR SEQ ID NO: 538 | TSGNLTR SEQ ID NO: 143 | RSDDLSR SEQ ID NO: 539 | QSANRTK SEQ ID NO: 540 |

TABLE 25B

Target Sequences for zinc finger proteins

| Zinc Finger Number | SEQ ID NO: | Target Sequence |
|---|---|---|
| 25686 | 432 | caCAACAAGACtGCGGGTtcggtggcgc |
| 25687 | 433 | gaTAGGTGGCAGTGGCAgtggcactggc |
| 25688 | 434 | taTCGGCACAACAAGACtgcgggttcgg |

TABLE 25B-continued

Target Sequences for zinc finger proteins

| Zinc Finger Number | SEQ ID NO: | Target Sequence |
|---|---|---|
| 25689 | 435 | tgGCAGTGGCAGTGGCActggcacggca |
| 25692 | 436 | caGCAGATGAGcGGAGCGatcgatcgcg |
| 25693 | 437 | caGTGGATAGAGCAGCGttggccgttgg |
| 25710 | 438 | agGAAGCCGGCGGTGAAtgtcgccgtgt |
| 25711 | 439 | cgTCGCCAcTCGGCACAAggctcatcag |
| 25712 | 440 | atCGGGCATCGGCGACTgatgagccttg |
| 25713 | 441 | gaTCAACGGAAGCGGATGGCccgcttct |
| 25716 | 442 | tgATCGCAtCGGGCATCGgcgactgatg |
| 25717 | 443 | cgGAAGCGGATGGCCCGcttctttagaa |

The Corn Event DAS-59132 zinc finger designs were incorporated into vectors encoding a protein having at least one finger with a CCHC structure. See, U.S. Patent Publication No. 2008/0182332. In particular, the last finger in each protein had a CCHC backbone for the recognition helix. The non-canonical zinc finger-encoding sequences were fused to the nuclease domain of the type IIS restriction enzyme FokI (amino acids 384-579 of the sequence of Wah et al. (1998) Proc. Natl. Acad. Sci. USA 95:10564-10569) via a four amino acid ZC linker and an opaque-2 nuclear localization signal derived from Zea mays to form Corn Event DAS-59132 zinc-finger nucleases (ZFNs). Expression of the fusion proteins in a bicistronic expression construct utilizing a 2A ribosomal stuttering signal as described in Shukla et al. (2009) Nature 459:437-441 was driven by a relatively strong, constitutive and ectopic promoter such as the CsVMV promoter.

The optimal zinc fingers were verified for cleavage activity using a budding yeast based system previously shown to identify active nucleases. See, e.g., U.S. Patent Publication No. 20090111119; Doyon et al. (2008) Nat. Biotechnol. 26:702-708; Geurts et al. (2009) Science 325:433. Zinc fingers for the various functional domains were selected for in-vivo use. Of the numerous ZFNs that were designed, produced and tested to bind to the putative Corn Event DAS-59132 genomic polynucleotide target sites, four pairs of ZFNs were identified as having in vivo activity at high levels, and selected for further experimentation. See, Table 25A. These ZFNs were characterized as being capable of efficiently binding and cleaving the four unique Corn Event DAS-59132 genomic polynucleotide target sites in planta.

FIG. 1 shows the genomic organization of the Corn Event DAS-59132 locus in relation to the ZFN polynucleotide binding/target sites of the four ZFN pairs. The first three ZFN pairs (E32 ZFN1, E32 ZFN2, and E32 ZFN3) bind upstream of the Corn Event DAS-59132 T-strand insert, the second three ZFN pairs (E32 ZFN4, E32 ZFN5, and E32 ZFN6) bind downstream of the Corn Event DAS-59132 T-strand insert. After testing the ZFN pairs in the budding yeast assay, ZFN pairs which optimally bound the Corn Event DAS-59132 locus were advanced for testing in a transient corn transformation assay.

Zinc Finger Nuclease Constructs for Expression in Maize

Plasmid vectors containing ZFN expression constructs of the four exemplary zinc finger nucleases, which were identified using the yeast assay and described in Example 2, were designed and completed using skills and techniques commonly known in the art. Each zinc finger-encoding sequence was fused to a sequence encoding an opaque-2 nuclear localization signal (Maddaloni et al. (1989) *Nuc. Acids Res* 0.17 (18):7532), that was positioned upstream of the zinc finger nuclease.

Figure 33:
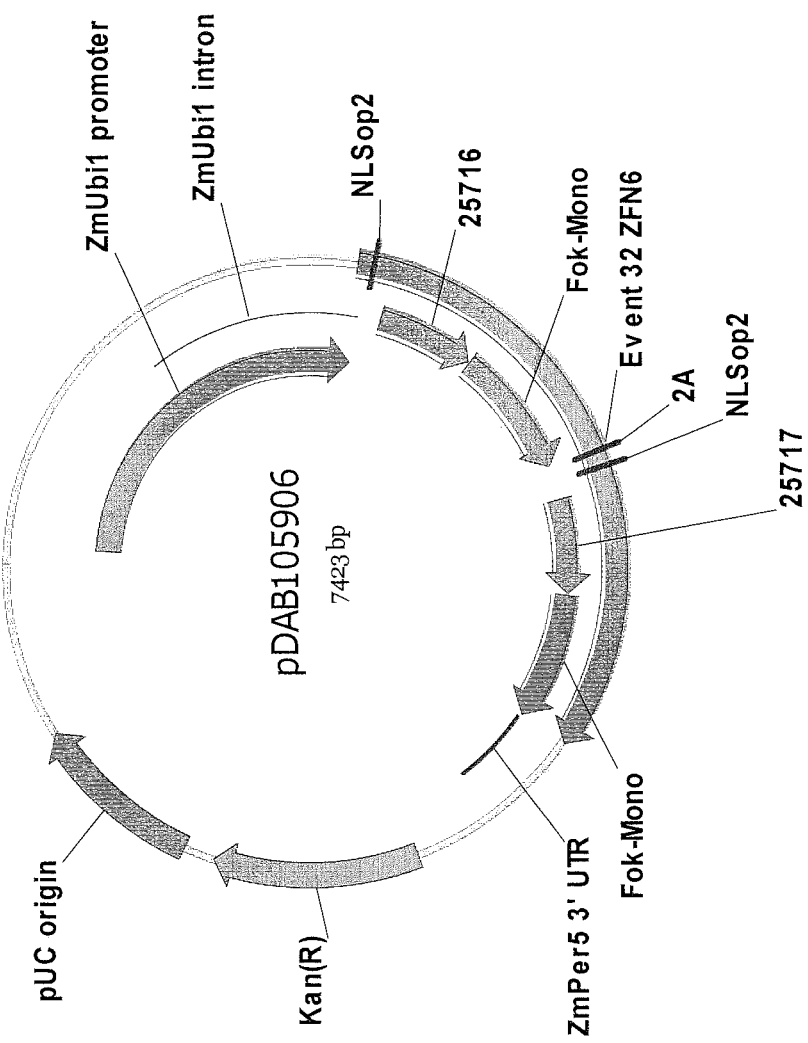
FIG. 33 shows a plasmid map of pDAB105906.
Figure 34:
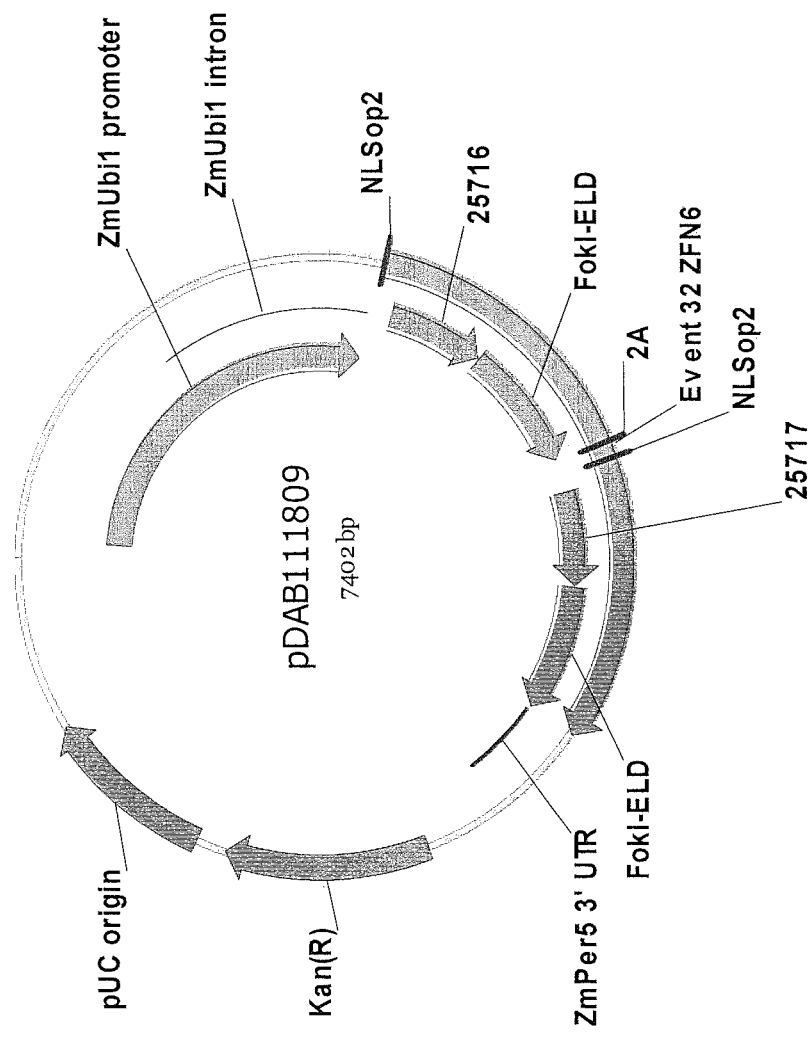
FIG. 34 shows a plasmid map of pDAB111809.

Next, the opaque-2 nuclear localization signal::zinc finger nuclease fusion sequence was paired with the complementary opaque-2 nuclear localization signal::zinc finger nuclease fusion sequence. As such, each construct consisted of a single open reading frame comprised of two opaque-2 nuclear localization signal::zinc finger nuclease fusion sequences separated by the 2A sequence from *Thosea asigna* virus (Mattion et al. (1996) *J. Virol.* 70:8124-8127). Expression of the ZFN coding sequence was driven by the highly expressing constitutive *Zea mays* Ubiquitin 1 Promoter (Christensen et al. (1992) Plant Mol. Biol. 18(4):675-89) and flanked by the *Zea mays* Per 5 3' polyA untranslated region (U.S. Pat. No. 6,699,984). The resulting four plasmid constructs were confirmed via restriction enzyme digestion and via DNA sequencing. FIGS. 33 and 34 provide a graphical representation of the completed plasmid construct. The ZFN expressed in plasmid construct, pDAB105906 (FIG. 33), contains "Fok-Mono" which is a wildtype FokI endonuclease. The ZFN expressed in plasmid construct, pDAB111809 (FIG. 34), contains "Fok1-ELD" which is a modified FokI endonuclease. The modified FokI endonuclease contains alterations as described in Doyon Y., Vo T., Mendel M., Greenberg S., Wang J., Xia D., Miller J., Urnov F., Gregory P., and Holmes M. (2010) Enhancing zinc-finger-nuclease activity with improved obligate heterodimeric architecture. *Nature Methods*, 8(1); 74-79.

Figure 35:
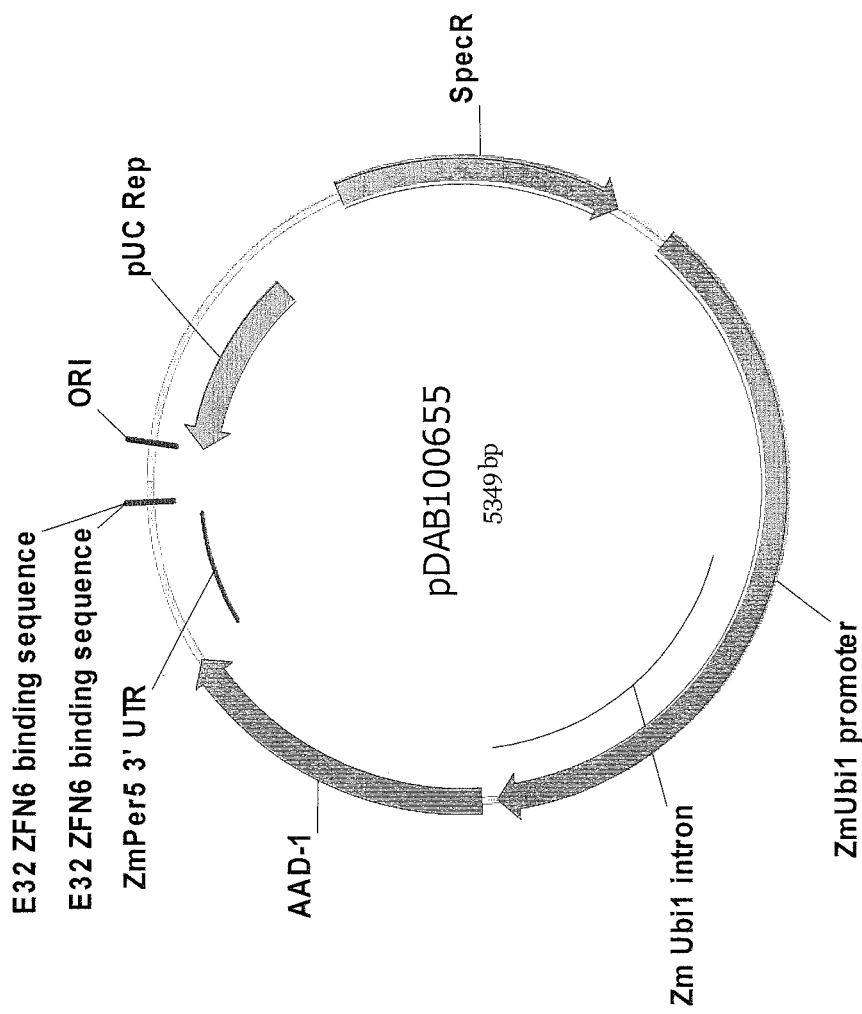
FIG. 35 shows a plasmid map of pDAB100655.

A donor construct was designed to integrate into the ZFN cleaved genomic DNA of the Corn Event DAS-59132 genomic locus. FIG. 35 illustrates the donor construct, pDAB100655, which consists of a single gene expression cassette. This single gene expression cassette is driven by the *Zea mays* Ubiquitin 1 promoter (Zm Ubi1 promoter):: the aad-1 coding sequence (AAD1; U.S. Pat. No. 7,838,733):: and is terminated by the *Zea mays* Per 5 3' untranslated region (ZmPer5 3'UTR). The construct contains a pair of repeated E32 ZFN6 binding sequences which were included downstream of the aad-1 gene expression cassette. The various gene elements were assembled in a high copy number pUC based plasmid.

Transient Transformation of Maize to Determine ZFN Efficiency

Maize Hi-II embryogenic cultures were produced as described in U.S. Pat. No. 7,179,902, and were used to evaluate and test the efficiencies of the different ZFNs. Plasmid DNA consisting of pDAB105901, pDAB105902, pDAB105903, pDAB105904, pDAB105905 and pDAB105906 were transiently transformed into maize callus cells to compare the cutting frequency of different ZFNs against a standard tested ZFN, pDAB7430, which was designed to the inositol polyphosphate 2-kinase gene locus within the maize genome as described in US Patent Application No. 2011/0119786.

From the cultures, 12 mL of packed cell volume (PCV) from a previously cryo-preserved cell line plus 28 mL of conditioned medium was subcultured into 80 mL of GN6 liquid medium (N6 medium (Chu et al., (1975) Sci Sin. 18:659-668), 2.0 mg/L 2,4-D, 30 g/L sucrose, pH 6.0) in a 500 mL Erlenmeyer flask, and placed on a shaker at 125 rpm at 28° C. This step was repeated two times using the same cell line, such that a total of 36 mL PCV was distributed across three flasks. After 24 hours, the contents were poured into sterile a PETRI™ dish and the GN6 liquid media was removed. Slightly moistened callus was transferred to a 2.5 cm diameter circle on GN6 S/M solid medium (N6 Medium (Chu et al., (1975) *Sci Sin*. 18:659-668), 2.0 mg/L 2,4-D, 30 g/L sucrose, 45.5 g/L sorbitol, 45.5 g/L mannitol, 100 mg/L myo-inositol, 2.5 g/L Gelrite, pH 6.0) containing filter paper. The plates were incubated in the dark for 4 hours at 28° C.

Microparticle gold (0.6 micron, BioRad, Hercules, Calif.,) was prepared for DNA precipitation by weighing out 21 mg into a sterile, siliconized 1.7 mL microcentrifuge tube (Sigma-Aldrich, St. Louis, Mo.) and 350 µL of ice cold 100% ethanol was added and vortexed for 1 minute. The gold was pelleted by centrifugation at 10,000 rpm for 15 seconds using a MINISPIN™ centrifuge (Eppendorf, Hauppauge, N.Y.). After removing the supernatant, 350 µL of ice cold, sterile water was added, mixed up and down with the pipette and centrifuged at 10,000 rpm for 15 seconds. The wash step was repeated one more time prior to suspending the gold in 350 µL of ice cold, sterile water. The washed gold was then stored at −20° C. until needed.

For each DNA precipitation, 3 mg of gold in 50 µL of water was aliqouted into a siliconized 1.7 mL microcentrifuge tube (Sigma-Aldrich, St. Louis, Mo.). Plasmid DNA (2.5 µg E32 ZFN in plasmids pDAB105901, pDAB105902, pDAB105903, pDAB105904, pDAB105905 or pDAB105906 and 2.5 µg IPPK2 ZFN in plasmid pDAB7430) was premixed in 0.6 mL microcentrifuge tubes (Fisher Scientific, Nazareth, Pa.) and added to the gold suspension gently pipetting up and down 5-10 times to mix thoroughly. Twenty microliters (20 µL) of cold 0.1 M spermidine was then added and gently mixed by pipetting up and down 5-10 times. Fifty microliters (50 µL) of ice cold 2.5 M calcium chloride was added slowly and gently mixed by pipetting up and down 5-10 times. The tube was then capped and allowed to incubate at room temperature for 10 minutes. After centrifuging for 15 seconds at 10,000 rpm, the supernatant was carefully removed and 60 µL of ice cold, 100% ethanol was added. The gold DNA mixture was resuspended by gently pipetting up and down 5-10 times.

For microparticle bombardment, sterilized macrocarriers (BioRad, Hercules, Calif.) were fit into stainless steel holders (BioRad, Hercules, Calif.) and autoclaved. Nine microliters (9 µL) of gold/DNA suspension was evenly spread in the center of the macrocarrier being sure to pipette up and down so as to keep suspension well mixed between aliquots. Macrocarriers were then placed onto a piece of sterile 125 mm Whatman #4 filter paper (GE Healthcare, Buckinghamshire, UK) on a bed of 8-mesh DRIERITE™ (W.A Hammond Drierite Co., Xenia, Ohio) in a 140×25 mm glass PETRI™ dish. The gold/DNA was allowed to dry completely for about 5-10 minutes. Rupture discs (1100 psi, BioRad, Hercules, Calif.) were sterilized by soaking for a few seconds in isopropyl alcohol then loaded into the retaining cap of a microparticle bombardment devise (PDS-1000, BioRad, Hercules, Calif.). An autoclaved stopping screen (BioRad, Hercules, Calif.) and a loaded macrocarrier was placed into the launch assembly, the lid was screwed on and slide into the bombardment chamber just under the nozzle. The PETRI™ dish containing target was uncovered and placed in the bombardment chamber 6 cm below the nozzle. A vacuum was pulled (−0.9 bar) and the devise was fired. Steps were repeated for each target blasted. Targets were incubated in dark at a temperature of 28° C. for 24 hours on the same blasting medium. Blasted cells were transferred to recovery GN6 solid recovery medium (N6 medium (Chu et al., (1975) Sci Sin. 18:659-668), 2.0 mg/L 2,4-D, 30 g/L sucrose, 2.5 g/L Gelrite, pH 6.0) and incubated for additional 48 hours @ 28° C. in the dark. Seventy-two hours post bombardment, the cells were harvested into 2 mL EPPENDORF MICROFUGE SAFE LOCK TUBES™ and lyophilized for 48 hours in a VIRTIS MODEL #50L VIRTUAL XL-70 LYOPHILIZER™ (SP Scientific, Gardiner N.Y.).

Next Generation Sequencing (NGS) Analysis of Transiently Transformed Maize

The transiently transformed maize callus tissue was analyzed to determine the cleavage efficiency of the zinc finger nuclease proteins.

Sample Preparation:

Maize callus tissue transiently transformed with the ZFN constructs and two control vectors, pDAB100664 and pDAB100665, were collected in 2 mL EPPENDORF™ tubes and lyophilized for 48 hrs. Genomic DNA (gDNA) was extracted from lyophilized tissue using the QIAGEN PLANT DNA EXTRACTION KIT™ (Valencia, Calif.) according to manufacturer's specifications. The isolated gDNA was resuspended in 200 µl of water and the concentration was determined using a NANODROP® spectrophotometer (Invitrogen, Carlsbad, Calif.). Integrity of the DNA was estimated by running all samples on a 0.8% agarose E-gels (Invitrogen). All gDNA samples were normalized (25 ng/µl) for PCR amplification to generate amplicons which would be analyzed via ILLUMINA™ sequencing (San Diego, Calif.).

PCR primers for amplification of the genomic regions which span each tested ZFN cleavage site and the control samples were purchased from Integrated DNA Technologies (Coralville, Iowa). Optimum amplification conditions for the primers were identified by gradient PCR using 0.2 µM appropriate primers, ACCUPRIME PFX SUPERMIX™ (1.1×, Invitrogen) and 100 ng of template genomic DNA in a 23.5 µL reaction. Cycling parameters were initial denaturation at 95° C. (5 min) followed by 35 cycles of denaturation (95° C., 15 sec), annealing (55-72° C., 30 sec), extension (68° C., 1 min) and a final extension (72° C., 7 min). Amplification products were analyzed on 3.5% TAE agarose gels. After identifying an optimum annealing temperature, preparative PCR reactions were carried out to validate each set of PCR primers and for generating the ILLUMINA™ sequencing amplicon.

For preparative PCR, 8-individual small scale PCR reactions were performed for each template using conditions described above and the resulting PCR products were pooled together and gel purified on 3.5% agarose gels using the QIAGEN MINELUTE GEL EXTRACTION/PURIFICATION KIT™ per manufacturer's recommendations. Concentrations of the gel purified amplicons were determined by NANODROP™ and the ILLUMINA™ sequencing samples were prepared by pooling approximately 100 ng of PCR amplicons from ZFN targeted and corresponding wild type controls. Primers used for the PCR amplicon generation are shown in Table 26 below.

TABLE 26

Oligonucleotides for amplification of ZFN binding sites

| Corn Event DAS-59132 Zinc Finger Number | Direction // SEQ ID NO: | Primer Sequence |
|---|---|---|
| 25686/25687 and | Forward // SEQ ID NO: 444 | 5'-CAGGCAGCGCCACCGAAC-3' |
| 25688/25689 | Reverse // SEQ ID NO: 445 | 5'-CGATCGATCGCGTGCCGT-3' |
| 256892/256893 | Forward // SEQ ID NO: 446 | 5'-CTGGCACGGCACGCGATC-3' |
| | Reverse // SEQ ID NO: 447 | 5'-CGGAGATCCGGCCCCAAC-3' |
| 25710/25711 | Forward // SEQ ID NO: 448 | 5'-GACACGGCACACACGGCG-3' |
| | Reverse // SEQ ID NO: 449 | 5'-TCGGGCATCGGCGACTGA-3' |
| 25712/25713 and 25716/25717 | Forward // SEQ ID NO: 450 | 5'-ACTCGGCACAAGGCTCAT-3' |
| | Reverse // SEQ ID NO: 451 | 5'-CCTGTGCCAATTCTAAAG-3' |
| 9149/9215 | Forward // SEQ ID NO: 452 | 5'-GCAGTGCATGTTATGAGC-3' |
| | Reverse // SEQ ID NO: 453 | 5'-CAGGACATAAATGAACTGAATC-3' |

Figure 36:
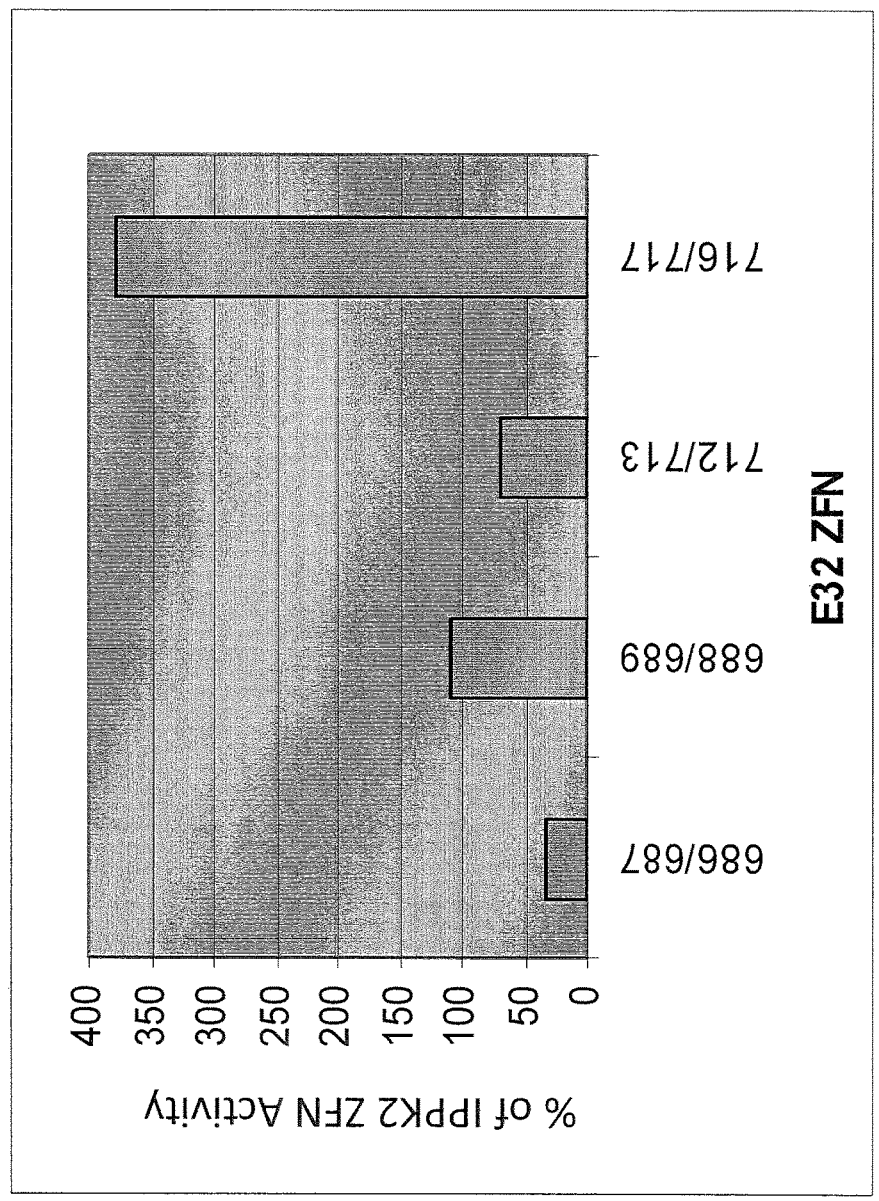
FIG. 36 depicts a graph showing evaluation of transiently expressed ZFNs in plants. Four ZFNs were evaluated in maize callus by transiently expressing the ZFNs and an internal control ZFN directed to the IPPK2 gene. After Next Generation Sequencing of PCR amplified fragments from the region surrounding the ZFN cleavage sites, the sequenced PCR amplified fragments were scored for the presence of sequence variants resulting from indels. The relative frequency of indels from each of the four E32 ZFN pairs as compared to IPPK2 ZFN activity are depicted. Event 32 ZFN6 which contains the 25716 ('716) and 25717 ('717) zinc finger binding domains cleaved the genomic locus of transgenic Corn Event DAS-59132 at 380 times the efficiency of the control IPPK2 zinc finger nuclease.

ILLUMINA™ Sequencing and Analysis:

The ZFNs were designed to recognize, bind and modify specific DNA sequences within the genomic locus of transgenic Corn Event DAS-59132. The efficiency by which the four ZFNs cleaved the genomic locus was assayed to determine which ZFN cleaved most efficiently. ILLUMINA™ sequencing was performed at Cofactor Genomics (St. Louis, Mo.) and sequences were analyzed using a sequence analysis script. Low quality sequences were filtered out and the remaining sequences were parsed according to unique DNA sequences identifiers. The unique DNA sequences identifiers were then aligned with the reference sequence and scored for insertions/deletions (Indels). To determine the level of cleavage activity, the region surrounding the ZFN cleavage site was scored for the presence of sequence variants which resulted from the INDELs. Cleavage activity for each ZFN in the study was calculated as the number of sequences with indels/1M high quality sequences or as a percentage of high quality sequences with indels. Next, the levels of cleavage efficiency were determined by normalizing the ZFN level of cleavage activity with the activity of a ZFN directed to the IPP2-K gene as described in U.S. Patent Publication No. 2011/0119786. FIG. 36 and Table 27 present the cleavage efficiency of the tested ZFNs.

Event 32 ZFN6 which contains the 25716 and 25717 zinc finger binding domains cleaved the genomic locus of transgenic Corn Event DAS-59132 with the highest efficiency. This ZFN functioned at 380 times the efficiency of the control IPPK2 zinc finger nuclease. Given the surprisingly high levels of cleavage activity of Event 32 ZFN6, this ZFN was selected for advancement to test the integration of a donor DNA fragment into a genomic locus via non homologous end-joining

TABLE 27

Cleavage efficiency of the tested eZFNs

| E32 ZFN Number | % IPPK2 ZFN Activity |
|---|---|
| 25686/25687 shown as "686/687" | 32 |
| 25688/25689 shown as "688/689" | 108 |
| 25712/25713 shown as "712/713" | 69 |
| 25716/25717 shown as "716/717" | 380 |

Transformation of ZFN in Protoplast

A system for gene targeting was established to target the endogenous genomic loci of Corn Event DAS-59132 and to optimize donor targeting parameters in maize. Double strand breaks were generated within the genome at Corn Event DAS-59132 and repaired by either the non-homologous end joining (NHEJ) or homology dependent repair (HDR).

Protoplast Isolation:

Maize Hi-II embryogenic suspension cultures were obtained and were maintained on a 3.5 day maintenance schedule. In a 50 mL sterile conical tube a 10 mL solution of sterile 6% (w/v) cellulase and a 10 mL solution of sterile 0.6% (w/v) pectolyase enzyme solutions were pipette into the conical tube using a 10 mL pipette tip. Next, 4 pack cell volumes (PCV) of Hi-II suspension cells were added into the 50 mL tube containing the digest solution and wrapped with parafilm. The tubes were placed on a platform rocker overnight at room temperature for ~16-18 hrs. The next morning, the tubes were removed from the shaker. In a sterile 50 mL conical tube the cells and enzyme solution were slowly filtered through a 100 µm cell strainer. Next, the cells were rinsed using a 100 µm cell strainer by pipetting 10 mLs of W5 media through the strainer. In a sterile 50 mL conical tube, the cells and enzyme solution were slowly filtered through a 70 µm cell strainer. This straining step was followed by a second straining step, wherein the cells and enzyme solution were slowly strained into a 50 mL conical tube through a 40 µm cell strainer. Using a 10 mL pipette tip, the 40 µm cell strainer was rinsed with 10 mL of W5 media to give a final volume of 40 mL and the tube was inverted. Very slowly, 8 mL of sucrose cushion was added to the bottom of the protoplast/enzyme solution. Using a centrifuge with a swing arm bucket rotor, the tubes were spun for 15 minutes at 1500 rpm. The protoplast cells were removed using a 5 mL narrow bore pipette tip. These cells (7-8 mLs) which were observed as a protoplast bane were removed very slowly and put into a sterile 50 mL conical tube. Next, 25 mL of W5 media was used to wash the tubes. The W5 media was added and the tubes were inverted slowly and centrifuge for 10 minutes at 1500 rpm. The supernatant was removed and 10 mL of MMG solution was added with slow inversion of the tube to resuspend protoplast pellet. The density of protoplasts were determined using a haemocytometer, the 4 PCV yields~30 million protoplasts.

Protoplast Transformation:

The protoplast cells were diluted to 1.6 million protoplasts per ml using an MMG solution. The protoplasts were gently resuspended by slowly inverting the tube. Next, 300 µL of protoplasts (~500 k protoplasts) were added to a sterile 2 mL tube, the tubes were inverted to evenly distribute the protoplast cells. Plasmid DNA of a concentration about 40-80 µg suspended in TE buffer was added to the protoplasts. The different experimental conditions are described in Table 28. The tubes were slowly rolled to suspend the DNA with the protoplasts and the tubes were incubated for 5-10 minutes at room temperature. Next 300 µL of PEG solution was added to the protoplast/DNA solution. Once all the PEG solution had been added, the PEG solution was mixed with the protoplast solution by gently inverting the tube. The cocktail was incubated at room temperature for 15-20 minutes with periodic inverting of the tube(s). After the incubation, 1 mL of W5 solution was slowly added to the tubes and the tubes were gently inverted. Finally, the solution was centrifuged at 1000 rpm for 15 minutes. The supernatant was carefully removed so as not to disturb the cell pellet. Finally, 1 mL of washing/incubating solution was added. The tubes were gently inverted to resuspend the cell pellet. The tubes were covered with aluminum foil to eliminate any exposure to light, and were laid on a rack on their side to incubate overnight. The cells were harvested 24 hours post-transformation for molecular analysis.

TABLE 28

Different treatment groups were used for the transformation of the protoplast cells. The differing concentrations of the DNA used for the transformations are described below.

| Treatment Groups | Donor DNA pDAB100651 (µg) | E32 ZFN6 pDAB105906 (µg) | pUC19 Filler (µg) | Salmon Sperm DNA Filler (µg) | Total DNA (µg) |
|---|---|---|---|---|---|
| E32 Donor alone + No enzyme control (filler-1) | pDAB100651 (40 µg) | N/A (0 µg) | pUC19 (40 µg) | N/A (0 µg) | 80 |
| E32 Donor alone + No enzyme control (filler-2) | pDAB100651 (40 µg) | N/A (0 µg) | N/A (0 µg) | ssDNA (40 µg) | 80 |
| E32 Donor alone control (no filler) | pDAB100651 (40 µg) | N/A (0 µg) | N/A (0 µg) | N/A (0 µg) | 40 |
| E32 ZFN6 alone control (no donor) filler1 | N/A (0 µg) | pDAB105906 (4 µg) | pUC19 (76 µg) | N/A (0 µg) | 80 |
| E32 ZFN6 alone control (no donor) filler2 | N/A (0 µg) | pDAB105906 (4 µg) | N/A (0 µg) | ssDNA (76 µg) | 80 |
| E32 ZFN6 wt FokI alone control (no donor) No filler | N/A (0 µg) | pDAB105906 (40 µg) | N/A (0 µg) | N/A (0 µg) | 40 |

TABLE 28-continued

Different treatment groups were used for the transformation of the protoplast cells. The differing concentrations of the DNA used for the transformations are described below.

| Treatment Groups | Donor DNA pDAB100651 (μg) | E32 ZFN6 pDAB105906 (μg) | pUC19 Filler (μg) | Salmon Sperm DNA Filler (μg) | Total DNA (μg) |
|---|---|---|---|---|---|
| E32 ZFN6 wt FokI + E32 Donor (1:10) filler1 | pDAB100651 (40 μg) | pDAB105906 (4 μg) | pUC19 (36 μg) | N/A (0 μg) | 80 |
| E32 ZFN6 wt FokI + E32 Donor (1:10) filler2 | pDAB100651 (40 μg) | pDAB105906 (4 μg) | N/A (0 μg) | ssDNA (36 μg) | 80 |

Sequence Validation of Targeting

The results of the ZFN cleavage activity in maize protoplasts were confirmed using the Next Generation Sequencing protocol described above. The sequenced PCR amplified fragments were scored for the presence of sequence variants resulting from indels. Event 32 ZFN6 cleaved the genomic locus of transgenic Corn Event DAS-59132 at about 1.5% of NHEJ/10 ng of targeted amplicon.

Targeting of an AAD-1 donor cassette into the genomic locus of transgenic Corn Event DAS-59132 into the Hi-II maize transgenic cell suspensions via Non Homologous End Joining (NHEJ) was confirmed via an in-out PCR reaction. The in-out PCR reaction was completed, wherein a first PCR reaction was designed to amplify the junction of the AAD-1 donor and genomic locus of transgenic Corn Event DAS-59132. The resulting amplicon was subjected to a second PCR reaction, wherein primers were designed to bind internally within the first amplicon. The combination of two independent PCR reactions resulted in the removal of background amplifications which may be false-positives. The in-out PCR results of the protoplast transformation experiments demonstrated that the genomic locus of transgenic Corn Event DAS-59132 could be reproducibly targeted with a 5.3 kb AAD1 plasmid donor and the E32 ZFN6 zinc finger nuclease at a ratio of 1:10 μg of DNA (with and without filler DNA comprised of either pUC19 plasmid DNA or salmon sperm DNA). Targeting via a NHEJ method was evidenced by the insertion of the AAD-1 donor cassette in both orientations. The sequence data produced from the PCR reactions resulted in three instances of perfect integration of the donor DNA. Thus it was possible to demonstrate donor targeting into an endogenous maize locus using ZFNs via a NHEJ-DSB repair mechanism.

WHISKERS™ Mediated Stable Transformation of ZFN and Donor for Targeted Integration Transgenic events were targeted to the endogenous genomic locus of Corn Event DAS-59132. Constructs as described in Example 2 include the donor sequence (pDAB100655) and Event 32 ZFN 6 (pDAB105906).

Maize callus cells, consisting of 12 mL of packed cell volume (PCV) from a previously cryo-preserved cell line plus 28 mL of conditioned medium was subcultured into 80 mL of GN6 liquid medium (N6 medium (Chu et al., (1975) Sci Sin. 18:659-668), 2.0 mg/L of 2,4-D, 30 g/L sucrose, pH 5.8) in a 500 mL Erlenmeyer flask, and placed on a shaker at 125 rpm at 28° C. This step was repeated two times using the same cell line, such that a total of 36 mL PCV was distributed across three flasks. After 24 hours, the GN6 liquid media was removed and replaced with 72 mL GN6 S/M osmotic medium (N6 Medium, 2.0 mg/L 2,4-D, 30 g/L sucrose, 45.5 g/L sorbitol, 45.5 g/L mannitol, 100 mg/L myo-inositol, pH 6.0). The flask was incubated in the dark for 30-35 minutes at 28° C. with moderate agitation (125 rpm). During the incubation period, a 50 mg/mL suspension of silicon carbide WHISKERS™ (Advanced Composite Materials, LLC, Greer, S.C.) was prepared by adding 8.1 mL of GN6 S/M liquid medium to 405 mg of sterile, silicon carbide WHISKERS™

Following incubation in GN6 S/M osmotic medium, the contents of each flask were pooled into a 250 mL centrifuge bottle. After all cells in the flask settled to the bottom, the content volume in excess of approximately 14 mL of GN6 S/M liquid was drawn off and collected in a sterile 1-L flask for future use. The pre-wetted suspension of WHISKERS™ was mixed at maximum speed on a vortex for 60 seconds, and then added to the centrifuge bottle.

In this example, 159 μg of pDAB100655 (donor sequence) and 11 μg of pDAB10506 (ZFN) plasmid DNA were added to each bottle. Once the plasmid DNA was added, the bottle was immediately placed in a modified RED DEVIL 5400™ commercial paint mixer (Red Devil Equipment Co., Plymouth, Minn.), and agitated for 10 seconds. Following agitation, the cocktail of cells, media, WHISKERS™ and plasmid DNA were added to the contents of a 1-L flask along with 125 mL fresh GN6 liquid medium to reduce the osmoticant. The cells were allowed to recover on a shaker set at 125 rpm for 2 hours. 6 mL of dispersed suspension was filtered onto Whatman #4 filter paper (5.5 cm) using a glass cell collector unit connected to a house vacuum line such that 60 filters were obtained per bottle. Filters were placed onto 60×20 mm plates of GN6 solid medium (same as GN6 liquid medium except with 2.5 g/L Gelrite gelling agent) and cultured at 28° C. under dark conditions for 1 week.

Identification and Isolation of Putative Targeted Events Integrated within the Corn Event DAS-59132 Genomic Locus One week post-DNA delivery, filter papers were transferred to 60×20 mm plates of GN6 (1H) selection medium (N6 Medium, 2.0 mg/L 2,4-D, 30 g/L sucrose, 100 mg/L myo-inositol, 2.5 g/L Gelrite, pH 5.8) containing a selective agent. These selection plates were incubated at 28° C. for one week in the dark. Following 1 week of selection in the dark, the tissue was embedded onto fresh media by scraping ½ the cells from each plate into a tube containing 3.0 mL of GN6 agarose medium held at 37-38° C. (N6 medium, 2.0 mg/L 2,4-D, 30 g/L sucrose, 100 mg/L myo-inositol, 7 g/L SEAPLAQUE® agarose, pH 5.8, autoclaved for 10 minutes at 121° C.).

The agarose/tissue mixture was broken up with a spatula and, subsequently, 3 mL of agarose/tissue mixture was evenly poured onto the surface of a 100×25 mm PETRI™ dish containing GN6 (1H) medium. This process was repeated for both halves of each plate. Once all the tissue was embedded, plates incubated at 28° C. under dark conditions for up to 10 weeks. Putatively transformed isolates that grew under these selection conditions were removed from the embedded plates and transferred to fresh selection medium in 60×20 mm plates. If sustained growth was evident after approximately 2 weeks, an event was deemed to be resistant to the applied herbicide (selective agent) and an aliquot of cells was subsequently harvested for genotype analysis. In this example, 24 events were recovered from 6 bottles treated. These events were advance for molecular analysis to confirm the integration of the AAD-1 gene within a genomic locus of Corn Event DAS-59132.

Molecular Analysis of NHEJ Targeting of the Corn Event DAS-59132 Genomic Locus

The 24 events that were recovered from the WHISKERS™ mediated transformation, as described above, were analyzed using several different molecular confirmation tools. As a result of the analysis events which contained a copy of the AAD-1 transgene integrated within the Corn Event DAS-59132 genomic locus were identified. Initially the 24 various events were confirmed to contain a copy of the AAD-1 transgene, next the events were analyzed to determine whether the genomic locus of Corn Event DAS-59132 which would suggest that a copy of the AAD-1 transgene had integrated via NHEJ within the genome of the maize cells. The events which were identified to contain a copy of the AAD-1 transgene within the genomic locus of Corn Event DAS-59132 were further confirmed via In-Out PCR and Southern blot reactions. These assays confirmed that events containing a copy of the AAD-1 transgene integrated within the Corn Event DAS-59132 genomic locus via an NHEJ mechanism.

DNA Extraction:

DNA was extracted from lyophilized maize callus tissue using a QIAGEN BIOSPRINT 96™ DNA isolation kit per manufacturer's recommendations. A pre-defined program was used for the automation extraction and DNA was eluted in 200 μl of 1:1 TE Buffer/distilled water. Two microliters (2 μl) of each sample was quantified on THERMOSCIENTIFIC NANODROP 8000™ and samples were normalized to 100 ng/μL using QIAGEN BIOROBOT 3000™. Normalized DNA was stored at 4° C. until further analysis.

Copy Number Estimation:

Transgene copy number determination by hydrolysis probe assay, analogous to TAQMAN® assay, was performed by real-time PCR using the LIGHTCYCLER®480 system (Roche Applied Science, Indianapolis, Ind.). Assays were designed for AAD-1 and the internal reference gene Invertase using LIGHTCYCLER® Probe Design Software 2.0. For amplification, LIGHTCYCLER®480 Probes Master mix (Roche Applied Science, Indianapolis, Ind.) was prepared at 1× final concentration in a 10 μL volume multiplex reaction containing 0.4 μM of each primer and 0.2 μM of each probe (Table 29). A two-step amplification reaction was performed with an extension at 60° C. for 40 seconds with fluorescence acquisition. Analysis of real time PCR copy number data was performed using LIGHTCYCLER® software release 1.5 using the relative quant module and is based on the ΔΔCt method. For this, a sample of gDNA from a single copy calibrator and a known two-copy check were included in each run.

TABLE 29

Primer/Probe Sequences for hydrolysis probe assay of AAD1 and internal reference (Inv).

| Primer Name | Sequence | Detection |
| --- | --- | --- |
| GAAD1F | SEQ ID NO: 454; 5' TGTTCGGTTCCCTCTACCAA 3' | — |
| GAAD1R | SEQ ID NO: 455; 5' CAACATCCATCACCTTGACTGA 3' | — |
| GAAD1R | SEQ ID NO: 456; 5' CACAGAACCGTCGCTTCAGCAACA 3' | FAM |
| IVF-Taq | SEQ ID NO: 457; 5' TGGCGGACGACGACTTGT 3' | — |
| IVR-Taq | SEQ ID NO: 458; 5' AAAGTTTGGAGGCTGCCGT 3' | — |
| IV-Probe | SEQ ID NO: 459; 5' CGAGCAGACCGCCGTGTACTTCTACC 3' | HEX |

Figure 37:
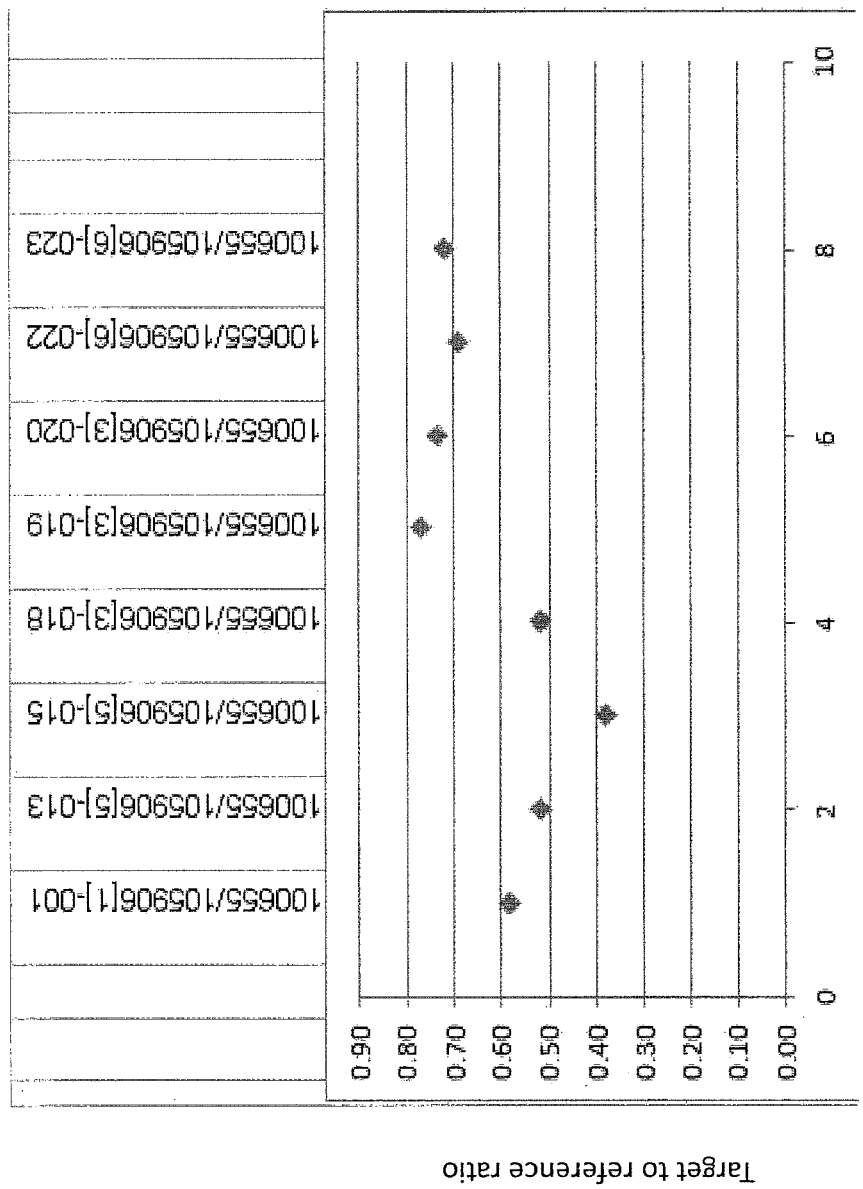
FIG. 37 depicts a graph of the ZFN locus disruption of Corn Event DAS-59132.

Corn Event DAS-59132 Genomic Locus Disruption Assay:

A genomic locus disruption assay for Corn Event DAS-59132 was performed by real-time PCR using the LIGHTCYCLER®480 system (Roche Applied Science, Indianapolis, Ind.). Assays were designed to monitor the specificity for which Event 32 ZFN6 (25716/25717) bound and cleaved genomic sequences of the Corn Event DAS-59132 locus and the internal reference gene IVF using the LIGHTCYCLER® Probe Design Software 2.0. For amplification, LIGHTCYCLER®480 Probes Master mix (Roche Applied Science, Indianapolis, Ind.) was prepared at 1× final concentration in a 10 μL volume multiplex reaction containing 0.4 μM of each primer and 0.2 μM of each probe (Table 30). A two-step amplification reaction was performed with an extension at 55° C. for 30 seconds with fluorescence acquisition. Analysis for the disruption assay was performed using target to reference ratio (FIG. 37). Four of the eight events were identified as containing an AAD-1 transgene integrated into the genomic locus of Corn Event DAS-59132. The following events, consisting of; Event 100655/105906[1]-001, Event 100655/105906[5]-013, Event 100655/105906[5]-015, and Event 100655/105906[3]-018, were advance for further molecular analysis to confirm the integration of the AAD-1 transgene within the genomic locus of Corn Event DAS-59132.

Corn Event DAS-59132 Locus Specific in-Out PCR:

The insertion of the AAD-1 donor within the genomic locus of Corn Event DAS-59132 via NHEJ can occur in one of two orientations. The integration of the AAD-1 transgene and the orientation of this integration were confirmed with an In-Out PCR assay. The In-Out PCR assay utilizes an "Out" primer that was designed to bind to the genomic locus of Corn Event DAS-59132 target sequence. In addition, an "In" primer was designed to bind to the AAD-1 donor sequence. The amplification reactions which were completed using these primers only amplify a donor gene which is inserted at the target site. The resulting PCR amplicon was produced from the two primers, and consisted of a sequence that spanned the junction of the insertion. For each sample, two sets of In-Out PCR primers were multiplexed into one reaction and were used to detect the NHEJ-mediated donor insertion which could occur in one of two different orientations. Positive and negative controls were included in the assay. Two positive control plasmids, pDAB100664 and pDAB100665, were constructed to simulate donor insertion at the genomic locus of Corn Event DAS-59132 in one of the two different orientations.

A DNA intercalating dye, SYTO-13, was used in the PCR mix in order to detect amplification in real time on a thermocycler with fluorescence detection capability. In addition, a melting temperature (Tm) analysis program was attached to a regular PCR program so the amplified products could be analyzed for their Tm profiles. The similarity in the Tm profile between an unknown sample and the positive control sample strongly suggests that the unknown sample has the same amplified product as that of the positive control. The PCR reactions were conducted using 10 ng of template genomic DNA, 0.2 µM dNTPs, 0.2 µM forward and reverse primers, 4 µM SYTO-13 and 0.15 µl of Ex Taq HS. Reactions were completed in two steps: the first step consisted of one cycle at 94° C. (2 minutes) and 35 cycles at 98° C. (12 seconds), 66° C. (30 seconds) and 68° C. (1.3 minutes); the second step was a Tm program covering 60-95° C. followed by 65° C. (30 seconds) and 72° C. (10 minutes) (Table 30). The amplicons were sent out for sequencing to confirm that the AAD-1 gene had integrated within the genomic locus of Corn Event DAS-59132.

The results of the real-time, In-Out PCR amplicons were visualized using the ABI software. These results were further confirmed using a gel shift assay, wherein the amplicons were run on a 1.2% TAE gel. Expected amplicon sizes were ~1.8 kb for the first orientation (as in pDAB100664) and ~2 kb for the second orientation (as in pDAB100665). The gel shift assay results confirmed the real-time, In-Out PCR reaction data. Both sets of data suggested that a copy of the AAD-1 transgene had integrated via NHEJ within the genome of the maize cells at the genomic locus of Corn Event DAS-59132.

alia, Calif.). Following tissue maceration the genomic DNA was isolated using the DNEASY PLANT MINI KIT™ (Qiagen, Germantown, Md.) according to the manufacturer's suggested protocol.

Southern Blot:

Genomic DNA (gDNA) was quantified using the QUANT-IT PICO GREEN DNA ASSAY KIT™ (Molecular Probes, Invitrogen, Carlsbad, Calif.). Quantified gDNA was adjusted to 4 µg for the Southern blot analysis. DNA samples were then digested using the NcoI restriction enzyme (New England BioLabs, Ipswich, Mass.) overnight at 37° C. followed with a clean-up using QUICK-PRECIP™ (Edge BioSystem, Gaithersburg, Md.) according to the manufacturer's suggested protocol. DNA was resuspended in 1× dye and electrophoresed for 5 hours on a 0.8% SEAKEM LE AGAROSE GEL™ (Lonza, Rockland, Me.) at 110 volts in a cold room. The gel was denatured, neutralized, and then transferred to a nylon charged membrane (Millipore, Bedford, Mass.) overnight and DNA was crosslinked to the membrane using the UV STRATA LINKER 1800™ (Stratagene, La Jolla, Calif.), and blots were prehybridized with 20 mL of PERFECTHYB PLUS™ (Sigma, St. Louis, Mo.). The 226 bp probe (SEQ ID NO:464) was labeled using PRIME-IT RMT RANDOM™ (Stratagene, La Jolla, Calif.) according to manufacturer's suggested protocol and purified using the PROBE QUANT G-50 MICRO COLUMNS™ (GE Healthcare, Buckinghamshire, UK) per manufacturer's suggested protocol. Approximately, 20,000,000 cpm of the labeled probe was added to the blots and incubated overnight. Blots were washed twice for 15 minutes per wash and placed on a phosphor image screen for 24 hours and analyzed by a STORM 860 SCANNER™ (Molecular Dynamics).

TABLE 30

Primers for In-Out PCR to detect NHEJ mediated targeting at Corn Event DAS-59132 in maize cells.

| Primer Name | Sequence | Expected Amplicon size/ control |
|---|---|---|
| E32-3R2 NJ-AAD1-Pri2 | Forward Primer SEQ ID NO: 460 5' GCC CTT ACA GTT CAT GGG CG 3' Reverser Primer SEQ ID NO: 461 5' GAC CAA GTC CTT GTC TGG GAC A 3' | 1.8 kB pDAB100664 |
| E32-5F1 NJ-AAD1-Pri2 | Forward Primer SEQ ID NO: 462 5' ACA AAC ACG TCC TCC AAG GCT 3' Reverse Primer SEQ ID NO: 463 5' GAC CAA GTC CTT GTC TGG GAC A 3' | 2.0 kB pDAB100665 |

Southern Blot Analysis:

The maize callus events identified above were further screened using a Southern blot assay. This assay was used to further confirm that the AAD-1 transgene had integrated via NHEJ within the genome of the maize cells at the genomic locus of Corn Event DAS-59132. The Southern blot analysis experiments generated data which demonstrated the integration and integrity of the AAD-1 transgene within the soybean genome.

DNA Extraction:

Genomic DNA was extracted from the callus tissue harvested from each individual event. Initially, the tissue samples were collected in 2 mL tubes and lyophilized for 2 days. Tissue maceration was performed with a KLECO TISSUE PULVERIZER™ and tungsten beads (Kleco, Vis- Expected and observed fragment sizes with the NcoI digest and probe, based on the known restriction enzyme sites AAD-1 and Corn Event DAS-59132 resulted from the Southern blots. Two DNA fragments were identified from these digests and hybridizations. Southern blots which produced results with bands at sizes of around 2.9 and 5.5 kb indicated that the AAD-1 transgene had integrated into the genomic locus of Corn Event DAS-59132 via an NHEJ mechanism.

Figure 38:
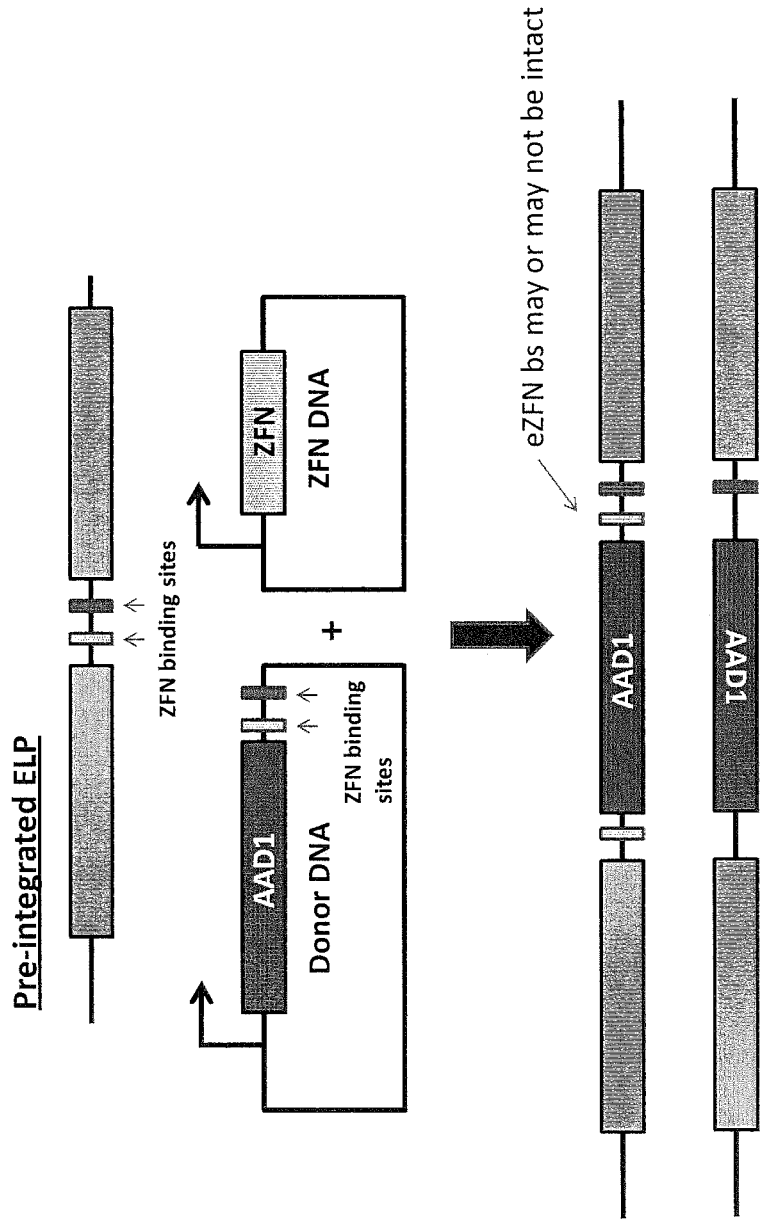
FIG. 38 is a schematic depicting the experimental system used for donor integration into the ELP of maize genome.

Example 9: Targeted Integration and Disruption of Corn Engineered Landing Pad Characterization of ELP Genomic Target Sequence The genomic locus in which an Engineered Landing Pad (ELP) integrated was selected as an endogenous genomic loci for gene targeting. The construction of the ELP sequences which comprise Zinc Finger binding sites (eZFN1 and eZFN3) and about 1.0 kb of random artificial sequences which flank the Zinc Finger binding sites, in addition to the Zinc Finger Nuclease proteins are described in International Patent Application WO2011091317, herein incorporated by reference in its entirety. To test NHEJ-mediated targeted integration within the ELP loci, two donor DNAs were constructed, both of which contain one of the two eZFN binding sites in a 5.3 kb plasmid comprising an aad-1 gene which confers resistance to the herbicide haloxyfop. FIG. 38 presents a representative schematic of the integration.

Regeneration of Transgenic Plant Events Comprising an ELP

Four transgenic ELP events produced from the transformation of pDAB100640, pDAB100641 and pDAB106685 (two for each ELP) were generated as described in International Patent Application WO2011091317, herein incorporated by reference in its entirety. The events were obtained and confirmed to be single copy and contain an intact PTU comprising the ELP. These events were regenerated to produce donor material for targeting. Healthy growing tissue was transferred first to 28(1H) (MS medium (Murashige and Skoog (1962) *Physiol Plant* 15:473-497), 0.025 mg/L 2,-4D, 5 mg/L BAP, 1.0 mg/L Herbiace, 30 g/L sucrose, 2.5 g/L gelrite, pH 5.7) and incubated in low light (14 $\mu E/m^2 \cdot sec$ 16 hr photoperiod) for 7 days followed by high light (89 $\mu E/m^2 \cdot sec$ 16 hr photoperiod) for another 7 days. Greening structures were transferred to 36(1H) which is the same as 28(1H) minus the BAP and 2,4-D and incubated in high light (40 $\mu E/m^2 \cdot sec$ 16 hr photoperiod) until shoot structures developed sufficient roots for transplanting to greenhouse. Plants were grown to maturity in greenhouse using mix of 95% METRO-MIX 360® and 5% clay/loam soil and pollinated dependent on health of plant. Vigorously growing plants were selfed or sibbed (plants from same event) and less vigorous plants were crossed with Hi-II or A188 to maintain embryogenic capacity of donor material. $T_1$ seed was planted in 4" pots and germinating seedlings were screened for zygosity via qPCR. Seedlings determined to be homozygous for the PAT gene were transferred to 5 gallon pots, grown to reproductive stage, outcrossed to Hi-II and $T_2$ embryos used for targeting via NHEJ mediated integration.

NHEJ Targeting of ELP Protoplasts

*Zea mays* Hi-II protoplasts were obtained and transformed using the previously described protoplast transformation protocol. Donor plasmid DNA of pDAB100651 was transformed with the ZFN plasmid DNA of pDAB105941. Likewise, donor plasmid DNA of pDAB100652 was transformed with the ZFN plasmid DNA of pDAB105943. The donor DNAs were transformed with Zinc Finger Nucleases into the ELP transgenic plants. Upon the introduction of the donor DNA and the eZFNs, both the donor DNA and the ELP loci with is integrated within the genomic target DNA were cleaved. The donor DNA was subsequently inserted into the genomic target. The insertion of the donor DNA within the ELP genomic loci can occur in either orientation. Insertion of the donor DNA in the direct orientation will result in a junction sequence that corresponds to the expected annealing and ligation of the 4 bp single-stranded complementary ends generated from ZFN cleavage. Insertions and deletions (indels) at the junctions are common. Insertion of the donor DNA in the reverse orientation will result in both junction fractions that contain indels.

Protoplast Isolation:

Maize Hi-II embryogenic suspension cultures were obtained and were maintained on a 3.5 day maintenance schedule. In a 50 mL sterile conical tube a 10 solution of sterile 6% (w/v) cellulase and a 10 mL solution of sterile 0.6% (w/v) pectolyase enzyme solutions were pipette into the conical tube using a 10 mL pipette tip. Next, 4 pack cell volumes (PCV) of Hi-II suspension cells were added into the 50 mL tube containing the digest solution and wrapped with parafilm. The tubes were placed on a platform rocker overnight at room temperature for ~16-18 hrs. The next morning, the tubes were removed from the shaker. In a sterile 50 mL conical tube the cells and enzyme solution were slowly filtered through a 100 µm cell strainer. Next, the cells were rinsed using a 100 µm cell strainer by pipetting 10 mLs of W5 media through the strainer. In a sterile 50 mL conical tube, the cells and enzyme solution were slowly filtered through a 70 µm cell strainer. This straining step was followed by a second straining step, wherein the cells and enzyme solution were slowly strained into a 50 mL conical tube through a 40 µm cell strainer. Using a 10 mL pipette tip, the 40 µm cell strainer was rinsed with 10 mL of W5 media to give a final volume of 40 mL and the tube was inverted. Very slowly, 8 mL of sucrose cushion was added to the bottom of the protoplast/enzyme solution. Using a centrifuge with a swing arm bucket rotor, the tubes were spun for 15 minutes at 1500 rpm. The protoplast cells were removed using a 5 mL narrow bore pipette tip. These cells (7-8 mLs) which were observed as a protoplast bane were removed very slowly and put into a sterile 50 mL conical tube. Next, 25 mL of W5 media was used to wash the tubes. The W5 media was added and the tubes were inverted slowly and centrifuge for 10 minutes at 1500 rpm. The supernatant was removed and 10 mL of MMG solution was added with slow inversion of the tube to resuspend protoplast pellet. The density of protoplasts were determined using a haemocytometer, the 4 PCV yields~30 million protoplasts.

Figure 39:
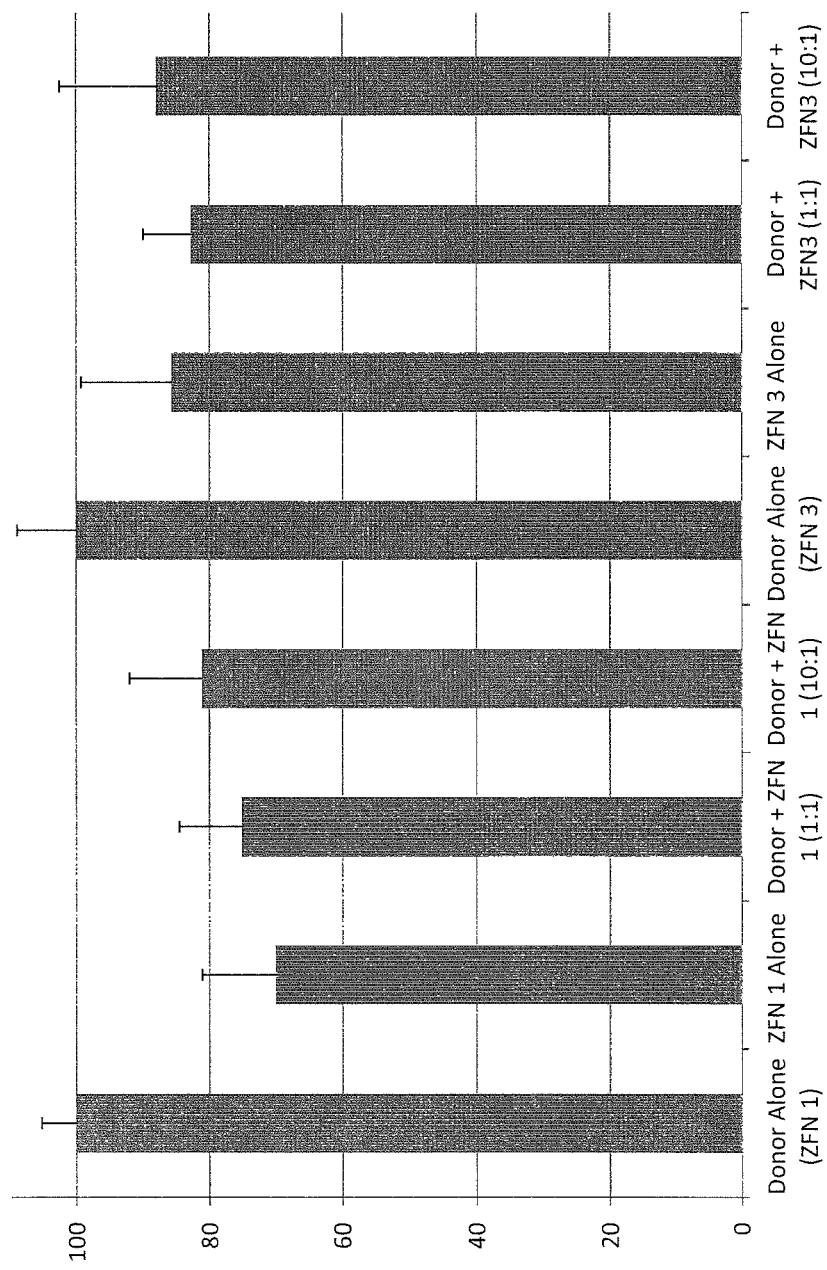
FIG. 39 is a graph illustrating the cleavage of genomic target DNA by eZFNs. DNA was isolated from each treatment group (6 replicates each) as indicated. TAQMAN™ assays were used to measure cleavage of the target DNA. Cleavage activity of the eZFNs is relative to the Donor DNA alone treatments. eZFNs (eZFN1 and eZFN3) levels were 1:1 or 1:10 ratios relative to the Donor DNA. Statistical groupings are indicated by lower case letters.

Protoplast Transformation:

The protoplast cells were diluted to 1.6 million protoplasts per ml using an MMG solution. The protoplasts were gently resuspended by slowly inverting the tube. Next, 300 µL of protoplasts (~500 k protoplasts) were added to a sterile 2 mL tube, the tubes were inverted to evenly distribute the protoplast cells. Plasmid DNA of a concentration about 80 µg was suspended in TE buffer was added to the protoplasts. Both the ZFN and donor plasmid constructs were transformed. The eZFN expressing plasmids (pDAB105941 and pDAB105943) were added alone or in combination at a 1:1 or 10:1 ratio of Donor DNA (pDAB100651 and pDAB100652) to eZFN DNA for each of the eZFN1 and eZFN3 treatments. The efficacy of the eZFNs had previously been tested and are described in more detail in International Patent Application WO2011091317, FIG. 39 is provided as a representation of the eZFN relative to the donor DNA. The tubes were slowly rolled to suspend the DNA with the protoplasts and the tubes were incubated for 5-10 minutes at room temperature. Next 300 µL of PEG solution was added to the protoplast/DNA solution. Once all the PEG solution had been added, the PEG solution was mixed with the protoplast solution by gently inverting the tube. The cocktail was incubated at room temperature for 15-20 minutes with periodic inverting of the tube(s). After the incubation, 1 mL of W5 solution was slowly added to the tubes and the tubes were gently inverted. Finally, the solution was centrifuged at 1000 rpm for 15 minutes. The supernatant was carefully removed so as not to disturb the cell pellet. Finally, 1 mL of washing/incubating solution was added. The tubes were gently inverted to resuspend the cell pellet. The tubes were covered with aluminum foil to eliminate any exposure to light, and were laid on a rack on their side to incubate overnight. The cells were harvested 24 hours post-transformation for molecular analysis to identify ELP loci which contained a donor integrated via NHEJ-mediated DNA repair.

TABLE 31

DNA concentrations and of the eZFN and Donor plasmid DNA that were transformed into the maize cells and integrated within the ELP loci.

| Treatment Groups | Donor DNA (pDAB) | Amount (µg) | eZFNs (pDAB) | Amount (µg) | Filler Plasmid (µg) | Total DNA (µg) |
|---|---|---|---|---|---|---|
| eZFN1 Donor alone | 100651 | 40 | — | — | 40 | 80 |
| eZFN1 alone | — | — | 105941 | 40 | 40 | 80 |
| eZFN1 Donor + eZFN1 (1:1) | 100651 | 40 | 105941 | 40 | 0 | 80 |
| eZFN1 Donor + eZFN1 (10:1) | 100651 | 40 | 105941 | 4 | 36 | 80 |
| — | — | — | — | — | — | — |
| eZFN3 Donor alone | 100652 | 40 | — | — | 40 | 80 |
| eZFN3 alone | — | — | 105943 | 40 | 40 | 80 |
| eZFN3 Donor + eZFN3 (1:1) | 100652 | 40 | 105943 | 40 | 0 | 80 |
| eZFN3 Donor + eZFN3 (10:1) | 100652 | 40 | 105943 | 4 | 36 | 80 |

Molecular Confirmation of Maize ELP Targeting by NHEJ in Protoplasts

DNA Extraction:

DNA was extracted from maize tissue using a Qiagen BIOSPRINT 96™ robot via automation and DNA was eluted in 200 µl of 1:1 TE Buffer/distilled water. DNA of each sample was quantified on THERMOSCIENTIFIC NANODROP 8000™ and samples were normalized to 100 ng/µL using QIAGEN BIOROBOT 3000™. Normalized DNA was stored at 4° C. till further analysis.

ELP Locus Disruption Assay:

After harvesting the protoplasts at 24 hr, DNA was extracted and analyzed using a disruption assay, junction analysis using PCR and sequencing of the DNAs produced by the junction PCR. The disruption assay is an indirect measure of relative eZFN cleavage activity. The TAQ-MAN™-based assay determines the loss of intact eZFN binding sites in the target DNA as would be expected due to misrepair of the DNA ends that can occur upon ligation of the ends.

The data from the TAQMAN™-based assay suggests that eZFN1 has a higher activity than does eZFN3 and also that there is significant cleavage of the target DNA by the eZFNs as demonstrated by the statistically significant reduction in the signal in the eZFN samples compared to the donor alone samples.

Figure 40:
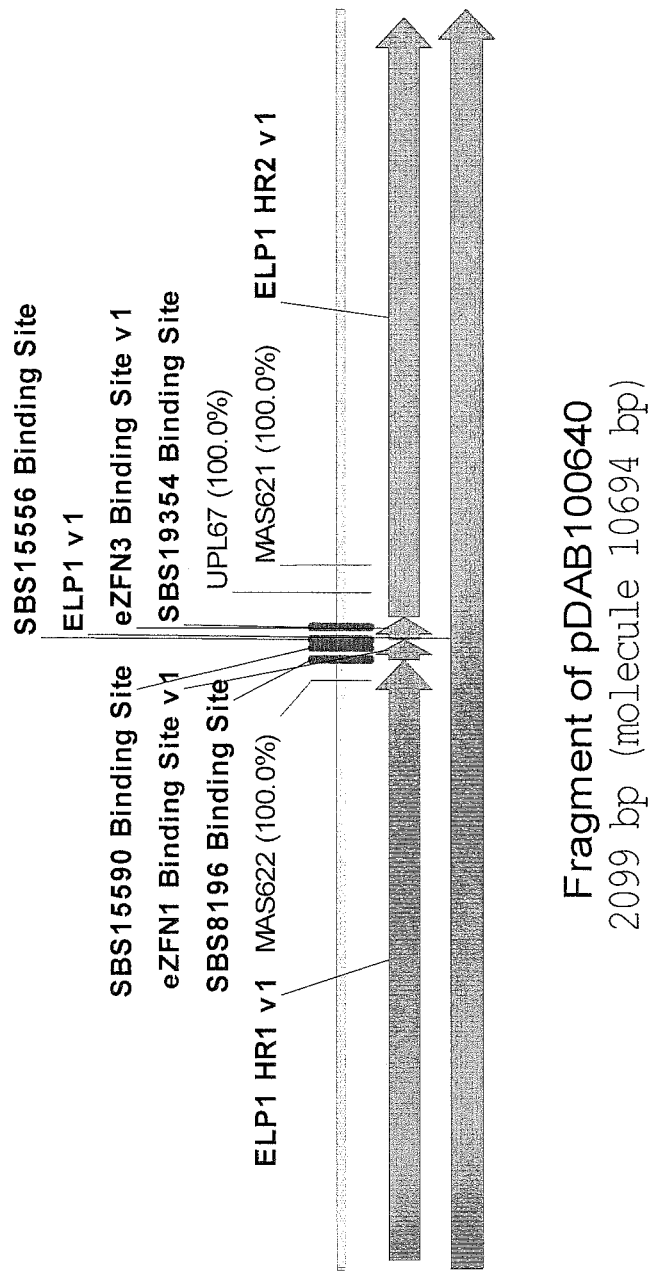
FIG. 40 illustrates the primer binding sites within the ELP loci of the corn genome.

Cleavage of genomic target DNA by eZFNs. DNA was isolated from each treatment group (6 replicates each) as indicated. Taqman assays were used to measure cleavage of the target DNA. ELP locus disruption assay was performed by real-time PCR using the LIGHTCYCLER®480 system (Roche Applied Science, Indianapolis, Ind.). Assays were designed to monitor eZFN1 and eZFN3 binding sequences within ELP1 and the internal reference gene IVF using LIGHTCYCLER® Probe Design Software 2.0. For amplification, LIGHTCYCLER®480 Probes Master mix (Roche Applied Science, Indianapolis, Ind.) was prepared at 1× final concentration in a 10 µL volume multiplex reaction containing 0.4 µM of each primer and 0.2 µM of each probe (Table 33). A two-step amplification reaction was performed with an extension at 55° C. for 30 seconds with fluorescence acquisition. Analysis for the disruption assay was performed using target to reference ratio. The location of the primers are shown in FIG. 40.

TABLE 33

Primer and probe sequences for the disruption assay

| Primer Name | Sequence | Detection |
|---|---|---|
| MAS622 | SEQ ID NO: 471; 5' TAGGAGTTCTCTTTTATGCCACCC 3' | — |
| MAS621 | SEQ ID NO: 472; 5' CCTTGGGATTTCAGTTGGTAGGTT 3' | — |
| UPL67 Probe | Obtained from Roche Biosciences, Indianapolis, IN | FAM |
| IVF-Taq | SEQ ID NO: 473; 5' TGGCGGACGACGACTTGT 3' | — |
| IVR-Taq | SEQ ID NO: 474; 5' AAAGTTTGGAGGCTGCCGT 3' | — |
| IV-Probe | SEQ ID NO: 475; 5' CGAGCAGACCGCCGTGTACTTCTACC 3' | HEX |

Locus Specific In-Out PCR:

Donor insertion at the expected ELP site using NHEJ-mediated repair can result in two different orientations. Two positive control plasmids, pDAB100660 and pDAB100662 were constructed and transformed into plants to simulate donor insertion within the ELP site. Transgenic plants which were produced with the pDAB100660 and pDAB100662 control constructs were assayed using an In-Out PCR design and the conditions for the In-Out PCR assay were determined on these plant materials.

The In-Out PCR assay has an "Out" primer in the ELP sequence while an "In" primer is placed in the donor sequence, so that only when the donor is inserted in the target site, the two primers would amplify a sequence that spans the junction of the insertion (Table 34). For each sample, two In-Out PCR reactions were used to detect donor insertion with two different orientations. Positive and negative controls were included in the assay.

A DNA intercalating dye, SYTO-13, was used in the PCR mix in order to detect amplification in real-time on a thermocycler with fluorescence detection capability. In addition, a melting temperature (Tm) analysis program was attached to a regular PCR program so the amplified products can be analyzed for their Tm profiles. Similarity of the Tm profile between an unknown sample and the positive control strongly suggests the unknown sample has the same amplified product as that of the positive control. Positive targeted samples identified in the real-time, In-Out PCR assay were further visualized using gel shift analysis. Expected amplicon sizes are ~1.5 kb for Orientation 1 (as in pDAB100662), and ~1.4 kb for Orientation 2 (as in pDAB100660).

TABLE 34

Primers for In-Out PCR to detect NHEJ mediated targeting at ELP1 in maize

| Primer Name | Sequence | Expected Amplicon size/control |
|---|---|---|
| ELP1-PriF1 | SEQ ID NO: 476 5' AGA CCT ACC ACC CAT TAG GGC 3' | 1.5 kB pDAB100662 |
| NJ-AAD1-Pri2 | SEQ ID NO: 477 5' GAC CAA GTC CTT GTC TGG GAC A 3' | |
| NJ-AAD1-Pri2 | SEQ ID NO: 478 5' GAC CAA GTC CTT GTC TGG GAC A 3' | 1.4 kB pDAB100660 |
| ELP2-PriR1 | SEQ ID NO: 479 5' GAT GGT GGT TAT GAC AGG CTC CT 3' | |

PCR reactions were conducted using 10 ng of template genomic DNA, 0.2 µM dNTPs, 0.2 µM forward and reverse primers, 4 µM SYTO-13 and 0.15 µl of Ex Taq HS. Reactions were completed in two steps: the first step consisted of one cycle at 94° C. (2 minutes) and 35 cycles at 98° C. (12 seconds), 66° C. (30 seconds) and 68° C. (1.3 minutes); the second step was a Tm program covering 60-95° C. followed by 65° C. (30 seconds) and 72° C. (10 minutes). Products were visualized using the ABI software as well as by running on a 1.2% TAE gel.

The In-out PCR junction analysis for eZFN1 and eZFN3 of NHEJ-directed targeting of donor treatments that included donor DNA alone, eZFN alone, or Donor DNA with eZFN DNA (at a ratio of either 1:1 or 10:1) were run out on agarose gels. The results indicated that the PCR amplicon size of the donor and eZFN DNA was that expected for an NHEJ targeted event.

Sequence of Target/Donor Junctions:

From the ELP targeted events which were confirmed via in-out PCR analysis, the PCR amplicon products were confirmed via sequencing and the target-donor junctions were validated by standard Sanger sequencing. Briefly, junction PCR analysis was performed on all replicates of each treatment group. PCR primers were chosen to amplify one side of the insert junction sequences that were either in the direct or reverse orientation. PCR products were observed in samples generated from the eZFN and Donor DNA samples, but not from the control samples, comprising the Donor DNA alone or eZFN alone samples. PCR products were evident in the majority of replicate samples from both ratios of eZFNs and Donor DNAs used.

Figure 41:
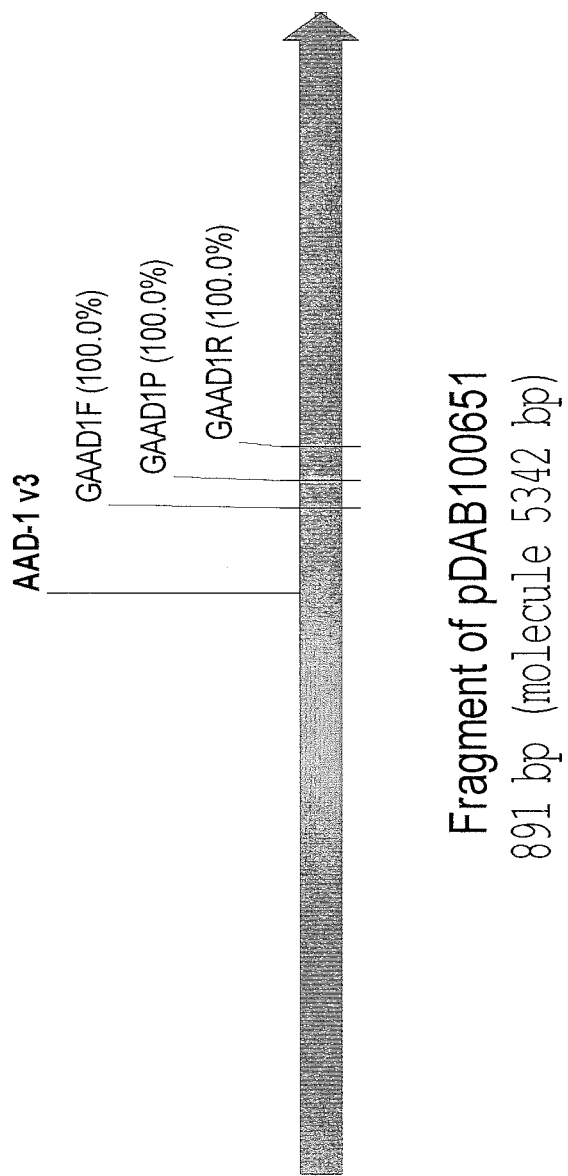
FIG. 41 illustrates the primer binding sites of the pDAB100651 fragment for copy number evaluation.

Representative samples of the PCR products were cloned and sequenced. For both the direct and reverse orientation, sequences of the PCR products from four different reactions are shown in FIG. 41. Nine unique haplotypes were observed for the direct orientation of the insert, as expected from misrepair to the junction ends. Three of the 16 sequences aligned with the sequence expected from annealing and ligation of intact ends of the inserted Donor DNA and the target sequence. All sequences of the PCR products in the reverse orientation had indels at the junctions as expected since the single-stranded ends of the Donor DNA and target DNA are not complementary.

Results of NHEJ-Mediated Donor Targeting in Maize Protoplasts

A maize protoplast-based transient assay system was developed that showed high, reproducible expression of reporter genes. Protoplasts were derived from a Hi-II maize suspension culture that was developed at DAS. A transgenic line of maize (maize line 106685[1]-007) that harbored an insert of the ELP was used for NHEJ mediated integration of the donor DNA sequence.

NHEJ Targeting of ELP Embryos Via Microparticle Bombardment

Three days prior to microparticle bombardment, 1.5-2.2 mm embryos were isolated from surface sterilized ears and placed (scutellum-up) onto N6 basal medium and vitamins (Phytotechnology Laboratories, Shawnee Mission, Kans.) with 2.0 mg/L 2,4-D, 2.8 g/L proline, 30 g/L sucrose, 100 mg/L casein enzymatic hydrolysate, 100 mg/L myo-inositol and 4.25 mg/L silver nitrate solidified with 2.5 g/L Gelzan (Phytotechnology Laboratories, Shawnee Mission, Kans.). Four hours prior to microparticle bombardment, ~35-40 embryos were placed (scutellum up) onto in the center of a 100×15 mm Petri dish containing the same medium with the addition of 36.4 g/L sorbitol and 36.4 g/L mannitol.

Microparticle gold (0.6 micron, BioRad, Hercules, Calif.,) was prepared for DNA precipitation by weighing out 15 mg into a sterile, siliconized 1.7 mL microcentrifuge tube (Sigma-Aldrich, St. Louis, Mo.) and 500 µL of ice cold 100% ethanol was slowly added. After a 15 second sonication in an FS-14 ultrasonic water bath (Fisher Scientific, Nazareth, Pa.), the gold was allowed to settle for 30 minutes at room temperature prior to centrifugation at 3,000 rpm for 60 seconds using a MiniSpin (Eppendorf, Hauppauge, N.Y.). After removing the supernatant, 1 mL of ice cold, sterile water was added, mixed up and down with the pipette and allowed to settle for 3-5 minutes prior to centrifugation at 3,000 for 60 seconds. The wash step was repeated one more time prior to suspending the gold in 500 µL of ice cold, sterile water. The washed gold was then aliquoted into separate 1.7 mL sterile, siliconized microcentrifuge tubes (50 µL per tube) being careful to keep the gold well mixed by pipetting up and down between tubes. The washed gold (~1.5 mg per 50 µL) was then stored at −20° C. until needed.

For DNA precipitation, one tube containing ~1.5 mg of gold in 50 µL of water was thawed for each 10 targets to be bombarded and sonicated in an ultrasonic water bath for 15 seconds then placed on ice. Plasmid DNA (0.5 µg ZFN+4.5 µg Donor) was premixed in 0.6 mL microcentrifuge tubes (Fisher Scientific, Nazareth, Pa.) and added to the gold suspension gently pipetting up and down several times to mix thoroughly. Fifty µL of ice cold 2.5 M calcium chloride was added and gently mixed by pipetting up and down several times. Twenty µL of cold 0.1 M spermidine was then added and gently mixed by pipetting up and down several times. The tube was then capped and placed onto a Vortex Genie 2 (Scientific Instruments Inc., Bohemia, N.Y.) and allowed to mix (set at 'shake 2') for 10 minutes after which the mixture was allowed to settle for 3-5 minutes. After centrifuging for 15 seconds at 5,000 rpm, the supernatant was carefully removed and 250 µL of ice cold, 100% ethanol was added, the tube capped and mixed vigorously by hand to dislodge the pellet. After a second centrifuge for 15 seconds at 5,000 rpm, 120 µL of ice cold, 100% ethanol was added, the tube capped and mixed vigorously by hand to dislodge the pellet.

For microparticle bombardment, sterilized macrocarriers (BioRad, Hercules, Calif.) were fit into stainless steel holders (BioRad, Hercules, Calif.) and autoclaved. Ten µL of gold/DNA suspension was evenly spread in the center of the macrocarrier being sure to pipette up and down so as to keep well mixed then placed onto a piece of sterile 125 mm Whatman #4 filter paper (GE Healthcare, Buckinghamshire, UK) on a bed of 8-mesh Drierite (W.A Hammond Drierite Co., Xenia, Ohio) in a 140×25 mm glass Petri dish. The gold/DNA was allowed to dry completely for about 10 minutes. Rupture discs (650 psi, BioRad, Hercules, Calif.) were sterilized by soaking for a few minutes in isopropyl alcohol then loaded into the retaining cap of a microparticle bombardment devise (PDS-1000, BioRad, Hercules, Calif.). An autoclaved stopping screen (BioRad, Hercules, Calif.) and a loaded macrocarrier was placed into the launch assembly, the lid was screwed on and slide into the bombardment chamber just under the nozzle. The Petri dish containing the screen-covered, leaf target was uncovered and placed in the bombardment chamber 6 cm below the nozzle. A vacuum was pulled (−0.9 bar) and the devise was fired.

Next day (16-20 hours after bombardment), the bombarded embryos were transferred (scutellum-up) to N6 basal medium and vitamins (Phytotechnology Laboratories, Shawnee Mission, Kans.) with 2.0 mg/L 2,4-D, 2.8 g/L proline, 30 g/L sucrose, 100 mg/L casein enzymatic hydrolysate, 100 mg/L myo-inositol and 4.25 mg/L silver nitrate solidified with 2.5 g/L Gelzan (Phytotechnology Laboratories, Shawnee Mission, Kans.). After 7 days-8 days-post-bombardment, 11 days from culture initiation—embryos were transferred to selection media N6 basal medium and vitamins (Phytotechnology Laboratories, Shawnee Mission, Kans.) with 2.0 mg/L 2,4-D, 2.8 g/L proline, 30 g/L sucrose, 100 mg/L casein enzymatic hydrolysate, 100 mg/L myo-inositol, 4.25 mg/L silver nitrate and 0.0362 mg/L R-haloxyfop acid solidified with 2.5 g/L Gelzan (Phytotechnology Laboratories, Shawnee Mission, Kans.). After two weeks, embryos were transferred to fresh selection N6 basal medium and vitamins (Phytotechnology Laboratories, Shawnee Mission, Kans.) with 2.0 mg/L 2,4-D, 2.8 g/L proline, 30 g/L sucrose, 100 mg/L casein enzymatic hydrolysate, 100 mg/L myo-inositol, 4.25 mg/L silver nitrate and 0.181 mg/L R-haloxyfop acid solidified with 2.5 g/L Gelzan (Phytotechnology Laboratories, Shawnee Mission, Kans.) and after an additional two weeks they were transferred to fresh medium of the same composition.

Callus growing on 0.181 mg/L R-haloxyfop was sampled for molecular analysis. Sampling involved placing either ~50 mg into 1.2 mL cluster tubes for PCR analysis or ~200 mg into 2.0 mL Safe Lock tubes (Eppendorf, Hauppauge, N.Y.) for Southern blot analysis surrounded by dry ice for rapid freezing. The tubes were then covered in 3M micropore tape (Fisher Scientific, Nazareth, Pa.) and lyophilized for 48 hours in a Virtual XL-70 (VirTis, Gardiner, N.Y.). Once the tissue was lyophilized, the tubes were capped and stored at 8° C. until analysis.

Molecular Confirmation of Maize ELP Targeting by NHEJ in Plants

DNA Extraction:

DNA was extracted from maize tissue using a Qiagen BIOSPRINT 96™ robot via automation and DNA was eluted in 200 µl of 1:1 TE Buffer/distilled water. Two µL of each sample was quantified on THERMOSCIENTIFIC NANODROP 8000™ and samples were normalized to 100 ng/µL using QIAGEN BIOROBOT 3000™. Normalized DNA was stored at 4° C. till further analysis.

Copy Number Estimation:

Transgene copy number determination by hydrolysis probe assay, analogous to TAQMAN® assay, was performed by real-time PCR using the LIGHTCYCLER®480 system (Roche Applied Science, Indianapolis, Ind.). Assays were designed for the aad-1 transgene and the internal reference gene Invertase using LIGHTCYCLER® PROBE DESIGN SOFTWARE 2.0. For amplification, LIGHTCYCLER®480 Probes Master mix (Roche Applied Science, Indianapolis, Ind.) was prepared at 1× final concentration in a 10 µL volume multiplex reaction containing 0.4 µM of each primer and 0.2 µM of each probe (Table 32). A two-step amplification reaction was performed with an extension at 60° C. for 40 seconds with fluorescence acquisition. Analysis of real time PCR copy number data was performed using LIGHTCYCLER® software release 1.5 using the relative quant module and is based on the ΔΔCt method. For this, a sample of gDNA from a single copy calibrator and known 2 copy check were included in each run. The location of the primers are shown in FIG. 41.

TABLE 32

Primer/Probe Sequences for hydrolysis probe assay of AAD1 and internal reference (Inv)

| Primer Name | Sequence | Detection |
|---|---|---|
| GAAD1F | SEQ ID NO: 465;<br>5' TGTTCGGTTCCCTCTACCAA 3' | — |
| GAAD1R | SEQ ID NO: 466;<br>5' CAACATCCATCACCTTGACTGA 3' | — |
| GAAD1R | SEQ ID NO: 467;<br>5' CACAGAACCGTCGCTTCAGCAACA 3' | FAM |
| IVF-Taq | SEQ ID NO: 468;<br>5' TGGCGGACGACGACTTGT 3' | — |
| IVR-Taq | SEQ ID NO: 469;<br>5' AAAGTTTGGAGGCTGCCGT 3' | — |
| IV-Probe | SEQ ID NO: 470;<br>5' CGAGCAGACCGCCGTGTACTTCTACC 3' | HEX |

Figure 42:
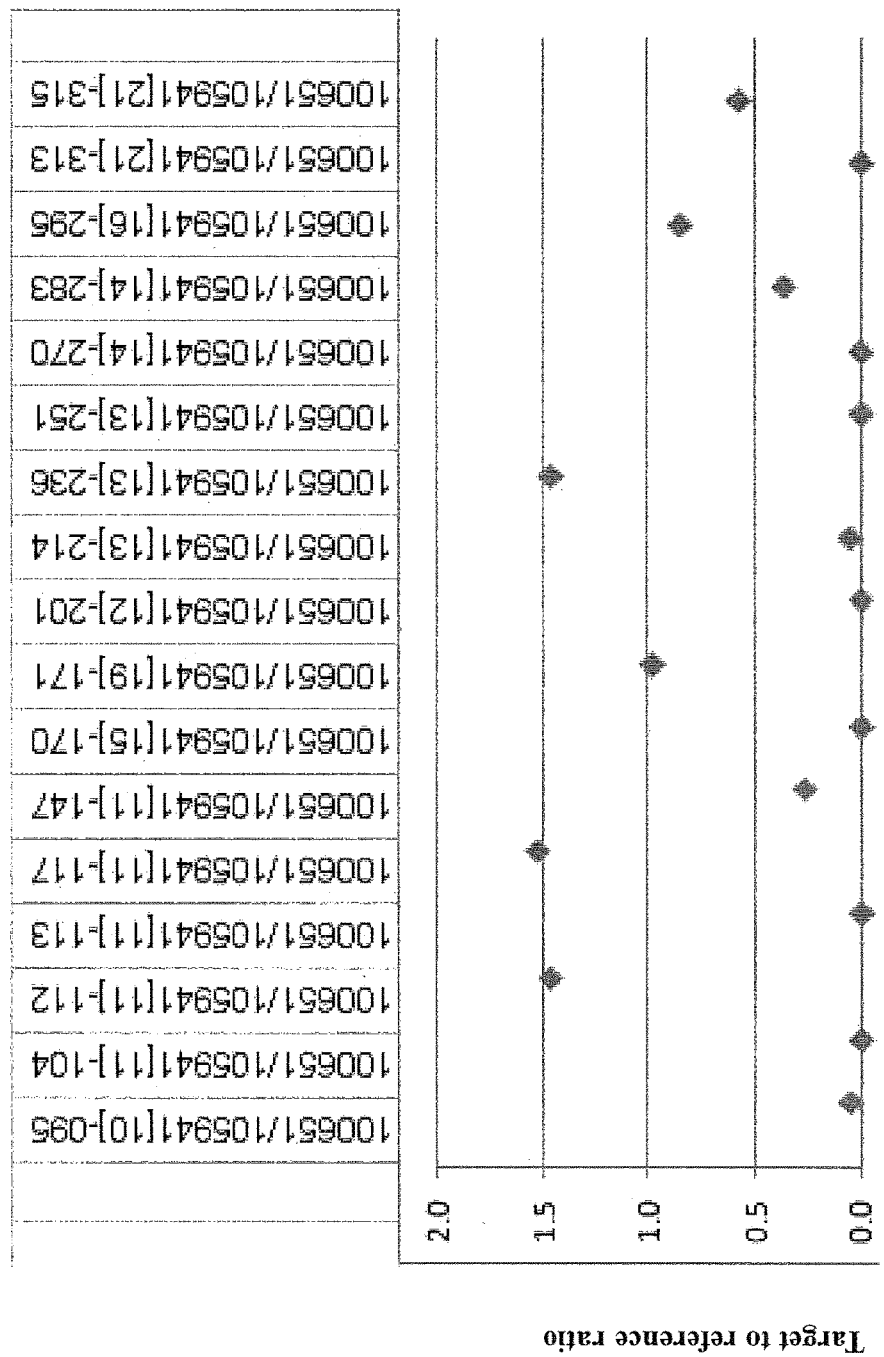
FIG. 42 shows the cleavage activity of the eZFNs is relative to the Donor DNA alone treatments. The eZFN (eZFN1 and eZFN3) cleavage levels were 1:1 or 1:10 ratios relative to the donor DNA. Statistical groupings are indicated by lower case letters.

ELP Locus Disruption Assay:

The ELP locus disruption assay was performed by real-time PCR using the LIGHTCYCLER®480 system (Roche Applied Science, Indianapolis, Ind.) as previously described above. Assays were designed to monitor eZFN1 and eZFN3 binding sequences within ELP1 and the internal reference gene IVF using LIGHTCYCLER® Probe Design Software 2.0. Analysis for the disruption assay was performed using target to reference ratio. The results are shown in FIG. 42.

Locus Specific In-Out PCR:

The In-Out PCR assay was completed as previously described above. The In-out PCR junction analysis for eZFN1 and eZFN3 of NHEJ-directed targeting of donor treatments that included donor DNA alone, eZFN alone, or Donor DNA with eZFN DNA (at a ratio of either 1:1 or 10:1) were run out on agarose gels. The results indicated that the PCR amplicon size of the donor and eZFN DNA was that expected for an NHEJ targeted event.

Sequence of Target/Donor Junctions:

From the ELP targeted events which were confirmed via in-out PCR analysis, the PCR amplicon products were confirmed via sequencing and the target-donor junctions were validated by standard Sanger sequencing. Briefly, junction PCR analysis was performed on all replicates of each treatment group. PCR primers were chosen to amplify one side of the insert junction sequences that were either in the direct or reverse orientation. PCR products were observed in samples generated from the eZFN and Donor DNA samples, but not from the control samples, comprising the Donor DNA alone or eZFN alone samples. PCR products were evident in the majority of replicate samples from both ratios of eZFNs and Donor DNAs used.

Figure 43:
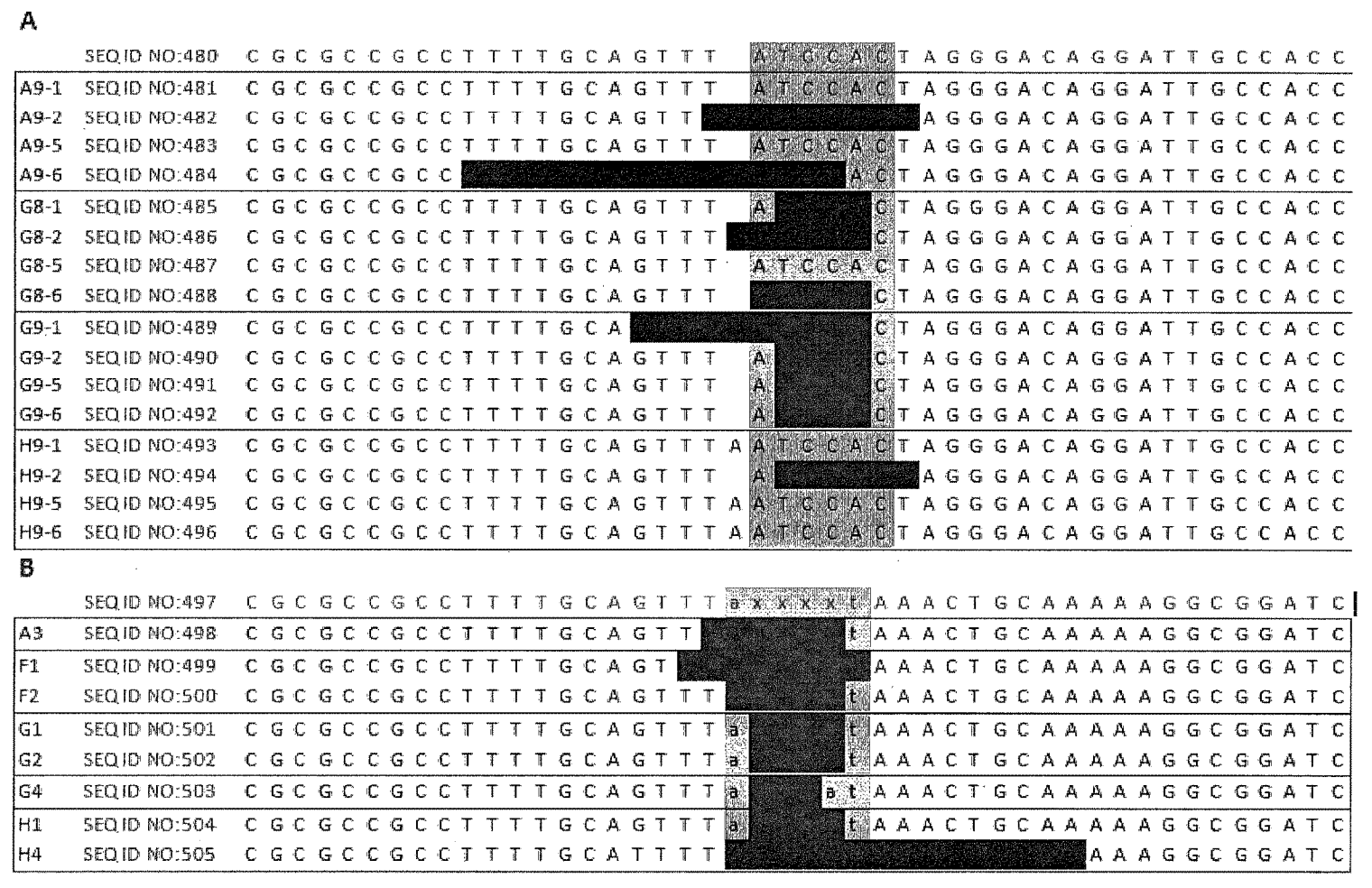

Representative samples of the PCR products were cloned and sequenced. For both the direct and reverse orientation, sequences of the PCR products from four different reactions are shown in FIG. 43. Nine unique haplotypes were observed for the direct orientation of the insert, as expected from misrepair to the junction ends. Three of the 16 sequences aligned with the sequence expected from annealing and ligation of intact ends of the inserted Donor DNA and the target sequence. All sequences of the PCR products in the reverse orientation had indels at the junctions as expected since the single-stranded ends of the Donor DNA and target DNA are not complementary.

Southern Blot Analysis:

Maize callus that were initially identified as containing a donor sequence integrated within the ELP locus via the locus specific disruption assay and the in-out PCR assay was selected for further analysis by Targeted Integration (TI) Southern blots. For T₁ Southerns, DNA was digested and probed with enzymes and probes at the target locus. For DNA extraction for Southerns, tissue samples were collected in 2 ml eppendorf tubes (Eppendorf) and lyophilized for 2 days. Tissue maceration was performed with a Kleco tissue pulverizer and tungsten beads (Kleco, Visalia, Calif.). Following tissue maceration the genomic DNA was isolated using the DNEASY PLANT MINI KIT™ (Qiagen, Germantown, Md.) according to the manufacturer's suggested protocol.

Genomic DNA (gDNA) was quantified by QUANT-IT PICO GREEN DNA™ assay kit (Molecular Probes, Invitrogen, Carlsbad, Calif.). Quantified gDNA was adjusted to 4 µg for the Southern blot analysis. DNA samples were then digested using the PmeI restriction enzyme (New England BioLabs) overnight at 37° C. followed with a clean-up using QUICK-PRECIP™ (Edge BioSystem, Gaithersburg, Md.) according to the manufacturer's suggested protocol. DNA was then resuspended in 1× dye and electrophoresed for 5 hours on a 0.8% SEAKEM LE agarose gel (Lonza, Rockland, Me.) at 110 volts in a cold room. The gel was denatured, neutralized, and then transferred to a nylon charged membrane (Millipore, Bedford, Mass.) overnight and DNA was crosslinked to the membrane using the UV STRATALINKER 1800™ (Stratagene, La Jolla, Calif.), and blots were pre-hybridized with 20 ml of PERFECTHYB PLUS™ (Sigma, St. Louis, Mo.). The probe was labeled using PRIME-IT RMT™ random (Stratagene, La Jolla, Calif.) according to manufacturer's suggested protocol and purified using PROBE QUANT G-50 MICRO COLUMNS™ (GE Healthcare, Buckinghamshire, UK) according to manufacturer's suggested protocol. Approximately 20,000,000 cpm of the labeled probed was added to the blots and incubated overnight. Blots were washed 2×15 minutes per wash, placed on a phosphor image screen for 24 hours and analyzed by a STORM 860 SCANNER™ (Molecular Dynamics). Results showed expected bands for targeted integration (~6.9 kB).

Results of ELP Loci Targeting Via NHEJ-Mediated Integration

The results of this study demonstrate precision insertion in maize of a donor DNA plasmid by NHEJ, subsequent to in vivo, ZFN-generated cleavage of the target DNA and the Donor DNA. Targeting of Donor DNAs occurred using two different donor DNAs (different by which eZFN binding sequences were contained in the ELP) and two different eZFNs within protoplasts and maize embryos. Integration within the ELP loci via an NHEJ repair mechanism occurred in both orientations. The donor DNA insert was detected in both of these orientations in the samples tested.

Precision targeting of genes using the NHEJ repair mechanism in the tissues of differing plant species provides significant advantage over known repair mechanisms such as homologous recombination mediated repair. The NHEJ repair mechanism is the dominate repair mechanism which operates in most if not all plant tissues. Conversely, the activity of the homologous recombination mediated repair pathway operates throughout the G2 phase of the cell cycle in plants. Resultingly, many plant tissues capable of transformation do not actively undergo cell division and, hence, would not support gene targeting by a homologous recombination mediated repair pathway. Another advantage of NHEJ repair mediated pathway for donor insertion within the genome of plants, is that unlike the homologous recombination mediated repair pathway, the NHEJ-mediated repair does not require extensive regions of homology, which reduces the size of the donor DNA sequences necessary for genomic insertion. Finally, donor DNA sequences of larger sizes can be successfully inserted into genomic loci using NHEJ repair mediated pathway as compared to the homologous recombination mediated repair pathway. Donor-DNA mediated integration within a genomic locus via the homologous recombination mediated repair pathway requires that a DNA polymerases copy the DNA template contained in the Donor DNA. In contrast, the NHEJ repair mediated pathway only requires interaction of the donor DNA with the target DNA at two points (their ends) and does not require template-dependent DNA synthesis. Accordingly the NHEJ repair mediated pathway can be utilized to integrate larger size donor DNA sequences within the targeted genomic locus.

Example 10: Exemplary Sequences

SEQ ID NO: 116

```
TCGCCCAAACCCTCGCCGCCGCCATGGCCGCAGCCACCTCCCCCGCCGTCGCATTCTC
GGGCGCCACCGCCGCCGCCATGCCCAAACCCGCCCGCCATCCTCTCCCGCGCCACCA
GCCCGTCTCGCGCCGCGCGCTCCCCGCCCGCGTCGTCAGGTGTTGCGCCGCGTCCCCC
GCCGCCACCTCCGCCGCGCCTCCCGCAACCGCGCTCCGGCCATGGGGCCCGTCCGAG
CCCCGCAAGGGCGCCGACATCCTCGTCGAGGCGCTCGAGCGCTGCGGCATCGTCGAC
GTCTTCGCCTACCCCGGCGGCGCCTCCATGGAGATCCACCAGGCGCTGACGCGCTCG
CCCGTCATCACCAACCACCTCTTCCGCCACGAGCAGGGGGAGGCGTTCGCGGCGTCC
GGCTACGCCCGCGCGTCCGGCCGCGTCGGCGTCTGCGTCGCCACCTCCGGCCCGGGG
GCCACCAACCTCGTCTCCGCGCTCGCCGACGCCCTCCTCGACTCCATCCCCATGGTCG
CCATCACGGGCCAGGTCCCCCGCCGCATGATCGGCACGGACGCGTTCCAGGAGACGC
CCATAGTGGAGGTCACGCGCTCCATCACCAAGCACAACTACCTGGTCCTTGACGTGG
AGGATATCCCCCGCGTCATCCAGGAAGCCTTCTTCCTTGCATCCTCTGGCCGCCCGGG
GCCGGTGCTAGTTGATATCCCCAAGGACATCCAGCAGCAGATGGCTGTGCCCGTCTG
GGACACTCCAATGAGTTTGCCAGGGTACATCGCCCGCCTGCCCAAGCCACCATCTAC
TGAATCGCTTGAGCAGGTCCTGCGTCTGGTTGGCGAGTCACGGCGCCCAATTCTGTA
TGTTGGTGGTGGCTGCGCTGCGTCTGGCGAGGAGTTGCGCCGCTTTGTTGAGCTTACT
```

-continued

```
GGGATTCCAGTTACAACTACTCTGATGGGCCTTGGCAACTTCCCCAGCGACGACCCA
CTGTCTCTGCGCATGCTTGGGATGCATGGCACTGTGTATGCAAATTATGCAGTAGAT
AAGGCTGACCTGTTGCTCGCATTTGGTGTGCGGTTTGATGATCGTGTGACTGGGAAA
ATCGAGGCTTTTGCAAGCAGGTCCAAGATTGAGCACATTGACATTGACCCAGCTGAG
ATTGGCAGAACAAGCAGCCACATGTCTCCATTTGTGCAGATGTTAAGCTTGCTTTAC
AGGGGTTGAATGATCTATTAAATGGGAGCAAAGCACAACAGGGTCTGGATTTTGGTC
CATGGCACAAGGAGTTGGATCAGCAGAAGAGGGAGTTTCCTCTAGGATTCAAGACTT
TTGGCGAGGCCATCCCGCCGCAATATGCTATCCAGGTACTGGATGAGCTGACAAAAG
GGGAGGCGATCATTGCCACTGGTGTTGGGCAGCACCAGATGTGGGCGGCTCAGTATT
ACACTTACAAGCGGCCACGGCAGTGGCTGTCTTCGTCTGGTTTGGGGGCAATGGGAT
TTGGGTTACCAGCTGCAGCTGGCGCTGCTGTGGCCAACCCAGGTGTTACAGTTGTTG
ACATTGATGGTGATGGTAGTTTCCTCATGAACATTCAGGAGTTGGCGTTGATCCGCAT
TGAGAACCTCCCAGTGAAGGTGATGATATTGAACAACCAGCATCTGGGAATGGTGGT
GCAGTGGGAGGATAGGTTTTACAAGGCCAATCGGGCGCACACATACCTTGGCAACCC
AGAAAATGAGAGTGAGATATATCCAGATTTTGTGACGATTGCTAAAGGATTCAACGT
TCCAGCAGTTCGAGTGACGAAGAAGAGCGAAGTCACTGCAGCAATCAAGAAGATGC
TTGAGACCCCAGGGCCATACTTGTTGGATATCATAGTCCCGCATCAGGAGCACGTGC
TGCCTATGATCCCAAGCGGTGGTGCTTTCAAGGACATGATCATGGAGGGTGATGGCA
GGACCTCGTACTGAAATTTCGACCTACAAGACCTACAAGTGTGACATGCGCAATCAG
CATGATGCCCGCGTTGTATCAACTACTAGGGGTTCAACTGTGAGCCATGCGTTTTC
TAGTTTGCTTGTTTCATTCATATAAGCTTGTATTACTTAGTTCCGAACCCTGTAGTTTT
GTAGTCTATGTTCTCTTTTGTAGGGATGTGCTGTCATAAGATGTCATGCAAGTTTCTT
GTCCTACATATCAATAATAAGTACTTCCATGNAANAAAAAAAAAAAAAAAAAAAAAAA
AAAAAAAAAAAAAAAAAAAAAAAAAAAAAA
```
SEQ ID NO: 117
```
TCGCCCAAACCCTCGCCGCCGCCATGGCCGCAGCCACCTCCCCCGCCGTCGCATTCTC
GGGCGCCGCCGCCGCCGCCGCCGCCATACCCAAACCCGCCCGCCAGCCTCTCCCGCG
CCACCAGCCCGCCTCGCGCCGCGCGCTCCCCGCCCGCATCGTCAGGTGCTGCGCCGC
GTCCCCGCCGCCACCTCCGTCGCGCCTCCCGCCACCGCGCTCCGGCCGTGGGCCC
CTCCGAGCCCCGCAAGGGCGCCGACATCCTCGTCGAGGCGCTGGAGCGCTGCGGCAT
CGTCGACGTCTTCGCCTACCCTGGCGGCGCGTCCATGGAGATCCACCAGGCGCTGAC
GCGCTCGCCAGTCATCACCAACCACCTCTTCCGCCACGAGCAGGGGGAGGCGTTCGC
GGGCGTCGGGTACGCCCGCGCGTCCGGCCGCGTCGGCGTCTGCGTCGGCCACCTCCGG
CCCGGGGGCCACCAACCTCGTCTCCGCGCTCGCCGACGCTCTCCTCGACTCCATCCCC
ATGGTCGCCATCACGGGCCAGGTCCCCGCCGCATGATCGGCACGGATGCGTTCCAG
GAGACGCCCATCGTGGAGGTCACGCGCTCCATCACCAAGCACAACTACCTGGTCCTT
GACGTGGAGGATATCCCCGCGTCATCCAGGAAGCCTTCTTCCTCGCGTCCTCTGGCC
GCCCGGGGCCGGTGCTGGTTGATATCCCCAAGGACATCCAGCAGCAGATGGCTGTGC
CTGTCTGGGACACGCCGATGAGTTTGCCAGGGTACATCGCCCGCCTGCCCAAGCCAC
CATCTACTGAATCGCTTGAGCAGGTCCTGCGTCTGGTTGGCGAGTCACGGCGCCCAA
TTCTGTATGTTGGTGGTGGCTGCGCTGCATCGGTGAGGAGTTGCGCGCTTTGTTGA
GCTCACTGGGATTCCAGTTACAACTACTCTTATGGGCCTTGGCAACTTCCCCAGTGAC
GACCCACTGTCTCTGCGCATGCTGGGGATGCATGGCACTGTGTATGCAAATTATGCA
GTAGATAAGGCTGACCTGTTGCTTGCATTTGGTGTGCGGTTTGATGATCGTGTGACCG
GGAAAATCGAGGCTTTTGCAAGCAGGTCCAAGATTGAGCACATTGACATTGACCCAG
CTGAGATTGGCAGAACAAGCAGCCACATGTCTCCATTTGTGCAGATGTTAAGCTTGC
TTTACAGGGGTTGAATGCTCTATTAAATGGGAGCAAAGCACAACAGGGTCTGGATTT
TGGTCCATGGCACAAGGAGTTGGATCAGCAGAAGAGGGAGTTTCCTCTAGGATTCAA
GACTTTTGGTGAGGCCATCCCGCCGCAATATGCTATCCAGGTACTGGATGAGCTGAC
AAAAGGGGAGGCGATCATTGCCACCGGTGTTGGGCAGCATCAGATGTGGGCGGCTC
AGTATTACACTTACAAGCGGCCACGGCAGTGGCTGTCTTCATCCGGTTTGGGTGCAA
TGGGATTTGGGTTGCCAGCTGCAGCTGGCGCTGCTGTGGCCAACCCAGGTGTTACAG
TTGTTGACATTGATGGGATGGTAGTTTCCTCATGAACATTCAGGAGTTGGCGTTGAT
CCGTATTGAGAACCTCCCAGTGAAGGTGATGATATTGAACAACCAGCATCTGGGAAT
GGTGGTGCAGTGGGAGGATAGGTTTTACAAGGCCAACCGGGCGCACACATACCTTG
GCAACCCAGAAAATGAGAGTGAGATATATCCAGATTTTGTGACGATTGCTAAAGGAT
TCAACGTTCCGGCAGTTCGTGTGACGAAGAAGAGCGAAGTCACTGCAGCAATCAAG
AAGATGCTTGAGACCCCAGGGCCATACTTGTTGGATATCATTGTCCCGCATCAGGAG
CACGTGCTGCCTATGATCCCAAGCGGTGGTGCTTTTAAGGACATGATCATGGAGGGT
GATGGCAGGACCTCGTACTGAAATTTCGACCTACAAGACCTACAAGTGTGACATGCG
CAATCAGCATGATACCTGCGTGTTGTATCAACTACTGGGGGTTCAACTGTGAACCAT
GCGTTTTCTAGTTTGCTTGTTTCATTCATATAAGCTTGTGTTACTTAGTTCCGAACCGT
GTAGTTTTGTAGTCTCTGTTCTCTTTTGTAGGGATGTGCTGTCATAAGATCATGCA
AGTTTCTTGTCCTACATATCAATAATAAGCACTTCCATGNAANAAAAAAAAAAAAAAA
AAAAAAAAAAAAAAAAAAAAAAAAAAAAAAAA
```
SEQ ID NO: 118
```
TCGCCCAAACCCTCGCCGCCGCCATGGCCGCNGCCACCTCCCCCGCCGTCGCATTCTC
GGGCGCCNCCGCCGCCGCCATNCCCAAACCCGCCCGCCANCCTCTCCCGCGCCACCA
GCCCGNCTCGCGCCGCGCGCTCCCCGCCCGCNTCGTCAGGTGNTGCGCCGCGTCCCC
CGCCGCCACCTCCGCGCGCCCCCGCCACCGCGCTCCGGCCTGGGGCCCGTCCGA
GCCCCGCAAGGGCGCCGACATCCTCGTCGAGGCGCTCGAGCGCTGCGGCATCGTCGA
CGTATTCGCCTACCCCGGCGGCGCGTCCATGGAGATCCACCAGGCGCTGACGCGCTC
GCCCGTCATCACCAACCACCTCTTCCGCCACGAGCAGGGGGAGGCGTTCGCGGCGTC
CGGCTACGCCCGCGCGTCCGGCCGCGTCGGCGTCTGCGTCGGCCACCTCCGGCCCGGG
GGCCACCAACCTCGTCTCCGCGCTCGCTGACGCCCTCCTCGACTCCATCCCCATGGTC
GCCATCACGGGCCAGGTCCCCGCCGCATGATCGGCACGGACGCGTTCCAGGAGAC
GCCCATAGTGGAGGTCACGCGCTCCATCACCAAGCACAACTACCTGGTCCTTGACGT
GGAGGATATCCCCCGCGTCATCCAGGAAGCCTTCTTCCTCGCGTCCTCTGGCCGCCCG
GGGCCGGTGCTGGTTGATATCCCCAAGGATATCCAGCAGCAGATGGCCGTGCCTATC
```

```
-continued
TGGGACACGCCGATGAGTTTGCCAGGGTACATCGCCCGCCTGCCCAAGCCACCATCT
ACTGAATCGCTTGAGCAGGTCCTGCGTCTGGTTGGCGAGTCACGGCGCCCAATTCTG
TATGTTGGTGGTGGCTGCGCTGCATCCGGCGAGGAGTTGCGCCGCTTTGTTGAGCTC
ACTGGGATTCCGGTTACAACTACTCTGATGGGCCTTGGCAACTTCCCCAGCGACGAC
CCACTGTCTCTGCGCATGCTTGGGATGCATGGCACTGTGTATGCAAATTATGCAGTCG
ATAAGGCTGACCTGTTGCTTGCATTTGGTGTGCGGTTTGATGATCGCGTGACTGGGA
AAATCGAGGCCTTTGCAAGCAGGTCCAAGATTGAGCACATTGACATTGACCCAGCTG
AGATTGGCAGAACAAGCAGCCACATGTCTCCATTTGTGCAGATGTTAAGCTTGCTTT
ACAGGGGTTGAATGCTCTATTAAATGGGAGCAAAGCACAACAGGGGTCTGGATTTTGG
TCCATGGCACAAGGAGTTGGATCAGCAGAAGAGGGAGTTTCCTCTAGGATTCAAGAC
TTTTGGCGAGGCCATCCCGCCGCAATATGCTATCCAGGTACTGGATGAGCTGACAAA
AGGGGAGGCGATCATTGCTACTGGTGTTGGGCAGCACCAGATGTGGGCGGCTCAGTA
TTACACTTACAAGCGGCCACGGCAGTGGCTGTCTTCGTCTGGTTTGGGGGCAATGGG
ATTTGGGTTACCAGCTGCAGCTGGCGCTGCTGGCCAACCCAGGTGTTACAGTTGTT
GACATTGATGGAGATGGTAGTTTCCTCATGAACATTCAGGAGTTGGCATTGATCCGT
ATTGAGAACCTCCCTGTGAAGGTGATGATATTGAACAACCAGCATCTGGGAATGGTG
GTGCAATGGGAGGATAGGTTTTACAAGGCCAATCGGGCGCACACATACCTTGGCAAC
CCAGAAAATGAGAGTGAGATATATCCAGATTTTGTGACGATTGCTAAAGGATTCAAC
GTTCCGGCAGTTCGTGTGACGAAGAAGAGCGAAGTCACTGCAGCAATCAAGAAGAT
GCTTGAGACCCCAGGGCCATACTTGTTGGATATCATCGTCCCGCATCAGGAGCACGT
GCTGCCTATGATCCCAAGCGGTGGTGCTTTCAAGGACATGATCATGGAGGGTGATGG
CAGGACCTCGTACTGAAATTTCGACCTACAAGACCTACAAGTGTGACATGCGCAATC
AGCATGGTGCCCGCGTGTTGTATCAACTACTAGGGGTTCAACTGTGAACCATGCGTT
TTCTAGTTTGCTTGTTTCATTCATATAAGCTTGTGTTACTTAGTTCCGAACCCTGTAGC
TTTGTAGTCTATGCTCTCTTTTGTAGGGATGTGCTGTCATAAGATATCATGCAAGTTT
CTTGTCCTACATATCAATAATAAGTACTTCCATGNAANAAAAAAAAAAAAAAAAAAA
AAAAAAAAAAAAAAAAAAAAAAAAAAAAAAA SEQ ID NO: 119
CGTTGTGCCTTGGCAGTCTCAGGTTGAGCCCTCACCATTGAAGTAGCATGGGTCATTG
GATTGACCCGATTTGACGGCGGATCTATTGGATCTTCCCTTTGTGTCGTTTTATACTG
GTATAGATGTTTAACACATATTTGGAAATATATTCAAAACATGTTTCTATAAAAA
GTTTAAACTATACATGTATAATGGAAGTCATTTATAAGAAATGTTTTACATGTATAAA
AGATGTACATCATATGTGCAAAAGTAGACATGTGTTAGAAAAATAAACAAACAAA
TACATAAAAAGAAAATCAAAGAAAAAACAACCCAAAAAACCAAAGAAAATAAAGA
AGAAGAAAAAAGAGAAAAAACATTGAAAATCAAAGAAGAAAAAAACATAAAGA
AAAGAAAACCGAAAAATACTGGCAAAAACACACAAAAAATGAAAAGAAAAAATAA
AGAAAACCGGACTTTACCAATCGAACGGAGCGATCGGACACGAATGAGCGAAGGCA
TGCATCGAGCAACACCGCTAATTGACCGGCCCGTAGTCGTTCGCCCGTAGACCATTC
ATAAGAATCGGTATCGGAGAGACATAGGGGTTCTTTGGTTTCTAACCATATCTTGTC
ACACTTTACCATACATCACCTTAGTCAAATCTGATCAAATTAGGTGAGTATTTGGTTC
TAGCCACATCTAAGGCAAGATTTGTTTTTCTGAGCAGTGAACCCCATATGTCATAGA
CAGAAAAATTGTGAAAAGATTCCTTTAGCACGGTCAAAGCGTGGTTAACAATTTAATC
AACTCAAGTAAGATAAATGCGATAAATGTGACAAAAATAATGTGTTATAGAAGTAT
GACAAAAATAATCACAATCCAAACAGTCTGATAGCTTGGCGAGTGCAAAATAGATA
CGAAATCTCTGGTGATATCACACGGGTCCAAAATAATTGCTTGTTTGAGCATCAGCC
TTTCTGCACAAAAAAAGCTAGCCCAAACAAACGAGTGGCGTCCCATCTGAACCACAC
GCTCACCCGCCGCGTGACAGCGCCAAAGACAAAACCATCACCCCTCCCCAATTCCAA
CCCTCTCTCCGCCTCACAGAAATCTCTCCCCTCGCCCAAACCCTCGCCGCCGCCATGG
CCGCCGCCACCTCCCCCGCCGTCGCATTCTCCGGCGCCGCCGCCGCCGCCGCCGCCA
TGCCCAAGCCCGCCCGCCAGCCTCTCCCGCGCCACCAGCCCGCCTCGCGCGCGCGC
TCCCCGCCCGCGTCGTCAGGTGCTGCGCCGCGCCCCCCGCTGCTGCCACCTCCGCCGC
GCCCCCCGCCACCGCGCTCCGGCCCTGGGGCCCGTCCGAGCCCCGCAAGGGCGCCGA
CATCCTCGTCGAGGCGCTCGAGCGCTGCGGCATCGTCGACGTATTCGCCTACCCCGG
CGGCGCGTCCATGGAGATCACCAGGCGCTGACGCGCTCGCCCGTCATCACCAACCA
CCTCTTCCGCCACGAGCAGGGGGAGGCGTTCGCGGCGTCCGGCTACGCCCGCGCGTC
CGGCCGCGTCGGCGTCTGCGTCGCCACCTCCGGCCCGGGGGCCACCAACCTCGTCTC
CGCGCTCGCTGACGCCCTCCTCGACTCCATCCCCATGGTCGCCATCACGGGCCAGGT
CCCCCGCCGCATGATCGGCACGGACGCGTTCCAGGAGACGCCCATAGTGGAGGTCAC
GCGCTCCATCACCAAGCACAACTACCTGGTCCTTGACGTGGAGGATATCCCCCGCGT
CATCCAGGAAGCCTTCTTCCTCGCGTCCTCTGGCCGCCCGGGGCCGGTGCTGGTTGAT
ATCCCCAAGGATATCCAGCAGCAGATGGCCGTGCCTATCTGGACACGCCGATGAGT
TTGCCAGGGTACATCGTCCCGCCTGCCCAAGCCACCATCTACTGAATCGCTTGAGCA
GGTCCTGCGTCTGGTTGGYGAGTCACGGCGCCCAATTCTGTATGTTGGTGGTGGCTG
CGCTGCATCCGGCGAGGAGTTGCGCCGCTTTGTTGAGCTCACTGGGATTCCGGTTAC
AACTACTCTGATGGGCCTTGGCAACTTCCCCAGCGACGACCCACTGTCTCTGCGCAT
GCTTGGGATGCATGGCACTGTGTATGCAAATTATGCAGTCGATAAGGCTGACCTGTT
GCTTGCATTTGGTGTGCGGTTTGATGATCGCGTGACTGGGAAAATCGAGGCCTTTGC
AAGCAGGTCCAAGATTGTGCACATTGACATTGACCCAGCTGAGATTGGCAAGAACA
AGCAGCCACATGTCTCCATTTGTGCAGATGTTAAGCTTGCTTTACAGGGGTTGAATGC
TCTATTAAATGGGAGCAAAGCACAACAGGGTCTGGATTTTGGTCCATGGCACAAGGA
GTTGGATCAGCAGAAGAGGGAGTTTCCTCTAGGATTCAAGACTTTTGGCGAGGCCAT
CCCGCCGCAATATGCTATCCAGGTACTGGATGAGCTGACAAAAGGGGAGGCGATCA
TTGCTACTGGTGTTGGGCAGCACCAGATGTGGGCGGCTCAGTATTACACTTACAAGC
GGCCACGGCAGTGGCTGTCTTCGTCTGGTTTGGGGGCAATGGGATTTGGGTTACCAG
CTGCAGCTGGCGCTGCTGTGGCCAACCCAGGTGTTACAGTTGTTGACATTGATGGAG
ATGGTAGTTTCCTCATGAACATTCAGGAGTTGGCATTGATCCGTATTGAGAACCTCCC
TGTGAAGGTGATGATATTGAACAACCAGCATCTGGGAATGGTGGTGCAATGGGAGG
ATAGGTTTTACAAGGCCAATCGGGCGCACACATACCTTGGCAACCCAGAAAATGAG
AGTGAGATATATCCAGATTTTGTGACGATTGCTAAAGGATTCAACGTTCCGGCAGTT
CGTGTGACGAAGAAGAGCGAAGTCACTGCAGCAATCAAGAAGATGCTTGAGACCCC
```

-continued

AGGGCCATACTTGTTGGATATCATCGTCCCGCATCAGGAGCACGTGCTGCCTATGAT
CCCAAGCGGTGGTGCTTTCAAGGACATGATCATGGAGGGTGATGGCAGGACCTCGTA
CTGAAATTTCGACCTACAAGACCTACAAGTGTGACATGCGCAATCAGCATGGTGCCC
GCGTGTTGTATCAACTACTAGGGGTTCAACTGTGAACCATGCGTTTTCTAGTTTGCTT
GTTTCATTCATATAAGCTTGTGTTACTTAGTTCCGAACCCTGTAGCTTTGTAGTCTATG
CTCTCTTTTGTAGGGATGTGCTGTCATAAGATATCATGCAAGTTTCTTGTCCTACATA
TCAATAATAAGTACTTCCATGGAATAATTCTCAGTTCTGTTTTGAATTTTGCATCTTCT
CACAAACAGTGTGCTGGTTCCTTTCTGTTACTTTACATGTCTGCCGTGTCCGGTTATG
ACATAATGACCGATGGAGGGTGGTCAGCAGGTTTTAGACGGGGAGTTGAAACTTTTT
TTTGGGGGGAAGAAATCTGAATACAGTTGGGAGGAAAGATAAAAGCATATACCTTG
ATTAATTTATTGAGCCCAATATCCAGCCTAATTTATCAAGCAATAGGCAGTGTAGGG
TGTTGGCATTCTTCTCTTCCTTGAGATCTGGTGTCGGGACCCCGATTCTAAGTCACAC
CGATCTAGCATGTAACACCTCATATCACTTTGCGGCCTCACGCACGGTATCCTCACGG
GTGTCGCCTTACCATGGCCCGGGACCGTTTGCGCCTTTTGGCTCACGTATATGATGGT
GTCGCTAGYATCCATATGACAGAGAACCCGGGCCGACATRGCTAGTCGTGAACCCAA
AGCGGCACAGACCTATGGAGACAGGCATACATGAATCACATCGAGCATGTCGGTCA
ACAGCGTATGAATCCGGCTGTAGCACTGGGCTAACAGGACTCCGGGGAACCCGGG
CTGTAGCAGGCTAGGCAGGACTCCGGAAGTCACCGCGTGACATTTCCCCGAAGGGAC
AGACATAGGAACGAAGTGGAACACATGCCGGCCAGTCAAGTGTTCTGAGCAGTAGT
GCTGGGCTAGCAGGACTCCGGTGAACCGGGCTGTAGCGGACTACTATGGCTCGAGGT
AGCACTAGACTACATTTCCCCATAAGAGAGGCTKCCAAGGATAAGCAACTAGATTGT
CGGRTCYCRSRYWTTGTCTCCGTGTGTTGTTATTGTTGTCATGCAAGTATGTTGTTGTA
CAACATGGCATCACAACATAACGCAAACTCATATAGATATAGGCTCAGAGAGCCAC
ATAGCATTAATACGAACAGGGTCACATGACCCATCATTCAGAGCATACAGCATGAAG
CATCATGTCTGAGTACAGACACTAC

SEQ ID NO: 120

CTGAAAATTCAATATGGCCCTCGGGCACCAATGCTCTTGCTTCCAATTTTCATAATTC
CCATTTGTAAAAAACACACCACAAAAATCACACTGTAGTAATCTACATGTTTGTTGA
GCCTATAAATCTTCATAAAATAATTGAGATTAATGCGGTTTGTTGCAAAAATATGGGG
TTGGTCATGTTTCTACATATTTCTATTTGCATTTCGTTAACTGGTGCTTGTTATTTTTGT
ACATAATGCATATCTCATTGTTATTATTTTTAACCTTTTGAGATGGTAACGAAGATCC
AAACATGCATAGATGATTCTCCGGATGATTTTTTGTAGCCTGCACTAGGAACTCCCA
AGAGCCAGAAGGTTGGGTTTGTACAAGATAACATTTGTTTGAACACACTCATAACCT
GCATGTGACATACATGACGTAACTTATAGTGATGATTCGACAAATGTCTCTTTGTCCA
ATTTTGTTATATATCCCGTGGCAACGCACGGGCATTCGACTAGTATATGTAAAGATAT
CAATGTGACGAGTCCCCATGGTCGTTGCGCTTGTCCACTACCGGCTCGCTAGAGGCG
ACTCTCACCTAGAAGTCGCTACGAGCAATACATAGTCGTTCTGGGCGCAGCTATGTT
CTGCCTTTTGCGACGCTCAGGCACGGCTTGCCTACAGCCTGAGGGTCGGGCTAGGAA
CCACTAATTGTGTCATGCTGATGTCACAATGACATCATGCATATTTTTATTTTCGTTTT
TCGCTTTCTCTTTAATTTTATTTGTATTTCAAATATTTTATATATTTTTTGAATTTTTT
CAATGTTGTATTTGAAAAATGTTAAACCTGTATAGAGAAAAATATTTTTGATATATAT
AAAGTATATAACATGAATGAAAAATGTATAAATGTTAATTATGTGTACCAAAAATG
TTGATAACAATTAGCAGTCTCACATATTTCAAATAAATGTATGTGGAATTAAAAAA
TATGTGTATTTAAGTTTAAAAAAAATGTTCATGTAATGTTCGTAAAATGTTTGATACA
TTCAATAAAAATTATGTCACATTTGAATAATTCTTCTCAAGCTTAACAAATGCGCTCA
TTATATTATCAAAAATTGTCTGTACAGTGTACACAAATGTTTATGTAGTTCAAAAAAA
ATGTTTTTTCAGTAAAAATATATTTGATCATGTATTTTATAAAAAACTGTTTAATATA
TATTTAGAAAATATATTCAAAACATGTTTCTGTAAAAAGTTAAAACTATACATGTATA
ATGTAAGTCATTTATAATAAATGTTTTACATGTATAAAAAATGTACAACATATGTGCA
AAAGTAGACATGTGTTGAAAAAATAAACAAATAACTAAATAAAAAGAAAATCAAAG
AAAAACACCAAAAACCAAAGAAATAAATAAAACCAAAGTATAAAGAAGARRAAAG
GAGAAAAAACATTGAAAATCAAAGARAAAAACATAAAGAAGAAAAAAACCGAAGA
AAACTAGCAAAAACACACACACAAAAAGAAAATGAAAAGAAATAATAAAGAAA
GCCGGACTGAACCGATCAAACGCAGCGATCGAACATGGATGGCTAAGGCATGCAT
CGAACAACACGGCTAATTGGCCGGCCCGTAGTCGTTCGCCCGTAGACCATTCCTACG
AATCGGTACCGGAGAGACATAGGGGCTGTATGGTTCCTAACCATACCTTGCCACACT
TTGTCACACCTCATCTTAGGCAAATTTAATCAAGTTATGTAGGTGTTTGGTTTTAGCC
ACATCTAAGGCAAGATTTATTTTCCTGAGCAGTGAACCCCATATGTTATAGACATAA
AAAGTGTGGGAAGATTCCCTTTAGTCAAACTGTGGCTAACAATTTATTAAGAATTAA
CTTAAGTAAGATAGGTGCAACAAATGTAGCAAAAATAATGTGGTATATATAGCAAA
GATAGCCACAACCGCGAGTGGAAATACCAGATACGAGATCTCTGGTCATATCACACG
AGTCCAAATTAATTGCTTTGTTTGAGGTTCAGCCTTTTGCATAAAAAAGCTAGCCCAA
ACAAACGAGTGGCGTCCCATCTGAACCACACACTCACCCGCCGCGTGACAGCGCCAA
AGACAAAACCATCACCCCTCCCCAATTCCAACCCTCTCTCTGCCTCACAGAAATCTCT
CCCTCGCCCAAACCCTCGCCGCCGCCATGGCCGCAGCCACCTCCCCCGCCGTCGCAT
TCTCGGGCGCCGCCGCCGCCGCCGCCGCCATACCCAAACCCGCCCGCCAGCCTCTCC
CGCGCCACCAGCCCGCCTCGCGCCGCGCGCTCCCCGCCCGCATCGTCAGGTGCTGCG
CCGCGTCCCCCGCCGCCACCTCCGTCGCGCCTCCCGCCACCGCGCTCCGGCCGTGGG
GCCCCTCCGAGCCCGCAAGGGCGCCGACATCCTCGTCGAGGCGCTGGAGCGCTGCG
GCATCGTCGACGTCTTCGCCTACCCTGGCGGCGCGTCCATGGAGATCCACCAGGCGC
TGACGCGCTCGCCAGTCATCACCAACCACCTCTTCCGCCACGAGCAGGGGGAGGCGT
TCGCGGCGTCCGGGTACGCCCGCGCGTCCGGCCGCGTCGGCGTCTGCGTCGCCACCT
CCGGCCCGGGGGCCACCAACCTCGTCTCCGCGCTCGCCGACGCTCTCCTCGACTCCA
TCCCCATGGTCGCCATCACGGGCCAGGTCCCCCGCCGCATGATCGGCACGGATGCGT
TCCAGGAGACGCCCATCGTGGAGGTCACGCGCTCCATCACCAAGCACAACTACCTGG
TCCTTGACGTGGAGGATATCCCCCGCGTCATCCAGGAAGCCTTCTTCCTCGCATCCTC
TGGCCGCCCGGGGCCGGTGCTGGTTGATATCCCCAAGGACATCCAGCAGCAGATGGC
TGTGCCTGTCTGGGACACGCCGATGAGTTTGCCAGGGTACATCGCCCGCCTGCCCAA
GCCACCATCTACTGAATCGCTTGAGCAGGTCCTGCGTCTGGTTGGCAGTCACGGCG
CCCAATTCTGTATGTTGGTGGTGGCTGCGCTGCATCTGGTGAGGAGTTGCGCCGCTTT

```
GTTGAGCTCACTGGGATTCCAGTTACAACTACTCTTATGGGCCTTGGCAACTTCCCCA
GTGACGACCCACTGTCTCTGCGCATGCTGGGGATGCATGGCACTGTGTATGCAAATT
ATGCAGTAGATAAGGCTGACCTGTTGCTTGCATTTGGTGTGCGGTTTGATGATCGTGT
GACCGGGAAAATCGAGGCTTTTGCAAGCAGGTCCAAGATTGTGCACATTGACATTGA
CCCAGCTGAGATTGGCAAGAACAAGCAGCCACATGTCTCCATTTGTGCAGATGTTAA
GCTTGCTTTACAGGGGTTGAATGCTCTATTAAATGGGAGCAAAGCACAACAGGGTCT
GGATTTTGGTCCATGGCACAAGGAGTTGGATCAGCAGAAGAGGGAGTTTCCTCTAGG
ATTCAAGACTTTTGGTGAGGCCATCCCGCCGCAATATGCTATCCAGGTACTGGATGA
GCTGACAAAAGGGGAGGCGATCATTGCCACCGGTGTTGGGCAGCATCAGATGTGGG
CGGCTCAGTATTACACTTACAAGCGGCCACGGCAGTGGCTGTCTTCATCCGGTTTGG
GTGCAATGGGATTTGGGTTGCCAGCTGCAGCTGGCGCTGCTGTGGCCAACCCAGGTG
TTACAGTTGTTGACATTGATGGGGATGGTAGTTTCCTCATGAACATTCAGGAGTTGGC
GTTGATCCGTATTGAGAACCTCCCAGTGAAGGTGATGATATTGAACAACCAGCATCT
GGGAATGGTGGTGCAGTGGGAGGATAGGTTTTACAAGGCCAACCGGGCGCACACAT
ACCTTGGCAACCCAGAAAATGAGAGTGAGATATATCCAGATTTTGTGACGATTGCTA
AAGGATTCAACGTTCCGGCAGTTCGTGTGACGAAGAAGAGCGAAGTCACTGCAGCA
ATCAAGAAGATGCTTGAGACCCCAGGGCCATACTTGTTGGATATCATTGTCCCGCAT
CAGGAGCACGTGCTGCCTATGATCCCAAGCGGTGGTGCTTTTAAGGACATGATCATG
GAGGGTGATGGCAGGACCTCGTACTGAAATTTCGACCTACAAGACCTACAAGTGTGA
CATGCGCAATCAGCATGATACCTGCGTGTTGTATCAACTACTGGGGGTTCAACTGTG
AACCATGCGTTTTCTAGTTTGCTTGTTTCATTCATATAAGCTTGTGTTACTTAGTTCCG
AACCGTGTAGTTTTGTAGTCTCTGTTCTCTTTTGTAGGGATGTGCTGTCATAAGATAT
CATGCAAGTTTCTTGTCCTACATATCAATAATAAGCACTTCCATGGAATAATTCTCAG
TTCTGTTTTGAATTTCACATCTTCTCACGAACAGTGTGCTGGTTCCTTTCTGTTACTTT
ACATGCCTGCCGTGTCAGGTTATGACATAACGACCGATGGAGGATTGGAGGGTGGTC
GGCTGGTTTTAGACGGGGAATTGAAACATTTTTCTGGAAGAAATCTGAATACAGTTG
GGAGGGGAAATGGAAGCATATATTTATCGAGCCCGCTATCCAGGCTAATTTATCAAG
CACTAGACAGTGTAGGGTGTTGGCATTCTTCTCTTCCTTGATATCCGGCTTGAGAGGA
GAGATTGAGGCTTCGGCTGTGTTGGTTGCTGATTTCTACAGCATTTTGAGAGAGAGA
GAGAGATGTTGCAACTGTGTTTTGTCTTGGTTGCTTGTACAGAGAAAGAGATGACAT
TTAGAGATATGCAGATCGTTTACCAGTTGTGCTGCGTTTATTCGTACTGATTGTTGTT
ATTGTTGCTATCATGTGCAAATTGTTGTGATGGAAAATCAACAAAATTTTGATATTTT
GCAAAGCGAGTTGGATTGAATGATTTGAGAAATGGTGACTTGTTGAGTGGCCTTGAG
AATTGGTGTTTCATAGGTGTGCAGTTGGTAATGAAAGGCGGCGGCTTGAAATTTCCG
AAAGGCAGGCAATGATACTTTCTGAAAGTGATGTTTTTCTTCCAGGTTTCCGGTGGA
ACAAGTCTACGTTGAGCCAATGTTTGTCAGCTTATTCTGCTCTTTAGTTTCAGTTGTTT
TGTTCACAGATTGCTGGGCAGAGCCCCATGATCGGCTGAGCCTCCAGGAGATCCTTG
ATTGCTCGACTGCGGATACGTTGAATCCTTTAAAATACTATAAGCTCCCTAGTTTTAG
TTTTAGAGAACTGAGAATCAATTGAGGGCAACATTAGTCGATTTTGGCTTCCGATTTT
GACTGGGTCGCCTCCCTGGGTCCTCTACAGTTTTGTGGGCCCTATATGTAAGTGCCCC
AGTGTTGTGGGCTTTCTGGTCTTTTCTGATGAAAGCGGCGTGGTGGCTGGGGGCTTTA
GAATATTTCATTGATTAACTAAAACAAATCAGATCCCTTTTTCCTGCTTCATGTGTGT
TTGACCAATCTTTTTTTAAAAATTTCTTTGATTTTATATTTGATGAGTAAATCTGGCT
GTGTCAACGGTAGTCCATTCGAAACCTGGAAATCGAAATCATTGTACTGCAGGTCTG
TTGCCTGTTAGTTTGTTCTTATATAAGATCTTTGACAGTTTATGAATTTGTCTTTGGAA
TTTGTATAAAGTTTCACAGATAGACAGGCCCTGTTGTTAAATACGTTCGTGCAATTAA
GTGTAAACATATCTGCCAGTGATTTTTCTCGGCTCGCATTAGTACGCATAAATTTTTA
GCACTTCTCTGAATTTTCTCATATGCAGACCACCTATGAAAAAAACGACATGCAAGT
AAATAAAACGATTTCAGGTTCATTTAGTAGCAAACCGTTTTTATGTCCTTTAAAAATC
AATTAGCAGAGCCACTCCATTCACCGGTCAGCAGAAAAGAAGCATGTGTGTTTTT
GGGCTATCATAGAGCTAAATAAATTTGATTCCCATCTGTAATGTTCATCGTTGTTTAC
ATCAGTGTTGGCTGTCGTGTGGTCGTGGAGACTAGCCTGTTCAGACAATATGTTTGAC
AAGAGTGTTGTTTTGTGAGATGCGGATGCGGTCGTTGCATCGTGTACTTGTTTTTGTGA
ATACCAGTTAGATGATCAGTTTTTGTGCACTTCTTGCCATGAATGGCTGTTAAATTGT
CACTTTTTAGGAACTTGTTGCCGTAATATCAATTAAATAATCAATTTTTGTGCATGGT
ATATCAATTAGATGGTCATTTTTTTCTAGTAGAGATGTCTATACATGCCAATGCAATG
TTCAGAGTTGTTCAAGGTCTCGACGGCGCGGCAAAGCGCGTCCTATGCTTCTAGTTTA
AGATGACAACCAAACACGACCCAAGTGTATGCTATGCTCATCCGGTTGGTCCTTGTT
GATGTTCAATGGGCGTGTCTCCATGGGCATCGACGGCGACAATGTTATCTTCTTCAAC
TGTCTGCTATATGCTCATTGGCATTTTTGAAACTTTGCAAGCAAGGTCGATAACTTGG
TCTGGGGATGTTGACGCCCTATGTATCTAGATTAGGGTGATGCTCCCGCCAGTATTT
TTTGGACGATTATCAACATTTGCGGCTGGTATACTATTGTGGCTAATCAACAAGGTTT
TTTTGTGTGTGGCTAATCAACAAGGTTTGGCGCTCGATGTTTTTTAATGTATTTCGAT
GACTCAATTTCTACGTCTGAACATTTCATTGAGCCAAGAGGCAGAACAACAGGTCAC
ATGTAACCGCCAGTGAAAAAGGTTCAAAGAAGAAAAAGATACGAACGACAGCGAGT
TTGTATKKCAGTTTTCGAACTAAGAGTAACACGGAGTRCAGTAGTACGATCCTTGTG
TMYTTCTGTATTTGGWTAKTTTTTTTCCGGAGTTGAGTATTWGWAACTTTCTTGTGCT
TTTTTTAACATTAGTACAGATGCAAGTGCTCATACATACGCGCTTTTTGATTTGTAAC
AATATTATGAAAGACGTAGTAATTATGTTTGCAGATCAATAAAGCTAGCCATCGTGT
GGTGTTCCCAAGAAAAAGATATTCACTATAGATTCACTACATCTTCTAAAAAAACTA
CACTGTAGATTCACTACAGACCAACAGAATATTCATGGTCACGTGGATAAAAACTTA
CTTTTTGAAAGTCTCAAGCATTTGGTTTGATTTTAAGAAAAAATAACTGACTCTATTT
TTGTGTACTCCTTGCAACGAACCTGGATAAAGATGGAGCCAGTCCGTTCCTGGTTACT
AGGAGTATCCATTTCCTGAAGACCATGGAGCAACCACGGCGGATCGGGCGATCGGC
AGCCTCCCAGCCGGCGACCATGGCGGATGCCACGAGCGCAGGAGCGACGCCTCTCCT
CCCTGGCCTCCTCGACGACATCGTAATCTGTGAGATCCTTGTCCGCCTCGCCCCCAA
AGCCATCCTCCGCTGCCGCGCCGTCACGCCGTGCCTGGCGCCGCACCACCTCCACCC
GCGACTTCCTCCTCGCCCACCACGCCCGCCAGCCCGCCCTCCTCATCACCTCCGGCCA
CAGTT
```

SEQ ID NO: 121

```
AAATTTTTATAATATTGTTTTTCCAAATTTTATGTTTAAACTCATTTTTGTTCAATTTTT
TGTGAATATATTTTAATCCATTGATAGATTTTGAAAATATAATAATTTTTCCAAACA
TTCTATAATTTCATAAACCTTTTTAACATTTCAAGAATAAGATTAGGAAATTTTGATT
CTTAAAATATATTTTTAATCTTGCAACTACATTTTTATATACAATTACATGAGCCAAT
TTATTTTGGTAGAAATCAACTGAAAAACAAAAGAAAAAATTGGAATAGCGGGAGT
TCTCTGCGCGAACTTGGGGGGGGGGGCGACAACCCTCTATCAATGAGCTAGGGATT
CCTATTACATCTCGCCTACAAGCCGCACTAGTTTTTTTYCCCATTTGTTTTATATCGGTT
TTTTACTACTTTTGCACCGGTTTTCTTCTGGTATTATTTCATTTTTCTTCTATACTTTCT
GTTGTTTTCTTCGTTTCCCCCTCCTGTTTTTTGTCTTTTTCTACAGTTTCCTTGTTTCTT
TCTTTGGTTTTCACCGATTTACTTTGTTTTTCACGTTTTTAAATTTTAATTTTAATCTTC
AGATACATAATTAACATTCATTAAATTATATACTTTTATGTCAAGTTTTTTCATACAC
ATTGTGCATTTTATACATATTAGGATTCTTAAATACATGATTAATATTTTATTCAGAC
ATAGAGTACTTGTTTTGAACACTTTTTCAAATACATGTTGAAATAATTTATTTTATGA
TATGAAATATGTTTTTTATTATGCAAACATTTTTATACACTTTATGTTTTTTTGAAAT
ATTACAAAATTTTTGCTTGAAACGTGTGAACATTTTTTAAAATGTAACATAATTTTTT
GAATGGTATGAAACTTTTTTGAACTGCGCGAACATTATTTTTACATTGTATATTATTTT
GATTCATTTTCTGTAAGTTATCGCCTGAATTGCTTGAAAAACGTGATTTTTTTTAAAT
GCCACATATATTGTTTTGAATGGTTCATGCATTTTCTGAAAGTTGATCGAACATGTT
TTTATATTGCATTTTTAAAATGTAATAACCACTTTTGAAAATTAACTAATGTATTTTCA
TAATATATGTATTTAATATTATTAAAAATAAAAAAAAGGTAAAAGAAAAAACAGATC
AACGCGATGAGACCCCATGGTTGTTGCGCTTGTCCACTACCGGCTCACTGAAGACGT
CTCTCACAGTAGGAGTCGCTACGAAGAATACATAGTCGCGCTGGGCGCGGTTATGTT
CCGCCTGTTGCGACGCCCAAGCATGGCTTGCCTACAGCTAGAGGGTCGGGCTAGGAA
CCACTAATTGTGTCATGCTGATGTCACAATGACATCATACATGCTTTTATTTTAATTTT
TCGCTTTCTCTTTAAATTTTTTTGTATTTCAAAATATTCTGTTTTTTTAAGAATGCTAGT
ATTGTATTTGAAAAATGTTAAACCTGTATAGAAAAATATATAACATGAATGAAAAT
GTATAGATGTTAATCATGTGTACAAAAAATGATTGTGACAATTAAGAATGTCACATA
TTTCAAATAAATGTATGTGGAATTTTGAAAAAATGTGTATATAATTTTTTTAATGGTC
ATGTAATTTTAAAAAAATGTGTGATACATTCAACAAAAAATATTTCACATTTGAATA
ATTCTTCTTGAGCTTAAGAAATGTGTTCATTATGTTATCAATTTTTTTGTACAGTGTAC
AAAAAATGTTTACATAGTTCAAAAAAATGTTTTTCAGTAAAATTACATTTCATTGTGTA
TTTAATATTTTAACACACATTTGGAAAATATATTTGAAACATGTTTTTGTAAAAAAAA
ATTTAAAACTATGCTTGTACTCCCTCCGTCCGAAAAAGGTTTACATGTATAAAAGTTT
TTTCGGAGGGAGGGATTATAATGTTAGTCATTTATAAGAAATGTTTTACATGTATGAA
AATGTATAGCATATGTGTAAAAGTAGACATGTGTTGAAAAAAAAAAGTAAAACAAC
CCAAAAAACCAATGAAAATAAAATAAAACCAAAGTACCAAGAAGAAGAAAAGGAG
AATAAACCATTGAAAAACAAAGAAAATAAAAAACATAAAGAAGAAAGAAACCCAA
AGAAAACTGGCAAAAATTAGACACAGAAAAGAAAAACGAAAAATATATAATAAA
RAAAACCGGACTGAACCGATCGGACACGGATGAGCGAAGGCATGCATCGAGCAACA
CAGCTAATTGGCCGGCCCATAGTCGTTCGCCCGCAGACCATTCATACGAATCGGTAC
CGGAGAGACATAGGGGCTATTTGGTTTGTAGCCACATTTTGTCATACATTTGTGACACC
GCATCTTATGCAAGTTTGACCAAATTAGGTGGATGTTTAGTTCTAACCACATGTAAG
GGAAGATTTTTTTTATGAGCATTGAACCCGTAGACACAAAAAGTGTAGGAAGATTA
CTTTAAACAAGCTAAAGTGTGGCTAACAATTTAAGCATCTCAGGTAAGATAAGTGCG
ACAAATATGGCAAAAATAATGTGGTATATATGACAAAGATAGTCACAATCCAAACA
GCCCATAGCCTGGCGAGTGCAAATAGATACGAGATCTCTGGTGATATCACAACCGTC
CAAATTAATTGCTTGTTTCAGCATCAGCCTTTTTGCATAAAGAAGCTAGCCCAATCTG
AACCACACACTCACCCGCCGCGTGACAGCGCCAAAGACAAAAACATCACCCCTCCCC
AATTCCAACCCTCTCTCTGCCTCACAGAAATCTCCCCCCTCGCCCAAACCCTCGCCGC
CGCCATGGCCGCCGCCACCTCCCCCGCCGTCGCATTCTCGGGCGCCACCGCCGCCGC
CATGCCCAAACCCGCCCGCCATCCTCTCCCGCGCCACCAGCCCGTCTCGCGCCGCGC
GCTCCCCGCCCGCGTCGTCAGGTGTTGCGCCGCGTCCCCCGCCGCCACCTCCGCCGC
GCCTCCCGCAACCGCGCTCCGGCCCTGGGGCCCGTCCGAGCCCCGCAAGGGCGCCGA
CATCCTCGTCGAGGCGCTCGAGCGCTGCGGCATCGTCGACGTCTTCGCCTACCCCGG
CGGCGCCTCCATGGAGATCCACCAGGCGCTGACGCGCTCGCCCGTCATCACCAACCA
CCTCTTCCGCCACGAGCAGGGGAGGCGTTCGCGGCGTCCGGCTACGCCCGCGCGTC
CGGCCGCGTCGGCGTCTGCGTCGCCACCTCCGGCCCGGGGGCCACCAACCTCGTCTC
CGCGCTCGCCGACGCCCTCCTCGACTCCATCCCCATGGTCGCCATCACGGGCCAGGT
CCCCCGCCGCATGATCGGCACGGACGCGTTCCAGGAGACGCCCATAGTGGAGGTCAC
GCGCTCCATCACCAAGCACAACTACCTGGTCCTTGACGTGGAGGATATCCCCCGCGT
CATCCAGGAAGCCTTCTTCCTTGCATCCTCTGGCCGCCCGGGGCCGGTGCTAGTTGAT
ATCCCCAAGGACATCCAGCAGCAGATGGCTGTGCCCGTCTGGGACACTCCAATGAGT
TTGCCAGGGTACATCGCCCGCCTGCCCAAGCCACCATCTACTGAATCGCTTGAGCAG
GTCCTGCGTCTGGTTGGCGAGTCACGGCGCCCAATTCTGTATGTTGGTGGTGGCTGCG
CTGCGTCTGGCGAGGAGTTGCGCCGCTTTGTTGAGCTTACTGGGATTCCAGTTCAAC
TACTCTGATGGGCCTTGGCAACTTCCCCAGCGACGACCCACTGTCTCTGCGCATGCTT
GGGATGCATGGCACTGTGTATGCAAATTATGCAGTAGATAAGGCTGACCTGTTGCTC
GCATTTGGTGTGCGGTTTGATGATCGTGTGACTGGGAAAATCGAGGCTTTTGCAAGC
AGGTCCAAGATTGTGCACATTGACATTGACCCAGCTGAGATTGGCAAGAACAAGCA
GCCACATGTCTCCATTTGTGCAGATGTTAAGCTTGCTTTACAGGGGTTGAATGATCTA
TTAAATGGGAGCAAAGCACAACAGGGTCTGGATTTTGGTCCATGGCACAAGGAGTTG
GATCAGCAGAAGAGGGAGTTTCCTCTAGGATTCAAGACTTTTGGCGAGGCCATCCCG
CCGCAATATGCTATCCAGGTACTGGATGAGCTGACAAAAGGGAGGCGATCATTGCC
ACTGGTGTTGGGCAGCACCAGATGTGGGCGGCTCAGTATTACACTTACAAGCGCCA
CGGCAGTGGCTGTCTTCGTCTGGTTTGGGGGCAATGGGATTTGGGTTACCAGCTGCA
GCTGGCGCTGCTGTGGCCAACCCAGGTGTTACAGTTGTTGACATTGATGGTGATGGT
AGTTTCCTCATGAACATTCAGGAGTTGGCGTTGATCCGCATTGAGAACCTCCCAGTG
AAGGTGATGATATTGAACAACCAGCATCTGGGAATGGTGGTGCAGTGGGAGGATAG
GTTTTACAAGGCCAATCGGGCGCACACATACCTTGGCAACCCAGAAAATGAGAGTG
```

```
AGATATATCCAGATTTTGTGACGATTGCTAAAGGATTCAACGTTCCAGCAGTTCGAG
TGACGAAGAAGAGCGAAGTCACTGCAGCAATCAAGAAGATGCTTGAGACCCCAGGG
CCATACTTGTTGGATATCATAGTCCCGCATCAGGAGCACGTGCTGCCTATGATCCCA
AGCGGTGGTGCTTTCAAGGACATGATCATGGAGGGTGATGGCAGGACCTCGTACTGA
AATTTCGACCTACAAGACCTACAAGTGTGACATGCGCAATCAGCATGATGCCCGCGT
GTTGTATCAACTACTAGGGGTTCAACTGTGAGCCATGCGTTTTCTAGTTTGCTTGTTT
CATTCATATAAGCTTGTATTACTTAGTTCCGAACCCTGTAGTTTTGTAGTCTATGTTCT
CTTTTGTAGGGATGTGCTGTCATAAGATGTCATGCAAGTTTCTTGTCCTACATATCAA
TAATAAGTACTTCCATGGAATAATTCTCAGTTCTGTTTTGAATTTTGCATCTTCTCACA
AACAGTGTGCTGGTTCCTTTCTGTTACTTTACATGTCTGCTGTGTCAGGTTCTGACAT
AACGACCGATGGAGGGTGGTCGGCAGGTTTTAGAAGGGGAATTGAAACTTTTTTTTG
GGAAGAAGTCTGAATACAGTTGGGAGGAAAAATAGAAGTATATACTTCGATTAATTT
ATCAAGCCCGCTATCCAGTCTAATTTATCAAGCACTAGACAGTGTAGGGTGTTGGCA
TTCTTCTCTTCCTTGAGATCCGGCTTGAGAGGAGAGACCGAGGCTTCGGCTGTGTTGG
TTGCTGATTTCTACAGCTTTTTGAGATAGAGAGAGAGATCCTGCAACTGTGGTTTGTC
TTGCTGCTTGTACAGCGAGAGAGACATTGAGAGATATGTAGATCGTTTACCAGTTGT
GCTGCTGTTATTCGTACTGGTACTGATTGTTGTTACTGTTGCTATCATGTGCAAATTGT
TGTGATGGAAAATCAACAAAATTTTGATATTTTGCAAAGCGAGTTGGATTGAATGAT
TTGAGAAATGGTGACTGCTTTCCCTCAGACTTGTTGAGTGGCCTTGAGAATTGGTGTT
TCATAGGTGGTGTATGCAGTTGCTAATGAAAGGCGACGGCTTGAAATTTCCGAAGG
CAGCCAATGATACTTTCTGAAAGTGATGTTTTTTTCGTCCAGGTTTCCGGTGGAGCAA
GTCTAGACACACGTTGAGCCAATGTTTGTCAGCTTATTCTGCTCTTTAGTTTCAGTTT
AGGTGCAGTTGTTTTGTTTACAGATTGCTGGGCAGAGCCCCGTGATCGGCTGAGCCT
CCAAGAGATCCTTGCTTGCTCGACTGCGGATACGCTGAATCCTTTAAAACGCTCCCTA
GTTTTAAGTTTTAGAGAACTGAGAATCAATTGGGGGCAACATTACTGGGTCGCCTCC
CTGGGCCTCTACAGTTTTGTGGGCCCTATATGTAAGTGCCCCAGTGTTGTGGGGATTT
GCGGCGTGGCGGGCGGCATTTGCGTCCTCTCTTCGGCGGCGCTGTTTCCCCCTCCTTC
TTGCTGCTTCTGGAGGAGGTGGTCGGCGGCGGGTGTTGTGGGGGGTCGCATTGGAGC
GGCGCGAACGCCGGTCCTGCTGCATCTGCCGCCATTGGTTGTT
```
SEQ ID NO: 140
```
CGTTCGCCCGTAGACCATTCATAAGAATCGGTATCGGAGAGACATAGGGGTTCTTTG
GTTTCTAACCATATCTTGTCACACTTTACCATACATCACCTTAGTCAAATCTGATCAA
ATTAGGTGAGTATTTGGTTCTAGCCACATCTAAGGCAAGATTTGTTTTTCTGAGCAGT
GAACCCCATATGTCATAGACAGAAAAATTGTGAAAAGATTCCTTTAGACGGTCAAG
CGTGGTTAACAATTTAATCAACTCAAGTAAGATAAATGCGATAAATGTGACAAAAAT
AATGTGTTATAGAAGTATGACAAAAATAATCACAATCCAAACAGTCTGATAGCTTGG
CGAGTGCAAAATAGATACGAAATCTCTGGTGATATCACACGGGTCCAAAATAATTGC
TTGTTTGAGCATCAGCCTTTCTGCACAAAAAAAGCTAGCCCAAACAAACGAGTGCG
TCCCATCTGAACCACACGCTCACCCGCCGCGTGACAGCGCCAAAGACAAAACCATCA
CCCCTCCCCAATTCCAACCCTCTCTCCGCCTCACAGAAATCTCTCCCCTCGCCCAAAC
CCTCGCCGCCGCCATGCCGCCGCCACCTCCCCCGCCGTCGCATTCTCCGGCGCCGCC
GCCGCCGCCGCCGCCATGCCCAAGCCCGCCGCCAGCCTCTCCCGCGCCACCAGCCC
GCCTCGCGCCGCGCGCTCCCCGCCCGCGTCGTCAGGTGCTGCGCCGCGCCCCCCGCT
GCTGCCACCTCCGCCGCGCCCCCGCCACCGCGCTCCGGCCCTCGGGGCCCGTCCGA
GCCCCGCAAGGGCGCCGACATCCTCGTCGAGGCGCTCGAGCGCTGCGGCATCGTCGA
CGTATTCGCCTACCCCGGCGGCGCGTCCATGGAGATCCACCAGGCGCTGACGCGCTC
GCCCGTCATCACCAACCACCTCCTTCCGCCACGAGCGAGGGGGAGGCGTTCGCGGCG
TCCGGCTACGCCCGCGCGTCCGGCCGCGTCGGCGTCTGCGTCGCCACCTCCGGCCCG
GGGGCCACCAACCTCGTCTCCGCGCTCGCTGACGCCCTCCTCGACTCCATCCCCATGG
TCGCCATCACGGGCCAGGTCCCCCGCCGCATGATCGGCACGGACGCGTTCCAGGAGA
CGCCCATAGTGGAGGTCACGCGCTCCATCACCAAGCACAACTACCTGGTCCTTGACG
TGGAGGATATCCCCCGCGTCATCCAGGAAGCCTTCTTCCTGCGTCCTCTGGCCGCCC
GGGGCCGGTGCTGGTTGATATCCCCAAGGATATCCAGCAGCAGATGGCCGTGCCTAT
CTGGGACACGCCGATGAGTTTGCCAGGGTACATCGTCCCGCCTGCCCAAGCCACCAT
CTACTGAATCGCTTGAGCAGGTCCTGCGTCTGGTTGGCGAGTCACGGCGCCCAATTC
TGTATGTTGGTGGTGGCTGCGCTGCATCCGGCGAGGAGTTGCGCCGCTTTGTTGAGCT
CACTGGGATTCCGGTTACAACTACTCTGATGGGCCTTGGCAACTTCCCCAGCGACGA
CCCACTGTCTCTGCGCATGCTTGGGATGCATGGCACTGTGTATGCAAATTATGCAGTC
GATAAGGCTGACCTGTTGCTTGCATTTGGTGTGCGGTTTGATGATCGCGTGACTGGG
AAAATCGAGGCCTTTGCAAGCAGGTCCAAGATTGTGCACATTGACATTGACCCAGCT
GAGATTGGCAAGAACAAGCAGCCACATGTCTCCATTTGTGCAGATGTTAAGCTTGCT
TTACAGGGGTTGAATGCTCTATTAAATGGGAGCAAAGCACAACAGGGTCTGGATTTT
GGTCCATGGCACAAGGAGTTGGATCAGCAGAAGAGGGAGTTTCCTCTAGGATTCAA
GACTTTTGGCGAGGCCATCCCGCCGCAATATGCTATCCAGGTACTGGATGAGCTGAC
AAAAGGGGAGGCGATCATTGCTACTGGTGTTGGGCAGCACCAGATGTGGGCGGCTC
AGTATTACACTTACAAGCGGCCACGGCAGTGGCTGTCTTCGTCTGGTTGGGGGCAAT
GGGATTTGGGTTACCAGCTGCAGCTGGCGCTGCTGTGGCCAACCCAGGGTGTTACAGT
TGTTGACATTGATGGAGATGGTAGTTTCCTCATGAACATTCAGGAGTTGGCATTGATC
CGTATTGAGAACCTCCCTGTGAAGGTGATGATATTGAACAACCAGCATCTGGGAATG
GTGGTGCAATGGGAGGATAGGTTTTACAAGGCCAATCGGGCGCACACATACCTTGGC
AACCCAGAAAATGAGAGTGAGATATATCCAGATTTTGTGACGATTGCTAAAGGATTC
AACGTTCCGGCAGTTCGTGTGACGAAGAAGAGCGAAGTCACTGCAGCAATCAAGAA
GATGCTTGAGACCCCAGGGCCATACTTGTTGGATATCATCGTCCCGCATCAGGAGCA
CGTGCTGCCTATGATCCCAAGCGGTGGTGCTTTCAAGGACATGATCATGGAGGGTGA
TGGCAGGACCTCGTACTGAAATTTCGACCTACAAGACCTACAAGTGTGACATGCGC
AATCAGCATGGTGCCCGCGTGTTGTATCAACTACTAGGGGTTCAACTGTGAACCATGC
GTTTTCTAGTTTGCTTGTTTCATTCATATAAGCTTGTGTTACTTAGTTCCGAACCCTGT
AGCTTTGTAGTCTATGCTCTCTTTTGTAGGGATGTGCTGTCATAAGATATCATGCAAG
TTTCTTGTCCTACATATCAATAATAAGTACTTCCATGGAATAATTCTCAGTTCTGTTTT
GAATTTTGCATCTTCTCACAAACAGTGTGCTGGTTCCTTTCTGTTACTTTACATGTCTG
```

-continued
```
CCGTGTCCGGTTATGACATAATGACCGATGGAGGGTGGTCAGCAGGTTTTAGACGGG
GAGTTGAAACTTTTTTTTGGGGGGAAGAAATCTGAATACAGTTGGGAGGAAAGATAA
AAGCATATACCTTGATTAATTTATTGAGCCCAATATCCAGCCTAATTTATCAAGCAAT
AGGCAGTGTAGGGTGTTG
```

SEQ ID NO: 141

```
CGTTCGCCCGTAGACCATTCCTACGAATCGGTACCGGAGAGACATAGGGGCTGTATG
GTTCCTAACCATACCTTGCCACACTTTGTCACACCTCATCTTAGGCAAATTTAATCAA
GTTATGTAGGTGTTTGGTTTTAGCCACATCTAAGGCAAGATTTATTTTCCTGAGCAGT
GAACCCCATATGTTATAGACATAAAAAGTGTGGGAAGATTCCCTTTAGTCAAACTGT
GGCTAACAATTTATTAAGAATTAACTTAAGTAAGATAGGTGCAACAAATGTAGCAAA
AATAATGTGGTATATATAGCAAAGATAGCCACAACCGCGAGTGGAAATACCAGATA
CGAGATCTCTGGTCATATCACACGAGTCCAAATTAATTGCTTTGTTTGAGGTTCAGCC
TTTTTGCATAAAAAAGCTAGCCCAAACAAACGAGTGGCGTCCCATCTGAACCACACA
CTCACCCGCCGCGTGACAGCGCCAAAGACAAAACCATCACCCCTCCCCAATTCCAAC
CCTCTCTCTGCCTCACAGAAATCTCTCCCTCGCCCAAACCCTCGCCGCCGCCATGGCC
GCAGCCACCTCCCCCGCCGTCGCATTCTCGGGCGCCGCCGCCGCCGCCGCCGCCATA
CCCAAACCCGCCCGCCAGCCTCTCCCGCGCCACCAGCCCGCCTCGCGCCGCGCGCTC
CCCGCCCGCATCGTCAGGTGCTGCGCCGCGTCCCCGCCGCCACCTCCGTCGCGCCTC
CCGCCACCGCGCTCCGGCCGTGGGGCCCCTCCGAGCCCCGCAAGGGCGCCGACATCC
TCGTCGAGGCGCTGGAGCGCTGCGGCATCGTCGACGTCTTCGCCTACCCTGGCGGCG
CGTCCATGGAGATCCACCAGGCGCTGACGCGCTCGCCAGTCATCACCAACCACCTCT
TCCGCCACGAGCAGGGGGAGGCGTTCGCGGCGTCCGGGTACGCCCGCGCGTCCGGC
CGCGTCGGCGTCTGCGTCGCCCACCTCCGGCCCGGGGGCCACCAACCTCGTCTCCGCG
CTCGCCGACGCTCTCCTCGACTCCATCCCCATGGTCGCCATCACGGGCCAGGTCCCCC
GCCGCATGATCGGCACGGATGCGTTCCAGGAGACGCCCATCGTGGAGGTCACGCGCT
CCATCACCAAGCACAACTACCTGGTCCTTGACGTGGAGGATATCCCCCGCGTCATCC
AGGAAGCCTTCTTCCTCGCATCCTCTGGCCGCCCGGGGCCGGTGCTGGTTGATATCCC
CAAGGACATCCAGCAGCAGATGGCTGTGCCTGTCTGGGACACGCCGATGAGTTTGCC
AGGGTACATCGCCCGCCTGCCCAAGCCACCATCTACTGAATGCTTGAGCAGGTCCT
GCGTCTGGTTGGCGAGTCACGGCGCCCAATTCTGTATGTTGGTGGTGGCTGCGCTGC
ATCTGGTGAGGAGTTGCGCCGCTTTGTTGAGCTCACTGGGATTCCAGTTACAACTACT
CTTATGGGCCTTGGCAACTTCCCCAGTGACGACCCACTGTCTCTGCGCATGCTGGGG
ATGCATGGCACTGTGTATGCAAATTATGCAGTAGATAAGGCTGACCTGTTGCTTGCA
TTTGGTGTGCGGTTTGATGATCGTGTGACCGGGAAAATCGAGGCTTTTGCAAGCAGG
TCCAAGATTGTGCACATTGACATTGACCCAGCTGAGATTGGCAAGAACAAGCAGCCA
CATGTCTCCATTTGTGCAGATGTTAAGCTTGCTTTACAGGGGTTGAATGCTCTATTAA
ATGGGAGCAAAGCACAACAGGGTCTGGATTTTGGTCCATGGCACAAGGAGTTGGAT
CAGCAGAAGAGGGAGTTTCCTCTAGGATTCAAGACTTTTGGTGAGGCCATCCCGCCA
CAATATGCTATCCAGGTACTGGATGAGCTGACAAAAGGGGAGGCGATCATTGCCACC
GGTGTTGGGCAGCATCAGATGTGGGCGGCTCAGTATTACACTTACAAGCGGCCACGG
CAGTGGCCGTGTCTTCATCCGGTTTGGGTGCAATGGGATTTGGGTTGCCAGCTGCAGCTG
GCGCTGCTGTGTGGCCAACCCAGGTGTTACAGTTGTTGACATTGATGGGGATGGTAGTT
TCCTCATGAACATTCAGGAGTTGGCGTTGATCCGTATTGAGAACCTCCCAGTGAAGG
TGATGATATTGAACAACCAGCATCTGGGAATGGTGGTGCAGTGGGAGGATAGGTTTT
ACAAGGCCAACCGGGCGCACACATACCTTGGCAACCCAGAAAATGAGAGTGAGATA
TATCCAGATTTTGTGACGATTGCTAAAGGATTCAACGTTCCGGCAGTTCGTGTGACG
AAGAAGAGCGAAGTCACTGCAGCAATCAAGAAGATGCTTGAGACCCCAGGGCCATA
CTTGTTGGATATCATTGTCCCGCATCAGGAGCACGTGCTGCCTATGATCCCAAGCGGT
GGTGCTTTTAAGGACATGATCATGGAGGGTGATGGCAGGACCTCGTACTGAAATTTC
GACCTACAAGACCTACAAGTGTGACATGCGCAATCAGCATGATACCTGCGTGTTGTA
TCAACTACTGGGGGTTCAACTGTGAACCATGCGTTTTCTAGTTTGCTTGTTTCATTCA
TATAAGCTTGTGTTACTTAGTTCCGAACCGTGTAGTTTTGTAGTCTCTGTTCTCTTTTG
TAGGGATGTGCTGTCATAAGATATCATGCAAGTTTCTTGTCCTACATATCAATAATAA
GCACTTCCATGGAATAATTCTCAGTTCTGTTTTGAATTTCACATCTTCTCACGAACAG
TGTGCTGGTTCCTTTCTGTTACTTTACATGCCTGCCGTGTCAGGTTATGACATAACGA
CCGATGGAGGATTGGAGGGTGGTCGGCTGGTTTTAGACGGGGAATTGAAACATTTTT
CTGGAAGAAATCTGAATACAGTTGGGAGGGGAAATGGAAGCATATATTTATCGAGC
CCGCTATCCAGGCTAATTTATCAAGCACTAGACAGTGTAGGGTGTTGGCATTCTTCTC
TTCCTTGATATCCGGCTTGAGAGGAGAGATTGAGGCTTCGGCTGTGTTGGTTGCTGAT
TTCTACAGCATTTTGAGAGAGAGAGAGAGATGTTGCAACTGTGTTTTGTCTTGGTTGC
TTGTACAGAGAAAGAGATGACATTTAGAGATATGCAGATCGTTTACCAGTTGTGCTG
CGTTTATTCGTACTGATTGTTGTTATTGTTGCTATCATGTGCAAATTGTTGTGATGGAA
AATCAACAAAATTTTGATATTTTGCAAAGCGAGTTGGATTGAATGATTTGAGAAATG
GTGACTTGTTGAGTGGCCTTGAGAATTGGTGTTTCATAGGTGTGCAGTTGGTAATGAA
AGGCGGCGGCTTGAAATTTCCGAAAGGCAGGCAATGATACTTTCTGAAAGTGATGTT
TTTTCTTCCAGGTTTCCGGTGGAACAAGTCTACGTTGAGCCAATGTTTGTCAGCTTAT
TCTGCTCTTTAGTTTCAGTTGTTTTGTTCACAGATTGCTGGGCAGAGCCCCATGATCG
GCTGAGCCTCCAGGAGATCCTTGATTGCTCGACTGC
```

SEQ ID NO: 142

```
CGTTCGCCCGTAGACCATTCATACGAATCGGTACCGGAGAGACATAGGGGCTATTTG
GTTTGTAGCCACATTTTGTCATACTTTGTGACACCGCATCTTATGCAAGTTTGATCAA
ATTAGGTGGATGTTTAGTTCTAACCACATGTAAGGGAAGATTTTTTTTTTATGAGCA
TTGAACCCGTAGACACAAAAGTGTAGGAAGATTACTTTAAACAAGCTAAAGTGTG
GCTAACAATTTAAGCATCTCAGGTAAGATAAGTGCGACAAATATGGCAAAAATAAT
GTGGTATATATGACAAAGATAGTCACAATCCAAACAGCCCATAGCCTGGCGAGTGCA
AATAGATACGAGATCTCTGGTGATATCACAACCGTCCAAATTAATTGCTTGTTTCAGC
ATCAGCCTTTTTGCATAAAGAAGCTAGCCCAATCTGAACCACACACTCACCCGCCGC
GTGACAGCGCCAAAGACAAAACCATCACCCCTCCCCAATTCCAACCCTCTCTCTGCC
TCACAGAAATCTCCCCCCTCGCCCAAACCCTCGCCGCCGCCATGGCCGCCGCCACCT
```

-continued
```
CCCCCGCCGTCGCATTCTCGGGCGCCACCGCCGCCGCCATGCCCAAACCCGCCCGCC
ATCCTCTCCCGCGCCACCAGCCCGTCTCGCGCCGCGCGCTCCCCGCCCGCGTCGTCAG
GTGTTGCGCCGCGTCCCCGCCGCCACCTCCGCCGCGCCTCCCGCAACCGCGCTCCG
GCCCTGGGGCCCGTCCGAGCCCCGCAAGGGCGCCGACATCCTCGTCGAGGCGCTCGA
GCGCTGCCGGCATCGTCGACGTCTTCGCCTACCCCGGCGGCGCCTCCATGGAGATCCA
CCAGGCGCTGACGCGCTCGCCCGTCATCACCAACCACCTCTTCCGCCACGAGCAGGG
GGAGGCGTTCGCGGCGTCCGGCTACGCCCGCGCGTCCGGCGCGTCGGCGTCTGCGT
CGCCACCTCCGGCCCGGGGGCCACCAACCTCGTCTCCGCGCTCGCCGACGCCCTCCT
CGACTCCATCCCCATGGTCGCCATCACGGGCCAGGTCCCCGCCGCATGATCGGCAC
GGACGCGTTCCAGGAGACGCCCATAGTGGAGGTCACGCGCTCCATCACCAAGCACA
ACTACCTGGTCCTTGACGTGGAGGATATCCCCCGCGTCATCCAGGAAGCCTTCTTCCT
TGCATCCTCTGGCCGCCCGGGGCCGGTGCTAGTTGATATCCCCAAGGACATCCAGCA
GCAGATGGCTGTGCCCGTCTGGGACACTCCAATGAGTTTGCCCAGGGTACATCGCCCG
CCTGCCCAAGCCACCATCTACTGAATCGCTTGAGCAGGTCCTGCGTCTGGTTGGCGA
GTCACGGCGCCCAATTCTGTATGTTGGTGGTGGCTGCGCTGCGTCTGGCGAGGAGTT
GCGCCGCTTTGTTGAGCTTACTGGGATTCCAGTTACAACTACTCTGATGGGCCTTGGC
AACTTCCCCAGCGACGACCCACTGTCTCTGCGCATGCTTGGGATGCATGGCACTGTG
TATGCAAATTATGCAGTAGATAAGGCTGACCTGTTGCTCGCATTTGGTGTGCGGTTTG
ATGATCGTGTGACTGGGAAAATCGAGGCTTTTGCAAGCAGGTCCAAGATTGTGCACA
TTGACATTGACCCAGCTGAGATTGGCAAGAACAAGCAGCCACATGTCTCCATTTGTG
CAGATGTTAAGCTTGCTTTACAGGGGTTGAATGATCTATTAAATGGGAGCAAAGCAC
AACAGGGTCTGGATTTTGGTCCATGGCACAAGGAGTTGGATCAGCAGAAGAGGGAG
TTTCCTCTAGGATTCAAGACTTTTGGCGAGGCCATCCCGCCGCAATATGCTATCCAGG
TACTGGATGAGCTGACAAAAGGGGAGGCGATCATTGCCACTGGTGTTGGGCAGCAC
CAGATGTGGGCGGCTCAGTATTACACTTACAAGCGGCCACGGCAGTGGCTGTCTTCG
TCTGGTTTGGGGGCAATGGGATTTGGGTTACCAGCTGCAGCTGGCGCTGGCTGTGGCC
AACCCAGGTGTTACAGTTGTTGACATTGATGGTGATGGTAGTTTCCTCATGAACATTC
AGGAGTTGGCGTTGATCCGCATTGAGAACCTCCCAGTGAAGGTGATGATATTGAACA
ACCAGCATCTGGGAATGGTGGTGCAGTGGAGGATAGGTTTTACAAGGCCAATCGG
GCGCACACACATACCTTGGCAACCCAGAAAATGAGAGTGAGATATATCCAGATTTTGTG
ACGATTGCTAAAGGATTCAACGTTCCAGCAGTTCGAGTGACGAAGAAGAGCGAAGT
CACTGCAGCAATCAAGAAGATGCTTGAGACCCCAGGGCCATACTTGTTGGATATCAT
AGTCCCGCATCAGGAGCACGTGCTGCCTATGATCCCAAGCGGTGGTGCTTTCAAGGA
CATGATCATGGAGGGTGATGGCAGGACCTCGTACTGAAATTTCGACCTACAAGACCT
ACAAGTGTGACATGCGCAATCAGCATGATGCCCGCGTGTTGTATCAACTACTAGGGG
TTCAACTGTGAGCCATGCGTTTTCTAGTTTGCTTGTTTCATTCATATAAGCTTGTATTA
CTTAGTTCCGAACCCTGTAGTTTTGTAGTCTATGTTCTCTTTTGTAGGGATGTGCTGTC
ATAAGATGTCATGCAAGTTTCTTGTCCTACATATCAATAATAAGTACTTCCATGGAAT
AATTCTCAGTTCTGTTTTGAATTTTGCATCTTCTCACAAACAGTGTGCTGGTTCTTTC
TGTTACTTTACATGTCTGCTGTGTCAGGTTCTGACATAACGACCGATGGAGGGTGGTC
GGCAGGTTTTAGAAGGGGAATTGAAACTTTTTTTGGGAAGAAGTCTGAATACAGTT
GGGAGGAAAAATAGAAGTATATACTTCGATTAATTTATCAAGCCCGCTATCCAGTCT
AATTTATCAAGCACTAGACAGTGTAGGGTGTTGGCATTCTTCTCTTCCTTGAGATCCG
GCTTGAGAGGAGAGACCGAGGCTTCGGCTGTGTTGGTTGCTGATTTCTACAGCTTTTT
GAGATAGAGAGAGATCCTGCAACTGTGTTTGTCTTGCTGCTTGTACAGCGAGAG
AGACATTGAGAGATATGTAGATCGTTTACCAGTTGTGCTGCTGTTATTCGTACTGGTA
CTGATTGTTGTTACTGTTGCTATCATGTGCAAATTGTTGTGATGAAAATCAACAAAA
TTTTGATATTTTGCAAAGCGAGTTGGATTGAATGATTTGAGAAATGGTGACTGCTTTC
CCTCAGACTTGTTGAGTGGCCTTGAGAATTGGTGTTTCATAGGTGGTGTATGCAGTTG
CTAATGAAAGGCGACGGCTTGAAATTTCCGAAAGGCAGCCAATGATACTTTCTGAAA
GTGATGTTTTTTCGTCCAGGTTTCCGGTGGAGCAAGTCTAGACACACGTTGAGCCAA
TGTTTGTCAGCTTATTCTGCTCTTTAGTTTCAGTTTAGGTGCAGTTGTTTTGTTTACAG
ATTGCTGGGCAGAGCCCCGTGATCGGCTGAGCCTCCAAGAGATCCT
```

SEQ ID NO: 175 tnantggtta ggtgctggtg gtccgaaggt ccacgccgcc aactacg

SEQ ID NO: 176

CNANTACGTAGTTGGCGGCGTGGACCTTCGGACCACCAGCACCTAAC

SEQ ID NO: 177

TNANTGGTTAGGTGCTGGTGGTCCGAAGGTCCACGCCGCCAACTACG

SEQ ID NO: 178

ANGNGTCGTAGTTGGCGGCGTGGACCTTCGGACCACCAGCACCTAAC

SEQ ID NO: 179

TGGATATCATAGTCCCGCATCAGGAGCACGTGCTGCCTATGATCCCAAGCGGTGGTG
CTTTCAAGGACATGATCATGGGTTAGGTGCTGGTGGTCCGAAGGTCCACGCCGCCAA
CTACGTGGATATCATAGTCCCGCATCAGGAGCACGTGCTGCCTATGATCCCAAGCGG
TGGTGCTTTCAAGGACATGATCATGG

SEQ ID NO: 180

CCATGATCATGTCCTTGAAAGCACCACCGCTTGGGATCATAGGCAGCACGTGCTCCT
GATGCGGGACTATGATATCCACGTAGTTGGCGGCGTGGACCTTCGGACCACCAGCAC
CTAACCCATGATCATGTCCTTGAAAGCACCACCGCTTGGGATCATAGGCAGCACGTG
CTCCTGATGCGGGACTATGATATCCA

SEQ ID NO: 181

TGGATATCATAGTCCCGCATCAGGAGCACGTGCTGCCTATGATCCCAAGCGGTGGTG
CTTTCAAGGACATGATCATGGGTTAGGTGCTGGTGGTCCGAAGGTCCACGCCGCCAA

-continued
CTACGGATGGCAGGACCTCGTACTGAAATTTCGACCTACAAGACCTACAAGTGTGAC
ATGCGCAATCAGCATGATGCCCGCGT

SEQ ID NO: 182

ACGCGGGCATCATGCTGATTGCGCATGTCACACTTGTAGGTCTTGTAGGTCGAAATTT
CAGTACGAGGTCCTGCCATCCGTAGTTGGCGGCGTGGACCTTCGGACCACCAGCACC
TAACCCATGATCATGTCCTTGAAAGCACCACCGCTTGGGATCATAGGCAGCACGTGC
TCCTGATGCGGGACTATGATATCCA

SEQ ID NO: 183

GGAGTTGGCGTTGATCCGNC

SEQ ID NO: 184

AACTACAGGGTTCGGAACTAAGTAANT

SEQ ID NO: 185

TGGCAGGATATATTGTGGTGTAAACAAATTGACGCTTAGACAACTTAATAACACATT
GCGGACGTTTTTAATGTACTGAATTAACGCCGAATTGAATTCGAGCTCGGTACCACT
GGATTTTGGTTTTAGGAATTAGAAATTTTATTGATAGAAGTATTTTACAAATACAAAT
ACATACTAAGGGTTTCTTATATGCTCAACACATGAGCGAAACCCTATAAGAACCCTA
ATTCCCTTATCTGGGAACTACTCACACATTATTCTGGAGAAAAATAGAGAGAGATAG
ATTTGTAGAGAGAGACTGGTGATTTTTGCGGACTCTATTAGATCTGGGTAACTGGCCT
AACTGGCCTTGGAGGAGCTGGCAACTCAAAATCCCTTTGCCAAAAACCAACATCATG
CCATCCACCATGCTTGTATCCAGCTGCGCAATGTACCCCGGGCTGTGTATCCCAA
AGCCTCATGCAACCTAACAGATGGATCGTTTGGAAGGCCTATAACAGCAACCACAGA
CTTAAAACCTTGCGCCTCCATAGACTTAAGCAAATGTGTGTACAATGTGGATCCTAG
GCCCAACCTTTGATGCCTATGTGACACGTAAACAGTACTCTCAACTGTCCAATCGTA
AGCGTTCCTAGCCTTCCAGGGCCCAGCGTAAGCAATACCAGCCACAACACCCTCAAC
CTCAGCAACCAACCAAGGGTATCTATCTTGCAACCTCTCGAGATCATCAATCCACTCT
TGTGGTGTTTGTGGCTCTGTCCTAAAGTTCACTGTAGACGTCTCAATGTAATGGTTAA
CGATATCACAAACCGCGGCCATATCAGCTGCTGTAGCTGGCCTAATCTCAACTGGTC
TCCTCTCCGGAGACATGGCTTCTACCTACAAAAAAGCTCCGCACGAGGCTGCATTTG
TCACAAATCATGAAAGAAAAACTACCGATGAACAATGCTGAGGGATTCAAATTCT
ACCCACAAAAAGAAGAAAGAAAGATCTAGCACATCTAAGCCTGACGAAGCAGCAGA
AATATATAAAAATATAAACCATAGTGCCCTTTTCCCCTCTTCCTGATCTTGTTTAGCA
TGGCGGAAATTTTAAACCCCCCATCATCTCCCCCAACAACGGCGGATCGCAGATCTA
CATCCGAGAGCCCCATTCCCCGCGAGATCCGGGCCGGATCCACGCCGGCGAGAGCCC
CAGCCGCGAGATCCCGCCCCTCCCGCGCACCGATCTGGGCGCGCACGAAGCCGCCTC
TCGCCCACCCAAACTACCAAGGCCAAAGATCGAGACCGAGACGGAAAAAAAAAACG
GAGAAAGAAAGAGGAGAGGGCGGGGTGGTTACCGGCGCGGCGGCGGCGGAGGGG
GAGGGGGGAGGAGCTCGTCGTCCGGCAGCGAGGGGGGAGGAGGTGGAGGTGGTGG
TGGTGGTGGTGGTAGGGTTGGGGGGATGGGAGGAGAGGGGGGGTATGTATATAGT
GGCGATGGGGGGCGTTTCTTTGGAAGCGGAGGGAGGGCCGGCCTCGTCGCTGGCTCG
CGATCCTCCTCGCGTTTCCGGCCCCCACGACCCGGACCCACCTGCTGTTTTTCTTTTT
CTTTTTTTTCTTTCTTTTTTTTTTTTTGGCTGCGAGACGTGCGGTGCGTGCGGACAACT
CACGGTGATAGTGGGGGGGTGTGGAGACTATTGTCCAGTTGGCTGGACTGGGGTGGG
TTGGGTTGGGTTGGGTTGGGCTGGGCTTGCTATGGATCGTGGATAGCACTTTGGGCTT
TAGGAACTTTAGGGGTTGTTTTTGTAAATGTTTTGAGTCTAAGTTTATCTTTTATTTTT
ACTAGAAAAAATACCCATGCGCTGCAACGGGGGAAAGCTATTTTAATCTTATTATTG
TTCATTGTGAGAATTCGCCTGAATATATATTTTTCTCAAAAATTATGTCAAATTAGCA
TATGGGTTTTTTTAAAGATATTTCTTATACAAATCCCTCTGTATTTACAAAAGCAAAC
GAACTTAAAACCCGACTCAAATACAGATATGCATTTCCAAAAGCGAATAAACTTAAA
AACCAATTCATACAAAAATGACGTATCAAAGTACCGACAAAAACATCCTCAATTTTT
ATAATAGTAGAAAAGAGTAAATTTCACTTTGGGCCACCTTTTATTACCGATATTTTAC
TTTATACCACCTTTTAACTGATGTTTTCACTTTTGACCAGGTAATCTTACCTTTGTTTT
ATTTTGGACTATCCCGACTCTCTTCTCAAGCATATGAATGACCTCGAGTATGCTAGTC
TAGAGTCGACCTGCAGGGTGCAGCGTGACCCGGTCGTGCCCCTCTCTAGAGATAATG
AGCATTGCATGTCTAAGTTATAAAAAATTACCACATATTTTTTTGTCACACTTGTTT
GAAGTGCAGTTTATCTATCTTTATACATATATTTAAACTTTACTCTGAATAATATA
ATCTATAGTACTACAATAATATCAGTGTTTTAGAGAATCATATAAATGAACAGTTAG
ACATGGTCTAAAGGACAATTGAGTATTTTGACAACAGGACTCTACAGTTTTATCTTTT
TAGTGTGCATGTGTTCTCCTTTTTTTTGCAAATAGCTTCACCTATATAATACTTCATC
CATTTTATTAGTACATCCATTTAGGGTTTAGGGTTAATGGTTTTTATAGACTAATTTTT
TTAGTACATCTATTTTATTCTATTTTAGCCTCTAAATTAAGAAAACTAAAACTCTATTT
TAGTTTTTTTATTTAATAATTTAGATATAAAATAGAATAAAATAAAGTGACTAAAAAT
TAAACAAATACCCTTTAAGAAATTAAAAAAACTAAGGAAACATTTTTCTTGTTTCGA
GTAGATAATGCCAGCCTGTTAAACGCCGTCGACGAGTCTAACGGACACCAACCAGCG
AACCAGCAGCGTCGCGTCGGGCCAAGCGAAGCAGACGGCACGGCATCTCTGTCGCT
GCCTCTGGACCCCTCTCGAGAGTTCCGCTCCACCGTTGGACTTGCTCCGCTGTCGGCA
TCCAGAAATTGCGTGGCGGAGCGGCAGACGTGAGCCGGCACGGCAGGCGGCCTCCT
CCTCCTCTCACGGCACGGCAGCTACGGGGATTCCTTTCCCACCGCTCCTTCGCTTTC
CCTTCCTCGCCCGCCGTAATAAATAGACACCCCCTCCACACCTCTTTCCCCAACCTC
GTGTTGTTCGGAGCGCACACACACACAACCAGATCTCCCCCAAATCCACCCGTCGGC
ACCTCCGCTTCAAGGTACGCCGCTCGTCCTCCCCCCCCCCCCTCTCTACCTTCTCTA
GATCGGCGTTCCGGTCCATGGTTAGGGCCCGGTAGTTCTACTTCTGTTCATGTTTGTG
TTAGATCCGTGTTTGTGTTAGATCCGTGCTGCTAGCGTTCGTACACGGATGCGACCTG
TACGTCAGACACGTTCTGATTGCTAACTTGCCAGTGTTTCTCTTTGGGGAATCCTGGG
ATGGCTCTAGCCGTTCCGCAGACGGGATCGATTTCATGATTTTTTTGTTTCGTTGCA
TAGGGTTTGGTTTGCCCTTTTCCTTTATTTCAATATATGCCGTGCACTTGTTTGTCGGG
TCATCTTTTCATGCTTTTTTTTGTCTTGGTTGTGATGATGTGGTCTGGTTGGGCGGTCG
TTCTAGATCGGAGTAGAATTCTGTTTCAAACTACCTGGTGGATTTATTAAATTTTGGAT

-continued

```
CTGTATGTGTGTGCCATACATATTCATAGTTACGAATTGAAGATGATGGATGGAAAT
ATCGATCTAGGATAGGTATACATGTTGATGCGGGTTTTACTGATGCATATACAGAGA
TGCTTTTTGTTCGCTTGGTTGTGATGATGTGGTGTGGTTGGGCGGTCGTTCATTCGTTC
TAGATCGGAGTAGAATACTGTTTCAAACTACCTGGTGTATTTATTAATTTTGGAACTG
TATGTGTGTGTCATACATCTTCATAGTTACGAGTTTAAGATGGATGGAAATATCGATC
TAGGATAGGTATACATGTTGATGTGGGTTTTACTGATGCATATACATGATGGCATATG
CAGCATCTATTCATATGCTCTAACCTTGAGTACCTATCTATTATAATAAACAAGTATG
TTTTATAATTATTTTGATCTTGATATACTTGGATGATGGCATATGCAGCAGCTATATG
TGGATTTTTTTAGCCCTGCCTTCATACGCTATTTATTTGCTTGGTACTGTTTCTTTTGTC
GATGCTCACCCTGTTGTTTGGTGTTACTTCTGCAGGAGGATCACAAGTTTGTACAAAA
AAGCAGGCTATGGCCGCCGCCACCTCCCCCGCCGTCGCATTCTCGGGCGCCACCGCC
GCCGCCATGCCCAAACCCGCCCGCCATCCTCTCCCGCGCCACCAGCCCGTCTCGCGC
CGCGCGCTCCCCGCCCGCGTCGTCAGGTGTTGCGCCGCGTCCCCCGCCGCCACCTCC
GCCGCGCCTCCCGCAACCGCGCTCCGGCCCTGGGGCCCGTCCGAGCCCGCCAAGGGC
GCCGACATCCTCGTCGAGGCGCTCGAGCGCTGCGGCATCGTCGACGTCTTCGCCTAC
CCCGGCGGCGCCTCCATGGAGATCCACCAGGCGCTGACGCGCTCGCCCGTCATCACC
AACCACCTCTTCCGCCACGAGCAGGGGAGGCGTTCGCGGCGTCCGGCTACGCCCGC
GCGTCCGGCCGCGTCGGCGTCTGCGTCGCCACCTCCGGCCCGGGGGCCACCAACCTC
GTCTCCGCGCTCGCCGACGCCCTCCTCGACTCCATCCCCATGGTCGCCATCACGGGCC
AGGTCCCCGCCGCATGATCGGCACGGACGCGTTCCAGGAGACGCCCATAGTGGAG
GTCACGCGCTCCATCACCAAGCACAACTACCTGGTCCTTGACGTGGAGGATATCCCC
CGCGTCATCCAGGAAGCCTTCTTCCTTGCATCCTCTGGCCGCCCGGGGCCGGTGCTAG
TTGATATCCCCAAGGACATCCAGCAGCAGATGGCTGTGCCCGTCTGGGACACTCCAA
TGAGTTTGCCAGGGTACATCGCCCGCCTGCCCAAGCCACCATCTACTGAATCGCTTG
AGCAGGTCCTGCGTCTGGTTGGCGAGTCACGGCGCCCAATTCTGTATGTTGGTGGTG
GCTGCGCTGCGTCTGGCGAGGAGTTGGCCCGCTTTGTTGAGCTTACTGGGATTCCAGT
TACAACTACTCTGATGGGCCTTGGCAACTTCCCCAGCGACGACCCACTGTCTCTGCGC
ATGCTTGGGATGCATGGCACTGTGTATGCAAATTATGCAGTAGATAAGGCTGACCTG
TTGCTCGCATTTGGTGTGCGGTTTGATGATCGTGTGACTGGGAAAATCGAGGCTTTTG
CAAGCAGGTCCAAGATTGTGCACATTGACATTGACCCAGCTGAGATTGGCAAGAACA
AGCAGCCACATGTCTCCATTTGTGCAGATGTTAAGCTTGCTTTACAGGGGTTGAATG
ATCTATTAAATGGGAGCAAAGCACAACAGGGTCTGGATTTTGGTCCATGGCACAAGG
AGTTGGATCAGCAGAAGAGGGAGTTTCCTCTAGGATTCAAGACTTTTGGCGAGGCCA
TCCCGCCGCAATATGCTATCCAGGTACTGGATGAGCTGACAAAAGGGGAGGCGATC
ATTGCCACTGGTGTTGGGCAGCACCAGATGTGGGCGGCTCAGTATTACACTTACAAG
CGGCCACGGCAGTGGCTGTCTTCGTCTGGTTTGGGGGCAATGGGATTTGGGTTACCA
GCTGCAGCTGGCGCTGCTGTGCCAACCCAGGTGTTACAGTTGTTGACATTGATGGT
GATGGTAGTTTCCTCATGAACATTCAGGAGTTGGCGTTGATCCGCATTGAGAACCTC
CCAGTGAAGGTGATGATATTGAACAACCAGCATCTGGGAATGGTGGTGCAGTGGGA
GGATAGGTTTTACAAGGCCAATCGGGCGCACACATACCTTGGCAACCCAGAAAATG
AGAGTGAGATATATCCAGATTTTGTGACGATTGCTAAAGGATTCAACGTTCCAGCAG
TTCGAGTGACGAAGAAGAGCGAAGTCACTGCAGCAATCAAGAAGATGCTTGAGACC
CCAGGGCCATACTTGTTGGATATCATAGTCCCGCATCAGGACGCACGTGCTGCCTATG
ATCCCAAATGGTGGTGCTTTCAAGGACATGATCATGGAGGGTGATGGCAGGACCTCG
TACTGATACCCAGCTTTCTTGTACAAAGTGGTGATCCTACTAGTAGAAGGAGTGCGT
CGAAGCAGATCGTTCAAACATTTGGCAATAAAGTTTCTTAAGATTGAATCCTGTTGC
CGGTCTTGCGATGATTATCATATAATTTCTGTTGAATTACGTTAAGCATGTAATAATT
AACATGTAATGCATGACGTTATTTATGAGATGGGTTTTTATGATTAGAGTCCCGCAAT
TATACATTTAATACGCGATAGAAACAAAATATAGCGCGCAAACTAGGATAAATTAT
CGCGCGCGGTGTCATCTATGTTACTAGATCGAAAGCTTAGCTTGAGCTTGGATCAGA
TTGTCGTTTCCCGCCTTCAGTTTAAACTATCAGTGTTTGACAGGATATATTGGCGGGT
AAAC
```

```
ATTTTCCATTCACTTGGCCC                                           SEQ ID NO: 186

TGCTATCTGGCTCAGCTGC                                            SEQ ID NO: 187

ATGGTGGAAGGGCGGTTGTGA                                          SEQ ID NO: 188

CTCCCGCGCACCGATCTG                                             SEQ ID NO: 189

CCCGCCCCTCTCCTCTTTC                                            SEQ ID NO: 190

AAGCCGCCTCTCGCCCACCCA                                          SEQ ID NO: 191

AYCAGATGTGGGCGGCTCAGTAT                                        SEQ ID NO: 192

GGGATATGTAGGACAAGAAACTTGCATGA                                  SEQ ID NO: 193

SEQ ID NO: 194
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
```

```
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATTCCCAATGGCGGCGCTTTCAAGGACA
TGATCATGGAGGGTGATGGCAGGACCTCGTACTGAAATGGTCCGAAGGTCCACGCCG
CCAACTACGAGTATGATCCCAAGCGGTGGTGCTTTCAAGGACATGATCATGGAGGGT
GATGGCAGGACCTCGTACTGAAATTTCGACCTACAAGACCTACAAGTGTGACATGCG
CAATCAGCATGGTGCCCGCGTGTTGTATCAACTACTAGGGGTTCAACTGTGAACCAT
GCGTTTTCTAGTTTGCTTGTTTCATTCATATAAGCTTGTGTTACTTAGTTCCGAACCCT
GTAGCTTTGTAGTCTATGCTCTCTTTTGTAGGGATGTGCTGTCATAAGATATCATGCA
AGTTTCTTGTCCTACATATC
```

SEQ ID NO: 195

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTTCCCAAGCGGTGGTGCTTTCAAGGACAT
GATCATGGAGGGTGATGGCAGGACCTCGTACTGAAATTTCGACCTACAAGACCTACA
AGTGTGACATGCGCAATCAGCATGGTGCCCGCGTGTTGTATCAACTACTAGGGGTTC
AACTGTGAACCATGCGTTTTCTAGTTTGCTTGTTTCATTCATATAAGCTTGTGTTACTT
AGTTCCGAACCCTGTAGCTTTGTAGTCTATGCTCTCTTTTGTAGGGATGTGCTGTCAT
AAGATATCATGCAAGTTTCTTGTCCTACATATC
```

SEQ ID NO: 196

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGAATGGCGGCGCTTTCAAGGACATGATCATGGAG
GGTGATGGCAGGACCTCGTACTGAAATGGTCCGAAGGTCCACGCCGCCAACTACGA
GTATGATCCCAAGCGGTGGTGCTTTTAAGGACATGATCATGGAGGGTGATGGCAGGA
CCTCGTACTGAAATTTCGACCTACAAGACCTACAAGTGTGACATGCGCAATCAGCAT
GATACCTGCGTGTTGTATCAACTACTGGGGGTTCAACTGTGAACCATGCGTTTTCTAG
TTTGCTTGTTTCATTCATATAAGCTTGTGTTACTTAGTTCCGAACCGTGTAGTTTTGTA
GTCTCTGTTCTCTTTTGTAGGGATGTGCTGTCATAAGATATCATGCAAGTTTCTTGTCC
TACATATC
```

SEQ ID NO: 197

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 198

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATCG
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCAGGGCCATACTTGTTGGATATC
ATAGTCCCGCATCAGGAGCACGTGCTGCCTAATGGCGGCGCTTTCAAGGACATGATCAT
GGAGGGTGATGGCAGGACCTCGTACTGAAATGGTCCGAAGGTCCACGCCGCCAACT
ACGAGTCCCAAGCGGTGGTGCTTTCAAGGACATGATCATGGAGGGTGATGGCAGGA
CCTCGTACTGAAATTTCGACCTACAAGACCTACAAGTGTGACATGCGCAATCAGCAT
GATGCCCGCGTGTTGTATCAACTACTAGGGGTTCAACTGTGAGCCATGCGTTTTCTAG
TTTGCTTGTTTCATTCATATAAGCTTGTATTACTTAGTTCCGAACCCTGTAGTTTTGTA
GTCTATGTTCTCTTTTGTAGGGATGTGCTGTCATAAGATGTCATGCAAGTTTCTTGTC
CTACATATC
```

SEQ ID NO: 199

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCCAGGGCCATACTTGTTGGATATC
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 200

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACAAGCGGTGGTGCTTTCAAGGACATGATCATGGAGGGT
GATGGCAGGACCTCGTACTGAAATTTCGACCTACAAGACCTACAAGTGTGACATGCG
CAATCAGCATGGTGCCCGCGTGTTGTATCAACTACTAGGGGTTCAACTGTGAACCAT
GCGTTTTCTAGTTTGCTTGTTTCATTCATATAAGCTTGTGTTACTTAGTTCCGAACCCT
GTAGCTTTGTAGTCTATGCTCTCTTTTGTAGGGATGTGCTGTCATAAGATATCATGCA
AGTTTCTTGTCCTACATATC
```

SEQ ID NO: 201

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATCCCAAGCGGTGGTGCTTTCAAGG
ACATGATCATGGAGGGTGATGGCAGGACCTCGTACTGAAATTTCGACCTACAAGACC
TACAAGTGTGACATGCGCAATCAGCATGGTGCCCGCGTGTTGTATCAACTACTAGGG
GTTCAACTGTGAACCATGCGTTTTCTAGTTTGCTTGTTTCATTCATATAAGCTTGTGTT
ACTTAGTTCCGAACCCTGTAGCTTTGTAGTCTATGCTCTCTTTTGTAGGGATGTGCTG
TCATAAGATATCATGCAAGTTTCTTGTCCTACATATC
```

SEQ ID NO: 202

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 203

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 204

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCAGGGCCATACTTGTTGGATATC
ATAGTCCCGCATCAGGAGCACGTGCTGCCTATGAttCCcAatGGcGGcGCTTTCAAGGA
CATGATCATGGAGGGTGATGGCAGGACCTCGTACTGAAATGGTCCGAAGGTCCACGC
CGCCAACTACGAGTCCCAAGCGGTGGTGCTTTCAAGGACATGATCATGGAGGGTGAT
GGCAGGACCTCGTACTGAAATTTCGACCTACAAGACCTACAAGTGTGACATGCGCAA
TCAGCATGATGCCCGCGTGTTGTATCAACTACTAGGGGTTCAACTGTGAGCCATGCG
TTTTCTAGTTTGCTTGTTTCATTCATATAAGCTTGTATTACTTAGTTCCGAACCCTGTA
GTTTTGTAGTCTATGTTCTCTTTTGTAGGGATGTGCTGTCATAAGATGTCATGCAAGT
TTCTTGTCCTACATATC
```

SEQ ID NO: 205

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCAGGGCCATACTTGTTGGATATC
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 206

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGAttCCcAatGGcGGcGCTTTCAAGGACA
TGATCATGGAGGGTGATGGCAGGACCTCGTACTGAAATGGTCCGAAGGTCCACGCCG
CCAACTACGAGTATGATCCCAAGCGGTGGTGCTTTCAAGGACATGATCATGGAGGGT
GATGGCAGGACCTCGTACTGAAATTTCGACCTACAAGACCTACAAGTGTGACATGCG
CAATCAGCATGGTGCCCGCGTGTTGTATCAACTACTAGGGGTTCAACTGTGAACCAT
GCGTTTTCTAGTTTGCTTGTTTCATTCATATAAGCTTGTGTTACTTAGTTCCGAACCCT
GTAGCTTTGTAGTCTATGCTCTCTTTTGTAGGGATGTGCTGTCATAAGATATCATGCA
AGTTTCTTGTCCTACATATC
```

SEQ ID NO: 207

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATCCCAAGCGGTGGTGCTTTCAAGG
ACATGATCATGGAGGGTGATGGCAGGACCTCGTACTGAAATTTCGACCTACAAGACC
TACAAGTGTGACATGCGCAATCATGGTGCCCGCGTGTTGTATCAACTACTAGGG
GTTCAACTGTGAACCATGCGTTTTCTAGTTTGCTTGTTTCATTCATATAAGCTTGTGTT
ACTTAGTTCCGAACCCTGTAGCTTTGTAGTCTATGCTCTCTTTTGTAGGGATGTGCTG
TCATAAGATATCATGCAAGTTTCTTGTCCTACATATC
```

SEQ ID NO: 208

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGACGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
```

```
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 209

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 210

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCAGGGCCATACTTGTTGGATATC
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 211

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCAGGGCCATACTTGTTGGATATC
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 212

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATcCcAatGGcGCGCTTTCAAGGACA
TGATCATGGAGGGTGATGGCAGGACCTCGTACTGAAATGGTCCGAAGGTCCACGCCG
CCAACTACGAGTATGATCCCAAGCGGTGGTGCTTTCAAGGACATGATCATGGAGGGT
GATGGCAGGACCTCGTACTGAAATTTCGACCTACAAGACCTACAAGTGTGACATGCG
CAATCAGCATGGTGCCCGCGTGTTGTATCAACTACTAGGGGTTCAACTGTGAACCAT
GCGTTTTCTAGTTTGCTTGTTTCATTCATATAAGCTTGTGTTACTTAGTTCCGAACCCT
GTAGCTTTGTAGTCTATGCTCTCTTTTGTAGGGATGTGCTGTCATAAGATATCATGCA
AGTTTCTTGTCCTACATATC
```

SEQ ID NO: 213

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATCCCAAGCGGTGGTGCTTTCAAGG
ACATGATCATGGAGGGTGATGGCAGGACCTCGTACTGAAATTTCGACCTACAAGACC
TACAAGTGTGACATGCGCAATCAGCATGGTGCCCGCGTGTTGTATCAACTACTAGGG
```

```
GTTCAACTGTGAACCATGCGTTTTCTAGTTTGCTTGTTTCATTCATATAAGCTTGTGTT
ACTTAGTTCCGAACCCTGTAGCTTTGTAGTCTATGCTCTCTTTTGTAGGGATGTGCTG
TCATAAGATATCATGCAAGTTTCTTGTCCTACATATC
```

SEQ ID NO: 214

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGTAGTTGGCGGCGCTTTCAAGGACATGATC
ATGGAGGGTGATGKCAGGACCTCGTACTGAAATGGTCCGAAGGTCCACGCCTCGTAT
GAAATGGTCCGAAGGTCCACGCCGCCAACTACGAGNNNNNNNNNNNNNNNNNNNN
NNNNNNNNNNTATGATTCCCAATGGCGGCTTCCCAATGGCGGCGCTTTCAAGGACAT
GATCATGGAGGGTGATGGCAGGACCTCGTACTGAAATGGTCCGAAGGTCCACGCCG
CCAACTACGATGATCCCAAGCGGTGGTGCTTTTAAGGACATGATCATGGAGGGTGAT
GGCAGGACCTCGTACTGAAATTTCGACCTACAAGACCTACAAGTGTGACATGCGCAA
TCAGCATGATACCTGCGTGTTGTATCAACTACTGGGGGTTCAACTGTGAACCATGCG
TTTTCTAGTTTGCTTGTTTCATTCATATAAGCTTGTGTTACTTAGTTCCGAACCGTGTA
GTTTTGTAGTCTCTGTTCTCTTTTGTAGGGATGTGCTGTCATAAGATATCATGCAAGTT
TCTTGTCCTACATATC
```

SEQ ID NO: 215

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 216

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCCAGGGCCATACTTGTTGGATATC
ATAGTCCCGCATCAGGAGCACGTGCTGCCTATGATtCCcAatGGcGGcGCTTTCAAGGA
CATGATCATGGAGGGTGATGGCAGGACCTCGTACTGAAATGGTCCGAAGGTCCACGC
CGCCAACTACGAGTATGATCCCAAGCGGTGGTGCTTTCAAGGACATGATCATGGAGG
GTGATGGCAGGACCTCGTACTGAAATTTCGACCTACAAGACCTACAAGTGTGACATG
CGCAATCAGCATGATGCCCGCGTGTTGTATCAACTACTAGGGGTTCAACTGTGAGCC
ATGCGTTTTCTAGTTTGCTTGTTTCATTCATATAAGCTTGTATTACTTAGTTCCGAACC
CTGTAGTTTTGTAGTCTATGTTCTCTTTTGTAGGGATGTGCTGTCATAAGATGTCATGC
AAGTTTCTTGTCCTACATATC
```

SEQ ID NO: 217

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCCAGGGCCATACTTGTTGGATATC
ATAGTCCCGCATCAGGAGCACGTGCTGCCTATGATTCCCAATGGCGGCGCTTTCAAG
GACATGATCATGGAGGGTGATGGCAGGACCTCGTACTGAAATGGTCCGAAGGTCC
ACGCCGCCACCTCGTACTGAAATGGTCCRAAGGTCCACGCCGCCAACTACGAGTATG
ATCCCAAGCGGTGGTGCTTTCAAGGACATGATCATGGAGGGTGATGGCAGGACCTCG
TACTGARATTTCGACCTACAAGACCTACAAGTGTGACATGCGCAATCAGCATGATGC
CCGCGTGTTGTATCAACTACTAGGGGTTCAACTGTGAGCCATGCGTTTTCTAGTTTGC
TTGTTTCATTCATATAAGCTTGTATTACTTAGTTCCGAACCCTGTAGTTTTGTAGTCTA
TGTTCTCTTTTGTAGGGATGTGCTGTCATAAGATGTCATGCAAGTTTCTTGTCCTACA
TATC
```

SEQ ID NO: 218

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
```

```
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATtCCcAatGGcGCgCTTTCAAGGACA
TGATCATGGAGGGTGATGGCAGGACCTCGTACTGAAATGGTCCGAAGGTCCACGCCG
CCAACTACGAGTATGATCCCAAGCGGTGGTGCTTTCAAGGACATGATCATGGAGGGT
GATGGCAGGACCTCGTACTGAAATTTCGACCTACAAGACCTACAAGTGTGACATGCG
CAATCAGCATGGTGCCCGCGTGTTGTATCAACTACTAGGGGTTCAACTGTGAACCAT
GCGTTTTCTAGTTTGCTTGTTTCATTCATATAAGCTTGTGTTACTTAGTTCCGAACCCT
GTAGCTTTGTAGTCTATGCTCTCTTTTGTAGGGATGTGCTGTCATAAGATATCATGCA
AGTTTCTTGTCCTACATATC
```

SEQ ID NO: 219
```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATCCCAAGCGGTGGTGCTTTCAAGG
ACATGATCATGGAGGGTGATGGCAGGACCTCGTACTGAAATTTCGACCTACAAGACC
TACAAGTGTGACATGCGCAATCAGCATGGTGCCCGCGTGTTGTATCAACTACTAGGG
GTTCAACTGTGAACCATGCGTTTTCTAGTTTGCTTGTTTCATTCATATAAGCTTGTGTT
ACTTAGTTCCGAACCCTGTAGCTTTGTAGTCTATGCTCTCTTTTGTAGGGATGTGCTG
TCATAAGATATCATGCAAGTTTCTTGTCCTACATATC
```

SEQ ID NO: 220
```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATGCTTTTAAGGACATGATCATGGAGGGTGATGGCAGGACCTCGTA
CTGAAATTTCGACCTACAAGACCTACAAGTGTGACATGCGCAATCAGCATGATACCT
GCGTGTTGTATCAACTACTGGGGTTCAACTGTGAACCATGCGTTTTCTAGTTTGCTT
GTTTCATTCATATAAGCTTGTGTTACTTAGTTCCGAACCGTGTAGTTTTGTAGTCTCTG
TTCTCTTTTGTAGGGATGTGCTGTCATAAGATATCATGCAAGTTTCTTGTCCTACATA
TC
```

SEQ ID NO: 221
```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 222
```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCCAGGGCCATACTTGTTGGATATC
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 223

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCCAGGGCCATACTTGTTGGATATC
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 224

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATCCCAAGCGGTGGTGCTTTCAAGG
ACATGATCATGGAGGGTGATGGCAGGACCTCGTACTGAAATTTCGACCTACAAGACC
TACAAGTGTGACATGCGCAATCAGCATGGTGCCCGCGTGTTGTATCAACTACTAGGG
GTTCAACTGTGAACCATGCGTTTTCTAGTTTGCTTGTTTCATTCATATAAGCTTGTGTT
ACTTAGTTCCGAACCCTGTAGCTTTGTAGTCTATGCTCTCTTTTGTAGGGATGTGCTG
TCATAAGATATCATGCAAGTTTCTTGTCCTACATATC
```

SEQ ID NO: 225

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATCCCAAGCGGTGGTGCTTTCAAGG
ACATGATCATGGAGGGTGATGGCAGGACCTCGTACTGAAATTTCGACCTACAAGACC
TACAAGTGTGACATGCGCAATCAGCATGGTGCCCGCGTGTTGTATCAACTACTAGGG
GTTCAACTGTGAACCATGCGTTTTCTAGTTTGCTTGTTTCATTCATATAAGCTTGTGTT
ACTTAGTTCCGAACCCTGTAGCTTTGTAGTCTATGCTCTCTTTTGTAGGGATGTGCTG
TCATAAGATATCATGCAAGTTTCTTGTCCTACATATC
```

SEQ ID NO: 226

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATtCCcAatGGcGGcGCTTTCAAGGA
CATGATCATGGAGGGTGATGGCAGGACCTCGTACTGAAATGGTCCGAAGGTCCACGC
CGCCAACTACGAGTATGATCCCAAGCGGTGGTGCTTTTAAGGACATGATCATGGAGG
GTGATGGCAGGACCTCGTACTGAAATTTCGACCTACAAGACCTACAAGTGTGACATG
CGCAATCAGCATGATACCTGCGTGTTGTATCAACTACTGGGGGTTCAACTGTGAACC
ATGCGTTTTCTAGTTTGCTTGTTTCATTCATATAAGCTTGTGTTACTTAGTTCCGAACC
GTGTAGTTTTGTAGTCTCTGTTCTCTTTTGTAGGGATGTGCTGTCATAAGATATCATGC
AAGTTTCTTGTCCTACATATC
```

SEQ ID NO: 227

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
```

```
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 228

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCAGGGCCATACTTGTTGGATATC
ATCGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGGTGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 229

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCAGGGCCATACTTGTTGGATATC
ATCGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGGTGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 230

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATtCCcAatGGcGCcGCTTTCAAGGACA
TGATCATGGAGGGTGATGGCAGGACCTCGTACTGAAATGGTCCGAAGGTCCACGCCG
CCAACTACGAGTATGATCCCAAGCGGTGGTGCTTTCAAGGACATGATCATGGAGGGT
GATGGCAGGACCTCGTACTGAAATTTCGACCTACAAGACCTACAAGTGTGACATGCG
CAATCAGCATGGTGCCCGCGTGTTGTATCAACTACTAGGGGTTCAACTGTGAACCAT
GCGTTTTCTAGTTTGCTTGTTTCATTCATATAAGCTTGTGTTACTTAGTTCCGAACCCT
GTAGCTTTGTAGTCTATGCTCTCTTTTGTAGGGATGTGCTGTCATAAGATATCATGCA
AGTTTCTTGTCCTACATATC
```

SEQ ID NO: 231

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATCCCAAGCGGTGGTGCTTTCAAGG
ACATGATCATGGAGGGTGATGGCAGGACCTCGTACTGAAATTTCGACCTACAAGACC
TACAAGTGTGACATGCGCAATCAGCATGGTGCCCGCGTGTTGTATCAACTACTAGGG
GTTCAACTGTGAACCATGCGTTTTCTAGTTTGCTTGTTTCATTCATATAAGCTTGTGTT
ACTTAGTTCCGAACCCTGTAGCTTTGTAGTCTATGCTCTCTTTTGTAGGGATGTGCTG
TCATAAGATATCATGCAAGTTTCTTGTCCTACATATC
```

SEQ ID NO: 232

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
```

```
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 233

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 234

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCCAGGGCCATACTTGTTGGATATC
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 235

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCCAGGGCCATACTTGTTGGATATC
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 236

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATCCCAAGCGGTGGTGCTTTCAAGG
ACATGATCATGGAGGGTGATGGCAGGACCTCGTACTGAAATTTCGACCTACAAGACC
TACAAGTGTGACATGCGCAATCAGCATGGTGCCCGCGTGTTGTATCAACTACTAGGG
GTTCAACTGTGAACCATGCGTTTTCTAGTTTGCTTGTTTCATTCATATAAGCTTGTGTT
ACTTAGTTCCGAACCCTGTAGCTTTGTAGTCTATGCTCTCTTTTGTAGGGATGTGCTG
TCATAAGATATCATGCAAGTTTCTTGTCCTACATATC
```

SEQ ID NO: 237

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATCCCAAGCGGTGGTGCTTTCAAGG
ACATGATCATGGAGGGTGATGGCAGGACCTCGTACTGAAATTTCGACCTACAAGACC
TACAAGTGTGACATGCGCAATCAGCATGGTGCCCGCGTGTTGTATCAACTACTAGGG
GTTCAACTGTGAACCATGCGTTTTCTAGTTTGCTTGTTTCATTCATATAAGCTTGTGTT
```

```
ACTTAGTTCCGAACCCTGTAGCTTTGTAGTCTATGCTCTCTTTTGTAGGGATGTGCTG
TCATAAGATATCATGCAAGTTTCTTGTCCTACATATC
```

SEQ ID NO: 238

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 239

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 240

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCCAGGGCCATACTTGTTGGATATC
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 241

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCCAGGGCCATACTTGTTGGATATC
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 242

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATtCCcAatGgCGGcGCTTTCAAGGACA
TGATCATGGAGGGTGATGGCAGGACCTCGTACTGAAATTGTCCGAAGGTCCACGCCG
CCAACTACGAGTATGATCCCAAGCGGTGGTGCTTTCAAGGACATGATCATGGAGGGT
GATGGCAGGACCTCGTACTGAAATTTCGACCTACAAGACCTACAAGTGTGACATGCG
CAATCAGCATGGTGCCCGCGTGTTGTATCAACTACTAGGGGTTCAACTGTGAACCAT
```

```
GCGTTTTCTAGTTTGCTTGTTTCATTCATATAAGCTTGTGTTACTTAGTTCCGAACCCT
GTAGCTTTGTAGTCTATGCTCTCTTTTGTAGGGATGTGCTGTCATAAGATATCATGCA
AGTTTCTTGTCCTACATATC
```

SEQ ID NO: 243

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATtCCcAatGGcGGcGCTTTCAAGGACA
TGATCATGGAGGGTGATGGCAGGACCTCGTACTGAAATGGTCCGAAGGTCCACGCCG
CCAACTACGAGTATGATCCCAAGCGGTGGTGCTTTCAAGGACATGATCATGGAGGGT
GATGGCAGGACCTCGTACTGAAATTTCGACCTACAAGACCTACAAGTGTGACATGCG
CAATCAGCATGGTGCCCGCGTGTTGTATCAACTACTAGGGGTTCAACTGTGAACCAT
GCGTTTTCTAGTTTGCTTGTTTCATTCATATAAGCTTGTGTTACTTAGTTCCGAACCCT
GTAGCTTTGTAGTCTATGCTCTCTTTTGTAGGGATGTGCTGTCATAAGATATCATGCA
AGTTTCTTGTCCTACATATC
```

SEQ ID NO: 244

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCtGcGCTTTCAAGGACATGATCATGGAGG
GTGATGGCAGGACCTCGTACTGAAATGGTCCGAAGGTCCACGCCGCCAACTACGAGT
ATGATCCCAAGCGGTGGTGCTTTTAAGGACATGATCATGGAGGGTGATGGCAGGACC
TCGTACTGAAATTTCGACCTACAAGACCTACAAGTGTGACATGCGCAATCAGCATGA
TACCTGCGTGTTGTATCAACTACTGGGGGTTCAACTGTGAACCATGCGTTTTCTAGTT
TGCTTGTTTCATTCATATAAGCTTGTGTTACTTAGTTCCGAACCGTGTAGTTTTGTAGT
CTCTGTTCTCTTTTGTAGGGATGTGCTGTCATAAGATATCATGCAAGTTTCTTGTCCTA
CATATC
```

SEQ ID NO: 245

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 246

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCAGGGCCATACTTGTTGGATATC
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 247

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCCAGGGCCATACTTGTTGGATATC
```

```
                -continued
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 248

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATtCCcAatGGcGGcGCTTTCAAGGACA
TGATCATGGAGGGTGATGGCAGGACCTCGTACTGAAATGGTCCAAGGTCCACGCCG
CCAACTACGAGTATGATCCCAAGCGGTGGTGCTTTCAAGGACATGATCATGGAGGGT
GATGGCAGGACCTCGTACTGAAATTTCGACCTACAAGACCTACAAGTGTGACATGCG
CAATCAGCATGGTGCCCGCGTGTTGTATCAACTACTAGGGGTTCAACTGTGAACCAT
GCGTTTTCTAGTTTGCTTGTTTCATTCATATAAGCTTGTGTTACTTAGTTCCGAACCCT
GTAGCTTTGTAGTCTATGCTCTCTTTTGTAGGGATGTGCTGTCATAAGATATCATGCA
AGTTTCTTGTCCTACATATC
```

SEQ ID NO: 249

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATCCCAAGCGGTGGTGCTTTCAAGG
ACATGATCATGGAGGGTGATGGCAGGACCTCGTACTGAAATTTCGACCTACAAGACC
TACAAGTGTGACATGCGCAATCAGCATGGTGCCCGCGTGTTGTATCAACTACTAGGG
GTTCAACTGTGAACCATGCGTTTTCTAGTTTGCTTGTTTCATTCATATAAGCTTGTGTT
ACTTAGTTCCGAACCCTGTAGCTTTGTAGTCTATGCTCTCTTTTGTAGGGATGTGCTG
TCATAAGATATCATGCAAGTTTCTTGTCCTACATATC
```

SEQ ID NO: 250

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 251

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 252

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
```

```
                                                       -continued
GTCACTGCAGCAATCAAGAAGATGCTTGAGACCCCAGGGCCATACTTGTTGGATATC
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 253

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCCAGGGCCATACTTGTTGGATATC
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 254

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATCCCAAGCGGTGGTGCTTTCAAGG
ACATGATCATGGAGGGTGATGGCAGGACCTCGTACTGAAATTTCGACCTACAAGACC
TACAAGTGTGACATGCGCAATCAGCATGGTGCCCGCGTGTTGTATCAACTACTAGGG
GTTCAACTGTGAACCATGCGTTTTCTAGTTTGCTTGTTTCATTCATATAAGCTTGTGTT
ACTTAGTTCCGAACCCTGTAGCTTTGTAGTCTATGCTCTCTTTTGTAGGGATGTGCTG
TCATAAGATATCATGCAAGTTTCTTGTCCTACATATC
```

SEQ ID NO: 255

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATCCCAAGCGGTGGTGCTTTCAAGG
ACATGATCATGGAGGGTGATGGCAGGACCTCGTACTGAAATTTCGACCTACAAGACC
TACAAGTGTGACATGCGCAATCAGCATGGTGCCCGCGTGTTGTATCAACTACTAGGG
GTTCAACTGTGAACCATGCGTTTTCTAGTTTGCTTGTTTCATTCATATAAGCTTGTGTT
ACTTAGTTCCGAACCCTGTAGCTTTGTAGTCTATGCTCTCTTTTGTAGGGATGTGCTG
TCATAAGATATCATGCAAGTTTCTTGTCCTACATATC
```

SEQ ID NO: 256

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATCCTGCGTGTTGTATCAACTACTAGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 257

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
```

```
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 258

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCAGGGCCATACTTGTTGGATATC
ATAGTCCCGCATCAGGAGCACGTGCTGCCTATGATtCCcAatGGcGGcGCTTTCAAGGA
CATGATCATGGAGGGTGATGGCAGGACCTCGTACTGAAATGTCCGAAGGTCCACGC
CGCCAACTACGAGTATGATCCCAAGCGGTGGTGCTTTCAAGGACATGATCATGGAGG
GTGATGGCAGGACCTCGTACTGAAATTTCGACCTACAAGACCTACAAGTGTGACATG
CGCAATCAGCATGATGCCCGCGTGTTGTATCAACTACTAGGGGTTCAACTGTGAGCC
ATGCGTTTTCTAGTTTGCTTGTTTCATTCATATAAGCTTGTATTACTTAGTTCCGAACC
CTGTAGTTTTGTAGTCTATGTTCTCTTTTGTAGGGATGTGCTGTCATAAGATGTCATGC
AAGTTTCTTGTCCTACATATC
```

SEQ ID NO: 259

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCAGGGCCATACTTGTTGGATATC
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 260

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATCCCAAGCGGTGGTGCTTTCAAGG
ACATGATCATGGAGGGTGATGGCAGGACCTCGTACTGAAATTTCGACCTACAAGACC
TACAAGTGTGACATGCGCAATCAGCATGGTCCCGCGTGTTGTATCAACTACTAGGG
GTTCAACTGTGAACCATGCGTTTTCTAGTTTGCTTGTTTCATTCATATAAGCTTGTGTT
ACTTAGTTCCGAACCCTGTAGCTTTGTAGTCTATGCTCTCTTTTGTAGGGATGTGCTG
TCATAAGATATCATGCAAGTTTCTTGTCCTACATATC
```

SEQ ID NO: 261

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATCCCAAGCGGTGGTGCTTTCAAGG
ACATGATCATGGAGGGTGATGGCAGGACCTCGTACTGAAATTTCGACCTACAAGACC
TACAAGTGTGACATGCGCAATCAGCATGGTCCCGCGTGTTGTATCAACTACTAGGG
GTTCAACTGTGAACCATGCGTTTTCTAGTTTGCTTGTTTCATTCATATAAGCTTGTGTT
ACTTAGTTCCGAACCCTGTAGCTTTGTAGTCTATGCTCTCTTTTGTAGGGATGTGCTG
TCATAAGATATCATGCAAGTTTCTTGTCCTACATATC
```

SEQ ID NO: 262

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
```

```
                                                                -continued
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC ATCAGATGTGGGCGGCTCAGTATTACACTTACAAGCGGCCACGGCAGTGGCTGTCTT                  SEQ ID NO: 263
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC ACCAGATGTGGGCGGCTCAGTATTACACTTACAAGCGGCCACGGCAGTGGCTGTCTT                  SEQ ID NO: 264
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCAGGGCCATACTTGTTGGATATC
ATAGTCCCGCATCAGGAGCACGTGTCCCAAGCGGTGGTGCTTTCAAGGACATGATCA
TGGAGGGTGATGGCAGGACCTCGTACTGAAATTTCGACCTACAAGACCTACAAGTGT
GACATGCGCAATCAGCATGATGCCCGCGTGTTGTATCAACTACTAGGGGTTCAACTG
TGAGCCATGCGTTTTCTAGTTTGCTTGTTTCATTCATATAAGCTTGTATTACTTAGTTC
CGAACCCTGTAGTTTTGTAGTCTATGTTCTCTTTTGTAGGGATGTGCTGTCATAAGAT
GTCATGCAAGTTTCTTGTCCTACATATC ACCAGATGTGGGCGGCTCAGTATTACACTTACAAGCGGCCACGGCAGTGGCTGTCTT                  SEQ ID NO: 265
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCCAGGGCCATACTTGTTGGATATC
ATAGTCCCGCATCAGGAGCACGTGCTGCCTATGATtCCcAatGGcGGcGCTTTCAAGGA
CATGATCATGGAGGGTGATGGCAGGACCTCGTACTGAAATGGTCCGAAGGTCAAGC
GGTGGTGCTTTCAAGGACATGATCATGGAGGGTGATGGCAGGACCTCGTACTGAAAT
TTCGACCTACAAGACCTACAAGTGTGACATGCGCAATCAGCATGATGCCCGCGTGTT
GTATCAACTACTAGGGGTTCAACTGTGAGCCATGCGTTTTCTAGTTTGCTTGTTTCAT
TCATATAAGCTTGTATTACTTAGTTCCGAACCCTGTAGTTTTGTAGTCTATGTTCTCTT
TTGTAGGGATGTGCTGTCATAAGATGTCATGCAAGTTTCTTGTCCTACATATC ACCAGATGTGGGCGGCTCAGTATTACACTTACAAGCGGCCACGGCAGTGGCTGTCTT                  SEQ ID NO: 266
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATtCCcAatGGcGGcGCTTTCAAGGACA
TGATCATGGAGGGTGATGGCAGGACCTCGTACTGAAATTTgcAgGGGTGGTGCTTTCAA
GGACATGATCATGGAGGGTGATGGCAGGACCTCGTACTGAAATTTCGACCTACAAGA
CCTACAAGTGTGACATGCGCAATCAGCATGGTGCCCGCGTGTTGTATCAACTACTAG
GGGTTCAACTGTGAACCATGCGTTTTCTAGTTTGCTTGTTTCATTCATATAAGCTTGT
GTTACTTAGTTCCGAACCCTGTAGCTTTGTAGTCTATGCTCTCTTTTGTAGGGATGTG
CTGTCATAAGATATCATGCAAGTTTCTTGTCCTACATATC ACCAGATGTGGGCGGCTCAGTATTACACTTACAAGCGGCCACGGCAGTGGCTGTCTT                  SEQ ID NO: 267
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTGT
```

-continued

```
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATCCCAAGCGGTGGTGCTTTCAAGG
ACATGATCATGGAGGGTGATGGCAGGACCTCGTACTGAAATTTCGACCTACAAGACC
TACAAGTGTGACATGCGCAATCAGCATGGTGCCCGCGTGTTGTATCAACTACTAGGG
GTTCAACTGTGAACCATGCGTTTTCTAGTTTGCTTGTTTCATTCATATAAGCTTGTGTT
ACTTAGTTCCGAACCCTGTAGCTTTGTAGTCTATGCTCTCTTTTGTAGGGATGTGCTG
TCATAAGATATCATGCAAGTTTCTTGTCCTACATATC
```

SEQ ID NO: 268

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 269

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 270

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCCAGGGCCATACTTGTTGGATATC
ATAGTCCCGCATCAGGAGCACGTGCTGCCTATGATtCCcAatGGcGGcGCTTTCAAGGA
CATGATCATGGAGGGTGATGGCAGGACCTCGTACTGAAATggtccgaaggtCAAGCGGTG
GTGCTTTCAAGGACATGATCATGGAGGGTGATGGCAGGACCTCGTACTGAAATTTCG
ACCTACAAGACCTACAAGTGTGACATGCGCAATCAGCATGATGCCCGCGTGTTGTAT
CAACTACTAGGGGTTCAACTGTGAGCCATGCGTTTTCTAGTTTGCTTGTTTCATTCAT
ATAAGCTTGTATTACTTAGTTCCGAACCCTGTAGTTTTGTAGTCTATGTTCTCTTTTGT
AGGGATGTGCTGTCATAAGTGTCATGCAAGTTTCTTGTCCTACATATC
```

SEQ ID NO: 271

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCCAGGGCCATACTTGTTGGATATC
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 272

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
```

-continued
```
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATtCCcAatGGcGGcGCTTTCAAGGACA
TGATCATGGAGGGTGATGGCAGGACCTCGTACTGAAATTTgcAggTACAAGATCCCAA
GCGGTGGTGCTTTCAAGGACATGATCATGGAGGGTGATGGCAGGACCTCGTACTGAA
ATTTCGACCTACAAGACCTACAAGTGTGACATGCGCAATCAGCATGGTGCCCGCGTG
TTGTATCAACTACTAGGGGTTCAACTGTGAACCATGCGTTTTCTAGTTTGCTTGTTTC
ATTCATATAAGCTTGTGTTACTTAGTTCCGAACCCTGTAGCTTTGTAGTCTATGCTCTC
TTTTGTAGGGATGTGCTGTCATAAGATATCATGCAAGTTTCTTGTCCTACATATC
```

SEQ ID NO: 273

```
ACCAGATGTGGGCGGCTCAGTATTACACTTACAAGCGGCCACGGCAGTGGCTGTCTT
CGTCTGGTTGGGGGCAATGGGATTTGGGTTACCAGCTGCAGCTGGCGCTGCTGTGGC
CAACCCAGGTGTTACAGTTGTTGACATTGATGGAGATGGTAGTTTCCTCATGAACATT
CAGGAGTTGGCATTGATCCGTATTGAGAACCTCCCTGTGAAGGTGATGATATTGAAC
AACCAGCATCTGGGAATGGTGGTGCAATGGGAGGATAGGTTTTACAAGGCCAATCG
GGCGCACACATACCTTGGCAACCCAGAAAATGAGAGTGAGATATATCCAGATTTTGT
GACGATTGCTAAAGGATTCAACGTTCCGGCAGTTCGTGTGACGAAGAAGAGCGAAG
TCACTGCAGCAATCAAGAAGATGCTTGAGACCCCAGGGCCATACTTGTTGGATATCA
TCGTCCCGCATCAGGAGCACGTGCTGCCTATGATCCCAAGCGGTGGTGCTTTCAAGG
ACATGATCATGGAGGGTGATGGCAGGACCTCGTACTGAAATTTCGACCTACAAGACC
TACAAGTGTGACATGCGCAATCAGCATGGTGCCCGCGTGTTGTATCAACTACTAGGG
GTTCAACTGTGAACCATGCGTTTTCTAGTTTGCTTGTTTCATTCATATAAGCTTGTGTT
ACTTAGTTCCGAACCCTGTAGCTTTGTAGTCTATGCTCTCTTTTGTAGGGATGTGCTG
TCATAAGATATCATGCAAGTTTCTTGTCCTACATATC
```

SEQ ID NO: 274

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 275

```
ATCAGATGTGGGCGGCTCAGTATTACACTTACAAGCGGCCACGGCAGTGGCTGTCTT
CATCCGGTTTGGGTGCAATGGGATTTGGGTTGCCAGCTGCAGCTGGCGCTGCTGTGG
CCAACCCAGGTGTTACAGTTGTTGACATTGATGGGGATGGTAGTTTCCTCATGAACA
TTCAGGAGTTGGCGTTGATCCGTATTGAGAACCTCCCAGTGAAGGTGATGATATTGA
ACAACCAGCATCTGGGAATGGTGGTGCAGTGGGAGGATAGGTTTTACAAGGCCAAC
CGGGCGCACACATACCTTGGCAACCCAGAAAATGAGAGTGAGATATATCCAGATTTT
GTGACGATTGCTAAAGGATTCAACGTTCCGGCAGTTCGTGTGACGAAGAAGAGCGA
AGTCACTGCAGCAATCAAGAAGATGCTTGAGACCCCAGGGCCATACTTGTTGGATAT
CATTGTCCCGCATCAGGAGCACGTGCTGCCTATGATCCCAAGCGGTGGTGCTTTTAA
GGACATGATCATGGAGGGTGATGGCAGGACCTCGTACTGAAATTTCGACCTACAAGA
CCTACAAGTGTGACATGCGCAATCAGCATGATACCTGCGTGTTGTATCAACTACTGG
GGGTTCAACTGTGAACCATGCGTTTTCTAGTTTGCTTGTTTCATTCATATAAGCTTGT
GTTACTTAGTTCCGAACCGTGTAGTTTTGTAGTCTCTGTTCTCTTTTGTAGGGATGTGC
TGTCATAAGATATCATGCAAGTTTCTTGTCCTACATATC
```

SEQ ID NO: 276

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
TGACGATTGCTAAAGGATTCAACGTTCCAGCAGTTCGAGTGACGAAGAAGAGCGAA
GTCACTGCAGCAATCAAGAAGATGCTTGAGACCCCAGGGCCATACTTGTTGGATATC
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC
```

SEQ ID NO: 277

```
ACCAGATGTGGGCGGCTCAGTATTACACTTACAAGCGGCCACGGCAGTGGCTGTCTT
CGTCTGGTTTGGGGGCAATGGGATTTGGGTTACCAGCTGCAGCTGGCGCTGCTGTGG
CCAACCCAGGTGTTACAGTTGTTGACATTGATGGTGATGGTAGTTTCCTCATGAACAT
TCAGGAGTTGGCGTTGATCCGCATTGAGAACCTCCCAGTGAAGGTGATGATATTGAA
CAACCAGCATCTGGGAATGGTGGTGCAGTGGGAGGATAGGTTTTACAAGGCCAATC
GGGCGCACACATACCTTGGCAACCCAGAAAATGAGAGTGAGATATATCCAGATTTTG
```

-continued
TGACGATTGCTAAAGGATTCAACGTTCCAGCAGTTCGAGTGACGAAGAAGAGCGAA
GTCACTGCAGCAATCAAGAAGATGCTTGAGACCCCAGGGCCATACTTGTTGGATATC
ATAGTCCCGCATCAGGAGCACGTGCTGCCTATGATCCCAAGCGGTGGTGCTTTCAAG
GACATGATCATGGAGGGTGATGGCAGGACCTCGTACTGAAATTTCGACCTACAAGAC
CTACAAGTGTGACATGCGCAATCAGCATGATGCCCGCGTGTTGTATCAACTACTAGG
GGTTCAACTGTGAGCCATGCGTTTTCTAGTTTGCTTGTTTCATTCATATAAGCTTGTAT
TACTTAGTTCCGAACCCTGTAGTTTTGTAGTCTATGTTCTCTTTTGTAGGGATGTGCTG
TCATAAGATGTCATGCAAGTTTCTTGTCCTACATATC TCCAAGGTTGCGGCCGCGCCCAAGGAACCCTTTTCTGGGCCAT::::::TACTCGGCCACG
ACTGGTAATTTAATTTTCAATTTATTT

SEQ ID NO: 299

SEQ ID NO: 326 tggcaggatatattgtggtgtaaacaaattgacgcttagacaacttaataacacattgcggacgt
ttttaatgtactgaattaacgccgaattgaattcgagctcggtaccactggattttggttttagg
aattagaaatttttattgatagaagtattttacaaatacaaatacactactaagggtttcttatatg
ctcaacacatgagcgaaacccctataagaaccctaattccctatctgggaactactcacacatta
ttctggagaaaaatagagagagatagatttgtagagagagactggtgattttttgcggactctatt
agatctgggtaactggcctaactggccttggaggagctggcaactcaaaatccctttgccaaaaa
ccaacatcatgccatccaccatgcttgtatccagctgcgcgcaatgtaccccgggctgtgtatcc
caaagcctcatgcaacctaacagatggatcgtttggaaggcctataacagcaaccacagacttaa
aaccttgcgcctccatagacttaagcaaatgtgtgtacaatgttggatcctaggcccaacctttga
tgcctatgtgacacgtaaacagtactctcaactgtccaatcgtaagcgttcctagccttccaggg
cccagcgtaagcaataccagccacaacaccctcaacctcagcaaccaaccaagggtatctatctt
gcaacctctcgagatcatcaatccactcttgtggtgtttgtggctctgtcctaaagttcactgta
gacgtctcaatgtaatggttaacgatatcacaaaccgcggccatatcagctgctgtagctggcct
aatctcaactggtctcctctccggagacatggcttctacctacaaaaaagctccgcacgaggctg
catttgtcacaaatcatgaaaagaaaaactaccgatgaacaatgctgagggattcaaattctacc
cacaaaaagaagaaagaaagatctagcacatctaagcctgacgaagcagcagaaatatataaaa
tataaaccatagtgcccttttccctcttcctgatcttgtttagcatggcggaaattttaaaccc
cccatcatctccccaacaacggcggatcgcagatctacatccgagagccccattccccgcgaga
tccgggccggatccacgccggcgagagcccagccgcgagatcccgcccctcccgcgcaccgatc
tgggcgcgcacgaagccgcctctcgcccacccaaactaccaaggccaaagatcgagaccgagacg
gaaaaaaaaacggagaaagaaagaggagagggcggggtggttaccggcggcggcggcggcggag
gggaggggggaggagctcgtcgtccggcagcgaggggggaggaggtggaggtggtggtggtggt
ggtggtagggttgggggatgggaggagaggggggggtatgtatatagtggcgatggggggcgtt
tctttggaagcggagggagggccggcctcgtcgctggctcgcgatcctcctcgcgtttccggccc
ccacgacccggacccacctgctgttttttctttttctttttttctttctttttttttttttttggc
tgcgagacgtgcggtgcgtgcggacaactcacggtgatagtgggggggtgtggagactattgtcc
agttggctggactggggtgggttgggttgggttgggttgggctgggcttgctatggatcgtggat
agcactttgggcttaggaactttaggggttgttttgtaaatgttttgagtctaagtttatctt
ttatttttactagaaaaaatacccatgcgctgcaacggggaaagctatttaatcttattattg
ttcattgtgagaattcgcctgaatatatattttttctcaaaaattatgtcaaattagcatatgggt
tttttttaaagatatttcttatacaaatccctctgtatttacaaaagcaaacgaacttaaaacccg
actcaaatacagatatgcatttccaaaagcgaataaacttaaaaaccaattcatacaaaaatgac
gtatcaaagtaccgacaaaaacatcctcaattttttataatagaaagaaagagtaaatttcacttt
gggccaccttttattaccgatattttactttataccaccttttaactgatgttttcacttttgac
caggtaatcttacctttgtttatttttggactatcccgactctcttctcaagcatatgaatgacc
tcgagtatgctagtctagagtcgacctgcagggtgcagcgtgacccggtcgtgccctctctaga
gataatgagcattgcatgtctaagttataaaaaattaccacatattttttttgtcacacttgttt
gaagtgcagtttatctatctttatacatatatttaaactttactctacgaataatataatctata
gtactacaataatatcagtgtttagagaatcatataaatgaacagttagacatggtctaaagga
caattgagtattttgacaacaggactctacagttttatcttttagtgtgcatgtgttctcctt
tttttttgcaaatagcttcacctatataatacttcatccatttttattagtacatccatttagggtt
tagggttaatggttttataagactaattttttttagtacatctatttttattctatttttagcctcta
aattaagaaaactaaaactctattttagttttttttatttaataatttagatataaaatagaataa
aataaagtgactaaaaattaaacaaatacccttttaagaaattaaaaaaactaaggaaacattttt
cttgtttcgagtagataatgccagcctgttaaacgccgtcgacgagtctaacggacaccaaccag
cgaaccagcagcgtcgcgtcgggccaagcgaagcagacggcacggcatctctgtcgctgcctctg
gaccccctcgagagttccgctccaccgttggacttgctccgctgtcggcatccagaaattgcgt
ggcggagcggcagacgtgagccggcacggcaggcggcctcctcctcctctcacggcacggcagct
acgggggattcctttcccaccgctccttcgctttcccttcctcgcccgccgtaataaatagacac
ccctccacaccctcttcccaacctcgtgttgttcggagcgcacacacacaaccagatctc
ccccaaatccaccgtcggcacctccgcttcaaggtacgccgctcgtcctccccccccccccctc
tctaccttctctagatcggcgttccggtccatggttagggcccggtagttctacttctgttcatg
tttgtgttagatccgtgtttgtgttagatccgtgctgctagcgttcgtacacggatgcgacctgt
acgtcagacacgttctgattgctaacttgccagtgtttctctttgggaatcctcgggatggctct
agccgttccgcagacgggatcgatttcatgatttttttttgtttcgttgcatagggtttggtttgc
ccttttcctttatttcaatatgccgtgcacttgtttgcgggtcatcttttcatgcttttttt
tgtcttggttgtgatgatgtggtctggttgggcggtcgttctagatcggagtagaattctgtttc
aaactacctggtggatttattaattttggatctgtgtgccatacatattcatagttacg
aattgaagatgatggatggaaaatcgatctaggataggtatacatgttgatgcgggttttactg
atgcatatacagagatgcttttgttcgcttggttgtgatgatgtggtgtggttgggcggtcgtt
cattcgttctagatcggagtagaatactgtttcaaactacctggtgtatttattaattttggaac
tgtatgtgtgtcatacatcttcatagttatgagtttaagatggatggaaatatctagga
taggtatacatgttgatgtgggttttactgatgcatatacatgatgcatatgcagcatctattc
atatgctctaacctgagtacctatctattataaataacaagtatgtttataattattttgatc
ttgatatacttggatgatggcatatgcagcagctatatgtggattttttagccctgccttcata
cgctatttatttgcttggtactgtttcttttgtcgatgctcaccctgttgtttggtgttacttct
gcaggaggatcacaagtttgtacaaaaaagcaggctatggccgccgcccacctcccccgccgtcgc -continued

```
attctcgggcgccaccgccgccgccatgcccaaaccgcccgccatcctctcccgcgccaccagc
ccgtctcgcgccgcgcgctccccgccgcgtcgtcaggtgttgcgccgcgtccccgccgccacc
tccgccgcgcctcccgcaaccgcgctccggccctggggcccgtccgagcccgcaagggcgccga
catcctcgtcgaggcgctcgagcgctgcggcatcgtcgacgtcttcgcctacccggcggcgcct
ccatggagatccaccaggcgctgacgcgctcgcccgtcatcaccaaccacctcttccgccacgag
caggggaggcgttcgcggcgtccggctacgcccgcgcgtccggccgcgtcggcgtctgcgtcgc
cacctccggcccgggggccaccaacctcgtctccgcgctcgccgacgccctcctcgactccatcc
ccatggtcgccatcacgggccaggtctcccgccgcatgatcggcacggacgcgttccaggagacg
cccatagtggaggtcacgcgctccatcaccaagcacaactacctggtccttgacgtggaggatat
ccccgcgtcatccaggaagccttcttccttgcatcctctgggcgccggggccggtgctagttg
atatccccaaggacatccagcagcagatggctgtgcccgtctgggacactccaatgagtttgcca
gggtacatcgcccgcctgcccaagccaccatctactgaatcgcttgagcaggtcctgcgtctggt
tggcgagtcacggcgcccaattctgtatgttggtggtggctgcgctgcgtctggcgaggagttgc
gccgcttgttgagcttactgggattccagttacaactactctgatgggccttggcaacttcccc
agcgacgacccactgtctctgcgcatgcttgggatgcatggcactgtgtatgcaaattatgcagt
agataaggctgaccgttgctcgcattggtgtgcggtttgatgatcgtgtgactgggaaaatcg
aggcttttgcaagcaggtccaagattgtgcacattgacattgacccagctgagattggcaagaac
aagcagccacatgtctccatttgtgcagatgttaagcttgctttacagggttgaatgatctatt
aaatgggagcaaagcacaacagggtctggattttggtccatggcacaaggagttggatcagcaga
agagggagtttcctctaggattcaagacttttggcgaggccatcccgccgcaatatgctatccag
gtactggatgagctgacaaaaggggaggcgatcattgccactggtgttgggcagcaccagatgtg
ggcggctcagtattacacttacaagcggccacggcagtgtcgtcttcgtctggtttggggggcaa
tgggatttgggttaccagctgcagctggcgctgctgtggccaacccaggtgttacagttgttgac
attgatggtgatggtagtttcctcatgaacattcaggagttggcgttgatccgcattgagaacct
cccagtgaaggtgatgatattgaacaaccagcatctgggaatggtggtgcagtggggaggatgagt
tttacaaggccaatcgggcgcacacataccttggcaacccagaaaatgagagtgagatatatcca
gattttgtgacgattgctaaaggattcaacgttccagcagttcgagtgacgaagaagagcgaagt
cactgcagcaatcaagaagatgcttgagaccccagggccatacttgttggatatcatagtcccgc
atcaggagcacgtgctgcctatgatcccaagcggtggtgctttcaaggacatgatcatggagggt
gatgcaggacctcgtactgataccccagctttcttgtacaaagtggtgatcctactagtagaagg
agtgcgtcgaagcagatcgttcaaacatttggcaataaagtttcttaagattgaatcctgttgcc
ggtcttgcgatgattatcatataatttctgttgaattacgttaagcatgtaataattaacatgta
atgcatgacgttatttatgagatgggtttttatgattagagtcccgcaattatacatttaatacg
cgatagaaaacaaaatatagcgcgcaaactaggataaattatcgcgcgcggtgtcatctatgtta
ctagatcgaaagcttagcttgagcttggatcagattgtcgtttcccgcccttcagtttaaactatc
agtgtttgacaggatatattggcgggtaaac
```
gcgaagatcc aggacaagga
SEQ ID NO: 327 ctgcttaccg gcaaagatga g
SEQ ID NO: 328 ttcccccgga ccagcagcgt
SEQ ID NO: 329 ccgacgagaa agaccagcaa
SEQ ID NO: 330 cttaagttgt cgatcgggac tgt
SEQ ID NO: 331 tgagcctctc gtcgccgatc acat
SEQ ID NO: 332

```
ccactcttgccctacacgacactgaagaccttatgattccaaacggcggcgccttcaaggacatg
atcatggagggtgatgcaggacctcgtactgaaatttcgacctacaagacctacaagtgtgaca
tgcgcaatcagcatggtgcccgcgtgttgtatcaactactaggggttcaactgtgaaccatgcgt
tttctagtttgcttgttcattcatataagcttgtgttacttagttccgaaccctgtagctttgt
agtctatgctctcttttgtagggatgtgctgtcataagatatcatgcaagtttcttgtcctacat
atcaataataagtacttccatggaataattctcagttctgttttgaattttgcatcttctcacaa
acagtgtgctggttcctttctgttcgctgacgccctcctcgactccatcccatggtcgccatca
cgggccaggtcccccgccgcatgatcggtagcgacttcgtgggcaggaaagccttcgtccaag
gtggtccctcctcgcaatcttgttggatggtgaatattataaaagcctgcccttctcgcgggtaa
gactcccgcccatccaggatgaggataccagccttttgcagtttatccactagggacaggattg
catcctgccgaaaccctgccaagcttgaggtagcctccaatttgacggtgccgccagcgacgccg
tctggaactgtcctttttgaggaccactccgtttgtctagaggtactggagatcatgacattaa
ggatgaccagttcgtaaaggtcctgcggtgtctattgcttttcataggttaataagtgtttgcta
gactgtggtgaaaggccaagactcccgcccatctctctatgcccgggacaagtgccaccccacag
tggggcaggatgaggatgaccaaagactcccgcccatctcactagggacaggattggccttttgc
agttatctctatgcccgggacaagtgtatccgaagtaaataaaccatcggactctcgtataag
actgtcgactcgaccggccgacgcataggttcatttgaagctgctattctatttaaattgaaact
cggacggtagcagtgtggtatgaggtcttcagcacactcggtaactccagtcac
```
SEQ ID NO: 333

```
ccactcttgccctacacgacactgaagacgtcgccattaccgggcaagtgacccgccgcatgatc
ggcacggacgcgttccaggagacgcccatagtggaggtcacgcgctccatcaccaagcacaacta
cctggtccttgacgtggaggatatccccgcgtcatccaggaagccttcttccttgcatcctctg
gccgccggggccggtgctagttgatatccccaaggacatccagcagcagatggctgtgcccgtc
tgggacactccaatgagtttgccagggtacatcgcccgcctgcccaagccaccatctactgaatc
```
SEQ ID NO: 334

-continued gcttgagcaggtcctgcgtctggttggcgagtcacggcgcccaattctgtatgttggtggtggct
gcgctgcgtctggcgaggagttgcgccgctttgttgagcttactgggattccagttacaactact
ctgatgggccttggcaacttccccagcgacgacccactgtctctgcgcatgcttgggatgcatgg
cactgtgtatgcaaattatgcagtagataaggctgacctgttgctcgcatttggtgtgcggtttg
atgatcgtgtgactgggaaaatcgaggcttttgcaagcaggtccaagattgtgcacattgacatt
gacccagctgagattggcaacaagcagccacatgtctccatttgtgcagatgttaagcttgc
tttacagggggttgaatgatctattaaatgggagcaaagcacaacagggtctggattttggtccat
ggcacaaggagttggatcagcagaagagggagtttcctctaggattcaagacttttggcgaggcc
atcccgcgcaatatgctatccaggtactggatgagctgacaaaaggggaggcgatcattgccac
tggtgttgggcagcaccagatgtgggcggctcagtattacacttacaagcggccacggcagtggc
tgtcttcgtctggtttgggggcaatgggatttggttaccagctgcagctggcgctgctgtggcc
aacccaggtgttacagttgttgacattgatggtgatggtagtttcctcatgaacattcaggagtt
ggcgttgatccgcattgagaacctcccagtgaaggtgatgatattgaacaaccagcatctgggaa
tggtggtgcagtgggaggataggttttacaaggccaatcgggcgcacacatccttggcaaccca
gaaaatgagagtgagatatatccagattttgtgacgattgctaaaggattcaacgttccagcagt
tcgagtgacgaagaagagcgaagtcactgcagcaatcaagaagatgcttgagaccccagggccat
acttgttggatatcatagtcccgcatcaggagcacgtgctgcctatgatcccaagcggtggtgct
ttcaaggacatgatcatggagggtgatggcaggacctcgtactgaaatttcgacctacaagacct
acaagtgtgacatgcgcaatcagcatggtgcccgcgtgttgtatcaactactaggggttcaactg
tgaaccatgcgttttctagtttgcttgtttcattcatataagcttgtgttacttagttccgaacc
ctgtagctttgtagtctatgctctcttttgtagggatgtgctgtcataagatatcatgcaagttt
cttgtcctacatatcaataatagtacttccatggaataattctcagttctgttttgaattttgc
atcttctcacaaacagtgtgctggttccttctgttctacgcccgcgcgtccggccgcgtcggcg
tctgcgtcgccacctccggcccggggccaccaacctcgtctccgtagcgacttcgtgggcgagg
aaagcctttcgtccaaggtggtccctcctcgcaatcttgttggatggtgaatattataaaagcct
gccctcctcgcgggtgagtccatgctcaacaccgtgcactagggacaggattggccttttgcagt
ttatccactagggacaggattgcatcctgccgaaaccctgccaagcttgaggtagcctccaattt
gacggtgccgccagcgacgccgtctggaactgtcctttttgaggaccactccgtttgtctagagg
tacctggagatcatgacattaaggatgaccagttcgtaaaggtcctgcggtgtctattgcttttc
ataggttaataagtgtttgctagactgtggtgaaaggccgcctttgcagttttatctctagaaag
actggagttgcagaaagactcccgcccatccaggatgaggatgaccatatccgaagtaaataaaa
ccatcggactctcgtataagactgtcgactcgaccggccgacgcataggttcatttgaagctgct
attctatttaaattgaaactcggacggtagcagtgtggtatgaggtcttcagcacactcggtaac
tccagtcac

SEQ ID NO: 335 tgagattggcaagaacaagcagccacatgtctccatttgtgcagatgttaagcttgctttacagg
ggttgaatgatctattaaatgggagcaaagcacaacagggtctggattttggtccatggcacaag
gagttggatcagcagaagagggagttcctctaggattcaagacttttggcgaggccatcccgcc
gcaatatgctatccaggtactggatgagctgacaaaaggggaggcgatcattgccactggtgttg
ggcagcaccagatgtgggcggctcagtattacacttacaagcggccacggcagtggctgtcttcg
tctggtttgggggcaatgggatttggttaccagctgcagctggcgctgctgtggccaacccagg
tgttacagttgttgacattgatggtgatggtagtttcctcatgaacattcaggagttggcgttga
tccgcattgagaacctcccagtgaaggtgatgatattgaacaaccagcatctgggaatggtggtg
cagtgggaggataggttttacaaggccaatcgggcgcacacatccttggcaacccagaaaatga
gagtgagatatatccagattttgtgacgattgctaaaggattcaacgttccagcagttcgagtga
cgaagaagagcgaagtcactgcagcaatcaagaagatgcttgagaccccagggccatacttgttg
gatatcatagtcccgcatcaggagcacgtgctgcctatgattccaaacggcggcgccttcaagga
catgatcatggagggtgatggcaggacctcgtactgaaatttcgacctacaagacctacaagtgt
gacatgcgcaatcagcatggtgcccgcgtgttgtatcaactactaggggttcaactgtgaaccat
gcgttttctagtttgcttgtttcattcatataagcttgtgttacttagttccgaacctgtagct
ttgtagtctatgctctcttttgtagggatgtgctgtcataagatatcatgcaagtttcttgtcct
acatatcaataatagtacttccatggaataattctcagttctgttttgaattttgcatcttctc
acaaacagtgtgctggttcctttctgttcgctgacgcccctcgactccatccccatggtcgcc
atcacgggccaggtccccgccgcatgtcggtagcgacttcgtgggcgaggaaagcctttcgtc
caaggtggtccctcctcgcaatcttgttggatggtgaatattataaaagcctgccctctcgcgg
gtaagactcccgcccatccaggatgaggatgaccagccttttgcagtttatccactagggacagg
attgcatcctgccgaaaccctgccaagcttgaggtagcctccaatttgacggtgccgccagcgac
gccgtctggaactgtcctttttgaggaccactccgtttgtctagaggtacctggagatcatgaca
ttaaggatgaccagttcgtaaaggtcctgcggtgtctattgcttttcataggttaataagtgttt
gctagactgtggtgaaaggccaagactcccgcccatctctctatgcccgggacaagtgccacccc
acagtggggcaggatgaggatgaccaaagactcccgcccatctcactagggacaggattggcctt
ttgcagtttatctctatgcccgggacaagtgtatccgaagtaaataaaaccatcggactctcgta
taagactgtcgactcgaccggccgacgcataggttcatttgaagctgctattctatttaaattga
aatcccaagcggtggtgctttcaaggacatgatcatggagggtgatggcaggacctcgtactgaa
atttcgacctacaagacctacaagtgtgacatgcgcaatcagcatgatgcccgcgtgttgtatca
actactaggggttcaactgtgagccatgcgttttctagtttgcttgtttcattcatataagcttg
tattacttagttccgaaccctgtagttttgtagtctatgtctctctttttgtagggatgtgctgtca
taagatgtcatgcaagtttcttgtcctacatatcaataatagtacttccatggaataattctca
gttctgttttgaattttgcatcttctcacaaacagtgtgctggttcctttctgttactttacatg
tctgctgtgtcaggttctgacataacgaccgatggagggtggtcggcaggttttagaaggggaat
tgaaactttttttgggaagaagtctgaatacagttgggaggaaaaatagaagtatatacttcga
ttaatttatcaagcccgctatccagtctaatttatcaagcactagacagtgtagggtgttggcat
tcttctcttcctgagatccggcttgagaggagagaccgaggcttcggctgtgttggttgctgat
ttctacagcttttgatagagagagatcctgcaactgtggtttgtcttgctgcttgtacag
cgagagagacattgagatatgtagatcgtttacc

SEQ ID NO: 350

CCAGAAGGTAATTATCCAAGATGTAGCATCAAGAATCCAATGTTTACGGGAAAAACT
ATGGAAGTATTATGTAAGCTCAGCAAGAAGCAGATCAATATGCGGCACATATGCAA
CCTATGTTCAAAAATGAAGAATGTACAGATACAAGATCCTATACTGCCAGAATACGA

```
AGAAGAATACGTAGAAATTGAAAAGAAGAACCAGGCGAAGAAAAGAATCTTGAA
GACGTAAGCACTGACGACAACAATGAAAAGAAGAAGATAAGGTCGGTGATTGTGAA
AGAGACATAGAGGACACATGTAAGGTGGAAAATGTAAGGGCGGAAAGTAACCTTAT
CACAAAGGAATCTTATCCCCCACTACTTATCCTTTTATATTTTTCCGTGTCATTTTGC
CCTTGAGTTTTCCTATATAAGGAACCAAGTTCGGCATTTGTGAAAACAAGAAAAAAT
TTGGTGTAAGCTATTTTCTTTGAAGTACTGAGGATACAACTTCAGAGAAATTTGTAAG
TTTGTAGATCTCCATGGCTCCAAGGAAGAGGAAGGAGTCTAACAGGGAGTCAGCTA
GGAGGTCAAGGTACAGGAAGGTGGGTATCCACGGGGTACCCGCCGCTATGGCTGAG
AGGCCCTTCCAGTGTCGAATCTGCATGCGTAACTTCAGTCGTAGTGACAACCTGAGC
AACCACATCCGCACCCACACAGGCGAGAAGCCTTTTGCCTGTGACATTTGTGGGAGG
AAATTTGCCACCAGCAGCAGCCGCATAAACCATACCAAGATACACACGGGCAGCCA
AAAGCCCTTCCAGTGTCGAATCTGCATGCGTAACTTCAGTCGTAGTGACAACCTGAG
CGAACACATCCGCACCCACACAGGCGAGAAGCCTTTTGCCTGTGACATTTGTGGGAG
GAAATTTGCCGCCAGCAAGACCCGCAAAAACCATACCAAGATACACACGGGCGAGA
AGCCCTTCCAGTGTCGAATCTGCATGCGTAAGTTTGCCCGCTCCGACGCCCTGACCCA
GCATGCCCAGAGATGCGGACTGCGGGGATCCCAACTTGTGAAATCAGAATTGGAAG
AGAAAAGTCTGAGCTTAGACACAAATTGAAGTACGTTCCACATGAATATATCGAAC
TTATCGAGATTGCTAGGAACTCAACACAGGACAGAATTTTGGAGATGAAGGTTATGG
AGTTCTTTATGAAAGTGTACGGATATAGGGGAAAGCACCTTGGTGGTTCTAGGAAAC
CTGATGGTGCAATCTACACTGTGGGATCACCTATTGACTATGGTGTTATCGTGGATAC
AAAGGCATACTCTGGTGGATACAATTTGCCAATCGGACAAGCTGACGAAATGCAGA
GATATGTTGAAGAGAACCAAACTAGAAACAAACATATTAATCAAATGAATGGTGG
AAGGTGTATCCTTCATCTGTTACAGAGTTCAAATTCCTTTTTGTGTCTGGACACTTTA
AGGGTAACTACAAAGCACAGCTTACTAGGTTGAACCATATTACAAATTGCAATGGTG
CTGTGTTGTCAGTTGAAGAGCTTTTGATCGGAGGTGAAATGATTAAGGCAGGAACAC
TTACTTTGGAGGAAGTTAGAAGAAAATTCAACAACGGTGAAATCAATTTTAGATCTG
GCGGCGAGAGGGCAGAGGAAGTCTTCTAACATGCGGTGACGTGGAGGAGAATCCC
GGCCCTAGGATGGCTCCAAGGAAGAGGAAGGAGTCTAACAGGGAGTCAGCTAGGAG
GTCAAGGTACAGGAAGGTGGGTATCCACGGGGTACCCGCCGCTATGGCTGAGAGGC
CCTTCCAGTGTCGAATCTGCATGCGTAACTTCAGTCGTAGTGACACCCTGAGCACGC
ACATCCGCACCCACACAGGCGAGAAGCCTTTTGCCTGTGACATTTGTGGGAGGAAAT
TTGCCGACAGGAGCAGCCGCATAAAGCATACCAAGATACACACGGGATCTCAGAAG
CCCTTCCAGTGTCGAATCTGCATGCGTAACTTCAGTCGCTCCGACGACCTGTCCAAGC
ACATCCGCACCCACACAGGCGAGAAGCCTTTTGCCTGTGACATTTGTGGGAGGAAGT
TTGCCGACAACTCCAACCGCATCAAGCATGCCCAGAGATGCGGACTGCGGGGATCCC
AACTTGTGAAATCAGAATTGGAAGAGAAAAAGTCTGAGCTTAGACACAAATTGAAG
TACGTTCCACATGAATATATCGAACTTATCGAGATTGCTAGGAACTCAACACAGGAC
AGAATTTTGGAGATGAAGGTTATGGAGTTCTTTATGAAAGTGTACGGATATAGGGGA
AAGCACCTTGGTGGTTCTAGGAAACCTGATGGTGCAATCTACACTGTGGGATCACCT
ATTGACTATGGTGTTATCGTGGATACAAAGGCATACTCTGGTGGATACAATTTGCCA
ATCGGACAAGCTGACGAAATGCAGAGATATGTTGAAGAGAACCAAACTAGAAACAA
ACATATTAATCCAAATGAATGGTGGAAGGTGTATCCTTCATCTGTTACAGAGTTCAA
ATTCCTTTTTGTGTCTGGACACTTTAAGGGTAACTACAAAGCACAGCTTACTAGGTTG
AACCATATTACAAATTGCAATGGTGCTGTGTTGTCAGTTGAAGAGCTTTTGATCGGA
GGTGAAATGATTAAGGCAGGAACACTTACTTTGGAGGAAGTTAGAAGAAAATTCAA
CAACGGTGAAATCAATTTTTGATAACTCGAGCTCGGTCACCAGCATAATTTTTATTAA
TGTACTAAATTACTGTTTTGTTAAATGCAATTTTGCTTTCTCGGGATTTTAATATCAAA
ATCTATTTAGAAATACACAATATTTTGTTGCAGGCTTGCTGGAGAATCGATCTGCTAT
CATAAAAATTACAAAAAAATTTTATTTGCCTCAATTATTTTAGGATTGGTATTAAGGA
CGCTTAAATTATTTGTCGGGTCACTACGCATCATTGTGATTGAGAAGATCAGCGATA
CGAAATATTCGTAGTACTATCGATAATTTATTTGAAAATTCATAAGAAAAGCAAACG
TTACATGAATTGATGAAACAATACAAAGACAGATAAAGCCACGCACATTTAGGATAT
TGGCCGAGATTACTGAATATTGAGTAAGATCACGGAATTTCTGACAGGAGCATGTCT
TCAATTCAGCCCAAATGGCAGTTGAAATACTCAAACCGCCCCATATGCAGGAGCGGA
TCATTCATTGTTTGTTTGGTTGCCTTTGCCAACATGGGAGTCCAAGGTT
```

SEQ ID NO: 351

```
CCAGAAGGTAATTATCCAAGATGTAGCATCAAGAATCCAATGTTTACGGGAAAAACT
ATGGAAGTATTATGTAAGCTCAGCAAGAAGCAGATCAATATGCGGCACATATGCAA
CCTATGTTCAAAAATGAAGAATGTACAGATACAAGATCCTATACTGCCAGAATACGA
AGAAGAATACGTAGAAATTGAAAAGAAGAACCAGGCGAAGAAAAGAATCTTGAA
GACGTAAGCACTGACGACAACAATGAAAAGAAGAAGATAAGGTCGGTGATTGTGAA
AGAGACATAGAGGACACATGTAAGGTGGAAAATGTAAGGGCGGAAAGTAACCTTAT
CACAAAGGAATCTTATCCCCCACTACTTATCCTTTTATATTTTTCCGTGTCATTTTGC
CCTTGAGTTTTCCTATATAAGGAACCAAGTTCGGCATTTGTGAAAACAAGAAAAAAT
TTGGTGTAAGCTATTTTCTTTGAAGTACTGAGGATACAACTTCAGAGAAATTTGTAAG
TTTGTAGATCTCCATGGCTCCAAGGAAGAGGAAGGAGTCTAACAGGGAGTCAGCTA
GGAGGTCAAGGTACAGGAAGGTGGGTATCCACGGGGTACCCGCCGCTATGGCTGAG
AGGCCCTTCCAGTGTCGAATCTGCATGCGTAACTTCAGTCAGTCCTCCGACCTGTCCC
GCCACATCCGCACCCACACCGGCGAGAAGCCTTTTGCCTGTGACATTTGTGGGAGGA
AATTTGCCCAGGCCGGCAACCTGTCCAAGCATACCAAGATACACACGCATCCCAGGG
CACCTATTCCCAAGCCCTTCCAGTGTCGAATCTGCATGCGTAAGTTTGCCCAGTCCGG
CGACCTGACCCGCCATACCAAGATACACACGGGCGAGAAGCCCTTCCAGTGTCGAAT
CTGCATGCGTAACTTCAGTACCTCCGGCTCCCTGTCCCGCCACATCCGCACCCACACC
GGCGAGAAGCCTTTTGCCTGTGACATTTGTGGGAGGAAATTTGCCCAGTCCGGCAAC
CTGGCCCGCCATGCCCAGAGATGCGGACTGCGGGGATCCCAACTTGTGAAATCAGAA
TTGGAAGAGAAAAGTCTGAGCTTAGACACAAATTGAAGTACGTTCCACATGAATAT
ATCGAACTTATCGAGATTGCTAGGAACTCAACACAGGACAGAATTTTGGAGATGAAG
GTTATGGAGTTCTTTATGAAAGTGTACGGATATAGGGGAAAGCACCTTGGTGGTTCT
AGGAAACCTGATGGTGCAATCTACACTGTGGGATCACCTATTGACTATGGTGTTATC
GTGGATACAAAGGCATACTCTGGTGGATACAATTTGCCAATCGGACAAGCTGACGAA
```

-continued

```
ATGCAGAGATATGTTGAAGAGAACCAAACTAGAAACAAACATATTAATCCAAATGA
ATGGTGGAAGGTGTATCCTTCATCTGTTACAGAGTTCAAATTCCTTTTTGTGTCTGGA
CACTTTAAGGGTAACTACAAAGCACAGCTTACTAGGTTGAACCATATTACAAATTGC
AATGGTGCTGTGTTGTCAGTTGAAGAGCTTTTGATCGGAGGTGAAATGATTAAGGCA
GGAACACTTACTTTGGAGGAAGTTAGAAGAAAATTCAACAACGGTGAAATCAATTTT
AGATCTGGCGGCGGAGAGGGCAGAGGAAGTCTTCTAACATGCGGTGACGTGGAGGA
GAATCCCGGCCCTAGGATGGCTCCAAGGAAGAGGAAGGAGTCTAACAGGGAGTCAG
CTAGGAGGTCAAGGTACAGGAAGGTGGGTATCCACGGGGTACCCGCCGCTATGGCT
GAGAGGCCCTTCCAGTGTCGAATCTGCATGCGTAACTTCAGTACCTCCGGCTCCCTGT
CCCGCCACATCCGCACCCACACCGGCGAGAAGCCTTTTGCCTGTGACATTTGTGGGA
GGAAATTTGCCCTGCGCCAGACCCTGCGCGACCATACCAAGATACACACGGGCAGCC
AAAAGCCCTTCCAGTGTCGAATCTGCATGCGTAACTTCAGTACCTCCGGCAACCTGA
CCCGCCACATCCGCACCCACACCGGCGAGAAGCCTTTTGCCTGTGACATTTGTGGGA
GGAAATTTGCCGACCGCTCCGCCCTGGCCCGCCATACCAAGATACACACGGGATCTC
AGAAGCCCTTCCAGTGTCGAATCTGCATGCGTAACTTCAGTCGCTCCGACGTGCTGTC
CGAGCACATCCGCACCCACACCGGCGAGAAGCCTTTTGCCTGTGACATTTGTGGGAG
GAAATTTGCCCGCAACTTCTCCCTGACCATGCATGCCCAGAGATGCGGACTGCGGGG
ATCCCAACTTGTGAAATCAGAATTGGAAGAGAAAAAGTCTGAGCTTAGACACAAATT
GAAGTACGTTCCACATGAATATATCGAACTTATCGAGATTGCTAGGAACTCAACACA
GGACAGAATTTTGGAGATGAAGGTTATGGAGTTCTTTATGAAAGTGTACGGATATAG
GGGAAAGCACCTTGGTGGTTCTAGGAAACCTGATGGTGCAATCTACACTGTGGGATC
ACCTATTGACTATGGTGTTATCGTGGATACAAAGGCATACTCTAGTTGGATACAATTT
GCCAATCGGACAAGCTGACGAAATGCAGAGATATGTTGAAGAGAACCAAACTAGAA
ACAAACATATTAATCCAAATGAATGGTGGAAGGTGTATCCTTCATCTGTTACAGAGT
TCAAATTCCTTTTTGTGTCTGGACACTTTAAGGGTAACTACAAAGCACAGCTTACTAG
GTTGAACCATATTACAAATTGCAATGGTGCTGTGTTGTCAGTTGAAGAGCTTTTGATC
GGAGGTGAAATGATTAAGGCAGGAACACTTACTTTGGAGGAAGTTAGAAGAAAATT
CAACAACGGTGAAATCAATTTTTGATAACTCGAGCTCGGTCACCAGCATAATTTTTAT
TAATGTACTAAATTACTGTTTTGTTAAATGCAATTTTGCTTTCTCGGGATTTTAATATC
AAAATCTATTTAGAAATACACAATATTTTGTTGCAGGCTTGCTGGAGAATCGATCTG
CTATCATAAAAATTACAAAAAAATTTTATTTGCCTCAATTATTTTAGGATTGGTATTA
AGGACGCTTAAATTATTGTCGGGTCACTACGCATCATTGTGATTGAGAAGATCAGC
GATACGAAATATTCGTAGTACTATCGATAATTTATTTGAAAATTCATAAGAAAAGCA
AACGTTACATGAATTGATGAAACAATACAAAGACAGATAAAGCCACGCACATTTAG
GATATTGGCCGAGATTACTGAATATTGAGTAAGATCACGGAATTTCTGACAGGAGCA
TGTCTTCAATTCAGCCCAAATGGCAGTTGAAATACTCAAACCGCCCCATATGCAGGA
GCGGATCATTCATTGTTTGTTTGGTTGCCTTTGCCAACATGGGAGTCCAAGGTT
```

SEQ ID NO: 352

```
GCCCAAGGAACCCTTTTCTGGGCCATCTTCGTACTCGGCCACGACTGGTAATTTAATG
GATCCAACCGACAACCACTTTGCGGACTTCCTTTCAAGAGAATTCAATAAGGTTAAT
TCCTAATTGAAATCCGAAGATAAGATTCCCACACACTTGTGGCTGATATCAAAGGC
TACTGCCTATTTAAACACATCTCTGGAGACTGAGAAAATCAGACCTCCAAGCATGAA
GAAGCCTGAGCTTACTGCTACTTCTGTTGAGAAGTTCCTCATCGAGAAGTTCGATTCT
GTGTCTGATCTTATGCAGCTCTCTGAGGGTGAGGAATCAAGAGCTTTCTCTTTCGATG
TTGGTGGAAGAGGATACGTTCTCAGAGTTAACTCTTGCGCTGACGGATTCTACAAGG
ATAGATACGTGTACAGACACTTCGCTTCAGCTGCTCTCCCTATCCCTGAAGTTCTTGA
TATCGGAGAGTTCTCTGAGTCTCTTACCTACTGTATCTCAAGAAGGGCTCAGGGTGTT
ACTCTTCAAGATCTTCCTGAGACTGAGCTTCCTGCTGTTCTTCAACCTGTTGCTGAGG
CTATGGATGCTATCGCTGCTGCTGATCTTTCTCAAACTTCTGGATTCGGACCTTTCGG
TCCTCAGGGAATCGGACAGTACACTACTTGGAGAGATTTTCATCTGCGCTATCGCTGA
TCCTCATGTTTACCATTGGCAGACCGTTATGGATGATACCGTTTCTGCTTCTGTTGCTC
AAGCTCTTGATGAGCTTATGCTTTGGGCTGAGGATTGTCCTGAGGTTAGACATCTTGT
TCACGCTGATTTCGGATCTAACAACGTTCTCACCGATAACGGAAGAATCACCGCTGT
TATCGATTGGTCTGAGGCTATGTTCGGAGATTCTCAATACGGATGGCCAACATATT
CTTTTTGGAGGCCTTGGCTTGCTTGTATGGAACAACAGACTAGATACTTCGAGAGAAG
GCATCCTGAGCTTGCTGGATCTCCTAGACTTAGAGCTTACATGCTTAGGATCGGACTT
GATCAGCTTTACCAGTCTCTCGTTGATGGAAACTTCGATGATGCTGCTTGGGCTCAGG
GAAGATGTGATGCTATCGTTAGATCTGGTGCTGGAACTGTTGGAAGAACTCAAATCG
CTAGAAGATCTGCTGCTGTTTGGACTGATGGATGTGTTGAAGTTCTCGCTGATTCTGG
AAACAGAAGGCCTTCTACTAGACCTAGAGCCAAGAAGTGAAGATCGGCGGCAATAG
CTTCTTAGCGCCATCCCGGGTTGATCCTATCTGTGTTGAAATAGTTGCGGTGGGCAAG
GCTCTCTTTCAGAAAGACAGGCGGCCAAAGGAACCCAAGGTGAGGTGGGCTATGGC
TCTCAGTTCCTTGTGGAAGCGCTTGGTCTAAGGTGCAGAGGTTTAGCGGGATGAAG
CAAAAGTGTCCGATTGTAACAAGATATGTTGATCCTACGTAAGGATATTAAAGTATG
TATTCATCACTAATATAATCAGTGTATTCCAATATGTACTACGATTTCCAATGTCTTT
ATTGTCGCCGTATGTAATCGGCGTCACAAAATAATCCCCGGTGACTTTCTTTTAATCC
AGGATGAAATAATATGTTATTATAATTTTTGCGATTTGGTCCGTTATAGGAATTGAAG
TGTGCTTGCGGTCGCCACCACTCCCATTTCATAATTTTACATGTATTTGAAAAATAAA
AATTTATGGTATTCAATTTAAACACGTATACTTGTAAAGAATGATATCTTGAAAGAA
ATATAGTTTAAATATTTATTGATAAAATAACAAGTCAGGTATTATAGTCCAAGCAAA
AACATAAATTTATTGATGCAAGTTTAAATTCAGAAATATTTCAATAACTGATTATATC
AGCTGGTACATTGCCGTAGATGAAAGACTGAGTGCGATATTATGGTGTAATACATAG
CGGCCGCGCCCAAGGAACCCTTTTCTGGGCCATCTTCGTACTCGGCCACGACTGGTA
ATTTAAT
```

SEQ ID NO: 353

```
gcccaaggaacccttttctgggccatcttcgtactcggccacgactggtaatttaatggatccactagtaacggccgccagtgtgctggaattc
gcccttcgtcgacctgcaggtcaacggatcaggatattcttgtttaagatgttgaactctatggaggtttgtatgaactgatgatctaggaccgga
taagttcccttcttcatagcgaacttattcaaagaatgttttgtgtatcattcttgttacattgttattaatgaaaaatatattggtcattggactgaac
acgagtgttaaatatggaccaggccccaaataagatccattgatatatgaattaaataacaagaatattaataagtcaccaaaccacttgcctttttt
```

-continued taacgagacttgttcaccaacttgatacaaaagtcattatcctatgcaaatcaataatcatacaaaaatatccaataacactaaaaaattaaaaga
aatggataatttcacaatatgttatacgataaagaagttacttttccaagaaattcactgattttataagcccacttgcattagatagaatggcaaaaa
aaaacaaaaggaaaagaaataaagcacgaagaattctagaaaatacgaaatacgcttcaatgcagtgggacccacggttcaattattgcca
attttcagctccaccgtatatttaaaaaataaaacgataatgctaaaaaaatataaatcgtaacgatcgttaaatctcaacggctggatcttatgac
gaccgttagaaattgtggttgtcgacgagtcagtaataaacggcgtcaaagtggttgcagccggcacacacgagtcgtgtttatcaactcaaa
gcacaaatacttttcctcaacctaaaaataaggcaattagccaaaaacaacttgcgtgtaaacaacgctcaatacacgtgtcattttattattagc
tattgcttcaccgccttagctttctcgtgacctagtcgtcctcgtcttttcttcttcttctataaaacaataccccaaagagctcttcttcttcacaatt
cagatttcaatttctcaaaatcttaaaaacttctctcaattctctctaccgtgatcaaggtaaatttctgtgttccttattctctcaaaatcttcgattttg
ttttcgttcgatcccaatttcgtatatgttctttggtttagattctgttaatcttagatcgaagacgattttctgggtttgatcgttagatatcatcttaat
tctcgattagggtttcatagatatcatccgatttgttcaaataatttgagttttgtcgaataattactcttcgatttgtgatttctatctagatctggtgtta
gtttctagtttgtgcgatcgaattgtcgattaatctcgagtttttctgattaacagatgagaggatctggatctgagtctgatgagtctggacttcctgct
atggaaatcgagtctagaatcactggaaccctaacggtgttgagttcgagcttgttggaggtggtgagggaactcctgagcagggaagaat
gactaacaagatgaagtctaccaagggtgctcttaccttctctccataccttctttctcacgttatgggatacggattctaccacttcggaacttac
ccatctggatacgagaaccctttccttcatgctatcaacaacggtggatacaccaacactaggatcgagaagtacgaggatggtggtgttcttc
acgttagcttctcttacagatacgaggctggaagagtgatcggagatttcaaggttatgggaacttgattccctgaggattctgttatcttcaccg
acaagatcatcaggtctaacgctactgttgagcatcttcatcctatgggagataacgatctcgatggatctttcaccagaaccttctcacttagag
atggtggttactactcttctgtggtggattctcacatgcacttcaagtctgctatccaccttctatccttcaaaacggtggacctatgttcgctttca
gaagagttgaggaagatcactctaacaccgagcttggaatctgatgtgctgtaaacaatgctcttcaagaccccctgatgctgatgctggtgaggaat
gataatatcaaaatctatttagaaatacacaatatttttgttgcaggcttgctggagaatcgatctgctatcataaaaattacaaaaaatttatttgc
ctcaattatttaggattggtattaaggacgcttaaattatttgtcgggtcactacgcatcattgtgattgagaagatcagcgatacgaaatattcgt
agtactatcgataaatttatttgaaaattcataagaaaagcaaacgttacatgaattgatgaaacaatacaaagacagatagaaagccacgcacattt
aggatattggccgagattactgaatattgagtaagatcacggaatttctgacaggagcatgtcttcaattcagcccaaatggcagttgaaatact
caaaccgcccatgcaggagcggatcattcattgtttgtttggttgcctttgccaacatgggagtccaaggttgcggccgcgcccaaggaa
ccctttctgggccatcttcgtactcggcacgactggtaatttaat

SEQ ID NO: 354

GCCCAAGGAACCCTTTTCTGGGCCATCTTCGTACTCGGCCACGACTGGTAATTTAATG
GATCCAACCGACAACCACTTTGCGGACTTCCTTTCAAGAGAATTCAATAAGGTTAAT
TCCTAATTGAAATCCGAAGATAAGATTCCCACACACTTGTGGCTGATATCAAAAGGC
TACTGCCTATTTAAACACATCTCTGGAGACTGAGAAAATCAGACCTCCAAGCATGAA
GAAGCCTGAGCTTACTGCTACTTCTGTTGAGAAGTTCCTCATCGAGAAGTTCGATTCT
GTGTCTGATCTTATGCAGCTCTCTGAGGGTGAGGAATCAAGAGCTTTCTCTTTCGATG
TTGGTGGAAGAGGATACGTTCTCAGAGTTAACTCTTGCGCTGACGGATTCTACAAGG
ATAGATACGTGTACAGACACTTCGCTTCAGCTGCTCTCCCTATCCCTGAAGTTCTTGA
TATCGGAGAGTTCTCTGAGTCTCTTACCTACTGTATCTCAAGAAGGGCTCAGGGTGTT
ACTCTTCAAGATCTTCCTGAGACTGAGCTTCCTGCTGTTCTTCAACCTGTTGCTGAGG
CTATGGATGCTATCGCTGCTGCTGATCTTTCTCAAACTTCTGGATTCGGACCTTTCGG
TCCTCAGGGAATCGGACAGTACACTACTTGGAGAGATTTCATCTGCGCTATCGCTGA
TCCTCATGTTTACCATTGGCAGACCGTTATGGATGATACCGTTTCTGCTTCTGTTGCTC
AAGCTCTTGATGAGCTTATGCTTTGGGCTGAGGATTGTCCTGAGGTTAGACATCTTGT
TCACGCTGATTTCGGATCTAACAACGTTCTCACCGATAACGGAAGAATCACCGCTGT
TATCGATTGGTCTGAGGCTATGTTCGGAGATTCTCAATACGAGGTGGCCAACATATT
CTTTTGGAGGCCTTGGCTTGCTTGTATGGAACAACAGACTAGATACTTCGAGAGAAG
GCATCCTGAGCTTGCTGGATCTCCTAGACTTAGAGCTTACATGCTTAGGATCGGACTT
GATCAGCTTTACCAGTCTCTCGTTGATGGAAACTTCGATGATGCTGCTTGGGCTCAGG
GAAGATGTGATGCTATCGTTAGATCTGGTGCTGGAACTGTTGGAAGAACTCAAATCG
CTAGAAGATCTGCTGCTGTTTGGACTGATGGATGTGTTGAAGTTCTCGCTGATTCTGG
AAACAGAAGGCCTTCTACTAGACCTAGAGCCAAGAAGTGAAGATCGGCGGCAATAG
CTTCTTAGCGCCATCCCGGGTTGATCCTATCTGTGTTGAAATAGTTGCGGTGGGCAAG
GCTCTCTTTCAGAAAGACAGGCGGCCAAAGGAACCCAAGGTGAGGTGGGCTATGGC
TCTCAGTTCCTTGTGGAAGCGCTTGGTCTAAGGTGCAGAGGTGTTAGCGGGATGAAG
CAAAAGTGTCCGATTGTAACAAGATATGTTGATCCTACGTAAGGATATTAAAGTATG
TATTCATCACTAATATAATCAGTGTATTCAATATGTACTACGATTTCCAATGTCTTT
ATTGTCGCCGTATGTAATCGGCGTCACAAAATAATCCCCGGTGACTTTCTTTTAATCC
AGGATGAAATAATATGTTATTATAATTTTTGCGATTTGGTCCGTTATAGGAATTGAAG
TGTGCTTGCGGTCGCCACCACTCCCATTTCATAATTTTACATGTATTTGAAAAATAAA
AATTTATGGTATTCAATTTAAACACGTATACTTGTAAAGAATGATATCTTGAAAGAA
ATATAGTTTAAATATTTATTGATAAAATAACAAGTCAGGTATTATAGTCCAAGCAAA
AACATAAATTTATTGATGCAAGTTTAAATTCAGAAATATTTCAATAACTGATTATATC
AGCTGGTACATTGCCGTAGATGAAAGACTGAGTGCGATATTATGGTGTAATACATAG
CGGCCGCAGCGAGAGAAAGCTTATTGCAACTTCAACTACTTGCTGGTCGATCGTGTT
GGCCACTC

SEQ ID NO: 355

GCCCAAGGAACCCTTTTCTGGGCCATCTTCGTACTCGGCCACGACTGGTAATTTAATG
GATCCACTAGTAACGGCCGCCAGTGTGCTGGAATTCGCCCTTCGTCGACCTGCAGGT
CAACGGATCAGGATATTCTTGTTTAAGATGTTGAACTCTATGGAGGTTTGTATGAACT
GATGATCTAGGACCGGATAAGTTCCCTTCTTCATAGCGAACTTATTCAAAGAATGTTT
TGTGTATCATTCTTGTTACATTGTTATTAATGAAAAAATATTATTGGTCATTGGACTG
AACACGAGTGTTAAATATGGACCAGGCCCAAATAAGATCCATTGATATATGAATTA
ATAACAAGAATAAATCGAGTCACCAAACCACTTGCCTTTTTAACGAGACTTGTTC
ACCAACTTGATACAAAAGTCATTATCCTATGCAAATCAATAATCATACAAAAATATC
CAATAACACTAAAAAATTAAAAGAAATGGATAATTTCACAATATGTTATACGATAAA
GAAGTTACTTTTCCAAGAAATTCACTGATTTTATAAGCCCACTTGCATTAGATAAATG
GCAAAAAAAACAAAAGGAAAAGAAATAAAGCACGAAGAATTCTAGAAAATACG
AAATACGCTTCAATGCAGTGGGACCCACGGTTCAATTATTGCCAATTTTCAGCTCCAC
CGTATATTTAAAAAATAAAACGATAATGCTAAAAAAATATAAATCGTAACGATCGTT
AAATCTCAACGGCTGGATCTTATGACGACCGTTAGAAATTGTGGTTGTCGACGAGTC
AGTAATAAACGGCGTCAAAGTGGTTGCAGCCGGCACACACGAGTCGTGTTTATCAAC
TCAAAGCACAAATACTTTTCCTCAACCTAAAAATAAGGCAATTAGCCAAAACAACT
TGCGTGTAAACAACGCTCAATACACGTGTCATTTTATTATTAGCTATTGCTTCACCG

-continued
```
CCTTAGCTTTCTCGTGACCTAGTCGTCCTCGTCTTTTCTTCTTCTTCTTCTATAAAACA
ATACCCAAAGAGCTCTTCTTCTTCACAATTCAGATTTCAATTTCTCAAAATCTTAAAA
ACTTTCTCTCAATTCTCTACCGTGATCAAGGTAAATTTCTGTGTTCCTTATTCTCTC
AAAATCTTCGATTTTGTTTTCGTTCGATCCCAATTTCGTATATGTTCTTTGGTTTAGAT
TCTGTTAATCTTAGATCGAAGACGATTTTCTGGGTTTGATCGTTAGATATCATCTTAA
TTCTCGATTAGGGTTTCATAGATATCATCCGATTTGTTCAAATAATTTGAGTTTTGTCG
AATAATTACTCTTCGATTTGTGATTTCTATCTAGATCTGGTGTTAGTTTCTAGTTTGTG
CGATCGAATTTGTCGATTAATCTGAGTTTTTCTGATTAACAGATGAGAGGATCTGGAT
CTGAGTCTGATGAGTCTGGACTTCCTGCTATGGAAATCGAGTGTAGAATCACTGGAA
CCCTTAACGGTGTTGAGTTCGAGCTTGTTGGAGGTGGTGAGGGAACTCCTGAGCAGG
GAAGAATGACTAACAAGATGAAGTCTACCAAGGGTGCTCTTACCTTCTCTCCATACC
TTCTTTCTCACGTTATGGGATACGGATTCTACCACTTCGGAACTTACCCATCTGGATA
CGAGAACCCTTTCCTTCATGCTATCAACAACGGTGGATACACCAACACTAGGATCGA
GAAGTACGAGGATGGTGGTGTTCTTCACGTTAGCTTCTCTTACAGATACGAGGCTGG
AAGAGTGATCGGAGATTTCAAGGTATGGGAACTGGATTCCCTGAGGATTCTGTTAT
CTTCACCGACAAGATCATCAGGTCTAACGCTACTGTTGAGCATCTTCATCCTATGGGA
GATAACGATCTCGATGGATCTTTCACCAGAACCTTCTCACTTAGAGATGGTGGTTACT
ACTCTTCTGTGGTGGATTCTCACATGCACTTCAAGTCTGCTATCCACCCTTCTATCCTT
CAAAACGGTGGACCTATGTTCGCTTTCAGAAGAGTTGAGGAAGATCACTCTAACACC
GAGCTTGGAATCGTTGAGTACCAACATGCTTTCAAGACCCCTGATGCTGATGCTGGT
GAGGAATGATAATATCAAATCTATTTAGAAATACACAATATTTTGTTGCAGGCTTG
CTGGAGAATCGATCTGCTATCATAAAAATTACAAAAAAATTTTATTTGCCTCAATTAT
TTTAGGATTGGTATTAAGGACGCTTAAATTATTTGTCGGGTCACTACGCATCATTGTG
ATTGAGAAGATCAGCGATACGAAATATTCGTAGTACTATCGATAATTTATTTGAAAA
TTCATAAGAAAAGCAAACGTTACATGAATTGATGAAACAATACAAAGACAGATAAA
GCCACGCACATTTAGGATATTGGCCGAGATTACTGAATATTGAGTAAGATCACGGAA
TTTCTGACAGGAGCATGTCTTCAATTCAGCCCAAATGGCAGTTGAAATACTCAAACC
GCCCCATATGCAGGAGCGGATCATTCATTGTTTGTTTGGTTGCCTTTGCCAACATGGG
AGTCCAAGGTTGCGGCCGCAGCGAGAGAAAGCTTATTGCAACTTCAACTACTTGCTG
GTCGATCGTGTTGGCCACTC
```

SEQ ID NO: 375
```
TTCTGGCCTCTTTATTGGGCCGCCCAAGGAACCCTTTTCTGGGCCATCTTCGTACTCG
GCCACGACTGGTAATTTAATGGATCCACTAGTAA
```

SEQ ID NO: 376
```
TTCTGGCCTCTTTATTGGGCCGCCCAAGGAACCCTTTTCTGGGCCATCTTCGTACTCG
GCCACGACTGGTAATTTAATGGATCCACTAGTAA
```

SEQ ID NO: 377
```
TTCTGGCCTCTTTATTGGGCCGCCCAAGGAACCCTTTTCTGGGCCATC:CAGTCGTGGC
CGAGTACGAAGATGGCCCAGA:::TACTCGGCCACGACTGGTAATTTAATGGATCCACT
AGTAA
```

SEQ ID NO: 378
```
TTCTGGCCTCTTTATTGGGCCGCCCAAGGAACCCTTTTCTGGGCCATC:::GTACTCGGC
CACGACTGGTAATTTAATGGATCCACTAGTAA
```

SEQ ID NO: 379
```
TTCTGGCCTCTTTATTGGGCCGCCCAAGGAACCCTTTTCTAGG::::::TAT
CTCAGTTCGGTGTAGGTCGTTCGCTCCAAGCTGGGCTGCGTGCACGAAC:CGTACTCG
GCCACGACTGGTAATTTAATGGATCCACTAGTAA
```

SEQ ID NO: 380
```
TTCTGGCCTCTTTATTGGGCCGCCCAAGGAACCCTTTTCTGGGCCA:::::::::::::::::GACTG
GTAATTTAATGGATCCACTAGTAA
```

SEQ ID NO: 381
```
TCCAAGGTTGCGGCCGCGCCCAAGGAACCCTTTTCTGGGCCATCTTCGTACTCGGCC
ACGACTGGTAATTTAATTTTCAATTTATTT
```

SEQ ID NO: 382
```
TCCAAGGTTGCGGCCGCGCCCAAGGAACCCTTTTCTGGGCCAT:T:::TACTCGGCCACG
ACTGGTAATTTAATTTTCAATTTATTT
```

SEQ ID NO: 383
```
:CGTACTCGGCCACGACTGGTAATTTAATTTTCAATTTATTT
```

SEQ ID NO: 384
```
TCCAAGGTTGCGGCCGCGCCCAAGGAACCCTTTTCTGGGCCATCTTCGTACTCG
GCCACGACTGGTAATTTAATTTTCAATTTATTT
```

SEQ ID NO: 385
```
TCCAAGGTTGCGGCCGCGCCCAAGGAACCCTTTTCTGGGCCATCTTC::::::::::::::TGGT
AATTTAATTTTCAATTTATTTTT
```

SEQ ID NO: 386
```
TCCAAGGTTGCGGCCGCGCCCAAGGAACCCTTTTCTGG::::::TAGCGGTGGTTTT
TTTGTTTGCAAGCAGCAGATTACGCGCAGAAAAAAGGA
TCGTACTCGGCCACGACTGGTAATTTAATTTTCAATTTATTT
```

```
TCCAAGGTTGCGGCCGCGCCCAAGGAACCCTTTTCTGGGCCATCTTACGAGCGT         SEQ ID NO: 387
AATGGCTGGCCTGTTGAACAAGTCTGGAAAGAAATGCATAAACATATCCCAGCC
ACGACT::::::::::::::::GGTAATTTAATTTTCAATTTATTT

SEQ ID NO: 388
TAGTTTATTTGCCCCAAGCGAGAGAAAGCTTATTGCAACTTCAACTCGTACTCGGCC
ACGACTGGTAATTTAATGGATCCACTAGTAA

SEQ ID NO: 389
TAGTTTATTTGCCCCAAGCGAGAGAAAGCTTATTGCAACTTCAACT

SEQ ID NO: 390
TAGTTTATTTGCCCCAAGCGAGAGAAAGCTTATTGCAACTTCAACG

SEQ ID NO: 391
TAGTTTATTTGCCCCAAGCGAGAGAAAGCTTATTGCAACTTCAACTTCGTACTCGGCC
ACGACTGGTAATTTAATGGATCCACTAGTAA

SEQ ID NO: 392
TAGTTTATTTGCCCCAAGCGAGAGAAAGCTTATTGCAACTTCAACTAT::GTACTCGGC
CACGACTGGTAATTTAATGGATCCACTAGTAA

SEQ ID NO: 393
TAGTTTATTTGCCCCAAGCGAGAGAAAGCTTATTGCAACTTCA:::::TACTCGGCCACG
ACTGGTAATTTAATGGATCCACTAGTAA

SEQ ID NO: 394
AGGTAATTTAATGGATCCACTAGTAA

SEQ ID NO: 395
TCCAAGGTTGCGGCCGCAGCGAGAGAAAGCTTATTGCAACTTCAACTACTTGCTGGT
CGATCGTGTTGGCCACTCTTGTTTATCTATCA

SEQ ID NO: 396
TCCAAGGTTGCGGCCGCAGCGAGAGAAAGCTTATTGCAACTTCA:::ACTTGCTGGTCG
ATCGTGTTGGCCACTCTTGTTTATCTATCA

SEQ ID NO: 397
TCCAAGGTTGCGGCCGC::::::::::::::::::::::::::::GCGCCGACCCAGCTTTCTTGTACAAAGTT
GGCATTATAAGAAAGCATTGCTTATCAATTTGTTGCAACGAACAGGTCACTATCAGT
CAAA:ACTTGCTGGTCGATCGTGTTGGCCACTCTTGTTTATCTATCA

SEQ ID NO: 398
TCCAAGGTTTGCGGCCGCAGCGAGAGAAAGCTTATTGCAACTTC::::::ACTTGCTGGT
CGATCGTGTTGGCCACTCTTGTTTATCTATCA

SEQ ID NO: 399
TCCAAGGTTGCGGCCGCAGCGAGAGAAAGCTTATTGCAACTTCA::GATAAAGTTGC
TCGCCTGTGTGGGTGTGGATGCT:ACTTGCTGGTCGATCGTGTTGGCCACTCTTGTTTA
TCTATCA

SEQ ID NO: 400
TCCAAGGTTGCGGCCGCAGCGAGAGAAAGCTTATTGCAACTTCAACTACACTACTTG
CTGGTCGATCGTGTTGGCCACTCTTGTTTATCTATCA

SEQ ID NO: 401
TCCAAGGTTGCGGCCGCAGCGAGAGAAAGCTTATTGCAACTTCAACTACTTGCTGGT
CGATCGTGTTGGCCACTCTTGTTTATCTATCA

SEQ ID NO: 402
CTTACATGCTTAGGATCGGACTTG

SEQ ID NO: 403
AGTTCCAGCACCAGATCTAACG

SEQ ID NO: 404
CCCTGAGCCCAAGCAGCATCATCG

SEQ ID NO: 405
CGGAGAGGGCGTGGAAGG

SEQ ID NO: 406
TTCGATTTGCTACAGCGTCAAC

SEQ ID NO: 407
AGGCACCATCGCAGGCTTCGCT

SEQ ID NO: 408
TTCTGGCCTCTTTATTGGGCCGCCCAAGGAACCCTTTTCTGGGCCATCTTCGTACTCG
GCCACGACTGGTAATTTAATGGATCCAACCGACAACCACTT
```

```
TTCTGGCCTCTTTATTGGGCCGCCCAAGGAACCCTTT::::::::::::::TACTCGGCCACGACT        SEQ ID NO: 409
GGTAATTTAATGGATCCAACCGACAACCACTT

TTCTGGCCTCTTTATTGGGCCGCCCAAGGAACCCTTTTCTGG::::::TCGTACTCGGCCA             SEQ ID NO: 410
CGACTGGTAATTTAATGGATCCAACCGACAACCACTT

TTCTGGCCTCTTTATTGGGCCGCCCAAGGAACCCTTTTCTGG                                SEQ ID NO: 411

TTCTGGCCTCTTTATTGGGCCGCCCAAGGAACCCTTTTCTGGGCCATCT:::::::CGGCCA            SEQ ID NO: 412
CGACTGGTAATTTAATGGATCCAACCGACAACCACTT

TTCTGGCCTCTTTATTGGGCCGCCCAAGGAACCCTTTTCTGGGCCAT::TCGTACTCGG               SEQ ID NO: 413
CCACGACTGGTAATTTAATGGATCCAACCGACAACCACTT

TTCTGGCCTCTTTATTGGGCCGCCCAAGGAACCCTTTTCTGGGCCATCT                         SEQ ID NO: 414

GTAATACATAGCGGCCGCGCCCAAGGAACCCTTTTCTGGGCCATCTTCGTACTCGGC                 SEQ ID NO: 415
CACGACTGGTAATTTAATTTTCAATTTATTTTTTCTTCAACTTCTTA

GTAATACATAGCGGCCGCGCCCAAGGAACCCTTTTCTGGGCCAT:::::::::::GCCACGACT          SEQ ID NO: 416
GGTAATTTAATTTTCAATTTATTTTTTCTTCAACTTCTTA

GTAATACATAGCGGCCGCGCCCAAGGAACCCTTTTCTGGGCCATCT::::::::::::::GACTG         SEQ ID NO: 417
GTAATTTAATTTTCAATTTATTTTTTCTTCAACTTCTTA

GTAATACATAGCGGCCGCGCCCAAGGAACCCTTTTCTGGGCCATCT::::::::::::::GACTG         SEQ ID NO: 418
GTAATTTAATTTTCAATTTATTTTTTCTTCAACTTCTTA

GTAATACATAGCGGCCGCGCCCAAGGAACCCTTTTCTGGGCCAT::::GTACTCGGCCA               SEQ ID NO: 419
CGACTGGTAATTTAATTTTCAATTTATTTTTTCTTCAACTTCTTA

::GTACTCGGCCACGACTGGTAATTTAATTTT:::::::::::TCTTTCAACTTCTTA                SEQ ID NO: 420

GTAATACATAGCGGCCGCGCCCAA:::::::::::::::::::::::TACTCGGCCACGACTGGTAATTT    SEQ ID NO: 421
AATTTTCAATTTATTTTTTCTTCAACTTCTTA

TGTAATACATAGCGGCCGCGCCCAAGGAACCCTTTACTCGGCCA:::::::::::::::::::::TAAT     SEQ ID NO: 422
TTAATTTTCAATTTATTTTTTCTTCAACTTCTTA tnantgattc ccaatggcgg cgctttcaag gacatgatca tggagggtga tggcaggacctcgtactgaa atggtccgaa     SEQ ID NO: 423
ggtccacgcc gccaactacg ag cnantactcg tagttggcgg cgtggacctt cggaccattt cagtacgagg tcctgccatcaccctccatg atcatgtcct     SEQ ID NO: 424
tgaaagcgcc gccattggga at tnantgattc ccaatggcgg cgctttcaag gacatgatca tggagggtga tggcaggacc tcgtactgaa atttgcaggt acaag     SEQ ID NO: 425 angngtcttg tacctgcaaa tttcagtacg aggtcctgcc atcaccctcc atgatcatgtccttgaaagc gccgccattg ggaat     SEQ ID NO: 426

GTTTACCCGCCAATATATCCTGTCAAACACTGATAGTTTAAACTGAAGGCGGGAAAC                 SEQ ID NO: 427
GACAATCTGATCATGAGCGGAGAATTAAGGGAGTCACGTTATGACCCCCGCCGATGA
CGCGGGACAAGCCGTTTTACGTTTGGAACTGACAGAACCGCAACGTTGAAGGAGCC
ACTCAGCAAGCTTACTAGTAGCGCTGTTTAAACGCTCTTCAACTGGAAGAGCGGTTA
CCCGGACCGAAGCTTGCATGCCTGCAGTCAGCGTGACCCGGTCGTGCCCCTCTCTA
GAGATAATGAGCATTGCATGTCTAAGTTATAAAAAATTACCACATATTTTTTTTGTCA
CACTTGTTTGAAGTGCAGTTTATCTATCTTTATACATATATTTAAACTTTACTCTACGA
ATAATATAATCTATAGTACTACAATAATATCAGTGTTTTAGAGAATCATATAAATGA
ACAGTTAGACATGGTCTAAAGGACAATTGAGTATTTTGACAACAGGACTCTACAGTT
TTATCTTTTTAGTGTGCATGTGTTCTCCTTTTTTTTTGCAAATAGCTTCACCTATATAA
TACTTCATCCATTTTATTAGTACATCCATTTAGGGTTTAGGGTTAATGGTTTTTATAGA
CTAATTTTTTTAGTACATCTATTTTATTCTATTTTAGCCTCTAAATTAAGAAAACTAAA
```

-continued

```
ACTCTATTTTAGTTTTTTTATTTAATAATTTAGATATAAAATAGAATAAAATAAAGTG
ACTAAAAATTAAACAAATACCCTTTAAGAAATTAAAAAAACTAAGGAAACATTTTTC
TTGTTTCGAGTAGATAATGCCAGCCTGTTAAACGCCGTCGACGAGTCTAACGGACAC
CAACCAGCGAACCAGCAGCGTCGCGTCGGGCAAGCGAAGCAGACGGCACGGCATC
TCTGTCGCTGCCTCTGGACCCCTCTCGAGAGTTCCGCTCCACCGTTGGACTTGCTCCG
CTGTCGGCATCCAGAAATTGCGTGGCGGAGCGGCAGACGTGAGCCGGCACGGCAGG
CGGCCTCCTCCTCCTCTCACGGCACCGGCAGCTACGGGGGATTCCTTTCCCACCGCTC
CTTCGCTTTCCCTTCCTCGCCCGCCGTAATAAATAGACACCCCCTCCACACCCTCTTT
CCCCAACCTCGTGTTGTTCGGAGCGCACACACACACAACCAGATCTCCCCCAAATCC
ACCCGTCGGCACCTCCGCTTCAAGGTACGCCGCTCGTCCTCCCCCCCCCCCCCTCTCT
ACCTTCTCTAGATCGGCGTTCCGGTCCATGGTTAGGGCCCGGTAGTTCTACTTCTGTT
CATGTTTGTGTTAGATCCGTGTTTGTGTTAGATCCGTGCTGCTAGCGTTCGTACACGG
ATGCGACCTGTACGTCAGACACGTTCTGATTGCTAACTTGCCAGTGTTTCTCTTTGGG
GAATCCTGGGATGGCTCTAGCCGTTCCGCAGACGGGATCGATTTCATGATTTTTTTTG
TTTCGTTGCATAGGGTTTGGTTTGCCCTTTTCCTTTATTTCAATATATGCCGTGCACTT
GTTTGTCGGGTCATCTTTTCATGCTTTTTTTTGTCTTGGTTGTGATGATGTGGTCTGGT
TGGGCGGTCGTTCTAGATCGGAGTAGAATTCTGTTTCAAACTACCTGGTGGATTTATT
AATTTTGGATCTGTATGTGTGTGCCATACATATTCATAGTTACGAATTGAAGATGATG
GATGGAAATATCGATCTAGGATAGGTATACATGTTGATGCGGGTTTTACTGATGCAT
ATACAGAGATGCTTTTTGTTCGCTTGGTTGTGATGATGTGGTGTGGTTGGGCGGTCGT
TCATTCGTTCTAGATCGGAGTAGAATACTGTTTCAAACTACCTGGTGTATTTATTAAT
TTTGGAACTGTATGTGTGTGTCATACATCTTCATAGTTACGAGTTTAAGATGGATGGA
AATATCGATGTAGGATAGGTATACATGTTGATGTGGGTTTTACTGATGCATATACATG
ATGGCATATGCAGCATCTATTCATATGCTCTAACCTTGAGTACCTATCTATTATAATA
AACAAGTATGTTTTATAATTATTTTGATCTTGATATACTTGGATGATGGCATATGCAG
CAGCTATATGTGGATTTTTTAGCCCTGCCTTCATACGCTATTTATTTGCTTGGTACTG
TTTCTTTTGTCGATGCTCACCCTGTTGTTGGTGTTACTTCTGCAGGTCGACTCTAGAG
GATCCACACGACACCATGTCCGCCCGCGAGGTGCACATCGACGTGAACAACAAGAC
CGGCCACACCCTCCAGCTGGAGGACAAGACCAAGCTCGACGGCGGCAGGTGGCGCA
CCTCCCCGACCAACGTGGCCAACGACCAGATCAAGACCTTCGTGGCCGAATCCAACG
GCTTCATGACCGGCACCGAGGGCACCATCTACTACTCAATTAATGGCGAGGCCGAGA
TCAGCCTCTACTTCGACAACCCGTTCGCCGGCTCCAACAAATACGACGGCCACTCCA
ACAAGTCCCAGTACGAGATCATCACCCAGGGCGGCTCCGGCAACCAGTCCCACGTGA
CCTACACCATCCAGCACCCTCCTCCCGCTACGGCCACAAGTCCTGAGTCATGAGTC
ATGAGTCAGTTAACCTAGACTTGTCCATCTTCTGGATTGGCAACTTAATTAATGTAT
GAAATAAAAGGATGCACACATAGTGACATGCTAATCACTATAATGTGGGCATCAAA
GTTGTGTGTTATGTGTAATTACTAGTTATCTGAATAAAAGAGAAAGAGATCATCCAT
ATTTCTTATCCTAAATGAATGTCACGTGTCTTTATAATTCTTTGATGAACCAGATGCA
TTTCATTAACCAAATCCATATACATATAAATATTAATCATATATAATTAATATCAATT
GGGTTAGCAAAACAAATCTAGTCTAGGTGTGTTTTGCGAATGCGGCCGCGGACCGAA
TTGGGGATCTGCATGAAAGAAACTGTCGCACTGCTGAACCGCACCTTGTCACTTTCA
TCGAACACGACCTGTGCCCAAGATGACGGTGCTGCGGTCAAGTGAGGCTGAATTGC
CTTGGACAGAAGCGGACTCCCTACAATTAGTTAGGCCAAACGGTGCATCCATGTGTA
GCTCCGGGCTCGGGCTGTATCGCCATCTGCAATAGCATCCATGGAGCTCGTTCCATGT
AGTTGGAGATGAACCAATGATCGGGCGTGTGGACGTATGTTCCTGTGTACTCCGATA
GTAGAGTACGTGTTAGCTCTTTCATGGTGCAAGTGAAATTTGTGTTGGTTTAATTACC
CCTACGTTAGTTGCGGGACAGGAGACACATCATGAATTTAAAGGCGATGATGTCCTC
TCCTGTAATGTTATTCTTTTGATGTGATGAATCAAAATGTCATATAAAACATTTGTTG
CTCTTTAGTTAGGCCTGATCGTAGAACGAAATGCTCGTGTAGCGGGGCTACGAGCCT
ATGACGCAATAACACTGGTTTGCCGGCCCGGAGTCGCTTGACAAAAAAAAGCATGTT
AAGTTTATTTACAATTCAAAACCTAACATATTATATTCCCTCAAAGCAGGTTCACGAT
CACACCTGTACCTAAAAAAAAACATGAAGAATATATTACTCCATTATTATGAGATGAA
CCACTTGGCAAGAGTGGTAAGCTATATAAAAAAAATGAACATTATTACGAGATGTTAT
ATGCCATTATATTGATTCGAAGATATATGTTTCTTTCTCCCACGGGCACCTAACGGAT
ACATGATAAGGCCAAGGCAGATCACGGGAAATTATTCGAATACATGTTACGCCCTAT
TGCCGGAAAAAAAATGCAGGGCAGGTGTTGGCCGTAGCGATTTAAGCACTTAAGCT
GGAGGTTGCCACACTTGGATGCAAGCGTCTGACCCTTCTAAAAAATCGGCGGCTTTG
TCCGTATCCGTATCCCCTATCCAACATCTAGCTGGCCACACGACGGGGCTGGGCAGA
TCGTGGATGCCGGGTCGACGTCGATCGTCAGCCATCATAGACCAATCGACCATCTGT
TATGGATGCTTGCTAGCTAGACTAGTCAGACATAAAATTTGGATACTTTCTCCCAACT
GGGAGACGGGGACTGATGTGCAGCTGCACGTGAGCTAAATTTTTCCCTATAAATATG
CATGAAATACTGCATTATCTTGCCACAGCCACTGCCACAGCCAGATAACAAGTGCAG
CTGGTAGCACGCAACGCATAGCTCTGGACTTGTAGCTAGGTAGCCAACCGGATCCAC
ACGACACCATGCTCGACACCAACAAGGTGTACGAGATCAGCAACCACGCCAACGGC
CTCTACGCCGCCACCTACCTCTCCCTCGACGACTCCGGCGTGTCCCTCATGAACAAGA
ACGACGACGACATCGACGACTACAACCTCAAGTGGTTCCTCTTCCCGATCGACGACG
ACCAGTACATCATCACCTCCTACGCCGCCAACAACTGCAAGGTGTGGAACGTGAACA
ACGACAAGATTAATGTGTCAACCTACTCCTCCACCAACTCCATCCAGAAGTGGCAGA
TCAAGGCCAACGGCTCCTCCTACGTGATCCAGTCCGACAACGGCAAGGTGCTCACCG
CCGGCACCGGCAGGCCCTCGGCCTCATCCGCCTCACCGACGAGTCCTCCAACAACC
CGAACCAGCAATGGAACCTGACGTCCGTGCAGACCATCCAGCTCCCGCGAGAAGCCG
ATCATCGACACCAAGCTCAAGGACTACCCCGAAGTACTCCCCGACCGGCAACATCGAC
AACGGCACCTCCCCGCAGCTCATGGGCTGGACCCTCGTGCCGTGCATCATGGTGAAC
GACCCGAACATCGACAAGAACACCCAGATCAAGACCACCCCGTACTACATCCTCAA
GAAGTACCAGTACTGGCAGAGGGCCGTGGGCTCCAACGTCGCGCTCCGCCCGCACG
AGAAGAAGTCCTACCACCTACGAGTGGGGCACCGAGATCGACGCAAGACCACCATC
ATCAACACCCTCGGCTTCCAGATCAACATCGACAGCGGCATGAAGTTCGACATCCCG
GAGGTGGGCGCGGTACCGACGAGATCAAGACCCAGCTCAACGAGGAGCTCAAGAT
CGAGTATTCACATGAGACGAAGATCATGGAGAAGTACCAGGAGCAGTCCGAGATCG
ACAACCCGACCGACCAGTCCATGAACTCCATCGGCTTCCTCACCATCACCTCCCTGG
AGCTCTACCGCTACAACGGCTCCGAGATCCGCATCATGCAGATCCAGACCTCCGACA
```

-continued

ACGACACCTACAACGTGACCTCCTACCCGAACCACCAGCAGGCCCTGCTGCTGCTGA
CCAACCACTCCTACGAGGAGGTGGAGGAGATCACCAACATCCCGAAGTCCACCCTCA
AGAAGCTCAAGAAGTACTACTTCTGAGTCATGAGTCATGAGTCAGTTAACCTAGACT
TGTCCATCTTCTGGATTGGCCAACTTAATTAATGTATGAAATAAAAGGATGCACACA
TAGTGACATGCTAATCACTATAATGTGGGCATCAAAGTTGTGTGTTATGTGTAATTAC
TAGTTATCTGAATAAAAGAGAAAGAGATCATCCATATTTCTTATCCTAAATGAATGT
CACGTGTCTTTATAATTCTTTGATGAACCAGATGCATTTCATTAACCAAATCCATATA
CATATAAATATTAATCATATATAATTAATATCAATTGGGTTAGCAAAACAAATCTAG
TCTAGGTGTGTTTTGCGAATTCCCATGGAGTCAAAGATTCAAATAGAGGACCTAACA
GAACTCGCCGTAAAGACTGGCGAACAGTTCATACAGAGTCTCTTACGACTCAATGAC
AAGAAGAAAATCTTCGTCAACATGGTGGAGCACGACACGCTTGTCTACTCCAAAAAT
ATCAAAGATACAGTCTCAGAAGACCAAAGGGCAATTGAGACTTTTCAACAAAGGGT
AATATCCGGAAACCTCCTCGGATTCCATTGCCCAGCTATCTGTCACTTTATTGTGAAG
ATAGTGGAAAAGGAAGGTGGCTCCTACAAATGCCATCATTGCGATAAAGGAAAGGC
CATCGTTGAAGATGCCTCTGCCGACAGTGGTCCCAAAGATGGACCCCCACCCACGAG
GAGCATCGTGGAAAAGAAGACGTTCCAACCACGTCTTCAAAGCAAGTGGATTGAT
GTGATATCTCCACTGACGTAAGGGATGACGCACAATCCCACTATCCTTCGCAAGACC
CTTCCTCTATATAAGGAAGTTCATTTCATTTGGAGAGGACAGGGTACCCGGGGATCC
ACCATGTCTCCGGAGAGGAGACCAGTTGAGATTAGGCCAGCTACAGCAGCTGATATG
GCCGCGGTTTGTGATATCGTTAACCATTACATTGAGACGTCTACAGTGAACTTTAGG
ACAGAGCCACAAACACCACAAGAGTGGATTGATGATCTAGAGAGGTTGCAAGATAG
ATACCCTTGGTTGGTTGCTGAGGTTGAGGGTGTTGTGGCTGGTATTGCTTACGCTGGG
CCCTGGAAGGCTAGGAACGCTTACGATTGGACAGTTGAGAGTACTGTTTACGTGTCA
CATAGGCATCAAAGGTTGGGCCTAGGATCCACATTGTACACACATTTGCTTAAGTCT
ATGGAGGCGCAAGGTTTTAAGTCTGTGGTTGCTGTTATAGGCCTTCCAAACGATCCA
TCTGTTAGGTTGCATGAGGCTTTGGGATACACAGCCCGGGGTACATTGCGCGCAGCT
GGATACAAGCATGGTGGATGGCATGATGTTGGTTTTTGGCAAAGGGATTTTGAGTTG
CCAGCTCCTCCAAGGCCAGTTAGGCCAGTTACCCAGATCTGAGTCGACCTGCAGGCA
TGCCCGCTGAAATCACCAGTCTCTCTCTACAAATCTATCTCTCTATAATAATGTGT
GAGTAGTTCCCAGATAAGGGAATTAGGGTTCTTATAGGGTTTCGCTCATGTGTTGAG
CATATAAGAAACCCTTAGTATGTATTTGTATTTGTAAAATACTTCTATCAATAAAATT
TCTAATTCCTAAAACCAAAATCCAGGGCGAGCTCGGTACCCGGGGATCCTCTAGAGT
CGACCTGCAGGCATGCCCGCGGATATCGATGGGCCCCGGCCGAAGCTTCGGTCCGGG
CCATCGTGGCCTCTTGCTCTTCAGGATGAAGAGCTATGTTTAAACGTGCAAGCGCTC
AATTCGCCCTATAGTGAGTCGTATTACAATCGTACGCAATTCAGTACATTAAAAACG
TCCGCAATGTGTTATTAAGTTGTCTAAGCGTCAATTTGTTTACACCACAATATATCCT
GCCA

SEQ ID NO: 428

GAGGCCGACACGGCACACACGGCGACATTCACCGCCGGCTTCCTCCGTCGCCACTCG
GCACAAGGCTCATCAGTCGCCGATGCCCGATGCGATCAACGGAAGCGGATGGCCCG
CTTCTTTAGAATTGGCACAGGAACACTGGCCACTGCCCTTGATGTGCAATTATGCCTG
CGAAAGCCTAGGCAACACACGCGAATAAACGAGCGAATGACACGGAAAGCTGATGT
GGTATGAATTATACAACATTATGGGCCAAAATATTATTCTATCCACCATTGTGTAGCC
ACAGCATCGGTATTTGAGTTGTGCGAGGACAAATCCCTCGTGAGGTCAAAAACAGCA
AATAATAAACCCATCTCCTGAAGACACCAAAAAAAAGGAGCAGCTCCTCGTGTCAAT
GAACAAGCGTCACAAGAAAAGGGAGCACGTAAATAACCTCTTCAATTGCTTCAGCAT
GAAAAGAACGGGAAGAAATGCAAGTCTACAGAGGAAAGTGCAGCTGTTTCGGCTGC
CATGGCAAGTTCCTACATGGGCGAGGAAAGCTGAACTGGATTCCAGTCTTCGCGCT
GTCATGCTCAGCTTGCTTTAGGATGCGGCAATAGTTCACCTGGATGAAAAAGATACA
AGTTAGTCTTGAAGCAGTCGAGTGGACATCCAAAGTATCAAATCGAAAGCTTGTAA
ATGGGGAAGGAAATATACCTCTACCCGGAAAAGTTTGGTAGGCAAAATAATCCCAA
CGCCAGCAGAGCTC

SEQ ID NO: 429

CGTGCAAGCGCTCAATTCGCCCTATAGTGAGTCGTATTACAATCGTACGCAATTCAG
TACATTAAAAACGTCCGCAATGTGTTATTAAGTTGTCTAAGCGTCAATTTGTTTACAC
CAGAGGCCGACACGGCACACACGGCGACATTCACCGCCGGCTTCCTCCGTCGCCACT
CGGCACAAGGCTCATCAGTCGCCGATGCCCGATGCGATCAACGGAAGCGGATGGCC
CGCTTCTTTAGAATTGGCACAGGAACACTGGCCACTGCCCTTGATGTGCAATTATGCC
TGCGAAAGCCTAGGCAACACACGCGAATAAACGAGCGAATGACACGGAAAGCTGAT
GTGGTATGAATTATACAACATTATGGGCCAAAATATTATTCTATCCACCATTGTGTAG
CCACAGCATCGGTATTTGAGTTGTGCGAGGACAAATCCCTCGTGAGGTCAAAAACAG
CAAATAATAAACCCATCTCCTGAAGACACCAAAAAAAAGGAGCAGCTCCTCGTGTC
AATGAACAAGCGTCACAAGAAAAGGGAGCACGTAAATAACCTCTTCAATTGCTTCA
GCATGAAAAGAACGGGAAGAAATGCAAGTCTACAGAGGAAAGTGCAGCTGTTTCGG
CTGCCATGGCAAGTTCCTACATGGGCGAGGAAAGCTGAACTGGATTCCAGTCTTCG
CGCTGTCATGCTCAGCTTGCTTTAGGATGCGGCAATAGTTCACCTGGATGAAAAAGA
TACAAGTTAGTCTTGAAGCAGTCGAGTGGACATCCAAAGTATCAAATCGAAAGCTT
GTAAATGGGGAAGGAAATATACCTCTACCCGGAAAAGTTTGGTAGGCAAAATAATC
CCAACGCCAGCAGAGCTC

SEQ ID NO: 430

AGTTGGGAAGGCAAAACGAATATAAGTGCATTCGGATTACTGTTTAGTCGAGTCATA
TTTAAGGAATTCATTGTAAATGTTCTAACCTAACCTAAGTATTAGGCAGCTATGGCTG
ATATGGATCTGATTGGACTTGATTTATCCATGATAAGTTTAAGAGCAACTCAAAGAG
GTTAGGTATATATGGTTTTGTAAAGGTAAATTTAGTTAATATTAGAAAAAAAAAGTG
TATCCAATAGGCTCTATAAACAACTCTTCAAATTTAGTGGCTTTCTATCCATCCACCT
TTGCTCTCTATTTTTGGATAGCCTGATTTACTCTCTATTCAGTCCGTAGGTTTAATGAG
TCTGTTGGATTAGCCTACACTTTTTCTGTAAAATCTATTTTAGATAGTAGCTAAATCA
GTAAATTTGGCTAGTATTTTTAGCTATTCTCTTGGAGTTTGCTATAAGACCAGAACAT

```
GTAAATTGGAAGTTTGTGGACCCGGACGAGAATGCATGACAAATCCAGAGTATTGAT
GATGGAATTCACCTATTTTACCCGACTCTTCCATTGTGTCCATTTCTCATCATCCCGG
GCGCTTTCTGCATCCGGTACAGCTGACATGACACGTTCACGCGTTACATGGCTGATG
GCTCACAAGTCACCCCCACATGTCTAGTGTTCGCCCAGGCAGATCGTCCTCGGCCTG
CGCTGCCGTGCTCTTGCCGCCGCTTGCTTGGGCCCTGCTGGCGCCCGCTGCCGATCAC
ACGGCCTACGCGGTGCAGGCAGCGCCACCGAACCCGCAGTCTTGTTGTGCCGATAGG
TGGCAGTGGCAGTGGCACTGGCACGGCACGCGATCGATCGCTCCGCTCATCTGCTGA
CAGTGGATAGAGCAGCGTTGGCCGTTGGGGCCGGATCTCCGTGAAGCGGTCGTCCCT
GCTGTACTGTGCCGCTATGGCGTGTCGCTTTCGCCATGTTTTCTTTTCTTTTTTTTCT
TTTTCTTTTTGCTAGGGCGGTTTCTCGTTCGCTGGTAACAGGGACCACTTCGGTTGAT
CCGTTGAATTTACTGAAAGAGATGGGAATGGTCGCTGTGCCCGGGACATTGAATGAG
ATGTTGTGTAAGTGAATATGGCTTTAGCCTTTTGCGAGTGGGAATGGATGCTAAACG
AACACAAACCGGGTTTAAACCAGAGGCCGACACGGCACACACGGCGACATTCACCG
CCGGCTTCCTCCGTCGCCACTCGGCACAAGGCTCATCAGTCGCCGATGCCCGATGCG
ATCAACGGAAGCGGATGGCCCGCTTCTTTAGAATTGGCACAGGAACACTGGCCACTG
CCCTTGATGTGCAATTATGCCTGCGAAAGCCTAGGCAACACACGCGAATAAACGAGC
GAATGACACGGAAAGCTGATGTGGTATGAATTATACAACATTATGGGCCAAAATATT
ATTCTATCCACCATTGTGTAGCCACAGCATCGGTATTTGAGTTGTGCGAGGACAAAT
CCCTCGTGAGGTCAAAAACAGCAAATAATAAACCCATCTCCTGAAGACACCAAAAA
AAAGGAGCAGCTCCTCGTGTCAATGAACAAGCGTCACAAGAAAGGGAGCACGTAA
ATAACCTCTTCAATTGCTTCAGCATGAAAAGAACGGGAAGAAATGCAAGTCTACAGA
GGAAAGTGCAGCTGTTTCGGCTGCCATGGCAAGTTCCTACATGGGCGAGGAAAAGCT
GAACTGGATTCCAGTCTTCGCGCTGTCATGCTCAGCTTGCTTTAGGATGCGGCAATAG
TTCACCTGGATGAAAAGATACAAGTTAGTCTTGAAGCAGTCGAGTGGACATCCAAA
GTATCAAAATCGAAAGCTTGTAAATGGGGAAGGAAATATACCTCTACCCGGAAAAG
TTTGGTAGGCAAAATAATCCCAACGCCAGCAGAGCTCCGGAACGTTTGCCGAAATTC
AGAAGCCGAAAAGTTCTTGTACTCACCCTCCGACAGTTTCGCAAGGTTTCCAGCAGT
AAGGAATGCGTGGCCATGGATTCCAGCGTCTCTGAATATCTTGAGGGGCAGATCAAA
AGAAAGGTCAGCGAAGGCAGACACGGCCAGATCACCTCCCAAGTAATCCCTTCCAG
GGTCAGCCGAGCCACTCTCCGAGTTATTAAGGACATGCCTCCGCGCCTCTGTTGGGC
CAACTCCCCTTAATCTGAAACCCAGCAGAGATGACGGTCCGCCCAAGCTGCACACTG
GAGAAGAATTACCTCCAAGATAAAACCTCTCTGGCACTGATGAAGTCGAATTCATGA
ATCCCCCTGCAAGCGGTAAAATGACACCCGCTCCTACACCAACGTTGAGAGCAGCAC
TATAAAATCCCAAAGGCACAGCACCCACGTACATCGAACTCCTGAGAGCAAACCCAA
CGGCAATATTTTCTAACGGACACCAACCAGCGAACCAGCAGCGTCGCGTCGGGCCAA
GCGAAGCAGACGGCACGGCATCTCTGTCGCTGCCTCTGGACCCCTCTCGAGAGTTCC
GCTCCACCGTTGGACTTGCTCCGCTGTCGGCATCCAGAAATTGCGTGGCGGAGCGGC
AGACGTGAGCCGGCACGGCAGGCGGCCTCCTCCTCCTCTCACGGCACCGGCAGCTAC
GGGGGATTCCTTTCCCACCGCTCCTTCGCTGTCCCTTCCTCGCCC
```

SEQ ID NO: 431

```
AGTTGGGAAGGCAAAACGAATATAAGTGCATTCGGATTACTGTTTAGTCGAGTCATA
TTTAAGGAATTCATTGTAAATGTTCTAACCTAACCTAAGTATTAGGCAGCTATGGCTG
ATATGGATCTGATTGGACTTGATTTATCCATGATAAGTTTAAGAGCAACTCAAAGAG
GTTAGGTATATATGGTTTTGTAAAGGTAAATTTAGTTAATATTAGAAAAAAAAAGTG
TATCCAATAGGCTCTATAAACAACTCTTCAAATTTAGTGGCTTTCTATCCATCCACCT
TTGCTCTCTATTTTTGGATAGCCTGATTTACTCTCTATTCAGTCCGTAGGTTTAATGAG
TCTGTTGGATTAGCCTACACTTTTTCTGTAAAATCTATTTTAGATAGTAGCTAAATCA
GTAAATTTGGCTAGTATTTTTAGCTATTCTCTTGGAGTTTGCTATAAGACCAGAACAT
GTAAATTGGAAGTTTGTGGACCCGGACGAGAATGCATGACAAATCCAGAGTATTGAT
GATGGAATTCACCTATTTTACCCGACTCTTCCATTGTGTCCATTTCTCATCATCCCGG
GCGCTTTCTGCATCCGGTACAGCTGACATGACACGTTCACGCGTTACATGGCTGATG
GCTCACAAGTCACCCCCACATGTCTAGTGTTCGCCCAGGCAGATCGTCCTCGGCCTG
CGCTGCCGTGCTCTTGCCGCCGCTTGCTTGGGCCCTGCTGGCGCCCGCTGCCGATCAC
ACGGCCTACGCGGTGCAGGCAGCGCCACCGAACCCGCAGTCTTGTTGTGCCGATAGG
TGGCAGTGGCAGTGGCACTGGCACGGCACGCGATCGATCGCTCCGCTCATCTGCTGA
CAGTGGATAGAGCAGCGTTGGCCGTTGGGGCCGGATCTCCGTGAAGCGGTCGTCCCT
GCTGTACTGTGCCGCTATGGCGTGTCGCTTTCGCCATGTTTTCTTTTCTTTTTTTTCT
TTTTCTTTTTGCTAGGGCGGTTTCTCGTTCGCTGGTAACAGGGACCACTTCGGTTGAT
CCGTTGAATTTACTGAAAGAGATGGGAATGGTCGCTGTGCCCGGGACATTGAATGAG
ATGTTGTGTAAGTGAATATGGCTTTAGCCTTTTGCGAGTGGGCGGCAATGCACGGC
ATGAACTATAATTTCCGGTCAAACTTTTGTGTGGAAATGGATGCTAAACGAACACAA
ACCGGGTTTAAACCAGAGGCCGACACGGCACACACGGCGACATTCACCGCCGGCTTC
CTCCGTCGCCACTCGGCACAAGGCTCATCAGTCGCCGATGCCCGATGCGATCAACGG
AAGCGGATGGCCCGCTTCTTTAGAATTGGCACAGGAACACTGGCCACTGCCCTTGAT
GTGCAATTATGCCTGCGAAAGCCTAGGCAACACACGCGAATAAACGAGCGAATGAC
ACGGAAAGCTGATGTGGTATGAATTATACAACATTATGGGCCAAAATATTATTCTAT
CCACCATTGTGTAGCCACAGCATCGGTATTTGAGTTGTGCGAGGACAAATCCCTCGT
GAGGTCAAAAACAGCAAATAATAAACCCATCTCCTGAAGACACCAAAAAAAAGGAG
CAGCTCCTCGTGTCAATGAACAAGCGTCACAAGAAAGGGAGCACGTAAATAACCT
CTTCAATTGCTTCAGCATGAAAAGAACGGGAAGAAATGCAAGTCTACAGAGGAAAG
TGCAGCTGTTTCGGCTGCCATGGCAAGTTCCTACATGGGCGAGGAAAAGCTGAACTG
GATTCCAGTCTTCGCGCTGTCATGCTCAGCTTGCTTTAGGATGCGGCAATAGTTCACC
TGGATGAAAAGATACAAGTTAGTCTTGAAGCAGTCGAGTGGACATCCAAAGTATC
AAAATCGAAAGCTTGTAAATGGGGAAGGAAATATACCTCTACCCGGAAAGTTTGG
TAGGCAAAATAATCCCAACGCCAGCAGAGCTCCGGAACGTTTGCCGAAATTCAGAA
GCCGAAAAGTTCTTGTACTCACCCTCCGACAGTTTCGCAAGGTTTCCAGCAGTAAGG
AATGCGTGGCCATGGATTCCAGCGTCTCTGAATATCTTGAGGGGCAGATCAAAAGAA
AGGTCAGCGAAGGCAGACACGGCCAGATCACCTCCCAAGTAATCCCTTCCAGGGTCA
GCCGAGCCACTCTCCGAGTTATTAAGGACATGCCTCCGCGCCTCTGTTGGGCCAACT
CCCCTTAATCTGAAACCCAGCAGAGATGACGGTCCGCCCAAGCTGCACACTGGAGAA
```

```
GAATTACCTCCAAGATAAAACCTCTCTGGCACTGATGAAGTCGAATTCATGAATCCC
CCTGCAAGCGGTAAAATGACACCCGCTCCTACACCAACGTTGAGAGCAGCACTATAA
AATCCCAAAGGCACAGCACCACGTACATCGAACTCCTGAGAGCAAACCCAACGGCA
ATATTTTTGTAATAGTGATGGTCAGAACTGAGAAGATCAGATAAAATTATACACTGA
TGCAATTATTTCATAGTTTCGCCCATGAACTGTAAGGGCTAGACAAAGCAAAAAGTA
AGACATGAAGGGCAAGAGAATAACCTGCCGGAAATATCTCAATCCTTTGCTATTCCA
TAGACCACCAACTTGAGAAGTTGACTGAAACGCATATCCTTTCGTTGGCCTAAGATG
TGAATCCCTCTTATCAATCTTGTATGTGTACTTCAATGCAGAAAGAAGGTTATGCCCT
AACTGCCTCCTTATGGCCTTTGATGAGACACGTGATGGATCAGTTAAGGTACGCCAC
GCAAGGTTGTATGACAAGTCATGGTTCCTTGTTGACAGCAAACCAAATGAAAGGCCA
AGTAGGCGCTCCTTGTATGATGAAAACTTCAGCCAATCTTGTGATGACAAAGATGCC
CGAGCCATCAATGGTGTTGGTATTGATTTAAACCTCGGTAGGCAGACTCCAACACCA
ACCTCTGTTGTTTGGTCCCAACCAAAGGATCCTGATGCATCCCAGATGTCACCATAGC
CAAACAAGTTCTTCAACTTAAGTGACCCTTCCAGCGACCAAGATCTTGCCTACAAGA
GTGGCAAGCACAGTCA
```

SEQ ID NO: 464
```
GTGCATTCGGATTACTGTTTAGTCGAGTCATATTTAAGGAATTCATTGTAAATGTTCT
AACCTAACCTAAGTATTAGGCAGCTATGGCTGATATGGATCTGATTGGACTTGATTT
ATCCATGATAAGTTTAAGAGCAACTCAAAGAGGTTAGGTATATATGGTTTTGTAAAG
GTAAATTTAGTTAATATTAGAAAAAAAAAGTGTATCCAATAGGCTCTATAAACA
```

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of integrating a transgene into an endogenous locus of a cell, the method comprising;
introducing one or more nucleases into the cell, the cell comprising a circular double-stranded plasmid donor, the double-stranded plasmid donor comprising: a transgene; and first and second sequences flanking the transgene, the first and second sequences flanking the transgene comprising paired target sites for one or more nucleases, the target sites flanking a spacer sequence, wherein at least one spacer sequence differs from the spacer sequence present in the genome of the cell, wherein the double-stranded plasmid does not comprise homology arms and further wherein the nucleases cleave the double-stranded plasmid in the sequences flanking the transgene and cleave the endogenous locus such that the transgene is integrated into the endogenous locus via homology-independent mechanisms.

2. The method of claim 1, wherein the transgene is integrated in a forward orientation.

3. The method of claim 1, wherein the transgene is integrated in a reverse orientation.

4. The method of claim 1, wherein the same nucleases cleave the endogenous locus and the double-stranded plasmid.

5. The method of claim 1, wherein different nucleases cleave the endogenous locus and the double-stranded plasmid.

6. The method of claim 1, wherein the spacer sequences comprise at least 5 nucleotides.

7. The method of claim 1, wherein the nucleases generate a deletion in the endogenous locus and the transgene is integrated into the deletion.

8. The method of claim 1, wherein the cell is a eukaryotic cell.

9. The method of claim 8, wherein the cell is a plant or mammalian cell.

10. The method of claim 9, wherein the plant cell is a dicotyledonous or a monocotyledonous plant cell.

* * * * *

SEQUENCE LISTING

```
<160> NUMBER OF SEQ ID NOS: 572

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tgtatctggc cactgat                                                    17

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tttgtctttg cctcctt                                                    17

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tgtcccctcc accccacagt ggggccacta gggacaggat tggtgacaga              50

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 4
gaccccaagc ccattcctgg gaactggaat ggtgcaggct gccataccaa                50

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtttcgtgtt cggagccgct ttaacccact ctgtggaagt gctcagcatt                50

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtcatcctca tcctgataaa ctgcaaaaga                                      30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cttttgcagt ttatcaggat gaggatgaca                                      30

<210> SEQ ID NO 8
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggccgtgtat ctggccactg atgacccttc tttgttaaag gaggcaaaga caaagtaa       58

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccccttacct ctctagtctg tgc                                             23

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 10
ggcgattaag ttgggtaacg                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggcctcttgg tcaagttgtt                                              20

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctcaggttct gggagagggt ag                                           22

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtaaaacgac ggccagt                                                 17

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
accagtgagt tttcattagg                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tggagcaaaa gacagtggtg                                              20

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 16
aagatggatt atcaagtgtc aagtcc                                          26

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
caaagtccca ctgggcg                                                    17

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atccgcatgg gagatcatct                                                 20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtgtatgttc gttcacccac                                                 20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
caaataggac cctgtgaagg a                                               21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gattaagttg ggtaacgcca g                                               21

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
``` ataggaccc tgtgaagga                                           19

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtgtggaatt gtgagcggat a                                       21

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agtccatgtc agacgcactg                                         20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agagtgaggc tctgtctcaa                                         20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tacgtatagg ctgcgcaact                                         20

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcacatgtag tctttgattt tg                                      22

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ttatctgtcc cctccacccc acagtggggc cactagggac aggattatcc atcacactgg    60

<210> SEQ ID NO 29
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cgaattctgc agatcacccc acagtggggc cactagggac aggattggtg acagaaaagc    60
c                                                                   61

<210> SEQ ID NO 30
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttatctgtcc cctccacccc acagtgggcc cactgtgggg tgatctgcag aattcg        56

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ttatctgtcc cctccacccc acagtggggt gatctgcaga attcg                    45

<210> SEQ ID NO 32
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ccagtgtgat ggataatcct gtccctagct agggacagga ttggtgacag aaaagc        56

<210> SEQ ID NO 33
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ttatctgtcc cctccacccc acagtggggc cactagggac aggattggtg acagaatcga    60

<210> SEQ ID NO 34
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ttatctgtcc cctccacccc acagtggggg ccactaggga caggattggt gacagaatcg    60
a                                                                    61

<210> SEQ ID NO 35
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ttatctgtcc cctccaccac tagggacagg attggtgaca gaatcga                  47

<210> SEQ ID NO 36
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ttatctgtcc cctccacccc acagccacta gggacaggat tggtgacaga atcga         55

<210> SEQ ID NO 37
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ttatctgtcc cctccacccc acagtggggc cacactaggg acaggattgg tgacagaatc    60
ga                                                                   62

<210> SEQ ID NO 38
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tcgattctgt caccaatcct gtccctagct agggacagga ttggtgacag aaaagc        56

<210> SEQ ID NO 39
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tcgattctgt caccaatcct gtccctaggg acaggattgg tgacagaaaa gc            52

<210> SEQ ID NO 40
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
tcgattctgt caccaatcca ggattggtga cagaaaagc                                   39

<210> SEQ ID NO 41
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tcgattctgt caccaatcct gtccctagtg cactaggga caggattggt gacagaaaag           60
c                                                                            61

<210> SEQ ID NO 42
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tcgattctgt caccaatcct gtccctagtg gccactaggg acaggattgg tgacagaaaa          60
gc                                                                           62

<210> SEQ ID NO 43
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tcgattctgt caccaatcct gtccctaggg acaggattgg tgacagaaaa gc                  52

<210> SEQ ID NO 44
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gtgggcaaca tgctggtcat cctcatcgat gaggatgacc aagggcgaat tctg               54

<210> SEQ ID NO 45
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gtgggcaaca tgctggtcat cctcatcctg atcaggatga ggatgaccaa gggcgaattc           60
tg                                                                           62

<210> SEQ ID NO 46

```
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gtgggcaaca tgctggtcat cctcatatca ggatgaggat gaccaagggc gaattctg          58

<210> SEQ ID NO 47
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gtgggcaaca tgctggtcat cctcatcctg atgatgagga tgaccaaggg cgaattctg         59

<210> SEQ ID NO 48
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
cagaattcgc ccttggtcat cctcatcctg ataaactgca aaaggctgaa gagcatgac         59

<210> SEQ ID NO 49
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cagaattcgc ccttggtcct gaagagcatg ac                                      32

<210> SEQ ID NO 50
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
cagaattcgc ccttggtcat ccgataaact gcaaaaggct gaagagcatg ac                52

<210> SEQ ID NO 51
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cagaattcgc ccttggtcat cctcatcctg atgataaact gcaaaaggct gaagagcatg        60
ac                                                                       62
```

```
<210> SEQ ID NO 52
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cagaattcgc ccttggtcac tgcaaaaggc tgaagagcat gac                    43

<210> SEQ ID NO 53
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cagaattcgc ccttggtcat cctcatcctg agttattttc tgcaaaaggc tgaagagcat    60
gac                                                                  63

<210> SEQ ID NO 54
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
agcaaccttt gaccccaagc ccattcctgg gaattcccag gaatgggctt ggggtcatcg    60
aattc                                                                65

<210> SEQ ID NO 55
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
agcaaccttt gaccccaagc ccattcctgg gaactggttc ccaggaatgg gcttggggtc    60
atcgaattc                                                            69

<210> SEQ ID NO 56
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
agcaaccttt gaccccaagc ccattcctgg ttcccaggaa tgggcttggg gtcatcgaat    60
tc                                                                   62

<210> SEQ ID NO 57
<211> LENGTH: 66
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 57
agcaaccttt gaccccaagc ccattcctgg gaacttccca ggaatgggct tggggtcatc    60
gaattc    66

<210> SEQ ID NO 58
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
agcaaccttt gaccccaagc ccattcctgg gaactagttc tcaggaatgg gcttggggtc    60
atcgaattc    69

<210> SEQ ID NO 59
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
agcaaccttt gaccccaagc ccattcctgg gaaccagttc ccaggaatgg gcttggggtc    60
atcgaattc    69

<210> SEQ ID NO 60
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
agcaaccttt gaccccaagc ccattcctgg gaagttccca ggaatgggct tggggtcatc    60
gaattc    66

<210> SEQ ID NO 61
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ggaattcgat gaccccaagc ccattcctgg gaactggaat ggtgcaggct gccataccaa    60
cttt    64

<210> SEQ ID NO 62
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62

```
ggaattcgat gaccccaagc ccattcctgg gtgcaggctg ccataccaac ttt        53
```

<210> SEQ ID NO 63
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63

```
ggaattcgat gaccccaagc ccattcctgg gaacctggaa tggtgcaggc tgccatacca    60
acttt                                                               65
```

<210> SEQ ID NO 64
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64

```
ggaattcgat gaccccaagc ccattcctgg gaactgggac tggaatggtg caggctgcca    60
taccaacttt                                                          70
```

<210> SEQ ID NO 65
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65

```
ggaattcgat gaccccaagc ccattcctgg gaactggctg gaatggtgca ggctgccata    60
ccaacttt                                                            68
```

<210> SEQ ID NO 66
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66

```
ggaattcgat gaccccaagc ccattcctgg gaaccatgga atggtgcagg ctgccatacc    60
aacttt                                                              66
```

<210> SEQ ID NO 67
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67

```
ggaattcgat gaccccaagc ccattcctgg gaataccaac ttt                     43
```

<210> SEQ ID NO 68
<211> LENGTH: 59
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 68
tcgatgtttc gtgttcggag ccgctttaac ccactctgtg gaagtgctca gcattggag       59

<210> SEQ ID NO 69
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tcgatgtttc gtgttcggag ccgctttaac cctgactctg tggaagtgct cagcattgga      60
g                                                                      61

<210> SEQ ID NO 70
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tcgatgtttc gtgttcggag ccgctttaac tctgtggaag tgctcagcat tggag           55

<210> SEQ ID NO 71
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tcgatgtttc gtgttcggag ccgctttaaa acccactctg tggaagtgct cagcattgga      60
g                                                                      61

<210> SEQ ID NO 72
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
agcaaccttt gacccccaagc ccattcctgg gaattcccag gaatgggctt ggggtcatcg     60
aattc                                                                  65

<210> SEQ ID NO 73
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
agcaaccttt gacccccaagc ccattcctgg gaaccagttc ccaggaatgg gcttggggtc     60
``` atcgaattc 69

<210> SEQ ID NO 74
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
agcaaccttt gaccccaagc ccattcctgg gaactgttcc caggaatggg cttggggtca    60
tcgaattc                                                            68

<210> SEQ ID NO 75
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
agcaaccttt gaccccaagc ccattcctgg gaaccagttc ccaggaatgg gcttggggtc    60
atcgaattc                                                           69

<210> SEQ ID NO 76
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
agcaaccttt gaccccaagc ccattcctgg gaaccagttc ccaggaatgg gcttggggtc    60
atcgaattc                                                           69

<210> SEQ ID NO 77
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
agcaaccttt gaccccaagc ccattcctgg gaactgttcc caggaatggg cttggggtca    60
tcgaattc                                                            68

<210> SEQ ID NO 78
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
agcaaccttt gaccccaagc ccattcctgg gaaccagttc ccaggaatgg gcttggggtc    60
atcgaattc                                                           69

```
<210> SEQ ID NO 79
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ttgatttggt atggcagcct gcaccattaa tggtgcaggc tgccatacca actttagcac    60
ca                                                                  62

<210> SEQ ID NO 80
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (60)..(60)
<223> OTHER INFORMATION: a, c, t, g, unknown or other
<220> FEATURE:
<221> NAME/KEY: modified_base
<222> LOCATION: (62)..(62)
<223> OTHER INFORMATION: a, c, t, g, unknown or other

<400> SEQUENCE: 80
ttgatttggt atggcagcct gcaccattcc ggaatggtgc aggcagcaat aaaaactttn    60 gnacct                                                              66

<210> SEQ ID NO 81
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tggataaaaa aagagtgtat ctggccactg atgacccttc tttgttaaag gaggcaaaga    60
caaagtaagg ccgcgaattc                                               80

<210> SEQ ID NO 82
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tggataaaaa aagagtgtat ctggccactg atgacccttc tttaaggagg caaagacaaa    60
gtaaggccgc gaattc                                                   76

<210> SEQ ID NO 83
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
tggataaaaa aagagtgtat ctggccactg atgaccctgt taaggaggc aaagacaaag    60
```
taaggccgcg aattc                                                      75

<210> SEQ ID NO 84
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tggataaaaa aagagtgtat ctggccactg atgacccttc atgttaaagg aggcaaagac    60
aaagtaaggc cgcgaattc                                                  79

<210> SEQ ID NO 85
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ttagcggccg tgtatctggc cactgatgac ccttctttgt taaggaggc aaagacaaag    60 taagttagac caacaagtgg                                                 80

<210> SEQ ID NO 86
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ttagcggccg tgtatctggc cactggttaa aggaggcaaa gacaaagtaa gttagaccaa    60
caagtgg                                                               67

<210> SEQ ID NO 87
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ttagcggccg tgtatctggc cactgatgac ccaggcaaag acaaagtaag ttagaccaac    60
aagtgg                                                                66

<210> SEQ ID NO 88
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ttagcggccg tgtatctggc cactgatgac ccttcttta aaggaggcaa agacaaagta    60
agttagacca acaagtgg                                                   78

```
<210> SEQ ID NO 89
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ttagcggccg tgtatctggc cactgatgac cctaaagaca agtaagtta gaccaacaag    60 tgg                                                                 63

<210> SEQ ID NO 90
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
tggataaaaa aagagtgtat ctggccactg atgacccttc ttaagaaggg tcatcagtgg   60
ccagatacac ggccgctaaa ttca                                          84

<210> SEQ ID NO 91
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
tggataaaaa aagagtgtat ctggccactg atgacccttc tacacggccg ctaaattca    59

<210> SEQ ID NO 92
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gaattcgcgg ccttactttg tctttgcctc ctttaacatg ttaaaggagg caaagacaaa   60
gtaagttaga ccaacaa                                                  77

<210> SEQ ID NO 93
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gaattcgcaa agacaaagta agttagacca acaa                               34

<210> SEQ ID NO 94
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 94
gaattcgcgg ccttactttg tctttgttaa aggaggcaaa gacaaagtaa gttagaccaa      60
caa                                                                   63

<210> SEQ ID NO 95
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gaattcgcgg ccttactttg tcttttgtta aaggaggcaa agacaaagta agttagacca      60
acaa                                                                  64

<210> SEQ ID NO 96
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gaattcgcgg ccttactttg tctttgcctc ctttaagtta aggaggcaa agacaaagta       60 agttagacca acaa                                                       74

<210> SEQ ID NO 97
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tggataaaaa aagagtgtat ctggccactg atgaccctta tttgttaaag gaggcaaaga     60
caaagtaagg ccgcgaattc                                                 80

<210> SEQ ID NO 98
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tggataaaaa aagagtgtat ctggccactg atgacccttt aaaggaggca aagacaaagt     60
aaggccgcga attc                                                       74

<210> SEQ ID NO 99
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tggataaaaa aagagtgtat ctggccactc tttgttaaag gaggcaaaga caaagtaagg     60
```

```
ccgcgaattc                                                            70

<210> SEQ ID NO 100
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tggataaaaa aagagtgtat ctggccactg atgttaaagg aggcaaagac aaagtaaggc     60
cgcgaattc                                                             69

<210> SEQ ID NO 101
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ttagcggccg tgtatctggc cactgatgac ccttcctttg ttaaaggagg caaagacaaa     60
gtaagttaga ccaacaagtg                                                 80

<210> SEQ ID NO 102
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
tggataaaaa aagagtgtat ctggccactg atgacccttg aagggtcatc agtggccaga     60
tacacggccg ctaaattcaa                                                 80

<210> SEQ ID NO 103
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
tggataaaaa aagagtgtat ctggccactg atgacccttc tacacggccg ctaaattcaa     60

<210> SEQ ID NO 104
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gaattcgcgg ccttactttg tctttgcctc ctttaacaaa gttttgttaa aggaggcaaa     60
gacaaagtaa gttagaccaa                                                 80

<210> SEQ ID NO 105
<211> LENGTH: 74
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 105
gaattcgcgg ccttactttg tctttgcctc ctttaatttg ttaaaggagg caaagacaaa    60
gtaagttaga ccaa                                                      74

<210> SEQ ID NO 106
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gaattcgcgg ccttactttg tctttgcctc ctctttgtta aaggaggcaa agacaaagta    60
agttagacca a                                                         71

<210> SEQ ID NO 107
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
accccacagt ggggccacta gggacaggat                                     30

<210> SEQ ID NO 108
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
atcctgtccc tagtggcccc actgtggggt                                     30

<210> SEQ ID NO 109
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
accccacagt ggg                                                       13

<210> SEQ ID NO 110
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
tggccccact gtggggt                                                   17
```

```
<210> SEQ ID NO 111
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
accccacagt gggtggccta gggacaggat                                          30

<210> SEQ ID NO 112
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
atcctgtccc taggccaccc actgtggggt                                          30

<210> SEQ ID NO 113
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
accccacagt ggg                                                            13

<210> SEQ ID NO 114
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gccacccact gtggggt                                                        17

<210> SEQ ID NO 115
<211> LENGTH: 9
<212> TYPE: PRT
<213> ORGANISM: Unknown
<220> FEATURE:
<223> OTHER INFORMATION: Description of Unknown: "LAGLIDADG" family
      motif peptide

<400> SEQUENCE: 115

Leu Ala Gly Leu Ile Asp Ala Asp Gly
1               5

<210> SEQ ID NO 116
<211> LENGTH: 2259
<212> TYPE: DNA
<213> ORGANISM: Triticum aestivum
<220> FEATURE:
<221> NAME/KEY: modified_base
<222> LOCATION: (2207)..(2207)
<223> OTHER INFORMATION: a, c, t, g, unknown or other
<220> FEATURE:
<221> NAME/KEY: modified_base
<222> LOCATION: (2210)..(2210)
<223> OTHER INFORMATION: a, c, t, g, unknown or other
```

<400> SEQUENCE: 116

```
tcgcccaaac cctcgccgcc gccatggccg cagccacctc cccgccgtc gcattctcgg      60
gcgccaccgc cgccgccatg cccaaacccg cccgccatcc tctcccgcgc caccagcccg    120
tctcgcgccg cgccgctcccc gcccgcgtcg tcaggtgttg cgccgcgtcc cccgccgcca   180
cctccgccgc gcctcccgca accgcgctcc ggccatgggg cccgtccgag ccccgcaagg    240
gcgccgacat cctcgtcgag gcgctcgagc gctgcggcat cgtcgacgtc ttcgcctacc    300
ccggcggcgc ctccatggag atccaccagg cgctgacgcg ctcgcccgtc atcaccaacc    360
acctcttccg ccacgagcag ggggaggcgt tcgcggcgtc cggctacgcc cgcgcgtccg    420
gccgcgtcgg cgtctgcgtc gccacctccg gcccgggggc caccaacctc gtctccgcgc    480
tcgccgacgc cctcctcgac tccatcccca tggtcgccat cacgggccag gtcccccgcc    540
gcatgatcgg cacggacgcg ttccaggaga cgcccatagt ggaggtcacg cgctccatca    600
ccaagcacaa ctacctggtc cttgacgtgg aggatatccc ccgcgtcatc caggaagcct    660
tcttccttgc atcctctggc cgcccggggc cggtgctagt tgatatcccc aaggacatcc    720
agcagcagat ggctgtgccc gtctgggaca ctccaatgag tttgccaggg tacatcgccc    780
gcctgcccaa gccaccatct actgaatcgc ttgagcaggt cctgcgtctg gttggcgagt    840
cacggcgccc aattctgtat gttggtggtg gctgcgctgc gtctggcgag gagttgcgcc    900
gctttgttga gcttactggg attccagtta caactactct gatgggcctt ggcaacttcc    960
ccagcgacga cccactgtct ctgcgcatgc ttgggatgca tggcactgtg tatgcaaatt   1020
atgcagtaga taaggctgac ctgttgctcg catttggtgt gcggtttgat gatcgtgtga   1080
ctgggaaaat cgaggctttt gcaagcaggt ccaagattga gcacattgac attgacccag   1140
ctgagattgg cagaacaagc agccacatgt ctccatttgt gcagatgtta agcttgcttt   1200
acaggggttg aatgatctat taaatgggag caaagcacaa cagggtctgg atttggtcc    1260
atggcacaag gagttggatc agcagaagag ggagtttcct ctaggattca agacttttgg   1320
cgaggccatc ccgccgcaat atgctatcca ggtactggat gagctgacaa aaggggaggc   1380
gatcattgcc actggtgttg ggcagcacca gatgtgggcg gctcagtatt acacttacaa   1440
gcggccacgg cagtggctgt cttcgtctgg tttgggggca atgggatttg ggttaccagc   1500
tgcagctggc gctgctgtgg ccaacccagg tgttacagtt gttgacattg atggtgatgg   1560
tagtttcctc atgaacattc aggagttggc gttgatccgc attgagaacc tcccagtgaa   1620
ggtgatgata ttgaacaacc agcatctggg aatggtggtg cagtgggagg ataggtttta   1680
caaggccaat cgggcgcaca catacctttgg caacccagaa aatgagagtg agatatatcc   1740
agattttgtg acgattgcta aaggattcaa cgttccagca gttcgagtga cgaagaagag   1800
cgaagtcact gcagcaatca agaagatgct tgagacccca gggccatact tgttggatat   1860
catagtcccg catcaggagc acgtgctgcc tatgatccca agcggtggtg ctttcaagga   1920
catgatcatg gagggtgatg gcaggacctc gtactgaaat ttcgacctac aagacctaca   1980
agtgtgacat gcgcaatcag catgatgccc gcgtgttgta tcaactacta ggggttcaac   2040
tgtgagccat gcgttttcta gtttgcttgt ttcattcata taagcttgta ttacttagtt   2100
ccgaaccctg tagttttgta gtctatgttc tcttttgtag ggatgtgctg tcataagatg   2160
tcatgcaagt ttcttgtcct acatatcaat aataagtact tccatgnaan aaaaaaaaa    2220
aaaaaaaaaa aaaaaaaaaa aaaaaaaaaa aaaaaaaa                          2259
```

```
<210> SEQ ID NO 117
<211> LENGTH: 2265
<212> TYPE: DNA
<213> ORGANISM: Triticum aestivum
<220> FEATURE:
<221> NAME/KEY: modified_base
<222> LOCATION: (2213)..(2213)
<223> OTHER INFORMATION: a, c, t, g, unknown or other
<220> FEATURE:
<221> NAME/KEY: modified_base
<222> LOCATION: (2216)..(2216)
<223> OTHER INFORMATION: a, c, t, g, unknown or other

<400> SEQUENCE: 117
```

| | | | | | |
|---|---|---|---|---|---|
| tcgcccaaac | cctcgccgcc | gccatggccg | cagccacctc | cccgccgtc | gcattctcgg | 60 |
| gcgccgccgc | cgccgccgcc | gccatcccca | aacccgcccg | ccagcctctc | ccgcgccacc | 120 |
| agcccgcctc | gcgccgcgcg | ctccccgccc | gcatcgtcag | gtgctgcgcc | gcgtcccccg | 180 |
| ccgccacctc | cgtcgcgcct | cccgccaccg | cgctccggcc | gtggggcccc | tccgagcccc | 240 |
| gcaagggcgc | cgacatcctc | gtcgaggcgc | tggagcgctg | cggcatcgtc | gacgtcttcg | 300 |
| cctaccctgg | cggcgcgtcc | atggagatcc | accaggcgct | gacgcgctcg | ccagtcatca | 360 |
| ccaaccacct | cttccgccac | gagcaggggg | aggcgttcgc | ggcgtccggg | tacgcccgcg | 420 |
| cgtccggccg | cgtcggcgtc | tgcgtcgcca | cctccggccc | ggggccacc | aacctcgtct | 480 |
| ccgcgctcgc | cgacgctctc | ctcgactcca | tccccatggt | cgccatcacg | gccaggtcc | 540 |
| cccgccgcat | gatcggcacg | gatgcgttcc | aggagacgcc | catcgtggag | gtcacgcgct | 600 |
| ccatcaccaa | gcacaactac | ctggtccttg | acgtggagga | tatccccgc | gtcatccagg | 660 |
| aagccttctt | cctcgcatcc | tctggccgcc | cgggccggt | gctggttgat | atccccaagg | 720 |
| acatccagca | gcagatggct | gtgcctgtct | gggacacgcc | gatgagtttg | ccagggtaca | 780 |
| tcgcccgcct | gcccaagcca | ccatctactg | aatcgcttga | gcaggtcctg | cgtctggttg | 840 |
| gcgagtcacg | gcgcccaatt | ctgtatgttg | gtggtggctg | cgctgcatct | ggtgaggagt | 900 |
| tgcgccgctt | tgttgagctc | actgggattc | cagttacaac | tactcttatg | ggccttggca | 960 |
| acttccccag | tgacgaccca | ctgtctctgc | gcatgctggg | gatgcatggc | actgtgtatg | 1020 |
| caaattatgc | agtagataag | gctgacctgt | tgcttgcatt | tggtgtgcgg | tttgatgatc | 1080 |
| gtgtgaccgg | gaaaatcgag | gcttttgcaa | gcaggtccaa | gattgagcac | attgacattg | 1140 |
| acccagctga | gattggcaga | acaagcagcc | acatgtctcc | atttgtgcag | atgttaagct | 1200 |
| tgctttacag | gggttgaatg | ctctattaaa | tgggagcaaa | gcacaacagg | gtctggattt | 1260 |
| tggtccatgg | cacaaggagt | tggatcagca | gaagagggag | tttcctctag | gattcaagac | 1320 |
| ttttggtgag | gccatcccgc | cgcaatatgc | tatccaggta | ctggatgagc | tgacaaaagg | 1380 |
| ggaggcgatc | attgccaccg | tgttgggca | gcatcagatg | tgggcggctc | agtattacac | 1440 |
| ttacaagcgg | ccacggcagt | ggctgtcttc | atccggttg | ggtgcaatgg | gatttgggtt | 1500 |
| gccagctgca | gctggcgctg | ctgtggccaa | cccaggtgtt | acagttgttg | acattgatgg | 1560 |
| ggatggtagt | ttcctcatga | acattcagga | gttggcgttg | atccgtattg | agaacctccc | 1620 |
| agtgaaggtg | atgatattga | acaaccagca | tctgggaatg | gtggtgcagt | gggaggatag | 1680 |
| gttttacaag | gccaaccggg | cgcacacata | ccttggcaac | ccagaaaatg | agagtgagat | 1740 |
| atatccagat | tttgtgacga | ttgctaaagg | attcaacgtt | ccggcagttc | gtgtgacgaa | 1800 |
| gaagagcgaa | gtcactgcag | caatcaagaa | gatgcttgag | accccagggc | catacttgtt | 1860 |
| ggatatcatt | gtcccgcatc | aggagcacgt | gctgcctatg | atcccaagcg | gtggtgcttt | 1920 |

| | |
|---|---|
| taaggacatg atcatggagg gtgatggcag gacctcgtac tgaaatttcg acctacaaga | 1980 |
| cctacaagtg tgacatgcgc aatcagcatg atacctgcgt gttgtatcaa ctactggggg | 2040 |
| ttcaactgtg aaccatgcgt tttctagttt gcttgtttca ttcatataag cttgtgttac | 2100 |
| ttagttccga accgtgtagt tttgtagtct ctgttctctt ttgtagggat gtgctgtcat | 2160 |
| aagatatcat gcaagtttct tgtcctacat atcaataata agcacttcca tgnaanaaaa | 2220 |
| aaaaaaaaaa aaaaaaaaaa aaaaaaaaaa aaaaaaaaaa aaaaa | 2265 |

```
<210> SEQ ID NO 118
<211> LENGTH: 2259
<212> TYPE: DNA
<213> ORGANISM: Triticum aestivum
<220> FEATURE:
<221> NAME/KEY: modified_base
<222> LOCATION: (32)..(32)
<223> OTHER INFORMATION: a, c, t, g, unknown or other
<220> FEATURE:
<221> NAME/KEY: modified_base
<222> LOCATION: (66)..(66)
<223> OTHER INFORMATION: a, c, t, g, unknown or other
<220> FEATURE:
<221> NAME/KEY: modified_base
<222> LOCATION: (80)..(80)
<223> OTHER INFORMATION: a, c, t, g, unknown or other
<220> FEATURE:
<221> NAME/KEY: modified_base
<222> LOCATION: (98)..(98)
<223> OTHER INFORMATION: a, c, t, g, unknown or other
<220> FEATURE:
<221> NAME/KEY: modified_base
<222> LOCATION: (121)..(121)
<223> OTHER INFORMATION: a, c, t, g, unknown or other
<220> FEATURE:
<221> NAME/KEY: modified_base
<222> LOCATION: (147)..(147)
<223> OTHER INFORMATION: a, c, t, g, unknown or other
<220> FEATURE:
<221> NAME/KEY: modified_base
<222> LOCATION: (158)..(158)
<223> OTHER INFORMATION: a, c, t, g, unknown or other
<220> FEATURE:
<221> NAME/KEY: modified_base
<222> LOCATION: (2207)..(2207)
<223> OTHER INFORMATION: a, c, t, g, unknown or other
<220> FEATURE:
<221> NAME/KEY: modified_base
<222> LOCATION: (2210)..(2210)
<223> OTHER INFORMATION: a, c, t, g, unknown or other

<400> SEQUENCE: 118
```

| | |
|---|---|
| tcgcccaaac cctcgccgcc gccatggccg cngccacctc cccgccgtc gcattctcgg | 60 |
| gcgccnccgc cgccgccatn cccaaacccg cccgccancc tctcccgcgc caccagcccg | 120 |
| nctcgcgccg cgccgctcccc gcccgcntcg tcaggtgntg cgccgcgtcc cccgccgcca | 180 |
| cctccgccgc gccccccgcc accgcgctcc ggccctgggg cccgtccgag ccccgcaagg | 240 |
| gcgccgacat cctcgtcgag gcgctcgagc gctgcggcat cgtcgacgta ttcgcctacc | 300 |
| ccggcggcgc gtccatggag atccaccagg cgctgacgcg ctcgcccgtc atcaccaacc | 360 |
| acctcttccg ccacgagcag ggggaggcgt tcgcggcgtc cggctacgcc cgcgcgtccg | 420 |
| gccgcgtcgg cgtctgcgtc gccacctccg gccggggggc caccaacctc gtctccgcgc | 480 |
| tcgctgacgc cctcctcgac tccatcccca tggtcgccat cacgggccag gtccccgcc | 540 |
| gcatgatcgg cacggacgcg ttccaggaga cgcccatagt ggaggtcacg cgctccatca | 600 |
| ccaagcacaa ctacctggtc cttgacgtgg aggatatccc ccgcgtcatc caggaagcct | 660 |
| tcttcctcgc gtcctctggc cgcccggggc cggtgctggt tgatatcccc aaggatatcc | 720 |

| | |
|---|---|
| agcagcagat ggccgtgcct atctgggaca cgccgatgag tttgccaggg tacatcgccc | 780 |
| gcctgcccaa gccaccatct actgaatcgc ttgagcaggt cctgcgtctg gttggcgagt | 840 |
| cacggcgccc aattctgtat gttggtggtg gctgcgctgc atccggcgag gagttgcgcc | 900 |
| gctttgttga gctcactggg attccggtta caactactct gatgggcctt ggcaacttcc | 960 |
| ccagcgacga cccactgtct ctgcgcatgc ttgggatgca tggcactgtg tatgcaaatt | 1020 |
| atgcagtcga taaggctgac ctgttgcttg catttggtgt gcggtttgat gatcgcgtga | 1080 |
| ctgggaaaat cgaggccttt gcaagcaggt ccaagattga gcacattgac attgacccag | 1140 |
| ctgagattgg cagaacaagc agccacatgt ctccatttgt gcagatgtta agcttgcttt | 1200 |
| acaggggttg aatgctctat taaatgggag caaagcacaa cagggtctgg attttggtcc | 1260 |
| atggcacaag gagttggatc agcagaagag ggagtttcct ctaggattca agacttttgg | 1320 |
| cgaggccatc ccgccgcaat atgctatcca ggtactggat gagctgacaa aaggggaggc | 1380 |
| gatcattgct actggtgttg ggcagcacca gatgtgggcg gctcagtatt acacttacaa | 1440 |
| gcggccacgg cagtggctgt cttcgtctgg tttgggggca atgggatttg ggttaccagc | 1500 |
| tgcagctggc gctgctgtgg ccaacccagg tgttacagtt gttgacattg atggagatgg | 1560 |
| tagtttcctc atgaacattc aggagttggc attgatccgt attgagaacc tccctgtgaa | 1620 |
| ggtgatgata ttgaacaacc agcatctggg aatggtggtg caatgggagg ataggtttta | 1680 |
| caaggccaat cgggcgcaca catccttgg caacccagaa aatgagagtg agatatatcc | 1740 |
| agattttgtg acgattgcta aaggattcaa cgttccggca gttcgtgtga cgaagaagag | 1800 |
| cgaagtcact gcagcaatca gaagatgct tgagaccca gggccatact tgttggatat | 1860 |
| catcgtcccg catcaggagc acgtgctgcc tatgatccca agcggtggtg ctttcaagga | 1920 |
| catgatcatg gagggtgatg gcaggacctc gtactgaaat ttcgacctac aagacctaca | 1980 |
| agtgtgacat gcgcaatcag catggtgccc gcgtgttgta tcaactacta ggggttcaac | 2040 |
| tgtgaaccat gcgttttcta gtttgcttgt ttcattcata taagcttgtg ttacttagtt | 2100 |
| ccgaaccctg tagctttgta gtctatgctc tcttttgtag ggatgtgctg tcataagata | 2160 |
| tcatgcaagt ttcttgtcct acatatcaat aataagtact tccatgnaan aaaaaaaaaa | 2220 |
| aaaaaaaaaa aaaaaaaaaa aaaaaaaaaa aaaaaaaa | 2259 |

<210> SEQ ID NO 119
<211> LENGTH: 4357
<212> TYPE: DNA
<213> ORGANISM: Triticum aestivum

<400> SEQUENCE: 119

| | |
|---|---|
| cgttgtgcct tggcagtctc aggttgagcc ctcaccattg aagtagcatg ggtcattgga | 60 |
| ttgacccgat ttgacggcgg atctattgga tcttcccttt gtgtcgtttt atactggtat | 120 |
| agatgtttaa cacatatttg gaaaatatat tcaaaacatg tttctataaa aaagtttaaa | 180 |
| ctatacatgt ataatggaag tcatttataa gaatgttttt acatgtataa aagatgtaca | 240 |
| tcatatgtgc aaaagtagac atgtgttaga aaaataaac aaacaaatac ataaaaagaa | 300 |
| aatcaaagaa aaaacaaccc aaaaaaccaa agaaaataaa gaagaagaag aaaaagagaa | 360 |
| aaaacattga aaatcaaaga agaaaaaaac ataagaaaa gaaaaccgaa aaatactggc | 420 |
| aaaaacacac aaaaaatgaa aagaaaaaat aagaaaaacc ggactttacc aatcgaacgg | 480 |
| agcgatcgga cacgaatgag cgaaggcatg catcgagcaa caccgctaat tgaccggccc | 540 |

```
gtagtcgttc gcccgtagac cattcataag aatcggtatc ggagagacat agggggttctt    600 tggtttctaa ccatatcttg tcacacttta ccatacatca ccttagtcaa atctgatcaa    660
attaggtgag tatttggttc tagccacatc taaggcaaga tttgtttttc tgagcagtga    720
accccatatg tcatagacag aaaaattgtg aaaagattcc tttagacggt caaagcgtgg    780
ttaacaattt aatcaactca agtaagataa atgcgataaa tgtgacaaaa ataatgtgtt    840
atagaagtat gacaaaaata atcacaatcc aaacagtctg atagcttggc gagtgcaaaa    900
tagatacgaa atctctggtg atatcacacg ggtccaaaat aattgcttgt ttgagcatca    960
gcctttctgc acaaaaaaag ctagcccaaa caaacgagtg gcgtcccatc tgaaccacac   1020
gctcacccgc cgcgtgacag cgccaaagac aaaaccatca cccctcccca attccaaccc   1080
tctctccgcc tcacagaaat ctctcccctc gcccaaaccc tcgccgccgc catggccgcc   1140
gccacctccc ccgccgtcgc attctccggc gccgccgccg ccgccgccgc catgcccaag   1200 cccgccgcc agcctctccc gcgccaccag cccgcctcgc gccgcgcgct ccccgcccgc   1260
gtcgtcaggt gctgcgccgc gccccccgct gctgccacct ccgccgcgcc cccgccacc   1320 gcgctccggc cctggggccc gtccgagccc cgcaagggcg ccgacatcct cgtcgaggcg   1380
ctcgagcgct gcggcatcgt cgacgtattc gcctaccccg gcggcgcgtc catggagatc   1440
caccaggcgc tgacgcgctc gcccgtcatc accaaccacc tcttccgcca cgagcagggg   1500
gaggcgttcg cggcgtccgg ctacgcccgc gcgtccggcc gcgtcggcgt ctgcgtcgcc   1560
acctccggcc cggggcccac caacctcgtc tccgcgctcg ctgacgccct cctcgactcc   1620
atccccatgg tcgccatcac gggccaggtc ccccgccgca tgatcggcac ggacgcgttc   1680
caggagacgc ccatagtgga ggtcacgcgc tccatcacca agcacaacta cctggtcctt   1740
gacgtggagg atatccccg cgtcatccag gaagccttct tcctcgcgtc ctctggccgc   1800
ccggggccgg tgctggttga tatccccaag gatatccagc agcagatggc cgtgcctatc   1860
tgggacacgc cgatgagttt gccagggtac atcgtcccgc ctgcccaagc caccatctac   1920
tgaatcgctt gagcaggtcc tgcgtctggt tggygagtca cggcgcccaa ttctgtatgt   1980
tggtggtggc tgcgctgcat ccggcgagga gttgcgccgc tttgttgagc tcactgggat   2040
tccggttaca actactctga tgggccttgg caacttcccc agcgacgacc cactgtctct   2100
gcgcatgctt gggatgcatg gcactgtgta tgcaaattat gcagtcgata aggctgacct   2160
gttgcttgca tttggtgtgc ggtttgatga tcgcgtgact gggaaaatcg aggcctttgc   2220
aagcaggtcc aagattgtgc acattgacat tgacccagct gagattggca agaacaagca   2280
gccacatgtc tccatttgtg cagatgttaa gcttgcttta caggggttga atgctctatt   2340
aaatgggagc aaagcacaac agggtctgga ttttggtcca tggcacaagg agttggatca   2400
gcagaagagg gagtttcctc taggattcaa gacttttggc gaggccatcc cgccgcaata   2460
tgctatccag gtactggatg agctgacaaa aggggaggcg atcattgcta ctggtgttgg   2520
gcagcaccag atgtgggcgg ctcagtatta cacttacaag cggccacggc agtggctgtc   2580
ttcgtctggt ttgggggcaa tgggatttgg gttaccagct gcagctggcg ctgctgtggc   2640
caacccaggt gttacagttg ttgacattga tggagatggt agtttcctca tgaacattca   2700
ggagttggca ttgatccgta ttgagaacct ccctgtgaag gtgatgatat tgaacaacca   2760
gcatctggga atggtggtgc aatgggagga taggttttac aaggccaatc gggcgcacac   2820
ataccttggc aacccagaaa atgagagtga gatatatcca gattttgtga cgattgctaa   2880
aggattcaac gttccggcag ttcgtgtgac gaagaagagc gaagtcactg cagcaatcaa   2940
```

```
gaagatgctt gagaccccag ggccatactt gttggatatc atcgtcccgc atcaggagca    3000
cgtgctgcct atgatcccaa gcggtggtgc tttcaaggac atgatcatgg agggtgatgg    3060
caggacctcg tactgaaatt tcgacctaca agacctacaa gtgtgacatg cgcaatcagc    3120
atggtgcccg cgtgttgtat caactactag gggttcaact gtgaaccatg cgttttctag    3180
tttgcttgtt tcattcatat aagcttgtgt tacttagttc cgaaccctgt agctttgtag    3240
tctatgctct cttttgtagg gatgtgctgt cataagatat catgcaagtt tcttgtccta    3300
catatcaata ataagtactt ccatggaata attctcagtt ctgttttgaa ttttgcatct    3360
tctcacaaac agtgtgctgg ttcctttctg ttactttaca tgtctgccgt gtccggttat    3420
gacataatga ccgatggagg gtggtcagca ggttttagac ggggagttga aacttttttt    3480 tgggggaag aaatctgaat acagttggga ggaaagataa aagcatatac cttgattaat     3540
ttattgagcc caatatccag cctaatttat caagcaatag gcagtgtagg gtgttggcat    3600
tcttctcttc cttgagatct ggtgtcggga ccccgattct aagtcacacc gatctagcat    3660
gtaacacctc atatcacttt gcggcctcac gcacggtatc ctcacgggtg tcgccttacc    3720
atggcccggg accgtttgcg ccttttggct cacgtatatg atggtgtcgc tagyatccat    3780
atgacagaga acccgggccg acatrgctag tcgtgaaccc aaagcggcac agacctatgg    3840
agacaggcat acatgaatca catcgagcat gtcggtcaac agcgtatgaa tccgggctgt    3900
agcactgggc taacaggact ccggggaacc cgggctgtag caggctaggc aggactccgg    3960
aagtcaccgc gtgacatttc cccgaaggga cagacatagg aacgaagtgg aacacatgcc    4020
ggccagtcaa gtgttctgag cagtagtgct gggctagcag gactccggtg aaccgggctg    4080
tagcggacta ctatggctcg aggtagcact agactacatt tccccataag agaggctkcc    4140
aaggataagc aactagattg tcggrtcycr srywttgtct ccgtgtgttg ttattgttgt    4200
catgcaagta tgtgttgtac aacatggcat cacaacataa cgcaaactca tatagatata    4260
ggctcagaga gccacatagc attaatacga acagggtcac atgacccatc attcagagca    4320
tacagcatga agcatcatgt ctgagtacag acactac                             4357
```

<210> SEQ ID NO 120
<211> LENGTH: 7585
<212> TYPE: DNA
<213> ORGANISM: Triticum aestivum

<400> SEQUENCE: 120

```
ctgaaaattc aatatggccc tcgggcacca atgctcttgc ttccaatttt cataattccc      60
atttgtaaaa aacacaccac aaaaatcaca ctgtagtaat ctacatgttt gttgagccta     120
taaatcttca taaataatt gagattaatg cggtttgtgc aaaaatatgg ggttggtcat      180
gtttctacat atttctattt gcatttcgtt aactggtgct tgttatttt gtacataatg      240 catatctcat tgttattatt tttaaccttt tgagatggta acgaagatcc aaacatgcat     300
agatgattct ccggatgatt ttttgtagcc tgcactagga actcccaaga gccagaaggt     360
tgggtttgta caagataaca tttgtttgaa cacactcata acctgcatgt gacatacatg     420
acgtaactta tagtgatgat tcgacaaatg tctctttgtc caattttgtt atatatcccg     480
tggcaacgca cgggcattcg actagtatat gtaaagatat caatgtgacg agtccccatg     540
gtcgttgcgc ttgtccacta ccggctcgct agaggcgact ctcacctaga agtcgctacg     600
agcaatacat agtcgttctg ggcgcagcta tgttctgcct tttgcgacgc tcaggcacgg     660
```

```
cttgcctaca gcctgagggt cgggctagga accactaatt gtgtcatgct gatgtcacaa    720
tgacatcatg catattttta ttttcgtttt tcgctttctc tttaattta tttgtatttc     780
aaaatatttt atatattttt tgaatttttt caatgttgta tttgaaaaat gttaaacctg    840
tatagagaaa aatattttg atatatataa agtatataa catgaatgaa aaatgtataa      900
atgttaatta tgtgtaccaa aaatgttgat aacaattagc agtctcacat atttcaaaat   960
aaatgtatgt ggaattaaaa aatatgtgta tttaagttta aaaaaaatgt tcatgtaatg   1020
ttcgtaaaat gtttgataca ttcaataaaa attatgtcac atttgaataa ttcttctcaa   1080
gcttaacaaa tgcgctcatt atattatcaa aaattgtctg tacagtgtac acaaatgttt   1140
atgtagttca aaaaaaatgt tttttcagta aaaatatatt tgatcatgta ttttataaaa   1200
aactgtttaa tatatattta gaaaatatat tcaaaacatg tttctgtaaa aagttaaaac   1260
tatacatgta taatgtaagt catttataat aaatgtttta catgtataaa aaatgtacaa   1320
catatgtgca aaagtagaca tgtgttgaaa aaataaacaa ataactaaat aaaaagaaaa   1380
tcaaagaaaa acaccaaaaa ccaaagaaat aaataaaacc aaagtataaa gaagarraaa   1440
ggagaaaaaa cattgaaaat caaagaraaa aacataaaga agaaaaaaac cgaagaaaac   1500
tagcaaaaaa cacacacaca aaaaagaaaa tgaaagaaaa taataaagaa agccggactg   1560
aaccgatcaa acgcagcgat cgaacatgga tgagctaagg catgcatcga caacacggc    1620
taattggccg gcccgtagtc gttcgcccgt agaccattcc tacgaatcgg taccggagag   1680
acataggggc tgtatggttc ctaaccatac cttgccacac tttgtcacac ctcatcttag   1740
gcaaatttaa tcaagttatg taggtgtttg gttttagcca catctaaggc aagatttatt   1800
ttcctgagca gtgaacccca tatgttatag acataaaaag tgtgggaaga ttcccttag    1860
tcaaactgtg gctaacaatt tattaagaat taacttaagt aagataggtg caacaaatgt   1920
agcaaaaata atgtggtata tatagcaaag atagccacaa ccgcgagtgg aaataccaga   1980
tacgagatct ctggtcatat cacacgagtc caaattaatt gctttgtttg aggttcagcc   2040
ttttgcataa aaaagctagc ccaaacaaac gagtggcgtc ccatctgaac cacacactca   2100
cccgccgcgt gacagcgcca aagacaaaac catcacccct ccccaattcc aaccctctct   2160
ctgcctcaca gaaatctctc cctcgcccaa acctcgccg ccgccatggc cgcagccacc    2220
tccccgccg tcgcattctc gggcgccgcc gccgccgccg ccgccatacc caaacccgcc    2280
cgccagcctc tcccgcgcca ccagcccgcc tcgcgccgcg cgctcccgc ccgcatcgtc     2340
aggtgctgcg ccgcgtcccc cgccgccacc tccgtcgcgc ctcccgccac cgcgctccgg   2400
ccgtggggcc cctccgagcc ccgcaagggc gccgacatcc tcgtcgaggc gctggagcgc   2460
tgcggcatcg tcgacgtctt cgcctaccct ggcggcgcgt ccatggagat ccaccaggcg   2520
ctgacgcgct cgccagtcat caccaaccac ctcttccgcc acgagcaggg ggaggcgttc   2580
gcggcgtccg ggtacgcccg cgcgtccggc gcgtcggcg tctgcgtcgc cacctccggc    2640
ccgggggcca ccaacctcgt ctccgcgctc gccgacgctc tcctcgactc catccccatg   2700
gtcgccatca cgggccaggt cccccgccgc atgatcggca cggatgcgtt ccaggagacg   2760
cccatcgtgg aggtcacgcg ctccatcacc aagcacaact acctggtcct tgacgtggag   2820
gatatccccc gcgtcatcca ggaagccttc ttcctcgcat cctctggccg cccggggccg   2880
gtgctggttg atatccccaa ggacatccag cagcagatgg ctgtgcctgt ctgggacacg   2940
ccgatgagtt tgccagggta catcgcccgc ctgcccaagc caccatctac tgaatcgctt   3000
gagcaggtcc tgcgtctggt tggcgagtca cggcgcccaa ttctgtatgt tggtggtggc   3060
```

```
tgcgctgcat ctggtgagga gttgcgccgc tttgttgagc tcactgggat tccagttaca    3120
actactctta tgggccttgg caacttcccc agtgacgacc cactgtctct gcgcatgctg    3180
gggatgcatg gcactgtgta tgcaaattat gcagtagata aggctgacct gttgcttgca    3240
tttggtgtgc ggtttgatga tcgtgtgacc gggaaaatcg aggcttttgc aagcaggtcc    3300
aagattgtgc acattgacat tgacccagct gagattggca agaacaagca gccacatgtc    3360
tccatttgtg cagatgttaa gcttgcttta caggggttga atgctctatt aaatgggagc    3420
aaagcacaac agggtctgga ttttggtcca tggcacaagg agttggatca gcagaagagg    3480
gagtttcctc taggattcaa gacttttggt gaggccatcc cgccgcaata tgctatccag    3540
gtactggatg agctgacaaa aggggaggcg atcattgcca ccggtgttgg gcagcatcag    3600
atgtgggcgg ctcagtatta cacttacaag cggccacggc agtggctgtc ttcatccggt    3660
ttgggtgcaa tgggatttgg gttgccagct gcagctggcg ctgctgtggc caacccaggt    3720
gttacagttg ttgacattga tggggatggt agtttcctca tgaacattca ggagttggcg    3780
ttgatccgta ttgagaacct cccagtgaag gtgatgatat tgaacaacca gcatctggga    3840
atggtggtgc agtgggagga taggttttac aaggccaacc gggcgcacac ataccttggc    3900
aacccagaaa atgagagtga gatatatcca gattttgtga cgattgctaa aggattcaac    3960
gttccggcag ttcgtgtgac gaagaagagc gaagtcactg cagcaatcaa gaagatgctt    4020
gagaccccag ggccatactt gttggatatc attgtcccgc atcaggagca cgtgctgcct    4080
atgatcccaa gcggtggtgc ttttaaggac atgatcatgg agggtgatgg caggacctcg    4140
tactgaaatt tcgacctaca agacctacaa gtgtgacatg cgcaatcagc atgataccctg    4200
```

```
tttctggtct tttctgatga aagcggcgtg gtggctgggg gctttagaat atttcattga    5460
ttaactaaaa caaatcagat ccctttttcc tgcttcatgt gtgtttgacc aatcttttt     5520
taaaaatttc tttgatttta tatttgatgg agtaaatctg gctgtgtcaa cggtagtcca    5580
ttcgaaacct ggaaatcgaa atcattgtac tgcaggtctg ttgcctgtta gtttgttctt    5640
atataagatc tttgacagtt tatgaatttg tctttggaat ttgtataaag tttcacagat    5700
agacaggccc tgttgttaaa tacgttcgtg caattaagtg taaacatatc tgccagtgat    5760
ttttctcggc tcgcattagt acgcataaat ttttagcact tctctgaatt ttctcatatg    5820
cagaccacct atgaaaaaaa cgacatgcaa gtaaataaaa cgatttcagg ttcatttagt    5880
agcaaaccgt ttttatgtcc tttaaaaatc aattagcaga gccactccat tcaccggtca    5940
gcagaaaaga agcatgtgtg tgttttgggg ctatcataga gctaaataaa tttgattccc    6000
atctgtaatg ttcatcgttg tttacatcag tgttggctgt cgtgtggtcg tggagactag    6060
cctgttcaga caatatgttt gacaagagtg ttgttttgtg agatgcggat gcggtgcttg    6120
catctgtact tgttttttgtg aataccagtt agatgatcag ttttttgtgca cttcttgcca    6180
tgaatggctg ttaaattgtc acttttttagg aacttgttgc cgtaatatca attaaataat    6240
caattttttgt gcatggtata tcaattagat ggtcattttt ttctagtaga gatgtctata    6300
catgccaatg caatgttcag agttgttcaa ggtctcgacg gcgcggcaaa gcgcgtccta    6360
tgcttctagt ttaagatgac aaccaaacac gacccaagtg tatgctatgc tcatccggtt    6420
ggtccttgtt gatgttcaat gggcgtgtct ccatgggcat cgacggcgac aatgttatct    6480
tcttcaactg tctgctatat gctcattggc attttttgaaa ctttgcaagc aaggtcgata    6540
acttggtctg gggatgttga cgcccctatg tatctagatt agggtgatgc tcccgccagt    6600
attttttgga cgattatcaa catttgcggc tggtatacta ttgtggctaa tcaacaaggt    6660
tttttttgtgt gtggctaatc aacaaggttt ggcgctcgat gttttttttaa tgtatttcga    6720
tgactcaatt tctacgtctg aacatttcat tgagccaaga ggcagaacaa caggtcacat    6780
gtaaccgcca gtgaaaaagg ttcaaagaag aaaagatac gaacgacagc gagtttgtat    6840
kkcagttttc gaactaagag taacacggag trcagtagta cgatccttgt gtmyttctgt    6900
atttggwtak ttttttttccg gagttgagta ttwgwaactt tcttgtgctt tttttaacat    6960
tagtacagat gcaagtgctc atacatacgc gcttttttgat ttgtaacaat attatgaaag    7020
acgtagtaat tatgtttgca gatcaataaa gctagccatc gtgtggtgtt cccaagaaaa    7080
agatattcac tatagattca ctacatcttc taaaaaaact acactgtaga ttcactacag    7140
accaacagaa tattcatggt cacgtggata aaaacttact ttttgaaagt ctcaagcatt    7200
tggtttgatt ttaagaaaaa ataactgact ctattttttgt gtactccttg caacgaacct    7260
ggataaagat ggagccagtc cgttcctggt tactaggagt atccatttcc tgaagaccat    7320
ggagcaacca cggcggatcg ggcgatcggc agcctcccag ccggcgacca tggcggatgc    7380
cacgagcgca ggagcgacgc ctctcctccc tggcctcctc gacgacatcg taatctgtga    7440
gatccttgtc cgcctcgccc cccaaagcca tcctccgctg ccgcgccgtc acgccgtgcc    7500
tggcgccgca ccacctccac ccgcgacttc tcctcgccc accacgcccg ccagcccgcc    7560
ctcctcatca cctccggcca cagtt                                          7585
```

<210> SEQ ID NO 121
<211> LENGTH: 6195
<212> TYPE: DNA
<213> ORGANISM: Triticum aestivum

<400> SEQUENCE: 121

```
aaatttttat aatattgttt ttccaaattt tatgtttaaa ctcatttttg ttcaattttt      60
tgtgaatata ttttaatcca ttgatagatt ttgaaaatat aataatttt ccaaaacatt     120
ctataatttc ataaacctt ttaacattc aagaataaga ttaggaaatt ttgattctta     180
aaatatattt ttaatcttgc aactacatt ttatatacaa ttacatgagc caatttattt     240
tggtagaaat caactgaaaa aacaaaagaa aaaattggaa tagcgggagt tctctgcgcg     300
aacttggggg ggggggcga caaccctcta tcaatgagct agggattcct attacatctc     360
gcctacaagc cgcactagtt ttttycccat ttgttttata tcggtttttt actacttttg     420
caccggtttt cttctggtat tatttcattt ttcttctata ctttctgttg ttttcttcgt     480
ttccccctcc tgttttttg tcttttttcta cagtttcctt gtttctttct ttggttttca     540
ccgatttact ttgttttttca cgttttttaaa ttttaatttt aatcttcaga tacataatta     600
acattcatta aattatatac ttttatgtca agttttttca tacacattgt gcattttata     660
catattagga ttcttaaata catgattaat attttattca gacatagagt acttgttttg     720
aacactttt caaatacatg ttgaaataat ttattttatg atatgaaata tgttttttta     780
ttatgcaaac attttttatac actttatgtt tttttgaaat attacaaaat ttttgcttga     840
aacgtgtgaa cattttttaa aatgtaacat aattttttga atggtatgaa actttttga     900
actgcgcgaa cattattttt acattgtata ttattttgat tcatttttctg taagttatcg     960
cctgaattgc ttgaaaaacg tgattttttt taaatgccac atatattgtt tttgaatggt    1020
tcatgcattt tctgaaagtt gatcgaacat gttttttatat tgcattttta aaatgtaata    1080
accactttg aaaattaact aatgtatttt cataatatat gtatttaata ttattaaaaa    1140
taaaaaaag gtaaagaaa aaacagatca acgcgatgag accccatggt tgttgcgctt    1200
gtccactacc ggctcactga agacgtctct cacagtagga gtcgctacga agaatacata    1260
gtcgcgctgg gcgcggttat gttccgcctg ttgcgacgcc caagcatggc ttgcctacag    1320
ctagagggtc gggctaggaa ccactaattg tgtcatgctg atgtcacaat gacatcatac    1380
atgctttat tttaattttt cgctttctct ttaaattttt ttgtatttca aaatattctg    1440
ttttttaag aatgctagta ttgtatttga aaaatgttaa acctgtatag aaaaatatat    1500
aacatgaatg aaaaatgtat agatgttaat catgtgtaca aaaatgatt gtgacaatta    1560
agaatgtcac atatttcaaa ataaatgtat gtggaatttt gaaaaatgt gtatataatt    1620
ttttaatggt catgtaattt taaaaaatg tgtgatacat tcaacaaaaa atatttcaca    1680
tttgaataat tcttcttgag cttaagaaat gtgttcatta tgttatcaat ttttttgtac    1740
agtgtacaaa aatgtttaca tagttcaaaa aaatgttttt cagtaaaatt acatttcatt    1800
gtgtatttaa tattttaaca cacatttgga aaatatattt gaaacatgtt tttgtaaaaa    1860
aaaatttaaa actatgcttg tactccctcc gtccgaaaaa ggtttacatg tataaaagtt    1920
ttttcggagg gagggattat aatgttagtc atttataaga aatgttttac atgtatgaaa    1980
atgtatagca tatgtgtaaa agtagacatg tgttgaaaaa aaaagtaaa acaacccaaa    2040
aaaccaatga aaataaaata aaaccaaagt accaagaaga agaaaaggag aataaaccat    2100
tgaaaaacaa agaaaataaa aaacataaag aagaagaaa cccaaagaaa actggcaaaa    2160
attagacaca gaaaagaaaa acgaaaaaat atataataaa raaaaccgga ctgaaccgat    2220
cggacacgga tgagcgaagg catgcatcga gcaacacagc taattggccg gcccatagtc    2280
```

```
gttcgcccgc agaccattca tacgaatcgg taccggagag acatagggc tatttggttt    2340 gtagccacat tttgtcatac tttgtgacac cgcatcttat gcaagtttga ccaaattagg    2400
tggatgttta gttctaacca catgtaaggg aagatttttt tttatgagca ttgaacccgt    2460
agacacaaaa agtgtaggaa gattacttta aacaagctaa agtgtggcta acaatttaag    2520
catctcaggt aagataagtg cgacaaatat ggcaaaaata atgtggtata tatgacaaag    2580
atagtcacaa tccaaacagc ccatagcctg gcgagtgcaa atagatacga gatctctggt    2640
gatatcacaa ccgtccaaat taattgcttg tttcagcatc agcctttttg cataaagaag    2700
ctagcccaat ctgaaccaca cactcacccg ccgcgtgaca cgccaaaga caaaaacatc    2760 accctcccc aattccaacc ctctctctgc ctcacagaaa tctcccccct cgcccaaacc    2820
ctcgccgccg ccatggccgc cgccacctcc ccgccgtcg cattctcggg cgccaccgcc    2880
gccgccatgc ccaaacccgc ccgccatcct ctcccgcgcc accagcccgt ctcgcgccgc    2940
gcgctccccg cccgcgtcgt caggtgttgc gccgcgtccc ccgccgccac ctccgccgcg    3000
cctcccgcaa ccgcgctccg gccctggggc ccgtccgagc cccgcaaggg cgccgacatc    3060
ctcgtcgagg cgctcgagcg ctgcggcatc gtcgacgtct tcgcctaccc cggcggcgcc    3120
tccatggaga tccaccaggc gctgacgcgc tcgcccgtca tcaccaacca cctcttccgc    3180
cacgagcagg gggaggcgtt cgcggcgtcc ggctacgccc gcgcgtccgg ccgcgtcggc    3240
gtctgcgtcg ccacctccgg cccgggggcc accaacctcg tctccgcgct cgccgacgcc    3300
ctcctcgact ccatccccat ggtcgccatc acgggccagg tcccccgccg catgatcggc    3360
acggacgcgt tccaggagac gcccatagtg gaggtcacgc gctccatcac caagcacaac    3420
tacctggtcc ttgacgtgga ggatatcccc cgcgtcatcc aggaagcctt cttccttgca    3480
tcctctggcc gccgggggcc ggtgctagtt gatatcccca aggacatcca gcagcagatg    3540
gctgtgcccg tctgggacac tccaatgagt ttgccagggt acatcgcccg cctgcccaag    3600
ccaccatcta ctgaatcgct tgagcaggtc ctgcgtctgg ttggcgagtc acggcgccca    3660
attctgtatg ttggtggtgg ctgcgctgcg tctggcgagg agttgcgccg ctttgttgag    3720
cttactggga ttccagttac aactactctg atgggccttg gcaacttccc cagcgacgac    3780
ccactgtctc tgcgcatgct tgggatgcat ggcactgtgt atgcaaatta tgcagtagat    3840
aaggctgacc tgttgctcgc atttggtgtg cggtttgatg atcgtgtgac tgggaaaatc    3900
gaggcttttg caagcaggtc caagattgtg cacattgaca ttgacccagc tgagattggc    3960
aagaacaagc agccacatgt ctccatttgt gcagatgtta agcttgcttt acaggggttg    4020
aatgatctat taaatgggag caaagcacaa cagggtctgg attttggtcc atggcacaag    4080
gagttggatc agcagaagag ggagtttcct ctaggattca agactttctgg cgaggccatc    4140 ccgccgcaat atgctatcca ggtactggat gagctgacaa aaggggaggc gatcattgcc    4200
actggtgttg gcagcacca gatgtgggcg gctcagtatt acacttacaa gcggccacgg    4260
cagtggctgt cttcgtctgg tttgggggca atgggatttg ggttaccagc tgcagctggc    4320
gctgctgtgg ccaacccagg tgttacagtt gttgacattg atggtgatgg tagtttcctc    4380
atgaacattc aggagttggc gttgatccgc attgagaacc tcccagtgaa ggtgatgata    4440
ttgaacaacc agcatctggg aatggtggtg cagtgggagg ataggtttta caaggccaat    4500
cgggcgcaca catacccttgg caacccagaa aatgagagtg agatatatcc agattttgtg    4560
acgattgcta aaggattcaa cgttccagca gttcgagtga cgaagaagag cgaagtcact    4620
gcagcaatca agaagatgct tgagaccca gggccatact tgttggatat catagtcccg    4680
```

-continued

```
catcaggagc acgtgctgcc tatgatccca agcggtggtg ctttcaagga catgatcatg    4740
gagggtgatg gcaggacctc gtactgaaat ttcgacctac aagacctaca agtgtgacat    4800
gcgcaatcag catgatgccc gcgtgttgta tcaactacta ggggttcaac tgtgagccat    4860
gcgttttcta gtttgcttgt ttcattcata taagcttgta ttacttagtt ccgaaccctg    4920
tagttttgta gtctatgttc tcttttgtag ggatgtgctg tcataagatg tcatgcaagt    4980
ttcttgtcct acatatcaat aataagtact tccatggaat aattctcagt tctgttttga    5040
attttgcatc ttctcacaaa cagtgtgctg gttcctttct gttactttac atgtctgctg    5100
tgtcaggttc tgacataacg accgatgagg ggtggtcggc aggttttaga aggggaattg    5160
aaactttttt ttgggaagaa gtctgaatac agttgggagg aaaaatagaa gtatatactt    5220
cgattaattt atcaagcccg ctatccagtc taatttatca agcactagac agtgtagggt    5280
gttggcattc ttctcttcct tgagatccgg cttgagagga gagaccgagg cttcggctgt    5340
gttggttgct gatttctaca gcttttgag atagagagag agatcctgca actgtggttt     5400
gtcttgctgc ttgtacagcg agagagacat tgagagatat gtagatcgtt taccagttgt    5460
gctgctgtta ttcgtactgg tactgattgt tgttactgtt gctatcatgt gcaaattgtt    5520
gtgatggaaa atcaacaaaa ttttgatatt ttgcaaagcg agttggattg aatgatttga    5580
gaaatggtga ctgctttccc tcagacttgt tgagtggcct tgagaattgg tgtttcatag    5640
gtggtgtatg cagttgctaa tgaaaggcga cggcttgaaa tttccgaaag gcagccaatg    5700
atactttctg aaagtgatgt ttttttcgtc caggtttccg gtggagcaag tctagacaca    5760
cgttgagcca atgtttgtca gcttattctg ctctttagtt tcagtttagg tgcagttgtt    5820
ttgtttacag attgctgggc agagccccgt gatcggctga gcctccaaga gatccttgct    5880
tgctcgactg cggatacgct gaatccttta aaacgctccc tagttttaag ttttagagaa    5940
ctgagaatca attgggggca acattactgg gtcgcctccc tgggcctcta cagttttgtg    6000
ggccctatat gtaagtgccc cagtgttgtg gggatttgcg gcgtggcggg cggcatttgc    6060
gtcctctctt cggcggcgct gtttcccccct ccttcttgct gcttctggag gaggtggtcg    6120
gcggcgggtg ttgtgggggg tcgcattgga gcggcgcgaa cgccggtcct gctgcatctg    6180
ccgccattgg ttgtt                                                     6195
```

<210> SEQ ID NO 122
<211> LENGTH: 26
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 122
tctgtaagtt atcgcctgaa ttgctt                                            26

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 123
cattgtgaca tcagcatgac acaa                                              24

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
aagcayggct tgcctacagc                                                    20

<210> SEQ ID NO 125
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
aaccaaatrc ccctatgtct ctcc                                               24

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cgttcgcccg tagaccattc                                                    20

<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127 ggagggtga tgkttttgtc ttt                                                 23

<210> SEQ ID NO 128
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tcgcccaaac cctcgcc                                                       17

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
gggtcgtcrc tggggaagtt                                                    20

```
<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
gccttcttcc tygcrtcctc tgg                                            23

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gcccgrttgg ccttgtaaaa cct                                            23

<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
aycagatgtg ggcggctcag tat                                            23

<210> SEQ ID NO 133
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gggatatgta ggacaagaaa cttgcatga                                      29

<210> SEQ ID NO 134
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
agggccatac ttgttggata tcatc                                          25

<210> SEQ ID NO 135
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
gccaacaccc tacactgcct at                                             22

<210> SEQ ID NO 136
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
tgcgcaatca gcatgatacc t                                            21

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
acgtatccgc agtcgagcaa t                                            21

<210> SEQ ID NO 138
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
gtagggatgt gctgtcataa gatg                                         24

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
ttggaggctc agccgatcac                                              20

<210> SEQ ID NO 140
<211> LENGTH: 3053
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
cgttcgcccg tagaccattc ataagaatcg gtatcggaga gacatagggg ttctttggtt    60
tctaaccata tcttgtcaca ctttaccata catcaccttc gtcaaatctg atcaaattag   120
gtgagtattt ggttctagcc acatctaagg caagatttgt ttttctgagc agtgaacccc   180
atatgtcata gacagaaaaa ttgtgaaaag attcctttag acggtcaaag cgtggttaac   240
aatttaatca actcaagtaa gataaatgcg ataaatgtga caaaaataat gtgttataga   300
agtatgacaa aaataatcac aatccaaaca gtctgatagc ttggcgagtg caaaatagat   360
acgaaatctc tggtgatatc acacgggtcc aaaataattg cttgtttgag catcagcctt   420
tctgcacaaa aaaagctagc ccaaacaaac gagtggcgtc ccatctgaac cacacgctca   480
cccgccgcgt gacagcgcca aagacaaaac catcaccccct ccccaattcc aaccctctct   540
```

-continued

```
ccgcctcaca gaaatctctc ccctcgccca aaccctcgcc gccgccatgg ccgccgccac    600 ctccccgcc gtcgcattct ccggcgccgc cgccgccgcc gccgccatgc ccaagcccgc     660
ccgccagcct ctcccgcgcc accagcccgc ctcgcgccgc gcgctcccg cccgcgtcgt     720 caggtgctgc gccgcgcccc ccgctgctgc cacctccgcc gcgcccccg ccaccgcgct     780 ccggccctcg gggcccgtcc gagccccgca agggcgccga catcctcgtc gaggcgctcg    840
agcgctgcgg catcgtcgac gtattcgcct accccggcgg cgcgtccatg gagatccacc    900
aggcgctgac gcgctcgccc gtcatcacca accacctcct tccgccacga gcgaggggga    960
ggcgttcgcg gcgtccggct acgcccgcgc gtccggccgc gtcggcgtct gcgtcgccac   1020
ctccggcccg ggggccacca acctcgtctc cgcgctcgct gacgccctcc tcgactccat   1080
ccccatggtc gccatcacgg gccaggtccc ccgccgcatg atcggcacgg acgcgttcca   1140
ggagacgccc atagtggagg tcacgcgctc catcaccaag cacaactacc tggtccttga   1200
cgtggaggat atccccgcg tcatccagga agccttcttc ctcgcgtcct ctggccgccc    1260
ggggccggtg ctggttgata tccccaagga tatccagcag cagatggccg tgcctatctg   1320
ggacacgccg atgagtttgc cagggtacat cgtcccgcct gcccaagcca ccatctactg   1380
aatcgcttga gcaggtcctg cgtctggttg gcgagtcacg gcgcccaatt ctgtatgttg   1440
gtggtggctg cgctgcatcc ggcgaggagt tgcgccgctt tgttgagctc actgggattc   1500
cggttacaac tactctgatg ggccttggca acttccccag cgacgaccca ctgtctctgc   1560
gcatgcttgg gatgcatggc actgtgtatg caaattatgc agtcgataag gctgacctgt   1620
tgcttgcatt tggtgtgcgg tttgatgatc gcgtgactgg gaaaatcgag gcctttgcaa   1680
gcaggtccaa gattgtgcac attgacattg acccagctga gattggcaag aacaagcagc   1740
cacatgtctc catttgtgca gatgttaagc ttgctttaca ggggttgaat gctctattaa   1800
atgggagcaa agcacaacag ggtctggatt ttggtccatg gcacaaggag ttggatcagc   1860
agaagaggga gtttcctcta ggattcaaga cttttggcga ggccatcccg ccgcaatatg   1920
ctatccaggt actggatgag ctgacaaaag gggaggcgat cattgctact ggtgttgggc   1980
agcaccagat gtgggcggct cagtattaca cttacaagcg gccacggcag tggctgtctt   2040
cgtctggttg ggggcaatgg gatttgggtt accagctgca gctggcgctg ctgtggccaa   2100
cccaggtgtt acagttgttg acattgatgg agatggtagt ttcctcatga acattcagga   2160
gttggcattg atccgtattg agaacctccc tgtgaaggtg atgatattga caaccagca    2220 tctgggaatg gtggtgcaat gggaggatag gttttacaag gccaatcggg cgcacacata   2280
ccttggcaac ccagaaaatg agagtgagat atatccagat tttgtgacga ttgctaaagg   2340
attcaacgtt ccggcagttc gtgtgacgaa gaagagcgaa gtcactgcag caatcaagaa   2400
gatgcttgag accccagggc catacttgtt ggatatcatc gtcccgcatc aggagcacgt   2460
gctgcctatg atcccaagcg gtggtgcttt caaggacatg atcatggagg gtgatggcag   2520
gacctcgtac tgaaatttcg acctacaaga cctacaagtg tgacatgcgc aatcagcatg   2580
gtgcccgcgt gttgtatcaa ctactagggg ttcaactgtg aaccatgcgt tttctagttt   2640
gcttgtttca ttcatataag cttgtgttac ttagttccga accctgtagc tttgtagtct   2700
atgctctctt ttgtagggat gtgctgtcat aagatatcat gcaagtttct tgtcctacat   2760
atcaataata agtacttcca tggaataatt ctcagttctg ttttgaattt tgcatcttct   2820
cacaaacagt gtgctggttc ctttctgtta ctttacatgt ctgccgtgtc cggttatgac   2880
ataatgaccg atggagggtg gtcagcaggt tttagacggg gagttgaaac ttttttttgg   2940
```

| | |
|---|---|
| ggggaagaaa tctgaataca gttgggagga aagataaaag catatacctt gattaattta | 3000 |
| ttgagcccaa tatccagcct aatttatcaa gcaataggca gtgtagggtg ttg | 3053 |

<210> SEQ ID NO 141
<211> LENGTH: 3589
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 141

| | |
|---|---|
| cgttcgcccg tagaccattc ctacgaatcg gtaccggaga gacatagggg ctgtatggtt | 60 |
| cctaaccata ccttgccaca ctttgtcaca cctcatctta ggcaaattta atcaagttat | 120 |
| gtaggtgttt ggttttagcc acatctaagg caagatttat tttcctgagc agtgaacccc | 180 |
| atatgttata gacataaaaa gtgtgggaag attcccttta gtcaaactgt ggctaacaat | 240 |
| ttattaagaa ttaacttaag taagataggt gcaacaaatg tagcaaaaat aatgtggtat | 300 |
| atatagcaaa gatagccaca accgcgagtg gaaataccag atacgagatc tctggtcata | 360 |
| tcacacgagt ccaaattaat tgctttgttt gaggttcagc cttttttgcat aaaaaagcta | 420 |
| gcccaaacaa acgagtggcg tcccatctga accacacact cacccgccgc gtgacagcgc | 480 |
| caaagacaaa accatcaccc ctccccaatt ccaaccctct ctctgcctca gaaatctc | 540 |
| tccctcgccc aaaccctcgc cgccgccatg ccgcagcca cctcccccgc cgtcgcattc | 600 |
| tcgggcgccc ccgccgccgc cgccgccata cccaaacccg cccgccagcc tctcccgcgc | 660 |
| caccagcccg cctcgcgccg cgcgctcccc gcccgcatcg tcaggtgctg cgccgcgtcc | 720 |
| cccgccgcca cctccgtcgc gcctcccgcc accgcgctcc ggccgtgggg ccctccgag | 780 |
| ccccgcaagg gcgccgacat cctcgtcgag gcgctggagc gctgcggcat cgtcgacgtc | 840 |
| ttcgcctacc ctggcggcgc gtccatggag atccaccagg cgctgacgcg ctcgccagtc | 900 |
| atcaccaacc acctcttccg ccacgagcag ggggaggcgt tcgcggcgtc cgggtacgcc | 960 |
| cgcgcgtccg gccgcgtcgg cgtctgcgtc gccacctccg gccgggggc caccaacctc | 1020 |
| gtctccgcgc tcgccgacgc tctcctcgac tccatcccca tggtcgccat cacgggccag | 1080 |
| gtcccccgcc gcatgatcgg cacggatgcg ttccaggaga cgcccatcgt ggaggtcacg | 1140 |
| cgctccatca ccaagcacaa ctacctggtc cttgacgtgg aggatatccc ccgcgtcatc | 1200 |
| caggaagcct tcttcctcgc atcctctggc cgcccggggc cggtgctggt tgatatcccc | 1260 |
| aaggacatcc agcagcagat ggctgtgcct gtctgggaca cgccgatgag tttgccaggg | 1320 |
| tacatcgccc gcctgcccaa gccaccatct actgaatcgc ttgagcaggt cctgcgtctg | 1380 |
| gttggcgagt cacggcgccc aattctgtat gttggtggtg gctgcgctgc atctggtgag | 1440 |
| gagttgcgcc gctttgttga gctcactggg attccagtta caactactct tatgggcctt | 1500 |
| ggcaacttcc ccagtgacga cccactgtct ctgcgcatgc tggggatgca tggcactgtg | 1560 |
| tatgcaaatt atgcagtaga taaggctgac ctgttgcttg catttggtgt gcggtttgat | 1620 |
| gatcgtgtga ccgggaaaat cgaggctttt gcaagcaggt ccaagattgt gcacattgac | 1680 |
| attgacccag ctgagattgg caagaacaag cagccacatg tctccatttg tgcagatgtt | 1740 |
| aagcttgctt tacaggggtt gaatgctcta ttaaatggga gcaaagcaca acagggtctg | 1800 |
| gattttggtc catggcacaa ggagttggat cagcagaaga gggagtttcc tctaggattc | 1860 |
| aagacttttg gtgaggccat cccgccgcaa tatgctatcc aggtactgga tgagctgaca | 1920 |

| | | | | |
|---|---|---|---|---|
| aaaggggagg | cgatcattgc | caccggtgtt | gggcagcatc | agatgtgggc ggctcagtat | 1980 |
| tacacttaca | agcggccacg | gcagtggctg | tcttcatccg | gtttgggtgc aatgggattt | 2040 |
| gggttgccag | ctgcagctgg | cgctgctgtg | gccaacccag | gtgttacagt tgttgacatt | 2100 |
| gatggggatg | tagtttcct | catgaacatt | caggagttgg | cgttgatccg tattgagaac | 2160 |
| ctcccagtga | aggtgatgat | attgaacaac | cagcatctgg | gaatggtggt gcagtgggag | 2220 |
| gataggtttt | acaaggccaa | ccgggcgcac | acataccttg | gcaacccaga aaatgagagt | 2280 |
| gagatatatc | cagattttgt | gacgattgct | aaaggattca | acgttccggc agttcgtgtg | 2340 |
| acgaagaaga | gcgaagtcac | tgcagcaatc | aagaagatgc | ttgagacccc agggccatac | 2400 |
| ttgttggata | tcattgtccc | gcatcaggag | cacgtgctgc | ctatgatccc aagcggtggt | 2460 |
| gcttttaagg | acatgatcat | ggagggtgat | ggcaggacct | cgtactgaaa tttcgaccta | 2520 |
| caagacctac | aagtgtgaca | tgcgcaatca | gcatgatacc | tgcgtgttgt atcaactact | 2580 |
| gggggttcaa | ctgtgaacca | tgcgttttct | agtttgcttg | tttcattcat ataagcttgt | 2640 |
| gttacttagt | tccgaaccgt | gtagttttgt | agtctctgtt | ctcttttgta gggatgtgct | 2700 |
| gtcataagat | atcatgcaag | tttcttgtcc | tacatatcaa | taataagcac ttccatggaa | 2760 |
| taattctcag | ttctgttttg | aatttcacat | cttctcacga | acagtgtgct ggttcctttc | 2820 |
| tgttacttta | catgcctgcc | gtgtcaggtt | atgacataac | gaccgatgga ggattggagg | 2880 |
| gtggtcggct | ggttttagac | ggggaattga | acattttc | tggaagaaat ctgaatacag | 2940 |
| ttgggagggg | aaatggaagc | atatatttat | cgagcccgct | atccaggcta atttatcaag | 3000 |
| cactagacag | tgtagggtgt | tggcattctt | ctcttccttg | atatccggct tgagaggaga | 3060 |
| gattgaggct | tcggctgtgt | tggttgctga | tttctacagc | attttgagag agagagagag | 3120 |
| atgttgcaac | tgtgttttgt | cttggttgct | tgtacagaga | aagagatgac atttagagat | 3180 |
| atgcagatcg | tttaccagtt | gtgctgcgtt | tattcgtact | gattgttgtt attgttgcta | 3240 |
| tcatgtgcaa | attgttgtga | tggaaaatca | acaaaatttt | gatattttgc aaagcgagtt | 3300 |
| ggattgaatg | atttgagaaa | tggtgacttg | ttgagtggcc | ttgagaattg gtgtttcata | 3360 |
| ggtgtgcagt | tggtaatgaa | aggcggcggc | ttgaaatttc | cgaaaggcag gcaatgatac | 3420 |
| tttctgaaag | tgatgttttt | tcttccaggt | ttccggtgga | acaagtctac gttgagccaa | 3480 |
| tgtttgtcag | cttattctgc | tctttagttt | cagttgtttt | gttcacagat tgctgggcag | 3540 |
| agccccatga | tcggctgagc | ctccaggaga | tccttgattg | ctcgactgc | 3589 |

<210> SEQ ID NO 142
<211> LENGTH: 3599
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 142

| | | | | |
|---|---|---|---|---|
| cgttcgcccg | tagaccattc | atacgaatcg | gtaccggaga | gacatagggg ctatttggtt | 60 |
| tgtagccaca | ttttgtcata | ctttgtgaca | ccgcatctta | tgcaagtttg atcaaattag | 120 |
| gtggatgttt | agttctaacc | acatgtaagg | gaagattttt | ttttttatga gcattgaacc | 180 |
| cgtagacaca | aaaagtgtag | gaagattact | ttaaacaagc | taaagtgtgg ctaacaattt | 240 |
| aagcatctca | ggtaagataa | gtgcgacaaa | tatggcaaaa | ataatgtggt atatatgaca | 300 |
| aagatagtca | caatccaaac | agcccatagc | ctggcgagtg | caaatagata cgagatctct | 360 |

```
ggtgatatca caaccgtcca aattaattgc ttgtttcagc atcagccttt ttgcataaag    420
aagctagccc aatctgaacc acacactcac ccgccgcgtg acagcgccaa agacaaaacc    480
atcacccctc cccaattcca accctctctc tgcctcacag aaatctcccc cctcgcccaa    540
accctcgccg ccgccatggc cgccgccacc tcccccgccg tcgcattctc gggcgccacc    600
gccgccgcca tgcccaaacc cgcccgccat cctctcccgc gccaccagcc cgtctcgcgc    660
cgcgcgctcc ccgcccgcgt cgtcaggtgt tgcgccgcgt cccccgccgc cacctccgcc    720
gcgcctcccg caaccgcgct ccggccctgg ggcccgtccg agcccgcaa  gggcgccgac    780 atcctcgtcg aggcgctcga gcgctgcggc atcgtcgacg tcttcgccta ccccggcggc    840
gcctccatgg agatccacca ggcgctgacg cgctcgcccg tcatcaccaa ccacctcttc    900
cgccacgagc aggggaggc  gttcgcgcg  tccggctacg cccgcgcgtc cggccgcgtc    960
ggcgtctgcg tcgccacctc cggcccgggg gccaccaacc tcgtctccgc gctcgccgac   1020
gccctcctcg actccatccc catggtcgcc atcacgggcc aggtcccccg ccgcatgatc   1080
ggcacggacg cgttccagga gacgcccata gtggaggtca cgcgctccat caccaagcac   1140
aactacctgg tccttgacgt ggaggatatc ccccgcgtca tccaggaagc cttcttcctt   1200
gcatcctctg gccgcccggg gccggtgcta gttgatatcc caaggacat  ccagcagcag   1260 atggctgtgc ccgtctggga cactccaatg agtttgccag ggtacatcgc ccgcctgccc   1320
aagccaccat ctactgaatc gcttgagcag gtcctgcgtc tggttggcga gtcacggcgc   1380
ccaattctgt atgttggtgg tggctgcgct gcgtctggcg aggagttgcg ccgctttgtt   1440
gagcttactg ggattccagt tacaactact ctgatgggcc ttggcaactt ccccagcgac   1500
gacccactgt ctctgcgcat gcttgggatg catggcactg tgtatgcaaa ttatgcagta   1560
gataaggctg acctgttgct cgcatttggt gtgcggtttg atgatcgtgt gactgggaaa   1620
atcgaggctt ttgcaagcag gtccaagatt gtgcacattg acattgaccc agctgagatt   1680
ggcaagaaca agcagccaca tgtctccatt tgtgcagatg ttaagcttgc tttacagggg   1740
ttgaatgatc tattaaatgg gagcaaagca caacagggtc tggattttgg tccatggcac   1800
aaggagttgg atcagcagaa gagggagttt cctctaggat tcaagacttt tggcgaggcc   1860
atcccgccgc aatatgctat ccaggtactg gatgagctga caaaagggga ggcgatcatt   1920
gccactggtg ttgggcagca ccagatgtgg gcggctcagt attacactta caagcggcca   1980
cggcagtggc tgtcttcgtc tggttttgggg gcaatgggat ttgggttacc agctgcagct   2040
ggcgctgctg tggccaaccc aggtgttaca gttgttgaca ttgatggtga tggtagtttc   2100
ctcatgaaca ttcaggagtt ggcgttgatc cgcattgaga acctcccagt gaaggtgatg   2160
atattgaaca accagcatct gggaatggtg gtgcagtggg aggataggtt ttacaaggcc   2220
aatcgggcgc acacatacct tggcaaccca gaaaatgaga gtgagatata tccagatttt   2280
gtgacgattg ctaaaggatt caacgttcca gcagttcgag tgacgaagaa gagcgaagtc   2340
actgcagcaa tcaagaagat gcttgagacc ccagggccat acttgttgga tatcatagtc   2400
ccgcatcagg agcacgtgct gcctatgatc ccaagcggtg gtgctttcaa ggacatgatc   2460
atggagggtg atggcaggac ctcgtactga aatttcgacc tacaagacct acaagtgtga   2520
catgcgcaat cagcatgatg cccgcgtgtt gtatcaacta ctaggggttc aactgtgagc   2580
catgcgtttt ctagttttgct tgtttcattc atataagctt gtattactta gttccgaacc   2640
ctgtagtttt gtagtctatg ttctcttttg tagggatgtg ctgtcataag atgtcatgca   2700
```

```
agtttcttgt cctacatatc aataataagt acttccatgg aataattctc agttctgttt    2760
tgaattttgc atcttctcac aaacagtgtg ctggttcctt tctgttactt tacatgtctg    2820
ctgtgtcagg ttctgacata acgaccgatg gagggtggtc ggcaggtttt agaagggaa     2880 ttgaaacttt tttttgggaa gaagtctgaa tacagttggg aggaaaaata gaagtatata    2940
cttcgattaa tttatcaagc ccgctatcca gtctaattta tcaagcacta gacagtgtag    3000
ggtgttggca ttcttctctt ccttgagatc cggcttgaga ggagagaccg aggcttcggc    3060
tgtgttggtt gctgatttct acagcttttt gagatagaga gagagatcct gcaactgtgg    3120
tttgtcttgc tgcttgtaca gcagagagaa cattgagaga tatgtagatc gtttaccagt    3180
tgtgctgctg ttattcgtac tggtactgat tgttgttact gttgctatca tgtgcaaatt    3240
gttgtgatgg aaaatcaaca aaattttgat attttgcaaa gcgagttgga ttgaatgatt    3300
tgagaaatgg tgactgcttt ccctcagact tgttgagtgg ccttgagaat tggtgtttca    3360
taggtggtgt atgcagttgc taatgaaagg cgacggcttg aaatttccga aaggcagcca    3420
atgatacttt ctgaaagtga tgttttttc gtccaggttt ccggtggagc aagtctagac     3480
acacgttgag ccaatgtttg tcagcttatt ctgctcttta gtttcagttt aggtgcagtt    3540
gttttgttta cagattgctg ggcagagccc cgtgatcggc tgagcctcca agagatcct    3599
```

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Thr Ser Gly Asn Leu Thr Arg
1               5

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

His Arg Thr Ser Leu Thr Asp
1               5

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gln Ser Ser Asp Leu Ser Arg
1               5

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 146

His Lys Tyr His Leu Arg Ser
1               5

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gln Trp Ser Thr Arg Lys Arg
1               5

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Arg Ser Asp Ser Leu Ser Ala
1               5

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Arg Ser Asp Ala Leu Ala Arg
1               5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Arg Ser Asp Asp Leu Thr Arg
1               5

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gln Lys Ser Asn Leu Ser Ser
1               5

<210> SEQ ID NO 152
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asp Ser Ser Asp Arg Lys Lys
1               5

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

His Ser Asn Ala Arg Lys Thr
1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gln Ser Gly Asn Leu Ala Arg
1               5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asp Arg Ser Ala Leu Ala Arg
1               5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Arg Ser Asp Asn Leu Ser Thr
1               5

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157
```

Ala Gln Trp Gly Arg Thr Ser
1               5

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gln Ser Gly Asp Leu Thr Arg
1               5

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Met Arg Asn Arg Leu Asn Arg
1               5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Asp Arg Ser Asn Leu Ser Arg
1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Trp Arg Ser Cys Arg Ser Ala
1               5

<210> SEQ ID NO 162
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gln Arg Ser Asn Leu Asp Ser
1               5

<210> SEQ ID NO 163
<211> LENGTH: 28
<212> TYPE: DNA
<213> ORGANISM: Triticum aestivum

<400> SEQUENCE: 163
aggcagcacg tgctcctgat gcgggact                                              28

<210> SEQ ID NO 164
<211> LENGTH: 28
<212> TYPE: DNA
<213> ORGANISM: Triticum aestivum

<400> SEQUENCE: 164
gatcccaagc ggtggtgctt tcaaggac                                              28

<210> SEQ ID NO 165
<211> LENGTH: 28
<212> TYPE: DNA
<213> ORGANISM: Triticum aestivum

<400> SEQUENCE: 165
tcttgtaggt cgaaatttca gtacgagg                                              28

<210> SEQ ID NO 166
<211> LENGTH: 28
<212> TYPE: DNA
<213> ORGANISM: Triticum aestivum

<400> SEQUENCE: 166
tacaagtgtg acatgcgcaa tcagcatg                                              28

<210> SEQ ID NO 167
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
acactctttc cctacacgac gctcttccga tcttcctcta ggattcaaga cttttgg             57

<210> SEQ ID NO 168
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gtgactggag ttcagacgtg tgctcttccg atctcgtggc cgcttgtaag tgtaa               55

<210> SEQ ID NO 169
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
acactctttc cctacacgac gctcttccga tctgagaccc cagggccata cttg                54

<210> SEQ ID NO 170
<211> LENGTH: 57
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 170
gtgactggag ttcagacgtg tgctcttccg atctcaagca aactagaaaa cgcatgg        57

<210> SEQ ID NO 171
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
acactctttc cctacacgac gctcttccga tctatggagg gtgatggcag gac            53

<210> SEQ ID NO 172
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gtgactggag ttcagacgtg tgctcttccg atctatgaca gcacatccct acaaaaga      58

<210> SEQ ID NO 173
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
acactctttc cctacacgac gctcttccga tctaacagtg tgctggttcc tttctg         56

<210> SEQ ID NO 174
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
gtgactggag ttcagacgtg tgctcttccg atcttytyyc ctcccaactg tattcaga      58

<210> SEQ ID NO 175
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 175
tnantggtta ggtgctggtg gtccgaaggt ccacgccgcc aactacg                   47
```

<210> SEQ ID NO 176
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 176
cnantacgta gttggcggcg tggaccttcg gaccaccagc acctaac                 47

<210> SEQ ID NO 177
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 177
tnantggtta ggtgctggtg gtccgaaggt ccacgccgcc aactacg                 47

<210> SEQ ID NO 178
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 178
angngtcgta gttggcggcg tggaccttcg gaccaccagc acctaac                 47

<210> SEQ ID NO 179
<211> LENGTH: 197
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 179
tggatatcat agtcccgcat caggagcacg tgctgcctat gatcccaagc ggtggtgctt    60
tcaaggacat gatcatgggt taggtgctgg tggtccgaag gtccacgccg ccaactacgt   120

```
ggatatcata gtcccgcatc aggagcacgt gctgcctatg atcccaagcg gtggtgcttt    180
caaggacatg atcatgg                                                   197
```

<210> SEQ ID NO 180
<211> LENGTH: 197
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180

```
ccatgatcat gtccttgaaa gcaccaccgc ttgggatcat aggcagcacg tgctcctgat    60
gcgggactat gatatccacg tagttggcgg cgtggacctt cggaccacca gcacctaacc   120
catgatcatg tccttgaaag caccaccgct tgggatcata ggcagcacgt gctcctgatg   180
cgggactatg atatcca                                                   197
```

<210> SEQ ID NO 181
<211> LENGTH: 197
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181

```
tggatatcat agtcccgcat caggagcacg tgctgcctat gatcccaagc ggtggtgctt    60
tcaaggacat gatcatgggt taggtgctgg tggtccgaag gtccacgccg ccaactacgg   120
atggcaggac ctcgtactga aatttcgacc tacaagacct acaagtgtga catgcgcaat   180
cagcatgatg cccgcgt                                                   197
```

<210> SEQ ID NO 182
<211> LENGTH: 197
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 182

```
acgcgggcat catgctgatt gcgcatgtca cacttgtagg tcttgtaggt cgaaatttca    60
gtacgaggtc ctgccatccg tagttggcgg cgtggacctt cggaccacca gcacctaacc   120
catgatcatg tccttgaaag caccaccgct tgggatcata ggcagcacgt gctcctgatg   180
cgggactatg atatcca                                                   197
```

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: a, c, t, g, unknown or other

<400> SEQUENCE: 183

```
ggagttggcg ttgatccgnc                                                20
```

```
<210> SEQ ID NO 184
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(26)
<223> OTHER INFORMATION: a, c, t, g, unknown or other

<400> SEQUENCE: 184
aactacaggg ttcggaacta agtaant                                            27

<210> SEQ ID NO 185
<211> LENGTH: 6661
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185
tggcaggata tattgtggtg taaacaaatt gacgcttaga caacttaata acacattgcg        60
gacgttttta atgtactgaa ttaacgccga attgaattcg agctcggtac cactggattt      120
tggttttagg aattagaaat tttattgata gaagtatttt acaaatacaa atacatacta      180
agggtttctt atatgctcaa cacatgagcg aaaccctata agaaccctaa ttcccttatc      240
tgggaactac tcacacatta ttctggagaa aaatagagag agatagattt gtagagagag      300
actggtgatt tttgcggact ctattagatc tgggtaactg gcctaactgg ccttggagga      360
gctggcaact caaaatccct ttgccaaaaa ccaacatcat gccatccacc atgcttgtat      420
ccagctgcgc gcaatgtacc ccgggctgtg tatcccaaag cctcatgcaa cctaacagat      480
ggatcgtttg gaaggcctat aacagcaacc acagacttaa aaccttgcgc tccatagac       540 ttaagcaaat gtgtgtacaa tgtggatcct aggcccaacc tttgatgcct atgtgacacg      600
taaacagtac tctcaactgt ccaatcgtaa gcgttcctag ccttccaggg cccagcgtaa      660
gcaataccag ccacaacacc ctcaacctca gcaaccaacc aagggtatct atcttgcaac      720
ctctcgagat catcaatcca ctcttgtggt gtttgtggct ctgtcctaaa gttcactgta      780
gacgtctcaa tgtaatggtt aacgatatca caaaccgcgg ccatatcagc tgctgtagct      840
ggcctaatct caactggtct cctctccgga gacatggctt ctacctacaa aaaagctccg      900
cacgaggctg catttgtcac aaatcatgaa aagaaaaact accgatgaac aatgctgagg      960
gattcaaatt ctacccacaa aaagaagaaa gaaagatcta gcacatctaa gcctgacgaa     1020
gcagcagaaa tatataaaaa tataaaccat agtgcccttt tcccctcttc ctgatcttgt     1080
ttagcatggc ggaaatttta aaccccccat catctccccc aacaacggcg gatcgcagat     1140
ctacatccga gagccccatt ccccgcgaga tccgggccgg atccacgccg gcgagagccc     1200
cagccgcgag atcccgcccc tcccgcgcac cgatctgggc gcgcacgaag ccgcctctcg     1260
cccacccaaa ctaccaaggc caaagatcga gaccgagacg gaaaaaaaaa acggagaaag     1320
aaagaggaga ggggcggggt ggttaccggc gcggcggcgg cggaggggga gggggagga     1380 gctcgtcgtc cggcagcgag ggggaggag gtggaggtgg tggtggtggt ggtggtaggg     1440 ttgggggat gggaggagag gggggggtat gtatatagtg gcgatggggg gcgtttcttt     1500
ggaagcggag ggagggccgg cctcgtcgct ggctcgcgat cctcctcgcg tttccggccc     1560
```

```
ccacgacccg acccacctg ctgtttttc tttttcttt ttttctttct tttttttttt    1620
ttggctgcga gacgtgcggt gcgtgcggac aactcacggt gatagtgggg gggtgtggag    1680
actattgtcc agttggctgg actggggtgg gttgggttgg gttgggttgg gctgggcttg    1740
ctatggatcg tggatagcac tttgggcttt aggaacttta ggggttgttt ttgtaaatgt    1800
tttgagtcta agtttatctt ttattttac tagaaaaaat acccatgcgc tgcaacgggg    1860
gaaagctatt ttaatcttat tattgttcat tgtgagaatt cgcctgaata tatatttttc    1920
tcaaaaatta tgtcaaatta gcatatgggt tttttaaag atatttctta tacaaatccc    1980
tctgtattta caaagcaaa cgaacttaaa acccgactca aatacagata tgcatttcca    2040
aaagcgaata aacttaaaaa ccaattcata caaaaatgac gtatcaaagt accgacaaaa    2100
acatcctcaa ttttataat agtagaaaag agtaaatttc actttgggcc acctttatt    2160
accgatattt tactttatac cacctttaa ctgatgtttt cacttttgac caggtaatct    2220
taccttgtt ttatttgga ctatcccgac tctcttctca agcatatgaa tgacctcgag    2280
tatgctagtc tagagtcgac ctgcagggtg cagcgtgacc cggtcgtgcc cctctctaga    2340
gataatgagc attgcatgtc taagttataa aaaattacca catattttt ttgtcacact    2400
tgtttgaagt gcagtttatc tatctttata catatatta aactttactc tacgaataat    2460
ataatctata gtactacaat aatatcagtg ttttagagaa tcatataaat gaacagttag    2520
acatggtcta aaggacaatt gagtattttg acaacaggac tctacagttt tatctttta    2580
gtgtgcatgt gttctccttt tttttgcaa atagcttcac ctatataata cttcatccat    2640
tttattagta catccattta gggtttaggg ttaatggttt ttatagacta atttttttag    2700
tacatctatt ttattctatt ttagcctcta aattaagaaa actaaaactc tattttagtt    2760
tttttattta ataattaga tataaaatag aataaaataa agtgactaaa aattaaacaa    2820
ataccttta agaaattaaa aaaactaagg aaacattttt cttgtttcga gtagataatg    2880
ccagcctgtt aaacgccgtc gacgagtcta acggacacca accagcgaac cagcagcgtc    2940
gcgtcgggcc aagcgaagca gacggcacgg catctctgtc gctgcctctg gaccccctctc    3000
gagagttccg ctccaccgtt ggacttgctc cgctgtcggc atccagaaat tgcgtggcgg    3060
agcggcagac gtgagccggc acggcaggcg gcctcctcct cctctcacgg cacggcagct    3120
acggggggatt cctttcccac cgctccttcg ctttcccttc ctcgcccgcc gtaataaata    3180
gacaccccct ccacaccctc tttccccaac ctcgtgttgt tcggagcgca cacacacaca    3240
accagatctc ccccaaatcc acccgtcggc acctccgctt caaggtacgc cgctcgtcct    3300
ccccccccccc ccctctctac cttctctaga tcggcgttcc ggtccatggt tagggcccgg    3360
tagttctact tctgttcatg tttgtgttag atccgtgttt gtgttagatc cgtgctgcta    3420
gcgttcgtac acggatgcga cctgtacgtc agacacgttc tgattgctaa cttgccagtg    3480
tttctctttg gggaatcctg ggatggctct agccgttccg cagacgggat cgatttcatg    3540
atttttttg tttcgttgca tagggttggg tttgcccttt tcctttattt caatatatgc    3600
cgtgcacttg tttgtcgggt catcttttca tgctttttt tgtcttggtt gtgatgatgt    3660
ggtctggttg ggcggtcgtt ctagatcgga gtagaattct gtttcaaact acctggtgga    3720
tttattaatt ttggatctgt atgtgtgtgc catacatatt catagttacg aattgaagat    3780
gatggatgga aatatcgatc taggataggt atacatgttg atgcgggttt tactgatgca    3840
tatacagaga tgcttttgt tcgcttggtt gtgatgatgt ggtgtggttg ggcggtcgtt    3900
cattcgttct agatcggagt agaatactgt ttcaaactac ctggtgtatt tattaatttt    3960
```

```
ggaactgtat gtgtgtgtca tacatcttca tagttacgag tttaagatgg atggaaatat    4020
cgatctagga taggtataca tgttgatgtg ggttttactg atgcatatac atgatggcat    4080
atgcagcatc tattcatatg ctctaacctt gagtacctat ctattataat aaacaagtat    4140
gttttataat tattttgatc ttgatatact tggatgatgg catatgcagc agctatatgt    4200
ggattttttt agccctgcct tcatacgcta tttatttgct tggtactgtt tcttttgtcg    4260
atgctcaccc tgttgtttgg tgttacttct gcaggaggat cacaagtttg tacaaaaaag    4320
caggctatgg ccgccgccac ctcccccgcc gtcgcattct cgggcgccac cgccgccgcc    4380
atgcccaaac ccgccgcca tcctctcccg cgccaccagc ccgtctcgcg ccgcgcgctc    4440
cccgcccgcg tcgtcaggtg ttgcgccgcg tccccgccg ccacctccgc cgcgcctccc    4500
gcaaccgcgc tccggccctg gggcccgtcc gagcccgca agggcgccga catcctcgtc    4560
gaggcgctcg agcgctgcgg catcgtcgac gtcttcgcct accccggcgg cgcctccatg    4620
gagatccacc aggcgctgac gcgctcgccc gtcatcacca accacctctt ccgccacgag    4680
caggggagg cgttcgcggc gtccggctac gcccgcgcgt ccggccgcgt cggcgtctgc    4740
gtcgccacct ccgccccggg ggccaccaac ctcgtctccg cgctcgccga cgccctcctc    4800
gactccatcc ccatggtcgc catcacgggc caggtccccc gccgcatgat cggcacggac    4860
gcgttccagg agacgcccat agtggaggtc acgcgctcca tcaccaagca caactacctg    4920
gtccttgacg tggaggatat cccccgcgtc atccaggaag ccttcttcct tgcatcctct    4980
ggccgcccgg ggccggtgct agttgatatc cccaaggaca tccagcagca gatggctgtg    5040
cccgtctggg acactccaat gagtttgcca gggtacatcg cccgcctgcc caagccacca    5100
tctactgaat cgcttgagca ggtcctgcgt ctggttggcg agtcacggcg cccaattctg    5160
tatgttggtg gtggctgcgc tgcgtctggc gaggagttgc gccgctttgt tgagcttact    5220
gggattccag ttacaactac tctgatgggc cttggcaact tccccagcga cgacccactg    5280
tctctgcgca tgcttgggat gcatggcact gtgtatgcaa attatgcagt agataaggct    5340
gacctgttgc tcgcatttgg tgtgcggttt gatgatcgtg tgactgggaa aatcgaggct    5400
tttgcaagca ggtccaagat tgtgcacatt gacattgacc cagctgagat tggcaagaac    5460
aagcagccac atgtctccat ttgtgcagat gttaagcttg ctttacaggg gttgaatgat    5520
ctattaaatg ggagcaaagc acaacagggt ctggattttg gtccatggca caaggagttg    5580
gatcagcaga gagggagtt tcctctagga ttcaagactt ttggcgaggc catcccgccg    5640
caatatgcta tccaggtact ggatgagctg acaaaagggg aggcgatcat tgccactggt    5700
gttgggcagc accagatgtg ggcggctcag tattcacttt acaagcggcc acggcagtgg    5760
ctgtcttcgt ctggtttggg ggcaatggga tttgggttac cagctgcagc tggcgctgct    5820
gtggccaacc caggtgttac agttgttgac attgatggtg atggtagttt cctcatgaac    5880
attcaggagt tggcgttgat ccgcattgag aacctcccag tgaaggtgat gatattgaac    5940
aaccagcatc tgggaatggt ggtgcagtgg gaggataggt tttacaaggc caatcgggcg    6000
cacacatacc ttggcaaccc agaaaatgag agtgagatat atccagattt tgtgacgatt    6060
gctaaaggat tcaacgttcc agcagttcga gtgacgaaga gagcgaagt cactgcagca    6120
atcaagaaga tgcttgagac cccagggcca tacttgttgg atatcatagt cccgcatcag    6180
gagcacgtgc tgcctatgat cccaaatggt ggtgctttca aggacatgat catggagggt    6240
gatggcagga cctcgtactg ataccagct ttccttgtaca aagtggtgat cctactagta    6300
```

```
gaaggagtgc gtcgaagcag atcgttcaaa catttggcaa taaagtttct taagattgaa    6360
tcctgttgcc ggtcttgcga tgattatcat ataatttctg ttgaattacg ttaagcatgt    6420
aataattaac atgtaatgca tgacgttatt tatgagatgg gtttttatga ttagagtccc    6480
gcaattatac atttaatacg cgatagaaaa caaaatatag cgcgcaaact aggataaatt    6540
atcgcgcgcg gtgtcatcta tgttactaga tcgaaagctt agcttgagct tggatcagat    6600
tgtcgtttcc cgccttcagt ttaaactatc agtgtttgac aggatatatt ggcgggtaaa    6660
c                                                                    6661
```

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
attttccatt cacttggccc                                                20

<210> SEQ ID NO 187
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
tgctatctgg ctcagctgc                                                 19

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 188
atggtggaag ggcggttgtg a                                              21

<210> SEQ ID NO 189
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
ctcccgcgca ccgatctg                                                  18

<210> SEQ ID NO 190
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
cccgcccctc tcctctttc                                                 19

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 191
aagccgcctc tcgcccaccc a                                              21

<210> SEQ ID NO 192
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
aycagatgtg ggcggctcag tat                                            23

<210> SEQ ID NO 193
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
gggatatgta ggacaagaaa cttgcatga                                      29

<210> SEQ ID NO 194
<211> LENGTH: 880
<212> TYPE: DNA
<213> ORGANISM: Triticum aestivum

<400> SEQUENCE: 194
accagatgtg ggcggctcag tattacactt acaagcggcc acggcagtgg ctgtcttcgt    60
ctggttgggg gcaatgggat tgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatt cccaatggcg gcgctttcaa ggacatgatc atggagggtg atggcaggac    540
ctcgtactga aatggtccga aggtccacgc cgccaactac gagtatgatc ccaagcggtg    600
gtgctttcaa ggacatgatc atggagggtg atggcaggac ctcgtactga aatttcgacc    660
tacaagacct acaagtgtga catgcgcaat cagcatggtg cccgcgtgtt gtatcaacta    720
ctaggggttc aactgtgaac catgcgtttt ctagtttgct tgtttcattc atataagctt    780
gtgttactta gttccgaacc ctgtagcttt gtagtctatg ctctcttttg tagggatgtg    840
ctgtcataag atatcatgca agtttcttgt cctacatatc                          880

<210> SEQ ID NO 195

```
<211> LENGTH: 776
<212> TYPE: DNA
<213> ORGANISM: Triticum aestivum

<400> SEQUENCE: 195
accagatgtg ggcggctcag tattacactt acaagcggcc acggcagtgg ctgtcttcgt    60
ctggttgggg gcaatgggat ttgggttacc agctgcagct ggcgctgctg tggccaaccc   120
aggtgttaca gttgttgaca ttgatggaga tggtagtttc ctcatgaaca ttcaggagtt   180
ggcattgatc cgtattgaga acctccctgt gaaggtgatg atattgaaca accagcatct   240
gggaatggtg gtgcaatggg aggataggtt ttacaaggcc aatcgggcgc acacatacct   300
tggcaaccca gaaaatgaga gtgagatata tccagatttt gtgacgattg ctaaaggatt   360
caacgttccg gcagttcgtg tgacgaagaa gagcgaagtc actgcagcaa tcaagaagat   420
gcttgagacc ccagggccat acttgttgga tatcatcgtc ccgcatcagg agcacgtgct   480
gccttcccaa gcggtggtgc tttcaaggac atgatcatgg agggtgatgg caggacctcg   540
tactgaaatt tcgacctaca agacctacaa gtgtgacatg cgcaatcagc atggtgcccg   600
cgtgttgtat caactactag gggttcaact gtgaaccatg cgttttctag tttgcttgtt   660
tcattcatat aagcttgtgt tacttagttc cgaaccctgt agctttgtag tctatgctct   720
cttttgtagg gatgtgctgt cataagatat catgcaagtt tcttgtccta catatc       776

<210> SEQ ID NO 196
<211> LENGTH: 866
<212> TYPE: DNA
<213> ORGANISM: Triticum aestivum

<400> SEQUENCE: 196
atcagatgtg ggcggctcag tattacactt acaagcggcc acggcagtgg ctgtcttcat    60
ccggtttggg tgcaatggga tttgggttgc cagctgcagc tggcgctgct gtggccaacc   120
caggtgttac agttgttgac attgatgggg atggtagttt cctcatgaac attcaggagt   180
tggcgttgat ccgtattgag aacctcccag tgaaggtgat gatattgaac aaccagcatc   240
tgggaatggt ggtgcagtgg gaggataggt tttacaaggc caaccgggcg cacacatacc   300
ttggcaaccc agaaaatgag agtgagatat atccagattt tgtgacgatt gctaaaggat   360
tcaacgttcc ggcagttcgt gtgacgaaga gagcgaagt cactgcagca atcaagaaga   420
tgcttgagac cccagggcca tacttgttgg atatcattgt cccgcatcag gagcacgtga   480
atggcggcgc tttcaaggac atgatcatgg agggtgatgg caggacctcg tactgaaatg   540
gtccgaaggt ccacgccgcc aactacgagt atgatcccaa gcggtggtgc ttttaaggac   600
atgatcatgg agggtgatgg caggacctcg tactgaaatt tcgacctaca agacctacaa   660
gtgtgacatg cgcaatcagc atgatacctg cgtgttgtat caactactgg gggttcaact   720
gtgaaccatg cgttttctag tttgcttgtt tcattcatat aagcttgtgt tacttagttc   780
cgaaccgtgt agttttgtag tctctgttct cttttgtagg gatgtgctgt cataagatat   840
catgcaagtt tcttgtccta catatc                                         866

<210> SEQ ID NO 197
<211> LENGTH: 781
<212> TYPE: DNA
<213> ORGANISM: Triticum aestivum

<400> SEQUENCE: 197
atcagatgtg ggcggctcag tattacactt acaagcggcc acggcagtgg ctgtcttcat    60
```

```
ccggtttggg tgcaatggga tttgggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga agagcgaagt cactgcagca atcaagaaga    420
tgcttgagac cccagggcca tacttgttgg atatcattgt cccgcatcag gagcacgtgc    480
tgcctatgat cccaagcggt ggtgcttta aggacatgat catggagggt gatggcagga    540
cctcgtactg aaatttcgac ctacaagacc tacaagtgtg acatgcgcaa tcagcatgat    600
acctgcgtgt tgtatcaact actgggggtt caactgtgaa ccatgcgttt tctagtttgc    660
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                    781

<210> SEQ ID NO 198
<211> LENGTH: 867
<212> TYPE: DNA
<213> ORGANISM: Triticum aestivum

<400> SEQUENCE: 198
accagatgtg ggcggctcag tattacactt acaagcggcc acggcagtgg ctgtcttcgt     60
ctggtttggg ggcaatggga tttgggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga agagcgaagt cactgcagca atcaagaaga    420
tgcttgagac cccagggcca tacttgttgg atatcatagt cccgcatcag gagcacgtgc    480
tgcctaatgg cggcgctttc aaggacatga tcatggaggg tgatggcagg acctcgtact    540
gaaatggtcc gaaggtccac gccgccaact acgagtccca agcggtggtg ctttcaagga    600
catgatcatg gagggtgatg gcaggacctc gtactgaaat ttcgacctac aagacctaca    660
agtgtgacat gcgcaatcag catgatgccc gcgtgttgta tcaactacta ggggttcaac    720
tgtgagccat gcgttttcta gtttgcttgt tcattcata taagcttgta ttacttagtt    780
ccgaaccctg tagttttgta gtctatgttc tcttttgtag ggatgtgctg tcataagatg    840
tcatgcaagt tcttgtcct acatatc                                         867

<210> SEQ ID NO 199
<211> LENGTH: 781
<212> TYPE: DNA
<213> ORGANISM: Triticum aestivum

<400> SEQUENCE: 199
accagatgtg ggcggctcag tattacactt acaagcggcc acggcagtgg ctgtcttcgt     60
ctggtttggg ggcaatggga tttgggttac cagctgcagc tggcgctgct gtggccaacc    120
caggtgttac agttgttgac attgatggtg atggtagttt cctcatgaac attcaggagt    180
```

```
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga gagcgaagt cactgcagca atcaagaaga    420
tgcttgagac cccagggcca tacttgttgg atatcatagt cccgcatcag gagcacgtgc    480
tgcctatgat cccaagcggt ggtgctttca aggacatgat catggagggt gatggcagga    540
cctcgtactg aaatttcgac ctacaagacc tacaagtgtg acatgcgcaa tcagcatgat    600
gcccgcgtgt tgtatcaact actaggggtt caactgtgag ccatgcgttt tctagtttgc    660
ttgtttcatt catataagct tgtattactt agttccgaac cctgtagttt tgtagtctat    720
gttctctttt gtagggatgt gctgtcataa gatgtcatgc aagtttcttg tcctacatat    780
c                                                                     781

<210> SEQ ID NO 200
<211> LENGTH: 763
<212> TYPE: DNA
<213> ORGANISM: Triticum aestivum

<400> SEQUENCE: 200
accagatgtg ggcggctcag tattacactt acaagcggcc acggcagtgg ctgtcttcgt     60
ctggttgggg gcaatgggat ttgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacaagcg    480
gtggtgcttt caaggacatg atcatggagg tgatggcagg acctcgtact gaaatttcg     540 acctacaaga cctacaagtg tgacatgcgc aatcagcatg tgcccgcgt gttgtatcaa    600 ctactagggg ttcaactgtg aaccatgcgt tttctagttt gcttgtttca ttcatataag    660
cttgtgttac ttagttccga accctgtagc tttgtagtct atgctctctt ttgtagggat    720
gtgctgtcat aagatatcat gcaagtttct tgtcctacat atc                      763

<210> SEQ ID NO 201
<211> LENGTH: 780
<212> TYPE: DNA
<213> ORGANISM: Triticum aestivum

<400> SEQUENCE: 201
accagatgtg ggcggctcag tattacactt acaagcggcc acggcagtgg ctgtcttcgt     60
ctggttgggg gcaatgggat ttgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
```

```
gcctatgatc ccaagcggtg gtgctttcaa ggacatgatc atggagggtg atggcaggac    540
ctcgtactga aatttcgacc tacaagacct acaagtgtga catgcgcaat cagcatggtg    600
cccgcgtgtt gtatcaacta ctaggggttc aactgtgaac catgcgtttt ctagtttgct    660
tgtttcattc atataagctt gtgttactta gttccgaacc ctgtagcttt gtagtctatg    720
ctctcttttg tagggatgtg ctgtcataag atatcatgca agtttcttgt cctacatatc    780
```

<210> SEQ ID NO 202
<211> LENGTH: 781
<212> TYPE: DNA
<213> ORGANISM: Triticum aestivum

<400> SEQUENCE: 202

```
atcagatgtg ggcggctcag tattacactt acaagcggcc acggcagtgg ctgtcttcat     60
ccggtttggg tgcaatggga tttggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga gagcgaagt cactgcagca atcaagaaga    420
tgcttgagac cccagggcca tacttgttgg atatcattgt cccgcatcag gagcacgtgc    480
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actgggggtt caactgtgaa ccatgcgttt tctagtttgc    660
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                   781
```

<210> SEQ ID NO 203
<211> LENGTH: 781
<212> TYPE: DNA
<213> ORGANISM: Triticum aestivum

<400> SEQUENCE: 203

```
atcagatgtg ggcggctcag tattacactt acaagcggcc acggcagtgg ctgtcttcat     60
ccggtttggg tgcaatggga tttggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga gagcgaagt cactgcagca atcaagaaga    420
tgcttgagac cccagggcca tacttgttgg atatcattgt cccgcatcag gagcacgtgc    480
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actgggggtt caactgtgaa ccatgcgttt tctagtttgc    660
ttgtttcatt catataagct tgtgttactt agttccgaac cgtgtagttt tgtagtctct    720
```

```
gttctctttt gtagggatgt gctgtcataa gatatcatgc aagtttcttg tcctacatat    780
c                                                                    781
```

<210> SEQ ID NO 204
<211> LENGTH: 876
<212> TYPE: DNA
<213> ORGANISM: Triticum aestivum

<400> SEQUENCE: 204

```
accagatgtg ggcggctcag tattacactt acaagcggcc acggcagtgg ctgtcttcgt     60
ctggtttggg ggcaatggga tttgggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga gagcgaagt cactgcagca atcaagaaga    420
tgcttgagac cccagggcca tacttgttgg atatcatagt cccgcatcag gagcacgtgc    480
tgcctatgat tcccaatggc ggcgctttca aggacatgat catggagggt gatggcagga    540
cctcgtactg aaatggtccg aaggtccacg ccgccaacta cgagtcccaa gcggtggtgc    600
tttcaaggac atgatcatgg agggtgatgg caggacctcg tactgaaatt cgacctaca    660
agacctacaa gtgtgacatg cgcaatcagc atgatgcccg cgtgttgtat caactactag    720
gggttcaact gtgagccatg cgttttctag tttgcttgtt tcattcatat aagcttgtat    780
tacttagttc cgaaccctgt agttttgtag tctatgttct cttttgtagg gatgtgctgt    840
cataagatgt catgcaagtt tcttgtccta catatc                              876
```

<210> SEQ ID NO 205
<211> LENGTH: 781
<212> TYPE: DNA
<213> ORGANISM: Triticum aestivum

<400> SEQUENCE: 205

```
accagatgtg ggcggctcag tattacactt acaagcggcc acggcagtgg ctgtcttcgt     60
ctggtttggg ggcaatggga tttgggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga gagcgaagt cactgcagca atcaagaaga    420
tgcttgagac cccagggcca tacttgttgg atatcatagt cccgcatcag gagcacgtgc    480
tgcctatgat cccaagcggt ggtgctttca aggacatgat catggagggt gatggcagga    540
cctcgtactg aaatttcgac ctacaagacc tacaagtgtg acatgcgcaa tcagcatgat    600
gcccgcgtgt tgtatcaact actagggggt caactgtgag ccatgcgttt tctagtttgc    660
ttgtttcatt catataagct tgtattactt agttccgaac cctgtagttt tgtagtctat    720
gttctctttt gtagggatgt gctgtcataa gatgtcatgc aagtttcttg tcctacatat    780
c                                                                    781
```

<210> SEQ ID NO 206
<211> LENGTH: 880
<212> TYPE: DNA
<213> ORGANISM: Triticum aestivum

<400> SEQUENCE: 206

```
accagatgtg ggcggctcag tattacactt acaagcggcc acggcagtgg ctgtcttcgt      60
ctggttgggg gcaatgggat ttgggttacc agctgcagct ggcgctgctg tggccaaccc     120
aggtgttaca gttgttgaca ttgatggaga tggtagtttc ctcatgaaca ttcaggagtt     180
ggcattgatc cgtattgaga acctccctgt gaaggtgatg atattgaaca accagcatct     240
gggaatggtg gtgcaatggg aggataggtt ttacaaggcc aatcgggcgc acacatacct     300
tggcaaccca gaaaatgaga gtgagatata ccagatttt gtgacgattg ctaaaggatt      360
caacgttccg gcagttcgtg tgacgaagaa gagcgaagtc actgcagcaa tcaagaagat     420
gcttgagacc ccagggccat acttgttgga tatcatcgtc ccgcatcagg agcacgtgct     480
gcctatgatt cccaatggcg cgctttcaa ggacatgatc atggagggtg atggcaggac      540
ctcgtactga atggtccga aggtccacgc cgccaactac gagtatgatc ccaagcggtg      600
gtgcttcaa ggacatgatc atggagggtg atggcaggac ctcgtactga aatttcgacc      660
tacaagacct acaagtgtga catgcgcaat cagcatggtg cccgcgtgtt gtatcaacta     720
ctaggggttc aactgtgaac catgcgtttt ctagtttgct tgtttcattc atataagctt     780
gtgttactta gttccgaacc ctgtagcttt gtagtctatg ctctcttttg tagggatgtg     840
ctgtcataag atatcatgca agtttcttgt cctacatatc                           880
```

<210> SEQ ID NO 207
<211> LENGTH: 780
<212> TYPE: DNA
<213> ORGANISM: Triticum aestivum

<400> SEQUENCE: 207

```
accagatgtg ggcggctcag tattacactt acaagcggcc acggcagtgg ctgtcttcgt      60
ctggttgggg gcaatgggat ttgggttacc agctgcagct ggcgctgctg tggccaaccc     120
aggtgttaca gttgttgaca ttgatggaga tggtagtttc ctcatgaaca ttcaggagtt     180
ggcattgatc cgtattgaga acctccctgt gaaggtgatg atattgaaca accagcatct     240
gggaatggtg gtgcaatggg aggataggtt ttacaaggcc aatcgggcgc acacatacct     300
tggcaaccca gaaaatgaga gtgagatata ccagatttt gtgacgattg ctaaaggatt      360
caacgttccg gcagttcgtg tgacgaagaa gagcgaagtc actgcagcaa tcaagaagat     420
gcttgagacc ccagggccat acttgttgga tatcatcgtc ccgcatcagg agcacgtgct     480
gcctatgatc ccaagcggtg gtgctttcaa ggacatgatc atggagggtg atggcaggac     540
ctcgtactga aatttcgacc tacaagacct acaagtgtga catgcgcaat cagcatggtg     600
cccgcgtgtt gtatcaacta ctaggggttc aactgtgaac catgcgtttt ctagtttgct    660
tgtttcattc atataagctt gtgttactta gttccgaacc ctgtagcttt gtagtctatg    720
ctctcttttg tagggatgtg ctgtcataag atatcatgca agtttcttgt cctacatatc    780
```

<210> SEQ ID NO 208
<211> LENGTH: 781
<212> TYPE: DNA
<213> ORGANISM: Triticum aestivum

<400> SEQUENCE: 208

```
atcagatgtg ggcggctcag tattacactt acaagcggcc acggcagtgg ctgtcttcat    60
ccggtttggg tgcaatggga tttgggttgc cagctgcagc tggcgctgct gtggccaacc   120
caggtgttac agttgttgac attgatgggg atggtagttt cctcatgaac attcaggagt   180
tggcgttgat ccgtattgag aacctcccag tgaaggtgat gatattgaac aaccagcatc   240
tgggaatggt ggtgcagtgg gaggataggt tttacaaggc caaccgggcg cacacatacc   300
ttggcaaccc agaaaatgag agtgagatat atccagattt tgtgacgatt gctaaaggat   360
tcaacgttcc ggcagttcgt gtgacgaaga gagcgaagt cactgcagca atcaagaaga   420
tgcttgagac cccagggcca tacttgttgg atatcattgt cccgcatcag gagcacgtgc   480
tgcctatgat cccaagcggt ggtgctttta aggacatgat catggagggt gatggcagga   540
cctcgtactg aaatttcgac ctacaagacc tacaagtgtg acatgcgcaa tcagcatgat   600
acctgcgtgt tgtatcaact actggggggtt caactgtgaa ccatgcgttt tctagtttgc   660
ttgtttcatt catataagct tgtgttactt agttccgaac cgtgtagttt tgtagtctct   720
gttctctttt gtagggatgt gctgtcataa gatatcatgc aagtttcttg tcctacatat   780
c                                                                  781

<210> SEQ ID NO 209
<211> LENGTH: 781
<212> TYPE: DNA
<213> ORGANISM: Triticum aestivum

<400> SEQUENCE: 209
atcagatgtg ggcggctcag tattacactt acaagcggcc acggcagtgg ctgtcttcat    60
ccggtttggg tgcaatggga tttgggttgc cagctgcagc tggcgctgct gtggccaacc   120
caggtgttac agttgttgac attgatgggg atggtagttt cctcatgaac attcaggagt   180
tggcgttgat ccgtattgag aacctcccag tgaaggtgat gatattgaac aaccagcatc   240
tgggaatggt ggtgcagtgg gaggataggt tttacaaggc caaccgggcg cacacatacc   300
ttggcaaccc agaaaatgag agtgagatat atccagattt tgtgacgatt gctaaaggat   360
tcaacgttcc ggcagttcgt gtgacgaaga gagcgaagt cactgcagca atcaagaaga   420
tgcttgagac cccagggcca tacttgttgg atatcattgt cccgcatcag gagcacgtgc   480
tgcctatgat cccaagcggt ggtgctttta aggacatgat catggagggt gatggcagga   540
cctcgtactg aaatttcgac ctacaagacc tacaagtgtg acatgcgcaa tcagcatgat   600
acctgcgtgt tgtatcaact actggggggtt caactgtgaa ccatgcgttt tctagtttgc   660
ttgtttcatt catataagct tgtgttactt agttccgaac cgtgtagttt tgtagtctct   720
gttctctttt gtagggatgt gctgtcataa gatatcatgc aagtttcttg tcctacatat   780
c                                                                  781

<210> SEQ ID NO 210
<211> LENGTH: 781
<212> TYPE: DNA
<213> ORGANISM: Triticum aestivum

<400> SEQUENCE: 210
accagatgtg ggcggctcag tattacactt acaagcggcc acggcagtgg ctgtcttcgt    60
ctggtttggg ggcaatggga tttgggttac cagctgcagc tggcgctgct gtggccaacc   120
caggtgttac agttgttgac attgatgGtg atggtagttt cctcatgaac attcaggagt   180
tggcgttgat ccgcattgag aacctcccag tgaaggtgat gatattgaac aaccagcatc   240
```

```
tgggaatggt ggtgcagtgg gaggataggt tttacaaggc caatcgggcg cacacatacc      300
ttggcaaccc agaaaatgag agtgagatat atccagattt tgtgacgatt gctaaaggat      360
tcaacgttcc agcagttcga gtgacgaaga agagcgaagt cactgcagca atcaagaaga      420
tgcttgagac cccagggcca tacttgttgg atatcatagt cccgcatcag gagcacgtgc      480
tgcctatgat cccaagcggt ggtgctttca aggacatgat catggagggt gatggcagga      540
cctcgtactg aaatttcgac ctacaagacc tacaagtgtg acatgcgcaa tcagcatgat      600
gcccgcgtgt tgtatcaact actaggggtt caactgtgag ccatgcgttt tctagtttgc      660
ttgtttcatt catataagct tgtattactt agttccgaac cctgtagttt tgtagtctat      720
gttctctttt gtagggatgt gctgtcataa gatgtcatgc aagtttcttg tcctacatat      780
c                                                                     781

<210> SEQ ID NO 211
<211> LENGTH: 781
<212> TYPE: DNA
<213> ORGANISM: Triticum aestivum

<400> SEQUENCE: 211
accagatgtg ggcggctcag tattacactt acaagcggcc acggcagtgg ctgtcttcgt       60
ctggtttggg ggcaatggga tttgggttac cagctgcagc tggcgctgct gtggccaacc      120
caggtgttac agttgttgac attgatggtg atggtagttt cctcatgaac attcaggagt      180
tggcgttgat ccgcattgag aacctcccag tgaaggtgat gatattgaac accagcatc       240 tgggaatggt ggtgcagtgg gaggataggt tttacaaggc caatcgggcg cacacatacc      300
ttggcaaccc agaaaatgag agtgagatat atccagattt tgtgacgatt gctaaaggat      360
tcaacgttcc agcagttcga gtgacgaaga agagcgaagt cactgcagca atcaagaaga      420
tgcttgagac cccagggcca tacttgttgg atatcatagt cccgcatcag gagcacgtgc      480
tgcctatgat cccaagcggt ggtgctttca aggacatgat catggagggt gatggcagga      540
cctcgtactg aaatttcgac ctacaagacc tacaagtgtg acatgcgcaa tcagcatgat      600
gcccgcgtgt tgtatcaact actaggggtt caactgtgag ccatgcgttt tctagtttgc      660
ttgtttcatt catataagct tgtattactt agttccgaac cctgtagttt tgtagtctat      720
gttctctttt gtagggatgt gctgtcataa gatgtcatgc aagtttcttg tcctacatat      780
c                                                                     781

<210> SEQ ID NO 212
<211> LENGTH: 880
<212> TYPE: DNA
<213> ORGANISM: Triticum aestivum

<400> SEQUENCE: 212
accagatgtg ggcggctcag tattacactt acaagcggcc acggcagtgg ctgtcttcgt       60
ctggttgggg gcaatgggat ttgggttacc agctgcagct ggcgctgctg tggccaaccc      120
aggtgttaca gttgttgaca ttgatggaga tggtagtttc ctcatgaaca ttcaggagtt      180
ggcattgatc cgtattgaga acctccctgt gaaggtgatg atattgaaca accagcatct      240
gggaatggtg gtgcaatggg aggataggtt ttacaaggcc aatcgggcgc acacatacct      300
tggcaaccca gaaaatgaga gtgagatata tccagatttt gtgacgattg ctaaaggatt      360
caacgttccg gcagttcgtg tgacgaagaa gagcgaagtc actgcagcaa tcaagaagat      420
```

| | |
|---|---|
| gcttgagacc ccagggccat acttgttgga tatcatcgtc ccgcatcagg agcacgtgct | 480 |
| gcctatgatt cccaatggcg gcgctttcaa ggacatgatc atggagggtg atggcaggac | 540 |
| ctcgtactga aatggtccga aggtccacgc cgccaactac gagtatgatc ccaagcggtg | 600 |
| gtgctttcaa ggacatgatc atggagggtg atggcaggac ctcgtactga aatttcgacc | 660 |
| tacaagacct acaagtgtga catgcgcaat cagcatggtg cccgcgtgtt gtatcaacta | 720 |
| ctaggggttc aactgtgaac catgcgtttt ctagtttgct tgtttcattc atataagctt | 780 |
| gtgttactta gttccgaacc ctgtagcttt gtagtctatg ctctcttttg tagggatgtg | 840 |
| ctgtcataag atatcatgca agtttcttgt cctacatatc | 880 |

<210> SEQ ID NO 213
<211> LENGTH: 780
<212> TYPE: DNA
<213> ORGANISM: Triticum aestivum

<400> SEQUENCE: 213

| | |
|---|---|
| accagatgtg ggcggctcag tattacactt acaagcggcc acggcagtgg ctgtcttcgt | 60 |
| ctggttgggg gcaatgggat ttgggttacc agctgcagct ggcgctgctg tggccaaccc | 120 |
| aggtgttaca gttgttgaca ttgatggaga tggtagtttc ctcatgaaca ttcaggagtt | 180 |
| ggcattgatc cgtattgaga acctccctgt gaaggtgatg atattgaaca accagcatct | 240 |
| gggaatggtg gtgcaatggg aggataggtt ttacaaggcc aatcgggcgc acacatacct | 300 |
| tggcaaccca gaaaatgaga gtgagatata tccagatttt gtgacgattg ctaaaggatt | 360 |
| caacgttccg gcagttcgtg tgacgaagaa gagcgaagtc actgcagcaa tcaagaagat | 420 |
| gcttgagacc ccagggccat acttgttgga tatcatcgtc ccgcatcagg agcacgtgct | 480 |
| gcctatgatc ccaagcggtg gtgctttcaa ggacatgatc atggagggtg atggcaggac | 540 |
| ctcgtactga aatttcgacc tacaagacct acaagtgtga catgcgcaat cagcatggtg | 600 |
| cccgcgtgtt gtatcaacta ctaggggttc aactgtgaac catgcgtttt ctagtttgct | 660 |
| tgtttcattc atataagctt gtgttactta gttccgaacc ctgtagcttt gtagtctatg | 720 |
| ctctcttttg tagggatgtg ctgtcataag atatcatgca agtttcttgt cctacatatc | 780 |

<210> SEQ ID NO 214
<211> LENGTH: 1041
<212> TYPE: DNA
<213> ORGANISM: Triticum aestivum
<220> FEATURE:
<221> NAME/KEY: modified_base
<222> LOCATION: (604)..(633)
<223> OTHER INFORMATION: a, c, t, g, unknown or other

<400> SEQUENCE: 214

| | |
|---|---|
| atcagatgtg ggcggctcag tattacactt acaagcggcc acggcagtgg ctgtcttcat | 60 |
| ccggtttggg tgcaatggga tttgggttgc cagctgcagc tggcgctgct gtggccaacc | 120 |
| caggtgttac agttgttgac attgatgggg atggtagttt cctcatgaac attcaggagt | 180 |
| tggcgttgat ccgtattgag aacctcccag tgaaggtgat gatattgaac aaccagcatc | 240 |
| tgggaatggt ggtgcagtgg gaggataggt tttacaaggc caaccgggcg cacacatacc | 300 |
| ttggcaaccc agaaaatgag agtgagatat atccagatttt gtgacgatt gctaaaggat | 360 |
| tcaacgttcc ggcagttcgt gtgacgaaga gagcgaagt cactgcagca atcaagaaga | 420 |
| tgcttgagac cccagggcca tacttgttgg atatcattgt cccgcatcag gagcacgtgc | 480 |
| tgtagttggc ggcgctttca aggacatgat catggagggt gatgkcagga cctcgtactg | 540 |

| aaatggtccg aaggtccacg cctcgtatga aatggtccga aggtccacgc cgccaactac | 600 |
| gagnnnnnn nnnnnnnnnn nnnnnnnnnn nnntatgatt cccaatggcg gcttcccaat | 660 |
| ggcggcgctt tcaaggacat gatcatggag ggtgatggca ggacctcgta ctgaaatggt | 720 |
| ccgaaggtcc acgccgccaa ctacgatgat cccaagcggt ggtgcttta aggacatgat | 780 |
| catggagggt gatggcagga cctcgtactg aaatttcgac ctacaagacc tacaagtgtg | 840 |
| acatgcgcaa tcagcatgat acctgcgtgt tgtatcaact actggggggtt caactgtgaa | 900 |
| ccatgcgttt tctagtttgc ttgtttcatt catataagct tgtgttactt agttccgaac | 960 |
| cgtgtagttt tgtagtctct gttctctttt gtagggatgt gctgtcataa gatatcatgc | 1020 |
| aagtttcttg tcctacatat c | 1041 |

<210> SEQ ID NO 215
<211> LENGTH: 781
<212> TYPE: DNA
<213> ORGANISM: Triticum aestivum

<400> SEQUENCE: 215

| atcagatgtg ggcggctcag tattacactt acaagcggcc acggcagtgg ctgtcttcat | 60 |
| ccggtttggg tgcaatggga tttggttgc cagctgcagc tggcgctgct gtggccaacc | 120 |
| caggtgttac agttgttgac attgatgggg atggtagttt cctcatgaac attcaggagt | 180 |
| tggcgttgat ccgtattgag aacctcccag tgaaggtgat gatattgaac aaccagcatc | 240 |
| tgggaatggt ggtgcagtgg gaggataggt tttacaaggc caaccgggcg cacacatacc | 300 |
| ttggcaaccc agaaaatgag agtgagatat atccagattt tgtgacgatt gctaaaggat | 360 |
| tcaacgttcc ggcagttcgt gtgacgaaga gagcgaagt cactgcagca atcaagaaga | 420 |
| tgcttgagac cccagggcca tacttgttgg atatcattgt cccgcatcag gagcacgtgc | 480 |
| tgcctatgat cccaagcggt ggtgctttta aggacatgat catggagggt gatggcagga | 540 |
| cctcgtactg aaatttcgac ctacaagacc tacaagtgtg acatgcgcaa tcagcatgat | 600 |
| acctgcgtgt tgtatcaact actgggggtt caactgtgaa ccatgcgttt tctagtttgc | 660 |
| ttgtttcatt catataagct tgtgttactt agttccgaac cgtgtagttt tgtagtctct | 720 |
| gttctctttt gtagggatgt gctgtcataa gatatcatgc aagtttcttg tcctacatat | 780 |
| c | 781 |

<210> SEQ ID NO 216
<211> LENGTH: 881
<212> TYPE: DNA
<213> ORGANISM: Triticum aestivum

<400> SEQUENCE: 216

| accagatgtg ggcggctcag tattacactt acaagcggcc acggcagtgg ctgtcttcgt | 60 |
| ctggtttggg ggcaatggga tttggttac cagctgcagc tggcgctgct gtggccaacc | 120 |
| caggtgttac agttgttgac attgatggtg atggtagttt cctcatgaac attcaggagt | 180 |
| tggcgttgat ccgcattgag aacctcccag tgaaggtgat gatattgaac aaccagcatc | 240 |
| tgggaatggt ggtgcagtgg gaggataggt tttacaaggc caatcgggcg cacacatacc | 300 |
| ttggcaaccc agaaaatgag agtgagatat atccagattt tgtgacgatt gctaaaggat | 360 |
| tcaacgttcc agcagttcga gtgacgaaga gagcgaagt cactgcagca atcaagaaga | 420 |
| tgcttgagac cccagggcca tacttgttgg atatcatagt cccgcatcag gagcacgtgc | 480 |

| | |
|---|---|
| tgcctatgat tcccaatggc ggcgctttca aggacatgat catggagggt gatggcagga | 540 |
| cctcgtactg aaatggtccg aaggtccacg ccgccaacta cgagtatgat cccaagcggt | 600 |
| ggtgctttca aggacatgat catggagggt gatggcagga cctcgtactg aaatttcgac | 660 |
| ctacaagacc tacaagtgtg acatgcgcaa tcagcatgat gcccgcgtgt tgtatcaact | 720 |
| actagggggtt caactgtgag ccatgcgttt tctagtttgc ttgtttcatt catataagct | 780 |
| tgtattactt agttccgaac cctgtagttt tgtagtctat gttctctttt gtagggatgt | 840 |
| gctgtcataa gatgtcatgc aagtttcttg tcctacatat c | 881 |

<210> SEQ ID NO 217
<211> LENGTH: 918
<212> TYPE: DNA
<213> ORGANISM: Triticum aestivum

<400> SEQUENCE: 217

| | |
|---|---|
| accagatgtg ggcggctcag tattacactt acaagcggcc acggcagtgg ctgtcttcgt | 60 |
| ctggtttggg ggcaatggga tttggttac cagctgcagc tggcgctgct gtggccaacc | 120 |
| caggtgttac agttgttgac attgatggta atggtagttt cctcatgaac attcaggagt | 180 |
| tggcgttgat ccgcattgag aacctcccag tgaaggtgat gatattgaac aaccagcatc | 240 |
| tgggaatggt ggtgcagtgg gaggataggt tttacaaggc caatcgggcg cacacatacc | 300 |
| ttggcaaccc agaaaatgag agtgagatat atccagattt tgtgacgatt gctaaaggat | 360 |
| tcaacgttcc agcagttcga gtgacgaaga gagcgaagt cactgcagca atcaagaaga | 420 |
| tgcttgagac cccagggcca tacttgttgg atatcatagt cccgcatcag gagcacgtgc | 480 |
| tgcctatgat tcccaatggc ggcgctttca aggacatgat catggagggt gatggcagga | 540 |
| cctcgtactg aaaatggtcc gaaggtccac gccgccacct cgtactgaaa tggtccraag | 600 |
| gtccacgccg ccaactacga gtatgatccc aagcggtggt gctttcaagg acatgatcat | 660 |
| ggagggtgat ggcaggacct cgtactgara tttcgaccta caagacctac aagtgtgaca | 720 |
| tgcgcaatca gcatgatgcc cgcgtgttgt atcaactact aggggttcaa ctgtgagcca | 780 |
| tgcgttttct agtttgcttg tttcattcat ataagcttgt attacttagt tccgaaccct | 840 |
| gtagttttgt agtctatgtt ctcttttgta gggatgtgct gtcataagat gtcatgcaag | 900 |
| tttcttgtcc tacatatc | 918 |

<210> SEQ ID NO 218
<211> LENGTH: 880
<212> TYPE: DNA
<213> ORGANISM: Triticum aestivum

<400> SEQUENCE: 218

| | |
|---|---|
| accagatgtg ggcggctcag tattacactt acaagcggcc acggcagtgg ctgtcttcgt | 60 |
| ctggttgggg gcaatgggat ttgggttacc agctgcagct ggcgctgctg tggccaaccc | 120 |
| aggtgttaca gttgttgaca ttgatggaga tggtagtttc ctcatgaaca ttcaggagtt | 180 |
| ggcattgatc cgtattgaga acctccctgt gaaggtgatg atattgaaca accagcatct | 240 |
| gggaatggtg gtgcaatggg aggataggtt ttacaaggcc aatcgggcgc acacatacct | 300 |
| tggcaaccca gaaaatgaga gtgagatata tccagatttt gtgacgattg ctaaaggatt | 360 |
| caacgttccg gcagttcgtg tgacgaagaa gagcgaagtc actgcagcaa tcaagaagat | 420 |
| gcttgagacc ccagggccat acttgttgga tatcatcgtc ccgcatcagg agcacgtgct | 480 |
| gcctatgatt cccaatggcg gcgctttcaa ggacatgatc atggagggtg atggcaggac | 540 |

| | |
|---|---:|
| ctcgtactga aatggtccga aggtccacgc cgccaactac gagtatgatc ccaagcggtg | 600 |
| gtgctttcaa ggacatgatc atggagggtg atggcaggac ctcgtactga aatttcgacc | 660 |
| tacaagacct acaagtgtga catgcgcaat cagcatggtg cccgcgtgtt gtatcaacta | 720 |
| ctaggggttc aactgtgaac catgcgtttt ctagtttgct tgtttcattc atataagctt | 780 |
| gtgttactta gttccgaacc ctgtagcttt gtagtctatg ctctcttttg tagggatgtg | 840 |
| ctgtcataag atatcatgca agtttcttgt cctacatatc | 880 |

<210> SEQ ID NO 219
<211> LENGTH: 780
<212> TYPE: DNA
<213> ORGANISM: Triticum aestivum

<400> SEQUENCE: 219

| | |
|---|---:|
| accagatgtg ggcggctcag tattacactt acaagcggcc acggcagtgg ctgtcttcgt | 60 |
| ctggttgggg gcaatgggat ttgggttacc agctgcagct ggcgctgctg tggccaaccc | 120 |
| aggtgttaca gttgttgaca ttgatggaga tggtagtttc ctcatgaaca ttcaggagtt | 180 |
| ggcattgatc cgtattgaga acctccctgt gaaggtgatg atattgaaca accagcatct | 240 |
| gggaatggtg gtgcaatggg aggataggtt ttacaaggcc aatcgggcgc acacatacct | 300 |
| tggcaaccca gaaaatgaga gtgagatata tccagatttt gtgacgattg ctaaaggatt | 360 |
| caacgttccg gcagttcgtg tgacgaagaa gagcgaagtc actgcagcaa tcaagaagat | 420 |
| gcttgagacc ccagggccat acttgttgga tatcatcgtc ccgcatcagg agcacgtgct | 480 |
| gcctatgatc ccaagcggtg gtgctttcaa ggacatgatc atggagggtg atggcaggac | 540 |
| ctcgtactga aatttcgacc tacaagacct acaagtgtga catgcgcaat cagcatggtg | 600 |
| cccgcgtgtt gtatcaacta ctaggggttc aactgtgaac catgcgtttt ctagtttgct | 660 |
| tgtttcattc atataagctt gtgttactta gttccgaacc ctgtagcttt gtagtctatg | 720 |
| ctctcttttg tagggatgtg ctgtcataag atatcatgca agtttcttgt cctacatatc | 780 |

<210> SEQ ID NO 220
<211> LENGTH: 745
<212> TYPE: DNA
<213> ORGANISM: Triticum aestivum

<400> SEQUENCE: 220

| | |
|---|---:|
| atcagatgtg ggcggctcag tattacactt acaagcggcc acggcagtgg ctgtcttcat | 60 |
| ccggtttggg tgcaatggga tttgggttgc agctgcagc tggcgctgct gtggccaacc | 120 |
| caggtgttac agttgttgac attgatgggg atggtagttt cctcatgaac attcaggagt | 180 |
| tggcgttgat ccgtattgag aacctcccag tgaaggtgat gatattgaac aaccagcatc | 240 |
| tgggaatggt ggtgcagtgg gaggataggt tttacaaggc caaccgggcg cacacatacc | 300 |
| ttggcaaccc agaaaatgag agtgagatat atccagattt tgtgacgatt gctaaaggat | 360 |
| tcaacgttcc ggcagttcgt gtgacgaaga agagcgaagt cactgcagca atcaagaaga | 420 |
| tgcttgagac cccagggcca tacttgttgg atatcattgt cccgcatgct tttaaggaca | 480 |
| tgatcatgga gggtgatggc aggacctcgt actgaaattt cgacctacaa gacctacaag | 540 |
| tgtgacatgc gcaatcagca tgatacctgc gtgttgtatc aactactggg ggttcaactg | 600 |
| tgaaccatgc gttttctagt ttgcttgttt cattcatata agcttgtgtt acttagttcc | 660 |
| gaaccgtgta gttttgtagt ctctgttctc ttttgtaggg atgtgctgtc ataagatatc | 720 |

```
atgcaagttt cttgtcctac atatc                                     745
```

<210> SEQ ID NO 221
<211> LENGTH: 781
<212> TYPE: DNA
<213> ORGANISM: Triticum aestivum

<400> SEQUENCE: 221

```
atcagatgtg ggcggctcag tattacactt acaagcggcc acggcagtgg ctgtcttcat    60
ccggtttggg tgcaatggga tttgggttgc cagctgcagc tggcgctgct gtggccaacc   120
caggtgttac agttgttgac attgatgggg atggtagttt cctcatgaac attcaggagt   180
tggcgttgat ccgtattgag aacctcccag tgaaggtgat gatattgaac aaccagcatc   240
tgggaatggt ggtgcagtgg gaggataggt tttacaaggc caaccgggcg cacacatacc   300
ttggcaaccc agaaaatgag agtgagatat atccagattt tgtgacgatt gctaaaggat   360
tcaacgttcc ggcagttcgt gtgacgaaga gagcgaagt cactgcagca atcaagaaga   420
tgcttgagac cccagggcca tacttgttgg atatcattgt cccgcatcag gagcacgtgc   480
tgcctatgat cccaagcggt ggtgctttta aggacatgat catggagggt gatggcagga   540
cctcgtactg aaatttcgac ctacaagacc tacaagtgtg acatgcgcaa tcagcatgat   600
acctgcgtgt tgtatcaact actgggggtt caactgtgaa ccatgcgttt tctagtttgc   660
ttgtttcatt catataagct tgtgttactt agttccgaac cgtgtagttt tgtagtctct   720
gttctctttt gtagggatgt gctgtcataa gatatcatgc aagtttcttg tcctacatat   780
c                                                                   781
```

<210> SEQ ID NO 222
<211> LENGTH: 781
<212> TYPE: DNA
<213> ORGANISM: Triticum aestivum

<400> SEQUENCE: 222

```
accagatgtg ggcggctcag tattacactt acaagcggcc acggcagtgg ctgtcttcgt    60
ctggtttggg ggcaatggga tttgggttac cagctgcagc tggcgctgct gtggccaacc   120
caggtgttac agttgttgac attgatggtg atggtagttt cctcatgaac attcaggagt   180
tggcgttgat ccgcattgag aacctcccag tgaaggtgat gatattgaac aaccagcatc   240
tgggaatggt ggtgcagtgg gaggataggt tttacaaggc caatcgggcg cacacatacc   300
ttggcaaccc agaaaatgag agtgagatat atccagattt tgtgacgatt gctaaaggat   360
tcaacgttcc agcagttcga gtgacgaaga gagcgaagt cactgcagca atcaagaaga   420
tgcttgagac cccagggcca tacttgttgg atatcatagt cccgcatcag gagcacgtgc   480
tgcctatgat cccaagcggt ggtgctttca aggacatgat catggagggt gatggcagga   540
cctcgtactg aaatttcgac ctacaagacc tacaagtgtg acatgcgcaa tcagcatgat   600
gcccgcgtgt tgtatcaact actaggggtt caactgtgag ccatgcgttt tctagtttgc   660
ttgtttcatt catataagct tgtattactt agttccgaac cctgtagttt tgtagtctat   720
gttctctttt gtagggatgt gctgtcataa gatgtcatgc aagtttcttg tcctacatat   780
c                                                                   781
```

<210> SEQ ID NO 223
<211> LENGTH: 781
<212> TYPE: DNA
<213> ORGANISM: Triticum aestivum

<400> SEQUENCE: 223

```
accagatgtg ggcggctcag tattacactt acaagcggcc acggcagtgg ctgtcttcgt    60
ctggtttggg ggcaatggga tttgggttac cagctgcagc tggcgctgct gtggccaacc   120
caggtgttac agttgttgac attgatggtg atggtagttt cctcatgaac attcaggagt   180
tggcgttgat ccgcattgag aacctcccag tgaaggtgat gatattgaac aaccagcatc   240
tgggaatggt ggtgcagtgg gaggataggt tttacaaggc caatcgggcg cacacatacc   300
ttggcaaccc agaaaatgag agtgagatat atccagattt tgtgacgatt gctaaaggat   360
tcaacgttcc agcagttcga gtgacgaaga gagcgaagt cactgcagca atcaagaaga   420
tgcttgagac cccagggcca tacttgttgg atatcatagt cccgcatcag gagcacgtgc   480
tgcctatgat cccaagcggt ggtgctttca aggacatgat catggagggt gatggcagga   540
cctcgtactg aaatttcgac ctacaagacc tacaagtgtg acatgcgcaa tcagcatgat   600
gcccgcgtgt tgtatcaact actaggggtt caactgtgag ccatgcgttt ctagtttgc    660
ttgtttcatt catataagct tgtattactt agttccgaac cctgtagttt tgtagtctat   720
gttctctttt gtagggatgt gctgtcataa gatgtcatgc aagtttcttg tcctacatat   780
c                                                                   781
```

<210> SEQ ID NO 224
<211> LENGTH: 780
<212> TYPE: DNA
<213> ORGANISM: Triticum aestivum

<400> SEQUENCE: 224

```
accagatgtg ggcggctcag tattacactt acaagcggcc acggcagtgg ctgtcttcgt    60
ctggttgggg gcaatgggat ttgggttacc agctgcagct ggcgctgctg tggccaaccc   120
aggtgttaca gttgttgaca ttgatggaga tggtagtttc ctcatgaaca ttcaggagtt   180
ggcattgatc cgtattgaga acctccctgt gaaggtgatg atattgaaca accagcatct   240
gggaatggtg gtgcaatggg aggataggtt ttacaaggcc aatcgggcgc acacatacct   300
tggcaaccca gaaaatgaga gtgagatata tccagatttt gtgacgattg ctaaaggatt   360
caacgttccg gcagttcgtg tgacgaagaa gagcgaagtc actgcagcaa tcaagaagat   420
gcttgagacc ccagggccat acttgttgga tatcatcgtc ccgcatcagg agcacgtgct   480
gcctatgatc ccaagcggtg gtgctttcaa ggacatgatc atggagggtg atggcaggac   540
ctcgtactga aatttcgacc tacaagacct acaagtgtga catgcgcaat cagcatggtg   600
cccgcgtgtt gtatcaacta ctaggggttc aactgtgaac catgcgtttt ctagtttgct   660
tgtttcattc ataagcttg tgttacttag ttccgaacct gtagctttg tagtctatg    720
ctctcttttg tagggatgtg ctgtcataag atatcatgca agtttcttgt cctacatatc   780
```

<210> SEQ ID NO 225
<211> LENGTH: 780
<212> TYPE: DNA
<213> ORGANISM: Triticum aestivum

<400> SEQUENCE: 225

```
accagatgtg ggcggctcag tattacactt acaagcggcc acggcagtgg ctgtcttcgt    60
ctggttgggg gcaatgggat ttgggttacc agctgcagct ggcgctgctg tggccaaccc   120
aggtgttaca gttgttgaca ttgatggaga tggtagtttc ctcatgaaca ttcaggagtt   180
```

```
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatc ccaagcggtg gtgctttcaa ggacatgatc atggagggtg atggcaggac    540
ctcgtactga aatttcgacc tacaagacct acaagtgtga catgcgcaat cagcatggtg    600
cccgcgtgtt gtatcaacta ctaggggttc aactgtgaac catgcgtttt ctagtttgct    660
tgtttcattc atataagctt gtgttactta gttccgaacc ctgtagcttt gtagtctatg    720
ctctcttttg tagggatgtg ctgtcataag atatcatgca agtttcttgt cctacatatc    780
```

<210> SEQ ID NO 226
<211> LENGTH: 881
<212> TYPE: DNA
<213> ORGANISM: Triticum aestivum

<400> SEQUENCE: 226

```
atcagatgtg ggcggctcag tattacactt acaagcggcc acggcagtgg ctgtcttcat    60
ccggtttggg tgcaatggga tttggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat accagatttt tgtgacgatt gctaaaggat    360
tcaacgttcc ggcagttcgt gtgacgaaga gagcgaagt cactgcagca atcaagaaga    420
tgcttgagac cccagggcca tacttgttgg atatcattgt cccgcatcag gagcacgtgc    480
tgcctatgat tcccaatggc ggcgctttca aggacatgat catggagggt gatggcagga    540
cctcgtactg aaatggtccg aaggtccacg ccgccaacta cgagtatgat cccaagcggt    600
ggtgctttta aggacatgat catggagggt gatggcagga cctcgtactg aaatttcgac    660
ctacaagacc tacaagtgtg acatgcgcaa tcagcatgat acctgcgtgt tgtatcaact    720
actgggggtt caactgtgaa ccatgcgttt tctagtttgc ttgtttcatt catataagct    780
tgtgttactt agttccgaac cgtgtagttt tgtagtctct gttctctttt gtagggatgt    840
gctgtcataa gatatcatgc aagtttcttg tcctacatat c                       881
```

<210> SEQ ID NO 227
<211> LENGTH: 781
<212> TYPE: DNA
<213> ORGANISM: Triticum aestivum

<400> SEQUENCE: 227

```
atcagatgtg ggcggctcag tattacactt acaagcggcc acggcagtgg ctgtcttcat    60
ccggtttggg tgcaatggga tttggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat accagatttt tgtgacgatt gctaaaggat    360
tcaacgttcc ggcagttcgt gtgacgaaga gagcgaagt cactgcagca atcaagaaga    420
```

| | |
|---|---|
| tgcttgagac cccagggcca tacttgttgg atatcattgt cccgcatcag gagcacgtgc | 480 |
| tgcctatgat cccaagcggt ggtgctttta aggacatgat catggagggt gatggcagga | 540 |
| cctcgtactg aaatttcgac ctacaagacc tacaagtgtg acatgcgcaa tcagcatgat | 600 |
| acctgcgtgt tgtatcaact actgggggtt caactgtgaa ccatgcgttt tctagtttgc | 660 |
| ttgtttcatt catataagct tgtgttactt agttccgaac cgtgtagttt tgtagtctct | 720 |
| gttctctttt gtagggatgt gctgtcataa gatatcatgc aagttcttg tcctacatat | 780 |
| c | 781 |

<210> SEQ ID NO 228
<211> LENGTH: 781
<212> TYPE: DNA
<213> ORGANISM: Triticum aestivum

<400> SEQUENCE: 228

| | |
|---|---|
| accagatgtg ggcggctcag tattacactt acaagcggcc acggcagtgg ctgtcttcgt | 60 |
| ctggtttggg ggcaatggga tttgggttac cagctgcagc tggcgctgct gtggccaacc | 120 |
| caggtgttac agttgttgac attgatggtg atggtagttt cctcatgaac attcaggagt | 180 |
| tggcgttgat ccgcattgag aacctcccag tgaaggtgat gatattgaac aaccagcatc | 240 |
| tgggaatggt ggtgcagtgg gaggataggt tttacaaggc caatcgggcg cacacatacc | 300 |
| ttggcaaccc agaaaatgag agtgagatat atccagattt tgtgacgatt gctaaaggat | 360 |
| tcaacgttcc agcagttcga gtgacgaaga gagcgaagt cactgcagca atcaagaaga | 420 |
| tgcttgagac cccagggcca tacttgttgg atatcatcgt cccgcatcag gagcacgtgc | 480 |
| tgcctatgat cccaagcggt ggtgctttca aggacatgat catggagggt gatggcagga | 540 |
| cctcgtactg aaatttcgac ctacaagacc tacaagtgtg acatgcgcaa tcagcatggt | 600 |
| gcccgcgtgt tgtatcaact actaggggtt caactgtgag ccatgcgttt tctagtttgc | 660 |
| ttgtttcatt catataagct tgtattactt agttccgaac cctgtagttt tgtagtctat | 720 |
| gttctctttt gtagggatgt gctgtcataa gatgtcatgc aagttcttg tcctacatat | 780 |
| c | 781 |

<210> SEQ ID NO 229
<211> LENGTH: 781
<212> TYPE: DNA
<213> ORGANISM: Triticum aestivum

<400> SEQUENCE: 229

| | |
|---|---|
| accagatgtg ggcggctcag tattacactt acaagcggcc acggcagtgg ctgtcttcgt | 60 |
| ctggtttggg ggcaatggga tttgggttac cagctgcagc tggcgctgct gtggccaacc | 120 |
| caggtgttac agttgttgac attgatggtg atggtagttt cctcatgaac attcaggagt | 180 |
| tggcgttgat ccgcattgag aacctcccag tgaaggtgat gatattgaac aaccagcatc | 240 |
| tgggaatggt ggtgcagtgg gaggataggt tttacaaggc caatcgggcg cacacatacc | 300 |
| ttggcaaccc agaaaatgag agtgagatat atccagattt tgtgacgatt gctaaaggat | 360 |
| tcaacgttcc agcagttcga gtgacgaaga gagcgaagt cactgcagca atcaagaaga | 420 |
| tgcttgagac cccagggcca tacttgttgg atatcatcgt cccgcatcag gagcacgtgc | 480 |
| tgcctatgat cccaagcggt ggtgctttca aggacatgat catggagggt gatggcagga | 540 |
| cctcgtactg aaatttcgac ctacaagacc tacaagtgtg acatgcgcaa tcagcatggt | 600 |

```
gcccgcgtgt tgtatcaact actaggggtt caactgtgag ccatgcgttt tctagtttgc    660
ttgtttcatt catataagct tgtattactt agttccgaac cctgtagttt tgtagtctat    720
gttctctttt gtagggatgt gctgtcataa gatgtcatgc aagtttcttg tcctacatat    780
c                                                                    781

<210> SEQ ID NO 230
<211> LENGTH: 880
<212> TYPE: DNA
<213> ORGANISM: Triticum aestivum

<400> SEQUENCE: 230
accagatgtg ggcggctcag tattacactt acaagcggcc acggcagtgg ctgtcttcgt     60
ctggttgggg gcaatgggat ttgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatt cccaatggcg cgctttcaa ggacatgatc atggagggtg atggcaggac    540
ctcgtactga aatggtccga aggtccacgc cgccaactac gagtatgatc ccaagcggtg    600
gtgctttcaa ggacatgatc atggagggtg atggcaggac ctcgtactga aatttcgacc    660
tacaagacct acaagtgtga catgcgcaat cagcatggtg cccgcgtgtt gtatcaacta    720
ctaggggttc aactgtgaac catgcgtttt ctagtttgct tgtttcattc atataagctt    780
gtgttactta gttccgaacc ctgtagcttt gtagtctatg ctctcttttg tagggatgtg    840
ctgtcataag atatcatgca agtttcttgt cctacatatc                          880

<210> SEQ ID NO 231
<211> LENGTH: 780
<212> TYPE: DNA
<213> ORGANISM: Triticum aestivum

<400> SEQUENCE: 231
accagatgtg ggcggctcag tattacactt acaagcggcc acggcagtgg ctgtcttcgt     60
ctggttgggg gcaatgggat ttgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatc ccaagcggtg gtgctttcaa ggacatgatc atggagggtg atggcaggac    540
ctcgtactga aatttcgacc tacaagacct acaagtgtga catgcgcaat cagcatggtg    600
cccgcgtgtt gtatcaacta ctaggggttc aactgtgaac catgcgtttt ctagtttgct    660
tgtttcattc atataagctt gtgttactta gttccgaacc ctgtagcttt gtagtctatg    720
ctctcttttg tagggatgtg ctgtcataag atatcatgca agtttcttgt cctacatatc    780
```

<210> SEQ ID NO 232
<211> LENGTH: 781
<212> TYPE: DNA
<213> ORGANISM: Triticum aestivum

<400> SEQUENCE: 232

```
atcagatgtg ggcggctcag tattacactt acaagcggcc acggcagtgg ctgtcttcat    60
ccggtttggg tgcaatggga tttggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga agagcgaagt cactgcagca atcaagaaga    420
tgcttgagac cccagggcca tacttgttgg atatcattgt cccgcatcag gagcacgtgc    480
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actgggggtt caactgtgaa ccatgcgttt tctagtttgc    660
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                     781
```

<210> SEQ ID NO 233
<211> LENGTH: 781
<212> TYPE: DNA
<213> ORGANISM: Triticum aestivum

<400> SEQUENCE: 233

```
atcagatgtg ggcggctcag tattacactt acaagcggcc acggcagtgg ctgtcttcat    60
ccggtttggg tgcaatggga tttggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga agagcgaagt cactgcagca atcaagaaga    420
tgcttgagac cccagggcca tacttgttgg atatcattgt cccgcatcag gagcacgtgc    480
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actgggggtt caactgtgaa ccatgcgttt tctagtttgc    660
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                     781
```

<210> SEQ ID NO 234
<211> LENGTH: 781
<212> TYPE: DNA
<213> ORGANISM: Triticum aestivum

<400> SEQUENCE: 234

```
accagatgtg ggcggctcag tattacactt acaagcggcc acggcagtgg ctgtcttcgt      60
ctggtttggg ggcaatggga tttgggttac cagctgcagc tggcgctgct gtggccaacc     120
caggtgttac agttgttgac attgatggtg atggtagttt cctcatgaac attcaggagt     180
tggcgttgat ccgcattgag aacctcccag tgaaggtgat gatattgaac aaccagcatc     240
tgggaatggt ggtgcagtgg gaggataggt tttacaaggc caatcgggcg cacacatacc     300
ttggcaaccc agaaaatgag agtgagatat atccagattt tgtgacgatt gctaaaggat     360
tcaacgttcc agcagttcga gtgacgaaga gagcgaagt cactgcagca atcaagaaga     420
tgcttgagac cccagggcca tacttgttgg atatcatagt cccgcatcag gagcacgtgc     480
tgcctatgat cccaagcggt ggtgctttca aggacatgat catggagggt gatggcagga     540
cctcgtactg aaatttcgac ctacaagacc tacaagtgtg acatgcgcaa tcagcatgat     600
gcccgcgtgt tgtatcaact actaggggtt caactgtgag ccatgcgttt tctagtttgc     660
ttgtttcatt catataagct tgtattactt agttccgaac cctgtagttt tgtagtctat     720
gttctctttt gtagggatgt gctgtcataa gatgtcatgc aagtttcttg tcctacatat     780
c                                                                    781
```

<210> SEQ ID NO 235
<211> LENGTH: 781
<212> TYPE: DNA
<213> ORGANISM: Triticum aestivum

<400> SEQUENCE: 235

```
accagatgtg ggcggctcag tattacactt acaagcggcc acggcagtgg ctgtcttcgt      60
ctggtttggg ggcaatggga tttgggttac cagctgcagc tggcgctgct gtggccaacc     120
caggtgttac agttgttgac attgatggtg atggtagttt cctcatgaac attcaggagt     180
tggcgttgat ccgcattgag aacctcccag tgaaggtgat gatattgaac aaccagcatc     240
tgggaatggt ggtgcagtgg gaggataggt tttacaaggc caatcgggcg cacacatacc     300
ttggcaaccc agaaaatgag agtgagatat atccagattt tgtgacgatt gctaaaggat     360
tcaacgttcc agcagttcga gtgacgaaga gagcgaagt cactgcagca atcaagaaga     420
tgcttgagac cccagggcca tacttgttgg atatcatagt cccgcatcag gagcacgtgc     480
tgcctatgat cccaagcggt ggtgctttca aggacatgat catggagggt gatggcagga     540
cctcgtactg aaatttcgac ctacaagacc tacaagtgtg acatgcgcaa tcagcatgat     600
gcccgcgtgt tgtatcaact actaggggtt caactgtgag ccatgcgttt tctagtttgc     660
ttgtttcatt catataagct tgtattactt agttccgaac cctgtagttt tgtagtctat     720
gttctctttt gtagggatgt gctgtcataa gatgtcatgc aagtttcttg tcctacatat     780
c                                                                    781
```

<210> SEQ ID NO 236
<211> LENGTH: 780
<212> TYPE: DNA
<213> ORGANISM: Triticum aestivum

<400> SEQUENCE: 236

```
accagatgtg ggcggctcag tattacactt acaagcggcc acggcagtgg ctgtcttcgt      60
ctggttgggg gcaatgggat ttgggttacc agctgcagct ggcgctgctg tggccaaccc     120
aggtgttaca gttgttgaca ttgatggaga tggtagtttc ctcatgaaca ttcaggagtt     180
```

```
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatc ccaagcggtg gtgctttcaa ggacatgatc atggagggtg atggcaggac    540
ctcgtactga aatttcgacc tacaagacct acaagtgtga catgcgcaat cagcatggtg    600
cccgcgtgtt gtatcaacta ctaggggttc aactgtgaac catgcgtttt ctagtttgct    660
tgtttcattc atataagctt gtgttactta gttccgaacc ctgtagcttt gtagtctatg    720
ctctcttttg tagggatgtg ctgtcataag atatcatgca agtttcttgt cctacatatc    780

<210> SEQ ID NO 237
<211> LENGTH: 780
<212> TYPE: DNA
<213> ORGANISM: Triticum aestivum

<400> SEQUENCE: 237
accagatgtg ggcggctcag tattacactt acaagcggcc acggcagtgg ctgtcttcgt     60
ctggttgggg gcaatgggat ttgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatc ccaagcggtg gtgctttcaa ggacatgatc atggagggtg atggcaggac    540
ctcgtactga aatttcgacc tacaagacct acaagtgtga catgcgcaat cagcatggtg    600
cccgcgtgtt gtatcaacta ctaggggttc aactgtgaac catgcgtttt ctagtttgct    660
tgtttcattc atataagctt gtgttactta gttccgaacc ctgtagcttt gtagtctatg    720
ctctcttttg tagggatgtg ctgtcataag atatcatgca agtttcttgt cctacatatc    780

<210> SEQ ID NO 238
<211> LENGTH: 781
<212> TYPE: DNA
<213> ORGANISM: Triticum aestivum

<400> SEQUENCE: 238
atcagatgtg ggcggctcag tattacactt acaagcggcc acggcagtgg ctgtcttcat     60
ccggtttggg tgcaatggga tttgggttgc agctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga gagcgaagt cactgcagca atcaagaaga    420
tgcttgagac cccagggcca tacttgttgg atatcattgt cccgcatcag gagcacgtgc    480
```

| | |
|---|---|
| tgcctatgat cccaagcggt ggtgctttta aggacatgat catggagggt gatggcagga | 540 |
| cctcgtactg aaatttcgac ctacaagacc tacaagtgtg acatgcgcaa tcagcatgat | 600 |
| acctgcgtgt tgtatcaact actgggggtt caactgtgaa ccatgcgttt tctagtttgc | 660 |
| ttgtttcatt catataagct tgtgttactt agttccgaac cgtgtagttt tgtagtctct | 720 |
| gttctctttt gtagggatgt gctgtcataa gatatcatgc aagtttcttg tcctacatat | 780 |
| c | 781 |

<210> SEQ ID NO 239
<211> LENGTH: 781
<212> TYPE: DNA
<213> ORGANISM: Triticum aestivum

<400> SEQUENCE: 239

| | |
|---|---|
| atcagatgtg ggcggctcag tattacactt acaagcggcc acggcagtgg ctgtcttcat | 60 |
| ccggtttggg tgcaatggga tttgggttgc cagctgcagc tggcgctgct gtggccaacc | 120 |
| caggtgttac agttgttgac attgatgggg atggtagttt cctcatgaac attcaggagt | 180 |
| tggcgttgat ccgtattgag aacctcccag tgaaggtgat gatattgaac aaccagcatc | 240 |
| tgggaatggt ggtgcagtgg gaggataggt tttacaaggc caaccgggcg cacacatacc | 300 |
| ttggcaaccc agaaaatgag agtgagatat atccagattt tgtgacgatt gctaaaggat | 360 |
| tcaacgttcc ggcagttcgt gtgacgaaga agagcgaagt cactgcagca atcaagaaga | 420 |
| tgcttgagac cccagggcca tacttgttgg atatcattgt cccgcatcag gagcacgtgc | 480 |
| tgcctatgat cccaagcggt ggtgctttta aggacatgat catggagggt gatggcagga | 540 |
| cctcgtactg aaatttcgac ctacaagacc tacaagtgtg acatgcgcaa tcagcatgat | 600 |
| acctgcgtgt tgtatcaact actgggggtt caactgtgaa ccatgcgttt tctagtttgc | 660 |
| ttgtttcatt catataagct tgtgttactt agttccgaac cgtgtagttt tgtagtctct | 720 |
| gttctctttt gtagggatgt gctgtcataa gatatcatgc aagtttcttg tcctacatat | 780 |
| c | 781 |

<210> SEQ ID NO 240
<211> LENGTH: 781
<212> TYPE: DNA
<213> ORGANISM: Triticum aestivum

<400> SEQUENCE: 240

| | |
|---|---|
| accagatgtg ggcggctcag tattacactt acaagcggcc acggcagtgg ctgtcttcgt | 60 |
| ctggtttggg ggcaatggga tttgggttac cagctgcagc tggcgctgct gtggccaacc | 120 |
| caggtgttac agttgttgac attgatggtg atggtagttt cctcatgaac attcaggagt | 180 |
| tggcgttgat ccgcattgag aacctcccag tgaaggtgat gatattgaac aaccagcatc | 240 |
| tgggaatggt ggtgcagtgg gaggataggt tttacaaggc caatcgggcg cacacatacc | 300 |
| ttggcaaccc agaaaatgag agtgagatat atccagattt tgtgacgatt gctaaaggat | 360 |
| tcaacgttcc agcagttcga gtgacgaaga agagcgaagt cactgcagca atcaagaaga | 420 |
| tgcttgagac cccagggcca tacttgttgg atatcatagt cccgcatcag gagcacgtgc | 480 |
| tgcctatgat cccaagcggt ggtgctttca aggacatgat catggagggt gatggcagga | 540 |
| cctcgtactg aaatttcgac ctacaagacc tacaagtgtg acatgcgcaa tcagcatgat | 600 |
| gcccgcgtgt tgtatcaact actaggggtt caactgtgag ccatgcgttt tctagtttgc | 660 |
| ttgtttcatt catataagct tgtattactt agttccgaac cctgtagttt tgtagtctat | 720 |

```
gttctctttt gtagggatgt gctgtcataa gatgtcatgc aagtttcttg tcctacatat    780
c                                                                    781

<210> SEQ ID NO 241
<211> LENGTH: 781
<212> TYPE: DNA
<213> ORGANISM: Triticum aestivum

<400> SEQUENCE: 241
accagatgtg gcggctcag tattacactt acaagcggcc acggcagtgg ctgtcttcgt     60
ctggtttggg ggcaatggga tttgggttac cagctgcagc tggcgctgct gtggccaacc   120
caggtgttac agttgttgac attgatggtg atggtagttt cctcatgaac attcaggagt   180
tggcgttgat ccgcattgag aacctcccag tgaaggtgat gatattgaac aaccagcatc   240
tgggaatggt ggtgcagtgg gaggataggt tttacaaggc caatcgggcg cacacatacc   300
ttggcaaccc agaaaatgag agtgagatat atccagattt tgtgacgatt gctaaaggat   360
tcaacgttcc agcagttcga gtgacgaaga gagcgaagt cactgcagca atcaagaaga   420
tgcttgagac cccagggcca tacttgttgg atatcatagt cccgcatcag gagcacgtgc   480
tgcctatgat cccaagcggt ggtgcttca aggacatgat catggagggt gatggcagga    540
cctcgtactg aaatttcgac ctacaagacc tacaagtgtg acatgcgcaa tcagcatgat   600
gcccgcgtgt tgtatcaact actaggggtt caactgtgag ccatgcgttt tctagtttgc   660
ttgtttcatt catataagct tgtattactt agttccgaac cctgtagttt tgtagtctat   720
gttctctttt gtagggatgt gctgtcataa gatgtcatgc aagtttcttg tcctacatat   780
c                                                                    781

<210> SEQ ID NO 242
<211> LENGTH: 880
<212> TYPE: DNA
<213> ORGANISM: Triticum aestivum

<400> SEQUENCE: 242
accagatgtg gcggctcag tattacactt acaagcggcc acggcagtgg ctgtcttcgt     60
ctggttgggg gcaatgggat ttgggttacc agctgcagct ggcgctgctg tggccaaccc   120
aggtgttaca gttgttgaca ttgatggaga tggtagtttc ctcatgaaca ttcaggagtt   180
ggcattgatc cgtattgaga acctccctgt gaaggtgatg atattgaaca accagcatct   240
gggaatggtg gtgcaatggg aggataggtt ttacaaggcc aatcgggcgc acacatacct   300
tggcaaccca gaaaatgaga gtgagatata tccagattt tgtgacgattg ctaaaggatt   360
caacgttccg gcagttcgtg tgacgaagaa gagcgaagtc actgcagcaa tcaagaagat   420
gcttgagacc ccagggccat acttgttgga tatcatcgtc ccgcatcagg agcacgtgct   480
gcctatgatt cccaatggcg gcgctttcaa ggacatgatc atggagggtg atggcaggac   540
ctcgtactga aatggtccga aggtccacgc cgccaactac gagtatgatc ccaagcggtg   600
gtgcttcaa ggacatgatc atggagggtg atggcaggac ctcgtactga aatttcgacc   660
tacaagacct acaagtgtga catgcgcaat cagcatggtc ccgcgtgtt gtatcaacta   720
ctaggggttc aactgtgaac catgcgtttt ctagtttgct tgtttcattc atataagctt   780
gtgttactta gttccgaacc ctgtagcttt gtagtctatg ctctcttttg tagggatgtg   840
ctgtcataag atatcatgca agtttcttgt cctacatatc                          880
```

<210> SEQ ID NO 243
<211> LENGTH: 880
<212> TYPE: DNA
<213> ORGANISM: Triticum aestivum

<400> SEQUENCE: 243

| | | | | | |
|---|---|---|---|---|---|
| accagatgtg | ggcggctcag | tattacactt | acaagcggcc | acggcagtgg | ctgtcttcgt | 60 |
| ctggttgggg | gcaatgggat | ttgggttacc | agctgcagct | ggcgctgctg | tggccaaccc | 120 |
| aggtgttaca | gttgttgaca | ttgatggaga | tggtagtttc | ctcatgaaca | ttcaggagtt | 180 |
| ggcattgatc | cgtattgaga | acctccctgt | gaaggtgatg | atattgaaca | accagcatct | 240 |
| gggaatggtg | gtgcaatggg | aggataggtt | ttacaaggcc | aatcgggcgc | acacatacct | 300 |
| tggcaaccca | gaaaatgaga | gtgagatata | tccagatttt | gtgacgattg | ctaaaggatt | 360 |
| caacgttccg | gcagttcgtg | tgacgaagaa | gagcgaagtc | actgcagcaa | tcaagaagat | 420 |
| gcttgagacc | ccagggccat | acttgttgga | tatcatcgtc | ccgcatcagg | agcacgtgct | 480 |
| gcctatgatt | cccaatggcg | gcgctttcaa | ggacatgatc | atggagggtg | atggcaggac | 540 |
| ctcgtactga | aatggtccga | aggtccacgc | cgccaactac | gagtatgatc | ccaagcggtg | 600 |
| gtgctttcaa | ggacatgatc | atggagggtg | atggcaggac | ctcgtactga | aatttcgacc | 660 |
| tacaagacct | acaagtgtga | catgcgcaat | cagcatggtg | cccgcgtgtt | gtatcaacta | 720 |
| ctaggggttc | aactgtgaac | catgcgtttt | ctagtttgct | tgtttcattc | atataagctt | 780 |
| gtgttactta | gttccgaacc | ctgtagcttt | gtagtctatg | ctctcttttg | tagggatgtg | 840 |
| ctgtcataag | atatcatgca | agtttcttgt | cctacatatc | | | 880 |

<210> SEQ ID NO 244
<211> LENGTH: 865
<212> TYPE: DNA
<213> ORGANISM: Triticum aestivum

<400> SEQUENCE: 244

| | | | | | |
|---|---|---|---|---|---|
| atcagatgtg | ggcggctcag | tattacactt | acaagcggcc | acggcagtgg | ctgtcttcat | 60 |
| ccggtttggg | tgcaatggga | tttgggttgc | cagctgcagc | tggcgctgct | gtggccaacc | 120 |
| caggtgttac | agttgttgac | attgatgggg | atggtagttt | cctcatgaac | attcaggagt | 180 |
| tggcgttgat | ccgtattgag | aacctcccag | tgaaggtgat | gatattgaac | aaccagcatc | 240 |
| tgggaatggt | ggtgcagtgg | gaggataggt | tttacaaggc | caaccgggcg | cacacatacc | 300 |
| ttggcaaccc | agaaaatgag | agtgagatat | atccagattt | tgtgacgatt | gctaaaggat | 360 |
| tcaacgttcc | ggcagttcgt | gtgacgaaga | agagcgaagt | cactgcagca | atcaagaaga | 420 |
| tgcttgagac | cccagggcca | tacttgttgg | atatcattgt | cccgcatcag | gagcacgtgc | 480 |
| tgcctgcgct | ttcaaggaca | tgatcatgga | gggtgatggc | aggacctcgt | actgaaatgg | 540 |
| tccgaaggtc | cacgccgcca | actacgagta | tgatcccaag | cggtggtgct | tttaaggaca | 600 |
| tgatcatgga | gggtgatggc | aggacctcgt | actgaaattt | cgacctacaa | gacctacaag | 660 |
| tgtgacatgc | gcaatcagca | tgatacctgc | gtgttgtatc | aactactggg | ggttcaactg | 720 |
| tgaaccatgc | gttttctagt | ttgcttgttt | cattcatata | agcttgtgtt | acttagttcc | 780 |
| gaaccgtgta | gttttgtagt | ctctgttctc | ttttgtaggg | atgtgctgtc | ataagatatc | 840 |
| atgcaagttt | cttgtcctac | atatc | | | | 865 |

<210> SEQ ID NO 245
<211> LENGTH: 781

```
<212> TYPE: DNA
<213> ORGANISM: Triticum aestivum

<400> SEQUENCE: 245
atcagatgtg ggcggctcag tattacactt acaagcggcc acggcagtgg ctgtcttcat    60
ccggtttggg tgcaatggga tttggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga agagcgaagt cactgcagca atcaagaaga    420
tgcttgagac cccagggcca tacttgttgg atatcattgt cccgcatcag gagcacgtgc    480
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actggggggtt caactgtgaa ccatgcgttt tctagtttgc    660
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                    781

<210> SEQ ID NO 246
<211> LENGTH: 781
<212> TYPE: DNA
<213> ORGANISM: Triticum aestivum

<400> SEQUENCE: 246
accagatgtg ggcggctcag tattacactt acaagcggcc acggcagtgg ctgtcttcgt    60
ctggtttggg ggcaatggga tttgggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga agagcgaagt cactgcagca atcaagaaga    420
tgcttgagac cccagggcca tacttgttgg atatcatagt cccgcatcag gagcacgtgc    480
tgcctatgat cccaagcggt ggtgctttca aggacatgat catggagggt gatggcagga    540
cctcgtactg aaatttcgac ctacaagacc tacaagtgtg acatgcgcaa tcagcatgat    600
gcccgcgtgt tgtatcaact actaggggtt caactgtgag ccatgcgttt tctagtttgc    660
ttgtttcatt catataagct tgtattactt agttccgaac cctgtagttt tgtagtctat    720
gttctctttt gtagggatgt gctgtcataa gatgtcatgc aagtttcttg tcctacatat    780
c                                                                    781

<210> SEQ ID NO 247
<211> LENGTH: 781
<212> TYPE: DNA
<213> ORGANISM: Triticum aestivum

<400> SEQUENCE: 247
accagatgtg ggcggctcag tattacactt acaagcggcc acggcagtgg ctgtcttcgt    60
```

```
ctggtttggg ggcaatggga tttgggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaggat    360 tcaacgttcc agcagttcga gtgacgaaga gagcgaagt cactgcagca atcaagaaga    420
tgcttgagac cccagggcca tacttgttgg atatcatagt cccgcatcag gagcacgtgc    480
tgcctatgat cccaagcggt ggtgctttca aggacatgat catggagggt gatggcagga    540
cctcgtactg aaatttcgac ctacaagacc tacaagtgtg acatgcgcaa tcagcatgat    600
gcccgcgtgt tgtatcaact actaggggtt caactgtgag ccatgcgttt ctagtttgc    660 ttgtttcatt catataagct tgtattactt agttccgaac cctgtagttt tgtagtctat    720
gttctctttt gtagggatgt gctgtcataa gatgtcatgc aagtttcttg tcctacatat    780
c                                                                   781

<210> SEQ ID NO 248
<211> LENGTH: 880
<212> TYPE: DNA
<213> ORGANISM: Triticum aestivum

<400> SEQUENCE: 248
accagatgtg ggcggctcag tattacactt acaagcggcc acggcagtgg ctgtcttcgt     60 ctggtttgggg gcaatgggat tgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaggatt    360 caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatt cccaatggcg gcgctttcaa ggacatgatc atggagggtg atggcaggac    540
ctcgtactga aatggtccga aggtccacgc cgccaactac gagtatgatc ccaagcggtg    600
gtgctttcaa ggacatgatc atggagggtg atggcaggac ctcgtactga aatttcgacc    660
tacaagacct acaagtgtga catgcgcaat cagcatggtg cccgcgtgtt gtatcaacta    720
ctaggggttc aactgtgaac catgcgtttt ctagtttgct tgtttcattc atataagctt    780
gtgttactta gttccgaacc tgtagctttt gtagtctatg ctctcttttg tagggatgtg    840
ctgtcataag atatcatgca agtttcttgt cctacatatc                          880

<210> SEQ ID NO 249
<211> LENGTH: 780
<212> TYPE: DNA
<213> ORGANISM: Triticum aestivum

<400> SEQUENCE: 249
accagatgtg ggcggctcag tattacactt acaagcggcc acggcagtgg ctgtcttcgt     60 ctggtttgggg gcaatgggat tgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
```

```
gggaatggtg gtgcaatggg aggataggtt ttacaaggcc aatcgggcgc acacatacct      300
tggcaaccca gaaaatgaga gtgagatata tccagatttt gtgacgattg ctaaaggatt      360
caacgttccg gcagttcgtg tgacgaagaa gagcgaagtc actgcagcaa tcaagaagat      420
gcttgagacc ccagggccat acttgttgga tatcatcgtc ccgcatcagg agcacgtgct      480
gcctatgatc ccaagcggtg gtgctttcaa ggacatgatc atggagggtg atggcaggac      540
ctcgtactga aatttcgacc tacaagacct acaagtgtga catgcgcaat cagcatggtg      600
cccgcgtgtt gtatcaacta ctaggggttc aactgtgaac catgcgtttt ctagtttgct      660
tgtttcattc atataagctt gtgttactta gttccgaacc ctgtagcttt gtagtctatg      720
ctctcttttg tagggatgtg ctgtcataag atatcatgca agtttcttgt cctacatatc      780

<210> SEQ ID NO 250
<211> LENGTH: 781
<212> TYPE: DNA
<213> ORGANISM: Triticum aestivum

<400> SEQUENCE: 250
atcagatgtg ggcggctcag tattacactt acaagcggcc acggcagtgg ctgtcttcat       60
ccggtttggg tgcaatggga tttggggttgc cagctgcagc tggcgctgct gtggccaacc      120
caggtgttac agttgttgac attgatgggg atggtagttt cctcatgaac attcaggagt      180
tggcgttgat ccgtattgag aacctcccag tgaaggtgat gatattgaac aaccagcatc      240
tgggaatggt ggtgcagtgg gaggataggt tttacaaggc caaccgggcg cacacatacc      300
ttggcaaccc agaaaatgag agtgagatat atccagattt tgtgacgatt gctaaaggat      360
tcaacgttcc ggcagttcgt gtgacgaaga gagcgaagt cactgcagca atcaagaaga       420
tgcttgagac cccagggcca tacttgttgg atatcattgt cccgcatcag gagcacgtgc      480
tgcctatgat cccaagcggt ggtgctttta aggacatgat catggagggt gatggcagga      540
cctcgtactg aaatttcgac ctacaagacc tacaagtgtg acatgcgcaa tcagcatgat      600
acctgcgtgt tgtatcaact actgggggtt caactgtgaa ccatgcgttt tctagtttgc      660
ttgtttcatt catataagct tgtgttactt agttccgaac cgtgtagttt tgtagtctct      720
gttctctttt gtagggatgt gctgtcataa gatatcatgc aagtttcttg tcctacatat      780
c                                                                      781

<210> SEQ ID NO 251
<211> LENGTH: 781
<212> TYPE: DNA
<213> ORGANISM: Triticum aestivum

<400> SEQUENCE: 251
atcagatgtg ggcggctcag tattacactt acaagcggcc acggcagtgg ctgtcttcat       60
ccggtttggg tgcaatggga tttggggttgc cagctgcagc tggcgctgct gtggccaacc      120
caggtgttac agttgttgac attgatgggg atggtagttt cctcatgaac attcaggagt      180
tggcgttgat ccgtattgag aacctcccag tgaaggtgat gatattgaac aaccagcatc      240
tgggaatggt ggtgcagtgg gaggataggt tttacaaggc caaccgggcg cacacatacc      300
ttggcaaccc agaaaatgag agtgagatat atccagattt tgtgacgatt gctaaaggat      360
tcaacgttcc ggcagttcgt gtgacgaaga gagcgaagt cactgcagca atcaagaaga       420
tgcttgagac cccagggcca tacttgttgg atatcattgt cccgcatcag gagcacgtgc      480
```

```
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actgggggtt caactgtgaa ccatgcgttt tctagtttgc    660
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                    781
```

<210> SEQ ID NO 252
<211> LENGTH: 781
<212> TYPE: DNA
<213> ORGANISM: Triticum aestivum

<400> SEQUENCE: 252

```
accagatgtg ggcggctcag tattacactt acaagcggcc acggcagtgg ctgtcttcgt     60
ctggtttggg ggcaatggga tttgggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga agagcgaagt cactgcagca atcaagaaga    420
tgcttgagac cccagggcca tacttgttgg atatcatagt cccgcatcag gagcacgtgc    480
tgcctatgat cccaagcggt ggtgctttca aggacatgat catggagggt gatggcagga    540
cctcgtactg aaatttcgac ctacaagacc tacaagtgtg acatgcgcaa tcagcatgat    600
gcccgcgtgt tgtatcaact actagggggtt caactgtgag ccatgcgttt tctagtttgc    660
ttgtttcatt catataagct tgtattactt agttccgaac cctgtagttt tgtagtctat    720
gttctctttt gtagggatgt gctgtcataa gatgtcatgc aagtttcttg tcctacatat    780
c                                                                    781
```

<210> SEQ ID NO 253
<211> LENGTH: 781
<212> TYPE: DNA
<213> ORGANISM: Triticum aestivum

<400> SEQUENCE: 253

```
accagatgtg ggcggctcag tattacactt acaagcggcc acggcagtgg ctgtcttcgt     60
ctggtttggg ggcaatggga tttgggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga agagcgaagt cactgcagca atcaagaaga    420
tgcttgagac cccagggcca tacttgttgg atatcatagt cccgcatcag gagcacgtgc    480
tgcctatgat cccaagcggt ggtgctttca aggacatgat catggagggt gatggcagga    540
cctcgtactg aaatttcgac ctacaagacc tacaagtgtg acatgcgcaa tcagcatgat    600
gcccgcgtgt tgtatcaact actagggggtt caactgtgag ccatgcgttt tctagtttgc    660
ttgtttcatt catataagct tgtattactt agttccgaac cctgtagttt tgtagtctat    720
```
gttctctttt gtagggatgt gctgtcataa gatgtcatgc aagtttcttg tcctacatat    780
c                                                                    781

<210> SEQ ID NO 254
<211> LENGTH: 780
<212> TYPE: DNA
<213> ORGANISM: Triticum aestivum

<400> SEQUENCE: 254
accagatgtg ggcggctcag tattacactt acaagcggcc acggcagtgg ctgtcttcgt     60
ctggttgggg gcaatgggat ttgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatc ccaagcggtg gtgctttcaa ggacatgatc atggagggtg atggcaggac    540
ctcgtactga aatttcgacc tacaagacct acaagtgtga catgcgcaat cagcatggtg    600
cccgcgtgtt gtatcaacta ctaggggttc aactgtgaac catgcgtttt ctagtttgct    660
tgtttcattc atataagctt gtgttactta gttccgaacc ctgtagcttt gtagtctatg    720
ctctcttttg tagggatgtg ctgtcataag atatcatgca agtttcttgt cctacatatc    780

<210> SEQ ID NO 255
<211> LENGTH: 780
<212> TYPE: DNA
<213> ORGANISM: Triticum aestivum

<400> SEQUENCE: 255
accagatgtg ggcggctcag tattacactt acaagcggcc acggcagtgg ctgtcttcgt     60
ctggttgggg gcaatgggat ttgggttacc agctgcagct ggcgctgctg tggccaaccc    120
aggtgttaca gttgttgaca ttgatggaga tggtagtttc ctcatgaaca ttcaggagtt    180
ggcattgatc cgtattgaga acctccctgt gaaggtgatg atattgaaca accagcatct    240
gggaatggtg gtgcaatggg aggataggtt ttacaaggcc aatcgggcgc acacatacct    300
tggcaaccca gaaaatgaga gtgagatata tccagatttt gtgacgattg ctaaaggatt    360
caacgttccg gcagttcgtg tgacgaagaa gagcgaagtc actgcagcaa tcaagaagat    420
gcttgagacc ccagggccat acttgttgga tatcatcgtc ccgcatcagg agcacgtgct    480
gcctatgatc ccaagcggtg gtgctttcaa ggacatgatc atggagggtg atggcaggac    540
ctcgtactga aatttcgacc tacaagacct acaagtgtga catgcgcaat cagcatggtg    600
cccgcgtgtt gtatcaacta ctaggggttc aactgtgaac catgcgtttt ctagtttgct    660
tgtttcattc atataagctt gtgttactta gttccgaacc ctgtagcttt gtagtctatg    720
ctctcttttg tagggatgtg ctgtcataag atatcatgca agtttcttgt cctacatatc    780

<210> SEQ ID NO 256
<211> LENGTH: 781
<212> TYPE: DNA
<213> ORGANISM: Triticum aestivum

<400> SEQUENCE: 256

```
atcagatgtg ggcggctcag tattacactt acaagcggcc acggcagtgg ctgtcttcat    60
ccggtttggg tgcaatggga tttgggttgc cagctgcagc tggcgctgct gtggccaacc   120
caggtgttac agttgttgac attgatgggg atggtagttt cctcatgaac attcaggagt   180
tggcgttgat ccgtattgag aacctcccag tgaaggtgat gatattgaac aaccagcatc   240
tgggaatggt ggtgcagtgg gaggataggt tttacaaggc caaccgggcg cacacatacc   300
ttggcaaccc agaaaatgag agtgagatat atccagattt tgtgacgatt gctaaaggat   360
tcaacgttcc ggcagttcgt gtgacgaaga agagcgaagt cactgcagca atcaagaaga   420
tgcttgagac cccagggcca tacttgttgg atatcattgt cccgcatcag gagcacgtgc   480
tgcctatgat cccaagcggt ggtgctttta aggacatgat catggagggt gatggcagga   540
cctcgtactg aaatttcgac ctacaagacc tacaagtgtg acatgcgcaa tcagcatgat   600
acctgcgtgt tgtatcaact actgggggtt caactgtgaa ccatgcgttt tctagtttgc   660
ttgtttcatt catataagct tgtgttactt agttccgaac cgtgtagttt tgtagtctct   720
gttctctttt gtagggatgt gctgtcataa gatatcatgc aagtttcttg tcctacatat   780
c                                                                  781
```

<210> SEQ ID NO 257
<211> LENGTH: 781
<212> TYPE: DNA
<213> ORGANISM: Triticum aestivum

<400> SEQUENCE: 257

```
atcagatgtg ggcggctcag tattacactt acaagcggcc acggcagtgg ctgtcttcat    60
ccggtttggg tgcaatggga tttgggttgc cagctgcagc tggcgctgct gtggccaacc   120
caggtgttac agttgttgac attgatgggg atggtagttt cctcatgaac attcaggagt   180
tggcgttgat ccgtattgag aacctcccag tgaaggtgat gatattgaac aaccagcatc   240
tgggaatggt ggtgcagtgg gaggataggt tttacaaggc caaccgggcg cacacatacc   300
ttggcaaccc agaaaatgag agtgagatat atccagattt tgtgacgatt gctaaaggat   360
tcaacgttcc ggcagttcgt gtgacgaaga agagcgaagt cactgcagca atcaagaaga   420
tgcttgagac cccagggcca tacttgttgg atatcattgt cccgcatcag gagcacgtgc   480
tgcctatgat cccaagcggt ggtgctttta aggacatgat catggagggt gatggcagga   540
cctcgtactg aaatttcgac ctacaagacc tacaagtgtg acatgcgcaa tcagcatgat   600
acctgcgtgt tgtatcaact actgggggtt caactgtgaa ccatgcgttt tctagtttgc   660
ttgtttcatt catataagct tgtgttactt agttccgaac cgtgtagttt tgtagtctct   720
gttctctttt gtagggatgt gctgtcataa gatatcatgc aagtttcttg tcctacatat   780
c                                                                  781
```

<210> SEQ ID NO 258
<211> LENGTH: 881
<212> TYPE: DNA
<213> ORGANISM: Triticum aestivum

<400> SEQUENCE: 258

```
accagatgtg ggcggctcag tattacactt acaagcggcc acggcagtgg ctgtcttcgt    60
ctggtttggg ggcaatggga tttgggttac cagctgcagc tggcgctgct gtggccaacc   120
caggtgttac agttgttgac attgatggtg atggtagttt cctcatgaac attcaggagt   180
```

-continued

```
tggcgttgat ccgcattgag aacctcccag tgaaggtgat gatattgaac aaccagcatc      240
tgggaatggt ggtgcagtgg gaggataggt tttacaaggc caatcgggcg cacacatacc      300
ttggcaaccc agaaaatgag agtgagatat atccagattt tgtgacgatt gctaaaggat      360
tcaacgttcc agcagttcga gtgacgaaga agagcgaagt cactgcagca atcaagaaga      420
tgcttgagac cccagggcca tacttgttgg atatcatagt cccgcatcag gagcacgtgc      480
tgcctatgat tcccaatggc ggcgctttca aggacatgat catggagggt gatggcagga      540
cctcgtactg aaatggtccg aaggtccacg ccgccaacta cgagtatgat cccaagcggt      600
ggtgctttca aggacatgat catggagggt gatggcagga cctcgtactg aaatttcgac      660
ctacaagacc tacaagtgtg acatgcgcaa tcagcatgat gcccgcgtgt tgtatcaact      720
actaggggtt caactgtgag ccatgcgttt tctagtttgc ttgtttcatt catataagct      780
tgtattactt agttccgaac cctgtagttt tgtagtctat gttctctttt gtagggatgt      840
gctgtcataa gatgtcatgc aagtttcttg tcctacatat c                         881
```

<210> SEQ ID NO 259
<211> LENGTH: 781
<212> TYPE: DNA
<213> ORGANISM: Triticum aestivum

<400> SEQUENCE: 259

```
accagatgtg ggcggctcag tattacactt acaagcggcc acggcagtgg ctgtcttcgt       60
ctggtttggg ggcaatggga tttgggttac cagctgcagc tggcgctgct gtggccaacc      120
caggtgttac agttgttgac attgatggtg atggtagttt cctcatgaac attcaggagt      180
tggcgttgat ccgcattgag aacctcccag tgaaggtgat gatattgaac aaccagcatc      240
tgggaatggt ggtgcagtgg gaggataggt tttacaaggc caatcgggcg cacacatacc      300
ttggcaaccc agaaaatgag agtgagatat atccagattt tgtgacgatt gctaaaggat      360
tcaacgttcc agcagttcga gtgacgaaga agagcgaagt cactgcagca atcaagaaga      420
tgcttgagac cccagggcca tacttgttgg atatcatagt cccgcatcag gagcacgtgc      480
tgcctatgat cccaagcggt ggtgctttca aggacatgat catggagggt gatggcagga      540
cctcgtactg aaatttcgac ctacaagacc tacaagtgtg acatgcgcaa tcagcatgat      600
gcccgcgtgt tgtatcaact actaggggtt caactgtgag ccatgcgttt tctagtttgc      660
ttgtttcatt catataagct tgtattactt agttccgaac cctgtagttt tgtagtctat      720
gttctctttt gtagggatgt gctgtcataa gatgtcatgc aagtttcttg tcctacatat      780
c                                                                     781
```

<210> SEQ ID NO 260
<211> LENGTH: 780
<212> TYPE: DNA
<213> ORGANISM: Triticum aestivum

<400> SEQUENCE: 260

```
accagatgtg ggcggctcag tattacactt acaagcggcc acggcagtgg ctgtcttcgt       60
ctggttgggg gcaatgggat ttgggttacc agctgcagct ggcgctgctg tggccaaccc      120
aggtgttaca gttgttgaca ttgatggaga tggtagtttc ctcatgaaca ttcaggagtt      180
ggcattgatc cgtattgaga acctccctgt gaaggtgatg atattgaaca accagcatct      240
gggaatggtg gtgcaatggg aggataggtt ttacaaggcc aatcgggcgc acacatacct      300
```

| | |
|---|---|
| tggcaaccca gaaaatgaga gtgagatata tccagatttt gtgacgattg ctaaaggatt | 360 |
| caacgttccg gcagttcgtg tgacgaagaa gagcgaagtc actgcagcaa tcaagaagat | 420 |
| gcttgagacc ccagggccat acttgttgga tatcatcgtc ccgcatcagg agcacgtgct | 480 |
| gcctatgatc ccaagcggtg gtgctttcaa ggacatgatc atggagggtg atggcaggac | 540 |
| ctcgtactga aatttcgacc tacaagacct acaagtgtga catgcgcaat cagcatggtg | 600 |
| cccgcgtgtt gtatcaacta ctaggggttc aactgtgaac catgcgtttt ctagtttgct | 660 |
| tgtttcattc atataagctt gtgttactta gttccgaacc ctgtagcttt gtagtctatg | 720 |
| ctctcttttg tagggatgtg ctgtcataag atatcatgca agtttcttgt cctacatatc | 780 |

<210> SEQ ID NO 261
<211> LENGTH: 780
<212> TYPE: DNA
<213> ORGANISM: Triticum aestivum

<400> SEQUENCE: 261

| | |
|---|---|
| accagatgtg ggcggctcag tattacactt acaagcggcc acggcagtgg ctgtcttcgt | 60 |
| ctggttgggg gcaatgggat ttgggttacc agctgcagct ggcgctgctg tggccaaccc | 120 |
| aggtgttaca gttgttgaca ttgatggaga tggtagtttc ctcatgaaca ttcaggagtt | 180 |
| ggcattgatc cgtattgaga acctccctgt gaaggtgatg atattgaaca accagcatct | 240 |
| gggaatggtg gtgcaatggg aggataggtt ttacaaggcc aatcgggcgc acacatacct | 300 |
| tggcaaccca gaaaatgaga gtgagatata tccagatttt gtgacgattg ctaaaggatt | 360 |
| caacgttccg gcagttcgtg tgacgaagaa gagcgaagtc actgcagcaa tcaagaagat | 420 |
| gcttgagacc ccagggccat acttgttgga tatcatcgtc ccgcatcagg agcacgtgct | 480 |
| gcctatgatc ccaagcggtg gtgctttcaa ggacatgatc atggagggtg atggcaggac | 540 |
| ctcgtactga aatttcgacc tacaagacct acaagtgtga catgcgcaat cagcatggtg | 600 |
| cccgcgtgtt gtatcaacta ctaggggttc aactgtgaac catgcgtttt ctagtttgct | 660 |
| tgtttcattc atataagctt gtgttactta gttccgaacc ctgtagcttt gtagtctatg | 720 |
| ctctcttttg tagggatgtg ctgtcataag atatcatgca agtttcttgt cctacatatc | 780 |

<210> SEQ ID NO 262
<211> LENGTH: 781
<212> TYPE: DNA
<213> ORGANISM: Triticum aestivum

<400> SEQUENCE: 262

| | |
|---|---|
| atcagatgtg ggcggctcag tattacactt acaagcggcc acggcagtgg ctgtcttcat | 60 |
| ccggtttggg tgcaatggga tttgggttgc agctgcagc tggcgctgct gtggccaacc | 120 |
| caggtgttac agttgttgac attgatgggg atggtagttt cctcatgaac attcaggagt | 180 |
| tggcgttgat ccgtattgag aacctcccag tgaaggtgat gatattgaac aaccagcatc | 240 |
| tgggaatggt ggtgcagtgg aggataggt tttacaaggc caaccgggcg cacacatacc | 300 |
| ttggcaaccc agaaaatgag agtgagatat atccagattt tgtgacgatt gctaaaggat | 360 |
| tcaacgttcc ggcagttcgt gtgacgaaga agagcgaagt cactgcagca atcaagaaga | 420 |
| tgcttgagac cccagggcca tacttgttgg atatcattgt cccgcatcag gagcacgtgc | 480 |
| tgcctatgat cccaagcggt ggtgctttta aggacatgat catggagggt gatggcagga | 540 |
| cctcgtactg aaatttcgac ctacaagacc tacaagtgtg acatgcgcaa tcagcatgat | 600 |
| acctgcgtgt tgtatcaact actgggggtt caactgtgaa ccatgcgttt tctagtttgc | 660 |

```
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                    781
```

<210> SEQ ID NO 263
<211> LENGTH: 781
<212> TYPE: DNA
<213> ORGANISM: Triticum aestivum

<400> SEQUENCE: 263

```
atcagatgtg gcggctcag tattacactt acaagcggcc acggcagtgg ctgtcttcat    60
ccggtttggg tgcaatggga tttgggttgc cagctgcagc tggcgctgct gtggccaacc   120
caggtgttac agttgttgac attgatgggg atggtagttt cctcatgaac attcaggagt   180
tggcgttgat ccgtattgag aacctcccag tgaaggtgat gatattgaac aaccagcatc   240
tgggaatggt ggtgcagtgg gaggataggt tttacaaggc caaccgggcg cacacatacc   300
ttggcaaccc agaaaatgag agtgagatat atccagattt tgtgacgatt gctaaaggat   360
tcaacgttcc ggcagttcgt gtgacgaaga agagcgaagt cactgcagca atcaagaaga   420
tgcttgagac cccagggcca tacttgttgg atatcattgt cccgcatcag gagcacgtgc   480
tgcctatgat cccaagcggt ggtgctttta aggacatgat catggagggt gatggcagga   540
cctcgtactg aaatttcgac ctacaagacc tacaagtgtg acatgcgcaa tcagcatgat   600
acctgcgtgt tgtatcaact actgggggtt caactgtgaa ccatgcgttt tctagtttgc   660
ttgtttcatt catataagct tgtgttactt agttccgaac cgtgtagttt tgtagtctct   720
gttctctttt gtagggatgt gctgtcataa gatatcatgc aagtttcttg tcctacatat   780
c                                                                    781
```

<210> SEQ ID NO 264
<211> LENGTH: 771
<212> TYPE: DNA
<213> ORGANISM: Triticum aestivum

<400> SEQUENCE: 264

```
accagatgtg gcggctcag tattacactt acaagcggcc acggcagtgg ctgtcttcgt    60
ctggtttggg ggcaatggga tttgggttac cagctgcagc tggcgctgct gtggccaacc   120
caggtgttac agttgttgac attgatggtg atggtagttt cctcatgaac attcaggagt   180
tggcgttgat ccgcattgag aacctcccag tgaaggtgat gatattgaac aaccagcatc   240
tgggaatggt ggtgcagtgg gaggataggt tttacaaggc caatcgggcg cacacatacc   300
ttggcaaccc agaaaatgag agtgagatat atccagattt tgtgacgatt gctaaaggat   360
tcaacgttcc agcagttcga gtgacgaaga agagcgaagt cactgcagca atcaagaaga   420
tgcttgagac cccagggcca tacttgttgg atatcatagt cccgcatcag gagcacgtgt   480
cccaagcggt ggtgctttca aggacatgat catggagggt gatggcagga cctcgtactg   540
aaatttcgac ctacaagacc tacaagtgtg acatgcgcaa tcagcatgat gcccgcgtgt   600
tgtatcaact actaggggtt caactgtgag ccatgcgttt tctagtttgc ttgtttcatt   660
catataagct tgtattactt agttccgaac cctgtagttt tgtagtctat gttctctttt   720
gtagggatgt gctgtcataa gatgtcatgc aagtttcttg tcctacatat c             771
```

<210> SEQ ID NO 265

<211> LENGTH: 854
<212> TYPE: DNA
<213> ORGANISM: Triticum aestivum

<400> SEQUENCE: 265

```
accagatgtg ggcggctcag tattacactt acaagcggcc acggcagtgg ctgtcttcgt      60
ctggtttggg ggcaatggga tttgggttac cagctgcagc tggcgctgct gtggccaacc     120
caggtgttac agttgttgac attgatggtg atggtagttt cctcatgaac attcaggagt     180
tggcgttgat ccgcattgag aacctcccag tgaaggtgat gatattgaac aaccagcatc     240
tgggaatggt ggtgcagtgg gaggataggt tttacaaggc caatcgggcg cacacatacc     300
ttggcaaccc agaaaatgag agtgagatat atccagattt tgtgacgatt gctaaaggat     360
tcaacgttcc agcagttcga gtgacgaaga gagcgaagt cactgcagca atcaagaaga     420
tgcttgagac cccagggcca tacttgttgg atatcatagt cccgcatcag gagcacgtgc     480
tgcctatgat tcccaatggc ggcgctttca aggacatgat catggagggt gatggcagga     540
cctcgtactg aaatggtccg aaggtcaagc ggtggtgctt tcaaggacat gatcatggag     600
ggtgatggca ggacctcgta ctgaaatttc gacctacaag acctacaagt gtgacatgcg     660
caatcagcat gatgcccgcg tgttgtatca actactaggg gttcaactgt gagccatgcg     720
tttttctagtt tgcttgtttc attcatataa gcttgtatta cttagttccg aaccctgtag     780
ttttgtagtc tatgttctct tttgtaggga tgtgctgtca aagatgtca tgcaagtttc     840
ttgtcctaca tatc                                                       854
```

<210> SEQ ID NO 266
<211> LENGTH: 843
<212> TYPE: DNA
<213> ORGANISM: Triticum aestivum

<400> SEQUENCE: 266

```
accagatgtg ggcggctcag tattacactt acaagcggcc acggcagtgg ctgtcttcgt      60
ctggttgggg gcaatgggat ttgggttacc agctgcagct ggcgctgctg tggccaaccc     120
aggtgttaca gttgttgaca ttgatggaga tggtagtttc ctcatgaaca ttcaggagtt     180
ggcattgatc cgtattgaga acctccctgt gaaggtgatg atattgaaca accagcatct     240
gggaatggtg gtgcaatggg aggataggtt ttacaaggcc aatcgggcgc acacatacct     300
tggcaaccca gaaaatgaga gtgagatata tccagatttt gtgacgattg ctaaaggatt     360
caacgttccg gcagttcgtg tgacgaagaa gagcgaagtc actgcagcaa tcaagaagat     420
gcttgagacc ccagggccat acttgttgga tatcatcgtc ccgcatcagg agcacgtgct     480
gcctatgatt cccaatggcg gcgctttcaa ggacatgatc atggagggtg atggcaggac     540
ctcgtactga aatttgcagg gtggtgcttt caaggacatg atcatggagg gtgatggcag     600
gacctcgtac tgaaatttcg acctacaaga cctacaagtg tgacatgcgc aatcagcatg     660
gtgcccgcgt gttgtatcaa ctactagggg ttcaactgtg aaccatgcgt ttctagttt     720
gcttgtttca ttcatataag cttgtgttac ttagttccga accctgtagc tttgtagtct     780
atgctctctt ttgtagggat gtgctgtcat aagatatcat gcaagtttct tgtcctacat     840
atc                                                                   843
```

<210> SEQ ID NO 267
<211> LENGTH: 780
<212> TYPE: DNA
<213> ORGANISM: Triticum aestivum

<400> SEQUENCE: 267

```
accagatgtg ggcggctcag tattacactt acaagcggcc acggcagtgg ctgtcttcgt      60
ctggttgggg gcaatgggat ttgggttacc agctgcagct ggcgctgctg tggccaaccc     120
aggtgttaca gttgttgaca ttgatggaga tggtagtttc ctcatgaaca ttcaggagtt     180
ggcattgatc cgtattgaga acctccctgt gaaggtgatg atattgaaca accagcatct     240
gggaatggtg gtgcaatggg aggataggtt ttacaaggcc aatcgggcgc acacatacct     300
tggcaaccca gaaaatgaga gtgagatata ccagatttt gtgacgattg ctaaaggatt      360
caacgttccg gcagttcgtg tgacgaagaa gagcgaagtc actgcagcaa tcaagaagat     420
gcttgagacc ccagggccat acttgttgga tatcatcgtc ccgcatcagg agcacgtgct     480
gcctatgatc ccaagcggtg gtgctttcaa ggacatgatc atggagggtg atggcaggac     540
ctcgtactga aatttcgacc tacaagacct acaagtgtga catgcgcaat cagcatggtg     600
cccgcgtgtt gtatcaacta ctaggggttc aactgtgaac catgcgtttt ctagtttgct     660
tgtttcattc atataagctt gtgttactta gttccgaacc ctgtagcttt gtagtctatg     720
ctctctttg tagggatgtg ctgtcataag atatcatgca agtttcttgt cctacatatc      780
```

<210> SEQ ID NO 268
<211> LENGTH: 781
<212> TYPE: DNA
<213> ORGANISM: Triticum aestivum

<400> SEQUENCE: 268

```
atcagatgtg ggcggctcag tattacactt acaagcggcc acggcagtgg ctgtcttcat      60
ccggtttggg tgcaatggga tttggggttgc cagctgcagc tggcgctgct gtggccaacc    120
caggtgttac agttgttgac attgatgggg atggtagttt cctcatgaac attcaggagt    180
tggcgttgat ccgtattgag aacctcccag tgaaggtgat gatattgaac aaccagcatc    240
tgggaatggt ggtgcagtgg aggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga agagcgaagt cactgcagca atcaagaaga    420
tgcttgagac cccagggcca tacttgttgg atatcattgt cccgcatcag gagcacgtgc    480
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actggggggtt caactgtgaa ccatgcgttt tctagtttgc    660
ttgtttcatt catataagct tgtgttactt agttccgaac cgtgtagttt gtagtctctc    720
gttctctttt gtagggatgt gctgtcataa gatatcatgc aagtttcttg tcctacatat    780
c                                                                     781
```

<210> SEQ ID NO 269
<211> LENGTH: 781
<212> TYPE: DNA
<213> ORGANISM: Triticum aestivum

<400> SEQUENCE: 269

```
atcagatgtg ggcggctcag tattacactt acaagcggcc acggcagtgg ctgtcttcat      60
ccggtttggg tgcaatggga tttggggttgc cagctgcagc tggcgctgct gtggccaacc    120
caggtgttac agttgttgac attgatgggg atggtagttt cctcatgaac attcaggagt    180
```

```
tggcgttgat ccgtattgag aacctcccag tgaaggtgat gatattgaac aaccagcatc    240
tgggaatggt ggtgcagtgg gaggataggt tttacaaggc caaccgggcg cacacatacc    300
ttggcaaccc agaaaatgag agtgagatat atccagattt tgtgacgatt gctaaaggat    360
tcaacgttcc ggcagttcgt gtgacgaaga agagcgaagt cactgcagca atcaagaaga    420
tgcttgagac cccagggcca tacttgttgg atatcattgt cccgcatcag gagcacgtgc    480
tgcctatgat cccaagcggt ggtgctttta aggacatgat catggagggt gatggcagga    540
cctcgtactg aaatttcgac ctacaagacc tacaagtgtg acatgcgcaa tcagcatgat    600
acctgcgtgt tgtatcaact actgggggtt caactgtgaa ccatgcgttt tctagtttgc    660
ttgtttcatt catataagct tgtgttactt agttccgaac cgtgtagttt tgtagtctct    720
gttctctttt gtagggatgt gctgtcataa gatatcatgc aagtttcttg tcctacatat    780
c                                                                    781

<210> SEQ ID NO 270
<211> LENGTH: 854
<212> TYPE: DNA
<213> ORGANISM: Triticum aestivum

<400> SEQUENCE: 270
accagatgtg ggcggctcag tattacactt acaagcggcc acggcagtgg ctgtcttcgt     60
ctggtttggg ggcaatggga tttgggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
tcaacgttcc agcagttcga gtgacgaaga agagcgaagt cactgcagca atcaagaaga    420
tgcttgagac cccagggcca tacttgttgg atatcatagt cccgcatcag gagcacgtgc    480
tgcctatgat tcccaatggc ggcgctttca aggacatgat catggagggt gatggcagga    540
cctcgtactg aaatggtccg aaggtcaagc ggtggtgctt tcaaggacat gatcatggag    600
ggtgatggca ggacctcgta ctgaaatttc gacctacaag acctacaagt gtgacatgcg    660
caatcagcat gatgcccgcg tgttgtatca actactaggg gttcaactgt gagccatgcg    720
ttttctagtt tgcttgtttc attcatataa gcttgtatta cttagttccg aaccctgtag    780
ttttgtagtc tatgttctct tttgtaggga tgtgctgtca taagatgtca tgcaagtttc    840
ttgtcctaca tatc                                                      854

<210> SEQ ID NO 271
<211> LENGTH: 781
<212> TYPE: DNA
<213> ORGANISM: Triticum aestivum

<400> SEQUENCE: 271
accagatgtg ggcggctcag tattacactt acaagcggcc acggcagtgg ctgtcttcgt     60
ctggtttggg ggcaatggga tttgggttac cagctgcagc tggcgctgct gtggccaacc    120
caggtgttac agttgttgac attgatggtg atggtagttt cctcatgaac attcaggagt    180
tggcgttgat ccgcattgag aacctcccag tgaaggtgat gatattgaac aaccagcatc    240
tgggaatggt ggtgcagtgg gaggataggt tttacaaggc caatcgggcg cacacatacc    300
ttggcaaccc agaaaatgag agtgagatat atccagattt tgtgacgatt gctaaaggat    360
```

| | |
|---|---|
| tcaacgttcc agcagttcga gtgacgaaga agagcgaagt cactgcagca atcaagaaga | 420 |
| tgcttgagac cccagggcca tacttgttgg atatcatagt cccgcatcag gagcacgtgc | 480 |
| tgcctatgat cccaagcggt ggtgctttca aggacatgat catggagggt gatggcagga | 540 |
| cctcgtactg aaatttcgac ctacaagacc tacaagtgtg acatgcgcaa tcagcatgat | 600 |
| gcccgcgtgt tgtatcaact actaggggtt caactgtgag ccatgcgttt tctagtttgc | 660 |
| ttgtttcatt catataagct tgtattactt agttccgaac cctgtagttt tgtagtctat | 720 |
| gttctctttt gtagggatgt gctgtcataa gatgtcatgc aagtttcttg tcctacatat | 780 |
| c | 781 |

<210> SEQ ID NO 272
<211> LENGTH: 859
<212> TYPE: DNA
<213> ORGANISM: Triticum aestivum

<400> SEQUENCE: 272

| | |
|---|---|
| accagatgtg ggcggctcag tattacactt acaagcggcc acggcagtgg ctgtcttcgt | 60 |
| ctggttgggg gcaatgggat ttgggttacc agctgcagct ggcgctgctg tggccaaccc | 120 |
| aggtgttaca gttgttgaca ttgatggaga tggtagtttc ctcatgaaca ttcaggagtt | 180 |
| ggcattgatc cgtattgaga acctccctgt gaaggtgatg atattgaaca accagcatct | 240 |
| gggaatggtg gtgcaatggg aggataggtt ttacaaggcc aatcgggcgc acacatacct | 300 |
| tggcaaccca gaaaatgaga gtgagatata tccagatttt gtgacgattg ctaaaggatt | 360 |
| caacgttccg gcagttcgtg tgacgaagaa gagcgaagtc actgcagcaa tcaagaagat | 420 |
| gcttgagacc ccagggccat acttgttgga tatcatcgtc ccgcatcagg agcacgtgct | 480 |
| gcctatgatt cccaatggcg gcgctttcaa ggacatgatc atggagggtg atggcaggac | 540 |
| ctcgtactga aatttgcagg tacaagatcc caagcggtgg tgctttcaag gacatgatca | 600 |
| tggagggtga tggcaggacc tcgtactgaa atttcgacct acaagaccta caagtgtgac | 660 |
| atgcgcaatc agcatggtgc cgcgtgttg tatcaactac taggggttca actgtgaacc | 720 |
| atgcgttttc tagtttgctt gtttcattca tataagcttg tgttacttag ttccgaaccc | 780 |
| tgtagctttg tagtctatgc tctcttttgt agggatgtgc tgtcataaga tatcatgcaa | 840 |
| gtttcttgtc ctacatatc | 859 |

<210> SEQ ID NO 273
<211> LENGTH: 780
<212> TYPE: DNA
<213> ORGANISM: Triticum aestivum

<400> SEQUENCE: 273

| | |
|---|---|
| accagatgtg ggcggctcag tattacactt acaagcggcc acggcagtgg ctgtcttcgt | 60 |
| ctggttgggg gcaatgggat ttgggttacc agctgcagct ggcgctgctg tggccaaccc | 120 |
| aggtgttaca gttgttgaca ttgatggaga tggtagtttc ctcatgaaca ttcaggagtt | 180 |
| ggcattgatc cgtattgaga acctccctgt gaaggtgatg atattgaaca accagcatct | 240 |
| gggaatggtg gtgcaatggg aggataggtt ttacaaggcc aatcgggcgc acacatacct | 300 |
| tggcaaccca gaaaatgaga gtgagatata tccagatttt gtgacgattg ctaaaggatt | 360 |
| caacgttccg gcagttcgtg tgacgaagaa gagcgaagtc actgcagcaa tcaagaagat | 420 |
| gcttgagacc ccagggccat acttgttgga tatcatcgtc ccgcatcagg agcacgtgct | 480 |

```
gcctatgatc ccaagcggtg gtgctttcaa ggacatgatc atggagggtg atggcaggac      540
ctcgtactga aatttcgacc tacaagacct acaagtgtga catgcgcaat cagcatggtg      600
cccgcgtgtt gtatcaacta ctaggggttc aactgtgaac catgcgtttt ctagtttgct      660
tgtttcattc atataagctt gtgttactta gttccgaacc ctgtagcttt gtagtctatg      720
ctctcttttg tagggatgtg ctgtcataag atatcatgca agtttcttgt cctacatatc      780
```

<210> SEQ ID NO 274
<211> LENGTH: 781
<212> TYPE: DNA
<213> ORGANISM: Triticum aestivum

<400> SEQUENCE: 274

```
atcagatgtg ggcggctcag tattacactt acaagcggcc acggcagtgg ctgtcttcat       60
ccggtttggg tgcaatggga tttggggttgc cagctgcagc tggcgctgct gtggccaacc      120
caggtgttac agttgttgac attgatgggg atggtagttt cctcatgaac attcaggagt      180
tggcgttgat ccgtattgag aacctcccag tgaaggtgat gatattgaac aaccagcatc      240
tgggaatggt ggtgcagtgg gaggataggt tttacaaggc caaccgggcg cacacatacc      300
ttggcaaccc agaaaatgag agtgagatat atccagattt tgtgacgatt gctaaaggat      360
tcaacgttcc ggcagttcgt gtgacgaaga gagcgaagt cactgcagca atcaagaaga      420
tgcttgagac cccagggcca tacttgttgg atatcattgt cccgcatcag gagcacgtgc      480
tgcctatgat cccaagcggt ggtgctttta aggacatgat catggagggt gatggcagga      540
cctcgtactg aaatttcgac ctacaagacc tacaagtgtg acatgcgcaa tcagcatgat      600
acctgcgtgt tgtatcaact actgggggtt caactgtgaa ccatgcgttt ctagtttgc      660 ttgtttcatt catataagct tgtgttactt agttccgaac cgtgtagttt tgtagtctct      720
gttctctttt gtagggatgt gctgtcataa gatatcatgc aagtttcttg tcctacatat      780
c                                                                        781
```

<210> SEQ ID NO 275
<211> LENGTH: 781
<212> TYPE: DNA
<213> ORGANISM: Triticum aestivum

<400> SEQUENCE: 275

```
atcagatgtg ggcggctcag tattacactt acaagcggcc acggcagtgg ctgtcttcat       60
ccggtttggg tgcaatggga tttggggttgc cagctgcagc tggcgctgct gtggccaacc      120
caggtgttac agttgttgac attgatgggg atggtagttt cctcatgaac attcaggagt      180
tggcgttgat ccgtattgag aacctcccag tgaaggtgat gatattgaac aaccagcatc      240
tgggaatggt ggtgcagtgg gaggataggt tttacaaggc caaccgggcg cacacatacc      300
ttggcaaccc agaaaatgag agtgagatat atccagattt tgtgacgatt gctaaaggat      360
tcaacgttcc ggcagttcgt gtgacgaaga gagcgaagt cactgcagca atcaagaaga      420
tgcttgagac cccagggcca tacttgttgg atatcattgt cccgcatcag gagcacgtgc      480
tgcctatgat cccaagcggt ggtgctttta aggacatgat catggagggt gatggcagga      540
cctcgtactg aaatttcgac ctacaagacc tacaagtgtg acatgcgcaa tcagcatgat      600
acctgcgtgt tgtatcaact actgggggtt caactgtgaa ccatgcgttt ctagtttgc      660 ttgtttcatt catataagct tgtgttactt agttccgaac cgtgtagttt tgtagtctct      720
gttctctttt gtagggatgt gctgtcataa gatatcatgc aagtttcttg tcctacatat      780
``` c                                                                               781

<210> SEQ ID NO 276
<211> LENGTH: 781
<212> TYPE: DNA
<213> ORGANISM: Triticum aestivum

<400> SEQUENCE: 276
accagatgtg ggcggctcag tattacactt acaagcggcc acggcagtgg ctgtcttcgt    60
ctggtttggg ggcaatggga tttgggttac cagctgcagc tggcgctgct gtggccaacc   120
caggtgttac agttgttgac attgatggtg atggtagttt cctcatgaac attcaggagt   180
tggcgttgat ccgcattgag aacctcccag tgaaggtgat gatattgaac aaccagcatc   240
tgggaatggt ggtgcagtgg gaggataggt tttacaaggc caatcgggcg cacacatacc   300
ttggcaaccc agaaaatgag agtgagatat atccagattt tgtgacgatt gctaaaggat   360
tcaacgttcc agcagttcga gtgacgaaga agagcgaagt cactgcagca atcaagaaga   420
tgcttgagac cccagggcca tacttgttgg atatcatagt cccgcatcag gagcacgtgc   480
tgcctatgat cccaagcggt ggtgctttca aggacatgat catggagggt gatggcagga   540
cctcgtactg aaatttcgac ctacaagacc tacaagtgtg acatgcgcaa tcagcatgat   600
gcccgcgtgt tgtatcaact actaggggtt caactgtgag ccatgcgttt tctagtttgc   660
ttgtttcatt catataagct tgtattactt agttccgaac cctgtagttt tgtagtctat   720
gttctctttt gtagggatgt gctgtcataa gatgtcatgc aagtttcttg tcctacatat   780
c                                                                               781

<210> SEQ ID NO 277
<211> LENGTH: 781
<212> TYPE: DNA
<213> ORGANISM: Triticum aestivum

<400> SEQUENCE: 277
accagatgtg ggcggctcag tattacactt acaagcggcc acggcagtgg ctgtcttcgt    60
ctggtttggg ggcaatggga tttgggttac cagctgcagc tggcgctgct gtggccaacc   120
caggtgttac agttgttgac attgatggtg atggtagttt cctcatgaac attcaggagt   180
tggcgttgat ccgcattgag aacctcccag tgaaggtgat gatattgaac aaccagcatc   240
tgggaatggt ggtgcagtgg gaggataggt tttacaaggc caatcgggcg cacacatacc   300
ttggcaaccc agaaaatgag agtgagatat atccagattt tgtgacgatt gctaaaggat   360
tcaacgttcc agcagttcga gtgacgaaga agagcgaagt cactgcagca atcaagaaga   420
tgcttgagac cccagggcca tacttgttgg atatcatagt cccgcatcag gagcacgtgc   480
tgcctatgat cccaagcggt ggtgctttca aggacatgat catggagggt gatggcagga   540
cctcgtactg aaatttcgac ctacaagacc tacaagtgtg acatgcgcaa tcagcatgat   600
gcccgcgtgt tgtatcaact actaggggtt caactgtgag ccatgcgttt tctagtttgc   660
ttgtttcatt catataagct tgtattactt agttccgaac cctgtagttt tgtagtctat   720
gttctctttt gtagggatgt gctgtcataa gatgtcatgc aagtttcttg tcctacatat   780
c                                                                               781

<210> SEQ ID NO 278
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 278

Arg Ser Ala Asp Leu Ser Arg
1               5

<210> SEQ ID NO 279
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Arg Ser Asp His Leu Ser Ala
1               5

<210> SEQ ID NO 280
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Gln Ser Ser Asp Leu Arg Arg
1               5

<210> SEQ ID NO 281
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Arg Ser Asp Asp Arg Lys Thr
1               5

<210> SEQ ID NO 282
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Arg Arg Ala Asp Arg Ala Lys
1               5

<210> SEQ ID NO 283
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Thr Ser Ser Asp Arg Lys Lys
1               5
```

```
<210> SEQ ID NO 284
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Arg Ser Ala Asp Leu Thr Arg
1               5

<210> SEQ ID NO 285
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Arg Asn Asp Asp Arg Lys Lys
1               5

<210> SEQ ID NO 286
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Asp Arg Ser Asn Leu Thr Arg
1               5

<210> SEQ ID NO 287
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Glu Arg Gly Thr Leu Ala Arg
1               5

<210> SEQ ID NO 288
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Asp Arg Ser Asp Leu Ser Arg
1               5

<210> SEQ ID NO 289
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 289

Asp Ser Ser Thr Arg Arg Arg
1               5

<210> SEQ ID NO 290
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Arg Ser Asp His Leu Ser Glu
1               5

<210> SEQ ID NO 291
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

His Ser Arg Thr Arg Thr Lys
1               5

<210> SEQ ID NO 292
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Arg Ser Asp Thr Leu Ser Glu
1               5

<210> SEQ ID NO 293
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Asn Asn Arg Asp Arg Thr Lys
1               5

<210> SEQ ID NO 294
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Asp Arg Ser Asp Leu Ser Arg
1               5

<210> SEQ ID NO 295
<211> LENGTH: 82

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
tccaaggttg cggccgcgcc caaggaaccc ttttctgggc cattactcgg ccacgactgg     60
taatttaatt ttcaatttat tt     82

<210> SEQ ID NO 296
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Arg Ser Asp His Leu Ser Arg
1               5

<210> SEQ ID NO 297
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Gln Gln Trp Asp Arg Lys Gln
1               5

<210> SEQ ID NO 298
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Asp Arg Ser His Leu Thr Arg
1               5

<210> SEQ ID NO 299
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Val Ser Ser Asn Leu Thr Ser
1               5

<210> SEQ ID NO 300
<211> LENGTH: 28
<212> TYPE: DNA
<213> ORGANISM: Triticum aestivum
<220> FEATURE:
<221> NAME/KEY: modified_base
<222> LOCATION: (2)..(2)
<223> OTHER INFORMATION: a, c, t, g, unknown or other

<400> SEQUENCE: 300

```
cngcggccat ggcggcggcg agggtttg                                              28

<210> SEQ ID NO 301
<211> LENGTH: 28
<212> TYPE: DNA
<213> ORGANISM: Triticum aestivum
<220> FEATURE:
<221> NAME/KEY: modified_base
<222> LOCATION: (24)..(24)
<223> OTHER INFORMATION: a, c, t, g, unknown or other

<400> SEQUENCE: 301
acctcccccg ccgtcgcatt ctcnggcg                                              28

<210> SEQ ID NO 302
<211> LENGTH: 28
<212> TYPE: DNA
<213> ORGANISM: Triticum aestivum
<220> FEATURE:
<221> NAME/KEY: modified_base
<222> LOCATION: (20)..(20)
<223> OTHER INFORMATION: a, c, t, g, unknown or other

<400> SEQUENCE: 302
ggccggacgc gcgggcgtan ccggacgc                                              28

<210> SEQ ID NO 303
<211> LENGTH: 28
<212> TYPE: DNA
<213> ORGANISM: Triticum aestivum

<400> SEQUENCE: 303
cgtcggcgtc tgcgtcgcca cctccggc                                              28

<210> SEQ ID NO 304
<211> LENGTH: 28
<212> TYPE: DNA
<213> ORGANISM: Triticum aestivum

<400> SEQUENCE: 304
acgccgacgc ggccggacgc gcgggcgt                                              28

<210> SEQ ID NO 305
<211> LENGTH: 28
<212> TYPE: DNA
<213> ORGANISM: Triticum aestivum

<400> SEQUENCE: 305
gcgtcgccac ctccggcccg ggggccac                                              28

<210> SEQ ID NO 306
<211> LENGTH: 28
<212> TYPE: DNA
<213> ORGANISM: Triticum aestivum

<400> SEQUENCE: 306
cagacgccga cgcggccgga cgcgcggg                                              28

<210> SEQ ID NO 307
<211> LENGTH: 28
<212> TYPE: DNA
<213> ORGANISM: Triticum aestivum

<400> SEQUENCE: 307
```

```
gtcgccacct ccggcccggg ggccacca                                              28

<210> SEQ ID NO 308
<211> LENGTH: 28
<212> TYPE: DNA
<213> ORGANISM: Triticum aestivum

<400> SEQUENCE: 308
gcgacgcaga cgccgacgcg gccggacg                                              28

<210> SEQ ID NO 309
<211> LENGTH: 28
<212> TYPE: DNA
<213> ORGANISM: Triticum aestivum

<400> SEQUENCE: 309
cctccggccc gggggccacc aacctcgt                                              28

<210> SEQ ID NO 310
<211> LENGTH: 28
<212> TYPE: DNA
<213> ORGANISM: Triticum aestivum
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 310
gggatggagt cgaggagngc gtcngcga                                              28

<210> SEQ ID NO 311
<211> LENGTH: 28
<212> TYPE: DNA
<213> ORGANISM: Triticum aestivum

<400> SEQUENCE: 311
tggtcgccat cacgggccag gtcccccg                                              28

<210> SEQ ID NO 312
<211> LENGTH: 28
<212> TYPE: DNA
<213> ORGANISM: Triticum aestivum
<220> FEATURE:
<221> NAME/KEY: modified_base
<222> LOCATION: (24)..(24)
<223> OTHER INFORMATION: a, c, t, g, unknown or other

<400> SEQUENCE: 312
accatgggga tggagtcgag gagngcgt                                              28

<210> SEQ ID NO 313
<211> LENGTH: 28
<212> TYPE: DNA
<213> ORGANISM: Triticum aestivum

<400> SEQUENCE: 313
ccatcacggg ccaggtcccc cgccgcat                                              28

<210> SEQ ID NO 314
<211> LENGTH: 28
<212> TYPE: DNA
<213> ORGANISM: Triticum aestivum
```

```
<220> FEATURE:
<221> NAME/KEY: modified_base
<222> LOCATION: (26)..(26)
<223> OTHER INFORMATION: a, c, t, g, unknown or other

<400> SEQUENCE: 314
cgaccatggg gatggagtcg aggagngc                                      28

<210> SEQ ID NO 315
<211> LENGTH: 28
<212> TYPE: DNA
<213> ORGANISM: Triticum aestivum

<400> SEQUENCE: 315
catcacgggc caggtccccc gccgcatg                                      28

<210> SEQ ID NO 316
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
acactctttc cctacacgac gctcttccga tcttccccaa ttccaaccct ctc          53

<210> SEQ ID NO 317
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
gtgactggag ttcagacgtg tgctcttccg atctcgtcag cgcctggtgg atct         54

<210> SEQ ID NO 318
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
acactctttc cctacacgac gctcttccga tctgcccgtc cgagcccgc aa            52

<210> SEQ ID NO 319
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
gtgactggag ttcagacgtg tgctcttccg atctcgtcag cgcctggtgg atct         54

<210> SEQ ID NO 320
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 320
acactctttc cctacacgac gctcttccga tctgcgctcg cccgtcatca c    51

<210> SEQ ID NO 321
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
gtgactggag ttcagacgtg tgctcttccg atctatgggg atggagtcga ggag    54

<210> SEQ ID NO 322
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
acactctttc cctacacgac gctcttccga tctcttccgc cacgagcagg g    51

<210> SEQ ID NO 323
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
gtgactggag ttcagacgtg tgctcttccg atctatgggg atggagtcga ggag    54

<210> SEQ ID NO 324
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
acactctttc cctacacgac gctcttccga tcttcgtctc cgcgctcgct ga    52

<210> SEQ ID NO 325
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
gtgactggag ttcagacgtg tgctcttccg atcttccact atgggcgtct cctg    54

<210> SEQ ID NO 326
<211> LENGTH: 6661
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 326

```
tggcaggata tattgtggtg taaacaaatt gacgcttaga caacttaata acacattgcg      60
gacgttttta atgtactgaa ttaacgccga attgaattcg agctcggtac cactggattt     120
tggttttagg aattagaaat tttattgata gaagtatttt acaaatacaa atacatacta     180
agggtttctt atatgctcaa cacatgagcg aaaccctata agaaccctaa ttcccttatc     240
tgggaactac tcacacatta ttctggagaa aaatagagag agatagattt gtagagagag     300
actggtgatt tttgcggact ctattagatc tgggtaactg gcctaactgg ccttggagga     360
gctggcaact caaaatccct tgccaaaaa ccaacatcat gccatccacc atgcttgtat      420
ccagctgcgc gcaatgtacc ccgggctgtg tatcccaaag cctcatgcaa cctaacagat     480
ggatcgtttg gaaggcctat aacagcaacc acagacttaa aaccttgcgc tccatagac      540
ttaagcaaat gtgtgtacaa tgtggatcct aggcccaacc tttgatgcct atgtgacacg     600
taaacagtac tctcaactgt ccaatcgtaa gcgttcctag ccttccaggg cccagcgtaa     660
gcaataccag ccacaacacc ctcaacctca gcaaccaacc aagggtatct atcttgcaac     720
ctctcgagat catcaatcca ctcttgtggt gtttgtggct ctgtcctaaa gttcactgta     780
gacgtctcaa tgtaatggtt aacgatatca caaaccgcgg ccatatcagc tgctgtagct     840
ggcctaatct caactggtct cctctccgga gacatggctt ctacctacaa aaaagctccg     900
cacgaggctg catttgtcac aaatcatgaa aagaaaaact accgatgaac aatgctgagg     960
gattcaaatt ctacccacaa aaagaagaaa gaaagatcta gcacatctaa gcctgacgaa    1020
gcagcagaaa tatataaaaa tataaaccat agtgcccttt tcccctcttc ctgatcttgt    1080
ttagcatggc ggaaatttta acccccccat catctccccc aacaacggcg gatcgcagat    1140
ctacatccga gagccccatt ccccgcgaga tccgggccgg atccacgccg gcgagagccc    1200
cagccgcgag atcccgcccc tcccgcgcac cgatctgggc gcgcacgaag ccgcctctcg    1260
cccacccaaa ctaccaaggc caaagatcga gaccgagacg gaaaaaaaaa acggagaaag    1320
aaagaggaga ggggcggggt ggttaccggc gcggcggcgg cggaggggga gggggagga     1380
gctcgtcgtc cggcagcgag ggggaggag gtggaggtgg tggtggtggt ggtggtaggg     1440
ttgggggat gggaggagag gggggggtat gtatatagtg gcgatggggg gcgtttcttt     1500
ggaagcggag ggagggccgg cctcgtcgct ggctcgcgat cctcctcgcg tttccggccc    1560
ccacgacccg gacccacctg ctgttttttc tttttctttt tttctttct tttttttttt    1620
ttggctgcga gacgtgcggt gcgtgcggac aactcacggt gatagtgggg gggtgtggag    1680
actattgtcc agttggctgg actggggtgg gttgggttgg gttgggttgg gctgggcttg    1740
ctatggatcg tggatagcac tttgggcttt aggaacttta ggggttgttt ttgtaaatgt    1800
tttgagtcta agtttatctt ttatttttac tagaaaaaat acccatgcgc tgcaacgggg    1860
gaaagctatt ttaatcttat tattgttcat tgtgagaatt cgcctgaata tatattttc    1920
tcaaaaatta tgtcaaatta gcatatgggt tttttaaag atatttctta tacaaatccc    1980
tctgtattta caaaagcaaa cgaacttaaa acccgactca aatacagata tgcatttcca    2040
aaagcgaata aacttaaaaa ccaattcata caaaaatgac gtatcaaagt accgacaaaa    2100
acatcctcaa ttttttataat agtagaaaag agtaaatttc actttgggcc accttttatt    2160
accgatattt tacttatac cacctttta ctgatgtttt cacttttgac caggtaatct      2220
tacctttgtt ttattttgga ctatcccgac tctcttctca agcatatgaa tgacctcgag    2280
tatgctagtc tagagtcgac ctgcagggtg cagcgtgacc cggtcgtgcc cctctctaga    2340
```

```
gataatgagc attgcatgtc taagttataa aaaattacca catattttt ttgtcacact    2400 tgtttgaagt gcagtttatc tatctttata catatattta aactttactc tacgaataat    2460
ataatctata gtactacaat aatatcagtg ttttagagaa tcatataaat gaacagttag    2520
acatggtcta aaggacaatt gagtattttg acaacaggac tctacagttt tatctttta     2580 gtgtgcatgt gttctccttt tttttgcaa atagcttcac ctatataata cttcatccat     2640
tttattagta catccattta gggtttaggg ttaatggttt ttatagacta atttttag      2700 tacatctatt ttattctatt ttagcctcta aattaagaaa actaaaactc tattttagtt    2760
tttttattta ataatttaga tataaaatag aataaaataa agtgactaaa aattaaacaa    2820
atacccttta agaaattaaa aaaactaagg aaacattttt cttgtttcga gtagataatg    2880
ccagcctgtt aaacgccgtc gacgagtcta acggacacca accagcgaac cagcagcgtc    2940
gcgtcgggcc aagcgaagca gacggcacgg catctctgtc gctgcctctg gaccctctc     3000 gagagttccg ctccaccgtt ggacttgctc cgctgtcggc atccagaaat tgcgtggcgg    3060
agcggcagac gtgagccggc acggcaggcg gcctcctcct cctctcacgg cacggcagct    3120 acggggatt cctttcccac cgctccttcg ctttcccttc ctcgcccgcc gtaataaata     3180
gacaccccct ccacaccctc ttccccaac ctcgtgttgt tcggagcgca cacacacaca    3240
accagatctc ccccaaatcc acccgtcggc acctccgctt caaggtacgc cgctcgtcct    3300
cccccccccc ccctctctac cttctctaga tcggcgttcc ggtccatggt tagggcccgg    3360
tagttctact tctgttcatg tttgtgttag atccgtgttt gtgttagatc cgtgctgcta    3420
gcgttcgtac acggatgcga cctgtacgtc agacacgttc tgattgctaa cttgccagtg    3480
tttctctttg gggaatcctg ggatggctct agccgttccg cagacgggat cgatttcatg    3540 atttttttg tttcgttgca tagggtttgg tttgcccttt tcctttattt caatatatgc     3600
cgtgcacttg tttgtcgggt catcttttca tgcttttttt tgtcttggtt gtgatgatgt    3660
ggtctggttg ggcggtcgtt ctagatcgga gtagaattct gtttcaaact acctggtgga    3720
tttattaatt ttggatctgt atgtgtgtgc catacatatt catagttacg aattgaagat    3780
gatggatgga aatatcgatc taggataggt atacatgttg atgcgggttt tactgatgca    3840
tatacagaga tgcttttgt tcgcttggtt gtgatgatgt ggtgtggttg ggcggtcgtt     3900
cattcgttct agatcggagt agaatactgt ttcaaactac ctggtgtatt tattaatttt    3960
ggaactgtat gtgtgtgtca tacatcttca tagttacgag tttaagatgg atggaaatat    4020
cgatctagga taggtataca tgttgatgtg ggttttactg atgcatatac atgatggcat    4080
atgcagcatc tattcatatg ctctaacctt gagtacctat ctattataat aaacaagtat    4140
gttttataat tattttgatc ttgatatact tggatgatgg catatgcagc agctatatgt    4200
ggattttttt agccctgcct tcatacgcta tttatttgct tggtactgtt tcttttgtcg    4260
atgctcaccc tgttgtttgg tgttacttct gcaggaggat cacaagtttg tacaaaaaag    4320
caggctatgg ccgccgccac ctcccccgcc gtcgcattct cgggcgccac cgccgccgcc    4380
atgcccaaac ccgccgcca tcctctcccg cgccaccagc ccgtctcgcg ccgcgcgctc    4440
cccgcccgcg tcgtcaggtg ttgcgccgcg tcccccgccg ccacctccgc cgcgcctccc    4500
gcaaccgcgc tccggccctg ggcccgtcc gagcccgca agggcgccga catcctcgtc     4560
gaggcgctcg agcgctgcgg catcgtcgac gtcttcgcct accccggcgg cgcctccatg    4620
gagatccacc aggcgctgac gcgctcgccc gtcatcacca accacctctt ccgccacgag    4680
```

```
caggggagg cgttcgcggc gtccggctac gcccgcgcgt ccggccgcgt cggcgtctgc    4740
gtcgccacct ccggcccggg ggccaccaac ctcgtctccg cgctcgccga cgccctcctc    4800
gactccatcc ccatggtcgc catcacgggc caggtctccc gccgcatgat cggcacggac    4860
gcgttccagg agacgcccat agtggaggtc acgcgctcca tcaccaagca caactacctg    4920
gtccttgacg tggaggatat cccccgcgtc atccaggaag ccttcttcct tgcatcctct    4980
ggccgcccgg ggccggtgct agttgatatc cccaaggaca tccagcagca gatggctgtg    5040
cccgtctggg acactccaat gagtttgcca gggtacatcg cccgcctgcc caagccacca    5100
tctactgaat cgcttgagca ggtcctgcgt ctggttggcg agtcacggcg cccaattctg    5160
tatgttggtg gtggctgcgc tgcgtctggc gaggagttgc gccgctttgt tgagcttact    5220
gggattccag ttacaactac tctgatgggc cttggcaact tccccagcga cgacccactg    5280
tctctgcgca tgcttgggat gcatggcact gtgtatgcaa attatgcagt agataaggct    5340
gacctgttgc tcgcatttgg tgtgcggttt gatgatcgtg tgactgggaa aatcgaggct    5400
tttgcaagca ggtccaagat tgtgcacatt gacattgacc cagctgagat tggcaagaac    5460
aagcagccac atgtctccat ttgtgcagat gttaagcttg ctttacaggg gttgaatgat    5520
ctattaaatg ggagcaaagc acaacagggt ctggattttg gtccatggca caaggagttg    5580
gatcagcaga gagggagtt tcctctagga ttcaagactt ttggcgaggc catcccgccg    5640
caatatgcta tccaggtact ggatgagctg acaaaagggg aggcgatcat tgccactggt    5700
gttgggcagc accagatgtg ggcggctcag tattacactt acaagcggcc acggcagtgg    5760
ctgtcttcgt ctggtttggg ggcaatggga tttgggttac cagctgcagc tggcgctgct    5820
gtggccaacc caggtgttac agttgttgac attgatggtg atggtagttt cctcatgaac    5880
attcaggagt tggcgttgat ccgcattgag aacctcccag tgaaggtgat gatattgaac    5940
aaccagcatc tgggaatggt ggtgcagtgg gaggataggt tttacaaggc caatcgggcg    6000
cacacatacc ttggcaaccc agaaaatgag agtgagatat atccagattt tgtgacgatt    6060
gctaaaggat tcaacgttcc agcagttcga gtgacgaaga gagcgaagt cactgcagca    6120 atcaagaaga tgcttgagac cccagggcca tacttgttgg atatcatagt cccgcatcag    6180
gagcacgtgc tgcctatgat cccaagcggt ggtgcttttca aggacatgat catggagggt    6240
gatggcagga cctcgtactg ataccccagct ttccttgtaca aagtggtgat cctactagta    6300
gaaggagtgc gtcgaagcag atcgttcaaa catttggcaa taaagtttct taagattgaa    6360
tcctgttgcc ggtcttgcga tgattatcat ataatttctg ttgaattacg ttaagcatgt    6420
aataattaac atgtaatgca tgacgttatt tatgagatgg ttttttatga ttagagtccc    6480
gcaattatac atttaatacg cgatagaaaa caaaatatag cgcgcaaact aggataaatt    6540
atcgcgcgcg gtgtcatcta tgttactaga tcgaaagctt agcttgagct tggatcagat    6600
tgtcgtttcc cgccttcagt ttaaactatc agtgtttgac aggatatatt ggcgggtaaa    6660
c                                                                    6661
```

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 327
gcgaagatcc aggacaagga                                          20

<210> SEQ ID NO 328
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
ctgcttaccg gcaaagatga g                                        21

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 329
ttcccccgga ccagcagcgt                                          20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
ccgacgagaa agaccagcaa                                          20

<210> SEQ ID NO 331
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
cttaagttgt cgatcgggac tgt                                      23

<210> SEQ ID NO 332
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 332
tgagcctctc gtcgccgatc acat                                     24

<210> SEQ ID NO 333
<211> LENGTH: 1159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 333
ccactcttgc cctacacgac actgaagacc ttatgattcc aaacggcggc gccttcaagg    60

```
acatgatcat ggagggtgat ggcaggacct cgtactgaaa tttcgaccta caagacctac      120
aagtgtgaca tgcgcaatca gcatggtgcc cgcgtgttgt atcaactact aggggttcaa      180
ctgtgaacca tgcgttttct agtttgcttg tttcattcat ataagcttgt gttacttagt      240
tccgaaccct gtagctttgt agtctatgct ctcttttgta gggatgtgct gtcataagat      300
atcatgcaag tttcttgtcc tacatatcaa taataagtac ttccatggaa taattctcag      360
ttctgttttg aattttgcat cttctcacaa acagtgtgct ggttcctttc tgttcgctga      420
cgccctcctc gactccatcc ccatggtcgc catcacgggc caggtccccc gccgcatgat      480
cggtagcgac ttcgtgggcg aggaaagcct tcgtccaag tggtccctc ctcgcaatct       540 tgttggatgg tgaatattat aaaagcctgc ccttctcgcg ggtaagactc cgcccatcc      600 aggatgagga tgaccagcct tttgcagttt atccactagg acaggattg catcctgccg       660 aaaccctgcc aagcttgagg tagcctccaa tttgacggtg ccgccagcga cgccgtctgg     720
aactgtcctt tttgaggacc actccgtttg tctagaggta cctggagatc atgacattaa     780
ggatgaccag ttcgtaaagg tcctgcggtg tctattgctt ttcataggtt aataagtgtt     840
tgctagactg tggtgaaagg ccaagactcc cgcccatctc tctatgcccg ggacaagtgc     900
caccccacag tggggcagga tgaggatgac caaagactcc cgcccatctc actagggaca     960
ggattggcct tttgcagttt atctctatgc ccgggacaag tgtatccgaa gtaaataaaa    1020
ccatcggact ctcgtataag actgtcgact cgaccggccg acgcataggt tcatttgaag    1080
ctgctattct atttaaattg aaactcggac ggtagcagtg tggtatgagg tcttcagcac    1140
actcggtaac tccagtcac                                                1159
```

<210> SEQ ID NO 334
<211> LENGTH: 2479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 334

```
ccactcttgc cctacacgac actgaagacg tcgccattac cgggcaagtg acccgccgca      60
tgatcggcac ggacgcgttc caggagacgc ccatagtgga ggtcacgcgc tccatcacca     120
agcacaacta cctggtcctt gacgtggagg atatccccg cgtcatccag gaagccttct      180
tccttgcatc ctctggccgc ccggggccgg tgctagttga tatccccaag gacatccagc     240
agcagatggc tgtgcccgtc tgggacactc caatgagttt gccagggtac atcgcccgcc     300
tgcccaagcc accatctact gaatcgcttg agcaggtcct cgtctggtt ggcgagtcac      360 ggcgcccaat tctgtatgtt ggtggtggct gcgctgcgtc tggcgaggag ttgcgccgct     420
ttgttgagct tactgggatt ccagttacaa ctactctgat gggccttggc aacttcccca     480
gcgacgaccc actgtctctg cgcatgcttg ggatgcatgg cactgtgtat gcaaattatg     540
cagtagataa ggctgacctg ttgctcgcat ttggtgtgcg gtttgatgat cgtgtgactg     600
ggaaaatcga ggcttttgca agcaggtcca agattgtgca cattgacatt gacccagctg     660
agattggcaa gaacaagcag ccacatgtct ccatttgtgc agatgttaag cttgctttac     720
aggggttgaa tgatctatta aatgggagca aagcacaaca gggtctggat tttggtccat     780
ggcacaagga gttggatcag cagaagaggg agtttcctct aggattcaag acttttggcg     840
aggccatccc gccgcaatat gctatccagg tactggatga gctgacaaaa ggggaggcga     900
```

```
tcattgccac tggtgttggg cagcaccaga tgtgggcggc tcagtattac acttacaagc     960
ggccacggca gtggctgtct tcgtctggtt tgggggcaat gggatttggg ttaccagctg    1020
cagctggcgc tgctgtggcc aacccaggtg ttacagttgt tgacattgat ggtgatggta    1080
gtttcctcat gaacattcag gagttggcgt tgatccgcat tgagaacctc ccagtgaagg    1140
tgatgatatt gaacaaccag catctgggaa tggtggtgca gtgggaggat aggttttaca    1200
aggccaatcg ggcgcacaca taccttggca acccagaaaa tgagagtgag atatatccag    1260
attttgtgac gattgctaaa ggattcaacg ttccagcagt tcgagtgacg aagaagagcg    1320
aagtcactgc agcaatcaag aagatgcttg agacccagg gccatacttg ttggatatca     1380
tagtcccgca tcaggagcac gtgctgccta tgatcccaag cggtggtgct ttcaaggaca    1440
tgatcatgga gggtgatggc aggacctcgt actgaaattt cgacctacaa gacctacaag    1500
tgtgacatgc gcaatcagca tggtgcccgc gtgttgtatc aactactagg ggttcaactg    1560
tgaaccatgc gttttctagt ttgcttgttt cattcatata agcttgtgtt acttagttcc    1620
gaaccctgta gctttgtagt ctatgctctc ttttgtaggg atgtgctgtc ataagatatc    1680
atgcaagttt cttgtcctac atatcaataa taagtacttc catggaataa ttctcagttc    1740
tgttttgaat tttgcatctt ctcacaaaca gtgtgctggt tcctttctgt tctacgcccg    1800
cgcgtccggc cgcgtcggcg tctgcgtcgc cacctccggc ccgggggcca ccaacctcgt    1860
ctccgtagcg acttcgtggg cgaggaaagc cttctgtcca aggtggtccc tcctcgcaat    1920
cttgttggat ggtgaatatt ataaaagcct gcccttctcg cgggtgagtc catgctcaac    1980
accgtgcact agggacagga ttggcctttt gcagtttatc cactagggac aggattgcat    2040
cctgccgaaa ccctgccaag cttgaggtag cctccaattt gacggtgccg ccagcgacgc    2100
cgtctggaac tgtcctttt gaggaccact ccgtttgtct agaggtacct ggagatcatg     2160
acattaagga tgaccagttc gtaaaggtcc tgcggtgtct attgcttttc ataggttaat    2220
aagtgtttgc tagactgtgg tgaaaggccg ccttttgcag tttatctcta gaaagactgg    2280
agttgcagaa agactcccgc ccatccagga tgaggatgac catatccgaa gtaaataaaa    2340
ccatcggact ctcgtataag actgtcgact cgaccggccg acgcataggt tcatttgaag    2400
ctgctattct atttaaattg aaactcggac ggtagcagtg tggtatgagg tcttcagcac    2460
actcggtaac tccagtcac                                                 2479
```

<210> SEQ ID NO 335
<211> LENGTH: 2571
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 335

```
tgagattggc aagaacaagc agccacatgt ctccatttgt gcagatgtta agcttgcttt      60
acaggggttg aatgatctat taaatgggag caaagcacaa cagggtctgg attttggtcc     120
atggcacaag gagttggatc agcagaagag ggagtttcct ctaggattca agactttgg      180 cgaggccatc ccgccgcaat atgctatcca ggtactggat gagctgacaa aaggggaggc    240
gatcattgcc actggtgttg ggcagcacca gatgtgggcg gctcagtatt acacttacaa    300
gcggccacgg cagtggctgt cttcgtctgg tttggggca atgggatttg ggttaccagc     360
tgcagctggc gctgctgtgg ccaacccagg tgttacagtt gttgacattg atggtgatgg    420
```

```
tagtttcctc atgaacattc aggagttggc gttgatccgc attgagaacc tcccagtgaa    480
ggtgatgata ttgaacaacc agcatctggg aatggtggtg cagtgggagg ataggtttta    540
caaggccaat cgggcgcaca cataccttgg caacccagaa aatgagagtg agatatatcc    600
agattttgtg acgattgcta aaggattcaa cgttccagca gttcgagtga cgaagaagag    660
cgaagtcact gcagcaatca agaagatgct tgagaccccca gggccatact tgttggatat    720
catagtcccg catcaggagc acgtgctgcc tatgattcca aacggcggcg ccttcaagga    780
catgatcatg gagggtgatg gcaggacctc gtactgaaat tcgacctac aagacctaca    840
agtgtgacat gcgcaatcag catggtgccc gcgtgttgta tcaactacta ggggttcaac    900
tgtgaaccat gcgttttcta gtttgcttgt tcattcata taagcttgtg ttacttagtt    960
ccgaaccctg tagctttgta gtctatgctc tcttttgtag gatgtgctg tcataagata   1020
tcatgcaagt ttcttgtcct acatatcaat aataagtact tccatggaat aattctcagt   1080
tctgttttga attttgcatc ttctcacaaa cagtgtgctg gttcctttct gttcgctgac   1140
gccctcctcg actccatccc catggtcgcc atcacgggcc aggtcccccg ccgcatgatc   1200
ggtagcgact cgtgggcga ggaaagcctt tcgtccaagg tggtccctcc tcgcaatctt   1260
gttggatggt gaatattata aaagcctgcc cttctcgcgg gtaagactcc cgcccatcca   1320
ggatgaggat gaccagcctt ttgcagttta tccactaggg acaggattgc atcctgccga   1380
aaccctgcca agcttgaggt agcctccaat ttgacggtgc cgccagcgac gccgtctgga   1440
actgtccttt ttgaggacca ctccgtttgt ctagaggtac ctggagatca tgacattaag   1500
gatgaccagt tcgtaaaggt cctgcggtgt ctattgcttt tcataggtta ataagtgttt   1560
gctagactgt ggtgaaaggc caagactccc gcccatctct ctatgcccgg acaagtgcc   1620
accccacagt ggggcaggat gaggatgacc aaagactccc gcccatctca ctagggacag   1680
gattggcctt ttgcagttta tctctatgcc cgggacaagt gtatccgaag taaataaaac   1740
catcggactc tcgtataaga ctgtcgactc gaccggccga cgcataggtt catttgaagc   1800
tgctattcta tttaaattga aatcccaagc ggtggtgctt tcaaggacat gatcatggag   1860
ggtgatggca ggacctcgta ctgaaatttc gacctacaag acctacaagt gtgacatgcg   1920
caatcagcat gatgcccgcg tgttgtatca actactaggg gttcaactgt gagccatgcg   1980
ttttctagtt tgcttgtttc attcatataa gcttgtatta cttagttccg aaccctgtag   2040
ttttgtagtc tatgttctct tttgtaggga tgtgctgtca taagatgtca tgcaagtttc   2100
ttgtcctaca tatcaataat aagtacttcc atggaataat tctcagttct gttttgaatt   2160
ttgcatcttc tcacaaacag tgtgctggtt cctttctgtt actttacatg tctgctgtgt   2220
caggttctga cataacgacc gatggagggt ggtcggcagg ttttagaagg ggaattgaaa   2280
cttttttttg ggaagaagtc tgaatacagt tgggaggaaa aatagaagta tatacttcga   2340
ttaatttatc aagcccgcta tccagtctaa tttatcaagc actagacagt gtagggtgtt   2400
ggcattcttc tcttccttga gatccggctt gagaggagag accgaggctt cggctgtgtt   2460
ggttgctgat ttctacagct ttttgagata gagagagaga tcctgcaact gtggtttgtc   2520
ttgctgcttg tacagcgaga gagacattga gagatatgta gatcgtttac c            2571
```

<210> SEQ ID NO 336
<211> LENGTH: 57
<212> TYPE: DNA
<213> ORGANISM: Brassica napus -continued

<400> SEQUENCE: 336
gcccaaggaa ccctttcctg ggccatcttc gtactcggcc acgactggta atttaat    57

<210> SEQ ID NO 337
<211> LENGTH: 58
<212> TYPE: DNA
<213> ORGANISM: Brassica napus

<400> SEQUENCE: 337
agcgagagaa agcttattgc aacttcaact acttgctggt cgatcgtgtt ggccactc    58

<210> SEQ ID NO 338
<211> LENGTH: 57
<212> TYPE: DNA
<213> ORGANISM: Brassica napus

<400> SEQUENCE: 338
gcccaaggaa ccctttcctg ggccatcttc gtactcggcc acgactggta atttaat    57

<210> SEQ ID NO 339
<211> LENGTH: 57
<212> TYPE: DNA
<213> ORGANISM: Brassica napus

<400> SEQUENCE: 339
gcccaaggaa ccctgttctg ggctatcttc gtactcggcc acgactggta atttaat    57

<210> SEQ ID NO 340
<211> LENGTH: 57
<212> TYPE: DNA
<213> ORGANISM: Brassica napus

<400> SEQUENCE: 340
gcccaaggaa ccctttcctg ggccatcttc gtcctcggcc acgactggta aagtttc    57

<210> SEQ ID NO 341
<211> LENGTH: 57
<212> TYPE: DNA
<213> ORGANISM: Brassica napus

<400> SEQUENCE: 341
gcccaaggaa ccctttcctg ggccatcttc gtcctcggcc acgactggta aagtttc    57

<210> SEQ ID NO 342
<211> LENGTH: 57
<212> TYPE: DNA
<213> ORGANISM: Brassica napus

<400> SEQUENCE: 342
gcccaaggaa ccctttcctg ggccatcttc gttcttggcc acgactggta aattaaa    57

<210> SEQ ID NO 343
<211> LENGTH: 57
<212> TYPE: DNA
<213> ORGANISM: Brassica napus

<400> SEQUENCE: 343
gcccaaggaa ccctttcctg ggccatcttc gttcttggcc acgactggta aattaaa    57

<210> SEQ ID NO 344
<211> LENGTH: 58
<212> TYPE: DNA
<213> ORGANISM: Brassica napus

<400> SEQUENCE: 344
agcgagagaa agcttattgc aacttcaact acttgctggt cgatcgtgtt ggccactc        58

<210> SEQ ID NO 345
<211> LENGTH: 58
<212> TYPE: DNA
<213> ORGANISM: Brassica napus

<400> SEQUENCE: 345
agcgagagaa agcttattgc aacttcaact acttgctggt cgatcatgtt ggccactc        58

<210> SEQ ID NO 346
<211> LENGTH: 58
<212> TYPE: DNA
<213> ORGANISM: Brassica napus

<400> SEQUENCE: 346
agcgagagaa agcttattgc aacttcaact acttgctggt ccataatgtt ggccattc        58

<210> SEQ ID NO 347
<211> LENGTH: 58
<212> TYPE: DNA
<213> ORGANISM: Brassica napus

<400> SEQUENCE: 347
agcgagagaa agcttattgc aacttcgact acttgctggt ccataatgtt ggcaattc        58

<210> SEQ ID NO 348
<211> LENGTH: 58
<212> TYPE: DNA
<213> ORGANISM: Brassica napus

<400> SEQUENCE: 348
agcgagagga agcttattgc aacttcaaca acttgctggt ccataatgtt ggccactc        58

<210> SEQ ID NO 349
<211> LENGTH: 58
<212> TYPE: DNA
<213> ORGANISM: Brassica napus

<400> SEQUENCE: 349
agcgagagga agcttattgc aacttcaact acttgctggt ccataatgtt ggccactc        58

<210> SEQ ID NO 350
<211> LENGTH: 3292
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 350
ccagaaggta attatccaag atgtagcatc aagaatccaa tgtttacggg aaaaactatg        60
gaagtattat gtaagctcag caagaagcag atcaatatgc ggcacatatg caacctatgt       120
tcaaaaatga agaatgtaca gatacaagat cctatactgc cagaatacga agaagaatac       180
gtagaaattg aaaaagaaga accaggcgaa gaaaagaatc ttgaagacgt aagcactgac       240
gacaacaatg aaaagaagaa gataaggtcg gtgattgtga agagacata gaggacacat        300 gtaaggtgga aaatgtaagg gcggaaagta accttatcac aaaggaatct tatccccac        360 tacttatcct tttatatttt tccgtgtcat ttttgccctt gagttttcct atataaggaa       420

```
ccaagttcgg catttgtgaa aacaagaaaa aatttggtgt aagctatttt ctttgaagta    480
ctgaggatac aacttcagag aaatttgtaa gtttgtagat ctccatggct ccaaggaaga    540
ggaaggagtc taacagggag tcagctagga ggtcaaggta caggaaggtg ggtatccacg    600
gggtacccgc cgctatggct gagaggccct tccagtgtcg aatctgcatg cgtaacttca    660
gtcgtagtga caacctgagc aaccacatcc gcacccacac aggcgagaag ccttttgcct    720
gtgacatttg tgggaggaaa tttgccacca gcagcagccg cataaaccat accaagatac    780
acacgggcag ccaaaagccc ttccagtgtc gaatctgcat gcgtaacttc agtcgtagtg    840
acaacctgag cgaacacatc cgcacccaca caggcgagaa gccttttgcc tgtgacattt    900
gtgggaggaa atttgccgcc agcaagaccc gcaaaaacca taccaagata cacacgggcg    960
agaagccctt ccagtgtcga atctgcatgc gtaagtttgc ccgctccgac gccctgaccc   1020
agcatgccca gagatgcgga ctgcggggat cccaacttgt gaaatcagaa ttggaagaga   1080
aaaagtctga gcttagacac aaattgaagt acgttccaca tgaatatatc gaacttatcg   1140
agattgctag gaactcaaca caggacagaa ttttggagat gaaggttatg gagttcttta   1200
tgaaagtgta cggatatagg ggaaagcacc ttggtggttc taggaaacct gatggtgcaa   1260
tctacactgt gggatcacct attgactatg tgttatcgt ggatacaaag gcatactctg   1320
gtggatacaa tttgccaatc ggacaagctg acgaaatgca gagatatgtt gaagagaacc   1380
aaactagaaa caaacatatt aatccaaatg aatggtggaa ggtgtatcct tcatctgtta   1440
cagagttcaa attccttttt gtgtctggac actttaaggg taactacaaa gcacagctta   1500
ctaggttgaa ccatattaca aattgcaatg gtgctgtgtt gtcagttgaa gagcttttga   1560
tcggaggtga aatgattaag gcaggaacac ttactttgga ggaagttaga agaaaattca   1620
acaacggtga atcaatttt agatctggcg gcggagaggg cagaggaagt cttctaacat   1680
gcggtgacgt ggaggagaat cccggcccta ggatggctcc aaggaagagg aaggagtcta   1740
acagggagtc agctaggagg tcaaggtaca ggaaggtggg tatccacggg gtacccgccg   1800
ctatggctga gaggcccttc agtgtcgaa tctgcatgcg taacttcagt cgtagtgaca   1860
ccctgagcac gcacatccgc acccacacag gcgagaagcc ttttgcctgt gacatttgtg   1920
ggaggaaatt tgccgacagg agcagccgca taaagcatac caagatacac acgggatctc   1980
agaagccctt ccagtgtcga atctgcatgc gtaacttcag tcgctccgac gacctgtcca   2040
agcacatccg cacccacaca ggcgagaagc cttttgcctg tgacatttgt gggaggaagt   2100
tgccgacaa ctccaaccgc atcaagcatg cccagagatg cggactgcgg ggatcccaac   2160
ttgtgaaatc agaattggaa gagaaaaagt ctgagcttag acacaaattg aagtacgttc   2220
cacatgaata tatcgaactt atcgagattg ctaggaactc aacacaggac agaattttgg   2280
agatgaaggt tatggagttc tttatgaaag tgtacggata taggggaaag caccttggtg   2340
gttctaggaa acctgatggt gcaatctaca ctgtgggatc acctattgac tatgtgttta   2400
tcgtggatac aaaggcatac tctggtggat acaatttgcc aatcggacaa gctgacgaaa   2460
tgcagagata tgttgaagag aaccaaacta gaaacaaaca tattaatcca aatgaatggt   2520
ggaaggtgta tccttcatct gttacagagt tcaaattcct ttttgtgtct ggacacttta   2580
agggtaacta caaagcacag cttactaggt tgaaccatat tacaaattgc aatggtgctg   2640
tgttgtcagt tgaagagctt ttgatcggag gtgaaatgat taaggcagga acacttactt   2700
tggaggaagt tagaagaaaa ttcaacaacg gtgaaatcaa ttttttgataa ctcgagctcg   2760
```

| | | | | |
|---|---|---|---|---|
| gtcaccagca | taatttttat | taatgtacta | aattactgtt | ttgttaaatg caattttgct | 2820 |
| ttctcgggat | tttaatatca | aaatctattt | agaaatacac | aatattttgt tgcaggcttg | 2880 |
| ctggagaatc | gatctgctat | cataaaaatt | acaaaaaaat | tttatttgcc tcaattattt | 2940 |
| taggattggt | attaaggacg | cttaaattat | ttgtcgggtc | actacgcatc attgtgattg | 3000 |
| agaagatcag | cgatacgaaa | tattcgtagt | actatcgata | atttatttga aaattcataa | 3060 |
| gaaaagcaaa | cgttacatga | attgatgaaa | caatacaaag | acagataaag ccacgcacat | 3120 |
| ttaggatatt | ggccgagatt | actgaatatt | gagtaagatc | acggaatttc tgacaggagc | 3180 |
| atgtcttcaa | ttcagcccaa | atggcagttg | aaatactcaa | accgccccat atgcaggagc | 3240 |
| ggatcattca | ttgtttgttt | ggttgccttt | gccaacatgg | gagtccaagg tt | 3292 |

<210> SEQ ID NO 351
<211> LENGTH: 3475
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 351

| | | | | |
|---|---|---|---|---|
| ccagaaggta | attatccaag | atgtagcatc | aagaatccaa | tgtttacggg aaaaactatg | 60 |
| gaagtattat | gtaagctcag | caagaagcag | atcaatatgc | ggcacatatg caacctatgt | 120 |
| tcaaaaatga | agaatgtaca | gatacaagat | cctatactgc | cagaatacga agaagaatac | 180 |
| gtagaaattg | aaaagaaga | accaggcgaa | gaaaagaatc | ttgaagacgt aagcactgac | 240 |
| gacaacaatg | aaaagaagaa | gataaggtcg | gtgattgtga | agagacata gaggacacat | 300 |
| gtaaggtgga | aatgtaagg | gcggaaagta | accttatcac | aaaggaatct tatcccccac | 360 |
| tacttatcct | tttatatttt | tccgtgtcat | ttttgcccctt | gagttttcct atataaggaa | 420 |
| ccaagttcgg | catttgtgaa | acaagaaaa | aatttggtgt | aagctatttt ctttgaagta | 480 |
| ctgaggatac | aacttcagag | aaatttgtaa | gtttgtagat | ctccatggct ccaaggaaga | 540 |
| ggaaggagtc | taacagggag | tcagctagga | ggtcaaggta | caggaaggtg ggtatccacg | 600 |
| gggtacccgc | cgctatggct | gagaggccct | tccagtgtcg | aatctgcatg cgtaacttca | 660 |
| gtcagtcctc | cgacctgtcc | cgccacatcc | gcacccacac | cggcgagaag ccttttgcct | 720 |
| gtgacatttg | tgggaggaaa | tttgcccagg | ccggcaacct | gtccaagcat accaagatac | 780 |
| acacgcatcc | cagggcacct | attcccaagc | ccttccagtg | tcgaatctgc atgcgtaagt | 840 |
| ttgcccagtc | cggcgacctg | acccgccata | ccaagataca | cacgggcgag aagcccttcc | 900 |
| agtgtcgaat | ctgcatgcgt | aacttcagta | cctccggctc | cctgtcccgc cacatccgca | 960 |
| cccacaccgg | cgagaagcct | tttgcctgtg | acatttgtgg | gaggaaattt gcccagtccg | 1020 |
| gcaacctggc | ccgccatgcc | cagagatgcg | gactgcgggg | atcccaactt gtgaaatcag | 1080 |
| aattggaaga | gaaaagtct | gagcttagac | acaaattgaa | gtacgttcca catgaatata | 1140 |
| tcgaacttat | cgagattgct | aggaactcaa | cacaggacag | aattttggag atgaaggtta | 1200 |
| tggagttctt | tatgaaagtg | tacggatata | ggggaaagca | ccttggtggt tctaggaaac | 1260 |
| ctgatggtgc | aatctacact | gtgggatcac | ctattgacta | tggtgttatc gtggatacaa | 1320 |
| aggcatactc | tggtggatac | aatttgccaa | tcggacaagc | tgacgaaatg cagagatatg | 1380 |
| ttgaagagaa | ccaaactaga | aacaaacata | ttaatccaaa | tgaatggtgg aaggtgtatc | 1440 |
| cttcatctgt | tacagagttc | aaattccttt | ttgtgtctgg | acactttaag ggtaactaca | 1500 |

| | |
|---|---|
| aagcacagct tactaggttg aaccatatta caaattgcaa tggtgctgtg ttgtcagttg | 1560 |
| aagagctttt gatcggaggt gaaatgatta aggcaggaac acttactttg gaggaagtta | 1620 |
| gaagaaaatt caacaacggt gaaatcaatt ttagatctgg cggcggagag ggcagaggaa | 1680 |
| gtcttctaac atgcggtgac gtggaggaga atcccggccc taggatggct ccaaggaaga | 1740 |
| ggaaggagtc taacagggag tcagctagga ggtcaaggta caggaaggtg ggtatccacg | 1800 |
| gggtacccgc cgctatggct gagaggccct tccagtgtcg aatctgcatg cgtaacttca | 1860 |
| gtacctccgg ctccctgtcc cgccacatcc gcacccacac cggcgagaag ccttttgcct | 1920 |
| gtgacatttg tgggaggaaa tttgccctgc ccagaccct gcgcgaccat accaagatac | 1980 |
| acacgggcag ccaaaagccc ttccagtgtc gaatctgcat gcgtaacttc agtacctccg | 2040 |
| gcaacctgac ccgccacatc cgcacccaca ccggcgagaa gccttttgcc tgtgacattt | 2100 |
| gtgggaggaa atttgccgac cgctccgccc tggcccgcca taccaagata cacacgggat | 2160 |
| ctcagaagcc cttccagtgt cgaatctgca tgcgtaactt cagtcgctcc gacgtgctgt | 2220 |
| ccgagcacat ccgcacccac accggcgaga agccttttgc ctgtgacatt tgtgggagga | 2280 |
| aatttgcccg caacttctcc ctgaccatgc atgcccagag atgcggactg cggggatccc | 2340 |
| aacttgtgaa atcagaattg gaagagaaaa agtctgagct tagacacaaa ttgaagtacg | 2400 |
| ttccacatga atatatcgaa cttatcgaga ttgctaggaa ctcaacacag gacagaattt | 2460 |
| tggagatgaa ggttatggag ttcttatga aagtgtacgg atataggga aagcaccttg | 2520 |
| gtggttctag gaaacctgat ggtgcaatct acactgtggg atcacctatt gactatggtg | 2580 |
| ttatcgtgga tacaaaggca tactctggtg gatacaattt gccaatcgga caagctgacg | 2640 |
| aaatgcagag atatgttgaa gagaaccaaa ctagaaacaa acatattaat ccaaatgaat | 2700 |
| ggtgaaggt gtatccttca tctgttacag agttcaaatt ccttttgtg tctggacact | 2760 |
| ttaagggtaa ctacaaagca cagcttacta ggttgaacca tattacaaat tgcaatggtg | 2820 |
| ctgtgttgtc agttgaagag cttttgatcg gaggtgaaat gattaaggca ggaacactta | 2880 |
| ctttggagga agttagaaga aaattcaaca acggtgaaat caattttga taactcgagc | 2940 |
| tcggtcacca gcataatttt tattaatgta ctaaattact gttttgttaa atgcaatttt | 3000 |
| gctttctcgg gattttaata tcaaaatcta tttagaaata cacaatattt tgttgcaggc | 3060 |
| ttgctggaga atcgatctgc tatcataaaa attacaaaaa aatttatttt gcctcaatta | 3120 |
| ttttaggatt ggtattaagg acgcttaaat tatttgtcgg gtcactacgc atcattgtga | 3180 |
| ttgagaagat cagcgatacg aaatattcgt agtactatcg ataatttatt tgaaaattca | 3240 |
| taagaaaagc aaacgttaca tgaattgatg aaacaataca aagacagata aagccacgca | 3300 |
| catttaggat attggccgag attactgaat attgagtaag atcacggaat ttctgacagg | 3360 |
| agcatgtctt caattcagcc caaatggcag ttgaaatact caaaccgccc catatgcagg | 3420 |
| agcggatcat tcattgtttg tttggttgcc tttgccaaca tgggagtcca aggtt | 3475 |

<210> SEQ ID NO 352
<211> LENGTH: 2019
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 352

| | |
|---|---|
| gcccaaggaa ccctttctg ggccatcttc gtactcggcc acgactggta atttaatgga | 60 |

```
tccaaccgac aaccactttg cggacttcct ttcaagagaa ttcaataagg ttaattccta      120
attgaaatcc gaagataaga ttcccacaca cttgtggctg atatcaaaag gctactgcct      180
atttaaacac atctctggag actgagaaaa tcagacctcc aagcatgaag aagcctgagc      240
ttactgctac ttctgttgag aagttcctca tcgagaagtt cgattctgtg tctgatctta      300
tgcagctctc tgagggtgag gaatcaagag cttttctcttt cgatgttggt ggaagaggat      360
acgttctcag agttaactct tgcgctgacg gattctacaa ggatagatac gtgtacagac      420
acttcgcttc agctgctctc cctatccctg aagttcttga tatcggagag ttctctgagt      480
ctcttaccta ctgtatctca agaagggctc agggtgttac tcttcaagat cttcctgaga      540
ctgagcttcc tgctgttctt caacctgttg ctgaggctat ggatgctatc gctgctgctg      600
atctttctca aacttctgga ttcggacctt tcggtcctca gggaatcgga cagtacacta      660
cttggagaga tttcatctgc gctatcgctg atcctcatgt ttaccattgg cagaccgtta      720
tggatgatac cgtttctgct tctgttgctc aagctcttga tgagcttatg ctttgggctg      780
aggattgtcc tgaggttaga catcttgttc acgctgattt cggatctaac aacgttctca      840
ccgataacgg aagaatcacc gctgttatcg attggtctga ggctatgttc ggagattctc      900
aatacgaggt ggccaacata ttcttttgga ggccttggct tgcttgtatg aacaacaga      960 ctagatactt cgagagaagg catcctgagc ttgctggatc tcctagactt agagcttaca     1020
tgcttaggat cggacttgat cagctttacc agtctctcgt tgatgaaaac ttcgatgatg     1080
ctgcttgggc tcagggaaga tgtgatgcta tcgttagatc tggtgctgga actgttggaa     1140
gaactcaaat cgctagaaga tctgctgctg tttggactga tggatgtgtt gaagttctcg     1200
ctgattctgg aaacagaagg ccttctacta gacctagagc caagaagtga agatcggcgg     1260
caatagcttc ttagcgccat cccggggttga tcctatctgt gttgaaatag ttgcggtggg     1320
caaggctctc tttcagaaag acaggcggcc aaaggaaccc aaggtgaggt gggctatggc     1380
tctcagttcc ttgtggaagc gcttggtcta aggtgcagag gtgttagcgg gatgaagcaa     1440
aagtgtccga ttgtaacaag atatgttgat cctacgtaag gatattaaag tatgtattca     1500
tcactaatat aatcagtgta ttccaatatg tactacgatt tccaatgtct ttattgtcgc     1560
cgtatgtaat cggcgtcaca aaataatccc cggtgactt cttttaatcc aggatgaaat      1620
aatatgttat tataattttt gcgatttggt ccgttatagg aattgaagtg tgcttgcgtt     1680
cgccaccact cccatttcat aatttacat gtatttgaaa ataaaaatt tatggtattc       1740 aatttaaaca cgtatacttg taaagaatga tatcttgaaa gaaatatagt ttaaatattt     1800
attgataaaa taacaagtca ggtattatag tccaagcaaa aacataaatt tattgatgca     1860
agtttaaatt cagaaatatt tcaataactg attatatcag ctggtacatt gccgtagatg     1920
aaagactgag tgcgatatta tggtgtaata catagcggcc gcgcccaagg aaccctttc      1980 tgggccatct tcgtactcgg ccacgactgg taatttaat                            2019
```

<210> SEQ ID NO 353
<211> LENGTH: 2666
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 353

```
gcccaaggaa ccctttttctg ggccatcttc gtactcggcc acgactggta atttaatgga      60
```

-continued

| | |
|---|---|
| tccactagta acggccgcca gtgtgctgga attcgccctt cgtcgacctg caggtcaacg | 120 |
| gatcaggata ttcttgttta agatgttgaa ctctatggag gtttgtatga actgatgatc | 180 |
| taggaccgga taagttccct tcttcatagc gaacttattc aaagaatgtt tgtgtatca | 240 |
| ttcttgttac attgttatta atgaaaaaat attattggtc attggactga acacgagtgt | 300 |
| taaatatgga ccaggcccca ataagatcc attgatatat gaattaaata caagaataa | 360 |
| atcgagtcac caaccacttt gcctttttta acgagacttg ttcaccaact tgatacaaaa | 420 |
| gtcattatcc tatgcaaatc aataatcata caaaaatatc caataacact aaaaaattaa | 480 |
| aagaaatgga taatttcaca atatgttata cgataaagaa gttacttttc caagaaattc | 540 |
| actgatttta taagcccact tgcattagat aaatggcaaa aaaaacaaa aaggaaaaga | 600 |
| aataaagcac gaagaattct agaaaatacg aaatacgctt caatgcagtg ggacccacgg | 660 |
| ttcaattatt gccaattttc agctccaccg tatatttaaa aaataaaacg ataatgctaa | 720 |
| aaaaatataa atcgtaacga tcgttaaatc tcaacggctg gatcttatga cgaccgttag | 780 |
| aaattgtggt tgtcgacgag tcagtaataa acggcgtcaa agtggttgca gccggcacac | 840 |
| acgagtcgtg tttatcaact caaagcacaa atacttttcc tcaacctaaa ataaggcaa | 900 |
| ttagccaaaa caactttgc gtgtaaacaa cgctcaatac acgtgtcatt ttattattag | 960 |
| ctattgcttc accgccttag ctttctcgtg acctagtcgt cctcgtcttt tcttcttctt | 1020 |
| cttctataaa acaatacca aagagctctt cttcttcaca attcagattt caatttctca | 1080 |
| aaatcttaaa aactttctct caattctctc taccgtgatc aaggtaaatt tctgtgttcc | 1140 |
| ttattctctc aaaatcttcg attttgtttt cgttcgatcc caatttcgta tatgttcttt | 1200 |
| ggtttagatt ctgttaatct tagatcgaag acgattttct gggtttgatc gttagatatc | 1260 |
| atcttaattc tcgattaggg tttcatagat atcatccgat ttgttcaaat aatttgagtt | 1320 |
| ttgtcgaata attactcttc gatttgtgat ttctatctag atctggtgtt agtttctagt | 1380 |
| ttgtgcgatc gaatttgtcg attaatctga gttttttctga ttaacagatg agaggatctg | 1440 |
| gatctgagtc tgatgagtct ggacttcctg ctatggaaat cgagtgtaga atcactggaa | 1500 |
| cccttaacgg tgttgagttc gagcttgttg gaggtggtga gggaactcct gagcagggaa | 1560 |
| gaatgactaa caagatgaag tctaccaagg gtgctcttac cttctctcca taccttcttt | 1620 |
| ctcacgttat gggatacgga ttctaccact tcggaactta cccatctgga tacgagaacc | 1680 |
| ctttccttca tgctatcaac aacggtggat acaccaacac taggatcgag aagtacgagg | 1740 |
| atggtggtgt tcttcacgtt agcttctctt acagatacga ggctggaaga gtgatcggag | 1800 |
| atttcaaggt tatgggaact ggattccctg aggattctgt tatcttcacc gacaagatca | 1860 |
| tcaggtctaa cgctactgtt gagcatcttc atcctatggg agataacgat ctcgatggat | 1920 |
| ctttcaccag aaccttctca cttagagatg gtggttacta ctcttctgtg gtggattctc | 1980 |
| acatgcactt caagtctgct atccacccctt ctatccttca aaacggtgga cctatgttcg | 2040 |
| ctttcagaag agttgaggaa gatcactcta acaccgagct tggaatcgtt gagtaccaac | 2100 |
| atgctttcaa gaccctgat gctgatgctg gtgaggaatg ataatatcaa aatctattta | 2160 |
| gaaatacaca atattttgtt gcaggcttgc tggagaatcg atctgctatc ataaaaatta | 2220 |
| caaaaaaatt ttatttgcct caattatttt aggattggta ttaaggacgc ttaaattatt | 2280 |
| tgtcgggtca ctacgcatca ttgtgattga gaagatcagc gatacgaaat attcgtagta | 2340 |
| ctatcgataa tttatttgaa aattcataag aaaagcaaac gttacatgaa ttgatgaaac | 2400 |
| aatacaaaga cagataaagc cacgcacatt taggatattg gccgagatta ctgaatattg | 2460 |

| | | | | |
|---|---|---|---|---|
| agtaagatca | cggaatttct | gacaggagca | tgtcttcaat tcagcccaaa tggcagttga | 2520 |
| aatactcaaa | ccgccccata | tgcaggagcg | gatcattcat tgtttgtttg gttgcctttg | 2580 |
| ccaacatggg | agtccaaggt | tgcggccgcg | cccaaggaac cctttctg gccatcttcg | 2640 |
| tactcggcca | cgactggtaa | tttaat | | 2666 |

<210> SEQ ID NO 354
<211> LENGTH: 2020
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 354

| | | | | |
|---|---|---|---|---|
| gcccaaggaa | ccctttctg | ggccatcttc | gtactcggcc acgactggta atttaatgga | 60 |
| tccaaccgac | aaccactttg | cggacttcct | ttcaagagaa ttcaataagg ttaattccta | 120 |
| attgaaatcc | gaagataaga | ttcccacaca | cttgtggctg atatcaaaag gctactgcct | 180 |
| atttaaacac | atctctggag | actgagaaaa | tcagacctcc aagcatgaag aagcctgagc | 240 |
| ttactgctac | ttctgttgag | aagttcctca | tcgagaagtt cgattctgtg tctgatctta | 300 |
| tgcagctctc | tgagggtgag | gaatcaagag | cttctctttt cgatgttggt ggaagaggat | 360 |
| acgttctcag | agttaactct | tgcgctgacg | gattctacaa ggatagatac gtgtacagac | 420 |
| acttcgcttc | agctgctctc | cctatccctg | aagttcttga tatcggagag ttctctgagt | 480 |
| ctcttaccta | ctgtatctca | agaagggctc | agggtgttac tcttcaagat cttcctgaga | 540 |
| ctgagcttcc | tgctgttctt | caacctgttg | ctgaggctat ggatgctatc gctgctgctg | 600 |
| atctttctca | aacttctgga | ttcggacctt | tcggtcctca gggaatcgga cagtacacta | 660 |
| cttggagaga | tttcatctgc | gctatcgctg | atcctcatgt ttaccattgg cagaccgtta | 720 |
| tggatgatac | cgtttctgct | tctgttgctc | aagctcttga tgagcttatg ctttgggctg | 780 |
| aggattgtcc | tgaggttaga | catcttgttc | acgctgattt cggatctaac aacgttctca | 840 |
| ccgataacgg | aagaatcacc | gctgttatcg | attggtctga ggctatgttc ggagattctc | 900 |
| aatacgaggt | ggccaacata | ttcttttgga | ggccttggct tgcttgtatg aacaacaga | 960 |
| ctagatactt | cgagagaagg | catcctgagc | ttgctggatc tcctagactt agagcttaca | 1020 |
| tgcttaggat | cggacttgat | cagctttacc | agtctctcgt tgatggaaac ttcgatgatg | 1080 |
| ctgcttgggc | tcagggaaga | tgtgatgcta | tcgttagatc tggtgctgga actgttggaa | 1140 |
| gaactcaaat | cgctagaaga | tctgctgctg | tttggactga tggatgtgtt gaagttctcg | 1200 |
| ctgattctgg | aaacagaagg | ccttctacta | gacctagagc caagaagtga agatcggcgg | 1260 |
| caatagcttc | ttagcgccat | cccgggttga | tcctatctgt gttgaaatag ttgcggtggg | 1320 |
| caaggctctc | tttcagaaag | acaggcggcc | aaaggaaccc aaggtgaggt gggctatggc | 1380 |
| tctcagttcc | ttgtggaagc | gcttggtcta | aggtgcagag tgttagcgg gatgaagcaa | 1440 |
| aagtgtccga | ttgtaacaag | atatgttgat | cctacgtaag gatattaaag tatgtattca | 1500 |
| tcactaatat | aatcagtgta | ttccaatatg | tactacgatt tccaatgtct ttattgtcgc | 1560 |
| cgtatgtaat | cggcgtcaca | aaataatccc | cggtgacttt cttttaatcc aggatgaaat | 1620 |
| aatatgttat | tataattttt | gcgatttggt | ccgttatagg aattgaagtg tgcttgcggt | 1680 |
| cgccaccact | cccatttcat | aattttacat | gtatttgaaa aataaaaatt tatggtattc | 1740 |
| aatttaaaca | cgtatacttg | taaagaatga | tatcttgaaa gaaatatagt ttaaatattt | 1800 |

| | |
|---|---|
| attgataaaa taacaagtca ggtattatag tccaagcaaa acataaaatt tattgatgca | 1860 |
| agtttaaatt cagaaatatt tcaataactg attatatcag ctggtacatt gccgtagatg | 1920 |
| aaagactgag tgcgatatta tggtgtaata catagcggcc gcagcgagag aaagcttatt | 1980 |
| gcaacttcaa ctacttgctg gtcgatcgtg ttggccactc | 2020 |

<210> SEQ ID NO 355
<211> LENGTH: 2667
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 355

| | |
|---|---|
| gcccaaggaa ccctttctg ggccatcttc gtactcggcc acgactggta atttaatgga | 60 |
| tccactagta acggccgcca gtgtgctgga attcgcccct cgtcgacctg caggtcaacg | 120 |
| gatcaggata ttcttgttta agatgttgaa ctctatggag gtttgtatga actgatgatc | 180 |
| taggaccgga taagttccct tcttcatagc gaacttattc aaagaatgtt ttgtgtatca | 240 |
| ttcttgttac attgttatta atgaaaaaat attattggtc attggactga acacgagtgt | 300 |
| taaatatgga ccaggcccca ataagatcc attgatatat gaattaaata caagaataa | 360 |
| atcgagtcac caaccacttt gccttttta acgagacttg ttcaccaact tgatacaaaa | 420 |
| gtcattatcc tatgcaaatc aataatcata caaaaatatc caataacact aaaaaattaa | 480 |
| aagaaatgga taatttcaca atatgttata cgataaagaa gttacttttc caagaaattc | 540 |
| actgattta taagcccact tgcattagat aaatggcaaa aaaaacaaa aaggaaaaga | 600 |
| aataaagcac gaagaattct agaaaatacg aaatacgctt caatgcagtg ggacccacgg | 660 |
| ttcaattatt gccaattttc agctccaccg tatatttaaa aataaaacg ataatgctaa | 720 |
| aaaaatataa atcgtaacga tcgttaaatc tcaacggctg gatcttatga cgaccgttag | 780 |
| aaattgtggt tgtcgacgag tcagtaataa acggcgtcaa agtggttgca gccggcacac | 840 |
| acgagtcgtg tttatcaact caaagcacaa atacttttcc tcaacctaaa ataaggcaa | 900 |
| ttagccaaaa acaactttgc gtgtaaacaa cgctcaatac acgtgtcatt ttattattag | 960 |
| ctattgcttc accgccttag cttttctcgtg acctagtcgt cctcgtcttt tcttcttctt | 1020 |
| cttctataaa acaatacca aagagctctt cttcttcaca attcagattt caatttctca | 1080 |
| aaatcttaaa aactttctct caattctctc taccgtgatc aaggtaaatt tctgtgttcc | 1140 |
| ttattctctc aaaatcttcg attttgtttt cgttcgatcc caatttcgta tatgttcttt | 1200 |
| ggtttagatt ctgttaatct tagatcgaag acgattttct gggtttgatc gttagatatc | 1260 |
| atcttaattc tcgattaggg tttcatagat atcatccgat ttgttcaaat aatttgagtt | 1320 |
| ttgtcgaata attactcttc gatttgtgat ttctatctag atctggtgtt agtttctagt | 1380 |
| ttgtgcgatc gaatttgtcg attaatctga gttttctga ttaacagatg agaggatctg | 1440 |
| gatctgagtc tgatgagtct ggacttcctg ctatggaaat cgagtgtaga atcactggaa | 1500 |
| cccttaacgg tgttgagttc gagccttgtt gaggtggtga gggaactcct gagcagggaa | 1560 |
| gaatgactaa caagatgaag tctaccaagg gtgctcttac cttctctcca taccttcttt | 1620 |
| ctcacgttat gggatacgga ttctaccact tcggaactta cccatctgga tacgagaacc | 1680 |
| ctttccttca tgctatcaac aacgtggat acaccaacac taggatcgag aagtacgagg | 1740 |
| atggtggtgt tcttcacgtt agcttctctt acagatacga ggctggaaga gtgatcggag | 1800 |

```
atttcaaggt tatgggaact ggattccctg aggattctgt tatcttcacc gacaagatca    1860
tcaggtctaa cgctactgtt gagcatcttc atcctatggg agataacgat ctcgatggat    1920
ctttcaccag aaccttctca cttagagatg gtggttacta ctcttctgtg gtggattctc    1980
acatgcactt caagtctgct atccaccctt ctatccttca aaacggtgga cctatgttcg    2040
ctttcagaag agttgaggaa gatcactcta acaccgagct tggaatcgtt gagtaccaac    2100
atgctttcaa gacccctgat gctgatgctg gtgaggaatg ataatatcaa aatctattta    2160
gaaatacaca atattttgtt gcaggcttgc tggagaatcg atctgctatc ataaaaatta    2220
caaaaaatt ttatttgcct caattatttt aggattggta ttaaggacgc ttaaattatt    2280
tgtcgggtca ctacgcatca ttgtgattga aagatcagc gatacgaaat attcgtagta    2340
ctatcgataa tttatttgaa aattcataag aaaagcaaac gttacatgaa ttgatgaaac    2400
aatacaaaga cagataaagc cacgcacatt taggatattg ccgagatta ctgaatattg    2460
agtaagatca cggaatttct gacaggagca tgtcttcaat tcagcccaaa tggcagttga    2520
aatactcaaa ccgccccata tgcaggagcg gatcattcat tgtttgtttg gttgcctttg    2580
ccaacatggg agtccaaggt tgcggccgca gcgagagaaa gcttattgca acttcaacta    2640
cttgctggtc gatcgtgttg gccactc                                        2667
```

```
<210> SEQ ID NO 356
<211> LENGTH: 28
<212> TYPE: DNA
<213> ORGANISM: Brassica napus

<400> SEQUENCE: 356
gcccaaggaa ccctttctg ggccatct                                        28

<210> SEQ ID NO 357
<211> LENGTH: 28
<212> TYPE: DNA
<213> ORGANISM: Brassica napus

<400> SEQUENCE: 357
cgtactcggc cacgactggt aatttaat                                       28

<210> SEQ ID NO 358
<211> LENGTH: 28
<212> TYPE: DNA
<213> ORGANISM: Brassica napus

<400> SEQUENCE: 358
agcgagagaa agcttattgc aacttcaa                                       28

<210> SEQ ID NO 359
<211> LENGTH: 28
<212> TYPE: DNA
<213> ORGANISM: Brassica napus

<400> SEQUENCE: 359
acttgctggt cgatcgtgtt ggccactc                                       28

<210> SEQ ID NO 360
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 360
gattcctaag cattgttggg tc                                              22

<210> SEQ ID NO 361
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
gaaaatctca tatcgaacgt gcgt                                            24

<210> SEQ ID NO 362
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
cgcttaccct ctctatctgg taa                                             23

<210> SEQ ID NO 363
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
ccttgcctct gtaccaaggc ag                                              22

<210> SEQ ID NO 364
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 364
gtgtgtggga atcttatctt cgg                                             23

<210> SEQ ID NO 365
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
caagtcaggt attatagtcc aagca                                           25

<210> SEQ ID NO 366
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 366
caagaatatc ctgatccgtt gac            23

<210> SEQ ID NO 367
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
tggcagttga atactcaaa cc            22

<210> SEQ ID NO 368
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
gtcctttgag atccatgagc tat            23

<210> SEQ ID NO 369
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369
gattcctaag cattgttggg ta            22

<210> SEQ ID NO 370
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
tgcgttcaag aaatcaaaga ca            22

<210> SEQ ID NO 371
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371
gaaaatctca tatcgaacgt gcgg            24

<210> SEQ ID NO 372
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 372
tctggtaaat cctaattcct c                                              21

<210> SEQ ID NO 373
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
ccttgcctct gtaccaaggc aa                                             22

<210> SEQ ID NO 374
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
cttgcctctg taccaaggca acttc                                          25

<210> SEQ ID NO 375
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
ttctggcctc tttattgggc cgcccaagga acctttcct gggccatctt cgtactcggc      60
cacgactggt aatttaatgg atccactagt aa                                  92

<210> SEQ ID NO 376
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
ttctggcctc tttattgggc cgcccaagga acctttcct gggccatctt cgtactcggc      60
cacgactggt aatttaatgg atccactagt aa                                  92

<210> SEQ ID NO 377
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 377
ttctggcctc tttattgggc cgcccaagga acctttcct gggccatcca gtcgtggccg      60
agtacgaaga tggcccagat actcggccac gactggtaat ttaatggatc cactagtaa    119

<210> SEQ ID NO 378
<211> LENGTH: 89
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 378
ttctggcctc tttattgggc cgcccaagga acccttttct gggccatcgt actcggccac    60
gactggtaat ttaatggatc cactagtaa                                      89

<210> SEQ ID NO 379
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 379
ttctggcctc tttattgggc cgcccaagga acccttttct aggtatctca gttcggtgta    60
ggtcgttcgc tccaagctgg gctgcgtgca cgaaccgtac tcggccacga ctggtaattt   120
aatggatcca ctagtaa                                                  137

<210> SEQ ID NO 380
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
ttctggcctc tttattgggc cgcccaagga acccttttct gggccagact ggtaatttaa    60
tggatccact agtaa                                                     75

<210> SEQ ID NO 381
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
tccaaggttg cggccgcgcc caaggaaccc ttttctgggc catcttcgta ctcggccacg    60
actggtaatt taattttcaa tttattt                                        87

<210> SEQ ID NO 382
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
tccaaggttg cggccgcgcc caaggaaccc ttttctgggc catttactcg gccacgactg    60
gtaatttaat tttcaattta ttt                                            83

<210> SEQ ID NO 383
<211> LENGTH: 41
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 383
cgtactcggc cacgactggt aatttaattt tcaatttatt t                    41

<210> SEQ ID NO 384
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
tccaaggttg cggccgcgcc caaggaaccc ttttctgggc catcttcgta ctcggccacg    60
actggtaatt taattttcaa tttattt                                       87

<210> SEQ ID NO 385
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
tccaaggttg cggccgcgcc caaggaaccc ttttctgggc catcttctgg taatttaatt    60
ttcaatttat tttt                                                     74

<210> SEQ ID NO 386
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 386
tccaaggttg cggccgcgcc caaggaaccc ttttctggta gcggtggttt ttttgtttgc    60
aagcagcaga ttacgcgcag aaaaaaagga tcgtactcgg ccacgactgg taatttaatt   120
ttcaatttat tt                                                      132

<210> SEQ ID NO 387
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 387
tccaaggttg cggccgcgcc caaggaaccc ttttctgggc catcttacga gcgtaatggc    60
tggcctgtta acaagtctg gaaagaaatg cataaacata tcccagccac gactggtaat    120
ttaattttca atttattt                                                138

<210> SEQ ID NO 388
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
tagtttattt gccccaagcg agagaaagct tattgcaact tcaactcgta ctcggccacg    60
actggtaatt taatggatcc actagtaa                                      88

<210> SEQ ID NO 389
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
tagtttattt gccccaagcg agagaaagct tattgcaact tcaact                  46

<210> SEQ ID NO 390
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
tagtttattt gccccaagcg agagaaagct tattgcaact tcaacg                  46

<210> SEQ ID NO 391
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
tagtttattt gccccaagcg agagaaagct tattgcaact tcaacttcgt actcggccac   60
gactggtaat ttaatggatc cactagtaa                                     89

<210> SEQ ID NO 392
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
tagtttattt gccccaagcg agagaaagct tattgcaact tcaactatgt actcggccac   60
gactggtaat ttaatggatc cactagtaa                                     89

<210> SEQ ID NO 393
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
tagtttattt gccccaagcg agagaaagct tattgcaact tcatactcgg ccacgactgg   60
taatttaatg gatccactag taa                                           83

<210> SEQ ID NO 394

```
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
aggtaattta atggatccac tagtaa                                          26

<210> SEQ ID NO 395
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
tccaaggttg cggccgcagc gagagaaagc ttattgcaac ttcaactact tgctggtcga     60
tcgtgttggc cactcttgtt tatctatca                                       89

<210> SEQ ID NO 396
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
tccaaggttg cggccgcagc gagagaaagc ttattgcaac ttcaacttgc tggtcgatcg     60
tgttggccac tcttgtttat ctatca                                          86

<210> SEQ ID NO 397
<211> LENGTH: 149
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 397
tccaaggttg cggccgcgcg ccgacccagc tttcttgtac aaagttggca ttataagaaa     60
gcattgctta tcaatttgtt gcaacgaaca ggtcactatc agtcaaaact tgctggtcga    120
tcgtgttggc cactcttgtt tatctatca                                      149

<210> SEQ ID NO 398
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
tccaaggttt gcggccgcag cgagagaaag cttattgcaa cttcacttgc tggtcgatcg     60
tgttggccac tcttgtttat ctatca                                          86

<210> SEQ ID NO 399
<211> LENGTH: 121
<212> TYPE: DNA
<213> ORGANISM: Artificial Sequence
<220> FEATURE:
```

```
<223> OTHER INFORMATION: Description of Artificial Sequence: Synthetic
      polynucleotide

<400> SEQUENCE: 399
tccaaggttg cggccgcagc gagagaaagc ttattgcaac ttcagataaa agttgctcgc    60
ctgtgtgggt gtggatgcta cttgctggtc gatcgtgttg gccactcttg tttatctatc   120
a                                                                  121

<210> SEQ ID NO 400
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
tccaaggttg cggccgcagc gagagaaagc ttattgcaac ttcaactaca ctacttgctg    60
gtcgatcgtg ttggccactc ttgtttatct atca                                94

<210> SEQ ID NO 401
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
tccaaggttg cggccgcagc gagagaaagc ttattgcaac ttcaactact tgctggtcga    60
tcgtgttggc cactcttgtt tatctatca                                      89

<210> SEQ ID NO 402
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 402
cttacatgct taggatcgga cttg                                           24

<210> SEQ ID NO 403
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 403
agttccagca ccagatctaa cg                                             22

<210> SEQ ID NO 404
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 404
ccctgagccc aagcagcatc atcg                                           24
```

<210> SEQ ID NO 405
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405
cggagagggc gtggaagg                                                 18

<210> SEQ ID NO 406
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 406
ttcgatttgc tacagcgtca ac                                            22

<210> SEQ ID NO 407
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 407
aggcaccatc gcaggcttcg ct                                            22

<210> SEQ ID NO 408
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
ttctggcctc tttattgggc cgcccaagga acccttttct gggccatctt cgtactcggc   60
cacgactggt aatttaatgg atccaaccga caaccactt                          99

<210> SEQ ID NO 409
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
ttctggcctc tttattgggc cgcccaagga acccttttac tcggccacga ctggtaattt   60
aatggatcca accgacaacc actt                                          84

<210> SEQ ID NO 410
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 410
ttctggcctc tttattgggc cgcccaagga acccttttct ggtcgtactc ggccacgact        60
ggtaatttaa tggatccaac cgacaaccac tt                                     92

<210> SEQ ID NO 411
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
ttctggcctc tttattgggc cgcccaagga acccttttct gg                          42

<210> SEQ ID NO 412
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
ttctggcctc tttattgggc cgcccaagga acccttttct gggccatctc ggccacgact        60
ggtaatttaa tggatccaac cgacaaccac tt                                     92

<210> SEQ ID NO 413
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
ttctggcctc tttattgggc cgcccaagga acccttttct gggccattcg tactcggcca        60
cgactggtaa tttaatggat ccaaccgaca accactt                                97

<210> SEQ ID NO 414
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
ttctggcctc tttattgggc cgcccaagga acccttttct gggccatct                   49

<210> SEQ ID NO 415
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 415
gtaatacata gcggccgcgc ccaaggaacc cttttctggg ccatcttcgt actcggccac        60
gactggtaat ttaattttca atttattttt tcttcaactt ctta                       104

<210> SEQ ID NO 416
```

```
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
gtaatacata gcggccgcgc ccaaggaacc cttttctggg ccatgccacg actggtaatt    60
taattttcaa tttattttttt cttcaacttc tta                                93

<210> SEQ ID NO 417
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
gtaatacata gcggccgcgc ccaaggaacc cttttctggg ccatctgact ggtaatttaa    60
ttttcaattt attttttctt caacttctta                                     90

<210> SEQ ID NO 418
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
gtaatacata gcggccgcgc ccaaggaacc cttttctggg ccatctgact ggtaatttaa    60
ttttcaattt attttttctt caacttctta                                     90

<210> SEQ ID NO 419
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 419
gtaatacata gcggccgcgc ccaaggaacc cttttctggg ccatgtactc ggccacgact    60
ggtaatttaa ttttcaattt attttttctt caacttctta                         100

<210> SEQ ID NO 420
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
gtactcggcc acgactggta atttaattttt tctttcaact tctta                   45

<210> SEQ ID NO 421
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 421
gtaatacata gcggccgcgc ccaatactcg gccacgactg gtaatttaat tttcaattta    60 tttttcttc aacttctta                                                  79

<210> SEQ ID NO 422
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
tgtaatacat agcggccgcg cccaaggaac cctttactcg gccataattt aattttcaat    60 ttatttttc ttcaacttct ta                                              82

<210> SEQ ID NO 423
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 423
tnantgattc ccaatggcgg cgcttttcaag gacatgatca tggagggtga tggcaggacc   60
tcgtactgaa atggtccgaa ggtccacgcc gccaactacg ag                      102

<210> SEQ ID NO 424
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 424
cnantactcg tagttggcgg cgtggacctt cggaccattt cagtacgagg tcctgccatc    60
accctccatg atcatgtcct tgaaagcgcc gccattggga at                     102

<210> SEQ ID NO 425
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
```

<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 425
tnantgattc ccaatggcgg cgctttcaag gacatgatca tggagggtga tggcaggacc    60
tcgtactgaa atttgcaggt acaag    85

<210> SEQ ID NO 426
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 426
angngtcttg tacctgcaaa tttcagtacg aggtcctgcc atcaccctcc atgatcatgt    60
ccttgaaagc gccgccattg ggaat    85

<210> SEQ ID NO 427
<211> LENGTH: 7390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 427
gtttacccgc caatatatcc tgtcaaacac tgatagttta aactgaaggc gggaaacgac    60
aatctgatca tgagcggaga attaagggag tcacgttatg accccgccg atgacgcggg    120 acaagccgtt ttacgtttgg aactgacaga accgcaacgt tgaaggagcc actcagcaag    180
cttactagta gcgctgttta aacgctcttc aactggaaga gcggttaccc ggaccgaagc    240
ttgcatgcct gcagtgcagc gtgacccggt cgtgcccctc tctagagata atgagcattg    300
catgtctaag ttataaaaaa ttaccacata ttttttttgt cacacttgtt tgaagtgcag    360
tttatctatc tttatacata tatttaaact ttactctacg aataatataa tctatagtac    420
tacaataata tcagtgtttt agagaatcat ataaatgaac agttagacat ggtctaaagg    480
acaattgagt attttgacaa caggactcta cagttttatc ttttttagtgt gcatgtgttc    540 tcctttttttt ttgcaaatag cttcacctat ataatacttc atccatttta ttagtacatc    600
catttagggt ttagggttaa tggttttat agactaattt tttagtaca tctattttat    660 tctattttag cctctaaatt aagaaaacta aaactctatt ttagtttttt tatttaataa    720
tttagatata aaatagaata aaataaagtg actaaaaatt aaacaaatac cctttaagaa    780
attaaaaaaa ctaaggaaac attttttcttg tttcgagtag ataatgccag cctgttaaac    840
gccgtcgacg agtctaacgg acaccaacca gcgaaccagc agcgtcgcgt cgggccaagc    900
gaagcagacg gcacggcatc tctgtcgctg cctctggacc cctctcgaga gttccgctcc    960
accgttggac ttgctccgct gtcggcatcc agaaattgcg tggcggagcg gcagacgtga   1020

```
gccggcacgg caggcggcct cctcctcctc tcacggcacc ggcagctacg ggggattcct    1080
ttcccaccgc tccttcgctt tcccttcctc gcccgccgta ataaatagac accccctcca    1140
caccctcttt ccccaacctc gtgttgttcg gagcgcacac acacacaacc agatctcccc    1200
caaatccacc cgtcggcacc tccgcttcaa ggtacgccgc tcgtcctccc ccccccccc     1260
tctctacctt ctctagatcg gcgttccggt ccatggttag ggcccggtag ttctacttct    1320
gttcatgttt gtgttagatc cgtgtttgtg ttagatccgt gctgctagcg ttcgtacacg    1380
gatgcgacct gtacgtcaga cacgttctga ttgctaactt gccagtgttt ctctttgggg    1440
aatcctggga tggctctagc cgttccgcag acgggatcga tttcatgatt ttttttgttt    1500
cgttgcatag ggtttggttt gccctttttcc tttatttcaa tatatgccgt gcacttgttt    1560
gtcgggtcat cttttcatgc ttttttttgt cttggttgtg atgatgtggt ctggttgggc    1620
ggtcgttcta gatcggagta gaattctgtt tcaaactacc tggtggattt attaattttg    1680
gatctgtatg tgtgtgccat acatattcat agttacgaat tgaagatgat ggatggaaat    1740
atcgatctag gataggtata catgttgatg cgggttttac tgatgcatat acagagatgc    1800
tttttgttcg cttggttgtg atgatgtggt gtggttgggc ggtcgttcat tcgttctaga    1860
tcggagtaga atactgtttc aaactacctg gtgtatttat taattttgga actgtatgtg    1920
tgtgtcatac atcttcatag ttacgagttt aagatggatg gaaatatcga tgtaggatag    1980
gtatacatgt tgatgtgggt tttactgatg catatacatg atggcatatg cagcatctat    2040
tcatatgctc taaccttgag tacctatcta ttataataaa caagtatgtt ttataattat    2100
tttgatcttg atatacttgg atgatggcat atgcagcagc tatatgtgga ttttttagc    2160
cctgccttca tacgctattt atttgcttgg tactgtttct tttgtcgatg ctcaccctgt    2220
tgtttggtgt tacttctgca ggtcgactct agaggatcca cacgacacca tgtccgcccg    2280
cgaggtgcac atcgacgtga acaacaagac cggccacacc ctccagctgg aggacaagac    2340
caagctcgac ggcggcaggt ggcgcacctc cccgaccaac gtggccaacg accagatcaa    2400
gaccttcgtg gccgaatcca acggcttcat gaccggcacc gagggcacca tctactactc    2460
aattaatggc gaggccgaga tcagcctcta cttcgacaac ccgttcgccg gctccaacaa    2520
atacgacggc cactccaaca gtcccagta cgagatcatc acccagggcg gctccggcaa    2580
ccagtcccac gtgacctaca ccatccgaac cacctcctcc cgctacgcc acaagtcctg    2640
agtcatgagt catgagtcag ttaacctaga cttgtccatc ttctggattg gccaacttaa    2700
ttaatgtatg aaataaaagg atgcacacat agtgacatgc taatcactat aatgtgggca    2760
tcaaagttgt gtgttatgtg taattactag ttatctgaat aaaagagaaa gagatcatcc    2820
atatttctta tcctaaatga atgtcacgtg tctttataat tctttgatga accagatgca    2880
tttcattaac caaatccata tacatataaa tattaatcat atataattaa tatcaattgg    2940
gttagcaaaa caaatctagt ctaggtgtgt tttgcgaatg cggccgcgga ccgaattggg    3000
gatctgcatg aaagaaactg tcgcactgct gaaccgcacc ttgtcacttt catcgaacac    3060
gacctgtgcc caagatgacg gtgctgcggt ctaagtgagg ctgaattgcc ttggacagaa    3120
gcggactccc tacaattagt taggccaaac ggtgcatcca tgtgtagctc cgggctcggg    3180
ctgtatcgcc atctgcaata gcatccatgg agctcgttcc atgtagttgg agatgaacca    3240
atgatcgggc gtgtggacgt atgttcctgt gtactccgat agtagagtac gtgttagctc    3300
tttcatggtg caagtgaaat ttgtgttggt ttaattaccc ctacgttagt tgcgggacag    3360
```

```
gagacacatc atgaatttaa aggcgatgat gtcctctcct gtaatgttat tcttttgatg    3420
tgatgaatca aaatgtcata taaaacattt gttgctcttt agttaggcct gatcgtagaa    3480
cgaaatgctc gtgtagcggg gctacgagcc tatgacgcaa taacactggt ttgccggccc    3540
ggagtcgctt gacaaaaaaa agcatgttaa gtttatttac aattcaaaac ctaacatatt    3600
atattccctc aaagcaggtt cacgatcaca cctgtaccta aaaaaaacat gaagaatata    3660
ttactccatt attatgagat gaaccacttg gcaagagtgg taagctatat aaaaaaatga    3720
acattattac gagatgttat atgccattat attgattcga agatatatgt ttctttctcc    3780
cacgggcacc taacggatac atgataaggc caaggcagat cacgggaaat tattcgaata    3840
catgttacgc cctattgccg gaaaaaaaat gcagggcagg tgttggccgt agcgatttaa    3900
gcacttaagc tggaggttgc cacacttgga tgcaagcgtc tgacccttct aaaaaatcgg    3960
cggctttgtc cgtatccgta tccccctatcc aacatctagc tggccacacg acggggctgg    4020
gcagatcgtg gatgccgggt cgacgtcgat cgtcagccat catagaccaa tcgaccatct    4080
gttatggatg cttgctagct agactagtca gacataaaat ttggatactt tctcccaact    4140
gggagacggg gactgatgtg cagctgcacg tgagctaaat ttttccctat aaatatgcat    4200
gaaatactgc attatcttgc cacagccact gccacagcca gataacaagt gcagctggta    4260
gcacgcaacg catagctctg gacttgtagc taggtagcca accggatcca cacgacacca    4320
tgctcgacac caacaaggtg tacgagatca gcaaccacgc caacggcctc tacgccgcca    4380
cctacctctc cctcgacgac tccggcgtgt ccctcatgaa caagaacgac gacgacatcg    4440
acgactacaa cctcaagtgg ttcctcttcc cgatcgacga cgaccagtac atcatcacct    4500
cctacgccgc caacaactgc aaggtgtgga acgtgaacaa cgacaagatt aatgtgtcaa    4560
cctactcctc caccaactcc atccagaagt ggcagatcaa ggccaacggc tcctcctacg    4620
tgatccagtc cgacaacggc aaggtgctca ccgccggcac cggccaggcc ctcggcctca    4680
tccgcctcac cgacgagtcc tccaacaacc cgaaccagca atggaacctg acgtccgtgc    4740
agaccatcca gctcccgcag aagccgatca tcgacaccaa gctcaaggac tacccgaagt    4800
actccccgac cggcaacatc gacaacggca cctccccgca gctcatgggc tggaccctcg    4860
tgccgtgcat catggtgaac gacccgaaca tcgacaagaa cacccagatc aagaccaccc    4920
cgtactacat cctcaagaag taccagtact ggcagagggc cgtgggctcc aacgtcgcgc    4980
tccgcccgca cgagaagaag tcctacacct acgagtgggg caccgagatc gaccagaaga    5040
ccaccatcat caacaccctc ggcttccaga tcaacatcga cagcggcatg aagttcgaca    5100 tccccggaggt gggcggcggt accgacgaga tcaagaccca gctcaacgag gagctcaaga    5160
tcgagtattc acatgagacg aagatcatgg agaagtacca ggagcagtcc gagatcgaca    5220
acccgaccga ccagtccatg aactccatcg gcttcctcac catcacctcc ctggagctct    5280
accgctacaa cggctccgag atccgcatca tgcagatcca gacctccgac aacgacacct    5340
acaacgtgac ctcctacccg aaccaccagc aggccctgct gctgctgacc aaccactcct    5400
acgaggaggt ggaggagatc accaacatcc gaagtccac cctcaagaag ctcaagaagt    5460
actacttctg agtcatgagt catgagtcag ttaacctaga cttgtccatc ttctggattg    5520
gccaacttaa ttaatgtatg aaataaaagg atgcacacat agtgacatgc taatcactat    5580
aatgtgggca tcaaagttgt gtgttatgtg taattactag ttatctgaat aaaagagaaa    5640
gagatcatcc atatttctta tcctaaatga atgtcacgtg tctttataat tctttgatga    5700
accagatgca tttcattaac caaatccata tacatataaa tattaatcat atataattaa    5760
```

-continued

```
tatcaattgg gttagcaaaa caaatctagt ctaggtgtgt tttgcgaatt cccatggagt    5820
caaagattca aatagaggac ctaacagaac tcgccgtaaa gactggcgaa cagttcatac    5880
agagtctctt acgactcaat gacaagaaga aaatcttcgt caacatggtg gagcacgaca    5940
cgcttgtcta ctccaaaaat atcaaagata cagtctcaga agaccaaagg gcaattgaga    6000
cttttcaaca aagggtaata tccggaaacc tcctcggatt ccattgccca gctatctgtc    6060
actttattgt gaagatagtg gaaaaggaag gtggctccta caaatgccat cattgcgata    6120
aaggaaaggc catcgttgaa gatgcctctg ccgacagtgg tcccaaagat ggaccccac    6180
ccacgaggag catcgtggaa aaagaagacg ttccaaccac gtcttcaaag caagtggatt    6240
gatgtgatat ctccactgac gtaagggatg acgcacaatc ccactatcct tcgcaagacc    6300
cttcctctat ataaggaagt tcatttcatt tggagaggac agggtacccg gggatccacc    6360
atgtctccgg agaggagacc agttgagatt aggccagcta cagcagctga tatggccgcg    6420
gtttgtgata tcgttaacca ttacattgag acgtctacag tgaactttag gacagagcca    6480
caaacaccac aagagtggat tgatgatcta gagaggttgc aagatagata cccttggttg    6540
gttgctgagg ttgagggtgt tgtggctggt attgcttacg ctgggccctg gaaggctagg    6600
aacgcttacg attggacagt tgagagtact gtttacgtgt cacataggca tcaaaggttg    6660
ggcctaggat ccacattgta cacacatttg cttaagtcta tggaggcgca aggttttaag    6720
tctgtggttg ctgttatagg ccttccaaac gatccatctg ttaggttgca tgaggctttg    6780
ggatacacag cccggggtac attgcgcgca gctggataca agcatggtgg atggcatgat    6840
gttggttttt ggcaaaggga ttttgagttg ccagctcctc caaggccagt taggccagtt    6900
acccagatct gagtcgacct gcaggcatgc ccgctgaaat caccagtctc tctctacaaa    6960
tctatctctc tctataataa tgtgtgagta gttcccagat aagggaatta gggttcttat    7020
agggtttcgc tcatgtgttg agcatataag aaacccttag tatgtatttg tatttgtaaa    7080
atacttctat caataaaatt tctaattcct aaaaccaaaa tccagggcga gctcggtacc    7140
cggggatcct ctagagtcga cctgcaggca tgcccgcgga tatcgatggg ccccggccga    7200
agcttcggtc cgggccatcg tggcctcttg ctcttcagga tgaagagcta tgtttaaacg    7260
tgcaagcgct caattcgccc tatagtgagt cgtattacaa tcgtacgcaa ttcagtacat    7320
taaaaacgtc cgcaatgtgt tattaagttg tctaagcgtc aatttgttta caccacaata    7380
tatcctgcca                                                           7390
```

<210> SEQ ID NO 428
<211> LENGTH: 753
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 428

```
gaggccgaca cggcacacac ggcgacattc accgccggct tcctccgtcg ccactcggca      60
caaggctcat cagtcgccga tgcccgatgc gatcaacgga agcggatggc ccgcttcttt     120
agaattggca caggaacact ggccactgcc cttgatgtgc aattatgcct gcgaaagcct     180
aggcaacaca cgcgaataaa cgagcgaatg acacggaaag ctgatgtggt atgaattata     240
caacattatg ggccaaaata ttattctatc caccattgtg tagccacagc atcggtattt     300
gagttgtgcg aggacaaatc cctcgtgagg tcaaaaacag caaataataa acccatctcc     360
```

```
tgaagacacc aaaaaaaagg agcagctcct cgtgtcaatg aacaagcgtc acaagaaaag    420
ggagcacgta aataacctct tcaattgctt cagcatgaaa agaacgggaa gaaatgcaag    480
tctacagagg aaagtgcagc tgtttcggct gccatggcaa gttcctacat gggcgaggaa    540
aagctgaact ggattccagt cttcgcgctg tcatgctcag cttgctttag gatgcggcaa    600
tagttcacct ggatgaaaaa gatacaagtt agtcttgaag cagtcgagtg gacatccaaa    660
gtatcaaaat cgaaagcttg taaatgggga aggaaatata cctctacccg gaaaagtttg    720
gtaggcaaaa taatcccaac gccagcagag ctc                                 753
```

<210> SEQ ID NO 429
<211> LENGTH: 870
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 429

```
cgtgcaagcg ctcaattcgc cctatagtga gtcgtattac aatcgtacgc aattcagtac     60
attaaaaacg tccgcaatgt gttattaagt tgtctaagcg tcaatttgtt tacaccagag    120
gccgacacgg cacacacggc gacattcacc gccggcttcc tccgtcgcca ctcggcacaa    180
ggctcatcag tcgccgatgc ccgatgcgat caacggaagc ggatggcccg cttctttaga    240
attggcacag gaacactggc cactgcccett gatgtgcaat tatgcctgcg aaagcctagg    300
caacacacgc gaataaacga gcgaatgaca cggaaagctg atgtggtatg aattatacaa    360
cattatgggc caaaatatta ttctatccac cattgtgtag ccacagcatc ggtatttgag    420
ttgtgcgagg acaaatccct cgtgaggtca aaaacagcaa ataataaacc catctcctga    480
agacaccaaa aaaaggagc agctcctcgt gtcaatgaac aagcgtcaca gaaaaggga    540 gcacgtaaat aacctcttca attgcttcag catgaaaaga acgggaagaa atgcaagtct    600
acagaggaaa gtgcagctgt ttcggctgcc atggcaagtt cctacatggg cgaggaaaag    660
ctgaactgga ttccagtctt cgcgctgtca tgctcagctt gctttaggat gcggcaatag    720
ttcacctgga tgaaaagat acaagttagt cttgaagcag tcgagtggac atccaaagta    780
tcaaaatcga aagcttgtaa atggggaagg aaatatacct ctacccggaa agtttggta    840 ggcaaaataa tcccaacgcc agcagagctc                                    870
```

<210> SEQ ID NO 430
<211> LENGTH: 2675
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 430

```
agttgggaag gcaaaacgaa tataagtgca ttcggattac tgtttagtcg agtcatattt     60
aaggaattca ttgtaaatgt tctaacctaa cctaagtatt aggcagctat ggctgatatg    120
gatctgattg gacttgattt atccatgata agtttaagag caactcaaag aggttaggta    180
tatatggttt tgtaaaggta aatttagtta atattagaaa aaaaagtgt atccaatagg    240 ctctataaac aactcttcaa atttagtggc tttctatcca tccacctttg ctctctattt    300
ttggatagcc tgatttactc tctattcagt ccgtaggttt aatgagtctg ttggattagc    360
```

```
ctacactttt tctgtaaaat ctattttaga tagtagctaa atcagtaaat ttggctagta    420
tttttagcta ttctcttgga gtttgctata agaccagaac atgtaaattg gaagtttgtg    480
gacccggacg agaatgcatg acaaatccag agtattgatg atggaattca cctatttac     540
ccgactcttc cattgtgtcc atttctcatc atccccgggc gctttctgca tccggtacag    600
ctgacatgac acgttcacgc gttacatggc tgatggctca caagtcaccc ccacatgtct    660
agtgttcgcc caggcagatc gtcctcggcc tgcgctgccg tgctcttgcc gccgcttgct    720
tgggccctgc tggcgcccgc tgccgatcac acggcctacg cggtgcaggc agcgccaccg    780
aacccgcagt cttgttgtgc cgataggtgg cagtggcagt ggcactggca cggcacgcga    840
tcgatcgctc cgctcatctg ctgacagtgg atagagcagc gttggccgtt ggggccggat    900
ctccgtgaag cggtcgtccc tgctgtactg tgccgctatg gcgtgtcgct ttcgccatgt    960
tttcttttct ttttttttc tttttcttt tgctagggcg gtttctcgtt cgctggtaac      1020
agggaccact tcggttgatc cgttgaattt actgaaagag atgggaatgg tcgctgtgcc    1080
cgggacattg aatgagatgt tgtgtaagtg aatatggctt tagccttttg cgagtgggaa    1140
tggatgctaa acgaacacaa accgggttta aaccagaggc cgacacggca cacacggcga    1200
cattcaccgc cggcttcctc cgtcgccact cggcacaagg ctcatcagtc gccgatgccc    1260
gatgcgatca acgaagcgg atggcccgct tctttagaat tggcacagga acactggcca     1320
ctgcccttga tgtgcaatta tgcctgcgaa agcctaggca acacacgcga ataaacgagc    1380
gaatgacacg gaaagctgat gtggtatgaa ttatacaaca ttatgggcca aaatattatt    1440
ctatccacca ttgtgtagcc acagcatcgg tatttgagtt gtgcgaggac aaatccctcg    1500
tgaggtcaaa acagcaaat aataaaccca tctcctgaag acaccaaaaa aaaggagcag    1560
ctcctcgtgt caatgaacaa gcgtcacaag aaaaggagc acgtaaataa cctcttcaat    1620
tgcttcagca tgaaaagaac gggaagaaat gcaagtctac agaggaaagt gcagctgttt    1680
cggctgccat ggcaagttcc tacatgggcg aggaaaagct gaactggatt ccagtcttcg    1740
cgctgtcatg ctcagcttgc tttaggatgc ggcaatagtt cacctggatg aaaaagatac    1800
aagttagtct tgaagcagtc gagtggacat ccaaagtatc aaaatcgaaa gcttgtaaat    1860
ggggaaggaa atatacctct acccggaaaa gtttggtagg caaaataatc ccaacgccag    1920
cagagctccg gaacgtttgc cgaaattcag aagccgaaaa gttcttgtac tcaccctccg    1980
acagtttcgc aaggtttcca gcagtaagga atgcgtggcc atggattcca gcgtctctga    2040
atatcttgag gggcagatca aaagaaaggt cagcgaaggc agacacggcc agatcacctc    2100
ccaagtaatc ccttccaggg tcagccgagc cactctccga gttattaagg acatgcctcc    2160
gcgcctctgt tgggccaact ccccttaatc tgaaacccag cagagatgac ggtccgccca    2220
agctgcacac tggagaagaa ttacctccaa gataaaacct ctctggcact gatgaagtcg    2280
aattcatgaa tccccctgca agcggtaaaa tgacacccgc tcctacacca acgttgagag    2340
cagcactata aaatcccaaa ggcacagcac acgtacatc gaactcctga gagcaaaccc     2400
aacggcaata ttttctaacg gacaccaacc agcgaaccag cagcgtcgcg tcgggccaag    2460
cgaagcagac ggcacggcat ctctgtcgct gcctctggac ccctctcgag agttccgctc    2520
caccgttgga cttgctccgc tgtcggcatc cagaaattgc gtggcggagc ggcagacgtg    2580
agccggcacg gcaggcggcc tcctcctcct ctcacggcac cggcagctac gggggattcc    2640
tttcccaccg ctccttcgct gtcccttcct cgccc                               2675
```

<210> SEQ ID NO 431
<211> LENGTH: 3102
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 431

| | | | | | |
|---|---|---|---|---|---|
| agttgggaag | gcaaaacgaa | tataagtgca | ttcggattac | tgtttagtcg | agtcatattt 60 |
| aaggaattca | ttgtaaatgt | tctaacctaa | cctaagtatt | aggcagctat | ggctgatatg 120 |
| gatctgattg | gacttgattt | atccatgata | agtttaagag | caactcaaag | aggttaggta 180 |
| tatatggttt | tgtaaaggta | aatttagtta | atattagaaa | aaaaaagtgt | atccaatagg 240 |
| ctctataaac | aactcttcaa | atttagtggc | tttctatcca | tccacctttg | ctctctattt 300 |
| ttggatagcc | tgatttactc | tctattcagt | ccgtaggttt | aatgagtctg | ttggattagc 360 |
| ctacactttt | tctgtaaaat | ctattttaga | tagtagctaa | atcagtaaat | ttggctagta 420 |
| tttttagcta | ttctcttgga | gtttgctata | agaccagaac | atgtaaattg | gaagtttgtg 480 |
| gacccggacg | agaatgcatg | acaaatccag | agtattgatg | atggaattca | cctattttac 540 |
| ccgactcttc | cattgtgtcc | atttctcatc | atccccgggc | gctttctgca | tccggtacag 600 |
| ctgacatgac | acgttcacgc | gttacatggc | tgatggctca | caagtcaccc | ccacatgtct 660 |
| agtgttcgcc | caggcagatc | gtcctcggcc | tgcgctgccg | tgctcttgcc | gccgcttgct 720 |
| tgggccctgc | tggcgcccgc | tgccgatcac | acggcctacg | cggtgcaggc | agcgccaccg 780 |
| aacccgcagt | cttgttgtgc | cgataggtgg | cagtggcagt | ggcactggca | cggcacgcga 840 |
| tcgatcgctc | cgctcatctg | ctgacagtgg | atagagcagc | gttggccgtt | ggggccggat 900 |
| ctccgtgaag | cggtcgtccc | tgctgtactg | tgccgctatg | gcgtgtcgct | ttcgccatgt 960 |
| tttctttctt | tttttttttc | tttttctttt | tgctagggcg | gtttctcgtt | cgctggtaac 1020 |
| agggaccact | tcgttgatc | cgttgaattt | actgaaagag | atgggaatgg | tcgctgtgcc 1080 |
| cgggacattg | aatgagatgt | tgtgtaagtg | aatatggctt | tagccttttg | cgagtggggc 1140 |
| ggcaatgcac | ggcatgaact | ataatttccg | gtcaaacttt | tgtgtggaaa | tggatgctaa 1200 |
| acgaacacaa | accgggttta | aaccagaggc | cgacacggca | cacacggcga | cattcaccgc 1260 |
| cggcttcctc | cgtcgccact | cggcacaagg | ctcatcagtc | gccgatgccc | gatgcgatca 1320 |
| acggaagcgg | atggcccgct | tctttagaat | tggcacagga | acactggcca | ctgcccttga 1380 |
| tgtgcaatta | tgcctgcgaa | agcctaggca | acacacgcga | ataaacgagc | gaatgacacg 1440 |
| gaaagctgat | gtggtatgaa | ttatacaaca | ttatgggcca | aaatattatt | ctatccacca 1500 |
| ttgtgtagcc | acagcatcgg | tatttgagtt | gtgcgaggac | aaatccctcg | tgaggtcaaa 1560 |
| aacagcaaat | aataaaccca | tctcctgaag | acaccaaaaa | aaaggagcag | ctcctcgtgt 1620 |
| caatgaacaa | gcgtcacaag | aaaagggagc | acgtaaataa | cctcttcaat | tgcttcagca 1680 |
| tgaaaagaac | gggaagaaat | gcaagtctac | agaggaaagt | gcagctgttt | cggctgccat 1740 |
| ggcaagttcc | tacatgggcg | aggaaaagct | gaactggatt | ccagtcttcg | cgctgtcatg 1800 |
| ctcagcttgc | tttaggatgc | ggcaatagtt | cacctgatg | aaaagatac | aagttagtct 1860 |
| tgaagcagtc | gagtggacat | ccaaagtatc | aaaatcgaaa | gcttgtaaat | ggggaaggaa 1920 |
| atatacctct | acccggaaaa | gtttggtagg | caaaataatc | ccaacgccag | cagagctccg 1980 |
| gaacgtttgc | cgaaattcag | aagccgaaaa | gttcttgtac | tcaccctccg | acagtttcgc 2040 |
| aaggtttcca | gcagtaagga | atgcgtggcc | atggattcca | gcgtctctga | atatcttgag 2100 |

```
gggcagatca aaagaaaggt cagcgaaggc agacacggcc agatcacctc ccaagtaatc    2160
ccttccaggg tcagccgagc cactctccga gttattaagg acatgcctcc gcgcctctgt    2220
tgggccaact cccttaatc tgaaacccag cagagatgac ggtccgccca agctgcacac     2280
tggagaagaa ttacctccaa gataaaacct ctctggcact gatgaagtcg aattcatgaa    2340 tcccctgca agcggtaaaa tgacacccgc tcctacacca acgttgagag cagcactata     2400
aaatcccaaa ggcacagcac cacgtacatc gaactcctga gagcaaaccc aacggcaata   2460
tttttgtaat agtgatggtc agaactgaga agatcagata aaattataca ctgatgcaat    2520
tatttcatag tttcgcccat gaactgtaag ggctagacaa agcaaaaagt aagacatgaa   2580
gggcaagaga ataacctgcc ggaaatatct caatcctttg ctattccata gaccaccaac   2640
ttgagaagtt gactgaaacg catatccttt cgttggccta agatgtgaat ccctcttatc   2700
aatcttgtat gtgtacttca atgcagaaag aaggttatgc cctaactgcc tccttatggc    2760
ctttgatgag acacgtgatg gatcagttaa ggtacgccac gcaaggttgt atgacaagtc   2820
atggttcctt gttgacagca aaccaaatga aaggccaagt aggcgctcct tgtatgatga    2880
aaacttcagc caatcttgtg atgacaaaga tgcccgagcc atcaatggtg ttggtattga    2940
tttaaacctc ggtaggcaga ctccaacacc aacctctgtt gtttggtccc aaccaaagga   3000
tcctgatgca tcccagatgt caccatagcc aaacaagttc ttcaacttaa gtgacccttc    3060
cagcgaccaa gatcttgcct acaagagtgg caagcacagt ca                       3102

<210> SEQ ID NO 432
<211> LENGTH: 28
<212> TYPE: DNA
<213> ORGANISM: Zea mays

<400> SEQUENCE: 432
cacaacaaga ctgcgggttc ggtggcgc                                       28

<210> SEQ ID NO 433
<211> LENGTH: 28
<212> TYPE: DNA
<213> ORGANISM: Zea mays

<400> SEQUENCE: 433
gataggtggc agtggcagtg gcactggc                                       28

<210> SEQ ID NO 434
<211> LENGTH: 28
<212> TYPE: DNA
<213> ORGANISM: Zea mays

<400> SEQUENCE: 434
tatcggcaca acaagactgc gggttcgg                                       28

<210> SEQ ID NO 435
<211> LENGTH: 28
<212> TYPE: DNA
<213> ORGANISM: Zea mays

<400> SEQUENCE: 435
tggcagtggc agtggcactg gcacggca                                       28

<210> SEQ ID NO 436
<211> LENGTH: 28
<212> TYPE: DNA
```

<213> ORGANISM: Zea mays

<400> SEQUENCE: 436
cagcagatga gcggagcgat cgatcgcg   28

<210> SEQ ID NO 437
<211> LENGTH: 28
<212> TYPE: DNA
<213> ORGANISM: Zea mays

<400> SEQUENCE: 437
cagtggatag agcagcgttg gccgttgg   28

<210> SEQ ID NO 438
<211> LENGTH: 28
<212> TYPE: DNA
<213> ORGANISM: Zea mays

<400> SEQUENCE: 438
aggaagccgg cggtgaatgt cgccgtgt   28

<210> SEQ ID NO 439
<211> LENGTH: 28
<212> TYPE: DNA
<213> ORGANISM: Zea mays

<400> SEQUENCE: 439
cgtcgccact cggcacaagg ctcatcag   28

<210> SEQ ID NO 440
<211> LENGTH: 28
<212> TYPE: DNA
<213> ORGANISM: Zea mays

<400> SEQUENCE: 440
atcgggcatc ggcgactgat gagccttg   28

<210> SEQ ID NO 441
<211> LENGTH: 28
<212> TYPE: DNA
<213> ORGANISM: Zea mays

<400> SEQUENCE: 441
gatcaacgga agcggatggc ccgcttct   28

<210> SEQ ID NO 442
<211> LENGTH: 28
<212> TYPE: DNA
<213> ORGANISM: Zea mays

<400> SEQUENCE: 442
tgatcgcatc gggcatcggc gactgatg   28

<210> SEQ ID NO 443
<211> LENGTH: 28
<212> TYPE: DNA
<213> ORGANISM: Zea mays

<400> SEQUENCE: 443
cggaagcgga tggcccgctt ctttagaa   28

<210> SEQ ID NO 444
<211> LENGTH: 18

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 444
caggcagcgc caccgaac                                                   18

<210> SEQ ID NO 445
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 445
cgatcgatcg cgtgccgt                                                   18

<210> SEQ ID NO 446
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 446
ctggcacggc acgcgatc                                                   18

<210> SEQ ID NO 447
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 447
cggagatccg gccccaac                                                   18

<210> SEQ ID NO 448
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 448
gacacggcac acacggcg                                                   18

<210> SEQ ID NO 449
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 449
tcgggcatcg gcgactga                                                   18

<210> SEQ ID NO 450
<211> LENGTH: 18
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 450
actcggcaca aggctcat                                                        18

<210> SEQ ID NO 451
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 451
cctgtgccaa ttctaaag                                                        18

<210> SEQ ID NO 452
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 452
gcagtgcatg ttatgagc                                                        18

<210> SEQ ID NO 453
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 453
caggacataa atgaactgaa tc                                                   22

<210> SEQ ID NO 454
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 454
tgttcggttc cctctaccaa                                                      20

<210> SEQ ID NO 455
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 455
caacatccat caccttgact ga                                                   22

<210> SEQ ID NO 456
<211> LENGTH: 24
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 456
cacagaaccg tcgcttcagc aaca                                         24

<210> SEQ ID NO 457
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 457
tggcggacga cgacttgt                                                18

<210> SEQ ID NO 458
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 458
aaagtttgga ggctgccgt                                               19

<210> SEQ ID NO 459
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 459
cgagcagacc gccgtgtact tctacc                                       26

<210> SEQ ID NO 460
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 460
gcccttacag ttcatgggcg                                              20

<210> SEQ ID NO 461
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 461
gaccaagtcc ttgtctggga ca                                           22

<210> SEQ ID NO 462
<211> LENGTH: 21
<212> TYPE: DNA
<213> ORGANISM: Artificial Sequence
<220> FEATURE:
```

<223> OTHER INFORMATION: Description of Artificial Sequence: Synthetic
       primer

<400> SEQUENCE: 462
acaaacacgt cctccaaggc t                                            21

<210> SEQ ID NO 463
<211> LENGTH: 22
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 463
gaccaagtcc ttgtctggga ca                                           22

<210> SEQ ID NO 464
<211> LENGTH: 226
<212> TYPE: DNA
<213> ORGANISM: Artificial Sequence
<220> FEATURE:
<223> OTHER INFORMATION: Description of Artificial Sequence: Synthetic
       probe

<400> SEQUENCE: 464
gtgcattcgg attactgttt agtcgagtca tatttaagga attcattgta aatgttctaa    60
cctaacctaa gtattaggca gctatggctg atatggatct gattggactt gatttatcca   120
tgataagttt aagagcaact caaagaggtt aggtatatat ggttttgtaa aggtaaattt   180
agttaatatt agaaaaaaaa agtgtatcca ataggctcta taaaca                 226

<210> SEQ ID NO 465
<211> LENGTH: 20
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 465
tgttcggttc cctctaccaa                                              20

<210> SEQ ID NO 466
<211> LENGTH: 22
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 466
caacatccat caccttgact ga                                           22

<210> SEQ ID NO 467
<211> LENGTH: 24
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 467
cacagaaccg tcgcttcagc aaca                                         24

```
<210> SEQ ID NO 468
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 468
tggcggacga cgacttgt                                                       18

<210> SEQ ID NO 469
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 469
aaagtttgga ggctgccgt                                                      19

<210> SEQ ID NO 470
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 470
cgagcagacc gccgtgtact tctacc                                              26

<210> SEQ ID NO 471
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 471
taggagttct cttttatgcc accc                                                24

<210> SEQ ID NO 472
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 472
ccttgggatt tcagttggta ggtt                                                24

<210> SEQ ID NO 473
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 473
tggcggacga cgacttgt                                                       18

<210> SEQ ID NO 474
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 474
aaagtttgga ggctgccgt                                                19

<210> SEQ ID NO 475
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 475
cgagcagacc gccgtgtact tctacc                                         26

<210> SEQ ID NO 476
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 476
agacctacca cccattaggg c                                              21

<210> SEQ ID NO 477
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 477
gaccaagtcc ttgtctggga ca                                             22

<210> SEQ ID NO 478
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 478
gaccaagtcc ttgtctggga ca                                             22

<210> SEQ ID NO 479
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 479
gatggtggtt atgacaggct cct                                            23

<210> SEQ ID NO 480
<211> LENGTH: 45
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
cgcgccgcct tttgcagttt atccactagg gacaggattg ccacc                   45

<210> SEQ ID NO 481
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
cgcgccgcct tttgcagttt atccactagg gacaggattg ccacc                   45

<210> SEQ ID NO 482
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
cgcgccgcct tttgcagtta gggacaggat tgccacc                            37

<210> SEQ ID NO 483
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
cgcgccgcct tttgcagttt atccactagg gacaggattg ccacc                   45

<210> SEQ ID NO 484
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
cgcgccgcca ctagggacag gattgccacc                                    30

<210> SEQ ID NO 485
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
cgcgccgcct tttgcagttt actagggaca ggattgccac c                       41

<210> SEQ ID NO 486
<211> LENGTH: 40
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 486
cgcgccgcct tttgcagttt ctagggacag gattgccacc                          40

<210> SEQ ID NO 487
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
cgcgccgcct tttgcagttt atccactagg gacaggattg ccacc                    45

<210> SEQ ID NO 488
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
cgcgccgcct tttgcagttt ctagggacag gattgccacc                          40

<210> SEQ ID NO 489
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
cgcgccgcct tttgcactag ggacaggatt gccacc                              36

<210> SEQ ID NO 490
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
cgcgccgcct tttgcagttt actagggaca ggattgccac c                        41

<210> SEQ ID NO 491
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
cgcgccgcct tttgcagttt actagggaca ggattgccac c                        41

<210> SEQ ID NO 492
<211> LENGTH: 41
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 492
cgcgccgcct tttgcagttt actagggaca ggattgccac c                          41

<210> SEQ ID NO 493
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
cgcgccgcct tttgcagttt aatccactag ggacaggatt gccacc                     46

<210> SEQ ID NO 494
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
cgcgccgcct tttgcagttt aagggacagg attgccacc                             39

<210> SEQ ID NO 495
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
cgcgccgcct tttgcagttt aatccactag ggacaggatt gccacc                     46

<210> SEQ ID NO 496
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
cgcgccgcct tttgcagttt aatccactag ggacaggatt gccacc                     46

<210> SEQ ID NO 497
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(25)
<223> OTHER INFORMATION: a, c, t, g, unknown or other

<400> SEQUENCE: 497
cgcgccgcct tttgcagttt annnntaaac tgcaaaaagg cggatc                     46

<210> SEQ ID NO 498
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
cgcgccgcct tttgcagttt aaactgcaaa aaggcggatc                                40

<210> SEQ ID NO 499
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
cgcgccgcct tttgcagtaa actgcaaaaa ggcggatc                                  38

<210> SEQ ID NO 500
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
cgcgccgcct tttgcagttt taaactgcaa aaggcggat c                               41

<210> SEQ ID NO 501
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
cgcgccgcct tttgcagttt ataaactgca aaaggcgga tc                              42

<210> SEQ ID NO 502
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
cgcgccgcct tttgcagttt ataaactgca aaaggcgga tc                              42

<210> SEQ ID NO 503
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
cgcgccgcct tttgcagttt aataaactgc aaaaggcgg atc                             43

<210> SEQ ID NO 504
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
cgcgccgcct tttgcagttt ataaactgca aaaggcgga tc                           42

<210> SEQ ID NO 505
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
cgcgccgcct tttgcatttt aaaggcggat c                                     31

<210> SEQ ID NO 506
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
tccaaggttg cggccgcagc gagagaaagc ttattgcaac ttcaactaca ctacttgctg      60
gtcgatcgtg ttggccactc ttgtttatct atca                                  94

<210> SEQ ID NO 507
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
tccaaggttg cggccgcagc gagagaaagc ttattgcaac ttcaactact tgctggtcga      60
tcgtgttggc cactcttgtt tatctatca                                        89

<210> SEQ ID NO 508
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
ttctggcctc tttattgggc cgcccaagga acccttttct gggccatctt cgtactcggc      60
cacgactggt aatttaatgg atccaaccga caaccactt                             99

<210> SEQ ID NO 509
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(40)
```

<223> OTHER INFORMATION: a, c, t, g, unknown or other

<400> SEQUENCE: 509

```
ttctggcctc tttattgggc cgcccaagga acccttnnn tactcggcca cgactggtaa      60
tttaatggat ccaaccgaca accactt                                         87
```

<210> SEQ ID NO 510
<211> LENGTH: 245
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (43)..(195)
<223> OTHER INFORMATION: a, c, t, g, unknown or other

<400> SEQUENCE: 510

```
ttctggcctc tttattgggc cgcccaagga accctttct ggnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnntcgta ctcggccacg actggtaatt taatggatcc aaccgacaac     240
cactt                                                                 245
```

<210> SEQ ID NO 511
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 511

```
ttctggcctc tttattgggc cgcccaagga accctttct gg                         42
```

<210> SEQ ID NO 512
<211> LENGTH: 462
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (50)..(419)
<223> OTHER INFORMATION: a, c, t, g, unknown or other

<400> SEQUENCE: 512

```
ttctggcctc tttattgggc cgcccaagga accctttct ggccatctn nnnnnnnnnn       60 nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnc    420
ggccacgact ggtaatttaa tggatccaac cgacaaccac tt                       462
```

<210> SEQ ID NO 513

```
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (48)..(83)
<223> OTHER INFORMATION: a, c, t, g, unknown or other

<400> SEQUENCE: 513
ttctggcctc tttattgggc cgcccaagga acccttttct gggccatnnn nnnnnnnnn        60 nnnnnnnnnn nnnnnnnnnn nnntcgtact cggccacgac tggtaattta atggatccaa      120
ccgacaacca ctt                                                         133

<210> SEQ ID NO 514
<211> LENGTH: 127
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (50)..(127)
<223> OTHER INFORMATION: a, c, t, g, unknown or other

<400> SEQUENCE: 514
ttctggcctc tttattgggc cgcccaagga acccttttct gggccatctn nnnnnnnnn        60 nnnnnnnnnn nnnnnnnnnn nnnnnnnnnn nnnnnnnnnn nnnnnnnnnn nnnnnnnnnn      120 nnnnnnn                                                                127

<210> SEQ ID NO 515
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 515
gtaatacata gcggccgcgc ccaaggaacc cttttctggg ccatcttcgt actcggccac        60
gactggtaat ttaattttca atttattttt tcttcaactt ctta                       104

<210> SEQ ID NO 516
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (45)..(48)
<223> OTHER INFORMATION: a, c, t, g, unknown or other

<400> SEQUENCE: 516
gtaatacata gcggccgcgc ccaaggaacc cttttctggg ccatnnnngc cacgactggt        60
aatttaattt tcaatttatt ttttcttcaa cttctta                                97

<210> SEQ ID NO 517
<211> LENGTH: 202
<212> TYPE: DNA
<213> ORGANISM: Artificial Sequence
```

```
<220> FEATURE:
<223> OTHER INFORMATION: Description of Artificial Sequence: Synthetic
      polynucleotide
<220> FEATURE:
<221> NAME/KEY: modified_base
<222> LOCATION: (47)..(158)
<223> OTHER INFORMATION: a, c, t, g, unknown or other

<400> SEQUENCE: 517
gtaatacata gcggccgcgc ccaaggaacc cttttctggg ccatctnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnga ctggtaattt aattttcaat      180 ttatttttc ttcaacttct ta                                                202

<210> SEQ ID NO 518
<211> LENGTH: 202
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (47)..(158)
<223> OTHER INFORMATION: a, c, t, g, unknown or other

<400> SEQUENCE: 518
gtaatacata gcggccgcgc ccaaggaacc cttttctggg ccatctnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnga ctggtaattt aattttcaat      180 ttatttttc ttcaacttct ta                                                202

<210> SEQ ID NO 519
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (45)..(278)
<223> OTHER INFORMATION: a, c, t, g, unknown or other

<400> SEQUENCE: 519
gtaatacata gcggccgcgc ccaaggaacc cttttctggg ccatnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnngt actcggccac gactggtaat      300
ttaattttca atttattttt tcttcaactt ctta                                  334

<210> SEQ ID NO 520
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
```
gtactcggcc acgactggta atttaattt tctttcaact tctta           45

<210> SEQ ID NO 521
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(33)
<223> OTHER INFORMATION: a, c, t, g, unknown or other

<400> SEQUENCE: 521
gtaatacata gcggccgcgc ccaannnnnn nnntactcgg ccacgactgg taatttaatt    60
ttcaatttat tttttcttca acttctta                                      88

<210> SEQ ID NO 522
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (45)..(51)
<223> OTHER INFORMATION: a, c, t, g, unknown or other

<400> SEQUENCE: 522
tgtaatacat agcggccgcg cccaaggaac cctttactcg gccannnnnn ntaatttaat    60
tttcaattta tttttcttc aacttctta                                      89

<210> SEQ ID NO 523
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
ctgcaggtga agacaggatg                                               20

<210> SEQ ID NO 524
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
ttctggcctc tttattgggc cgcccaagga acccttttct gggccatctt cgtactcggc    60
cacgactggt aatttaatgg atccaaccga caaccactt                          99

<210> SEQ ID NO 525
<211> LENGTH: 305
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (50)..(255)

```
<223> OTHER INFORMATION: a, c, t, g, unknown or other

<400> SEQUENCE: 525
ttctggcctc tttattgggc cgcccaagga acccttttct gggccatctn nnnnnnnnn       60 nnnnnnnnnn nnnnnnnnnn nnnnnnnnnn nnnnnnnnnn nnnnnnnnnn nnnnnnnnnn      120
nnnnnnnnnn nnnnnnnnnn nnnnnnnnnn nnnnnnnnnn nnnnnnnnnn nnnnnnnnnn      180
nnnnnnnnnn nnnnnnnnnn nnnnnnnnnn nnnnnnnnnn nnnnnnnnnn nnnnnnnnnn      240
nnnnnnnnnn nnnnntcgta ctcggccacg actggtaatt taatggatcc aaccgacaac      300
cactt                                                                  305

<210> SEQ ID NO 526
<211> LENGTH: 465
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (50)..(422)
<223> OTHER INFORMATION: a, c, t, g, unknown or other

<400> SEQUENCE: 526
ttctggcctc tttattgggc cgcccaagga acccttttct gggccatctn nnnnnnnnn       60 nnnnnnnnnn nnnnnnnnnn nnnnnnnnnn nnnnnnnnnn nnnnnnnnnn nnnnnnnnnn      120
nnnnnnnnnn nnnnnnnnnn nnnnnnnnnn nnnnnnnnnn nnnnnnnnnn nnnnnnnnnn      180
nnnnnnnnnn nnnnnnnnnn nnnnnnnnnn nnnnnnnnnn nnnnnnnnnn nnnnnnnnnn      240
nnnnnnnnnn nnnnnnnnnn nnnnnnnnnn nnnnnnnnnn nnnnnnnnnn nnnnnnnnnn      300
nnnnnnnnnn nnnnnnnnnn nnnnnnnnnn nnnnnnnnnn nnnnnnnnnn nnnnnnnnnn      360
nnnnnnnnnn nnnnnnnnnn nnnnnnnnnn nnnnnnnnnn nnnnnnnnnn nnnnnnnnnn      420
nncggccacg actggtaatt taatggatcc aaccgacaac cactt                      465

<210> SEQ ID NO 527
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (45)..(49)
<223> OTHER INFORMATION: a, c, t, g, unknown or other

<400> SEQUENCE: 527
ttctggcctc tttattgggc cgcccaagga acccttttct gggcnnnnnt cggccacgac       60
tggtaattta atggatccaa ccgacaacca ctt                                   93

<210> SEQ ID NO 528
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 528
gtaatacata gcggccgcag cgagagaaag cttattgcaa cttcaactac ttgctggtcg       60
```
atcgtgttgg ccactcttgt ttatctatca ttcctcgttg gtc         103

<210> SEQ ID NO 529
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (48)..(276)
<223> OTHER INFORMATION: a, c, t, g, unknown or other

<400> SEQUENCE: 529
gtaatacata gcggccgcag cgagagaaag cttattgcaa cttcaacnnn nnnnnnnnnn    60
nnnnnnnnnn nnnnnnnnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnnnnnn nnnnnnnnnn nnnnnnnnnn nnnnnnnnnn nnnnnnnnnn   240
nnnnnnnnnn nnnnnnnnnn nnnnnnnnnn nnnnnncttg ctggtcgatc gtgttggcca   300
ctcttgttta tctatcattc ctcgttggtc                                    330

<210> SEQ ID NO 530
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (48)..(73)
<223> OTHER INFORMATION: a, c, t, g, unknown or other

<400> SEQUENCE: 530
gtaatacata gcggccgcag cgagagaaag cttattgcaa cttcaacnnn nnnnnnnnnn    60
nnnnnnnnnn nnntacttgc tggtcgatcg tgttggccac tcttgtttat ctatcattcc   120
tcgttggtc                                                           129

<210> SEQ ID NO 531
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (48)..(80)
<223> OTHER INFORMATION: a, c, t, g, unknown or other

<400> SEQUENCE: 531
gtaatacata gcggccgcag cgagagaaag cttattgcaa cttcaacnnn nnnnnnnnnn    60
nnnnnnnnnn nnnnnnnnnn acttgctggt cgatcgtgtt ggccactctt gtttatctat   120
cattcctcgt tggtc                                                    135

<210> SEQ ID NO 532
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide

```
<220> FEATURE:
<221> NAME/KEY: modified_base
<222> LOCATION: (48)..(64)
<223> OTHER INFORMATION: a, c, t, g, unknown or other

<400> SEQUENCE: 532
gtaatacata gcggccgcag cgagagaaag cttattgcaa cttcaacnnn nnnnnnnnn      60 nnnncttgct ggtcgatcgt gttggccact cttgtttatc tatcattcct cgttggtc     118

<210> SEQ ID NO 533
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Arg Ser Asp Asp Leu Ser Lys
1               5

<210> SEQ ID NO 534
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Gln Ser Gly Ser Leu Thr Arg
1               5

<210> SEQ ID NO 535
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Arg Ser Asp Asn Leu Arg Glu
1               5

<210> SEQ ID NO 536
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536

Asp Thr Gly Ala Arg Leu Lys
1               5

<210> SEQ ID NO 537
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Arg Ser Ala Asp Arg Lys Thr
```

<210> SEQ ID NO 538
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Asp Arg Ser His Leu Ser Arg
1               5

<210> SEQ ID NO 539
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 539

Arg Ser Asp Asp Leu Ser Arg
1               5

<210> SEQ ID NO 540
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

Gln Ser Ala Asn Arg Thr Lys
1               5

<210> SEQ ID NO 541
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
tgtcccctcc accccacagt gggtggccta gggacaggat tggtgacaga            50

<210> SEQ ID NO 542
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
cccactagaa agaacatgtt                                             20

<210> SEQ ID NO 543
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 543
gccactaggg acaggat                                                        17

<210> SEQ ID NO 544
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
atcctgtccc tag                                                            13

<210> SEQ ID NO 545
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
tggcctaggg acaggat                                                        17

<210> SEQ ID NO 546
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
atcctgtccc tag                                                            13

<210> SEQ ID NO 547
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
ttctggcctc tttattgggc cgcccaagga acccttttct gggccatctt cgtactcggc         60
cacgactggt aatttaatgg atccactagt aa                                       92

<210> SEQ ID NO 548
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
ttctggcctc tttattgggc cgcccaagga acccttttct gggccatctt cgtactcggc         60
cacgactggt aatttaatgg atccactagt aa                                       92

<210> SEQ ID NO 549
<211> LENGTH: 119
<212> TYPE: DNA
<213> ORGANISM: Artificial Sequence
<220> FEATURE:

-continued

<223> OTHER INFORMATION: Description of Artificial Sequence: Synthetic
      polynucleotide

<400> SEQUENCE: 549
ttctggcctc tttattgggc cgcccaagga acccttttct gggccatcca gtcgtggccg      60
agtacgaaga tggcccagat actcggccac gactggtaat ttaatggatc cactagtaa    119

<210> SEQ ID NO 550
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
ttctggcctc tttattgggc cgcccaagga acccttttct gggccatcgt actcggccac      60
gactggtaat ttaatggatc cactagtaa                                        89

<210> SEQ ID NO 551
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 551
ttctggcctc tttattgggc cgcccaagga acccttttct aggtatctca gttcggtgta      60
ggtcgttcgc tccaagctgg gctgcgtgca cgaaccgtac tcggccacga ctggtaattt    120
aatggatcca ctagtaa                                                   137

<210> SEQ ID NO 552
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552
ttctggcctc tttattgggc cgcccaagga acccttttct gggccagact ggtaatttaa      60
tggatccact agtaa                                                       75

<210> SEQ ID NO 553
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
tccaaggttg cggccgcgcc caaggaaccc ttttctgggc catcttcgta ctcggccacg      60
actggtaatt taattttcaa tttattt                                          87

<210> SEQ ID NO 554
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
tccaaggttg cggccgcgcc caaggaaccc ttttctgggc cattactcgg ccacgactgg    60
taatttaatt ttcaatttat tt                                            82

<210> SEQ ID NO 555
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
tccaaggttg cggccgcgcc caaggaaccc ttttctgggc catttactcg gccacgactg    60
gtaatttaat tttcaattta ttt                                           83

<210> SEQ ID NO 556
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
cgtactcggc cacgactggt aatttaattt caatttatt t                        41

<210> SEQ ID NO 557
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
tccaaggttg cggccgcgcc caaggaaccc ttttctgggc catcttcgta ctcggccacg    60
actggtaatt taattttcaa tttattt                                       87

<210> SEQ ID NO 558
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 558
tccaaggttg cggccgcgcc caaggaaccc ttttctgggc catcttctgg taatttaatt    60
ttcaatttat tttt                                                     74

<210> SEQ ID NO 559
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 559
tccaaggttg cggccgcgcc caaggaaccc ttttctggta gcggtggttt ttttgtttgc    60
aagcagcaga ttacgcgcag aaaaaaagga tcgtactcgg ccacgactgg taatttaatt   120
ttcaatttat tt              132

<210> SEQ ID NO 560
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 560
tccaaggttg cggccgcgcc caaggaaccc ttttctgggc catcttacga gcgtaatggc    60
tggcctgttg aacaagtctg gaaagaaatg cataaacata tcccagccac gactggtaat   120
ttaattttca atttattt              138

<210> SEQ ID NO 561
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561 tagtttatt gccccaagcg agagaaagct tattgcaact tcaactcgta ctcggccacg    60
actggtaatt taatggatcc actagtaa              88

<210> SEQ ID NO 562
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562 tagtttatt gccccaagcg agagaaagct tattgcaact tcaact              46

<210> SEQ ID NO 563
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563 tagtttatt gccccaagcg agagaaagct tattgcaact tcaacg              46

<210> SEQ ID NO 564
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 564 tagtttatt gccccaagcg agagaaagct tattgcaact tcaacttcgt actcggccac    60
gactggtaat ttaatggatc cactagtaa              89

<210> SEQ ID NO 565
<211> LENGTH: 89

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
tagtttattt gccccaagcg agagaaagct tattgcaact tcaactatgt actcggccac    60
gactggtaat ttaatggatc cactagtaa                                      89

<210> SEQ ID NO 566
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566
tagtttattt gccccaagcg agagaaagct tattgcaact tcatactcgg ccacgactgg    60
taatttaatg gatccactag taa                                            83

<210> SEQ ID NO 567
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
aggtaattta atggatccac tagtaa                                         26

<210> SEQ ID NO 568
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568
tccaaggttg cggccgcagc gagagaaagc ttattgcaac ttcaactact tgctggtcga    60
tcgtgttggc cactcttgtt tatctatca                                      89

<210> SEQ ID NO 569
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
tccaaggttg cggccgcagc gagagaaagc ttattgcaac ttcaacttgc tggtcgatcg    60
tgttggccac tcttgtttat ctatca                                         86

<210> SEQ ID NO 570
<211> LENGTH: 149
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 570
tccaaggttg cggccgcgcg ccgacccagc tttcttgtac aaagttggca ttataagaaa      60
gcattgctta tcaatttgtt gcaacgaaca ggtcactatc agtcaaaact tgctggtcga     120
tcgtgttggc cactcttgtt tatctatca                                       149

<210> SEQ ID NO 571
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
tccaaggttt gcggccgcag cgagagaaag cttattgcaa cttcacttgc tggtcgatcg      60
tgttggccac tcttgtttat ctatca                                          86

<210> SEQ ID NO 572
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 572
tccaaggttg cggccgcagc gagagaaagc ttattgcaac ttcagataaa agttgctcgc      60
ctgtgtgggt gtggatgcta cttgctggtc gatcgtgttg ccactcttg tttatctatc     120 a                                                                    121
```